United States Patent
Lee et al.

(10) Patent No.: US 10,141,516 B2
(45) Date of Patent: *Nov. 27, 2018

(54) COMPOUND FOR ORGANIC ELECTRIC ELEMENT, ORGANIC ELECTRIC ELEMENT COMPRISING THE SAME AND ELECTRONIC DEVICE THEREOF

(71) Applicant: DUK SAN NEOLUX CO., LTD., Cheonan-si, Chungcheongnam-do (KR)

(72) Inventors: Bumsung Lee, Cheonan-si (KR); Yeonhee Choi, Cheonan-si (KR); Daesung Kim, Yongin-si (KR); Soungyun Mun, Yongin-si (KR); Jungcheol Park, Cheonan-si (KR); Kiho So, Cheonan-si (KR); Jinho Yun, Cheonan-si (KR); Daehwan Oh, Cheonan-si (KR); Seungwon Yeo, Daejeon (KR)

(73) Assignee: DUK SAN NEOLUX CO., LTD., Cheonan-si, Chungcheon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/650,110

(22) PCT Filed: Dec. 3, 2013

(86) PCT No.: PCT/KR2013/011089
§ 371 (c)(1),
(2) Date: Jun. 5, 2015

(87) PCT Pub. No.: WO2014/088285
PCT Pub. Date: Jun. 12, 2014

(65) Prior Publication Data
US 2015/0303379 A1    Oct. 22, 2015

(30) Foreign Application Priority Data

Dec. 6, 2012 (KR) .................. 10-2012-0141364
Nov. 1, 2013 (KR) .................. 10-2013-0132013

(51) Int. Cl.
| | |
|---|---|
| *C07D 209/86* | (2006.01) |
| *C07D 333/76* | (2006.01) |
| *H01L 51/00* | (2006.01) |
| *C07D 209/82* | (2006.01) |
| *C09K 11/06* | (2006.01) |
| *H05B 33/14* | (2006.01) |
| *C07D 401/12* | (2006.01) |
| *C07D 405/04* | (2006.01) |
| *C07D 405/14* | (2006.01) |
| *C07D 409/04* | (2006.01) |
| *C07D 409/12* | (2006.01) |
| *C07D 409/14* | (2006.01) |
| *G09G 3/3225* | (2016.01) |
| *H01L 51/50* | (2006.01) |

(52) U.S. Cl.
CPC ........ *H01L 51/0061* (2013.01); *C07D 209/82* (2013.01); *C07D 209/86* (2013.01); *C07D 401/12* (2013.01); *C07D 405/04* (2013.01); *C07D 405/14* (2013.01); *C07D 409/04* (2013.01); *C07D 409/12* (2013.01); *C07D 409/14* (2013.01); *C09K 11/06* (2013.01); *G09G 3/3225* (2013.01); *H01L 51/006* (2013.01); *H01L 51/0072* (2013.01); *H05B 33/14* (2013.01); *C09K 2211/1007* (2013.01); *C09K 2211/1011* (2013.01); *C09K 2211/1014* (2013.01); *C09K 2211/1029* (2013.01); *C09K 2211/1088* (2013.01); *C09K 2211/1092* (2013.01); *H01L 51/0052* (2013.01); *H01L 51/0056* (2013.01); *H01L 51/0058* (2013.01); *H01L 51/0067* (2013.01); *H01L 51/0068* (2013.01); *H01L 51/0073* (2013.01); *H01L 51/0074* (2013.01); *H01L 51/5004* (2013.01); *H01L 51/5012* (2013.01); *H01L 51/5056* (2013.01); *H01L 51/5072* (2013.01); *H01L 51/5088* (2013.01); *H01L 51/5092* (2013.01); *H01L 2251/552* (2013.01); *Y02E 10/549* (2013.01)

(58) Field of Classification Search
CPC .. C07D 209/86; C07D 333/76; H01L 51/0061
USPC ........................................................ 548/440
See application file for complete search history.

(56) References Cited

U.S. PATENT DOCUMENTS

2015/0325795 A1* 11/2015 Lee ................. C07D 209/82
257/40

FOREIGN PATENT DOCUMENTS

| | | | | |
|---|---|---|---|---|
| JP | 2008-78362 A | 4/2008 | | |
| JP | 2008-195841 A | 8/2008 | | |
| KR | 10-2010-0021907 A | 2/2010 | | |
| KR | 10-2010-0033265 A | 3/2010 | | |
| KR | 10-2010-0131629 A | 12/2010 | | |
| KR | 101029082 B1 * | 4/2011 | ........... | C07D 307/91 |
| KR | WO 2011133007 A2 * | 10/2011 | ........... | C09K 11/06 |
| KR | 10-2012-0100031 A | 9/2012 | | |
| KR | 10-2012-0111670 A | 10/2012 | | |
| KR | 10-2013-0096334 A | 8/2013 | | |
| WO | WO 2011055932 A2 * | 5/2011 | ........... | C07D 209/82 |
| WO | WO 2011133007 A2 * | 10/2011 | ........... | C09K 11/06 |
| WO | 2011155742 A2 | 12/2011 | | |
| WO | WO-2012090806 A1 * | 7/2012 | ........... | C07D 209/86 |

OTHER PUBLICATIONS

Machine Translation of the claims of JP-2008195841, obtained from https://worldwide.espacenet.com, accessed on Mar. 4, 2017.*

(Continued)

*Primary Examiner* — Matthew P Coughlin
*Assistant Examiner* — Sagar Patel
(74) *Attorney, Agent, or Firm* — Vorys, Sater, Seymour & Pease LLP; Mih Suhn Koh

(57) ABSTRACT

Provides herein are a compound capable of improving light emitting efficiency, stability, and lifespan of the element, an organic element using the same, and an electric device for the same.

13 Claims, 1 Drawing Sheet

(56) References Cited

OTHER PUBLICATIONS

Machine Translation of the specification of JP-2008195841, obtained from https://worldwide.espacenet.com, accessed on Mar. 4, 2017.*
Machine Translation of KR-101029082, obtained from http://eng.kipris.or.kr/enghome/main.jsp, accessed on Jun. 21, 2017.*
Machine Translation of WO-2012090806-A1, obtained from https://worldwide.espacenet.com/publicationDetails/biblio?II=0&ND=3&adjacent=true&locale=en_EP&FT=D&date=20120705&CC=WO&NR=2012090806A1&KC=A1, accessed on Dec. 28, 2017. (Year: 2012).*

* cited by examiner

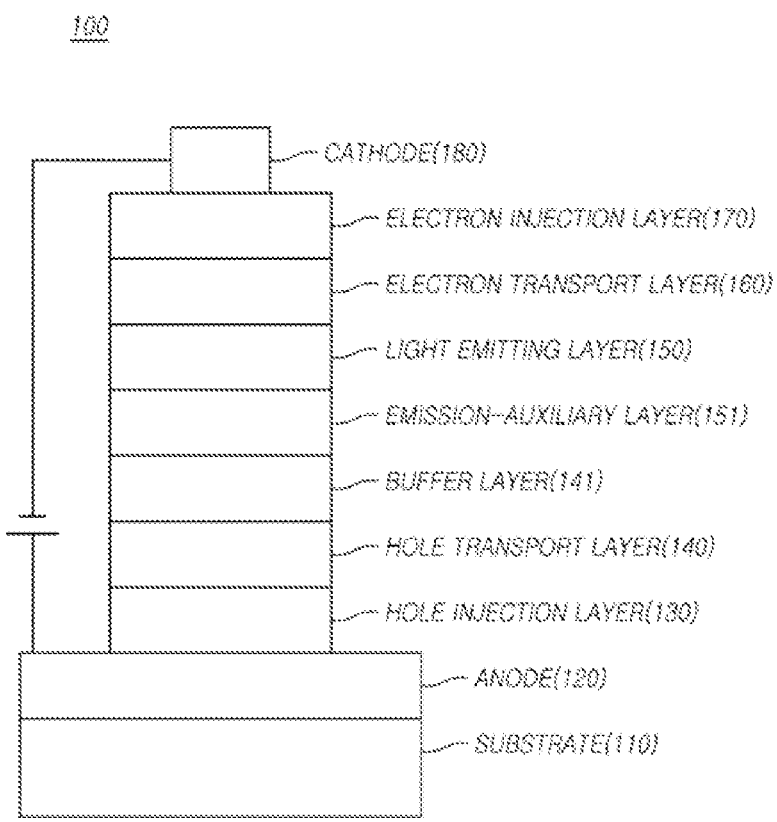

COMPOUND FOR ORGANIC ELECTRIC ELEMENT, ORGANIC ELECTRIC ELEMENT COMPRISING THE SAME AND ELECTRONIC DEVICE THEREOF

CROSS-REFERENCE TO RELATED APPLICATION

This application claims priority from and the benefit under U.S.C. § 119(a) of Korean Patent Application No. 10-2012-0141364, filed on Dec. 6, 2012, and Korean Patent Application No. 10-2013-0132013, filed on Nov. 1, 2013, the contents of which are hereby incorporated by reference for all purposes as if fully set forth herein.

JOINT RESEARCH AGREEMENT

The claimed invention was made by or on behalf of parties to a joint research agreement under AIA 35 U.S.C. 102(c). The parties were DUK SAN NEOLUX CO., LTD and SAMSUNG DISPLAY CO., LTD. The agreement was in effect on or before the effective filing date of the claimed invention, and the claimed invention was made as a result of activities undertaken within the scope of the joint research agreement.

BACKGROUND

Technical Field

The present invention relates to compounds for organic electric elements, organic electric elements using the same, and electronic devices thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. Here, in many cases, the organic material layer may have a multi-layered structure including multiple layers made of different materials in order to improve the efficiency and stability of an organic electric element, and for example, may include a hole injection layer, a hole transport layer, a light emitting layer, an electron transport layer, an electron injection layer, and the like.

A material used as an organic material layer in an organic electric element may be classified into a light emitting material and a charge transport material, for example, a hole injection material, a hole transport material, an electron transport material, an electron injection material, and the like according to its function.

The most problematic issues in an organic electric element are life span and efficiency, and the situation is such that this life span or efficiency issue must be solved as displays become larger and larger. Efficiency, life span, driving voltage, and the like are correlated with each other.

For example, if efficiency is increased, then driving voltage is relatively lowered, and the crystallization of an organic material due to Joule heating generated during operation is reduced as driving voltage is lowered, as a result of which life span shows a tendency to increase.

However, efficiency cannot be maximized only by simply improving the organic material layer. This is because long life span and high efficiency can be simultaneously achieved when an optimal combination of energy levels and T1 values, inherent material properties (mobility, interfacial properties, etc.), and the like among the respective layers included in the organic material layer is given.

Further, in order to solve the emission problem with a hole transport layer in a recent organic electric element, an emission-auxiliary layer is present between the hole transport layer and a light emitting layer, and it is time to develop different emission-auxiliary layers according to respective light emitting layers (R, G, B).

In general, an electron transferred from an electron transport layer to a light emitting layer and a hole transferred from a hole transport layer to the light emitting layer are recombined to form an exciton.

However, since a material used in a hole transporting layer should have a low HOMO value, it mainly has a low T1 value. Due to this, excitons generated from a light emitting layer are transported to the hole transporting layer, resulting in a charge unbalance in the light emitting layer. Thus, light emission occurs in the hole transporting layer or at an interface of the hole transporting layer so that the organic electroluminescent device is reduced in color purity, efficiency, and lifespan.

When used, a material with rapid hole mobility can reduce a driving voltage in the organic electroluminescent device, but is apt to cause a charge unbalance due to its hole mobility being faster than its electron mobility. Hence, the organic electroluminescent device also suffers from the disadvantage of a reduction in color purity, efficiency, and lifespan.

Therefore, there is an urgent need to develop an emission-auxiliary layer which has a high T1 value and the HOMO level of which is between the HOMO energy level of a hole transport layer and the HOMO energy level of a light emitting layer.

In addition, it is required to develop a hole injection layer material that retards penetration/diffusion of metal oxides from an anode electrode (ITO) into an organic layer, which is one cause for the shortened life span of an organic electric element, and has stability against Joule heat generated during the operation of an organic electric element, that is, a high glass transition temperature. Also, it has been reported that a low glass transition temperature of a hole transport layer material has a great effect on the life span of an organic electric element because the uniformity of a thin film surface collapses during the operation of the element. In general, deposition is a main method of forming an OLED, and thus there is an actual need to develop a material that is durable to such a deposition method, that is, a highly heat-resistant material.

In order to allow an organic electric element to fully exhibit the above-mentioned excellent features, it should be prerequisite to support a material constituting an organic material layer in the element, for example, a hole injection material, a hole transport material, a light emitting material, an electron transport material, an electron injection material, or the like, by a stable and efficient material. However, such a stable and efficient organic material layer material for an organic electric element has not yet been fully developed. Accordingly, there is a continuous need to develop new materials for an organic material layer.

SUMMARY

An object of the present invention is to provide a compound that is configured to both have a high T1 value and a wide band gap, and which allows for an excellent charge balance by introducing a carbazole core, which is widely used as a hole transporting material, with a non-linear linker (thus, resulting in a bent structure upon linkage with an amine group) and with a bulky substituent at the nitrogen position thereof, thereby guaranteeing that the device has high luminous efficiency, low driving voltage, high thermal resistance, high color purity, and long longevity, an organic electroluminescent device using the same, and an electronic device using the device.

In accordance with an aspect of the present invention, there is provided compounds represented by the formula below.

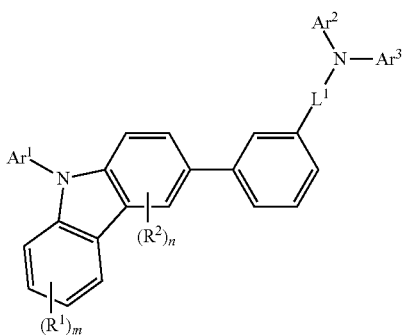

In another aspect of the present invention, there are provided organic electric elements using the compound represented by the formula above and electronic devices including the organic electric element.

By using the compound according to embodiments of the present invention, an organic electric element according to one or more embodiments of the present invention not only has high luminous efficiency, low driving voltage and high heat-resistant and, but can also be significantly improved in color purity, luminous efficiency, and life span.

BRIEF DESCRIPTION OF THE DRAWINGS

FIG. 1 illustrates an example of an organic light emitting diode according to an embodiment of the present invention.

DETAILED DESCRIPTION

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

As used in the specification and the accompanying claims, unless otherwise stated, the following is the meaning of the term as follows.

Unless otherwise stated, the term "halo" or "halogen" as used herein includes fluorine, chlorine, bromine, or iodine.

Unless otherwise stated, the term "alkyl" or "alkyl group" as used herein has a single bond of 1 to 60 carbon atoms, and means aliphatic functional radicals including a linear alkyl group, a branched chain alkyl group, a cycloalkyl group (alicyclic), or an alkyl group substituted with a cycloalkyl.

Unless otherwise stated, the term "haloalkyl" or "halogen alkyl" as used herein includes an alkyl group substituted with a halogen.

Unless otherwise stated, the term "heteroalkyl" as used herein means alkyl substituted one or more carbon atoms with heteroatom.

Unless otherwise stated, the term "alkenyl" or "alkynyl" as used herein has, but not limited to, double or triple bonds of 2 to 60 carbon atoms, and includes a linear alkyl group, or a branched chain alkyl group, Unless otherwise stated, the term "cycloalkyl" as used herein means, but not limited to, alkyl forming a ring having 3 to 60 carbon atoms.

The term "alkoxyl group", "alkoxy group" or "alkyloxy group" as used herein means an oxygen radical attached to an alkyl group, but not limited to, and has 1 to 60 carbon atoms.

The term "alkenoxyl group", "alkenoxy group", "alkenyloxy group" or "alkenyloxy group" as used herein means an oxygen radical attached to an alkenyl group, but not limited to, and has 2 to 60 carbon atoms.

The term "aryloxyl group" or "aryloxy group" as used herein means an oxygen radical attached to an aryl group, but not limited to, and has 6 to 60 carbon atoms.

Unless otherwise stated, the term "aryl group" or "arylene group" as used herein has, but not limited to, 6 to 60 carbon atoms. Herein, the aryl group or arylene group means a monocyclic or polycyclic aromatic group, and may also be formed in conjunction with an adjacent group. Examples of "aryl group" or "arylene group" may include a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substitutes with an arylcarbonyl, wherein the arylcarbonyl may be a carbonyl substituted with an aryl.

Unless otherwise stated, the term "heteroalkyl" as used herein means alkyl containing one or more heteroatoms. Unless otherwise stated, the term "heteroaryl group" or "heteroarylene group" as used herein means, but not limited to, a $C_2$ to $C_{60}$ aryl or arylene group containing one or more heteroatoms, includes both monocyclic and polycyclic rings, and may also be formed in conjunction with an adjacent group.

Unless otherwise stated, the term "heterocyclic group" as used herein contains one or more heteroatoms, but not limited to, has 2 to 60 carbon atoms, includes both monocyclic and polycyclic rings, and may include alicyclic and/or aromatic group containing heteroatoms. Also, the heterocyclic group may also be formed in conjunction with an adjacent group.

Unless otherwise stated, the term "heteroatom" as used herein represents at least one of N, O, S, P, and Si.

Also, the term "heterocyclic group" may include SO$_2$ instead of carbon consisting of cycle. For example, "heterocyclic group" includes compound below.

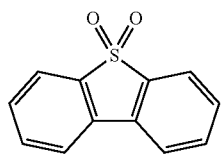 [SMILES: O=S1(=O)c2ccccc2-c2ccccc21]

Unless otherwise stated, the term "aliphatic" as used herein means an aliphatic hydrocarbon having 1 to 60 carbon atoms, and the term "aliphatic ring" as used herein means an aliphatic hydrocarbon ring having 3 to 60 carbon atoms.

Unless otherwise stated, the term "ring" means an aliphatic ring having 3 to 60 carbon atoms, an aromatic ring having 6 to 60 carbon atoms, a hetero ring having 2 to 60 carbon atoms, or a fused ring formed by the combination of them, and includes a saturated or unsaturated ring.

Hetero compounds or hetero radicals other than the above-mentioned hetero compounds each contain, but not limited to, one or more heteroatoms.

Unless otherwise stated, the term "carbonyl" as used herein is represented by —COR', wherein R' may be hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "ether" as used herein is represented by —R—O—R', wherein R' may be hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynl having 2 to 20 carbon atoms, or the combination of these.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthio group, a $C_6$-$C_{20}$ arylthio group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a $C_6$-$C_{20}$ aryl group substituted by deuterium, a $C_8$-$C_{20}$ arylalkenyl group, a silane group, a boron group, a germanium group, and a $C_5$-$C_{20}$ heterocyclic group.

Otherwise specified, the Formulas used in the present invention are as defined in the index definition of the substituent of the following Formula.

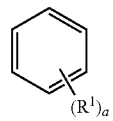

Wherein, when a is an integer of zero, the substituent $R^1$ is absent, when a is an integer of 1, the sole $R^1$ is linked to any one of the carbon atoms constituting the benzene ring, when a is an integer of 2 or 3, the substituent $R^1$s may be the same and different, and are linked to the benzene ring as follows. when a is an integer of 4 to 6, the substituents $R^1$s may be the same and different, and are linked to the benzene ring in a similar manner to that when a is an integer of 2 or 3, hydrogen atoms linked to carbon constituents of the benzene ring being not represented as usual.

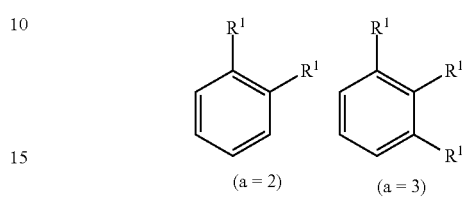

FIG. 1 illustrates an organic electric element according to an embodiment of the present invention.

Referring to FIG. 1, an organic electric element 100 according to an embodiment of the present invention includes a first electrode 120 formed on a substrate 110, a second electrode 180, and an organic material layer between the first electrode 110 and the second electrode 180, which contains the inventive compound. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer includes a hole injection layer 130, a hole transport layer 140, a light emitting layer 150, an electron transport layer 160, and an electron injection layer 170 formed in sequence on the first electrode 120. Here, the layers included in the organic material layer, except the light emitting layer 150, may not be formed. The organic material layer may further include a hole blocking layer, an electron blocking layer, an emission-auxiliary layer 151, a buffer layer 141, etc., and the electron transport layer 160 and the like may serve as the hole blocking layer.

Although not shown, the organic electric element according to an embodiment of the present invention may further include at least one protective layer or one capping layer formed on at least one of the sides the first and second electrodes, which is a side opposite to the organic material layer.

The inventive compound employed in the organic material layer may be used as a host material, a dopant material, or a capping layer material in the hole injection layer 130, the hole transport layer 140, the electron transport layer 160, the electron injection layer 170, or the light emitting layer 150. For example, the inventive compound may be used as the light emitting layer 150, the hole transport layer 140, and/or the emission-auxiliary layer 151.

Since depending on the type and position of a substituent to be attached, a band gap, electrical properties, interfacial properties, and the like may vary even in the same core, it is very important what the types of core and a combination of substituent attached to the core are. Specially, long life span and high efficiency can be simultaneously achieved when an optimal combination of energy levels and T1 values, inherent material properties (mobility, interfacial properties, etc.), and the like among the respective layers included in the organic material layer is given.

As already described above, in order to solve the emission problem with a hole transport layer in a conventional organic electric element, an emission-auxiliary layer is preferably formed between the hole transport layer and a light emitting layer, and it is time to develop different emission-auxiliary layers according to respective light emitting layers (R, G, B). However, even when a similar core is used, it is very difficult to infer the characteristics of an emission-auxiliary layer if a used organic material layer varies because the correlation between the emission-auxiliary layer and a hole transport layer and the correlation between the emission-auxiliary layer and a light emitting layer (host) mused be discovered.

Accordingly, in the present invention, a combination of energy levels and T1 values, inherent material properties (mobility, interfacial properties, etc.), and the like among the respective layers included in the organic material layer is optimized by forming a light emitting layer or an emission-auxiliary layer by using the compound represented by Formula 1, and thus the life span and efficiency of the organic electric element can be improved at the same time.

The organic electric element according to an embodiment of the present invention may be manufactured using a PVD (physical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon.

Also, the organic material layer may be manufactured in such a manner that a smaller number of layers are formed using various polymer materials by a soluble process or solvent process, for example, spin coating, dip coating, doctor blading, screen printing, inkjet printing, or thermal transfer, instead of deposition. Since the organic material layer according to the present invention may be formed in various ways, the scope of protection of the present invention is not limited by a method of forming the organic material layer.

According to used materials, the organic electric element according to an embodiment of the present invention may be of a top emission type, a bottom emission type, or a dual emission type.

A WOLED (White Organic Light Emitting Device) readily allows for the formation of ultra-high definition images, and is of excellent processability as well as enjoying the advantage of being produced using conventional color filter technologies for LCDs. In this regard, various structures for WOLEDs, used as back light units, have been, in the most part, suggested and patented. Representative among the structures are a parallel side-by-side arrangement of R(Red), G(Green), B(Blue) light-emitting units, a vertical stack arrangement of RGB light-emitting units, and a CCM (color conversion material) structure in which electroluminescence from a blue (B) organic light emitting layer, and photoluminescence from an inorganic luminescent using the electroluminescence are combined. The present invention is applicable to these WOLEDs.

Further, the organic electric element according to an embodiment of the present invention may be any one of an organic light emitting diode (OLED), an organic solar cell, an organic photo conductor (OPC), an organic transistor (organic TFT), and an element for monochromatic or white illumination.

Another embodiment of the present invention provides an electronic device including a display device, which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, a compound according to an aspect of the present invention will be described.

The compound according to an aspect of the present invention is represented by Formula 1 below.

[Formula 1]

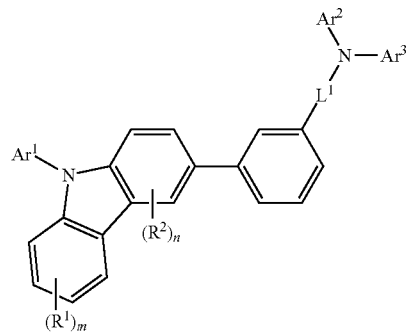

In Formula 1 above, m is an integer from 1 to 4, and n is an integer from 1 to 3.

$R^1$ and $R^2$ may be independently selected from the group consisting of hydrogen, deuterium, tritium, halogen, a $C_6$-$C_{60}$ aryl group, a fluorenyl group, a $C_2$-$C_{60}$ heterocyclic group containing at least one heteroatom selected from the group consisting of O, N, S, Si, and P, a $C_1$-$C_{50}$ alkyl group, a $C_2$-$C_{20}$ alkenyl group, -$L^2$-N($Ar^2$)($Ar^3$), a $C_1$-$C_{30}$ alkoxy group, and a $C_6$-$C_{30}$ aryloxy group. For example, $R^1$ and $R^2$ may be independently hydrogen, a phenyl group, or a naphthyl group and so on.

In Formula 1 above, $Ar^1$ may be selected from the group consisting of a fluorenyl group, a $C_6$-$C_{60}$ aryl group, a $C_2$-$C_{20}$ alkenyl group, a $C_2$-$C_{60}$ heterocyclic group containing at least one heteroatom selected from the group consisting of O, N, S, Si, and P, a $C_1$-$C_{50}$ alkyl group, -$L^2$-N($Ar^2$)($Ar^3$), and a fused ring group of a $C_3$-$C_{60}$ aliphatic ring and a $C_6$-$C_{60}$ aromatic ring. For example, $Ar^1$ may be an ethyl group, a phenyl group, a biphenylyl group, a naphthyl group, a terphenylyl group, a 9,9-dimethyl-9H-fluorenyl group, a 9,9-diphenyl-9H-fluorenyl group, a 9,9-spiro-bifluorenyl group, a pyridyl group, an isoquinolyl group, a dibenzothienyl group, or a dibenzofuranyl group and so on.

In Formula 1 above, $L^1$ and $L^2$ may be independently selected from the group consisting of a single bond, a $C_6$-$C_{60}$ arylene group, a fluorenylene group, and a $C_2$-$C_{60}$ bivalent heterocyclic group containing at least one heteroatom selected from the group consisting of O, N, S, Si, and P, a bivalent fused ring group of a $C_3$-$C_{60}$ aliphatic ring and a $C_6$-$C_{60}$ aromatic ring, and a bivalent aliphatic hydrocarbon group. For example, $L^1$ and $L^2$ may be independently a single bond, a phenylene group, a biphenylene group, a naphthylene group, a 9,9-dimethyl-9H-fluorenylene group, a 9,9-diphenyl-9H-fluorenylene group, a dibenzothienylene group, or a dibenzofuranylene group and so on.

In Formula 1 above, Ar² and Ar³ may be independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a $C_1$-$C_{50}$ alkyl group, a fused ring group of a $C_3$-$C_{60}$ aliphatic ring and a $C_6$-$C_{60}$ aromatic ring, and a $C_2$-$C_{20}$ alkenyl group. For example, Ar² and Ar³ may be independently a phenyl group, a biphenylyl group, a terphenylyl group, a naphthyl group, a phenanthryl group, a 9,9-dimethyl-9H-fluorenyl group, a 9,9-diphenyl-9H-fluorenyl group, a 9,9-spiro-bifluorenyl group, a dibenzothienyl group, a dibenzofuranyl group, a phenyl group substituted by fluoro, a phenyl group substituted by propenyl, a pyridyl group, a isoquinolyl group, a quinolyl group, a phenyl group substituted by methyl, a phenyl group substituted by deuterium, a benzothienyl group, a thienyl group, an indolyl group, or a benzoquinolyl group and so on.

With the provisos that, the aryl group, heterocyclic group, fluorenyl group, alkyl group, alkenyl group, fused ring group, alkoxy group, aryloxy group, arylene group, fluorenylene group and aliphatic hydrocarbon group may be substituted by one or more substituents selected from the group consisting of deuterium, halogen, a silane group, a boron group, a germanium group, a cyano group, a nitro group, -L'-N(R')(R") (wherein, L' may be selected from the group consisting of a single bond, a $C_6$-$C_{60}$ arylene group, a fluorenylene group, a $C_2$-$C_{60}$ heterocyclic group containing at least one heteroatom selected from the group consisting of O, N, S, Si, and P; a fused ring group of a $C_3$-$C_{60}$ aliphatic ring and a $C_6$-$C_{60}$ aromatic ring, and a $C_2$-$C_{60}$ bivalent aliphatic hydrocarbon group, and the R' and R" may be independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a $C_1$-$C_{20}$ alkyl group, and a $C_2$-$C_{20}$ alkenyl group.), a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted by deuterium, a $C_2$-$C_{20}$ heterocyclic group, a $C_3$-$C_{20}$ cycloalkyl group, a $C_7$-$C_{20}$ arylalkyl group, and a $C_8$-$C_{20}$ arylalkenyl group.

Also, in Formula 1 above, L¹ may be any one of groups below.

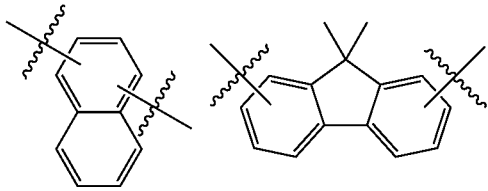

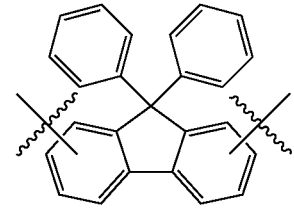

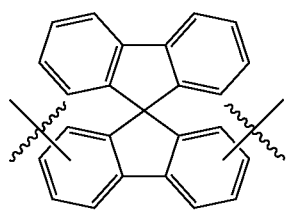

Also, in Formula 1 above, Ar² and Ar³ are independently any one of groups below.

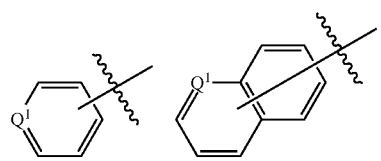

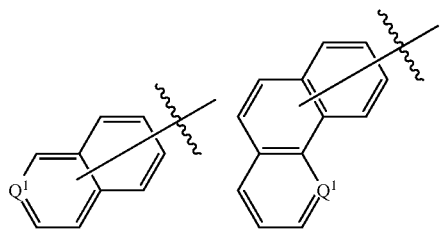

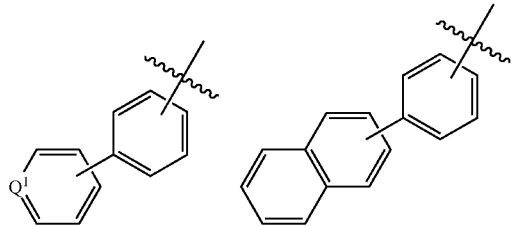

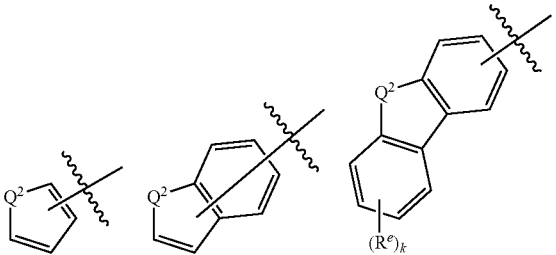

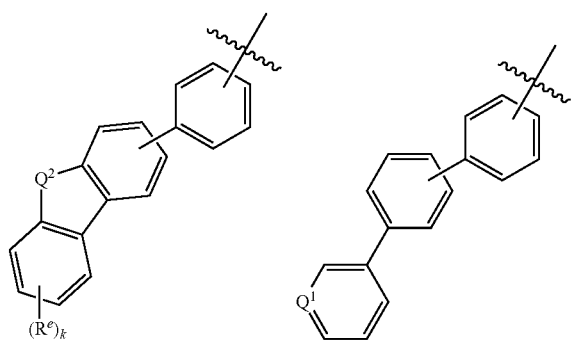

-continued

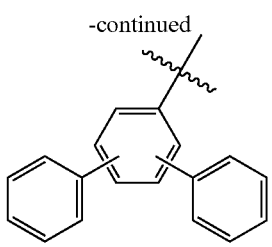

In groups above, $Q^1$ may be $C(R^a)$ or N, and $Q^2$ may be selected form the group consisting of $C(R^b)(R^c)$, $N(R^d)$, S and O. k may be an integer from 1 to 4. $R^a$ and $R^e$ may be independently selected from the group consisting of hydrogen, deuterium, a $C_6$-$C_{60}$ aryl group, a $C_2$-$C_{60}$ heterocyclic group containing at least one heteroatom selected from the group consisting of O, N, S, Si, and P, a $C_1$-$C_{50}$ alkyl group, a $C_2$-$C_{20}$ alkenyl group, a $C_1$-$C_{30}$ alkoxy group, and a fluorenyl group, or any two adjacent groups of $R^e$s can be optionally linked together to form at least one aromatic ring.

$R^b$ to $R^d$ may be independently selected from the group consisting of a $C_6$-$C_{60}$ aryl group, a $C_2$-$C_{60}$ heterocyclic group containing at least one heteroatom selected from the group consisting of O, N, S, Si, and P, a $C_1$-$C_{50}$ alkyl group, a $C_2$-$C_{20}$ alkenyl group, and a $C_1$-$C_{30}$ alkoxy group, or $R^b$ and $R^c$ can be optionally linked together to form at least one spiro compound.

Specially, the compound represented by Formula 1 above may be represented by one of Formula 2 or Formula 3 below.

[Formula 2]

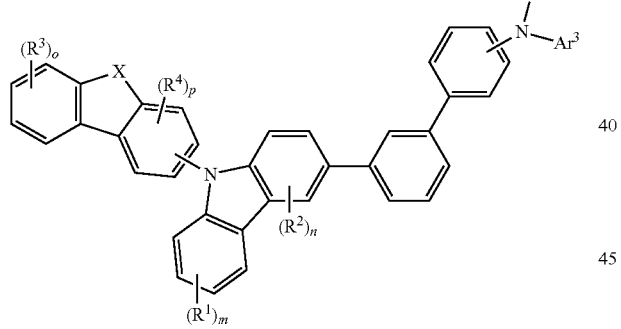

[Formula 3]

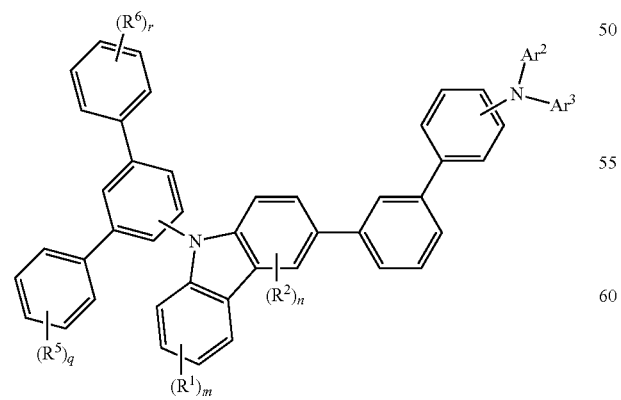

In Formula 2 and Formula 3 above, $Ar^2$, $Ar^3$, $R^1$, $R^2$, m and n may be as defined in Formula 1 above.

In Formula 2 above, X may be selected form the group consisting of $C(R^f)(R^g)$, S and O. $R^f$ and $R^g$ may be independently selected from the group consisting of a $C_6$-$C_{60}$ aryl group, a $C_2$-$C_{60}$ heterocyclic group containing at least one heteroatom selected from the group consisting of O, N, S, Si, and P, a $C_1$-$C_{50}$ alkyl group, a $C_2$-$C_{20}$ alkenyl group, and a $C_1$-$C_{30}$ alkoxy group, or $R^f$ and $R^g$ can be optionally linked together to form at least one spiro compound.

In Formula 2 and Formula 3 above, o is an integer from 1 to 4, p is an integer from 1 to 3, and q and r are independently an integer from 1 to 5.

In Formula 2 and Formula 3 above, $R^3$ to $R^6$ may be independently selected from the group consisting of hydrogen, deuterium, tritium, halogen, a $C_6$-$C_{60}$ aryl group, a $C_2$-$C_{60}$ heterocyclic group containing at least one heteroatom selected from the group consisting of O, N, S, Si, and P, a $C_1$-$C_{50}$ alkyl group, a $C_2$-$C_{20}$ alkenyl group, a $C_1$-$C_{30}$ alkoxy group, and a $C_6$-$C_{30}$ aryloxy group, or any two adjacent groups of $R^3$s to $R^6$s can be optionally linked together to form at least one aromatic ring.

Specially, the compound represented by Formula 1 above may be represented by one of Formula 4 or Formula 5 below.

[Formula 4]

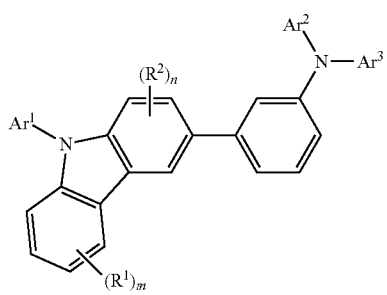

[Formula 5]

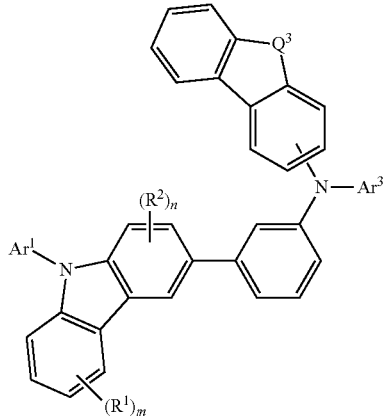

In Formula 4 and Formula 5 above, $Ar^1$ to $Ar^3$, $R^1$, $R^2$, m and n may be as defined in Formula 1 above.

In Formula 5 above, $Q^3$ may be selected form the group consisting of $C(R^h)(R^i)$, $N(R^j)$, S and O. $R^h$ to $R^j$ may be independently selected from the group consisting of a $C_6$-$C_{60}$ aryl group, a $C_2$-$C_{60}$ heterocyclic group containing at least one heteroatom selected from the group consisting of O, N, S, Si, and P, a $C_1$-$C_{50}$ alkyl group, a $C_2$-$C_{20}$ alkenyl group, and a $C_1$-$C_{30}$ alkoxy group, or $R^h$ and $R^i$ can be optionally linked together to form at least one spiro compound.

More specially, the compound represented by Formula 1 to Formula 5 above may be represented by one of compounds below.

| A1 | A2 |
|---|---|
| 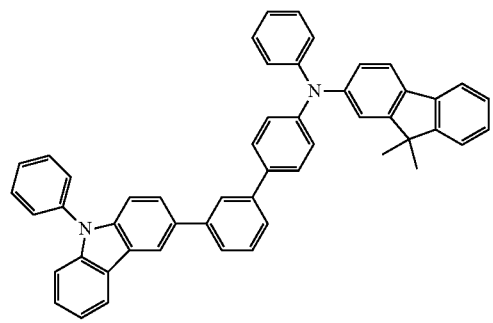 | 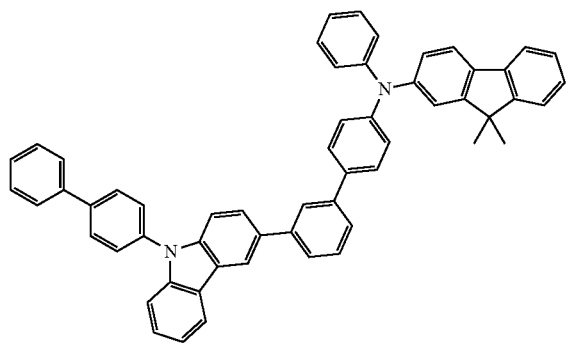 |
| A6 | A7 |
| 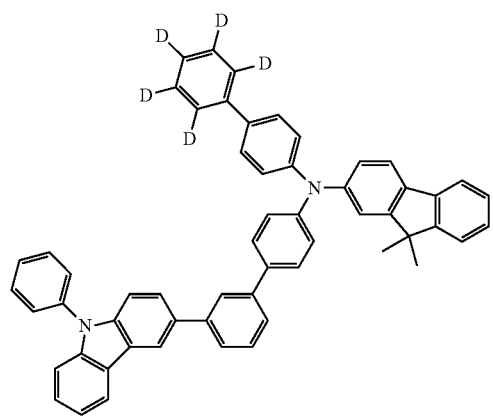 | 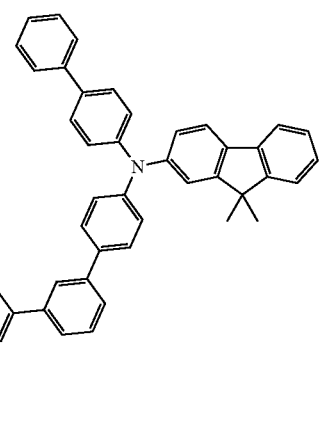 |
| A11 | A12 |
| 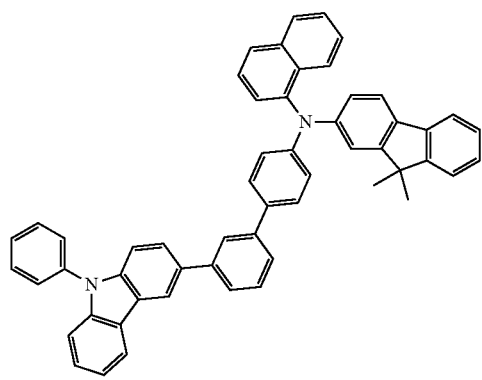 | 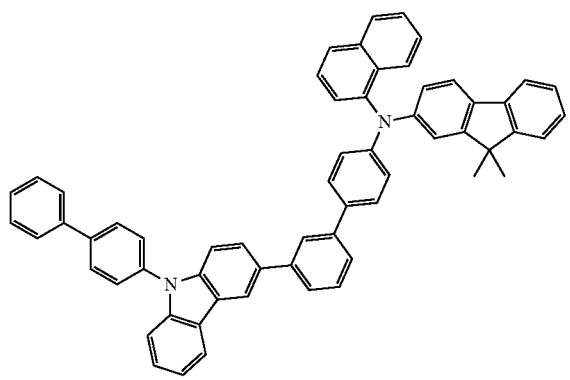 |
| A16 | A17 |
| 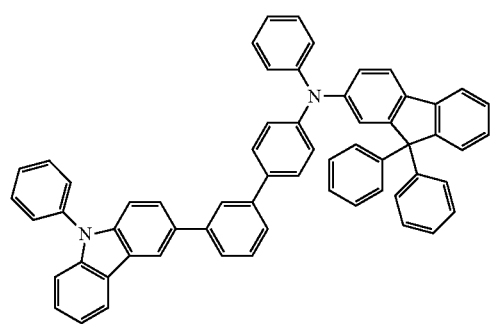 | 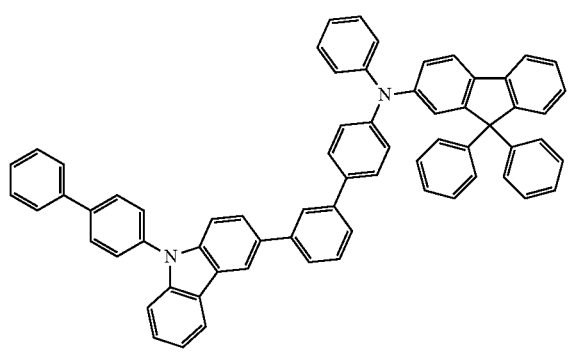 |

-continued
A19
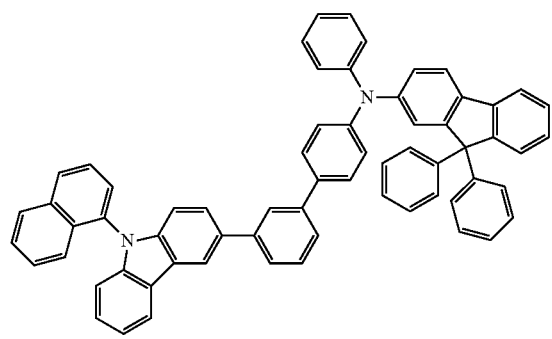
A21
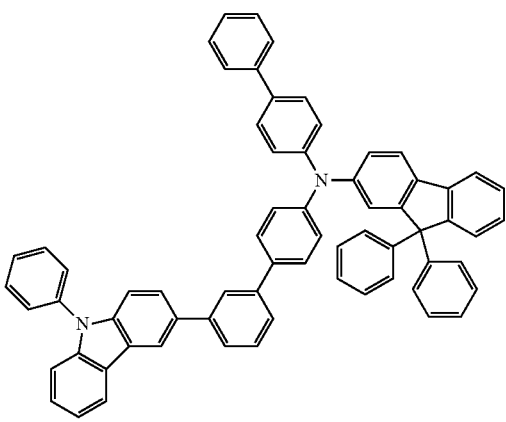
A22
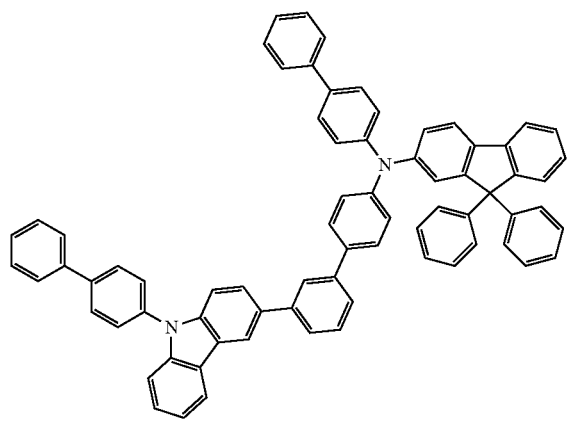
A23
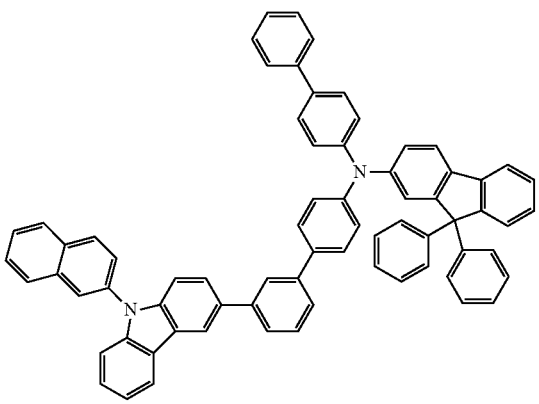
A24
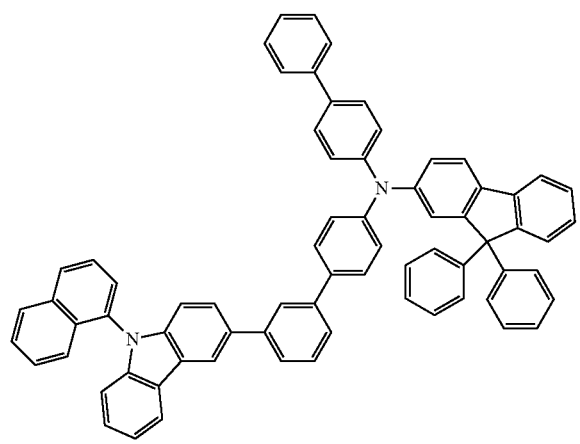
A25
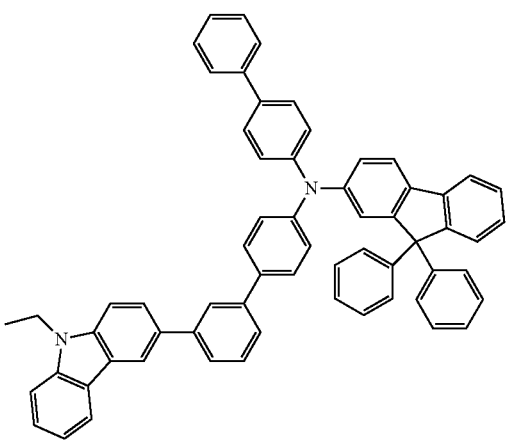

-continued
A26
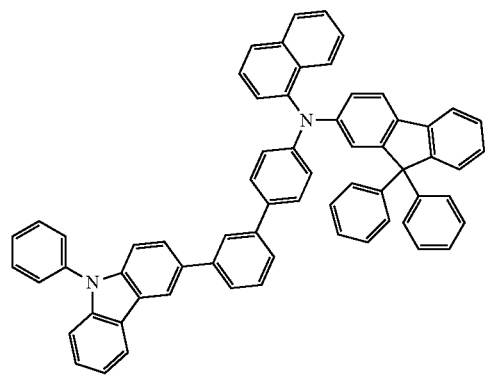
A27
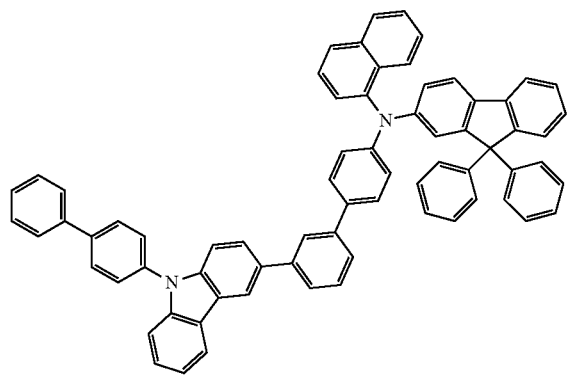
A31
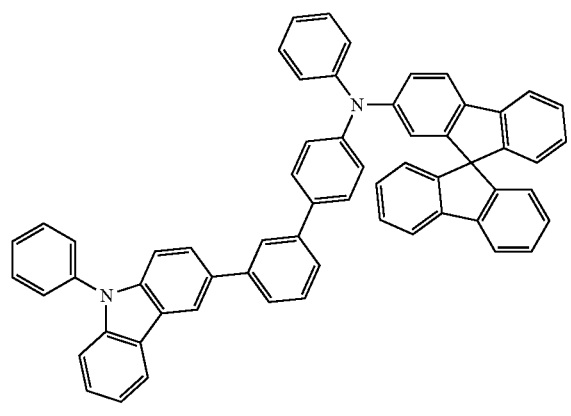
A36
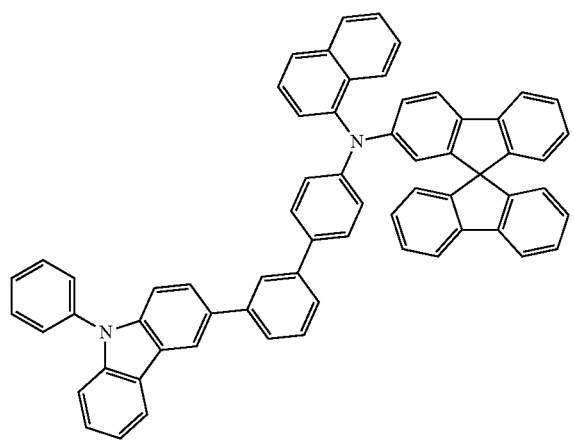
A47
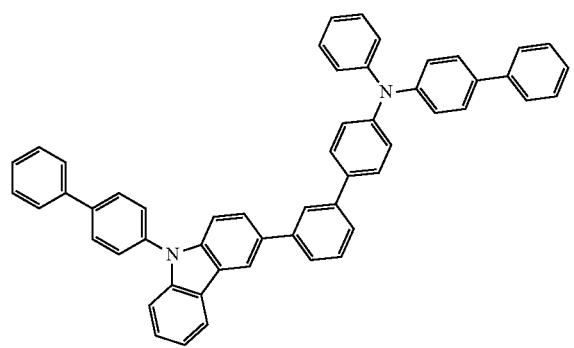
A51
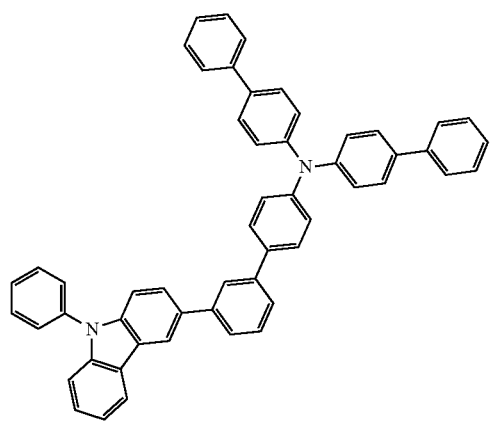

-continued
A56
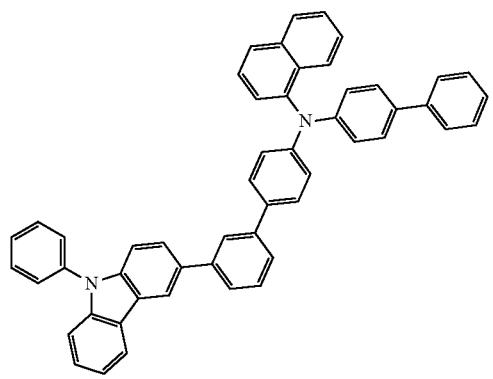
A62
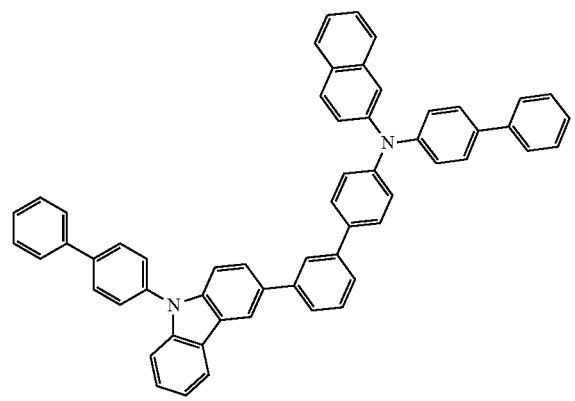
A66
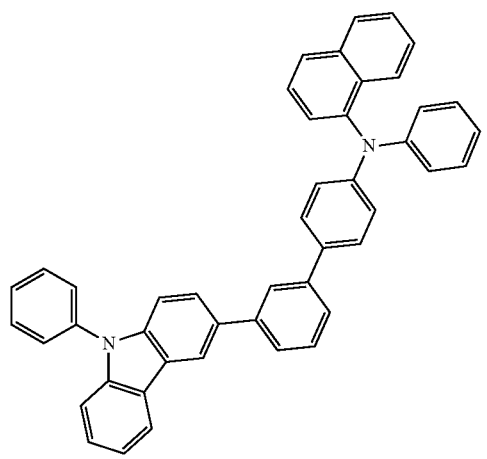
A72
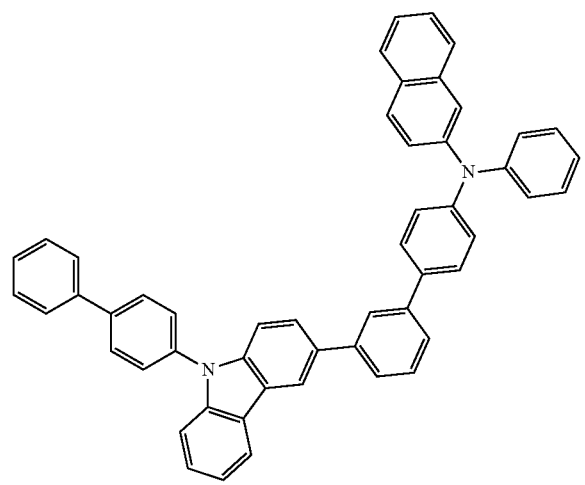
A87
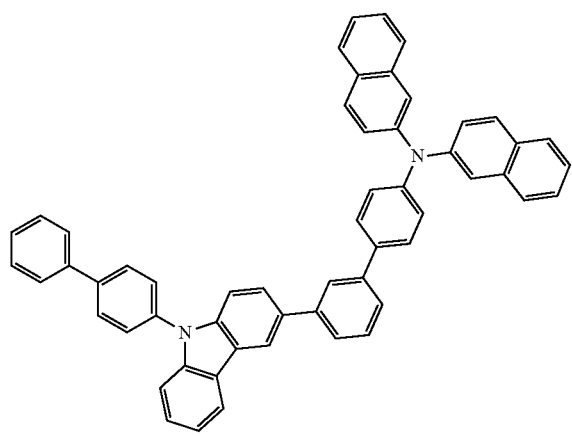
A97
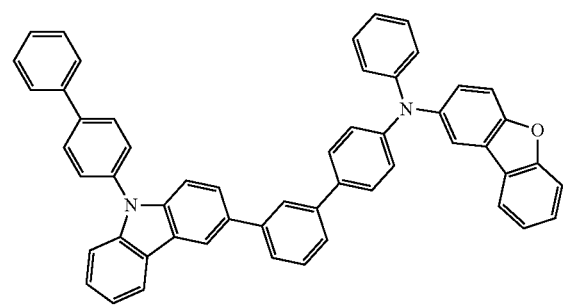

-continued
A101
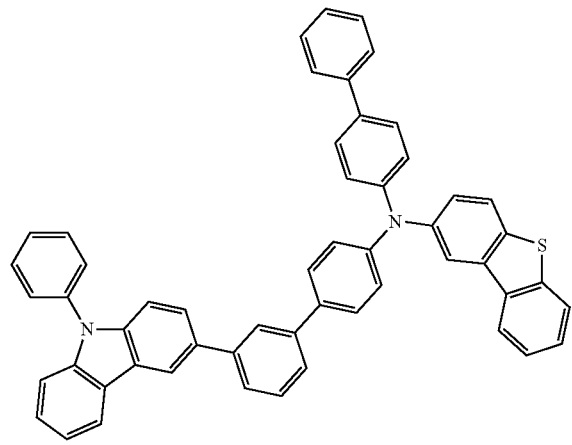
A121
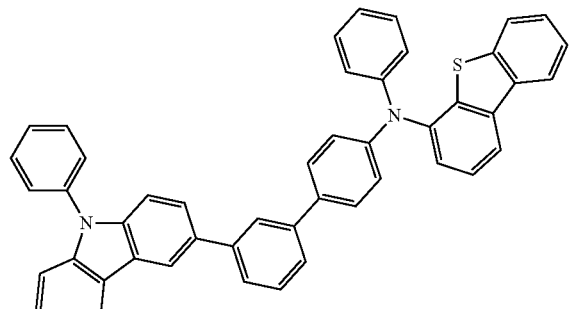
A123
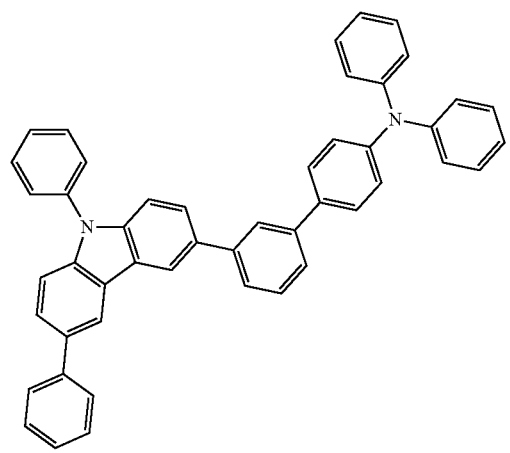
A124
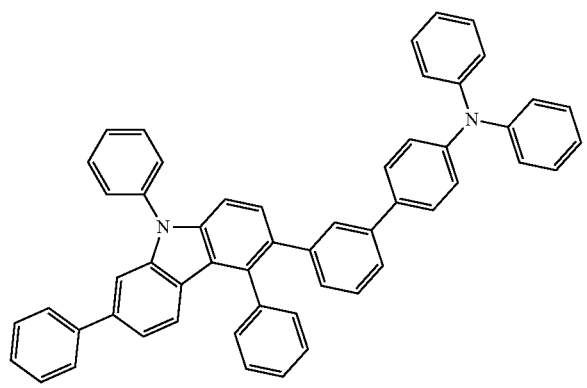
A125
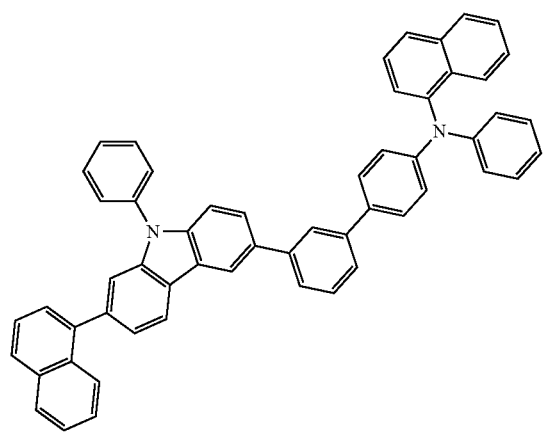
A127
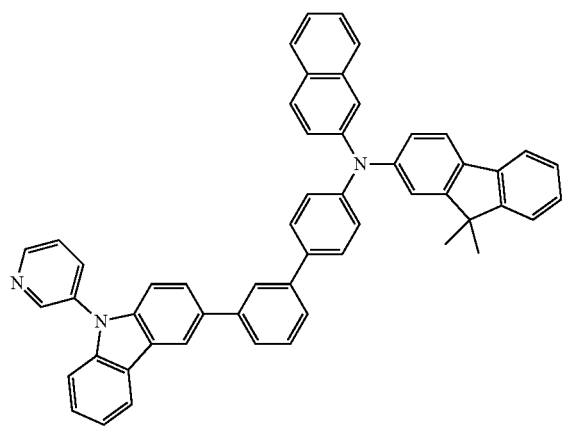

-continued
A128
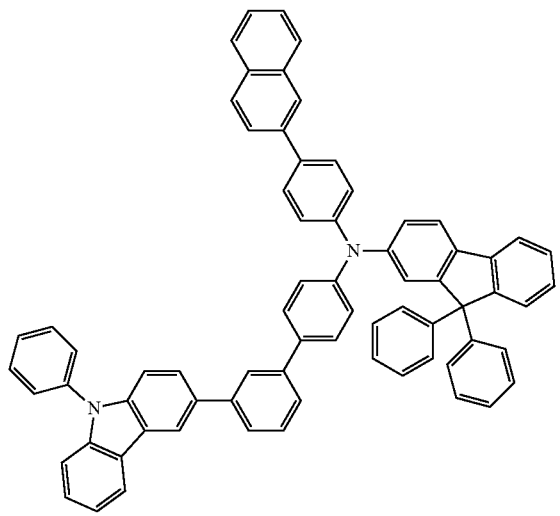
A129
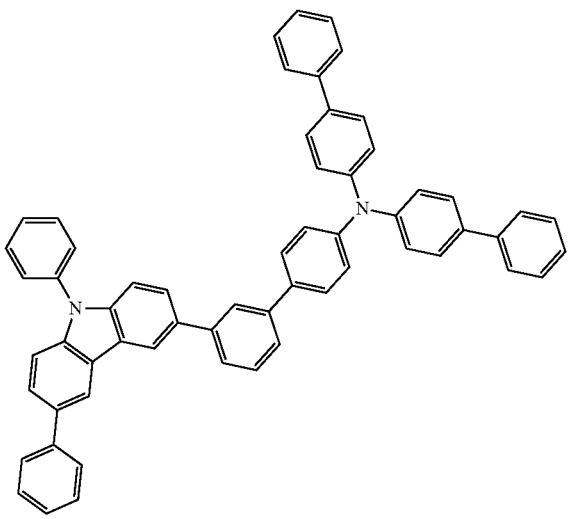
A130
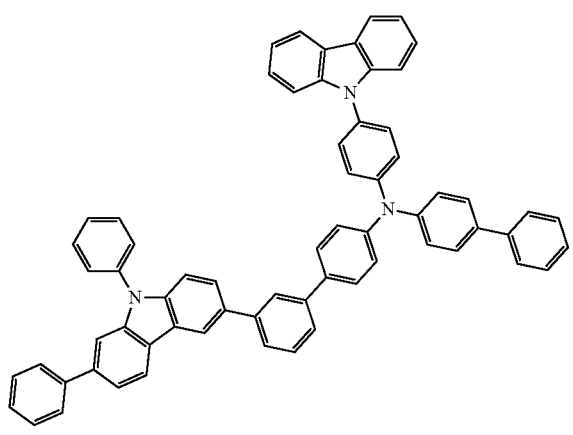
A131
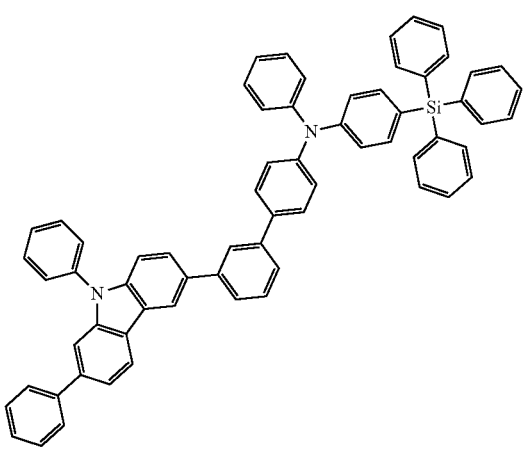
A134
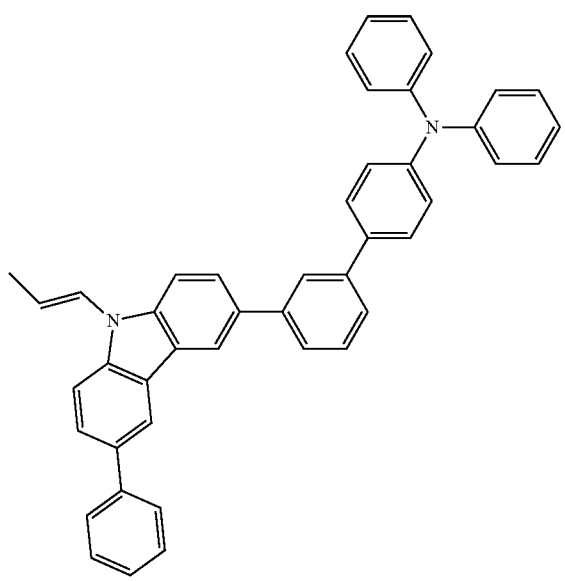
A135
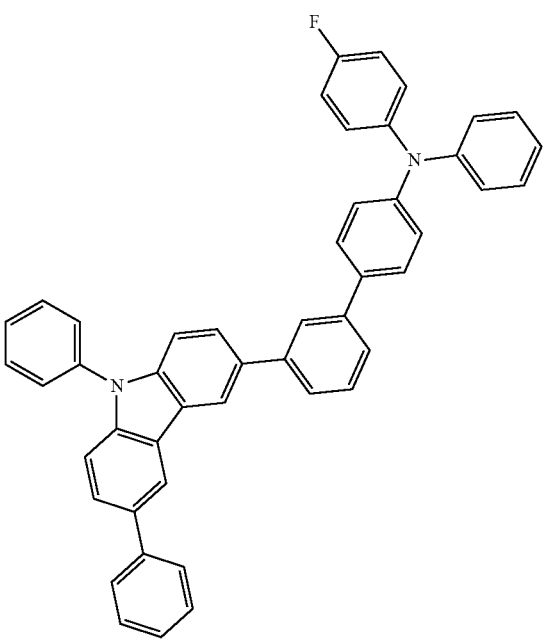

-continued
A142
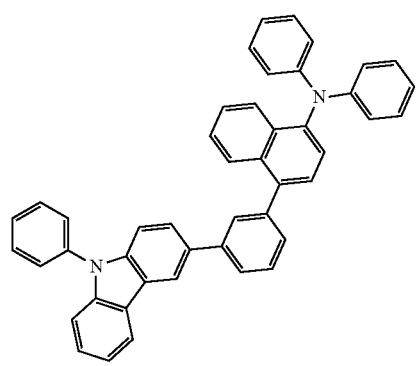
A146
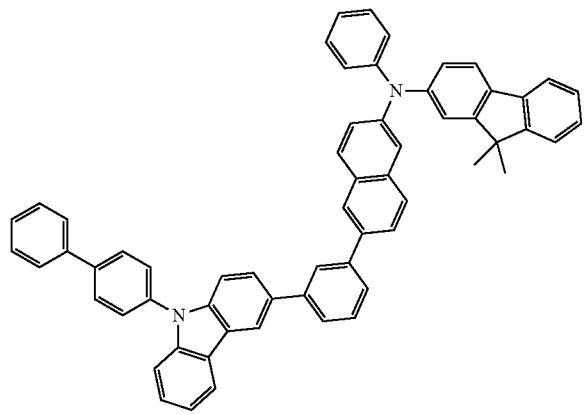
A161
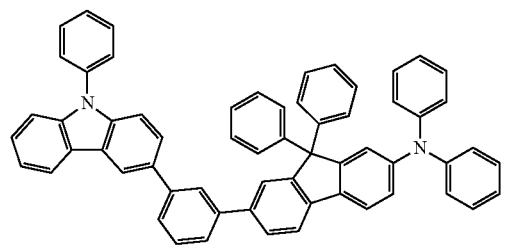
A162
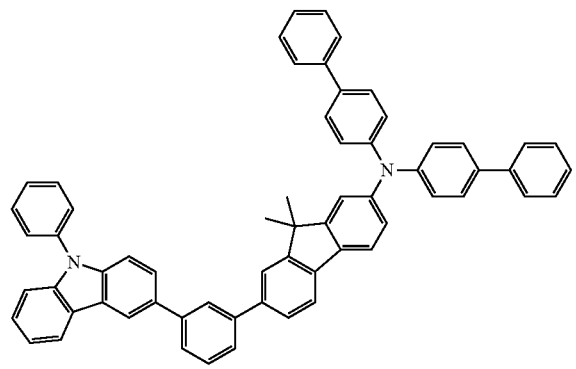
A165
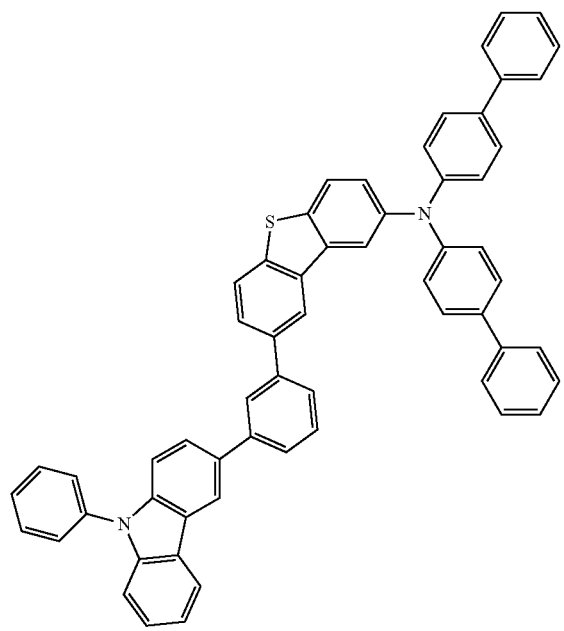
A168
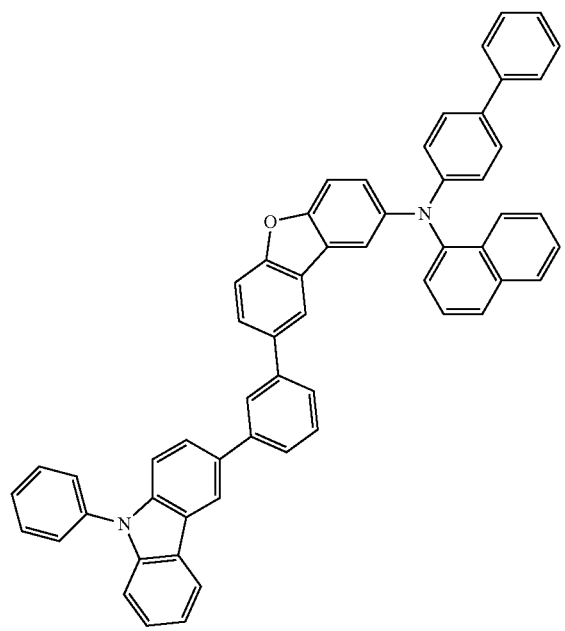

-continued
A169
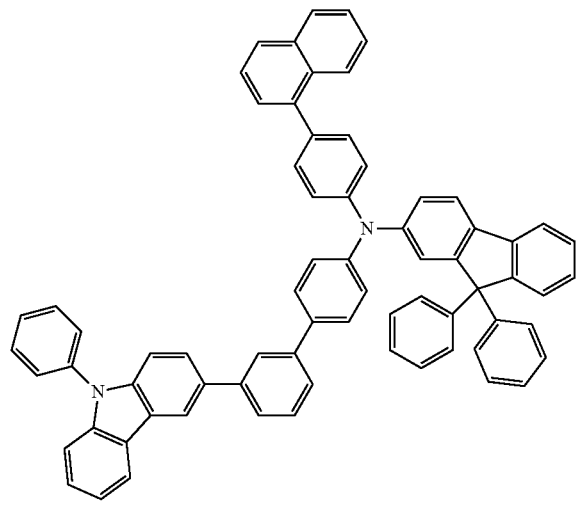
A170
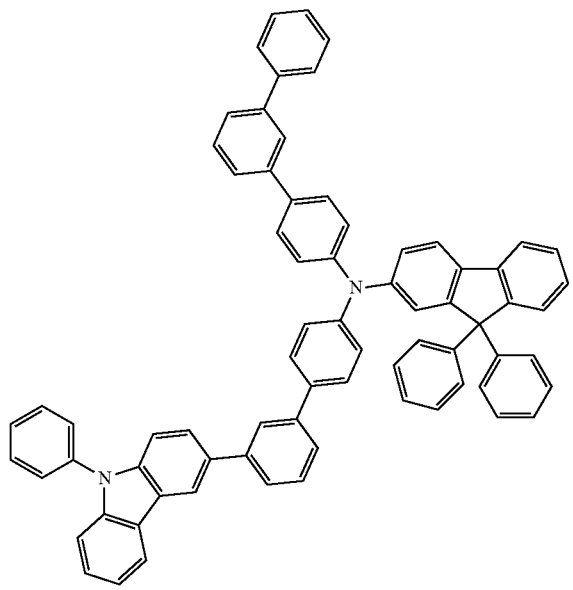
A171
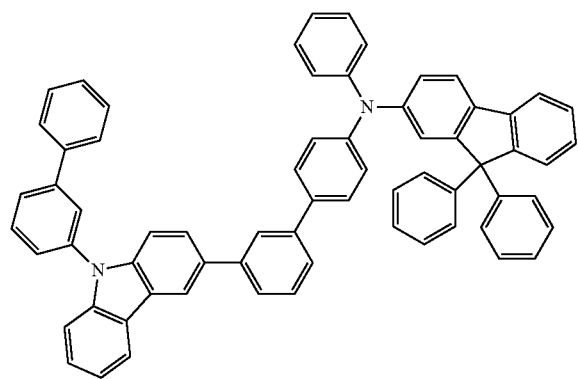
A172
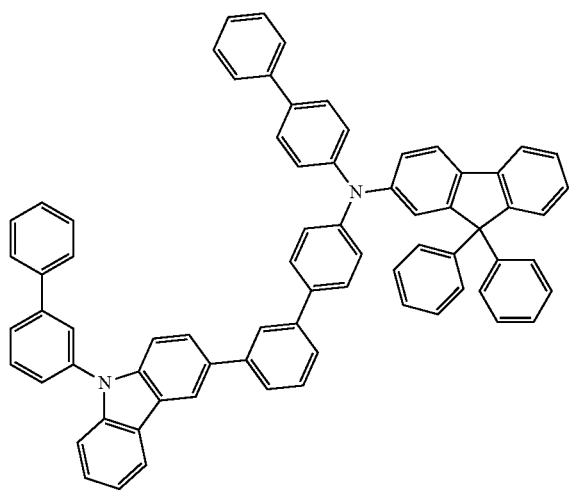
A173
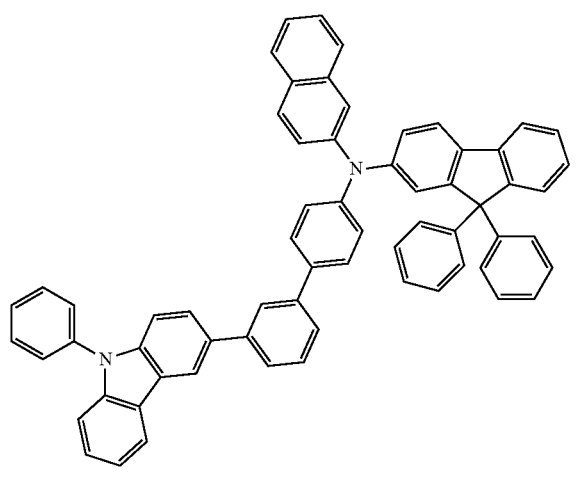
A174
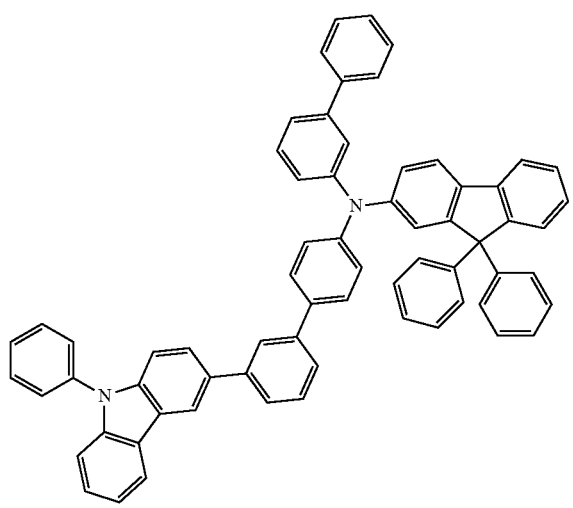

-continued
A175
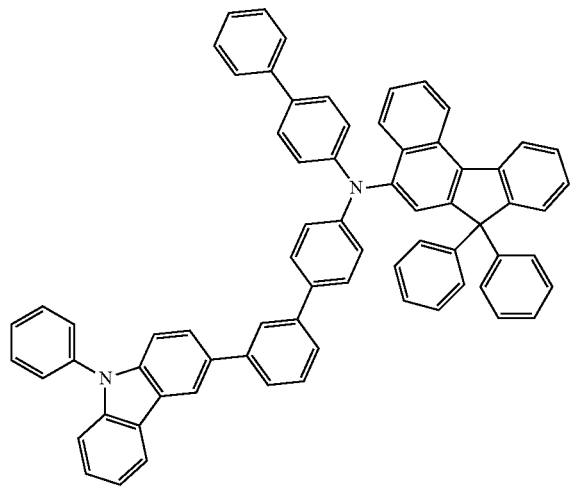
A176
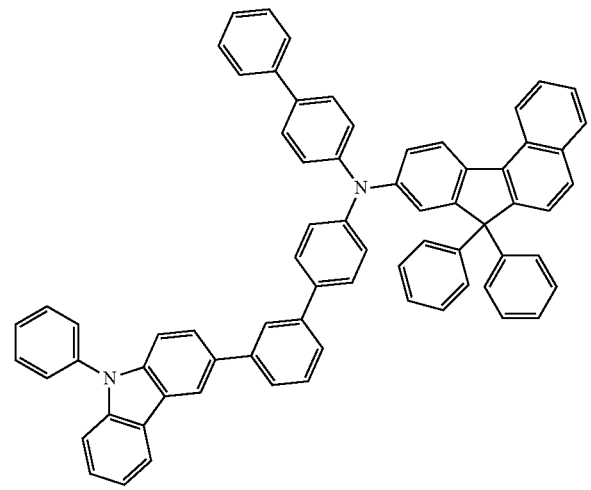
A177
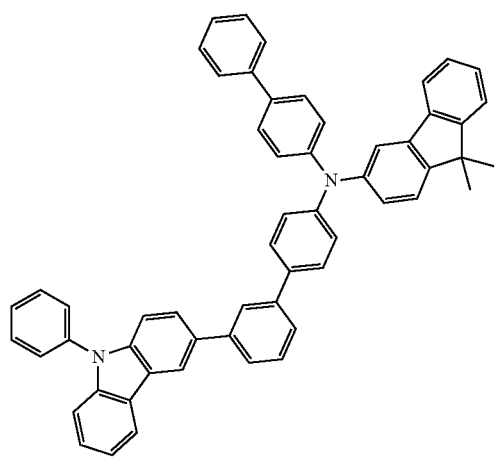
A178
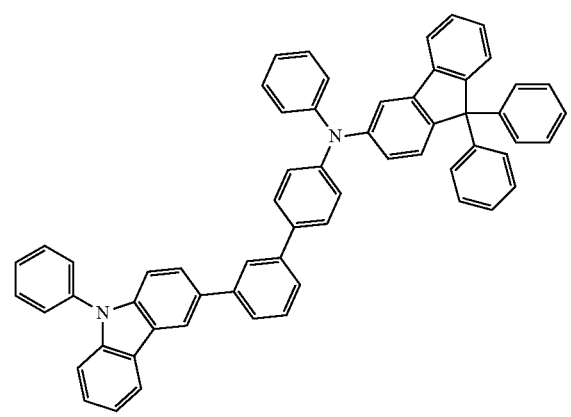
A179
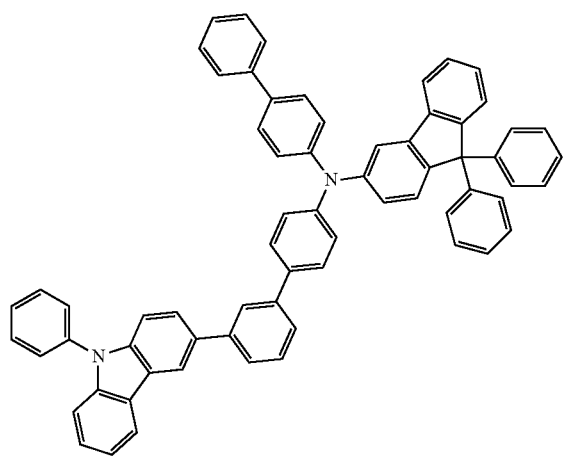
A180
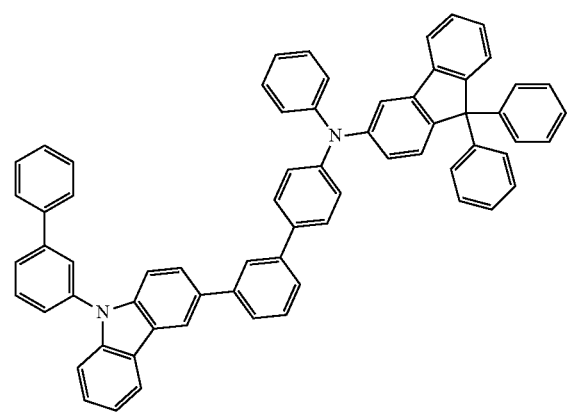

-continued
A181
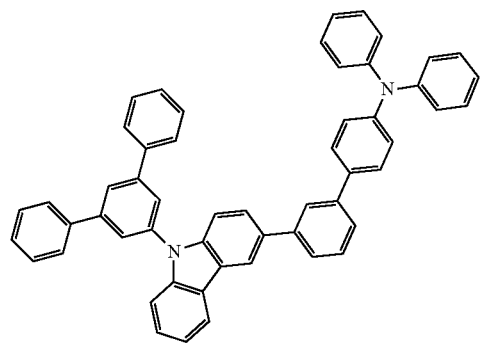
A182
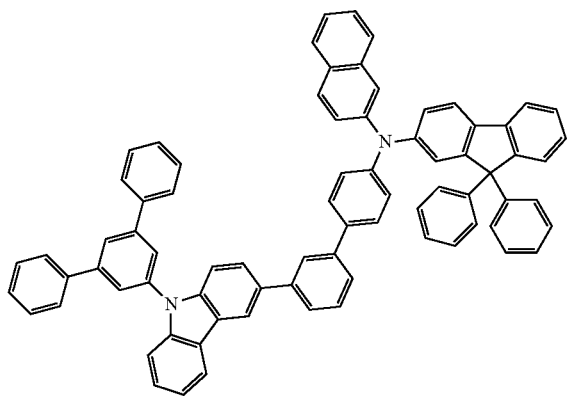
A183
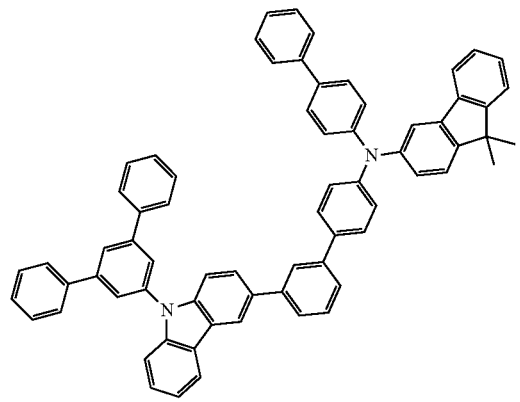
A184
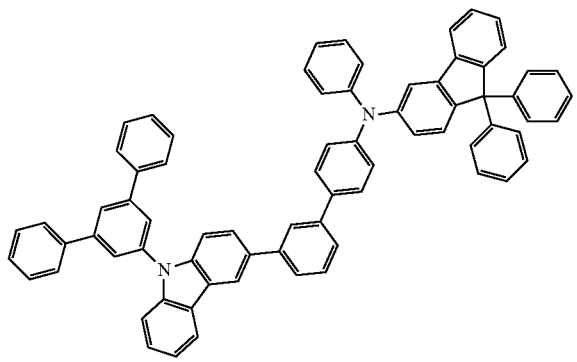
A185
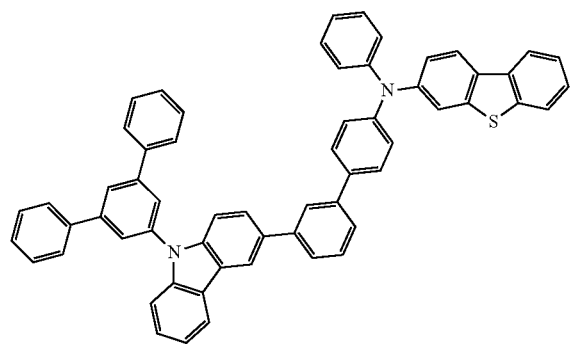
A186
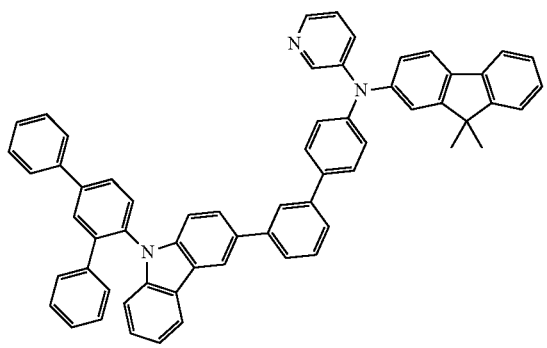
A187
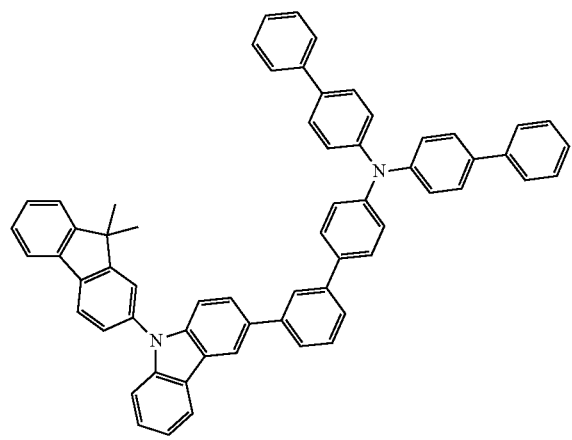
A188
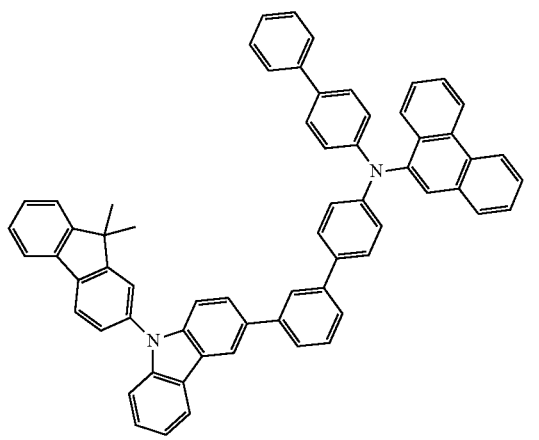

-continued
A189
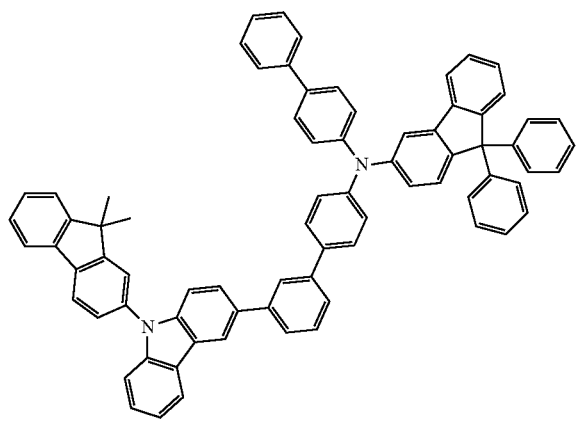
A190
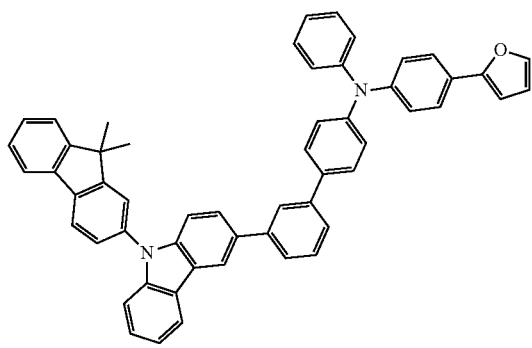
A191
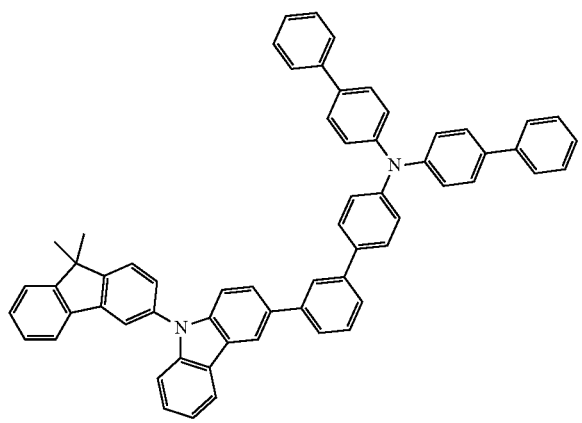
A192
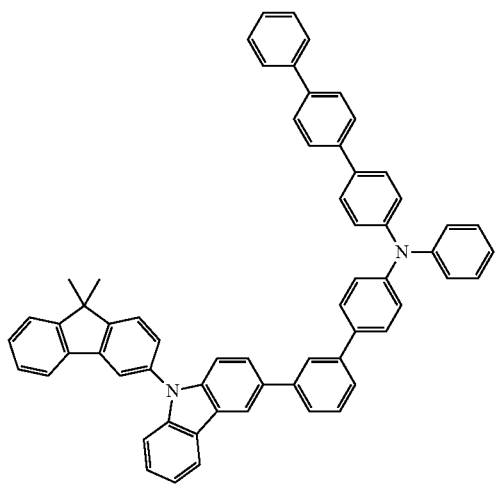
A193
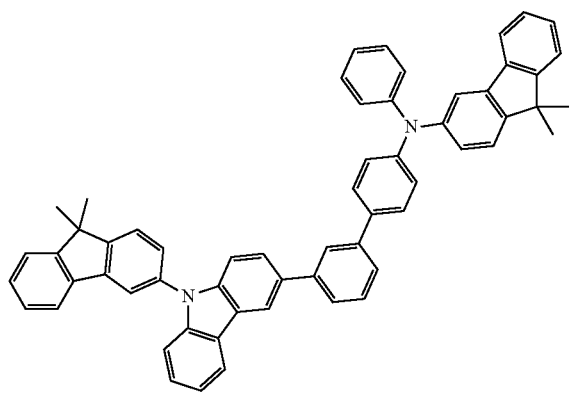
A194
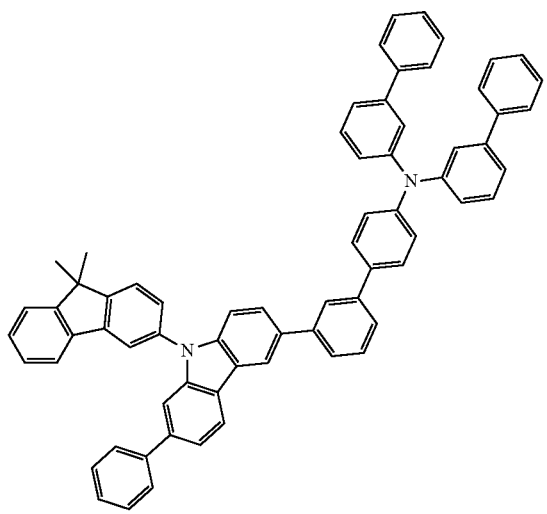

-continued
A195
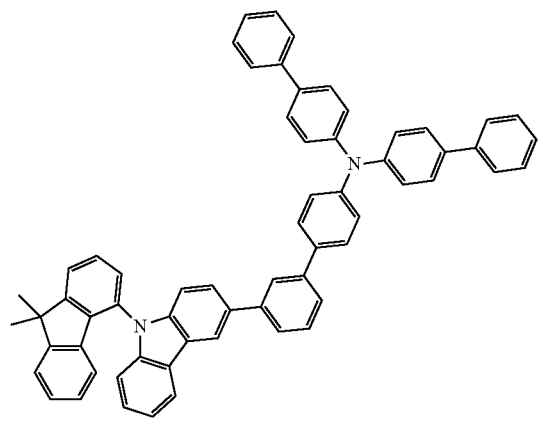
A196
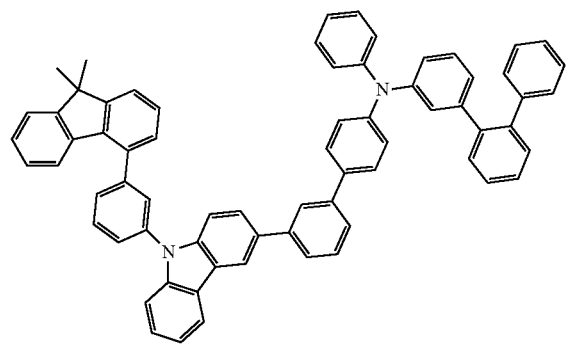
A197
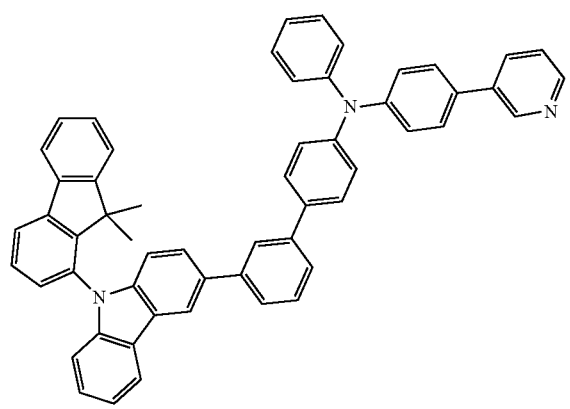
A198
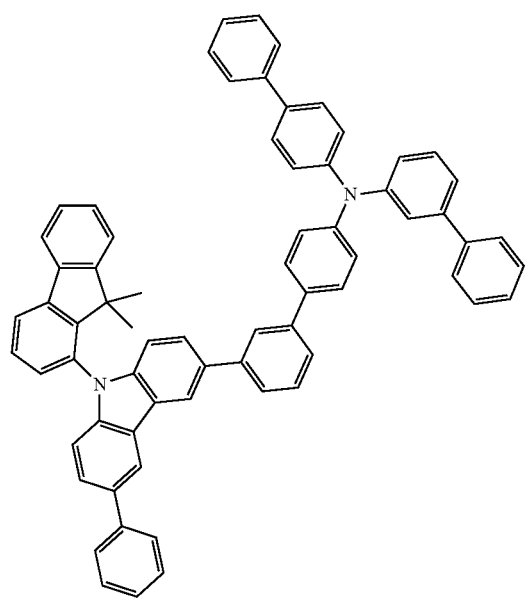
A199
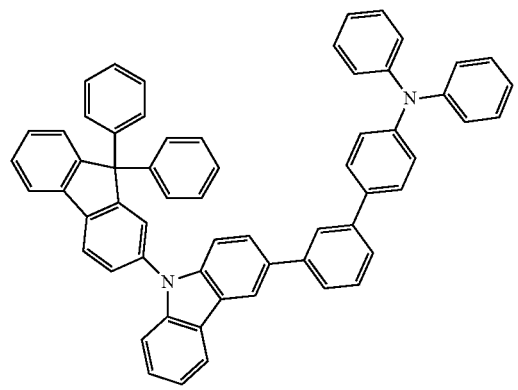
A200
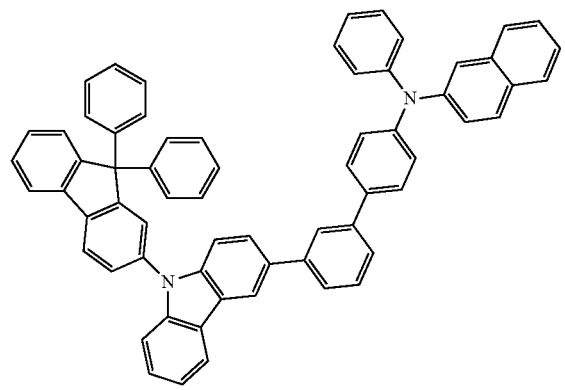

-continued
A201
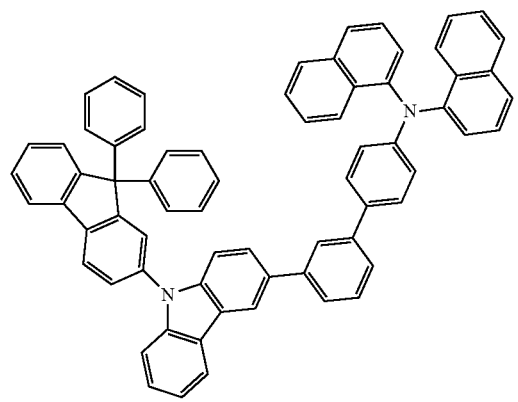
A202
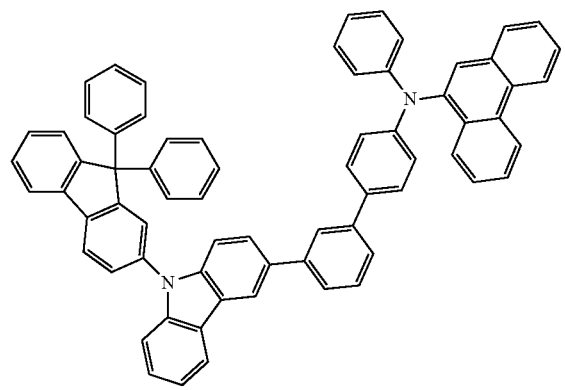
A203
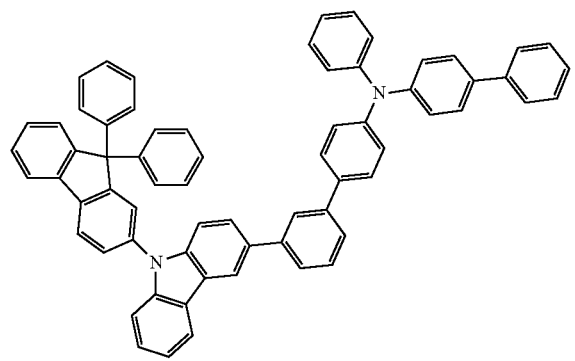
A204
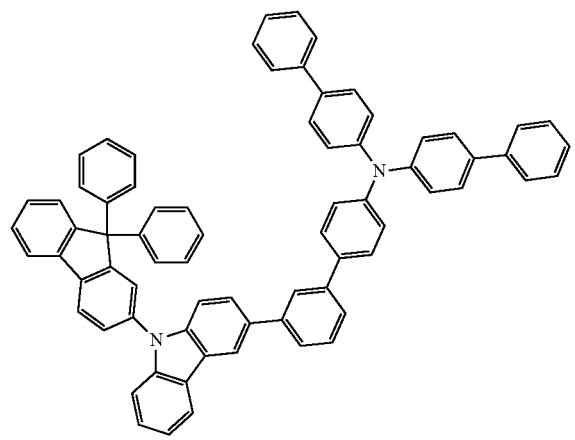
A205
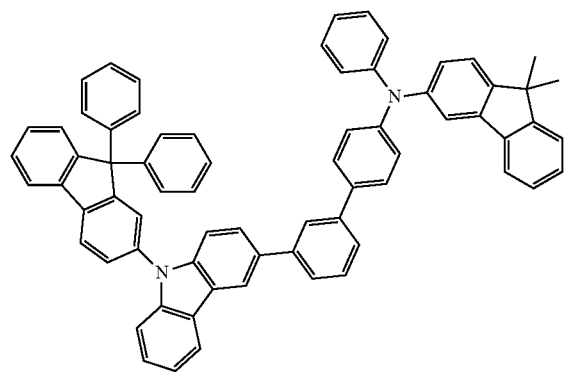
A206
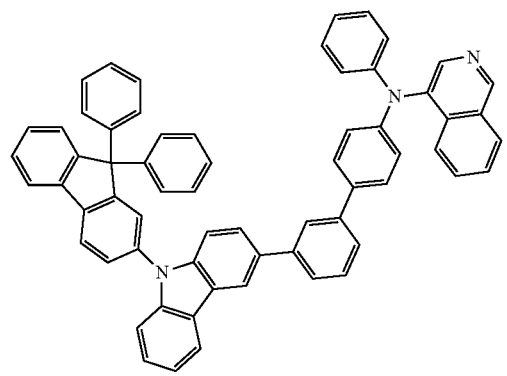

-continued
A207
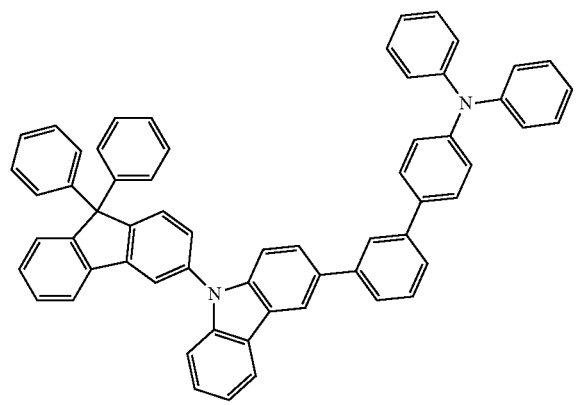
A208
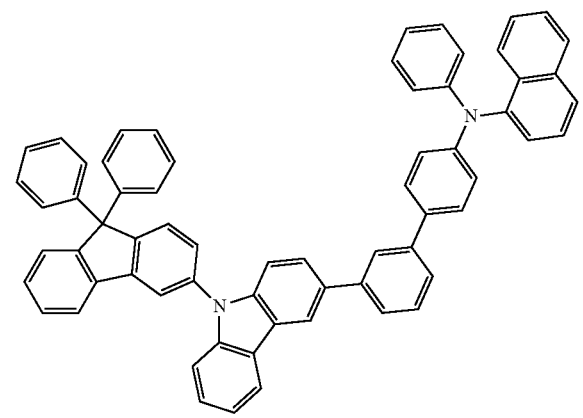
A209
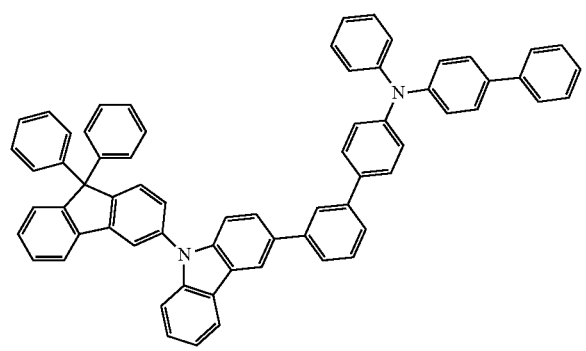
A210
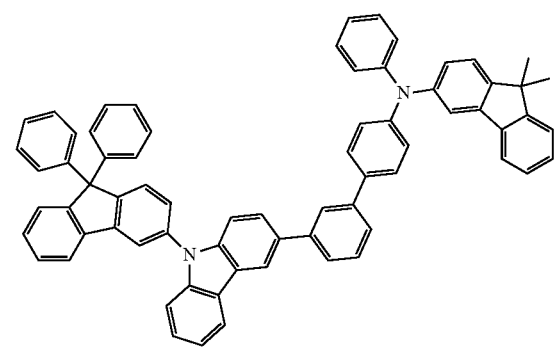
A211
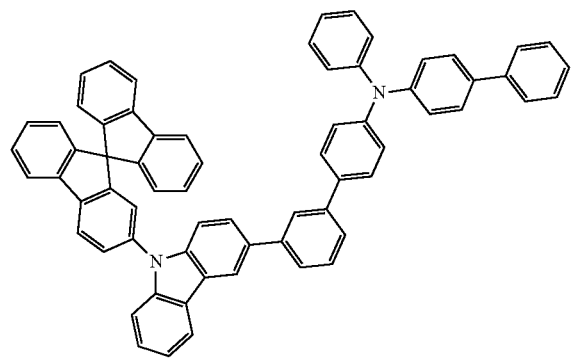
A212
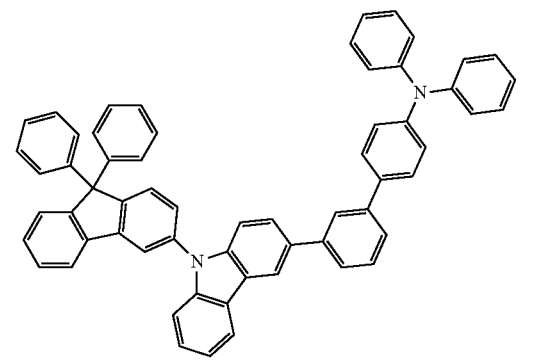
A213
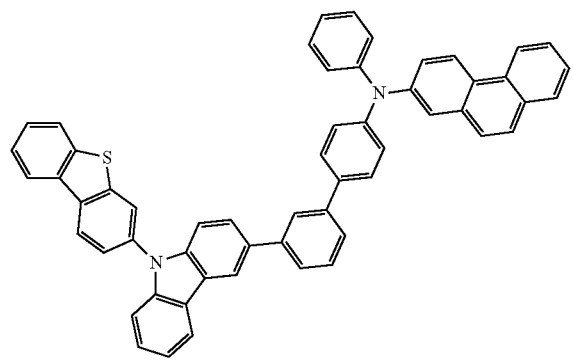
A214
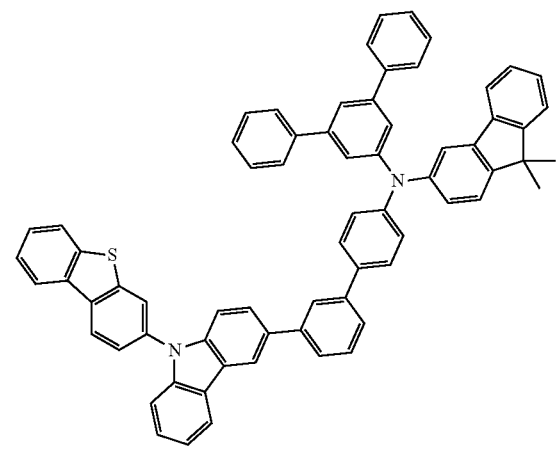

-continued
A215
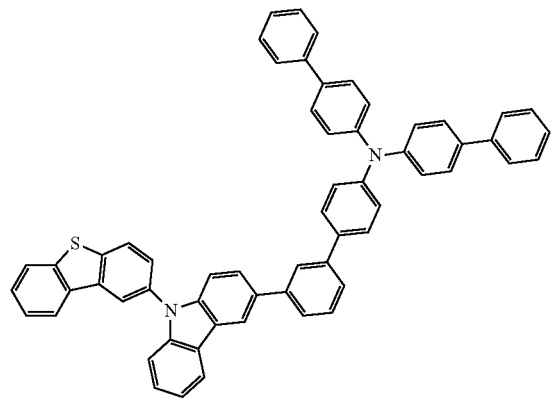
A216
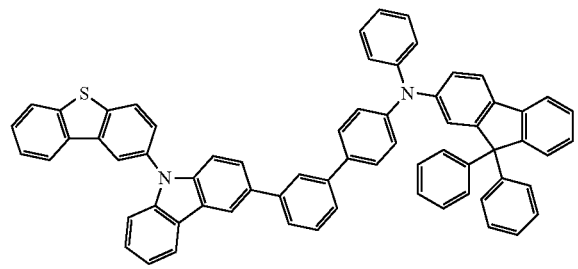
A217
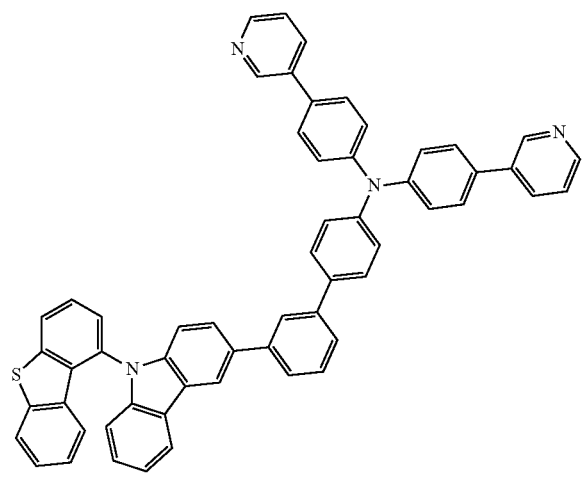
A218
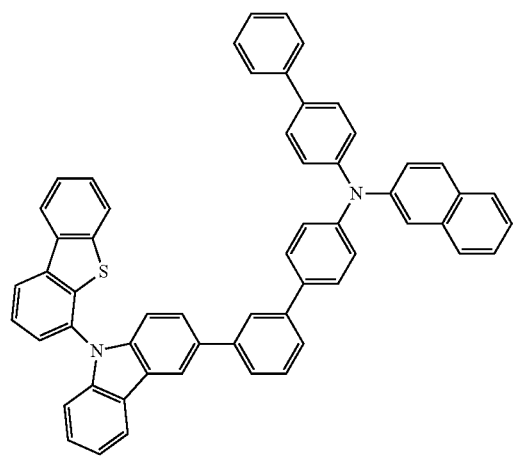
A219
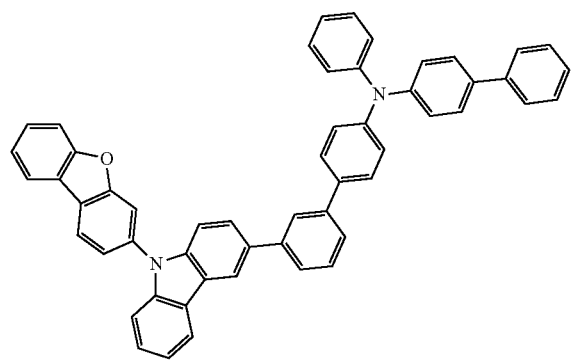
A220
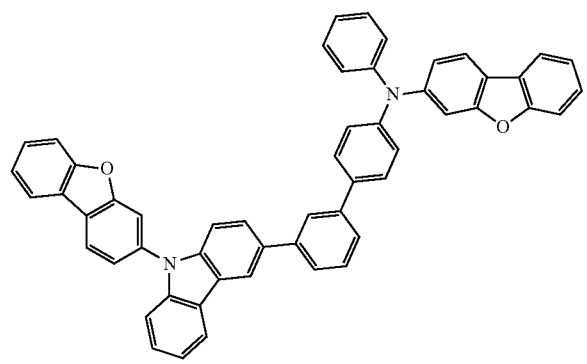

A221
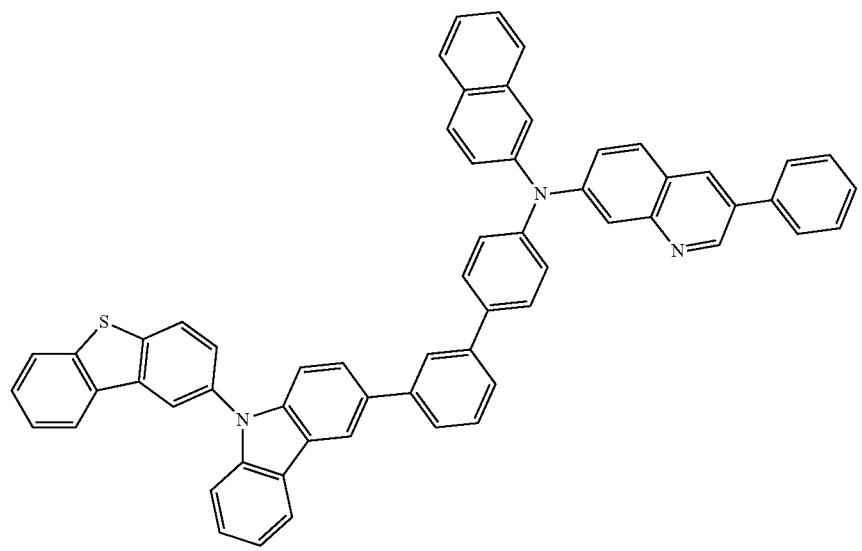
A222
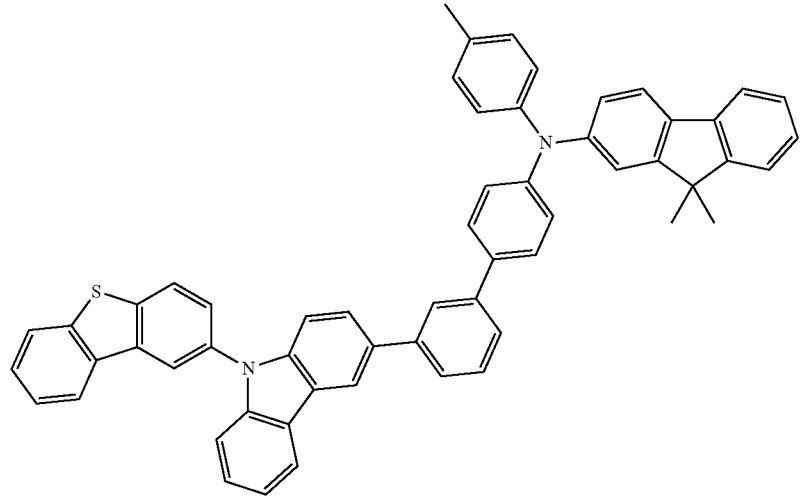
A223 A224
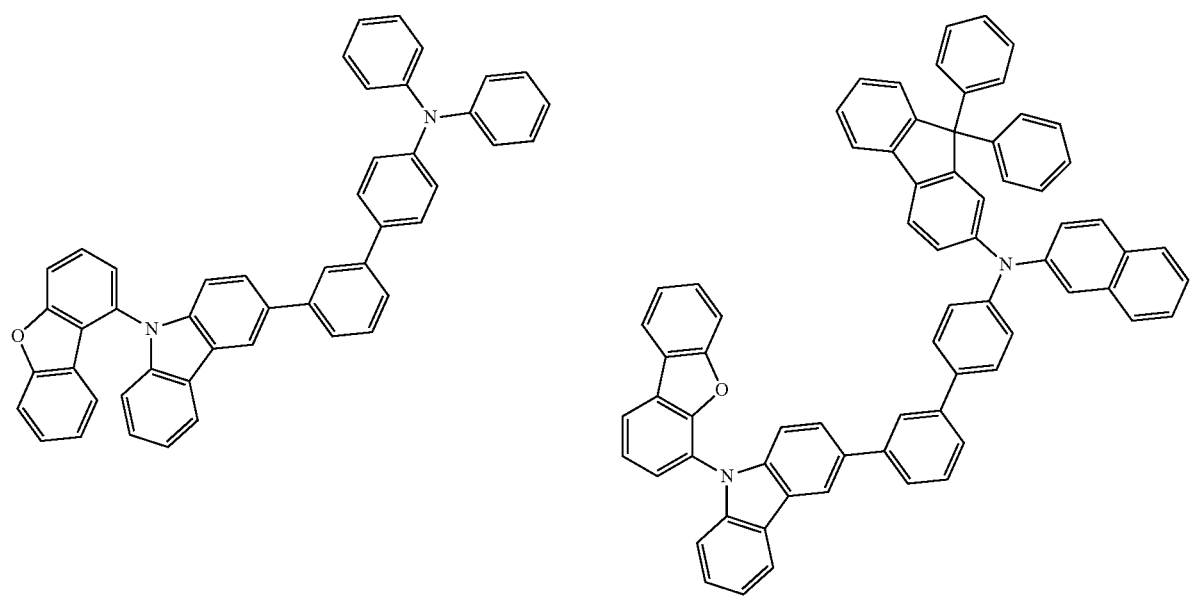

-continued
A225
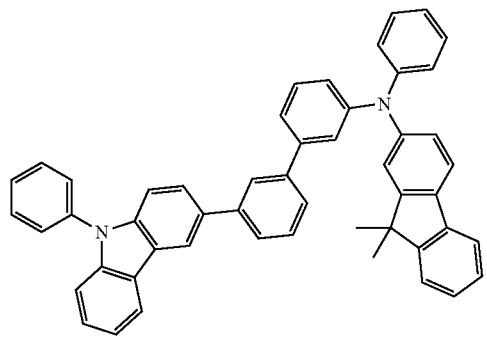
A226
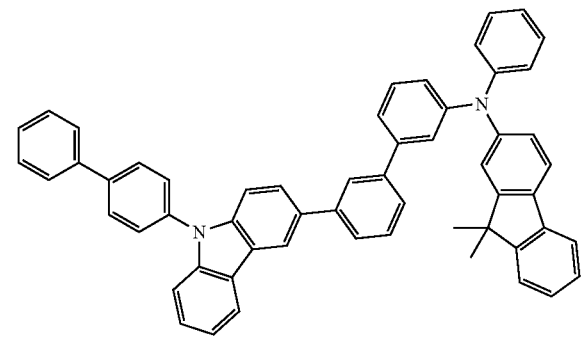
A227
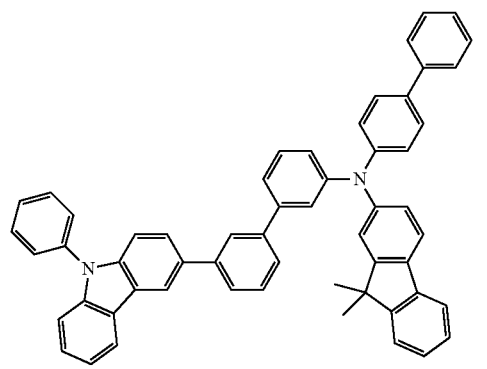
A228
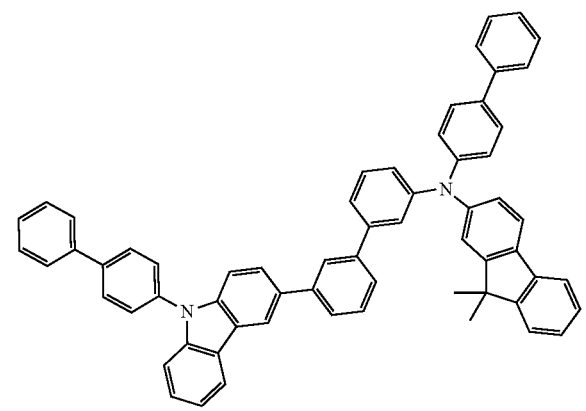
A229
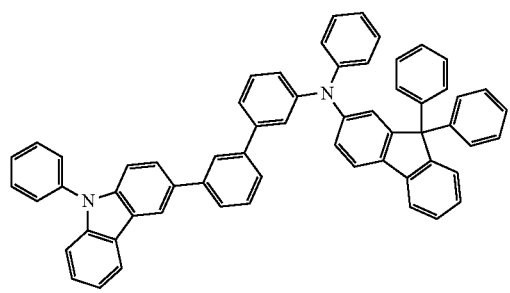
A230
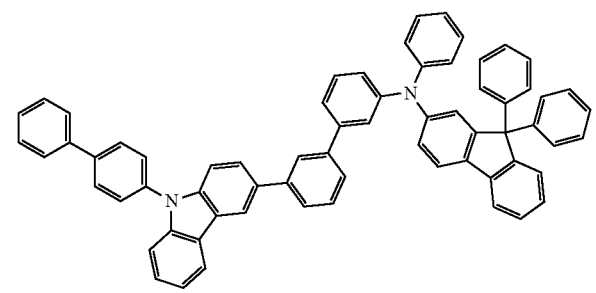
A231
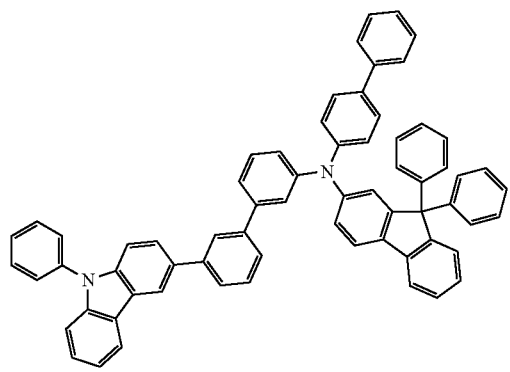
A232
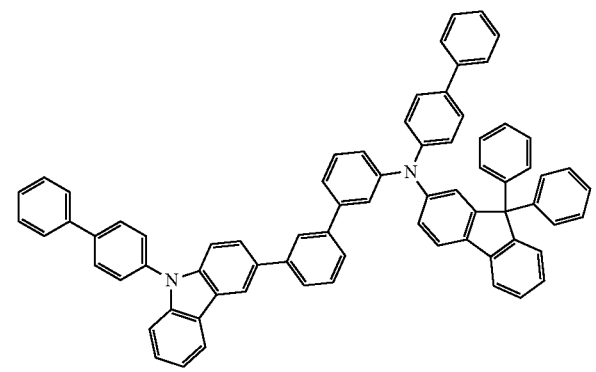

-continued
A233 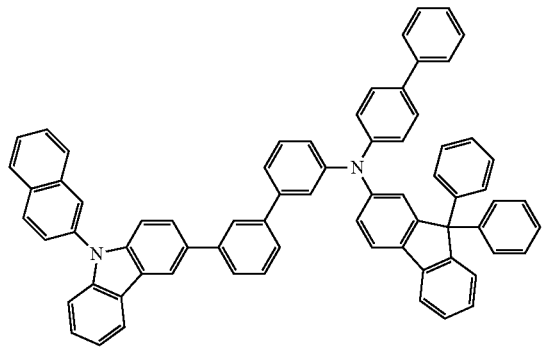
A234 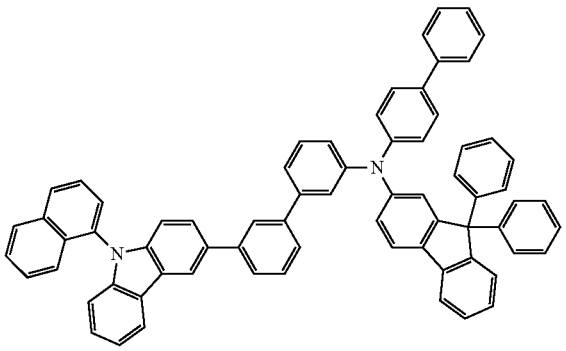
A235 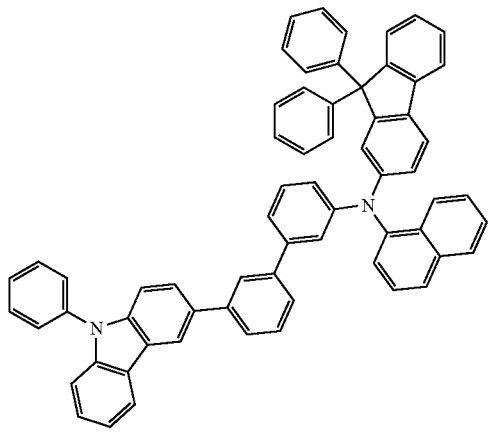
A236 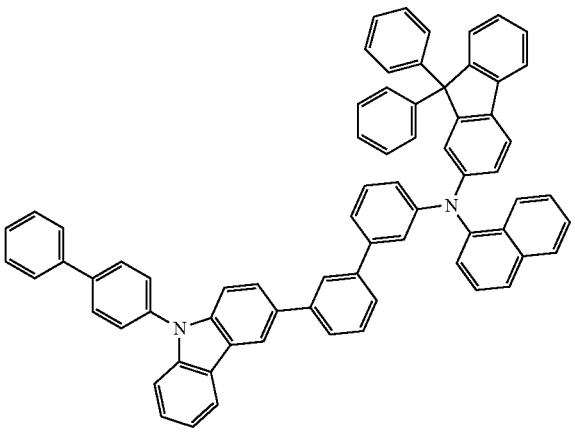
A237 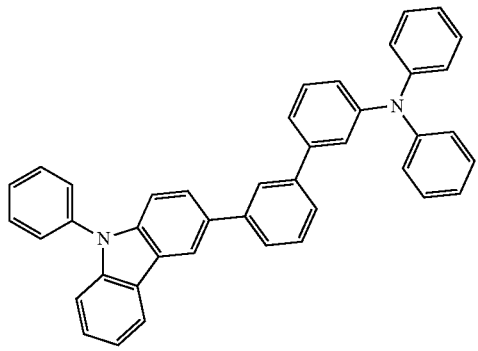
A238 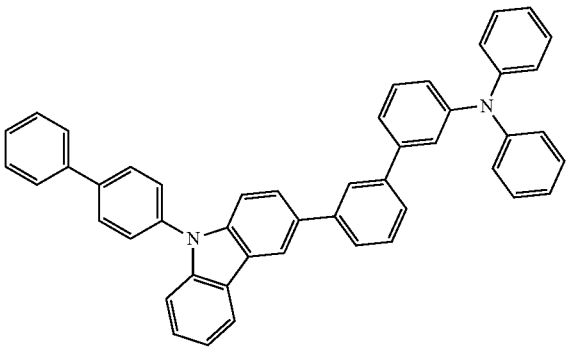
A239 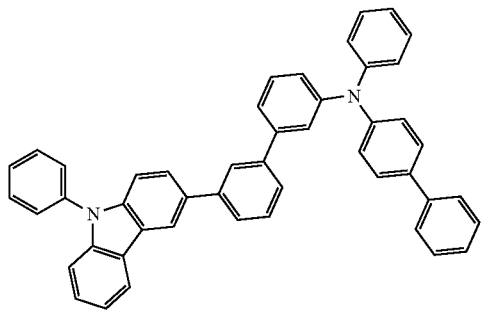
A240 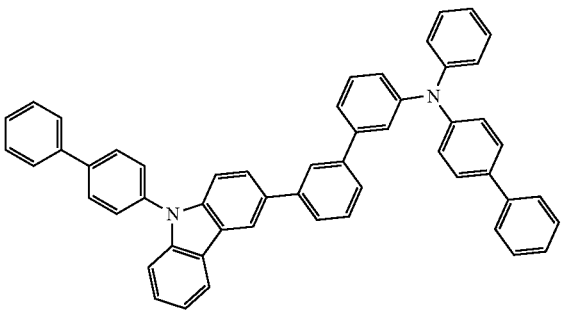

-continued
A241
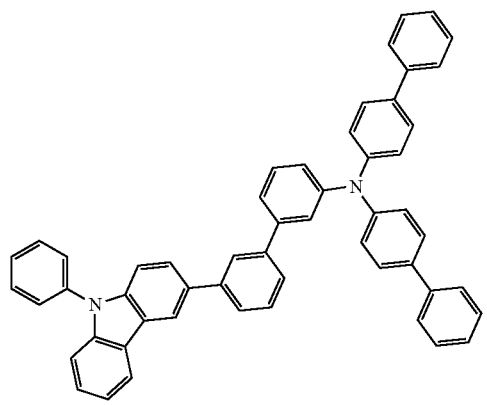
A242
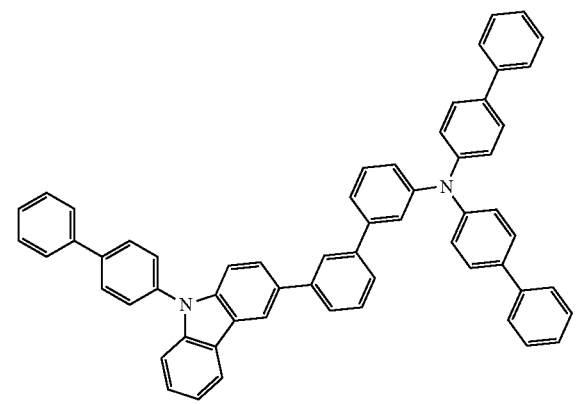
A243
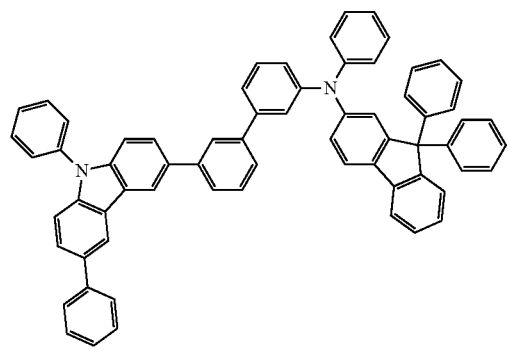
A244
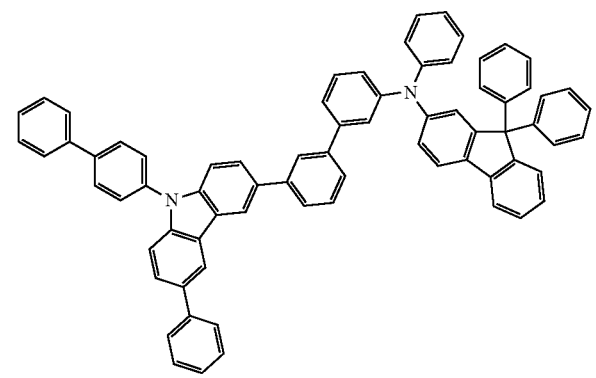
A245
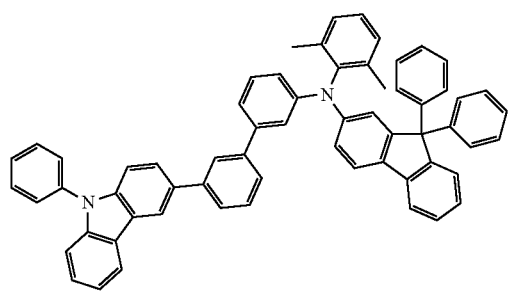
A246
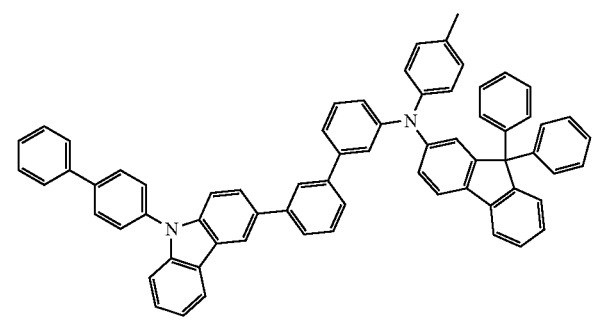
A247
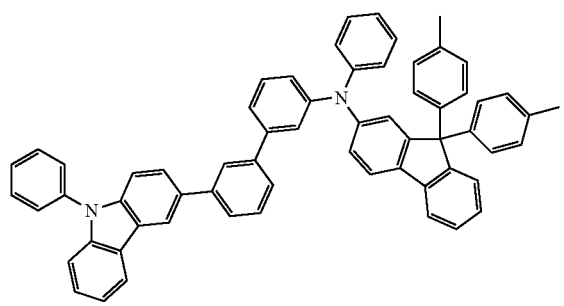
A248
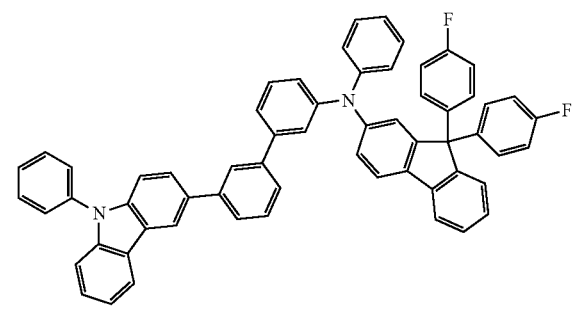

-continued
A249
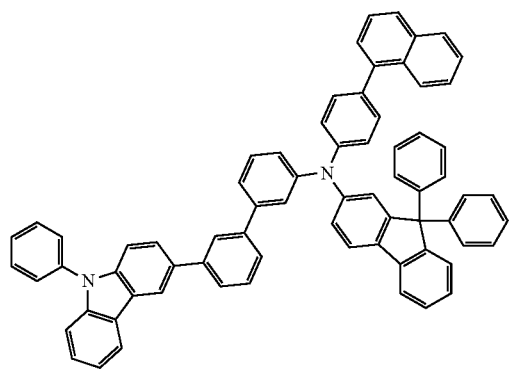
A250
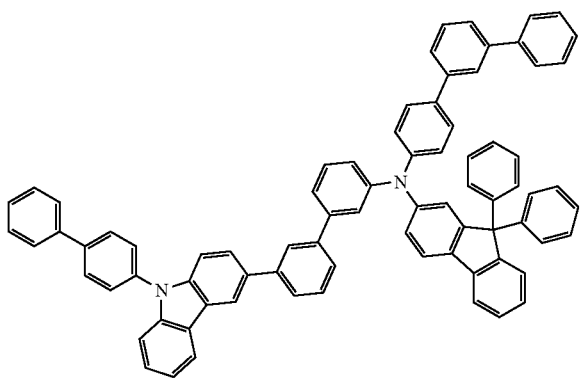
A251
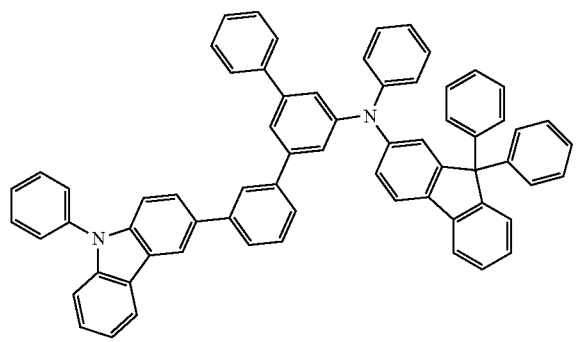
A252
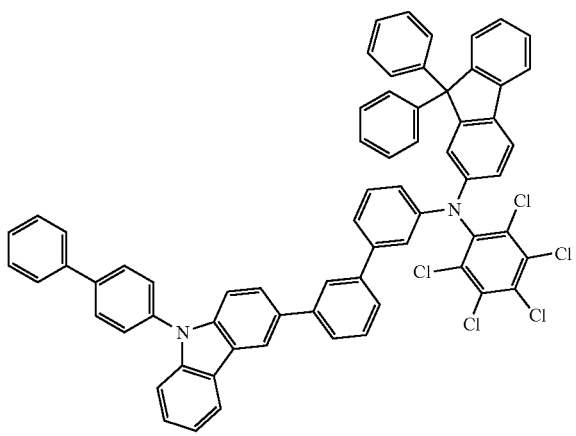
A253
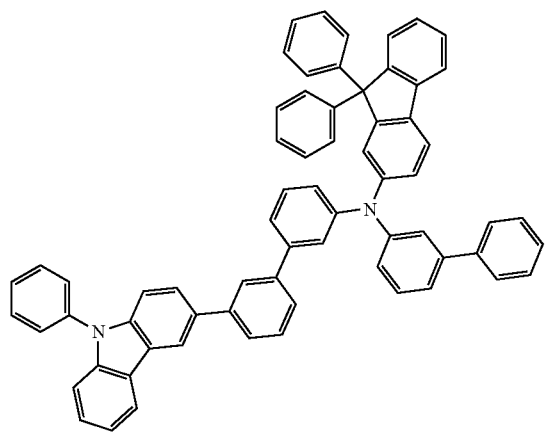
A254
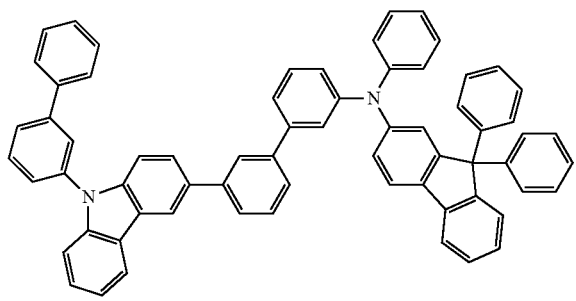

-continued
A255
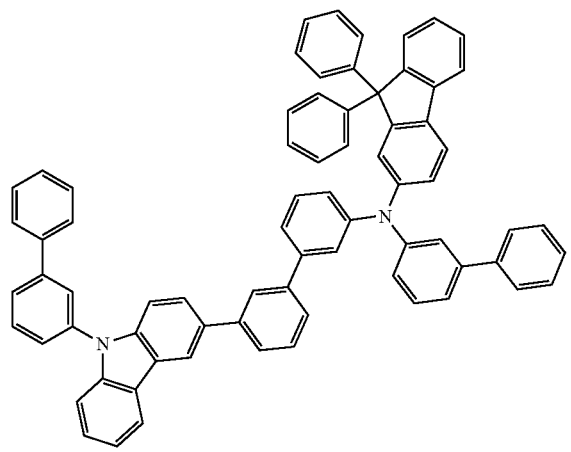
A256
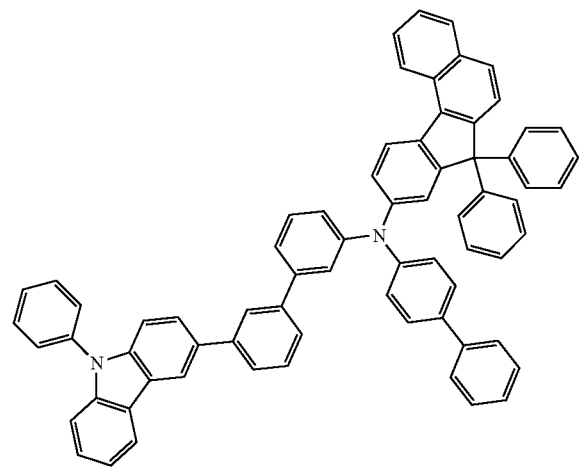
A257
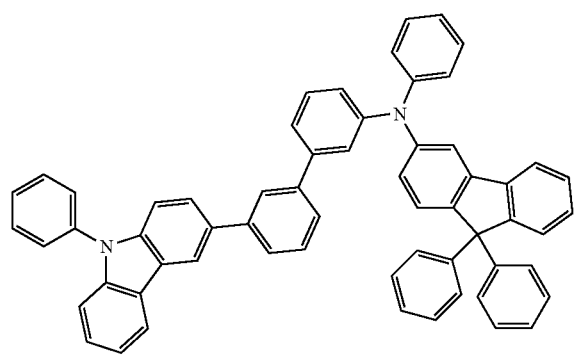
A258
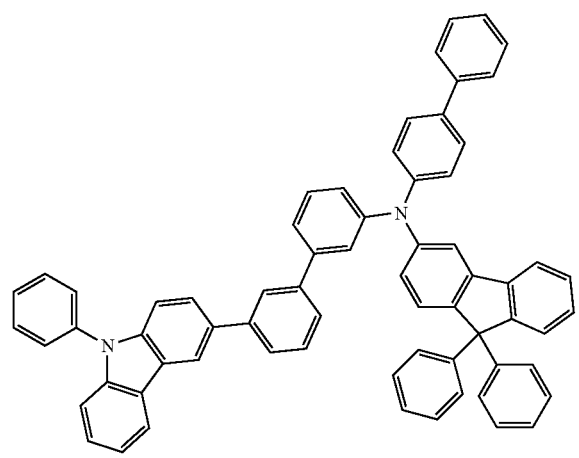
A259
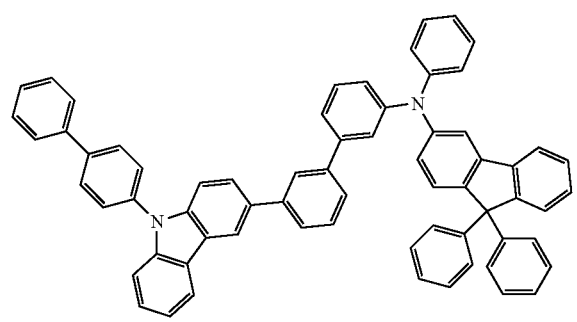
A260
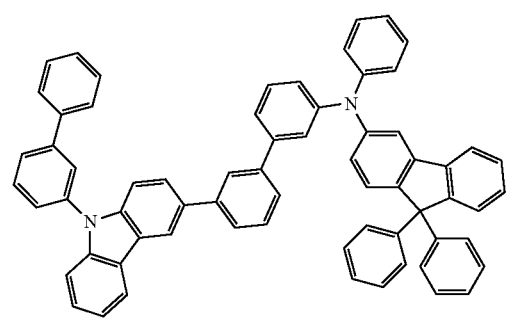

-continued
A261
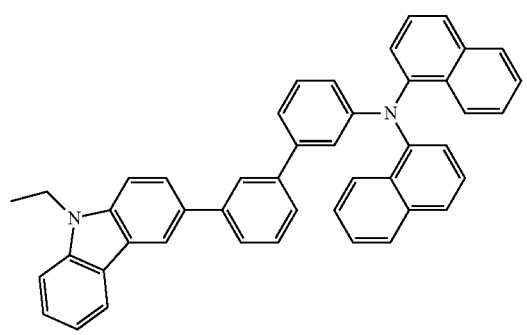
A262
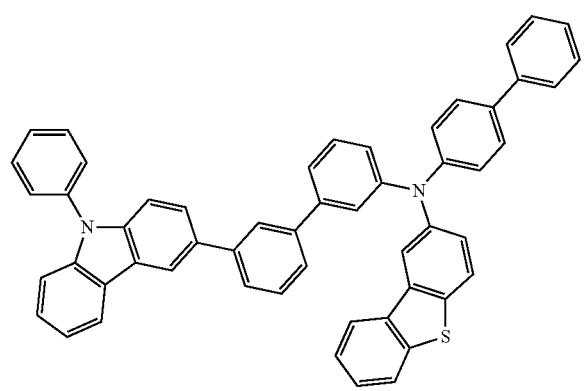
A263
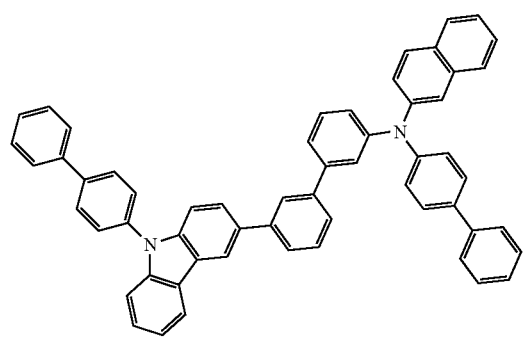
A264
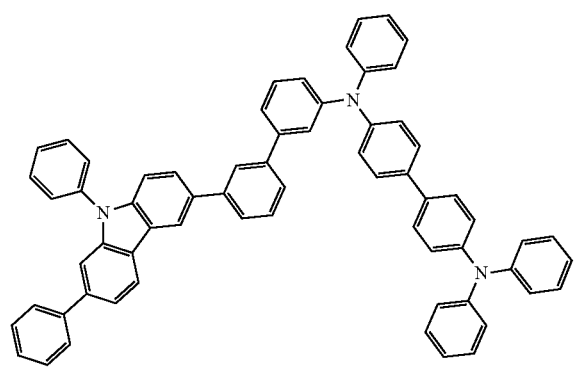
A265
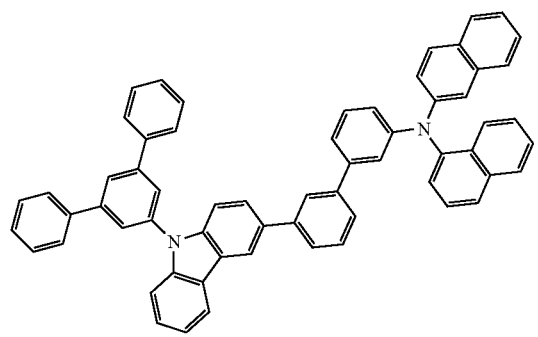
A266
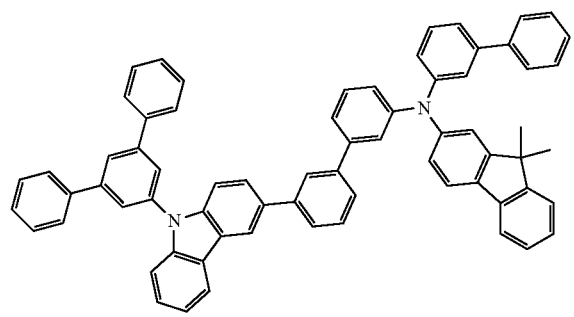
A267
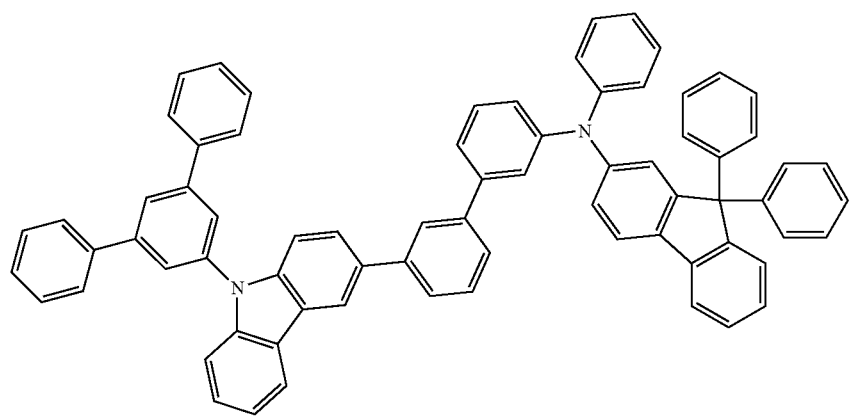

-continued
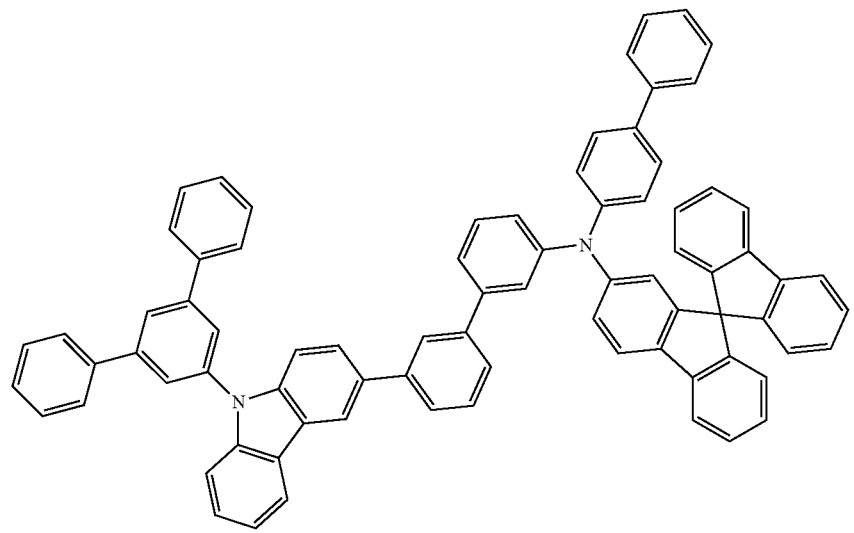
A268
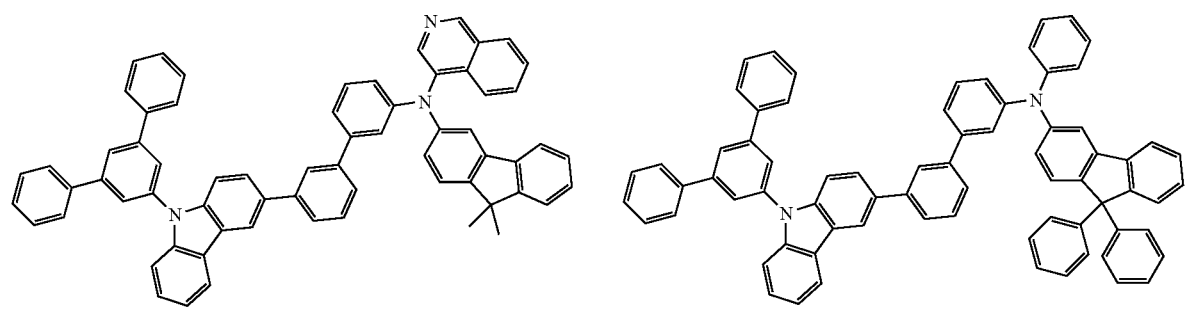
A269  A270
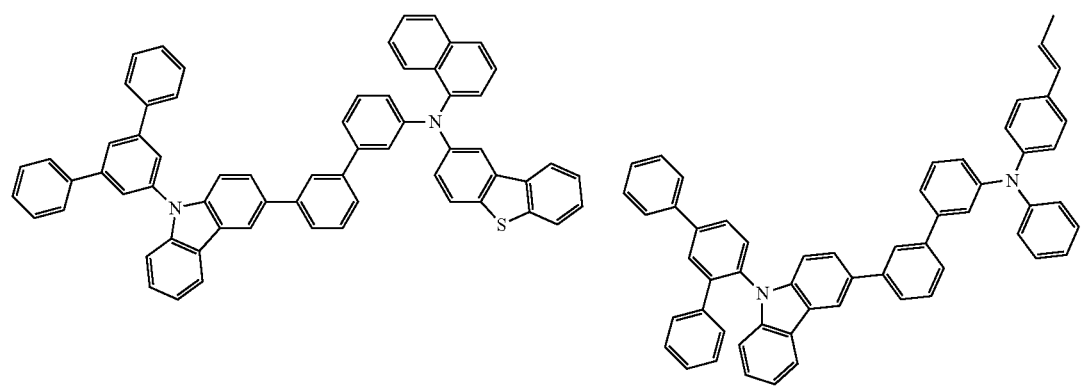
A271  A272

-continued
A273
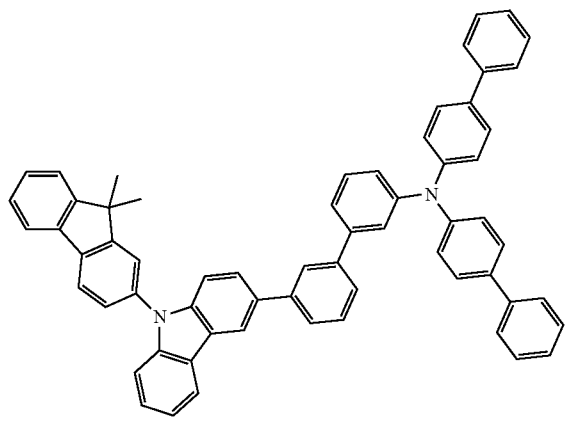
A274
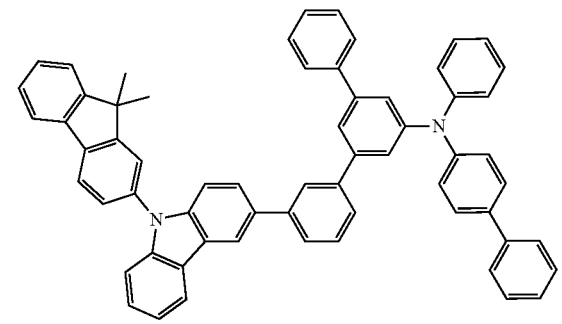
A275
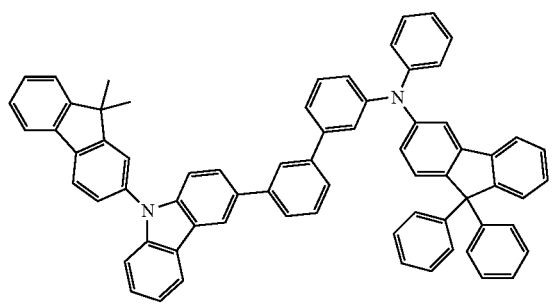
A276
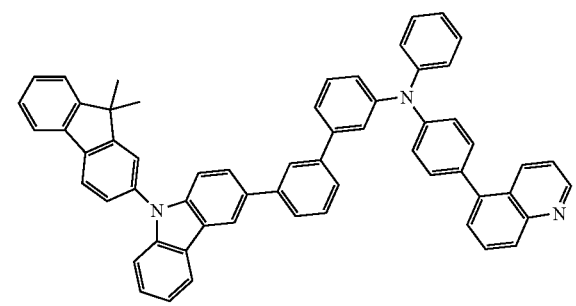
A277
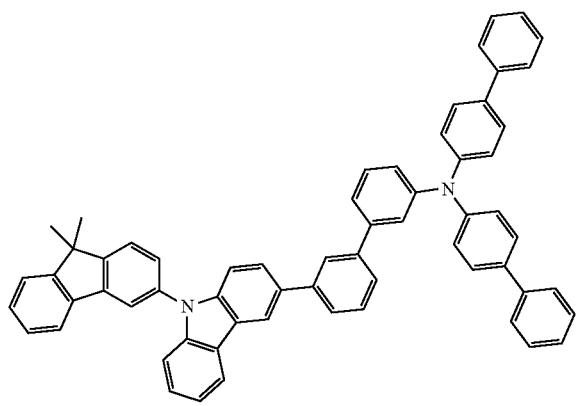
A278
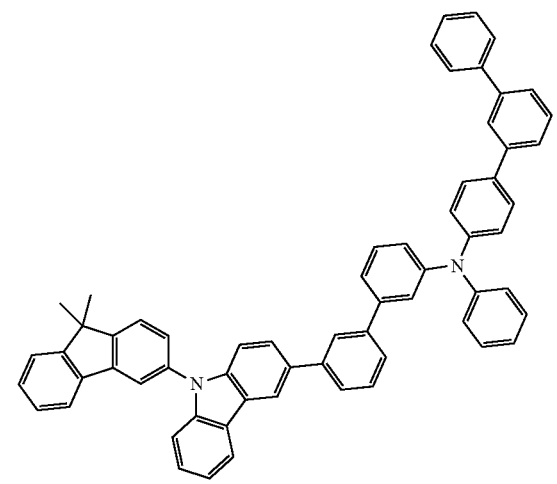
A279
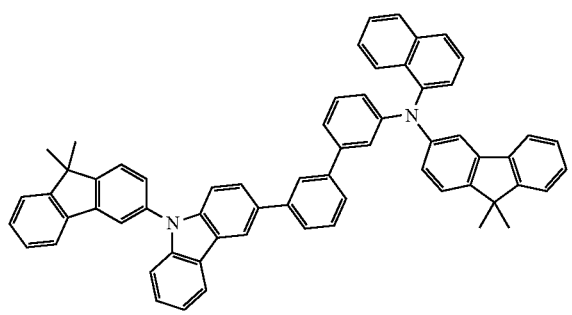
A280
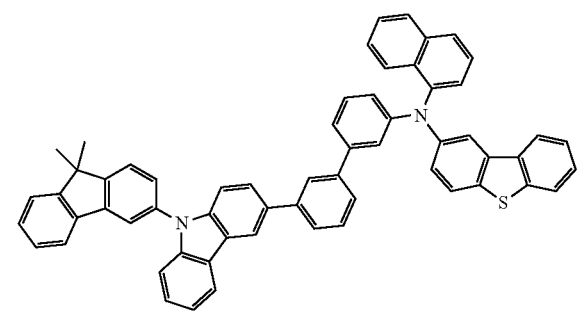

-continued
A281
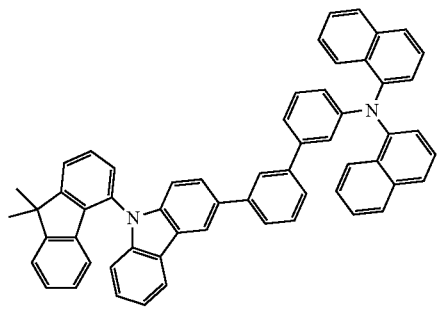
A282
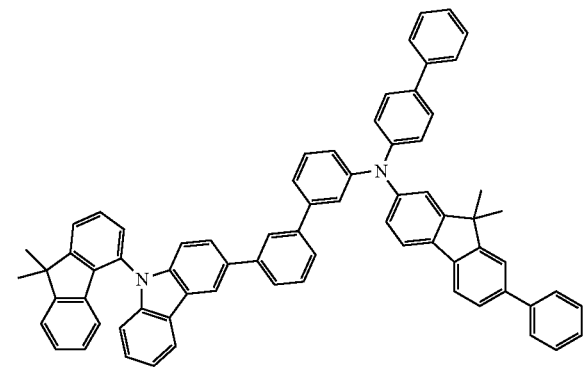
A283
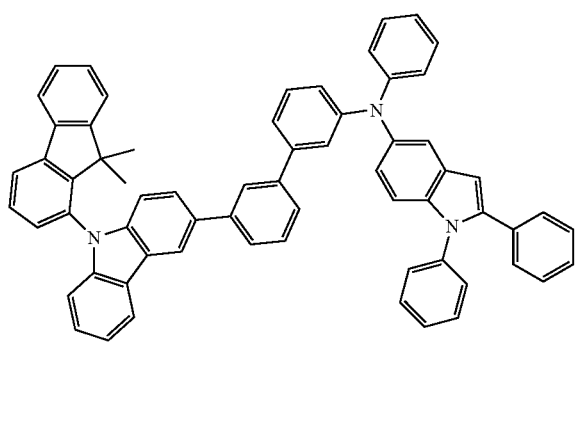
A284
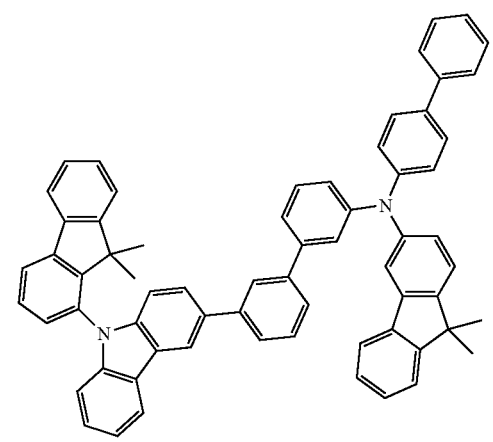
A285
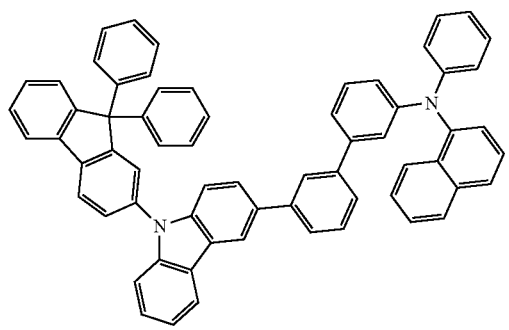
A286
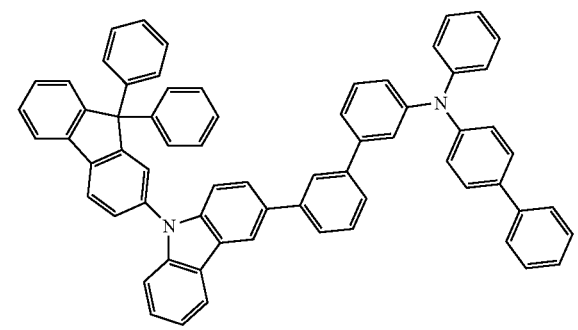
A287
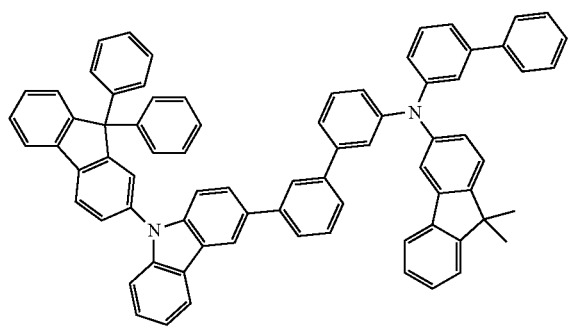
A288
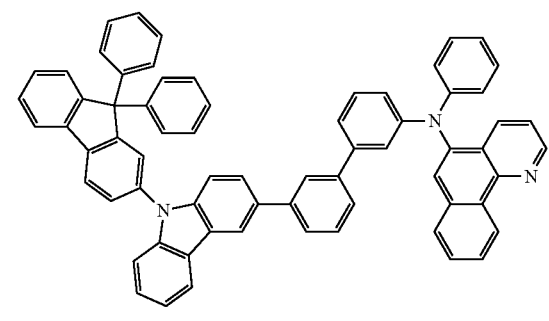

-continued
A289
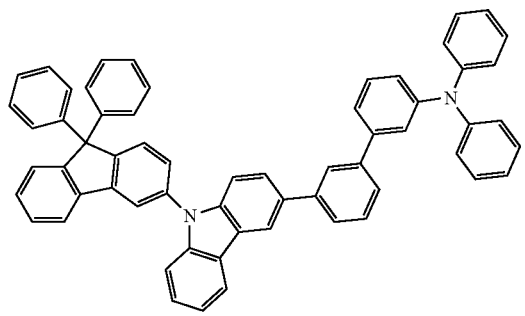
A290
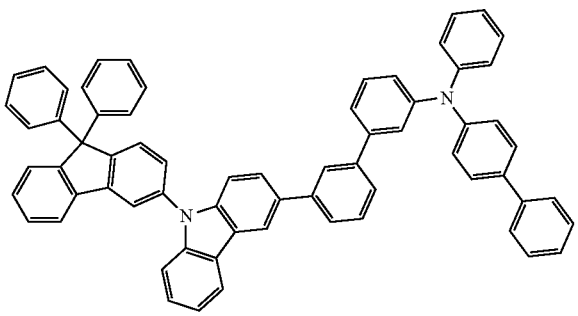
A291
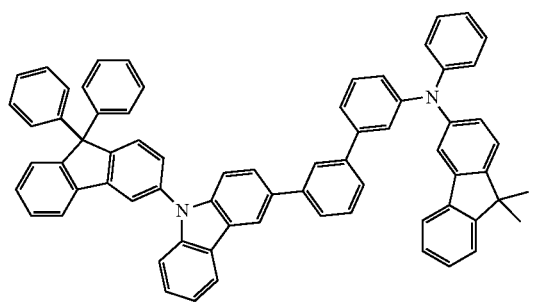
A292
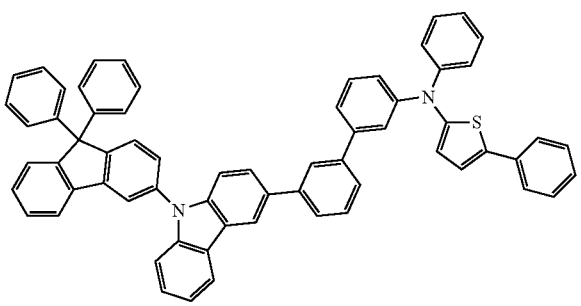
A293
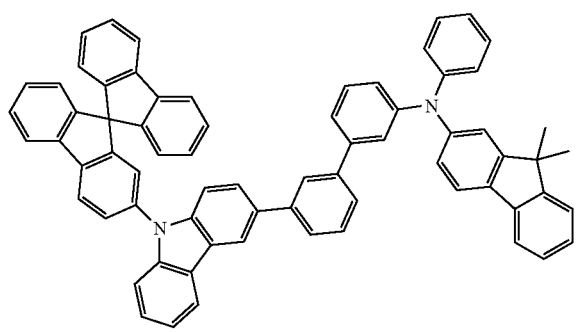
A294
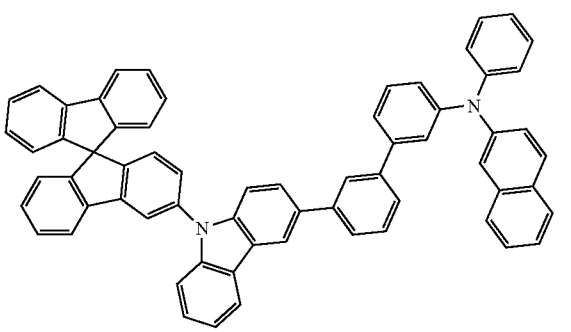
A295
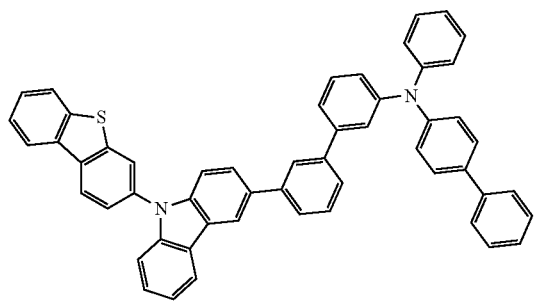
A296
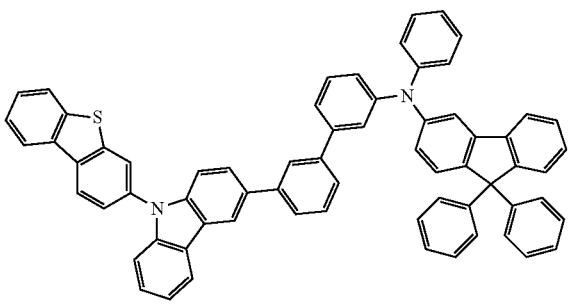

A297
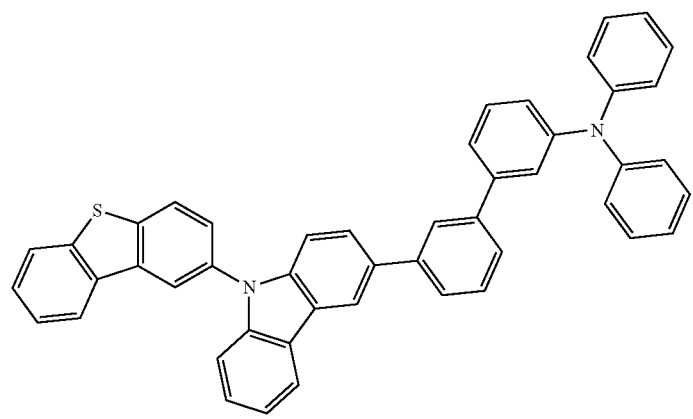
A298
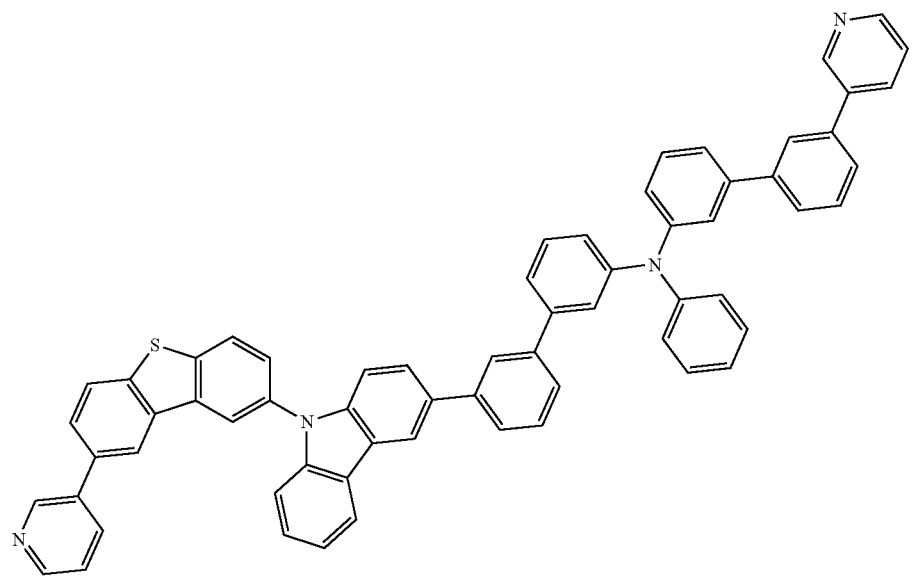
A299
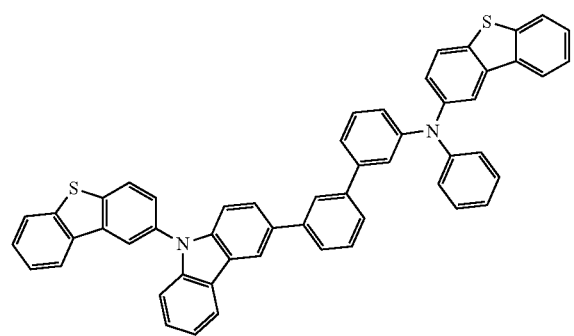
A300
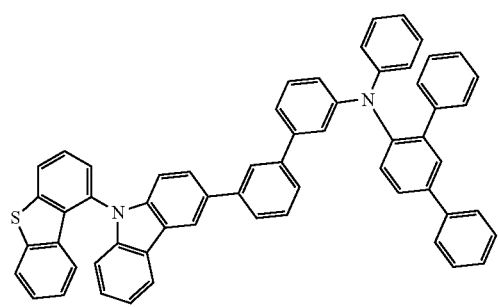

-continued
A301
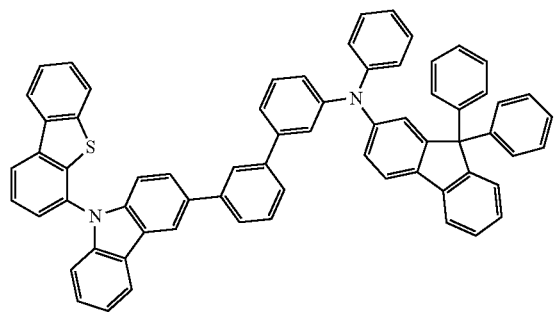
A302
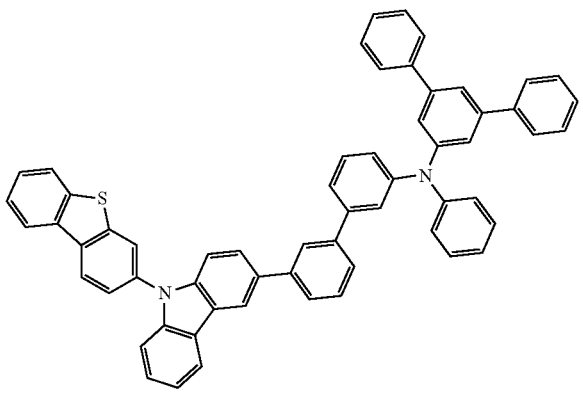
A303
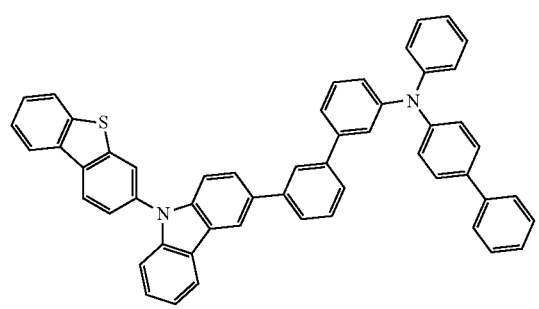
A304
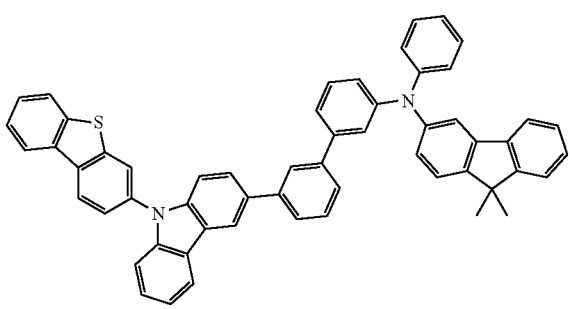
A305
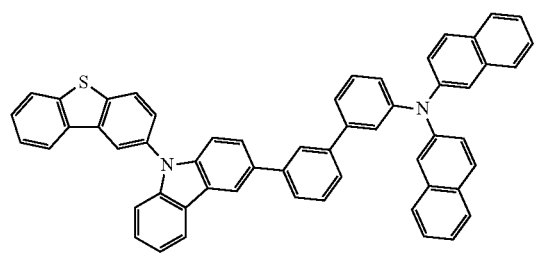
A306
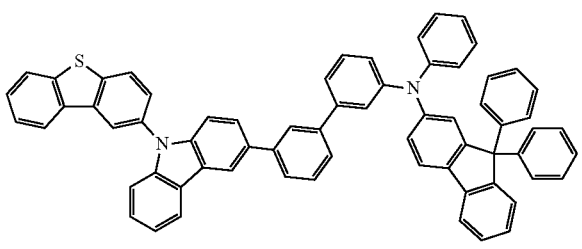
A307
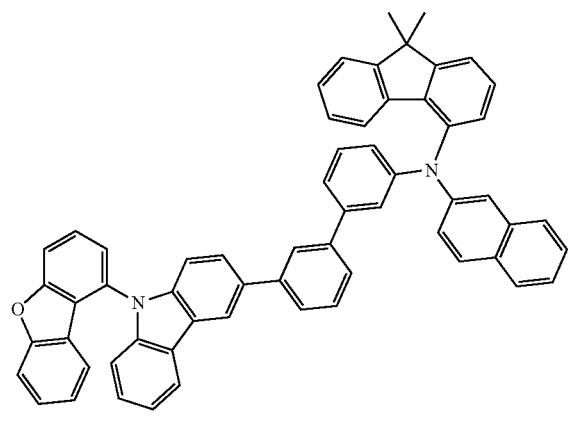
A308
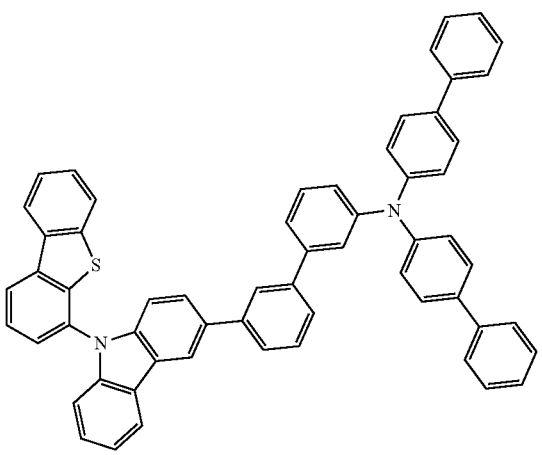

-continued
A309
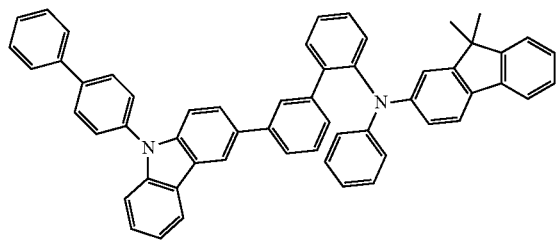
A310
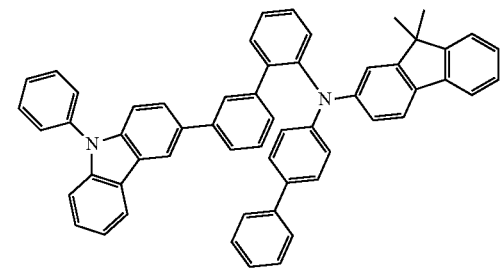
A311
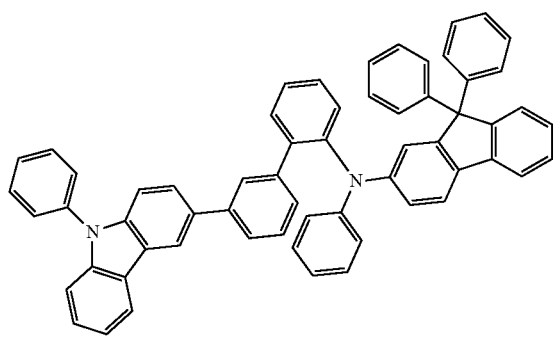
A312
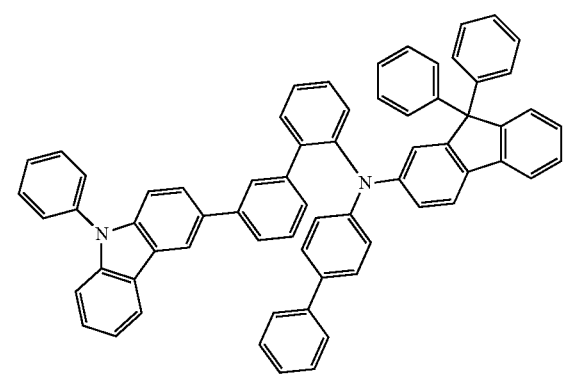
A313
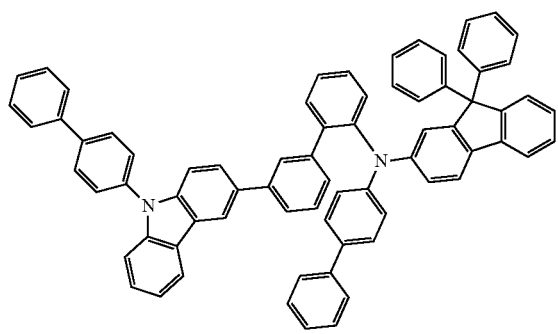
A314
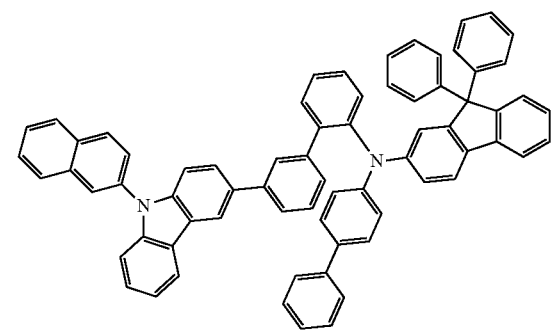
A315
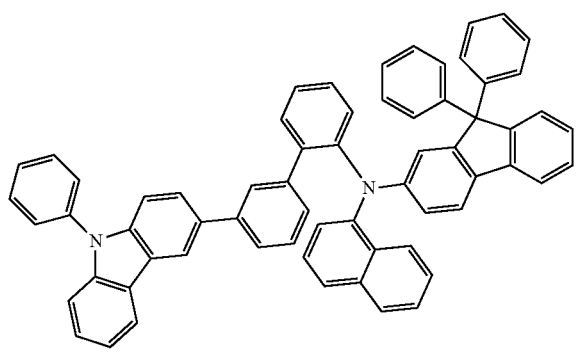
A316
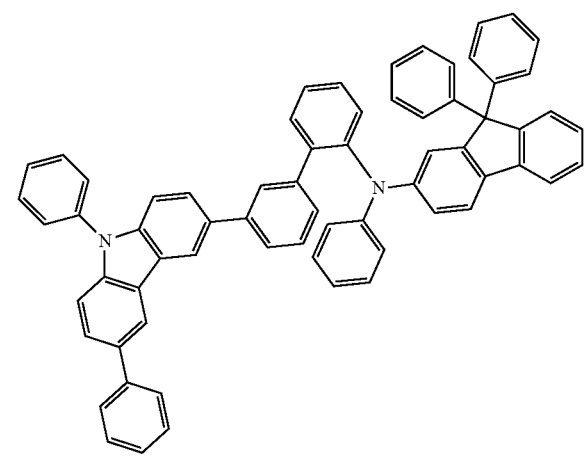

-continued
A317
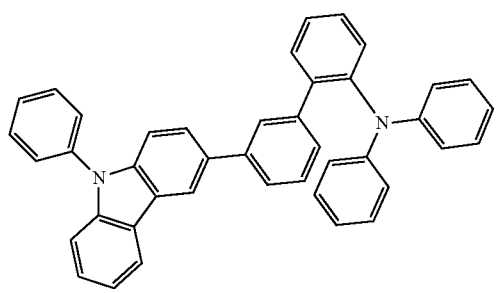
A318
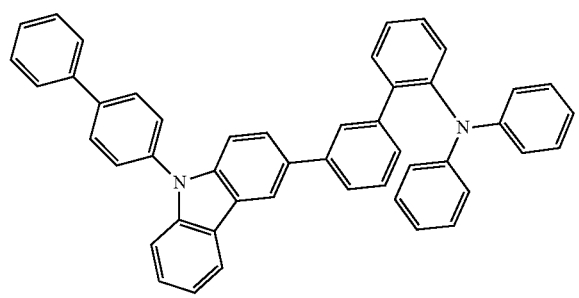
A319
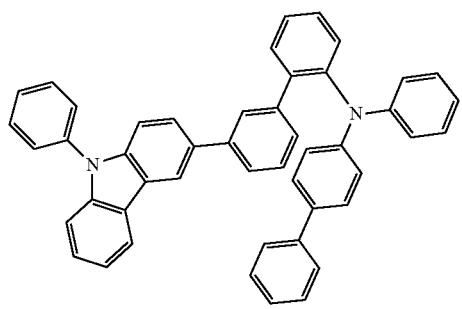
A320
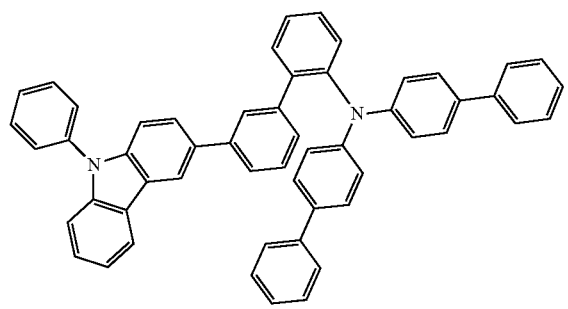
A321
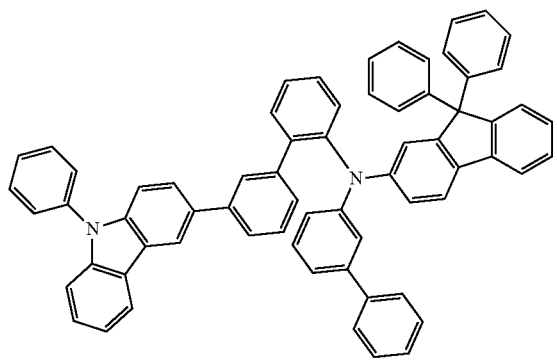
A322
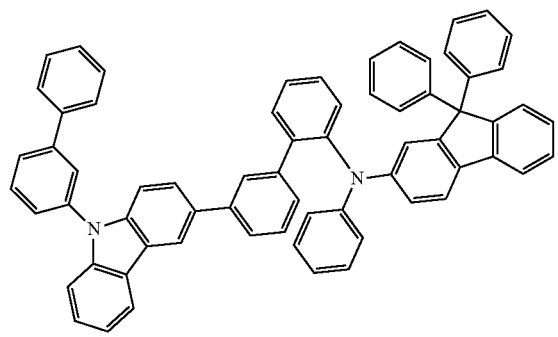
A323
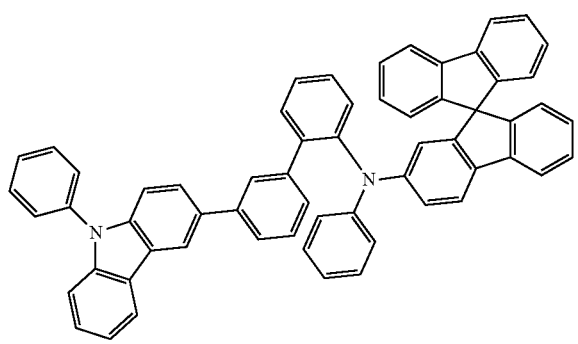
A324
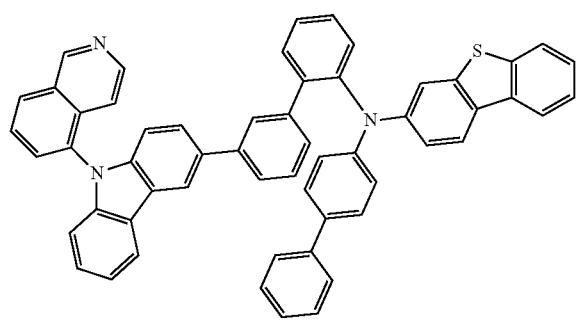

-continued
A325
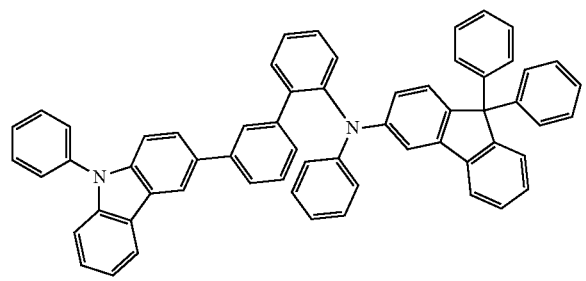
A326
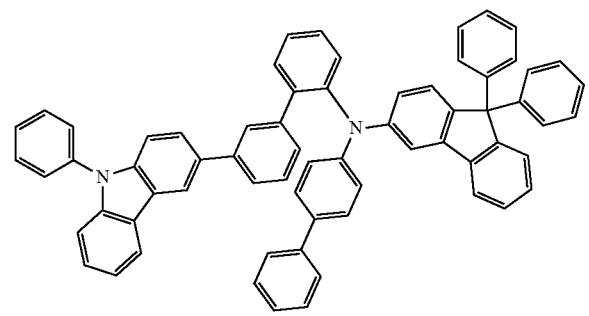
A327
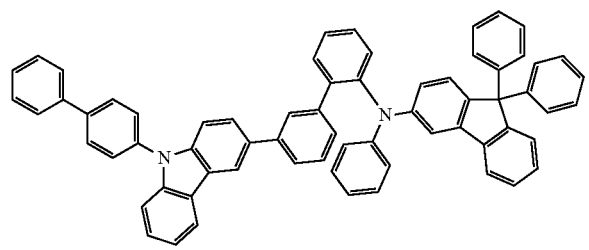
A328
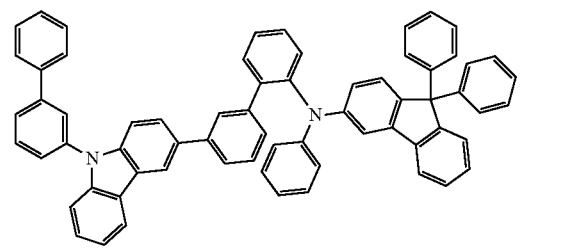
A329
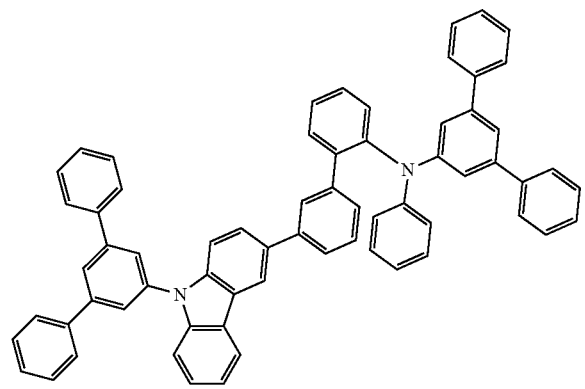
A330
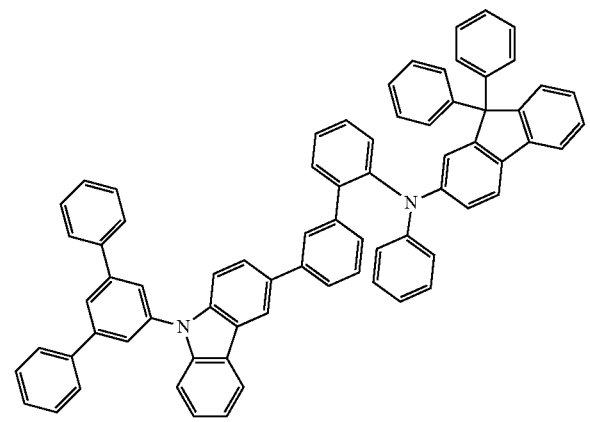
A331
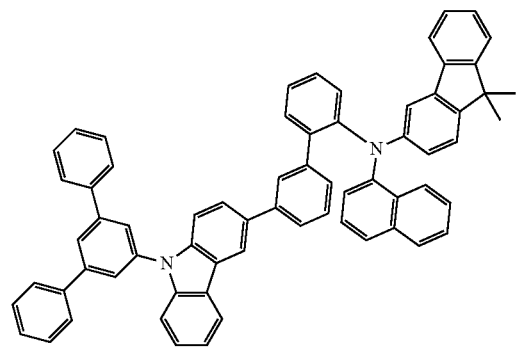
A332
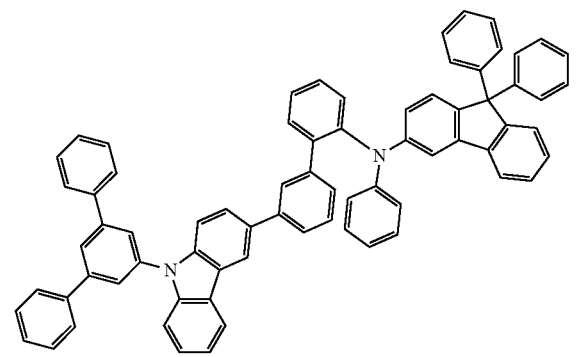

-continued
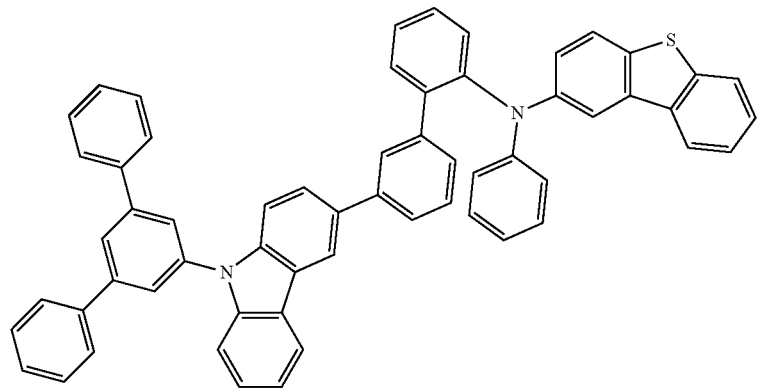
A333
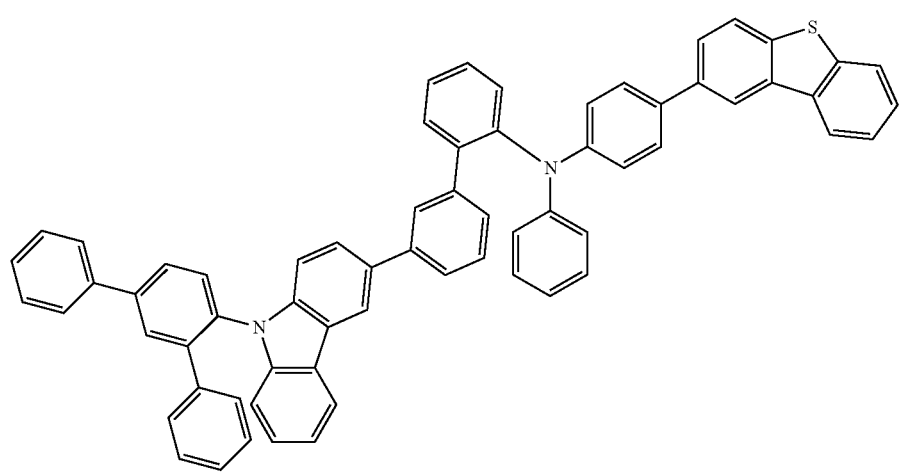
A334
A335 A336
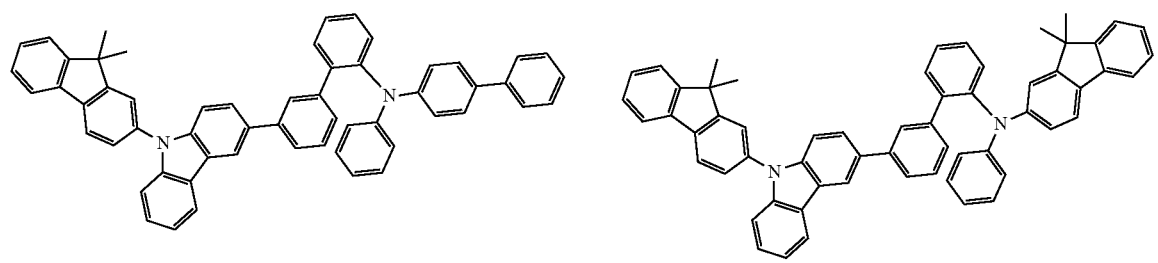
A337 A338
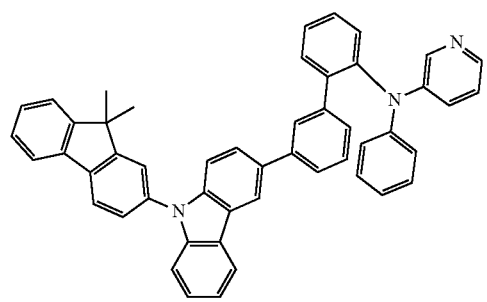
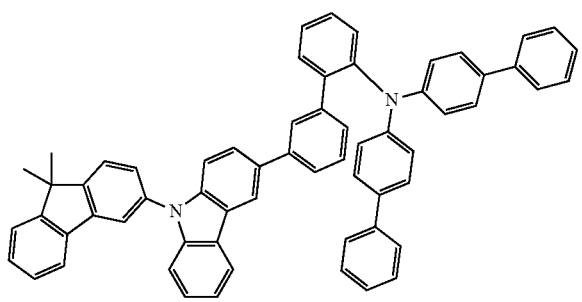

-continued
A339
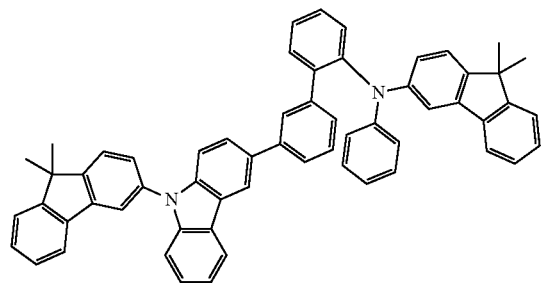
A340
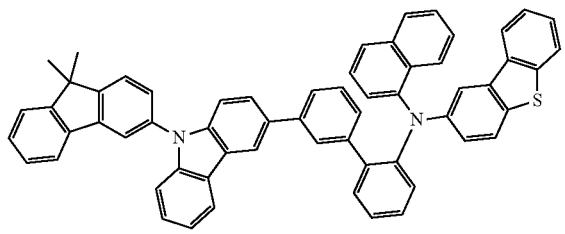
A341
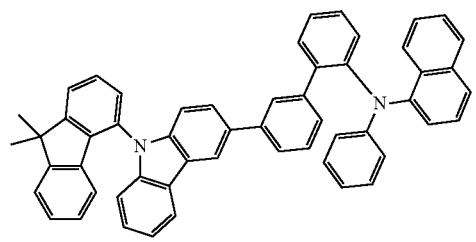
A342
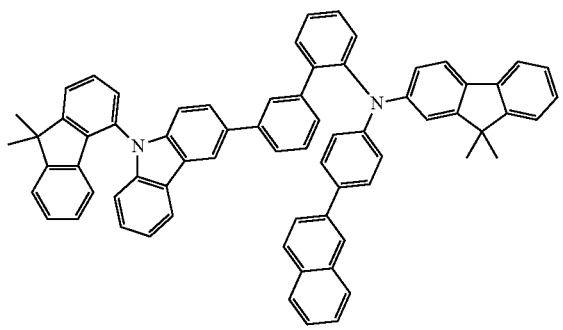
A343
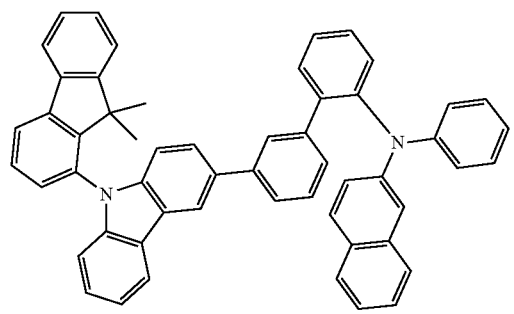
A344
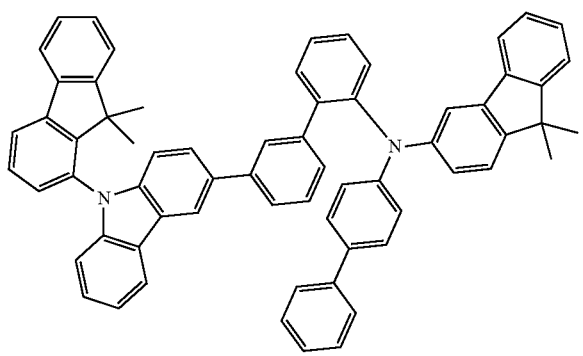
A345
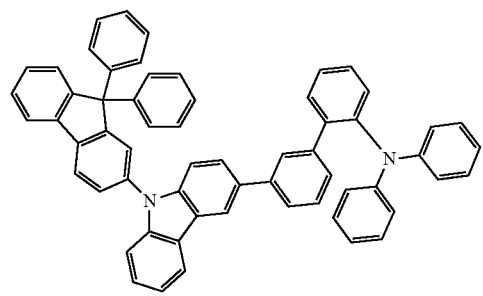
A346
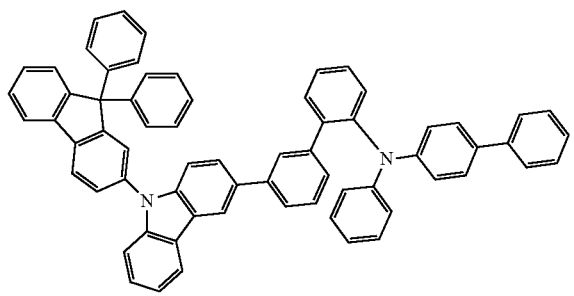

-continued
A347
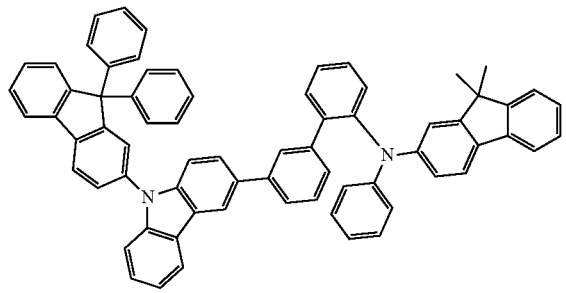
A348
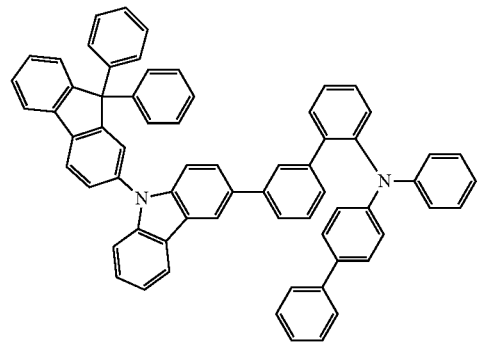
A349
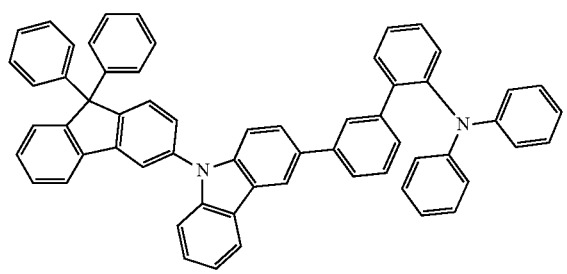
A350
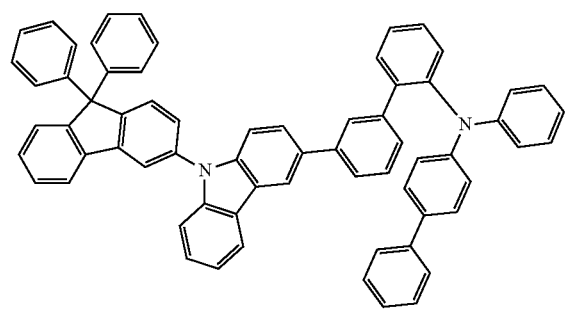
A351
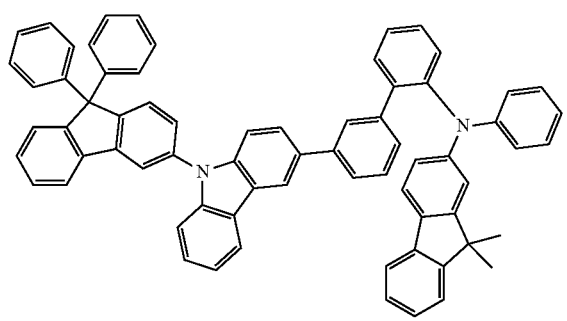
A352
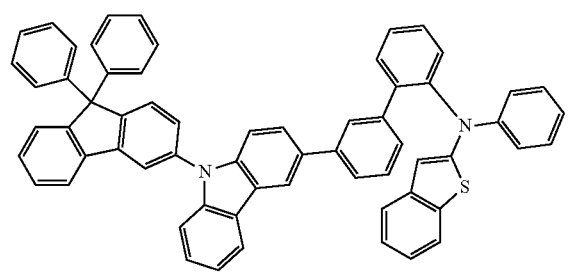
A353
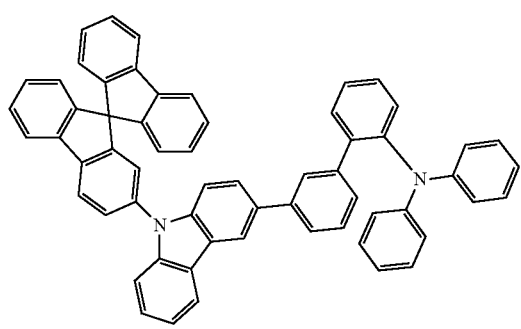
A354
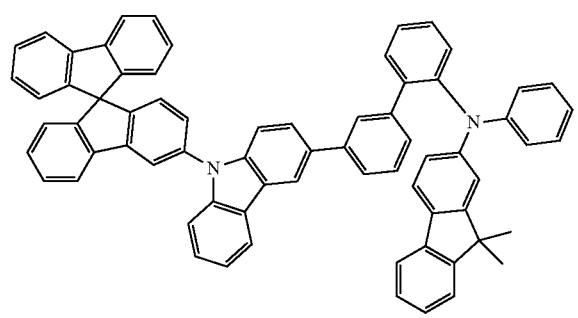

-continued
| A355 | A356 |
|---|---|
| 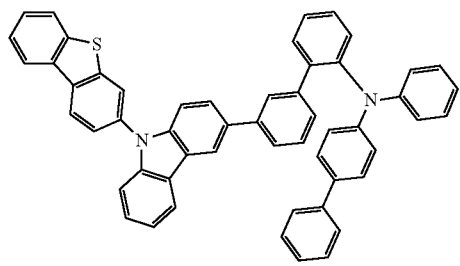 | 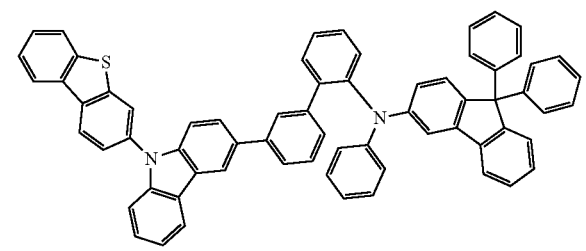 |
| A357 | A358 |
| 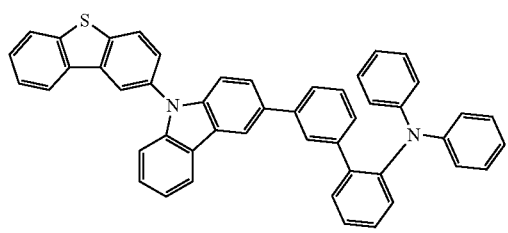 | 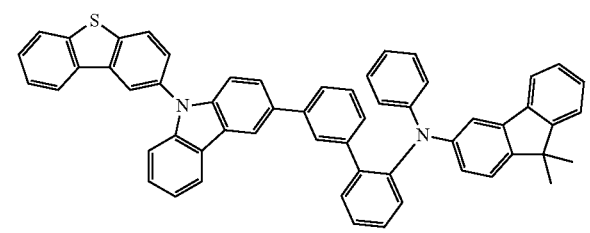 |
| A359 | A360 |
| 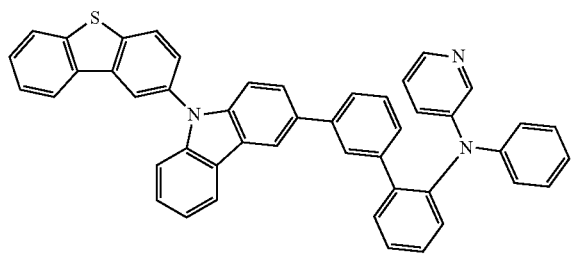 | 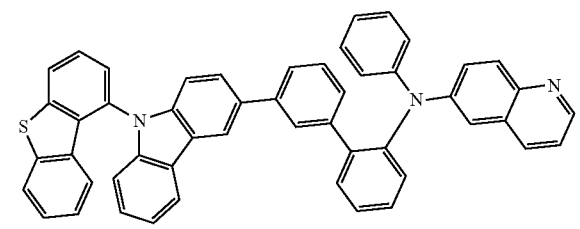 |
| A361 | A362 |
| 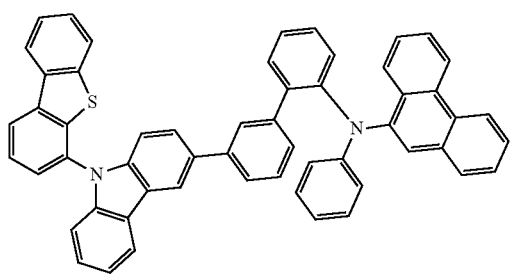 | 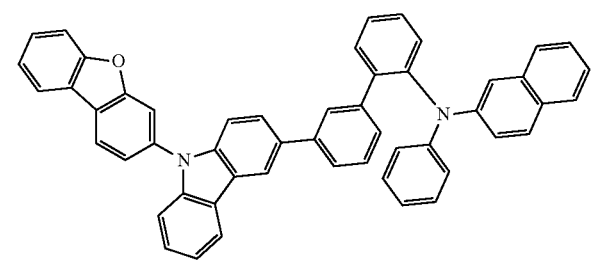 |
| A363 | A364 |
| 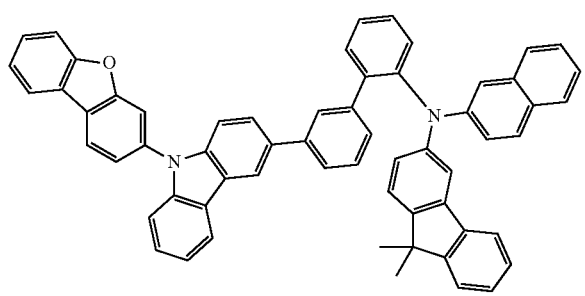 | 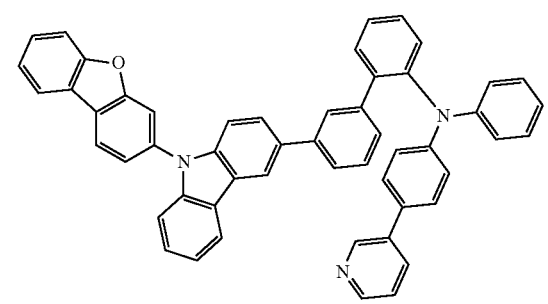 |

-continued
A365
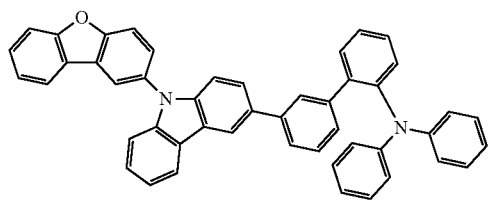
A366
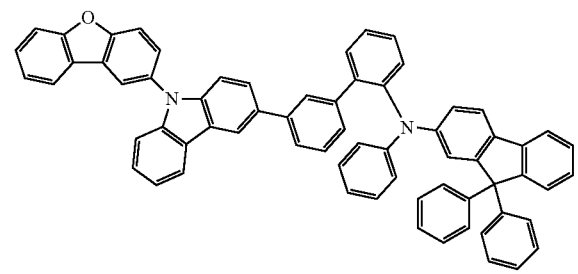
A367
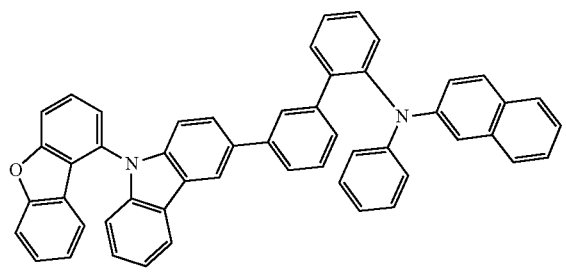
A368
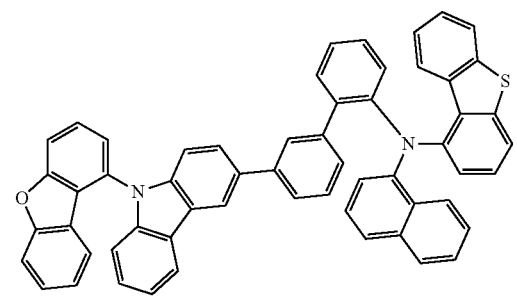
A369
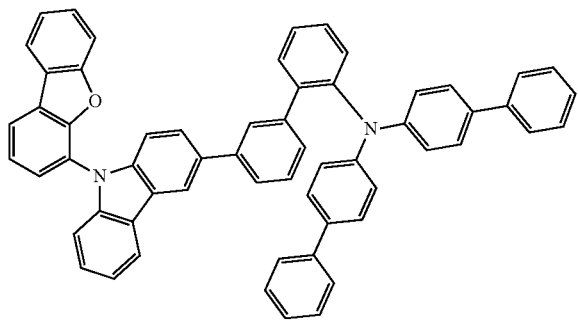
A370
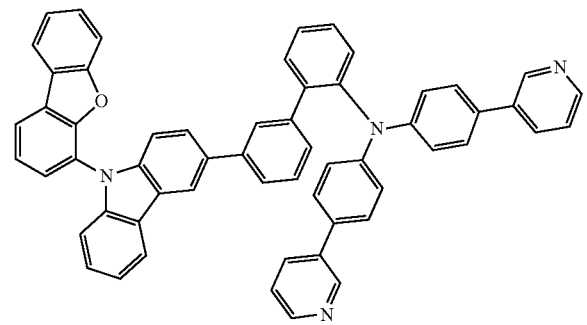
A371
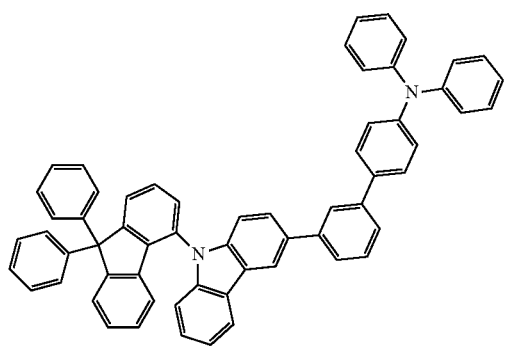
A372
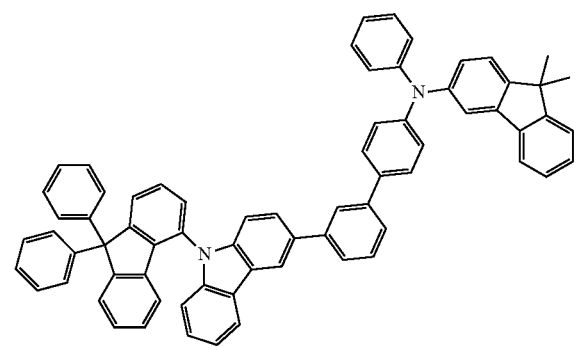

-continued
A373
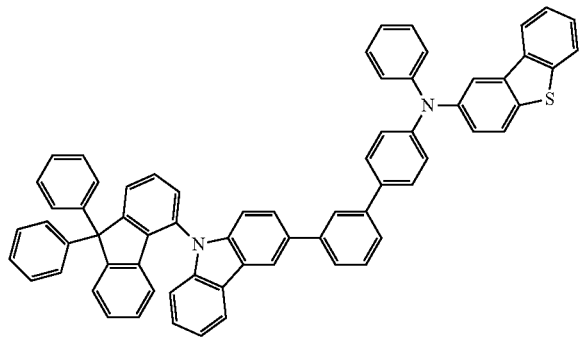
A374
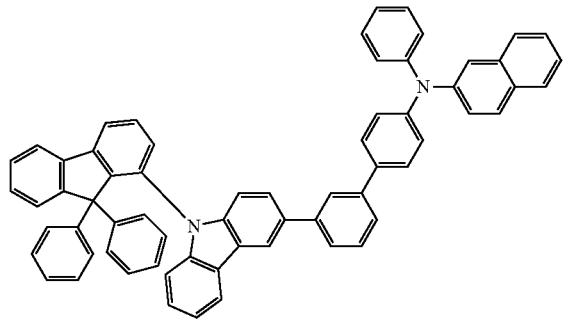
A375
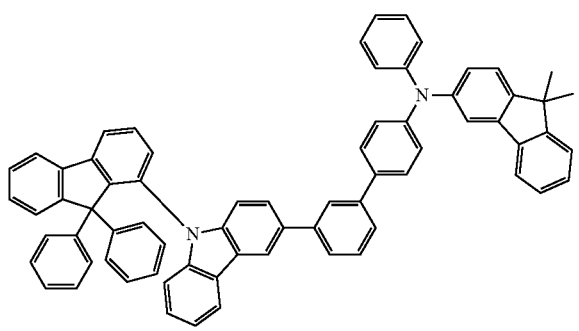
A376
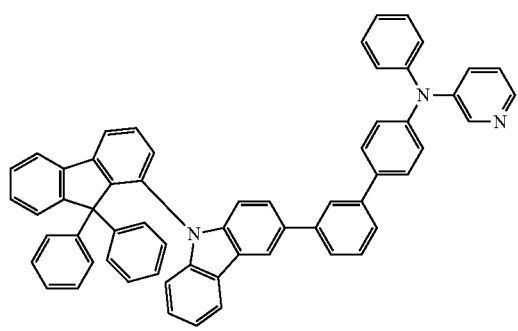
A377
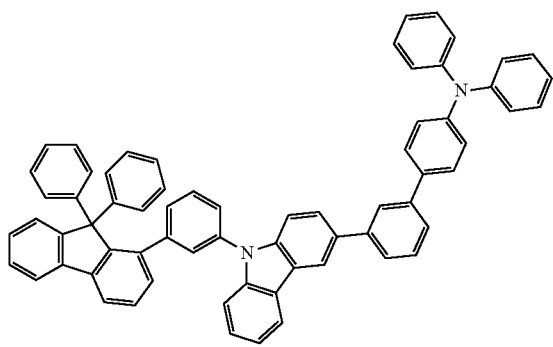
A378
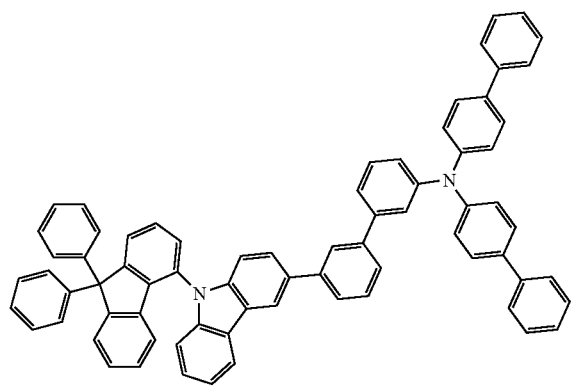
A379
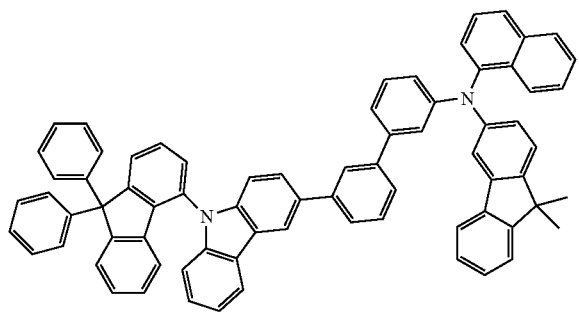
A380
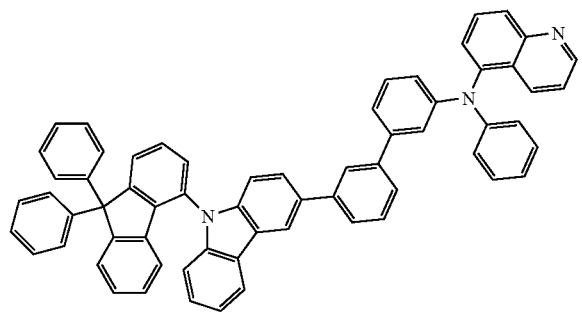

-continued
A381
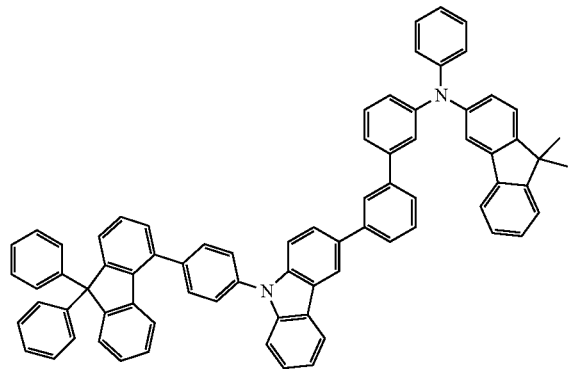
A382
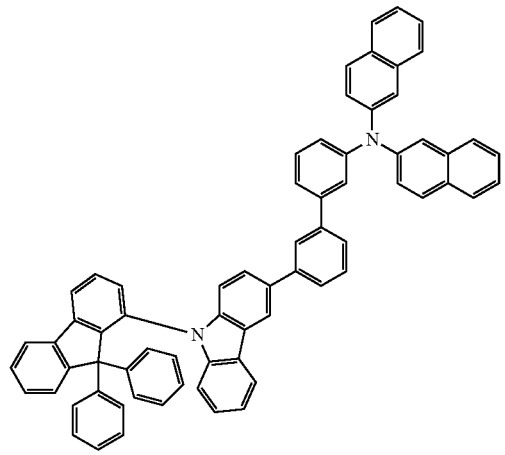
A383
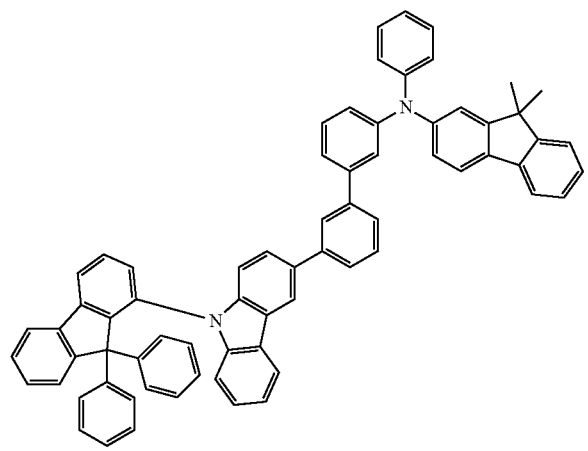
A384
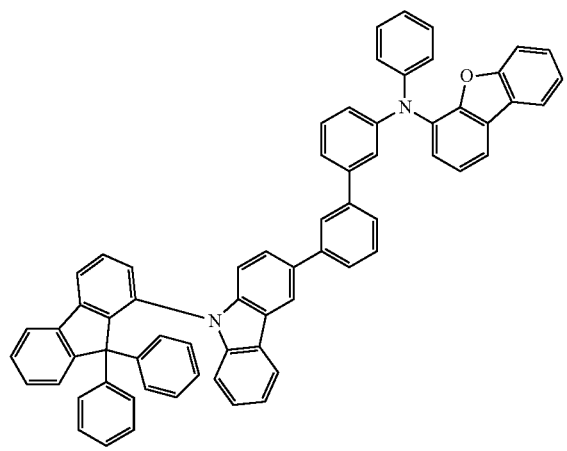
A385
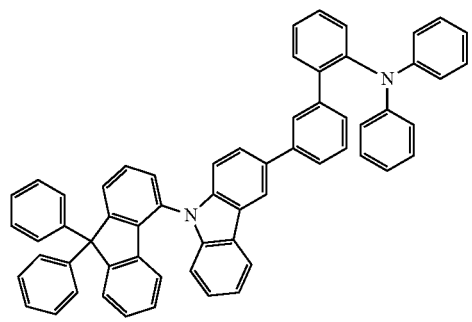
A386
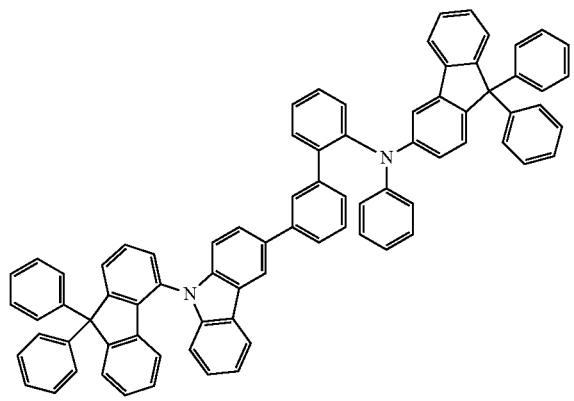

A387
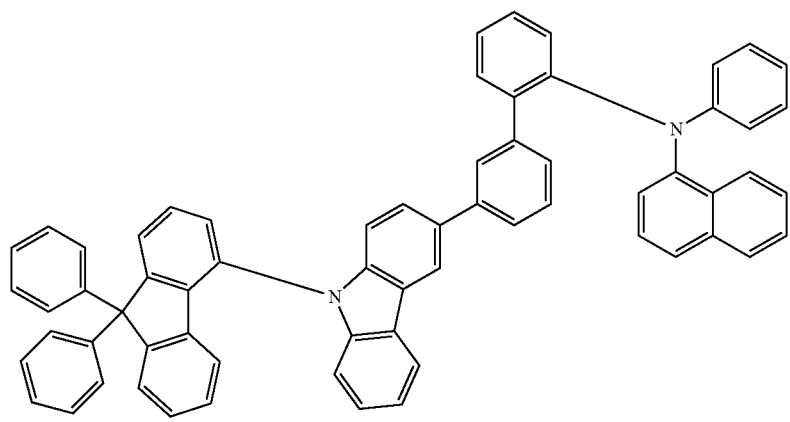
A388
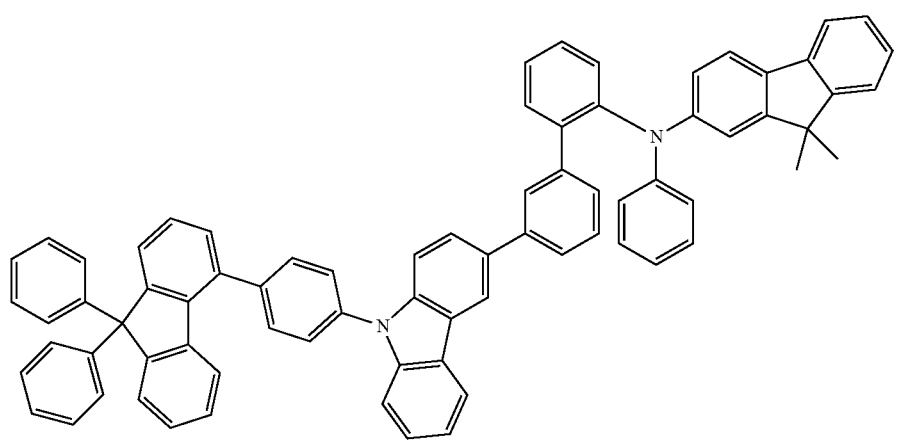
A389
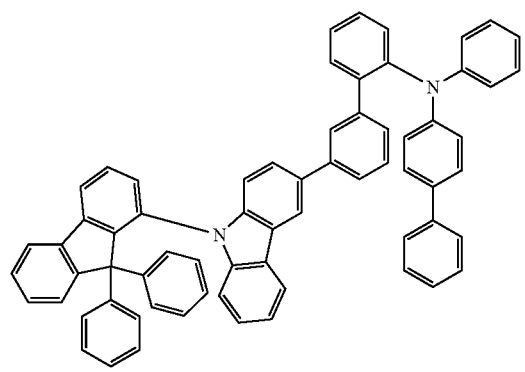
A390
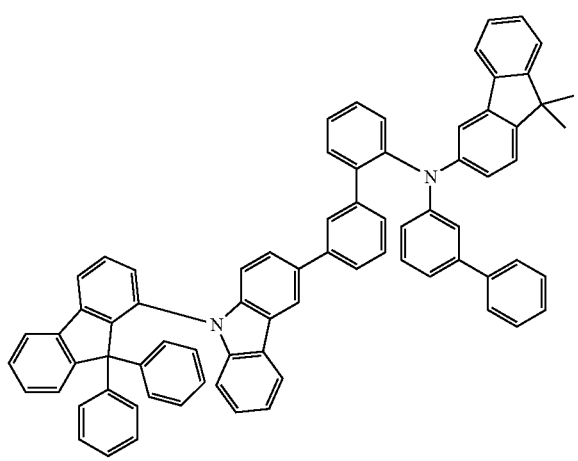

A391
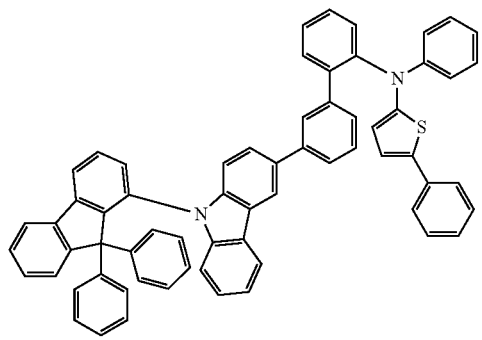
A392
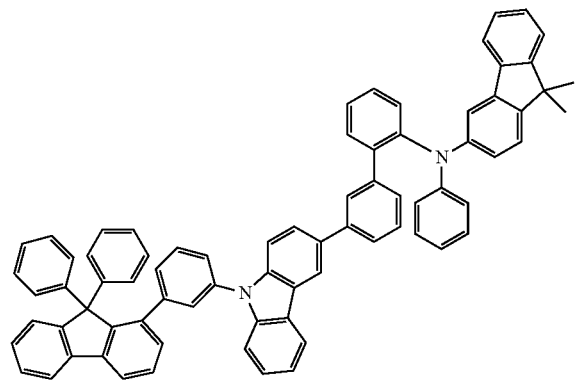
C1
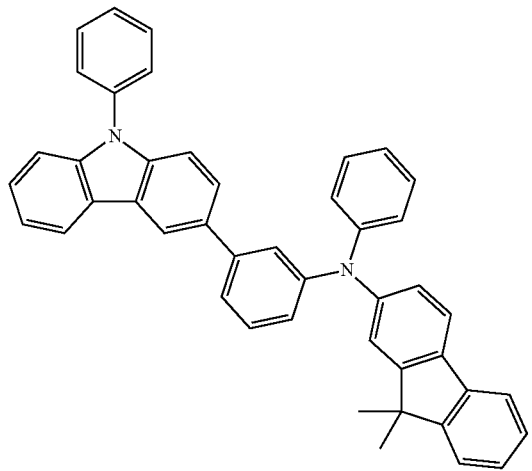
C2
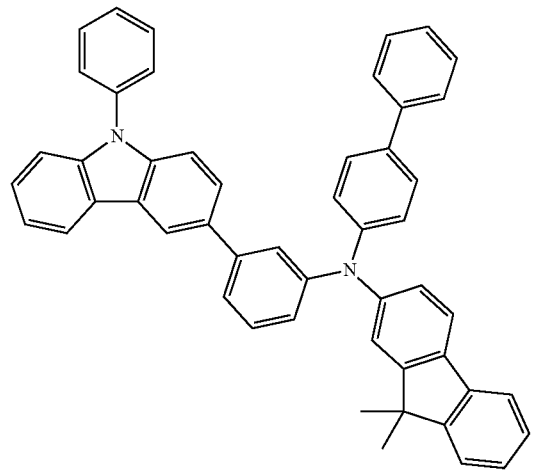
C3
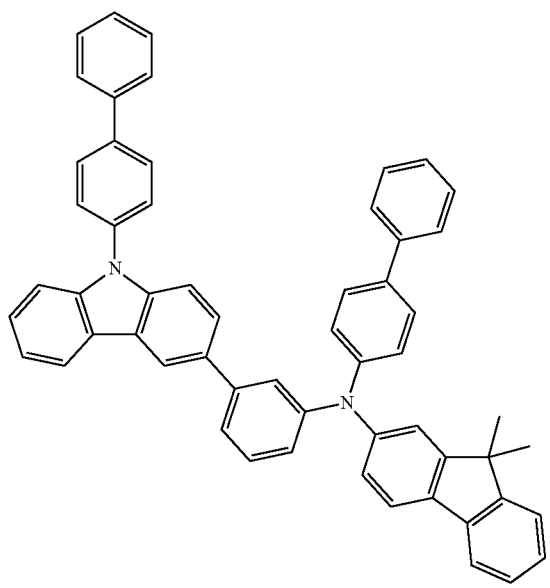
C4
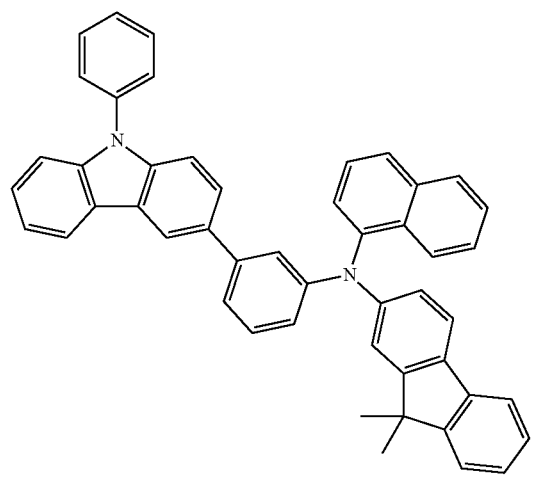

-continued
C5
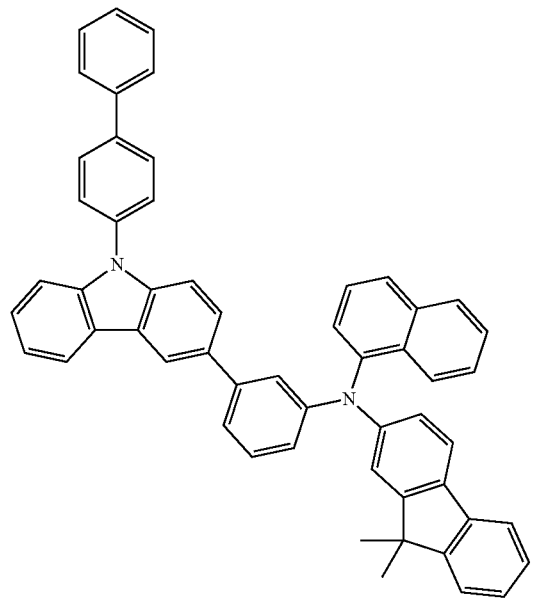
C6
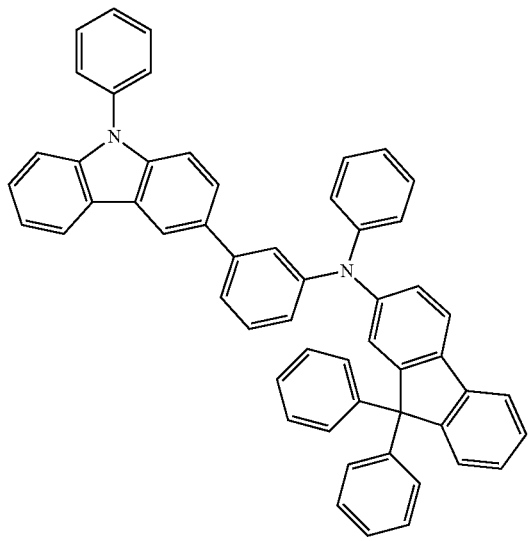
C7
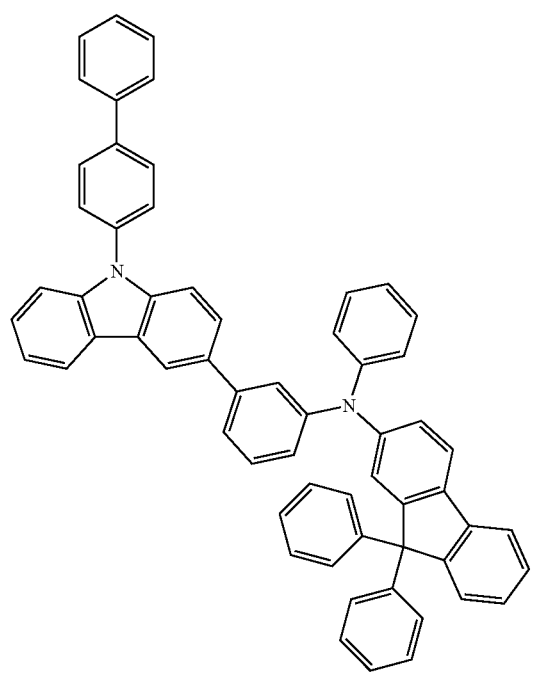
C8
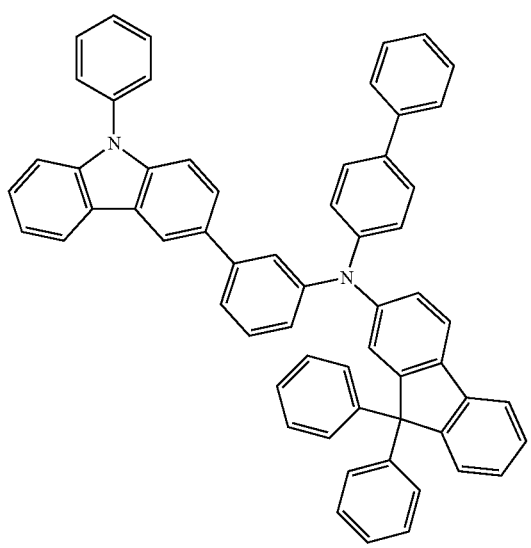

-continued
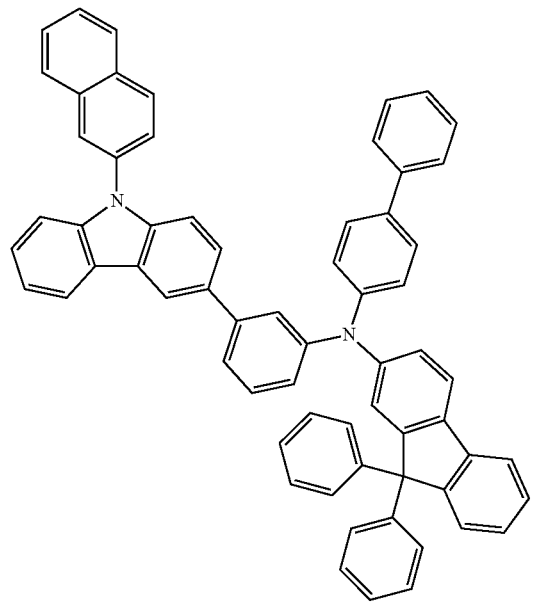
C9
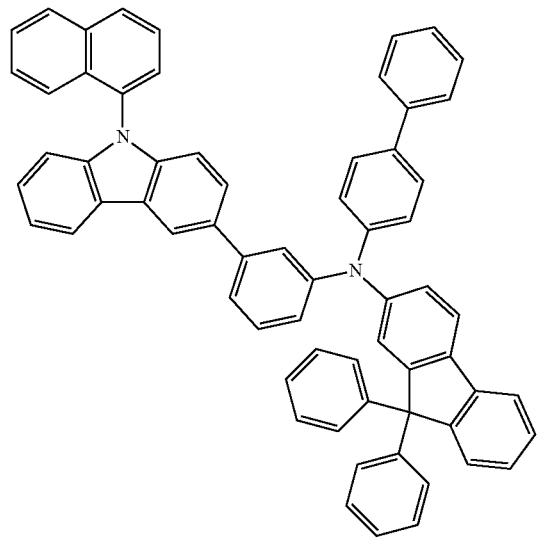
C10
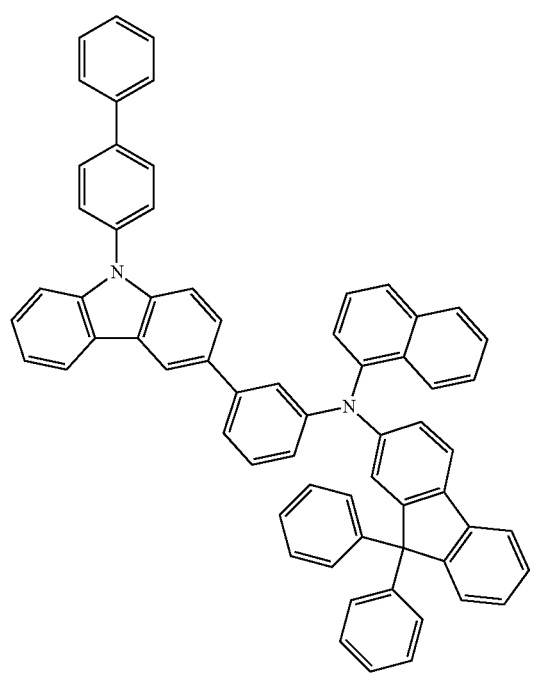
C11
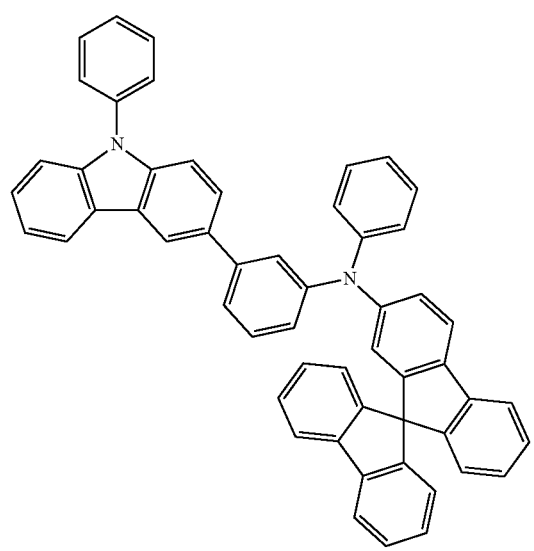
C12

-continued
C13
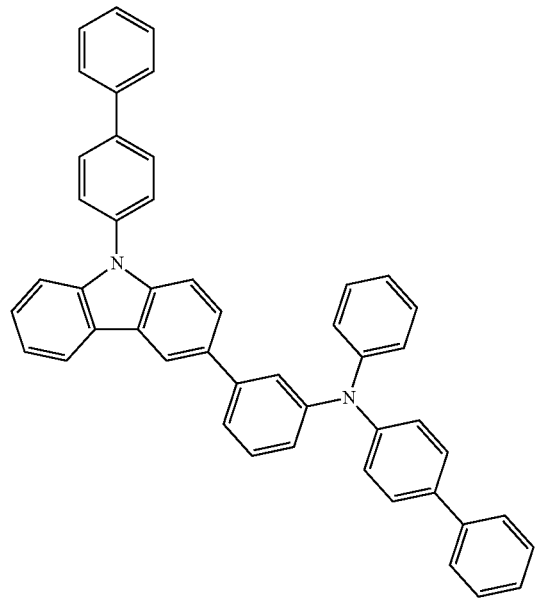
C14
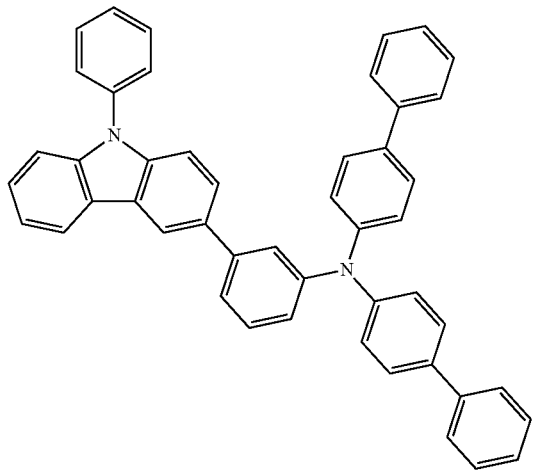
C15
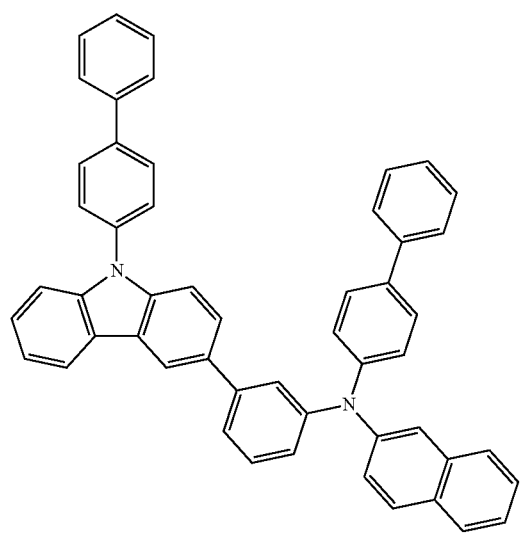
C16
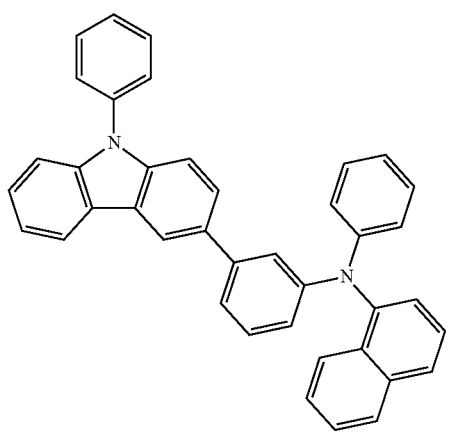
C17
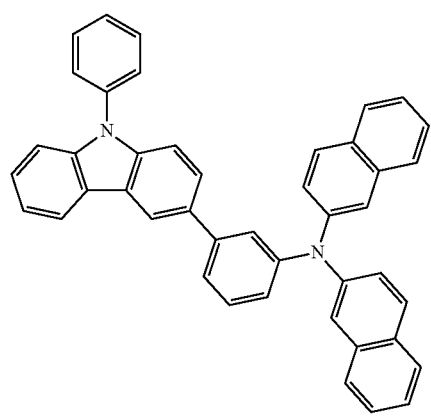
C18
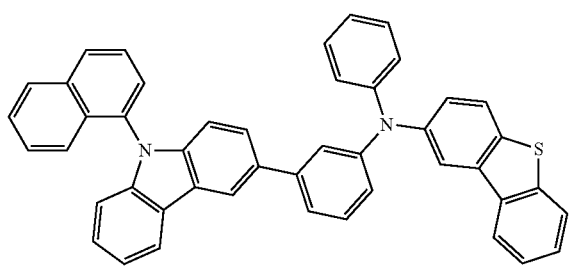

-continued
C19
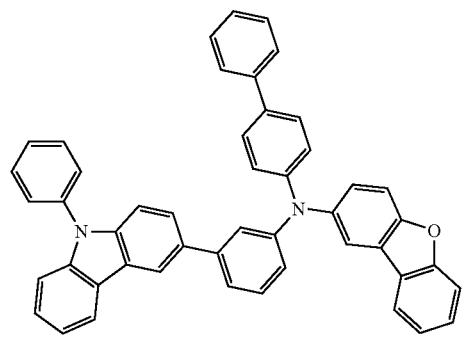
C20
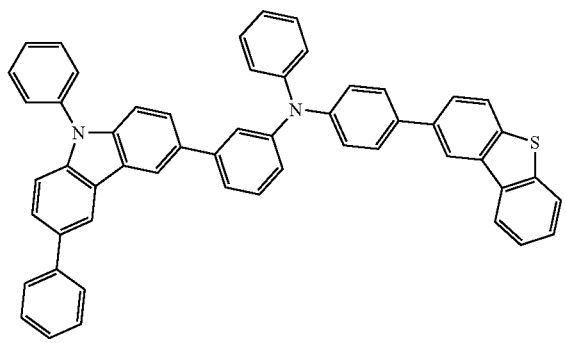
C21
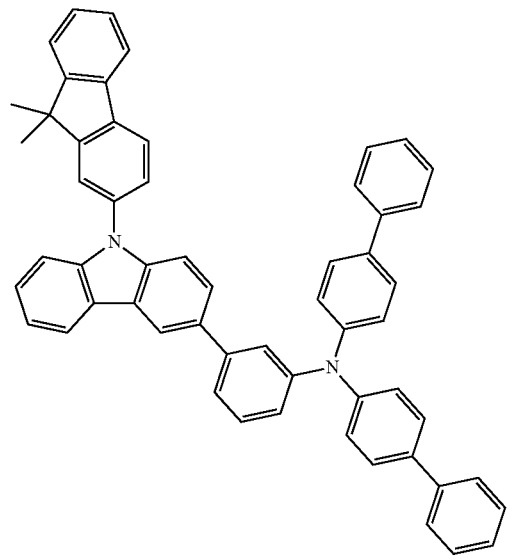
C22
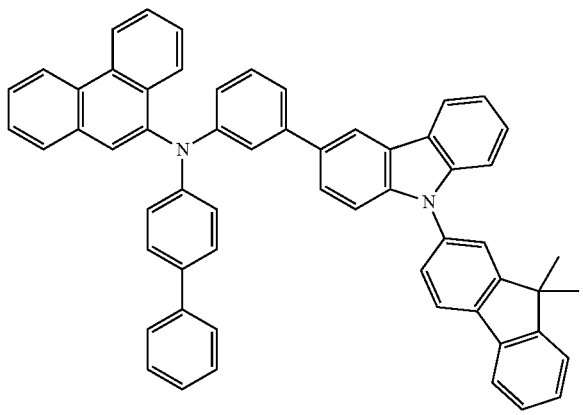
C23
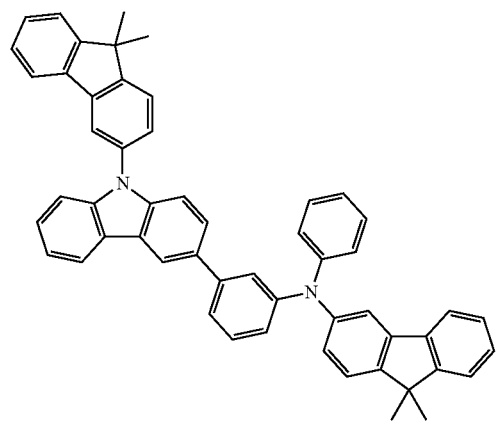
C24
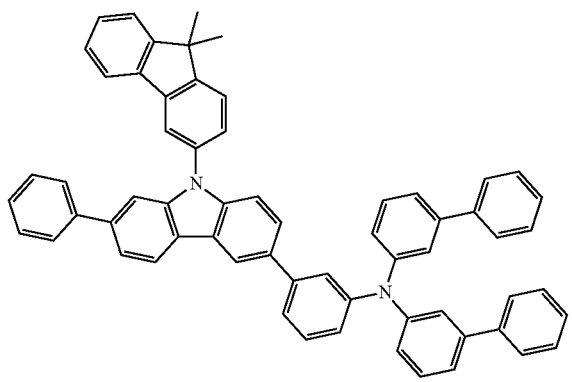

-continued
C25
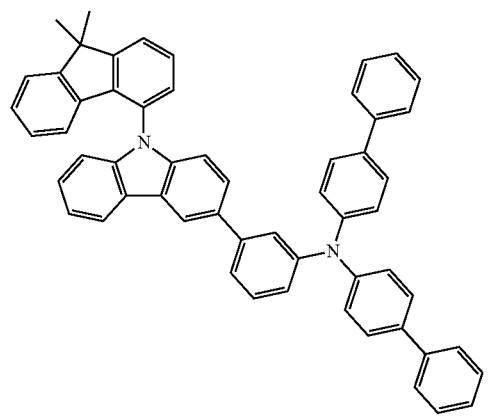
C26
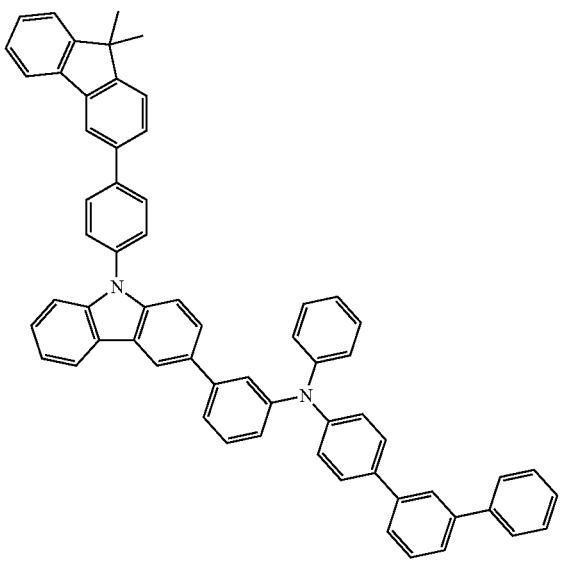
C27
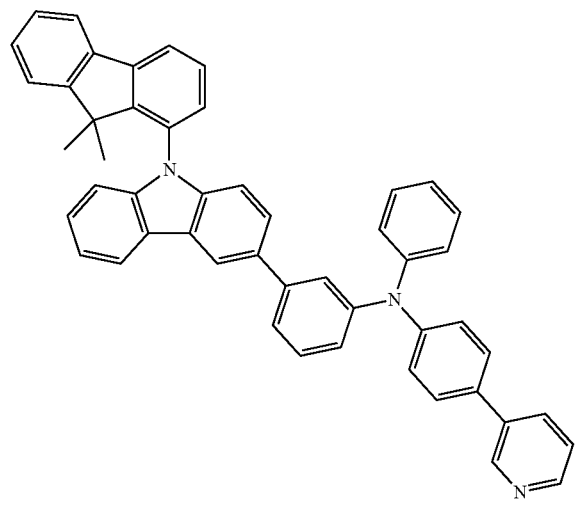
C28
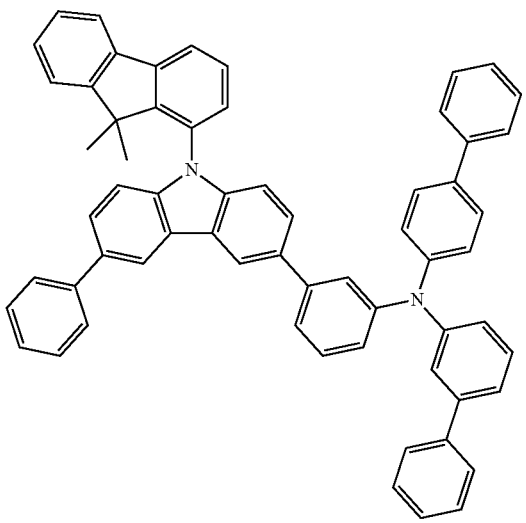

-continued
C29
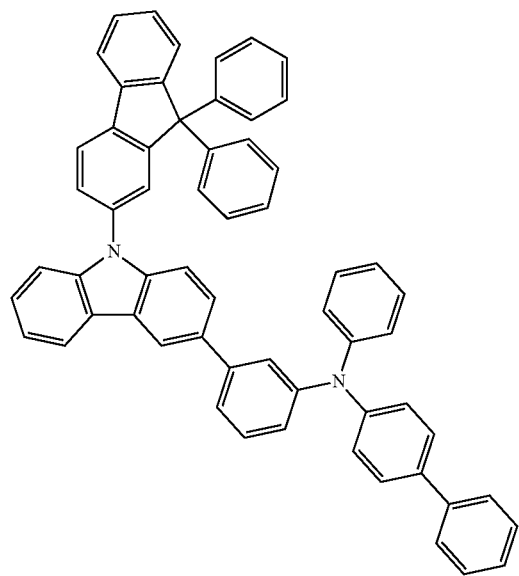
C30
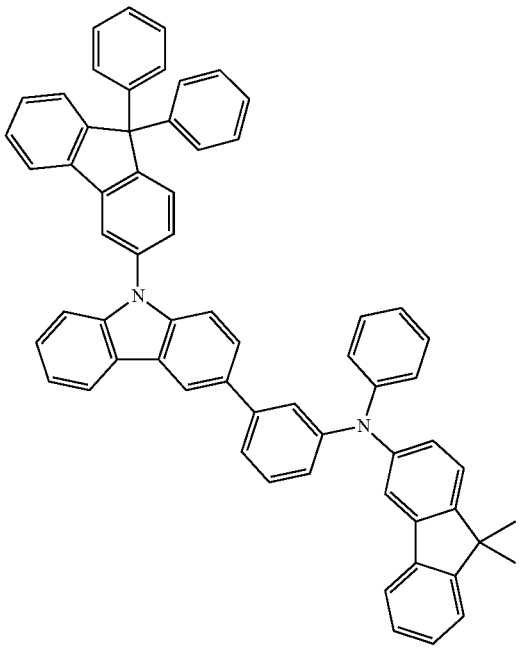
C31
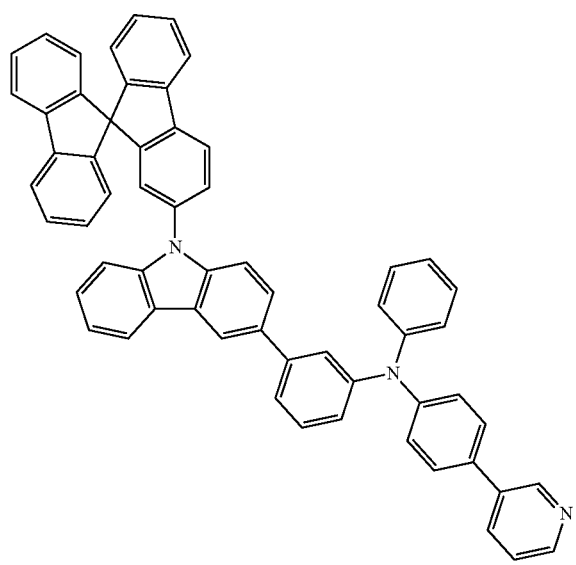
C32
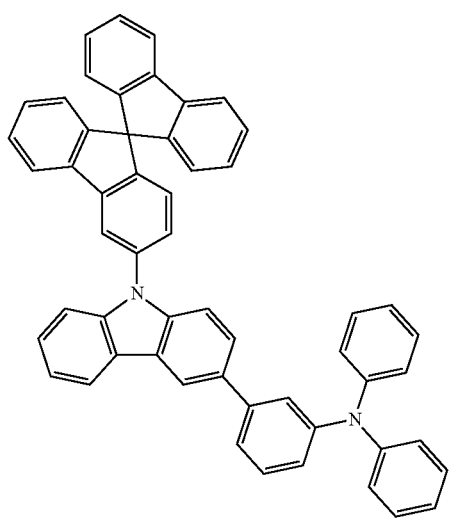
C33
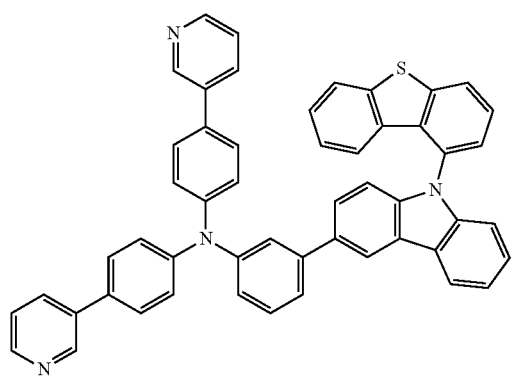
C34
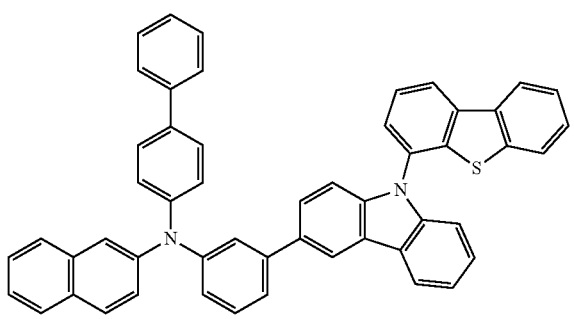

C35

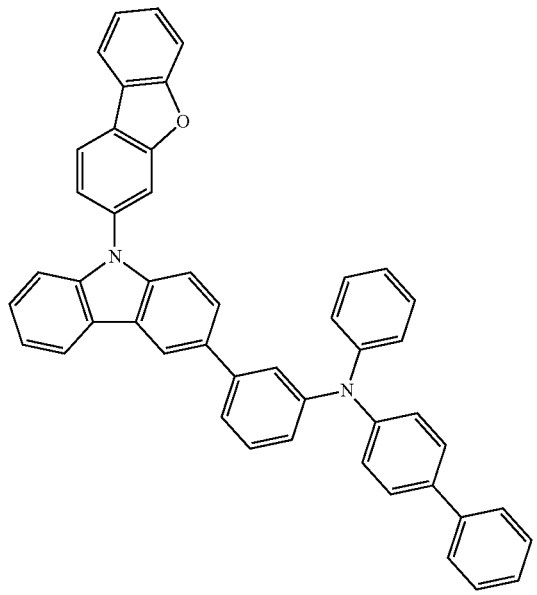

C36

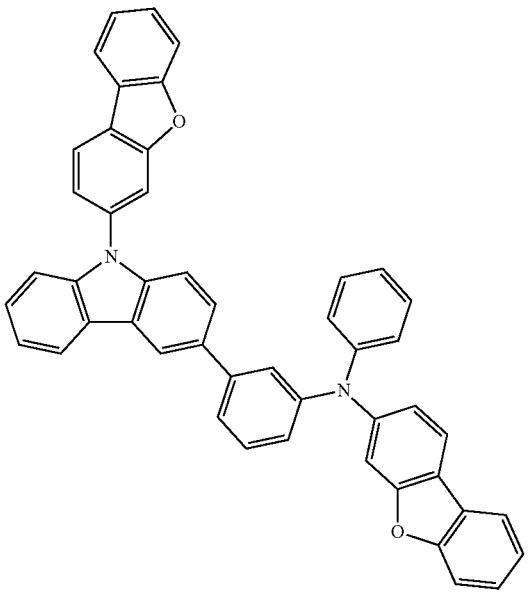

C37 C38

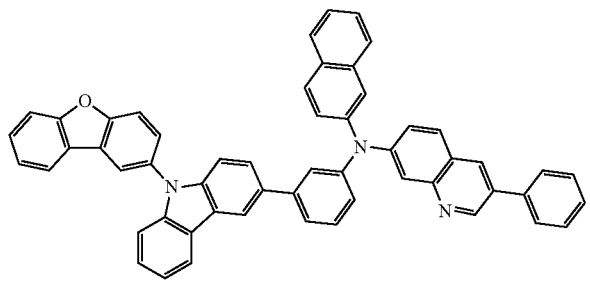

C39

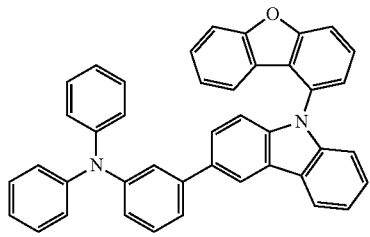

C40

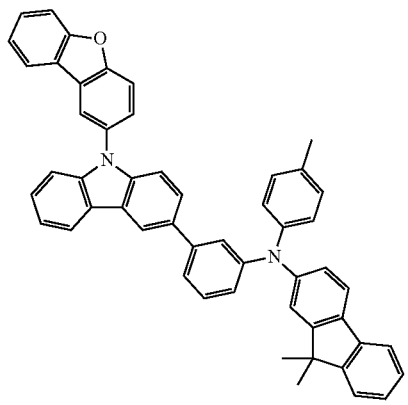

In another aspect of the present invention, there is provided a compound for an organic electric element represented by Formula 1 above.

In another aspect of the present invention, there is provided an organic electric element comprising the compound represented by Formula 1 above.

The organic electric element can comprise a first electrode, a second electrode, and an organic material layer disposed between the first electrode and the second electrode. The organic material layer can comprise the compound represented by Formula 1. The compound by represented Formula 1 can be contained in at least one layer of a hole injection layer, a hole transport layer, an emission-auxiliary layer, or a light emitting layer of the organic material layer. The compound represented by Formula 1 may be used a material in the hole injection layer, a material in the hole transport layer, a material in the emission-auxiliary layer, or a material in the light emitting layer. There is provided the organic electric element comprising the organic material layer comprising at least one of the compounds represented by Formula 2 to Formula 5. Specially, there is provided and the organic electric element comprising the organic material layer comprising at least one of the compounds represented by the individual formulas.

In another aspect of the present invention, the present invention provides an organic electric element further including at least a layer to improve luminous efficiency which is formed on at least one of the sides the first and second electrodes, which is opposite to the organic material layer.

Hereinafter, Synthesis Examples of the inventive compound represented by Formula 1 above and Preparation Examples of an organic electric element will be described in detail by way of example. However, the following examples are only for illustrative purposes and are not intended to limit the scope of the invention.

Synthesis Example

The final product according to the present invention can be synthesized by reaction between Sub 1 and Sub 2 as illustrated in, but not limited to, the following Reaction Scheme 1.

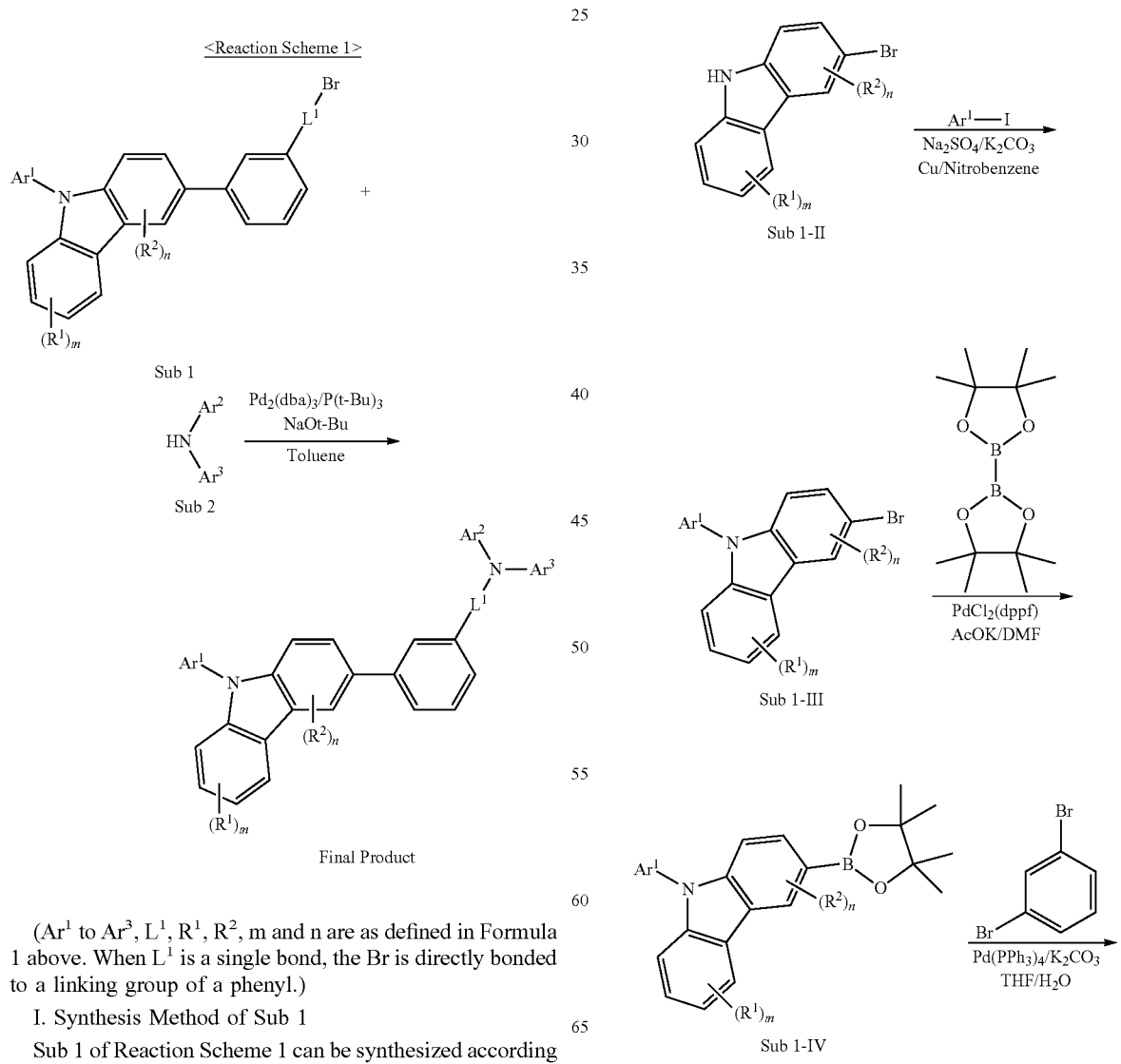

($Ar^1$ to $Ar^3$, $L^1$, $R^1$, $R^2$, m and n are as defined in Formula 1 above. When $L^1$ is a single bond, the Br is directly bonded to a linking group of a phenyl.)

I. Synthesis Method of Sub 1

Sub 1 of Reaction Scheme 1 can be synthesized according to, but not limited to, the following Reaction Scheme 2.

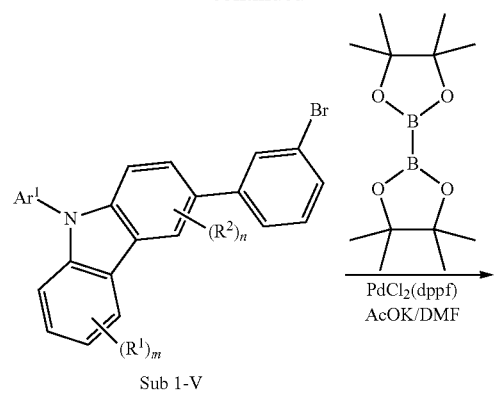
Sub 1-V
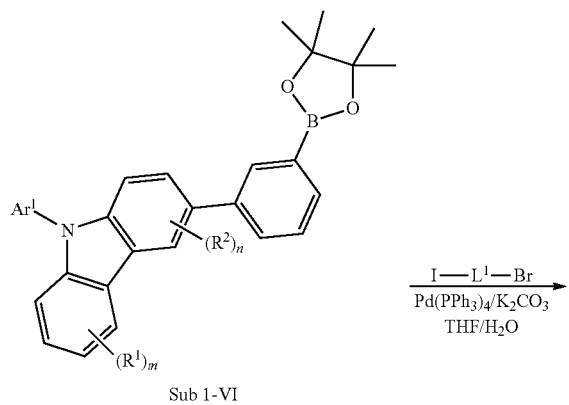
Sub 1-VI
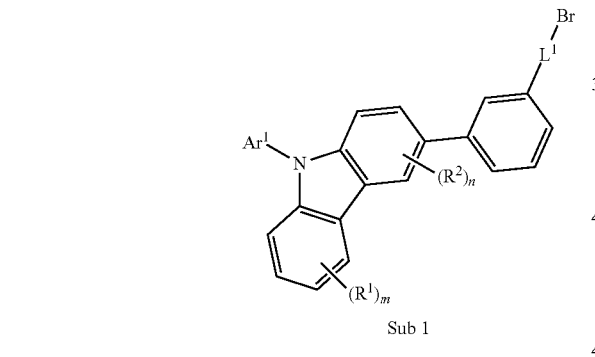
Sub 1
Synthesis Examples of the compounds of Sub 1 will be described in detail.
1. Synthesis Method of Sub 1-A1
<Reaction Scheme 3>
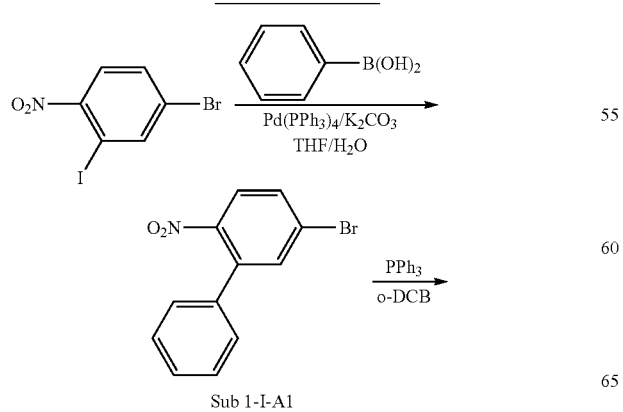
Sub 1-I-A1
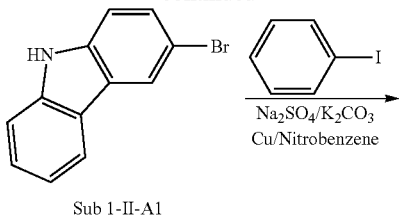
Sub 1-II-A1
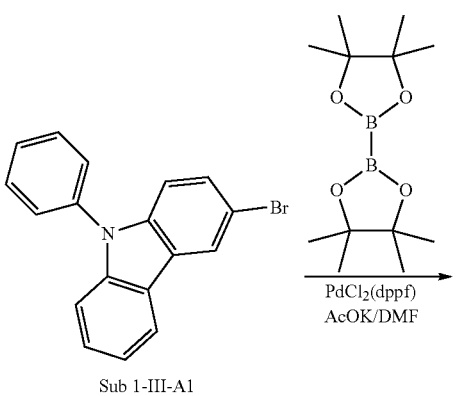
Sub 1-III-A1
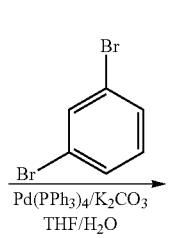
Sub 1-IV-A1
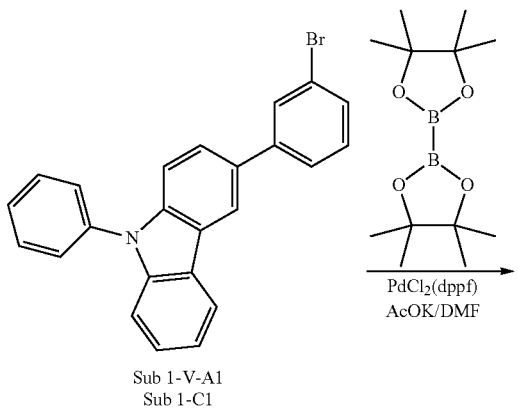
Sub 1-V-A1
Sub 1-C1

-continued

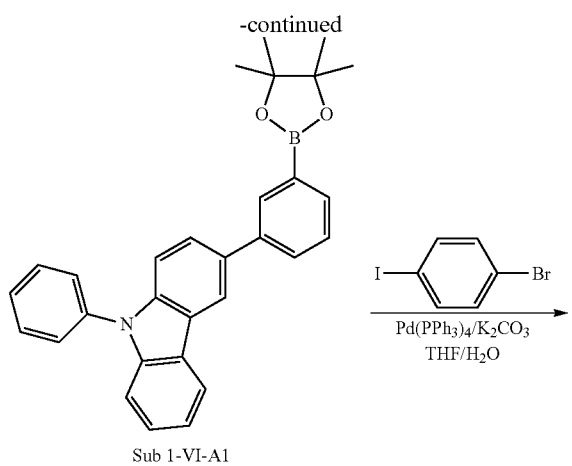

Sub 1-VI-A1

Sub 1-A1

(1) Synthesis Method of Sub 1-I-A1 phenylboronic acid (412.96 g, 3386.9 mmol) as the starting material was dissolved in THF in a round bottom flask, and 4-bromo-2-iodo-1-nitrobenzene (1665.83 g, 5080.3 mmol), Pd(PPh$_3$)$_4$ (195.69 g, 169.3 mmol), K$_2$CO$_3$ (1404.29 g, 10160.6 mmol), and water were added to the reaction solution, followed by stirring at 80° C. Upon completion of the reaction, the reaction product was extracted with CH$_2$Cl$_2$ and water. The extracted organic layer was dried with MgSO$_4$ and concentrated, and then the produced organic material was separated by a silica gel column and recrystallized to obtain 659.32 g of product (yield: 70%).

(2) Synthesis Method of Sub 1-II-A1

The obtained Sub 1-I-A1 (659.32 g, 2370.8 mmol) was dissolved in o-dichlorobenzene in a round bottom flask, and triphenylphosphine (1554.59 g, 5927 mmol) was added to the reaction solution, followed by stirring at 200° C. Upon completion of the reaction, o-dichlorobenzene was removed by distillation, and the reaction product was extracted with CH$_2$Cl$_2$ and water. The extracted organic layer was dried with MgSO$_4$ and concentrated, and then the produced organic material was separated by a silica gel column and recrystallized to obtain 431.76 g of product (yield: 74%).

(3) Synthesis Method of Sub 1-III-A1

The obtained Sub 1-II-A1 (50.69 g, 206 mmol) was dissolved in nitrobenzene in a round bottom flask, and iodobenzene (63.03 g, 309 mmol), Na$_2$SO$_4$ (29.26 g, 206 mmol), K$_2$CO$_3$ (28.47 g, 206 mmol), and Cu (3.93 g, 61.8 mmol) were added to the reaction solution, followed by stirring at 200° C. Upon completion of the reaction, nitrobenzene was removed by distillation, and the reaction product was extracted with CH$_2$Cl$_2$ and water. The extracted organic layer was dried with MgSO$_4$ and concentrated, and then the produced organic material was separated by a silica gel column and recrystallized to obtain 48.45 g of product (yield: 73%).

(4) Synthesis Method of Sub 1-IV-A1

The obtained Sub 1-III-A1 (48.45 g, 150.4 mmol) was dissolved in DMF in a round bottom flask, and Bis(pinacolato)diboron (42 g, 165.4 mmol), Pd(dppf)Cl$_2$ (3.68 g, 4.5 mmol) and KOAc (44.27 g, 451.1 mmol) were added to the reaction solution, followed by stirring at 90° C. Upon completion of the reaction, DMF was removed by distillation, and the reaction product was extracted with CH$_2$Cl$_2$ and water. The extracted organic layer was dried with MgSO$_4$ and concentrated, and then the produced organic material was separated by a silica gel column and recrystallized to obtain 46.64 g of product (yield: 84%).

(5) Synthesis Method of Sub 1-V-A1(Sub 1-C1)

The obtained Sub 1-IV-A1 (46.64 g, 126.3 mmol) was dissolved in THF in a round bottom flask, and 1,3-dibromobenzene (44.69 g, 189.5 mmol), Pd(PPh$_3$)$_4$ (7.3 g, 6.3 mmol), K$_2$CO$_3$ (52.37 g, 378.9 mmol), and water were added to the reaction solution, followed by stirring at 80° C. Upon completion of the reaction, the reaction product was extracted with CH$_2$Cl$_2$ and water. The extracted organic layer was dried with MgSO$_4$ and concentrated, and then the produced organic material was separated by a silica gel column and recrystallized to obtain 36.22 g of product (yield: 72%).

(6) Synthesis Method of Sub 1-VI-A1

The obtained Sub 1-V-A1 (36.22 g, 90.9 mmol) was dissolved in DMF in a round bottom flask, and Bis(pinacolato)diboron (25.4 g, 100 mmol), Pd(dppf)Cl$_2$ (2.23 g, 2.7 mmol) and KOAc (26.77 g, 272.8 mmol) were added to the reaction solution, followed by stirring at 90° C. Upon completion of the reaction, DMF was removed by distillation, and the reaction product was extracted with CH$_2$Cl$_2$ and water. The extracted organic layer was dried with MgSO$_4$ and concentrated, and then the produced organic material was separated by a silica gel column and recrystallized to obtain 33.21 g of product (yield: 82%).

(7) Synthesis Method of Sub 1-A1

The obtained Sub 1-VI-A1 (10.52 g, 23.6 mmol) was dissolved in THF in a round bottom flask, and 1-bromo-4-iodobenzene (10.02 g, 35.4 mmol), Pd(PPh$_3$)$_4$ (1.36 g, 1.2 mmol), K$_2$CO$_3$ (9.79 g, 70.9 mmol) and water were added to the reaction solution, followed by stirring at 80° C. Upon completion of the reaction, the reaction product was extracted with CH$_2$Cl$_2$ and water. The extracted organic layer was dried with MgSO$_4$ and concentrated, and then the produced organic material was separated by a silica gel column and recrystallized to obtain 9.08 g of product (yield: 81%).

2. Synthesis Method of Sub 1-A2
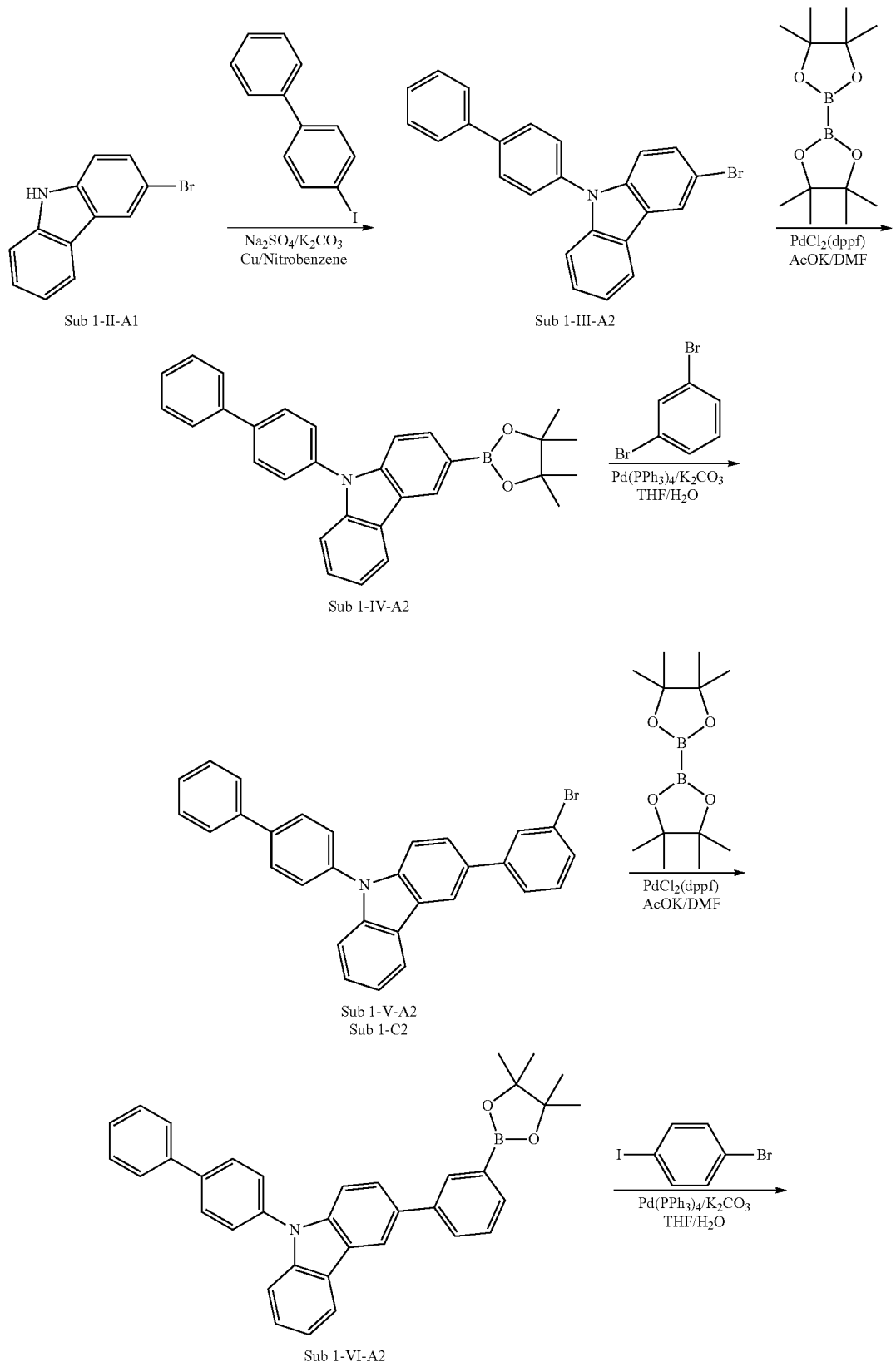

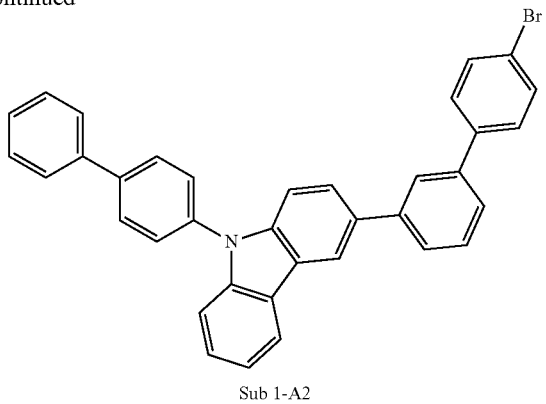

Sub 1-A2

(1) Synthesis Method of Sub 1-III-A2

Using the obtained Sub 1-II-A1 (23.94 g, 97.3 mmol) plus 4-iodo-1,1'-biphenyl (40.87 g, 145.9 mmol), Na$_2$SO$_4$ (13.82 g, 97.3 mmol), K$_2$CO$_3$ (13.44 g, 97.3 mmol), Cu (1.85 g, 29.2 mmol), and nitrobenzene, the same procedure as described in the synthesis method of Sub 1-III-A1 was carried out to obtain 27.51 g of product (yield: 71%).

(2) Synthesis Method of Sub 1-IV-A2

Using the obtained Sub 1-III-A2 (27.51 g, 69.1 mmol) plus Bis(pinacolato)diboron (19.29 g, 76 mmol), Pd(dppf)Cl$_2$ (1.69 g, 2.1 mmol), KOAc (20.34 g, 207.2 mmol) and DMF, the same procedure as described in the synthesis method of Sub 1-IV-A1 was carried out to obtain 26.76 g of product (yield: 87%).

(3) Synthesis Method of Sub 1-V-A2(Sub 1-C2)

Using the obtained Sub 1-IV-A2 (26.76 g, 60.1 mmol) plus 1,3-dibromobenzene (21.26 g, 90.1 mmol), Pd(PPh$_3$)$_4$ (3.47 g, 3 mmol), K$_2$CO$_3$ (24.91 g, 180.3 mmol), THF and water, the same procedure as described in the synthesis method of Sub 1-V-A1 was carried out to obtain 22.23 g of product (yield: 78%).

(4) Synthesis Method of Sub 1-VI-A2

Using the obtained Sub 1-V-A2 (22.23 g, 46.9 mmol) plus Bis(pinacolato)diboron (13.09 g, 51.5 mmol), Pd(dppf)Cl$_2$ (1.15 g, 1.4 mmol), KOAc (13.8 g, 140.6 mmol) and DMF, the same procedure as described in the synthesis method of Sub 1-VI-A1 was carried out to obtain 20.53 g of product (yield: 84%).

(5) Synthesis Method of Sub 1-A2

Using the obtained Sub 1-VI-A2 (8.69 g, 16.7 mmol) plus 1-bromo-4-iodobenzene (7.07 g, 25 mmol), Pd(PPh$_3$)$_4$ (0.96 g, 0.8 mmol), K$_2$CO$_3$ (6.91 g, 50 mmol), THF and water, the same procedure as described in the synthesis method of Sub 1-A1 was carried out to obtain 7.61 g of product (yield: 83%).

3. Synthesis Method of Sub 1-A21

<Reaction Scheme 5>

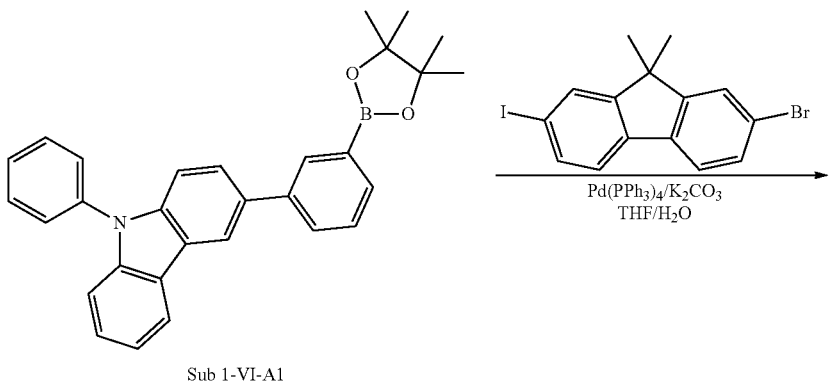

Sub 1-VI-A1

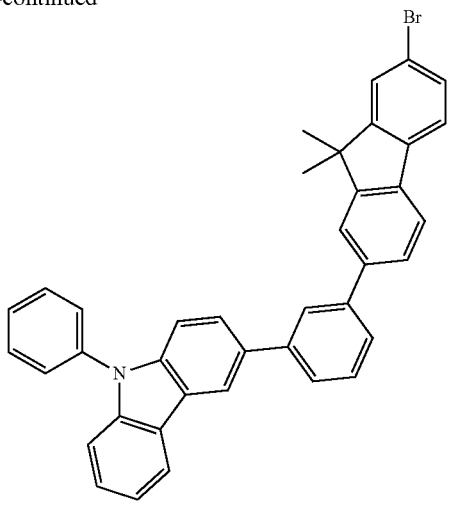
Sub 1-A21
Using the obtained Sub 1-VI-A1 (12.36 g, 27.8 mmol) plus 2-bromo-7-iodo-9,9-dimethyl-9H-fluorene (16.61 g, 41.6 mmol), Pd(PPh$_3$)$_4$ (1.6 g, 1.4 mmol), K$_2$CO$_3$ (11.51 g, 83.3 mmol), THF and water, the same procedure as described in the synthesis method of Sub 1-A1 was carried out to obtain 12.95 g of product (yield: 79%).
4. Synthesis Method of Sub 1-A26
<Reaction Scheme 6>
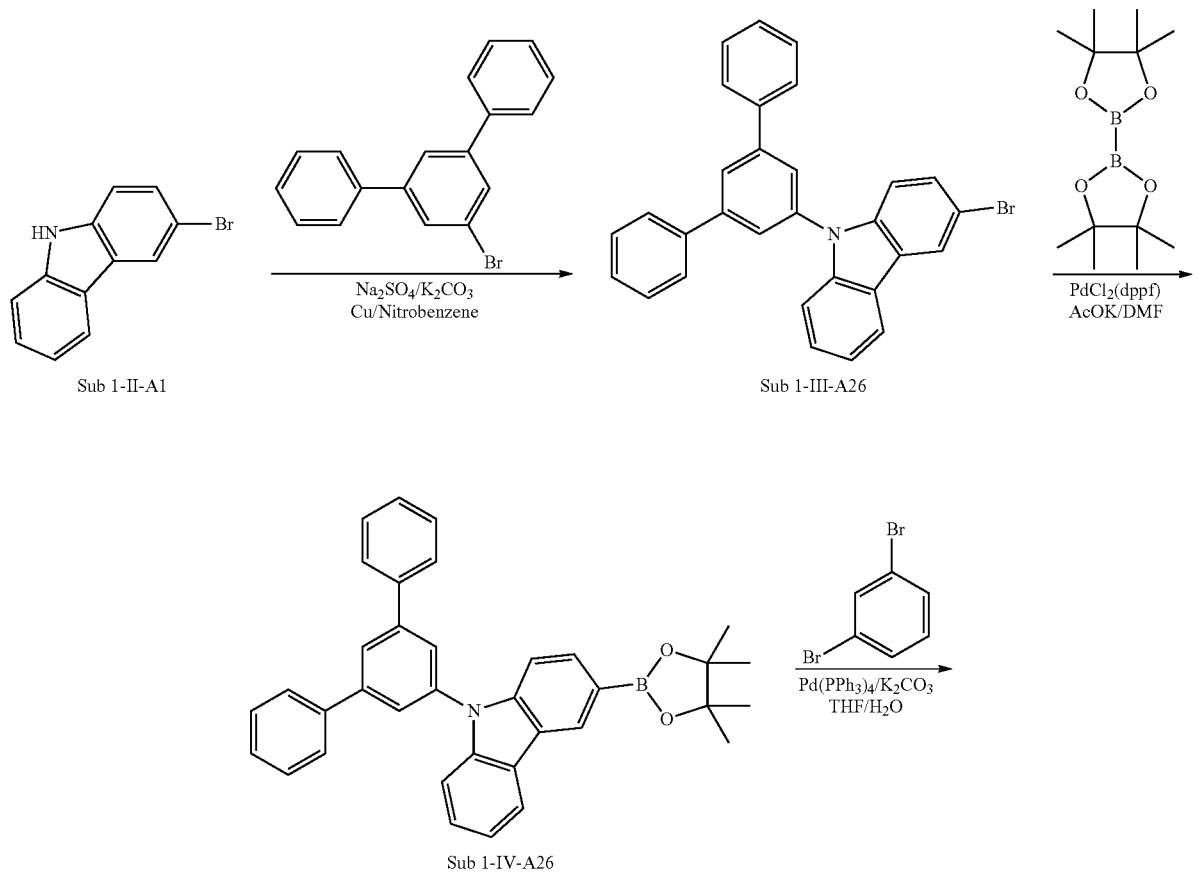

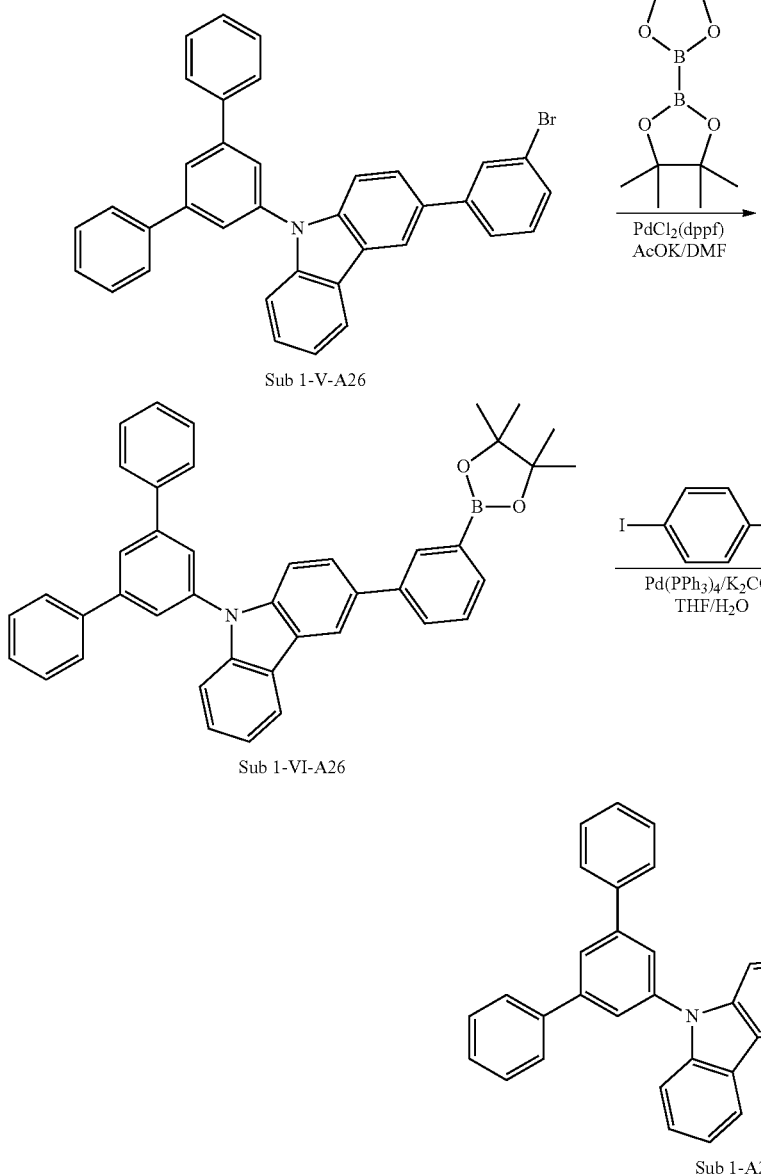

(1) Synthesis Method of Sub 1-III-A26

Using the obtained Sub 1-II-A1 (48.04 g, 195.2 mmol) plus 5'-bromo-1,1':3',1''-terphenyl (90.54 g, 292.8 mmol), Na₂SO₄ (27.73 g, 195.2 mmol), K₂CO₃ (26.98 g, 195.2 mmol), Cu (3.72 g, 58.6 mmol) and nitrobenzene, the same procedure as described in the synthesis method of Sub 1-III-A1 was carried out to obtain 62.97 g of product (yield: 68%).

(2) Synthesis Method of Sub 1-IV-A26

Using the obtained Sub 1-III-A26 (62.97 g, 132.7 mmol) plus Bis(pinacolato)diboron (37.08 g, 146 mmol), Pd(dppf)Cl₂ (3.25 g, 4 mmol), KOAc (39.08 g, 398.2 mmol) and DMF, the same procedure as described in the synthesis method of Sub 1-IV-A1 was carried out to obtain 56.07 g of product (yield: 81%).

(3) Synthesis Method of Sub 1-V-A26

Using the obtained Sub 1-IV-A26 (56.07 g, 107.5 mmol) plus 1,3-dibromobenzene (38.05 g, 161.3 mmol), Pd(PPh₃)₄ (6.21 g, 5.4 mmol), K₂CO₃ (44.58 g, 322.6 mmol), THF and water, the same procedure as described in the synthesis method of Sub 1-V-A1 was carried out to obtain 41.43 g of product (yield: 70%).

(4) Synthesis Method of Sub 1-VI-A26

Using the obtained Sub 1-V-A26 (41.43 g, 75.3 mmol) plus Bis(pinacolato)diboron (21.02 g, 82.8 mmol), Pd(dppf)Cl₂ (1.84 g, 2.3 mmol), KOAc (22.16 g, 225.8 mmol) and DMF, the same procedure as described in the synthesis method of Sub 1-VI-A1 was carried out to obtain 35.08 g of product (yield: 78%).

(5) Synthesis Method of Sub 1-A26

Using the obtained Sub 1-VI-A26 (10.69 g, 17.9 mmol) plus 1-bromo-4-iodobenzene (7.59 g, 26.8 mmol), Pd(PPh₃)₄ (1.03 g, 0.9 mmol), K₂CO₃ (7.42 g, 53.7 mmol), THF and water, the same procedure as described in the synthesis method of Sub 1-A1 was carried out to obtain 8.52 g of product (yield: 76%).

5. Synthesis Method of Sub 1-A29
<Reaction Scheme 7>
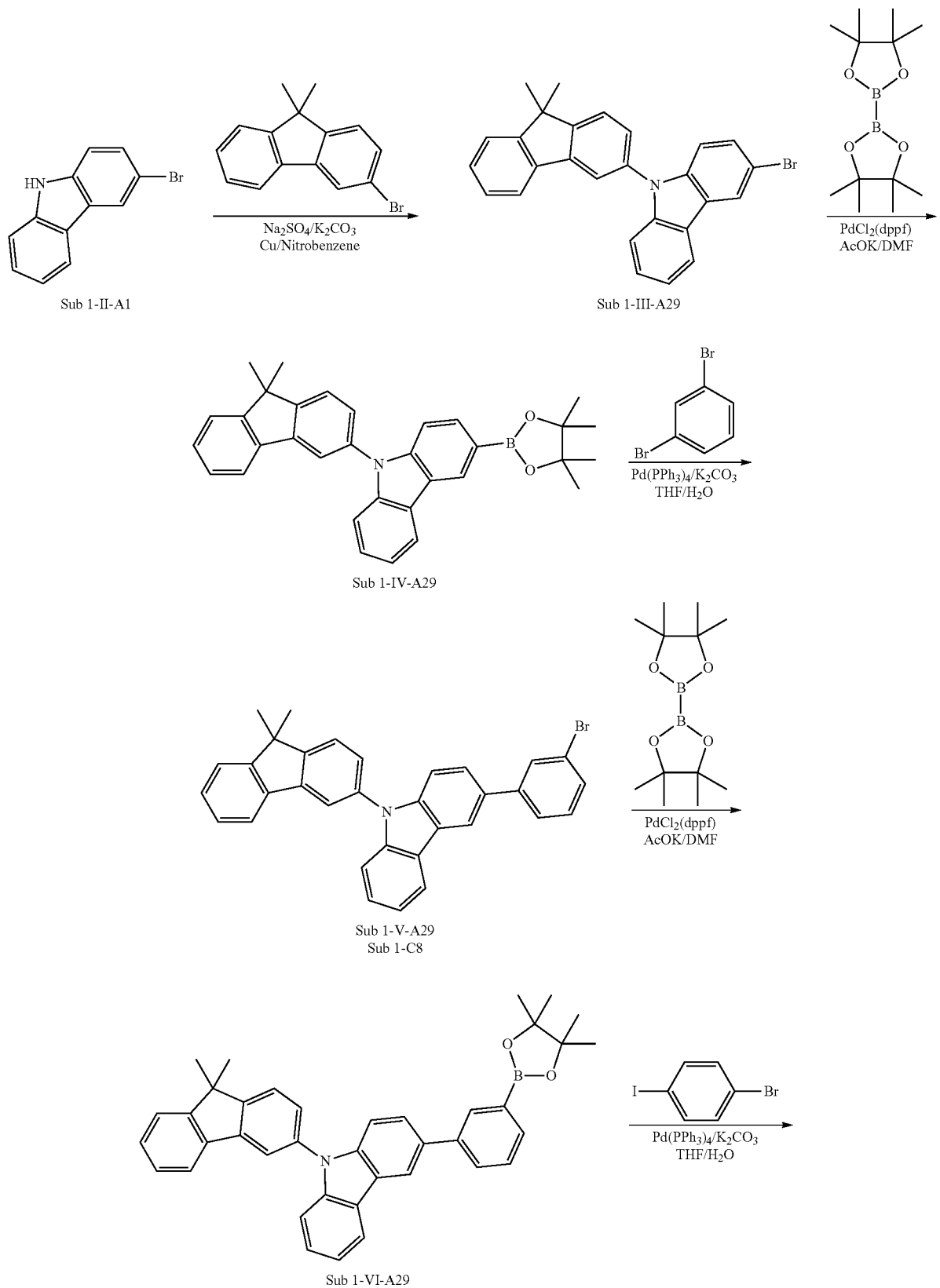

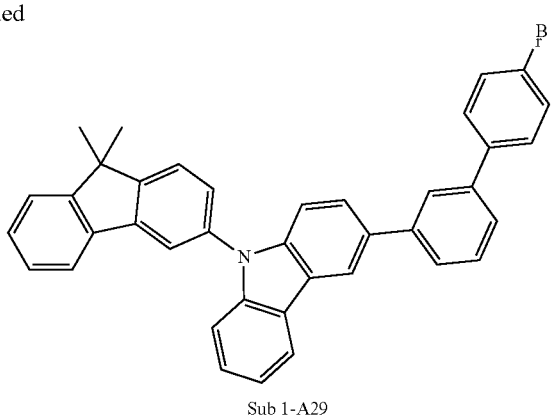

Sub 1-A29

(1) Synthesis Method of Sub 1-III-A29

Using the obtained Sub 1-II-A1 (41.09 g, 167 mmol) plus 3-bromo-9,9-dimethyl-9H-fluorene (68.41 g, 250.4 mmol), $Na_2SO_4$ (23.72 g, 167 mmol), $K_2CO_3$ (23.08 g, 167 mmol), Cu (3.18 g, 50.1 mmol), and nitrobenzene, the same procedure as described in the synthesis method of Sub 1-III-A1 was carried out to obtain 51.23 g of product (yield: 70%).

(2) Synthesis Method of Sub 1-IV-A29

Using the obtained Sub 1-III-A29 (51.23 g, 116.9 mmol) plus Bis(pinacolato)diboron (32.65 g, 128.6 mmol), Pd(dppf)$Cl_2$ (2.86 g, 3.5 mmol), KOAc (34.41 g, 350.6 mmol) and DMF, the same procedure as described in the synthesis method of Sub 1-IV-A1 was carried out to obtain 48.22 g of product (yield: 85%).

(3) Synthesis Method of Sub 1-V-A29(Sub 1-C8)

Using the obtained Sub 1-IV-A29 (48.22 g, 99.3 mmol) plus 1,3-dibromobenzene (35.15 g, 149 mmol), Pd(PPh$_3$)$_4$ (5.74 g, 5 mmol), $K_2CO_3$ (41.19 g, 298 mmol), THF and water, the same procedure as described in the synthesis method of Sub 1-V-A1 was carried out to obtain 38.84 g of product (yield: 76%).

(4) Synthesis Method of Sub 1-VI-A29

Using the obtained Sub 1-V-A29 (38.84 g, 75.5 mmol) plus Bis(pinacolato)diboron (21.09 g, 83 mmol), Pd(dppf)$Cl_2$ (1.85 g, 2.3 mmol), KOAc (22.23 g, 226.5 mmol) and DMF, the same procedure as described in the synthesis method of Sub 1-VI-A1 was carried out to obtain 33.91 g of product (yield: 80%).

(5) Synthesis Method of Sub 1-A29

Using the obtained Sub 1-VI-A29 (9.61 g, 17.1 mmol) plus 1-bromo-4-iodobenzene (7.26 g, 25.7 mmol), Pd(PPh$_3$)$_4$ (0.99 g, 0.9 mmol), $K_2CO_3$ (7.1 g, 51.3 mmol), THF and water, the same procedure as described in the synthesis method of Sub 1-A1 was carried out to obtain 8.09 g of product (yield: 80%).

6. Synthesis Method of Sub 1-A35

<Reaction Scheme 8>

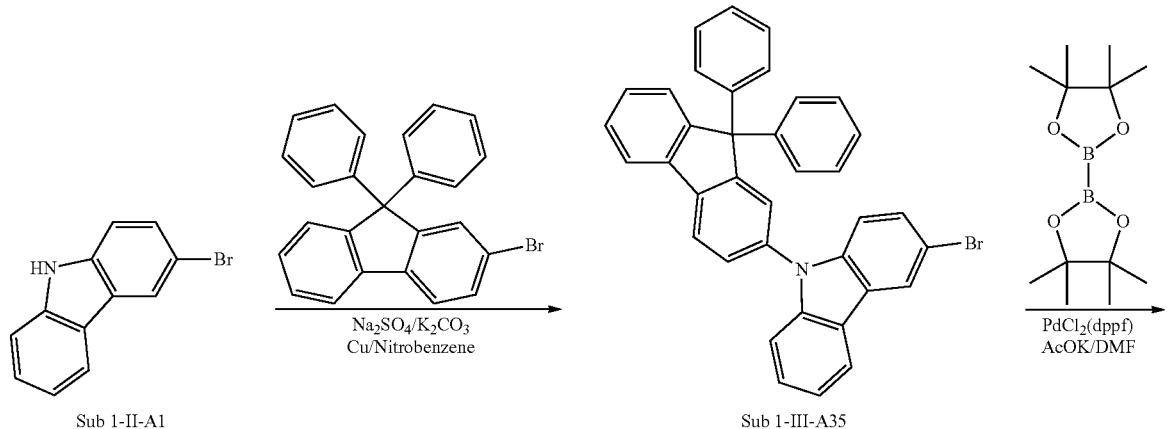

-continued
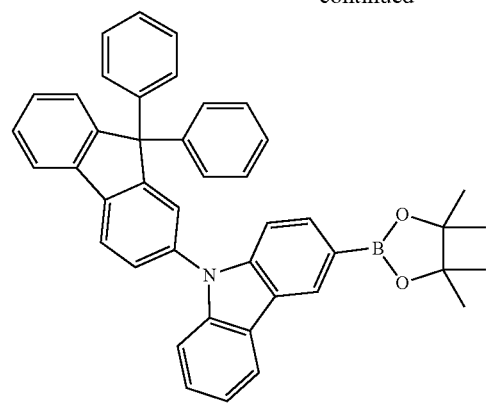 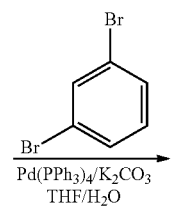
Sub 1-IV-A35
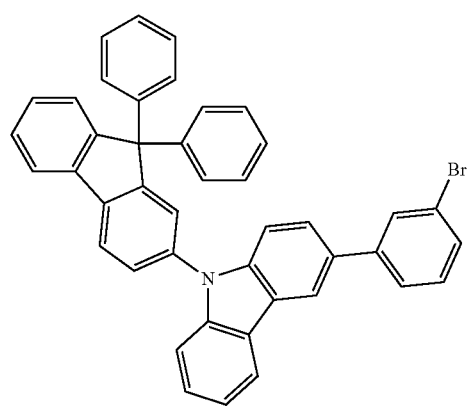 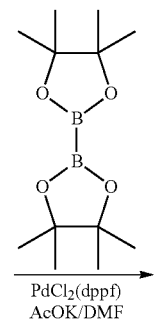
Sub 1-V-A35
Sub 1-C12
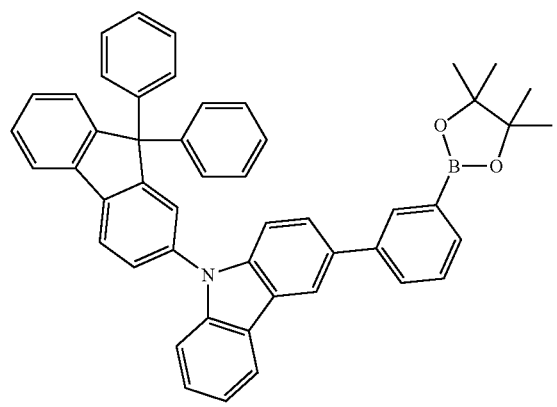 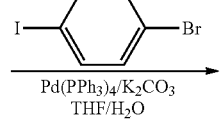
Sub 1-VI-A35

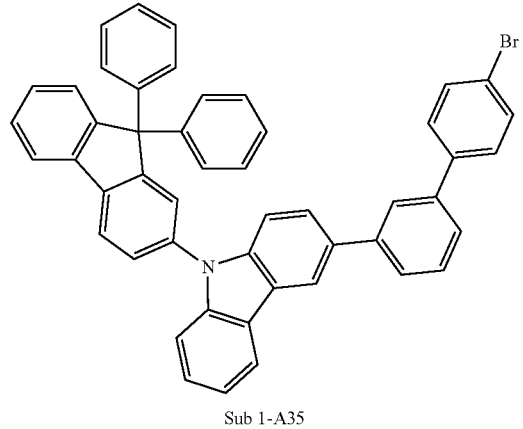

Sub 1-A35

(1) Synthesis Method of Sub 1-III-A35

Using the obtained Sub 1-II-A1 (63.72 g, 258.9 mmol) plus 2-bromo-9,9-diphenyl-9H-fluorene (154.31 g, 388.4 mmol), $Na_2SO_4$ (36.78 g, 258.9 mmol), $K_2CO_3$ (35.79 g, 258.9 mmol), Cu (4.94 g, 77.7 mmol) and nitrobenzene, the same procedure as described in the synthesis method of Sub 1-III-A1 was carried out to obtain 88.84 g of product (yield: 61%).

(2) Synthesis Method of Sub 1-IV-A35

Using the obtained Sub 1-III-A35 (88.84 g, 157.9 mmol) plus Bis(pinacolato)diboron (44.12 g, 173.7 mmol), Pd(dppf)$Cl_2$ (3.87 g, 4.7 mmol), KOAc (46.5 g, 473.8 mmol) and DMF, the same procedure as described in the synthesis method of Sub 1-IV-A1 was carried out to obtain 74.13 g of product (yield: 77%).

(3) Synthesis Method of Sub 1-V-A35(Sub 1-C12)

Using the obtained Sub 1-IV-A35 (74.13 g, 121.6 mmol) plus 1,3-dibromobenzene (43.03 g, 182.4 mmol), Pd(PPh$_3$)$_4$ (7.03 g, 6.1 mmol), $K_2CO_3$ (50.42 g, 364.8 mmol), THF and water, the same procedure as described in the synthesis method of Sub 1-V-A1 was carried out to obtain 54.36 g of product (yield: 70%).

(4) Synthesis Method of Sub 1-VI-A35

Using the obtained Sub 1-V-A35 (54.36 g, 85.1 mmol) plus Bis(pinacolato)diboron (23.78 g, 93.6 mmol), Pd(dppf)$Cl_2$ (2.09 g, 2.6 mmol), KOAc (25.06 g, 255.4 mmol) and DMF, the same procedure as described in the synthesis method of Sub 1-VI-A1 was carried out to obtain 43.19 g of product (yield: 74%).

(5) Synthesis Method of Sub 1-A35

Using the obtained Sub 1-VI-A35 (12.29 g, 17.9 mmol) plus 1-bromo-4-iodobenzene (7.61 g, 26.9 mmol), Pd(PPh$_3$)$_4$ (1.04 g, 0.9 mmol), $K_2CO_3$ (7.43 g, 53.8 mmol), THF and water, the same procedure as described in the synthesis method of Sub 1-A1 was carried out to obtain 9.61 g of product (yield: 75%).

7. Synthesis Method of Sub 1-A36

<Reaction Scheme 9>

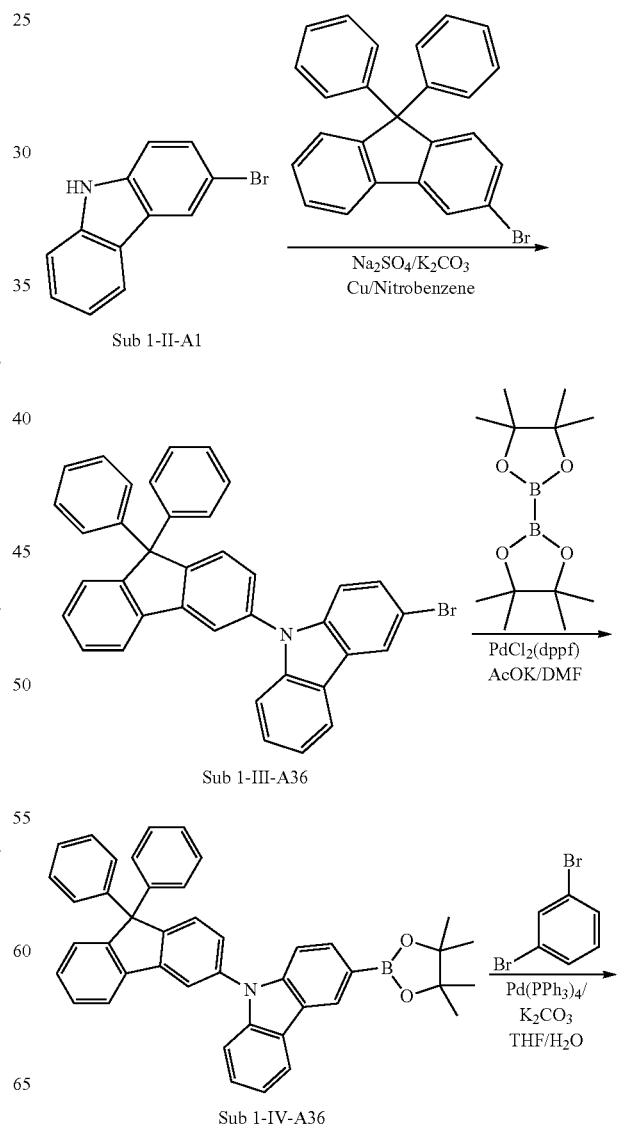

-continued

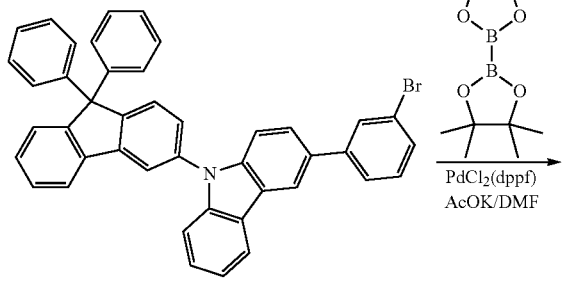

Sub 1-V-A36
Sub 1-C13

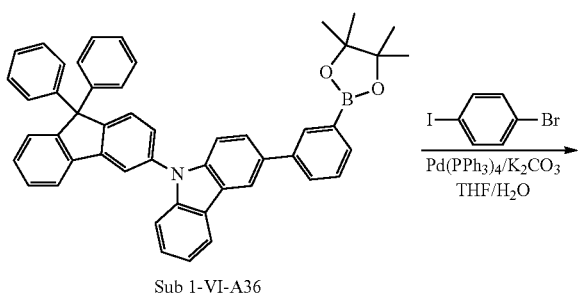

Sub 1-VI-A36

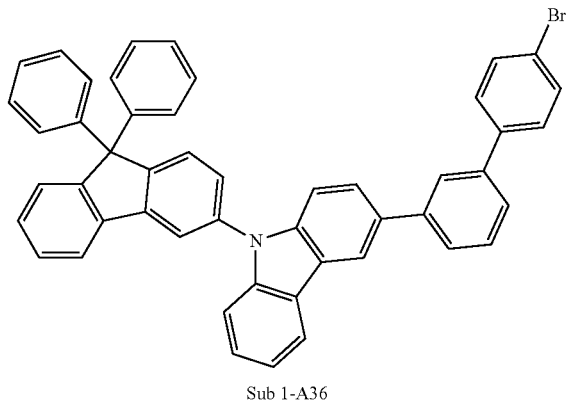

Sub 1-A36

(1) Synthesis Method of Sub 1-III-A36

Using the obtained Sub 1-II-A1 (59.25 g, 240.8 mmol) plus 3-bromo-9,9-diphenyl-9H-fluorene (143.48 g, 361.1 mmol), $Na_2SO_4$ (34.2 g, 240.8 mmol), $K_2CO_3$ (33.27 g, 240.8 mmol), Cu (4.59 g, 72.2 mmol) and nitrobenzene, the same procedure as described in the synthesis method of Sub 1-III-A1 was carried out to obtain 85.32 g of product (yield: 63%).

(2) Synthesis Method of Sub 1-IV-A36

Using the obtained Sub 1-III-A36 (85.32 g, 151.7 mmol) plus Bis(pinacolato)diboron (42.37 g, 166.8 mmol), Pd(dppf)$Cl_2$ (3.72 g, 4.6 mmol), KOAc (44.66 g, 455 mmol) and DMF, the same procedure as described in the synthesis method of Sub 1-IV-A1 was carried out to obtain 73.04 g of product (yield: 79%).

(3) Synthesis Method of Sub 1-V-A36(Sub 1-C13)

Using the obtained Sub 1-IV-A36 (73.04 g, 119.8 mmol) plus 1,3-dibromobenzene (42.4 g, 179.7 mmol), Pd(PPh$_3$)$_4$ (6.92 g, 6 mmol), $K_2CO_3$ (49.68 g, 359.5 mmol), THF and water, the same procedure as described in the synthesis method of Sub 1-V-A1 was carried out to obtain 55.86 g of product (yield: 73%).

(4) Synthesis Method of Sub 1-VI-A36

Using the obtained Sub 1-V-A36 (55.86 g, 87.5 mmol) plus Bis(pinacolato)diboron (24.43 g, 96.2 mmol), Pd(dppf)$Cl_2$ (2.14 g, 2.6 mmol), KOAc (25.75 g, 262.4 mmol) and DMF, the same procedure as described in the synthesis method of Sub 1-VI-A1 was carried out to obtain 42.58 g of product (yield: 71%).

(5) Synthesis Method of Sub 1-A36

Using the obtained Sub 1-VI-A36 (11.85 g, 17.3 mmol) plus 1-bromo-4-iodobenzene (7.33 g, 25.9 mmol), Pd(PPh$_3$)$_4$ (1 g, 0.9 mmol), $K_2CO_3$ (7.17 g, 51.8 mmol), THF and water, the same procedure as described in the synthesis method of Sub 1-A1 was carried out to obtain 9.39 g of product (yield: 76%).

8. Synthesis Method of Sub 1-A43

<Reaction Scheme 10>

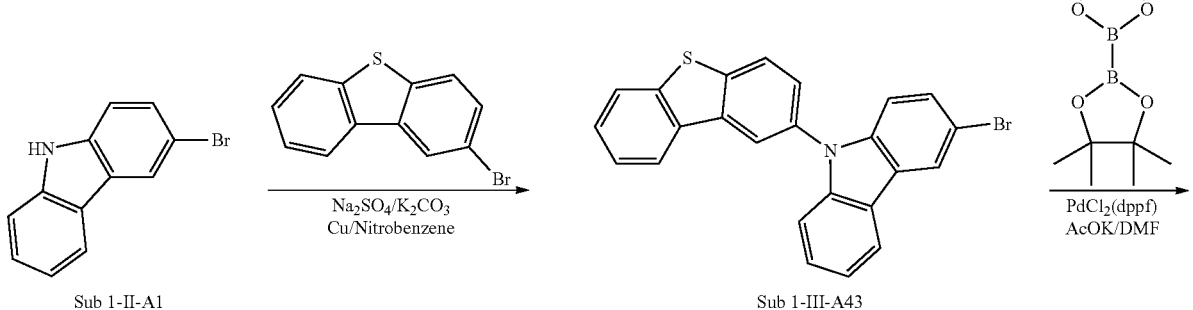

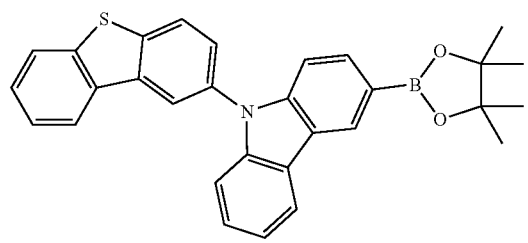

Sub 1-IV-A43

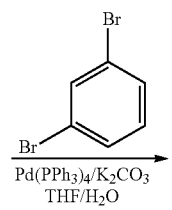

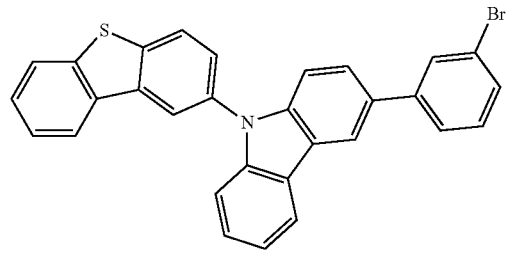

Sub 1-V-A43

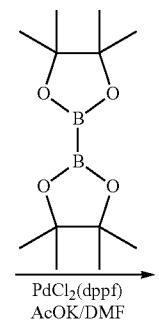

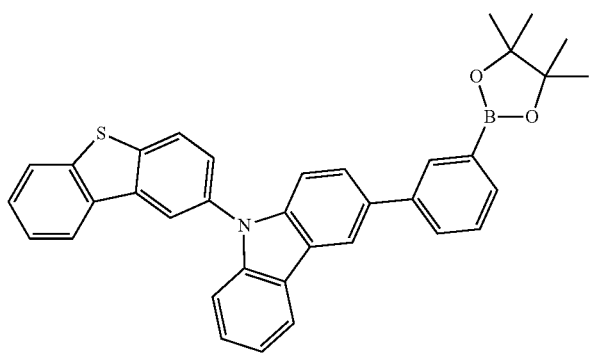

Sub 1-VI-A43

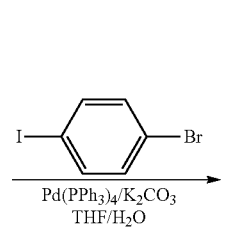

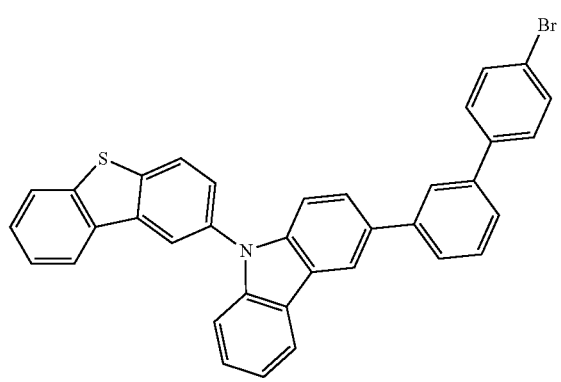

Sub 1-A43

(1) Synthesis Method of Sub 1-III-A43

Using the obtained Sub 1-II-A1 (52.13 g, 211.8 mmol) plus 2-bromodibenzo[b,d]thiophene (83.61 g, 317.7 mmol), Na$_2$SO$_4$ (30.09 g, 211.8 mmol), K$_2$CO$_3$ (29.28 g, 211.8 mmol), Cu (4.04 g, 63.5 mmol) and nitrobenzene, the same procedure as described in the synthesis method of Sub 1-III-A1 was carried out to obtain 62.61 g of product (yield: 69%).

(2) Synthesis Method of Sub 1-IV-A43

Using the obtained Sub 1-III-A43 (62.61 g, 146.2 mmol) plus Bis(pinacolato)diboron (40.83 g, 160.8 mmol), Pd(dppf)Cl$_2$ (3.58 g, 4.4 mmol), KOAc (43.04 g, 438.5 mmol) and DMF, the same procedure as described in the synthesis method of Sub 1-IV-A1 was carried out to obtain 58.37 g of product (yield: 84%).

(3) Synthesis Method of Sub 1-V-A43

Using the obtained Sub 1-IV-A43 (58.37 g, 122.8 mmol) plus 1,3-dibromobenzene (43.45 g, 184.2 mmol), Pd(PPh$_3$)$_4$ (7.09 g, 6.1 mmol), K$_2$CO$_3$ (50.91 g, 368.3 mmol), THF and water, the same procedure as described in the synthesis method of Sub 1-V-A1 was carried out to obtain 46.45 g of product (yield: 75%).

(4) Synthesis Method of Sub 1-VI-A43

Using the obtained Sub 1-V-A43 (46.45 g, 92.1 mmol) plus Bis(pinacolato)diboron (25.72 g, 101.3 mmol), Pd(dppf)Cl$_2$ (2.26 g, 2.8 mmol), KOAc (27.11 g, 276.2 mmol) and DMF, the same procedure as described in the synthesis method of Sub 1-VI-A1 was carried out to obtain 40.63 g of product (yield: 80%).

(5) Synthesis Method of Sub 1-A43

Using the obtained Sub 1-VI-A43 (9.78 g, 17.7 mmol) plus 1-bromo-4-iodobenzene (7.53 g, 26.6 mmol), Pd(PPh$_3$)$_4$ (1.02 g, 0.9 mmol), K$_2$CO$_3$ (7.35 g, 53.2 mmol), THF and water, the same procedure as described in the synthesis method of Sub 1-A1 was carried out to obtain 8.13 g of product (yield: 79%).

9. Synthesis Method of Sub 1-A46

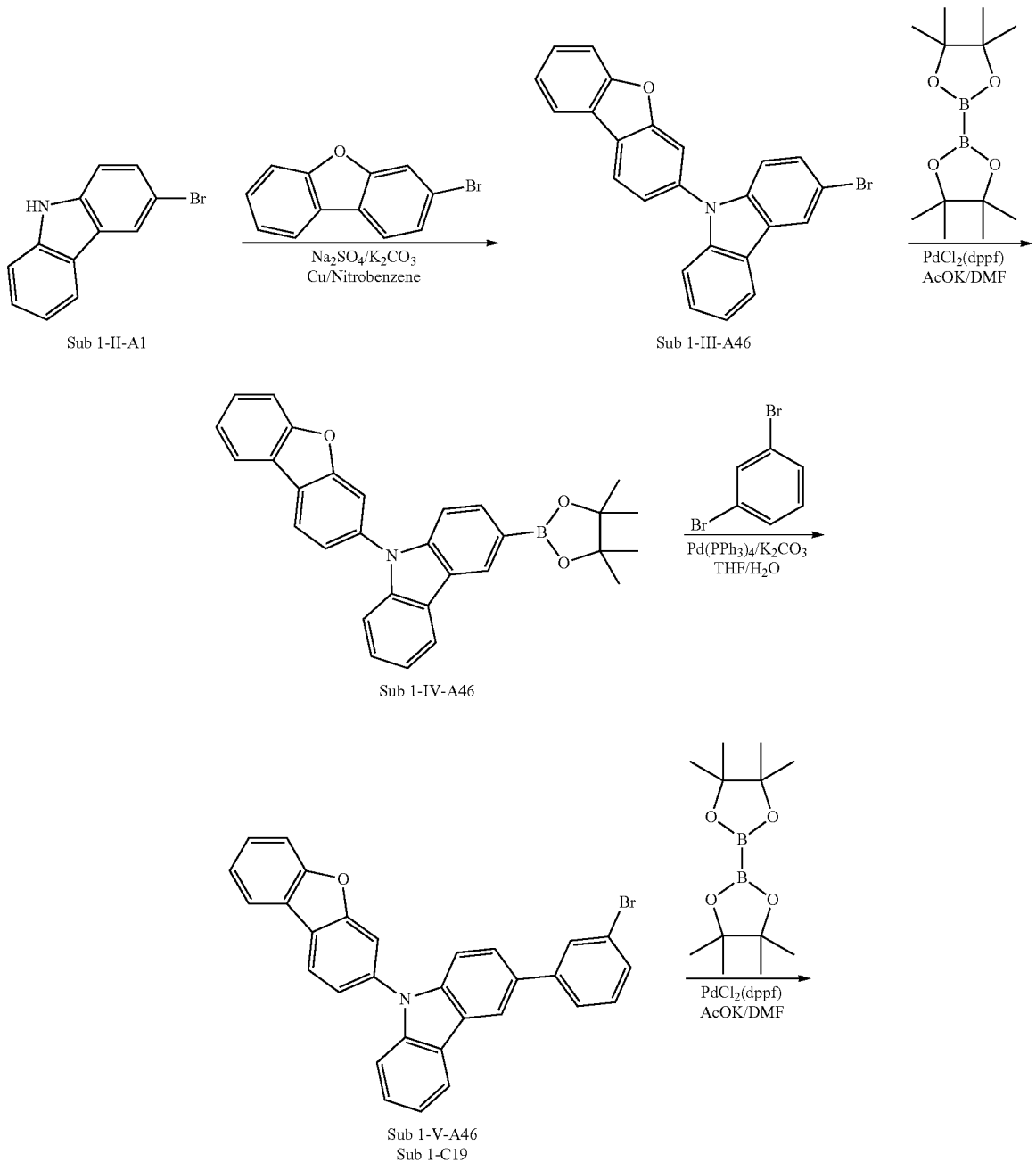

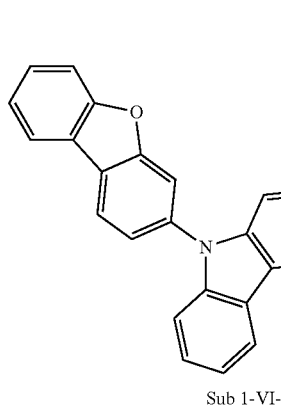

Sub 1-VI-A46

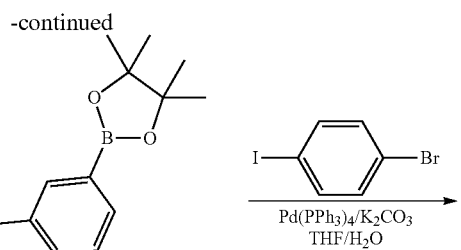

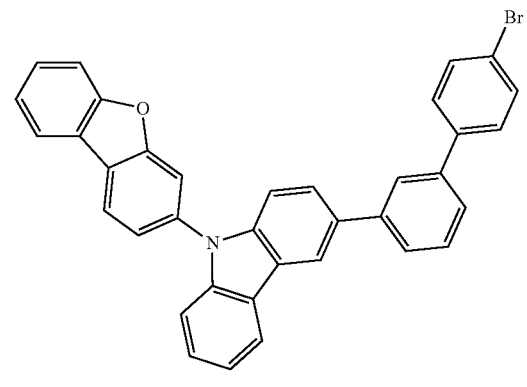

Sub 1-A46

(1) Synthesis Method of Sub 1-III-A46

Using the obtained Sub 1-II-A1 (57.92 g, 235.4 mmol) plus 3-bromodibenzo[b,d]furan (87.23 g, 353 mmol), Na$_2$SO$_4$ (33.43 g, 235.4 mmol), K$_2$CO$_3$ (32.53 g, 235.4 mmol), Cu (4.49 g, 70.6 mmol), and nitrobenzene, the same procedure as described in the synthesis method of Sub 1-III-A1 was carried out to obtain 63.07 g of product (yield: 65%).

(2) Synthesis Method of Sub 1-IV-A46

Using the obtained Sub 1-III-A46 (63.07 g, 153 mmol) plus Bis(pinacolato)diboron (42.73 g, 168.3 mmol), Pd(dppf)Cl$_2$ (3.75 g, 4.6 mmol), KOAc (45.04 g, 458.9 mmol) and DMF, the same procedure as described in the synthesis method of Sub 1-IV-A1 was carried out to obtain 55.51 g of product (yield: 79%).

(3) Synthesis Method of Sub 1-V-A46(Sub 1-C19)

Using the obtained Sub 1-IV-A46 (55.51 g, 120.8 mmol) plus 1,3-dibromobenzene (42.76 g, 181.3 mmol), Pd(PPh$_3$)$_4$ (6.98 g, 6 mmol), K$_2$CO$_3$ (50.11 g, 362.5 mmol), THF and water, the same procedure as described in the synthesis method of Sub 1-V-A1 was carried out to obtain 44.26 g of product (yield: 75%).

(4) Synthesis Method of Sub 1-VI-A46

Using the obtained Sub 1-V-A46 (44.26 g, 90.6 mmol) plus Bis(pinacolato)diboron (25.32 g, 99.7 mmol), Pd(dppf)Cl$_2$ (2.22 g, 2.7 mmol), KOAc (26.68 g, 271.9 mmol) and DMF, the same procedure as described in the synthesis method of Sub 1-VI-A1 was carried out to obtain 37.36 g of product (yield: 77%).

(5) Synthesis Method of Sub 1-A46

Using the obtained Sub 1-VI-A46 (10.65 g, 19.9 mmol) plus 1-bromo-4-iodobenzene (8.44 g, 29.8 mmol), Pd(PPh$_3$)$_4$ (1.15 g, 1 mmol), K$_2$CO$_3$ (8.25 g, 59.7 mmol), THF and water, the same procedure as described in the synthesis method of Sub 1-A1 was carried out to obtain 8.98 g of product (yield: 80%).

10. Synthesis Method of Sub 1-A51

<Reaction Scheme 12>

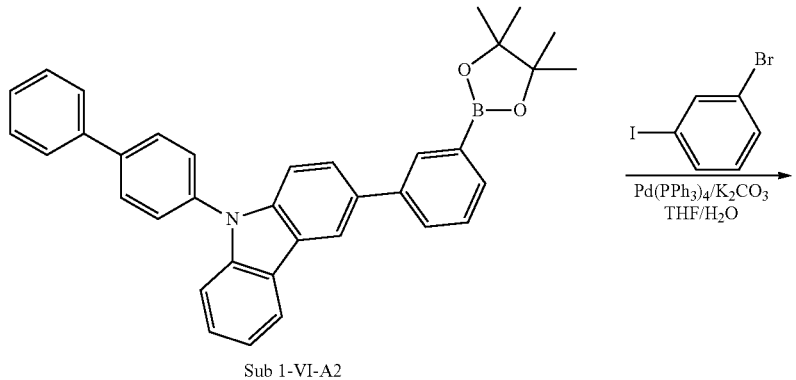

Sub 1-VI-A2

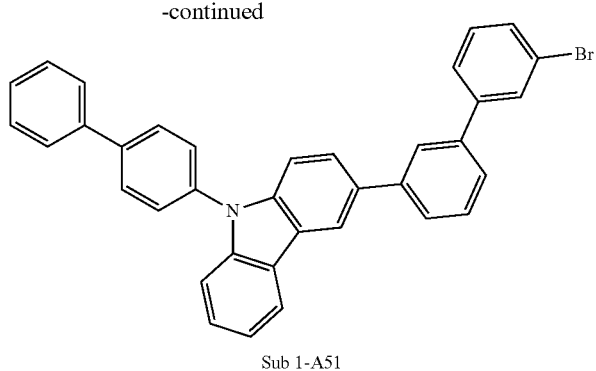

Sub 1-A51

Using the obtained Sub 1-VI-A2 (10.16 g, 19.5 mmol) plus 1-bromo-3-iodobenzene (8.27 g, 29.2 mmol), Pd(PPh$_3$)$_4$ (1.13 g, 1 mmol), K$_2$CO$_3$ (8.08 g, 58.5 mmol), THF, and water, the same procedure as described in the synthesis method of Sub 1-A1 was carried out to obtain 7.94 g of product (yield: 74%).

11. Synthesis Method of Sub 1-A59

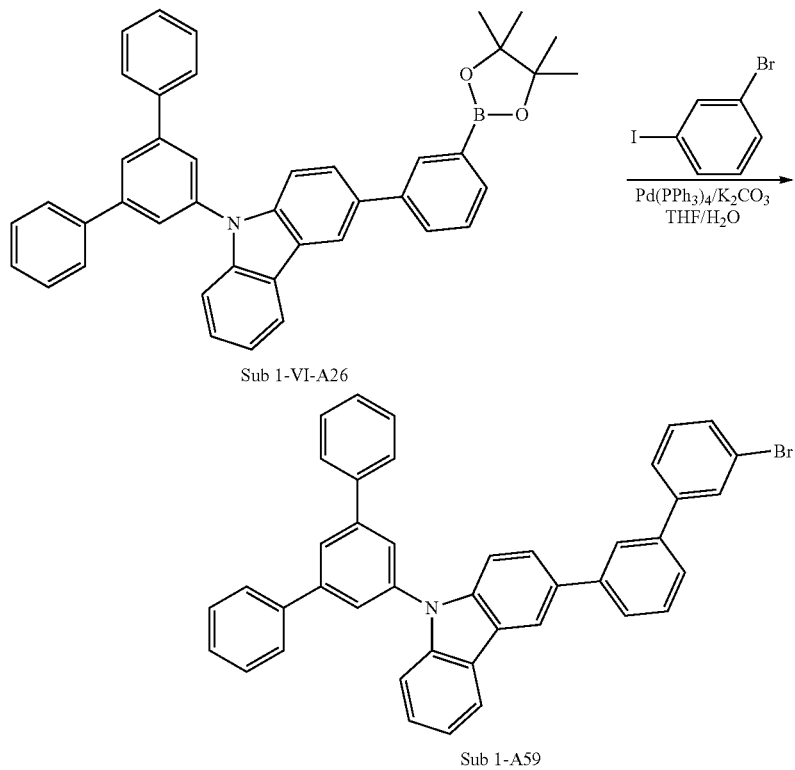

Using the obtained Sub 1-VI-A26 (10.81 g, 18.1 mmol) plus 1-bromo-3-iodobenzene (7.68 g, 27.1 mmol), Pd(PPh$_3$)$_4$ (1.05 g, 0.9 mmol), K$_2$CO$_3$ (7.5 g, 54.3 mmol), THF, and water, the same procedure as described in the synthesis method of Sub 1-A1 was carried out to obtain 8.05 g of product (yield: 71%).

12. Synthesis Method of Sub 1-A64
Reaction Scheme 14
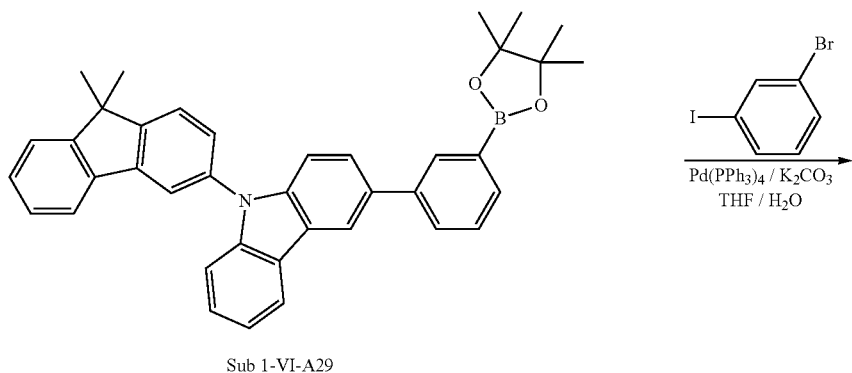
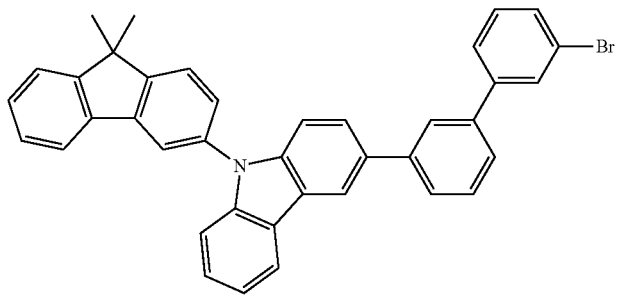
Using the obtained Sub 1-VI-A29 (10.29 g, 18.3 mmol) plus 1-bromo-3-iodobenzene (7.78 g, 27.5 mmol), Pd(PPh$_3$)$_4$ (1.06 g, 0.9 mmol), K$_2$CO$_3$ (7.6 g, 55 mmol), THF, and water, the same procedure as described in the synthesis method of Sub 1-A1 was carried out to obtain 8.33 g of product (yield: 77%).
13. Synthesis Method of Sub 1-A67
<Reaction Scheme 15>
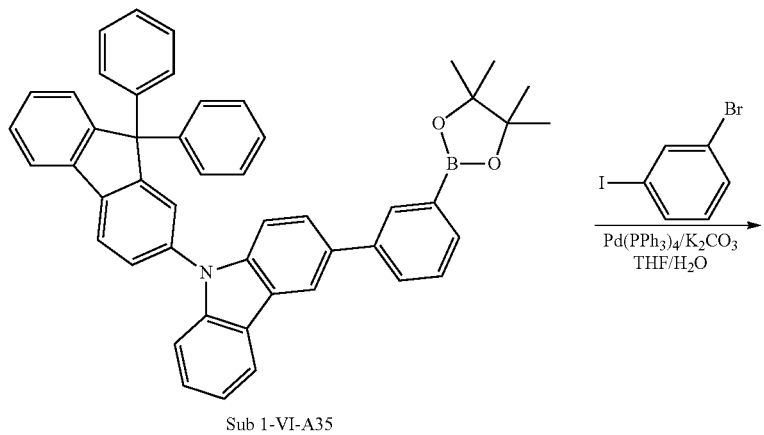

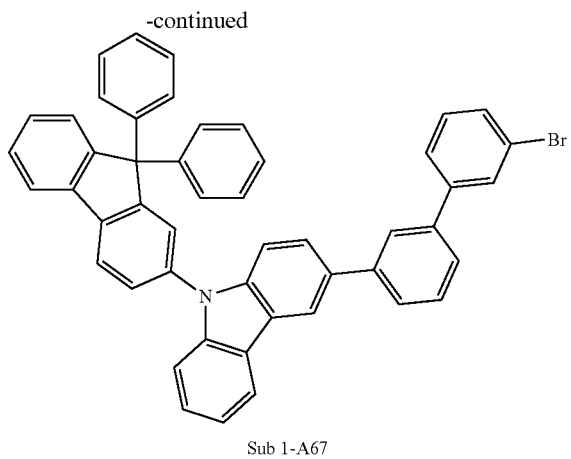

Sub 1-A67

Using the obtained Sub 1-VI-A35 (13.62 g, 19.9 mmol) plus 1-bromo-3-iodobenzene (8.43 g, 29.8 mmol), Pd(PPh$_3$)$_4$ (1.15 g, 1 mmol), K$_2$CO$_3$ (8.24 g, 59.6 mmol), THF, and water, the same procedure as described in the synthesis method of Sub 1-A1 was carried out to obtain 9.94 g of product (yield: 70%).

14. Synthesis Method of Sub 1-A68

Reaction Scheme 16

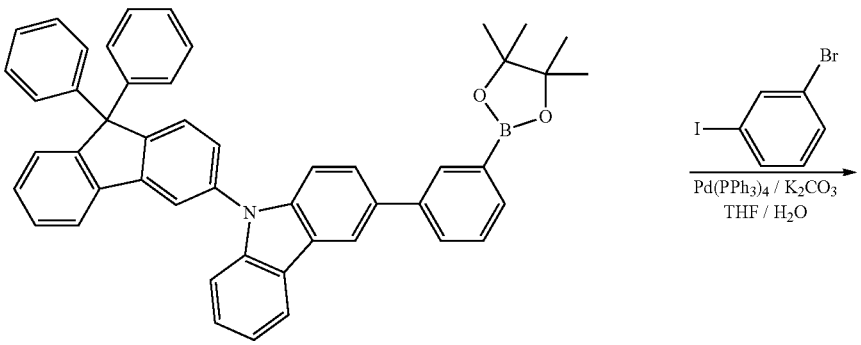

Sub 1-VI-A36

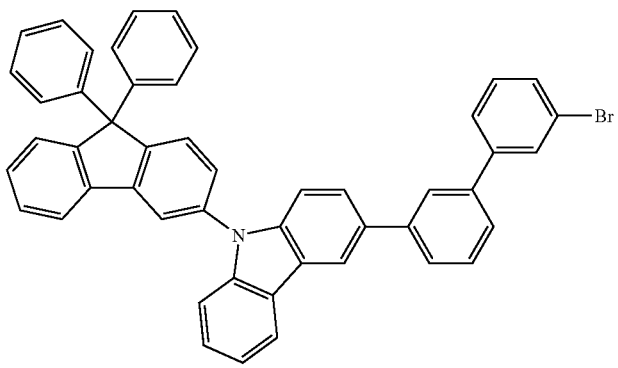

Sub 1-A68

Using the obtained Sub 1-VI-A36 (12.87 g, 18.8 mmol) plus 1-bromo-3-iodobenzene (7.97 g, 28.2 mmol), Pd(PPh$_3$)$_4$ (1.08 g, 0.9 mmol), K$_2$CO$_3$ (7.78 g, 56.3 mmol), THF, and water, the same procedure as described in the synthesis method of Sub 1-A1 was carried out to obtain 9.66 g of product (yield: 72%).

15. Synthesis Method of Sub 1-A75
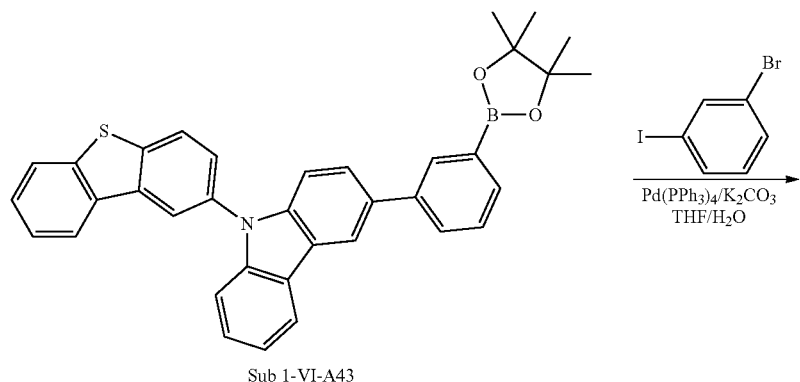
Sub 1-VI-A43
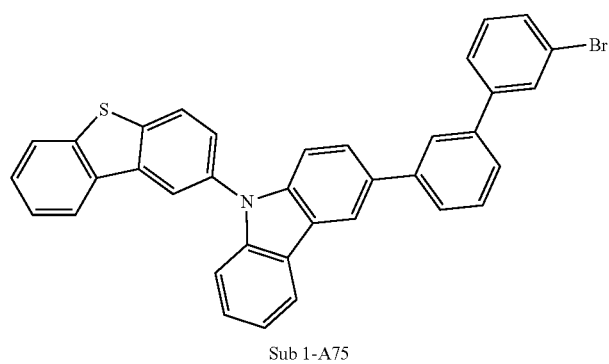
Sub 1-A75
Using the obtained Sub 1-VI-A43 (12.29 g, 22.3 mmol) plus 1-bromo-3-iodobenzene (9.46 g, 33.4 mmol), Pd(PPh$_3$)$_4$ (1.29 g, 1.1 mmol), K$_2$CO$_3$ (9.24 g, 66.9 mmol), THF, and water, the same procedure as described in the synthesis method of Sub 1-A1 was carried out to obtain 10.09 g of product (yield: 78%).
16. Synthesis Method of Sub 1-A79
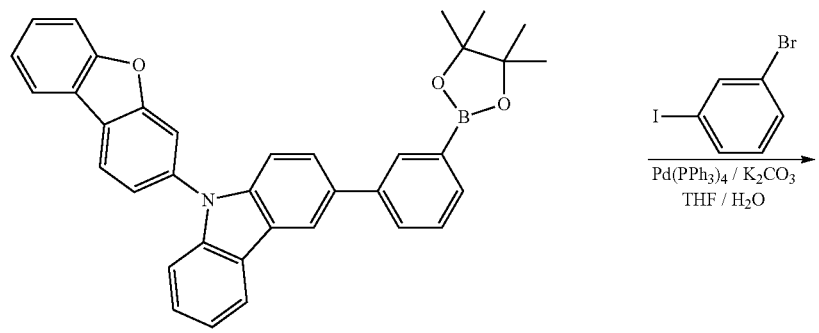
Sub 1-VI-A46

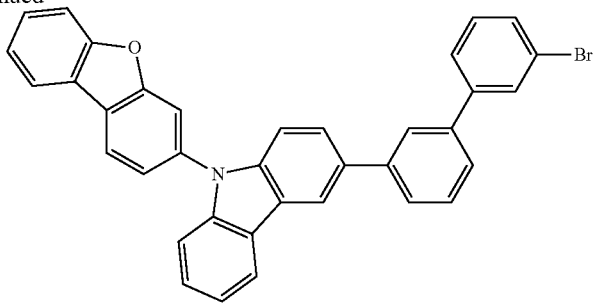

Sub 1-A79

Using the obtained Sub 1-VI-A46 (11.93 g, 22.3 mmol) plus 1-bromo-3-iodobenzene (9.45 g, 33.4 mmol), Pd(PPh$_3$)$_4$ (1.29 g, 1.1 mmol), K$_2$CO$_3$ (9.24 g, 66.8 mmol), THF, and water, the same procedure as described in the synthesis method of Sub 1-A1 was carried out to obtain 9.43 g of product (yield: 75%).

17. Synthesis Method of Sub 1-A83

<Reaction Scheme 19>

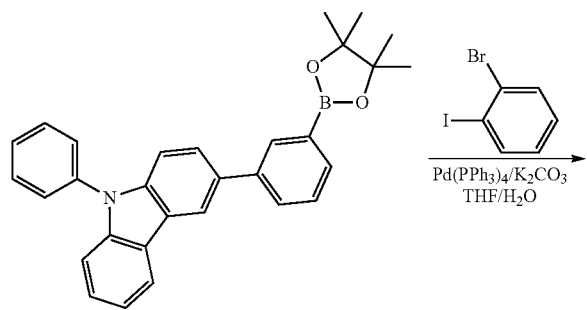

Sub 1-VI-A1

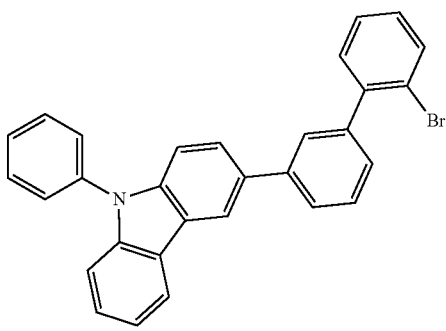

Sub 1-A83

Using the obtained Sub 1-VI-A1 (9.38 g, 21.1 mmol) plus 1-bromo-2-iodobenzene (8.94 g, 31.6 mmol), Pd(PPh$_3$)$_4$ (1.22 g, 1.1 mmol), K$_2$CO$_3$ (8.73 g, 63.2 mmol), THF, and water, the same procedure as described in the synthesis method of Sub 1-A1 was carried out to obtain 6.99 g of product (yield: 70%).

18. Synthesis Method of Sub 1-A89

Reaction Scheme 20

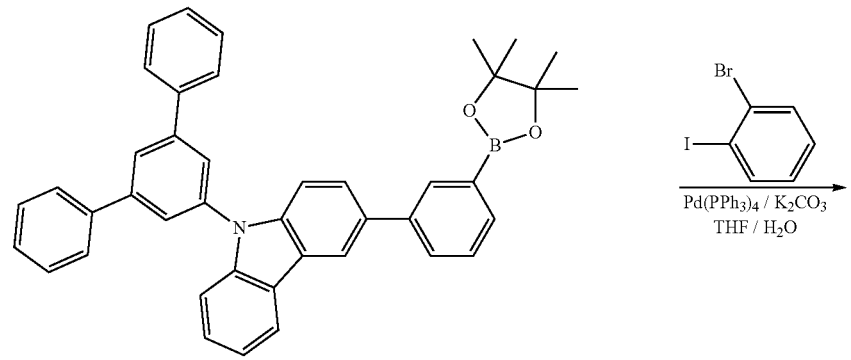

Sub 1-VI-A26

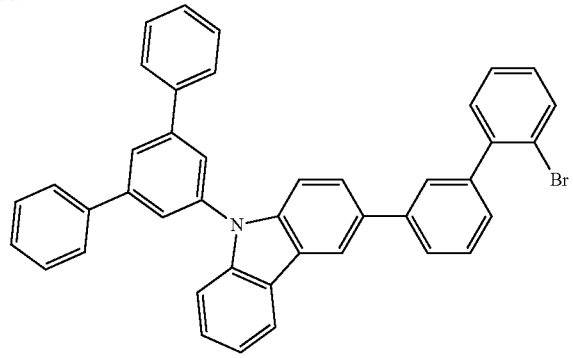

Sub 1-A89

Using the obtained Sub 1-VI-A26 (11.57 g, 19.4 mmol) plus 1-bromo-2-iodobenzene (8.22 g, 29 mmol), Pd(PPh$_3$)$_4$ (1.12 g, 1 mmol), K$_2$CO$_3$ (8.03 g, 58.1 mmol), THF, and water, the same procedure as described in the synthesis method of Sub 1-A1 was carried out to obtain 7.76 g of product (yield: 64%).

19. Synthesis Method of Sub 1-A92

<Reaction Scheme 21>

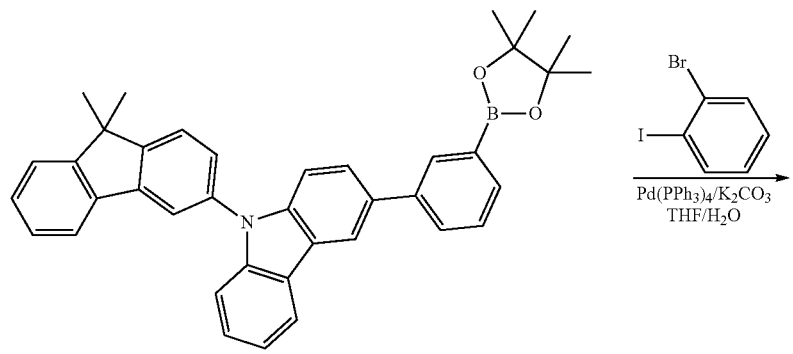

Sub 1-VI-A29

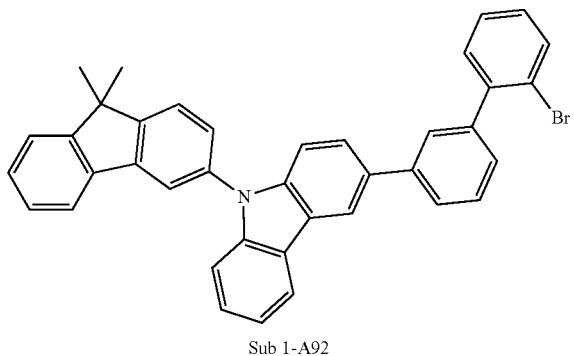

Sub 1-A92

Using the obtained Sub 1-VI-A29 (12.08 g, 21.5 mmol) plus 1-bromo-2-iodobenzene (9.13 g, 32.3 mmol), Pd(PPh$_3$)$_4$ (1.24 g, 1.1 mmol), K$_2$CO$_3$ (8.92 g, 64.5 mmol), THF, and water, the same procedure as described in the synthesis method of Sub 1-A1 was carried out to obtain 8.64 g of product (yield: 68%).

20. Synthesis Method of Sub 1-A95
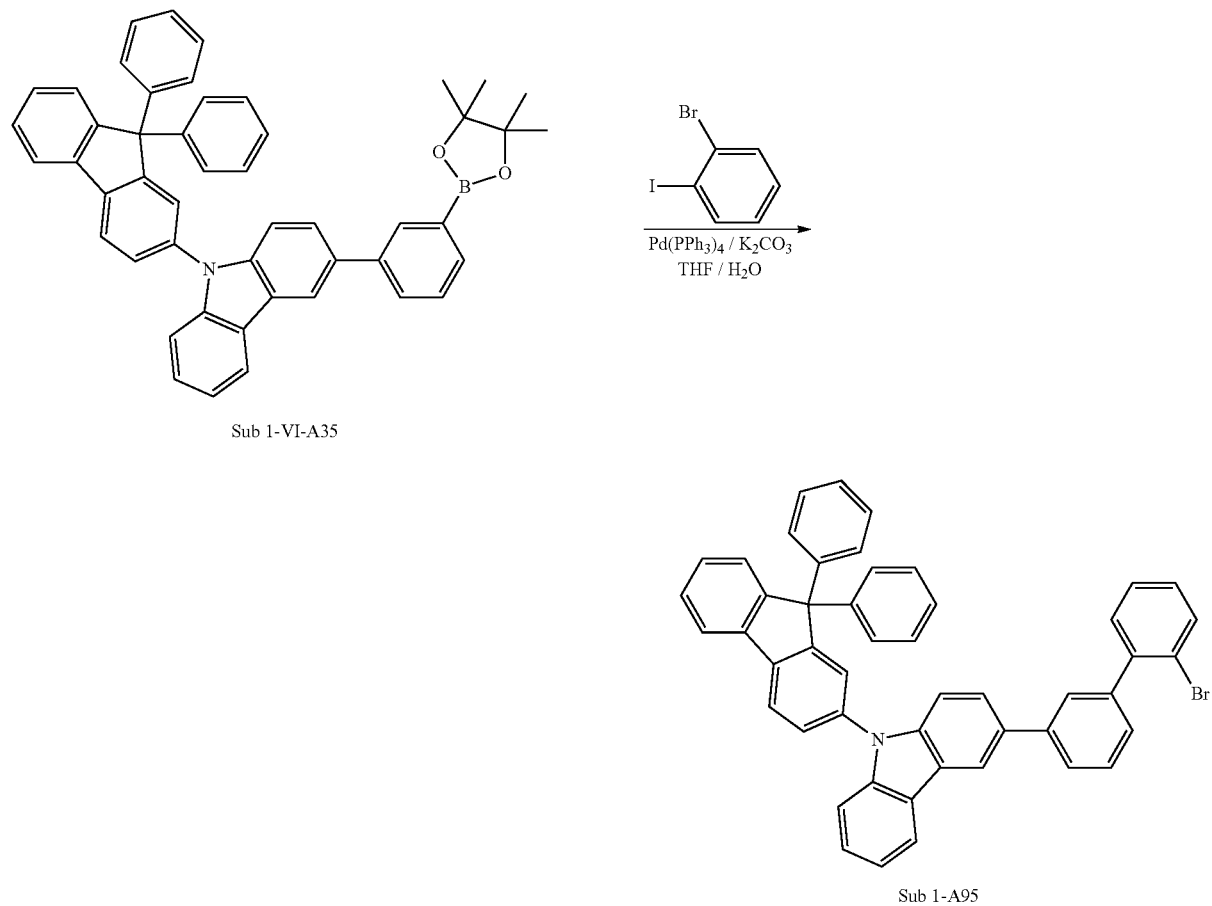
Using the obtained Sub 1-VI-A35 (16.56 g, 24.2 mmol) plus 1-bromo-2-iodobenzene (10.25 g, 36.2 mmol), Pd(PPh$_3$)$_4$ (1.4 g, 1.2 mmol), K$_2$CO$_3$ (10.01 g, 72.5 mmol), THF, and water, the same procedure as described in the synthesis method of Sub 1-A1 was carried out to obtain 10.18 g of product (yield: 59%).
21. Synthesis Method of Sub 1-A96
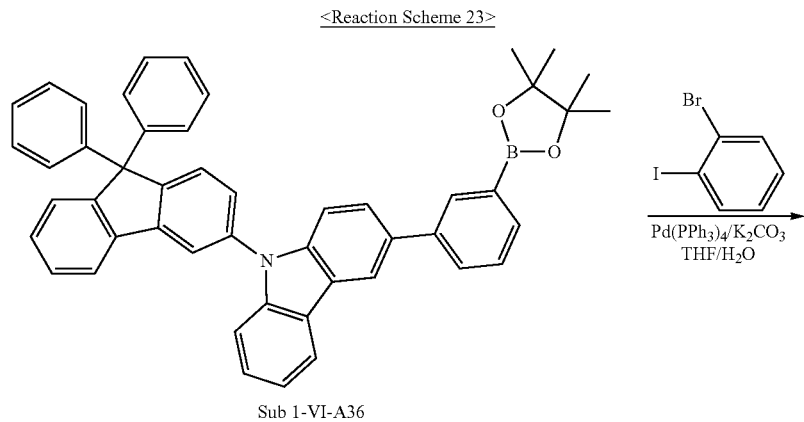

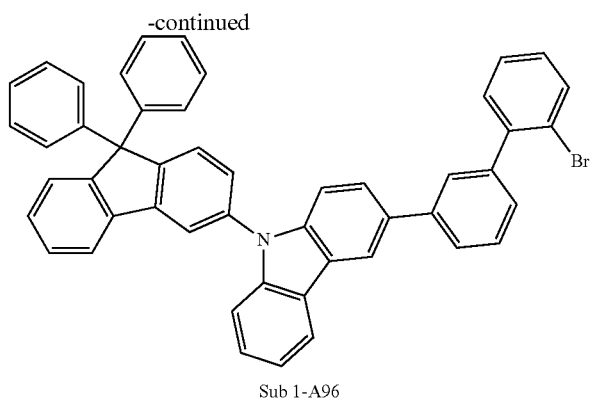
Sub 1-A96
Using the obtained Sub 1-VI-A36 (15.69 g, 22.9 mmol) plus 1-bromo-2-iodobenzene (9.71 g, 34.3 mmol), Pd(PPh$_3$)$_4$ (1.32 g, 1.1 mmol), K$_2$CO$_3$ (9.49 g, 68.6 mmol), THF, and water, the same procedure as described in the synthesis method of Sub 1-A1 was carried out to obtain 9.81 g of product (yield: 60%).
22. Synthesis Method of Sub 1-A101
Reaction Scheme 24
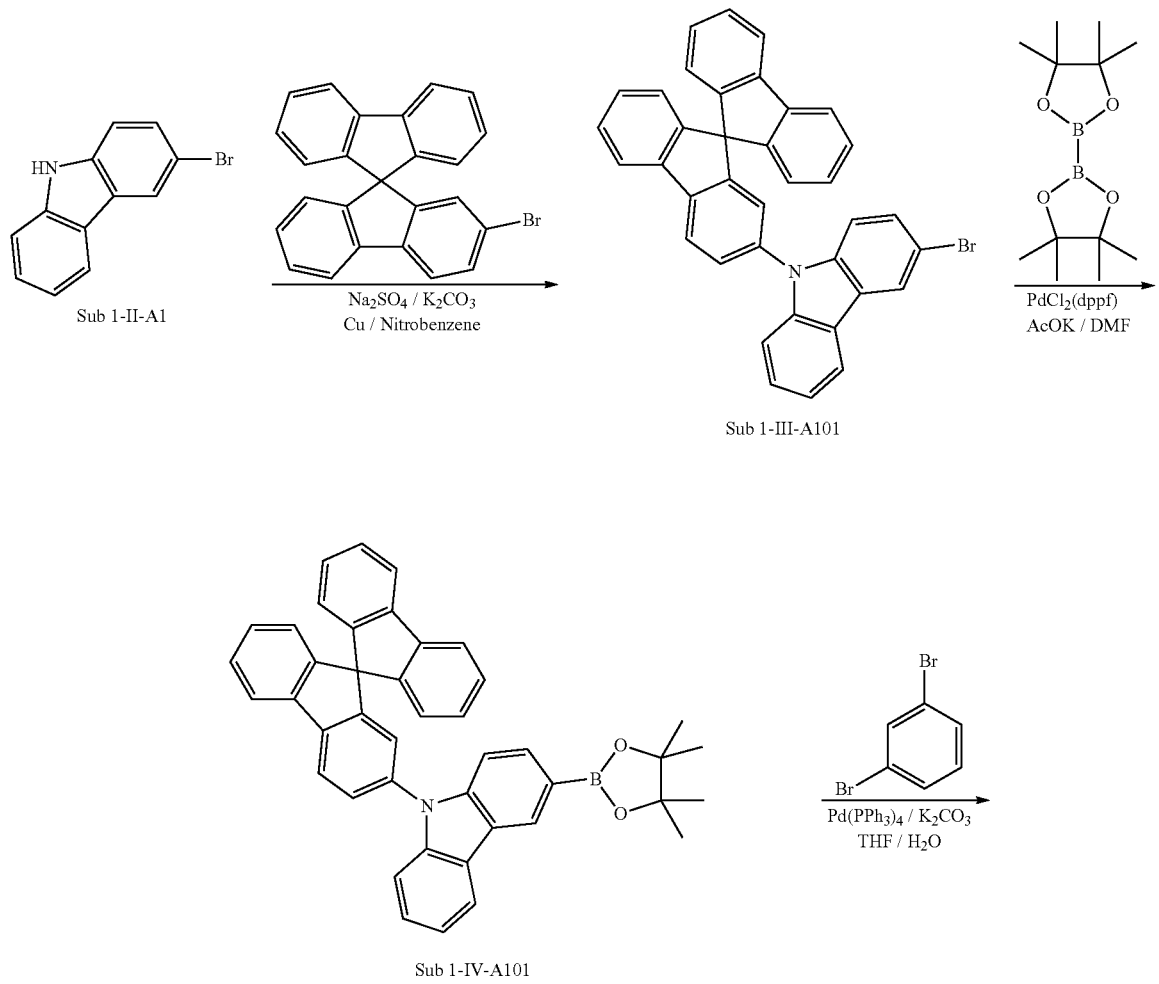

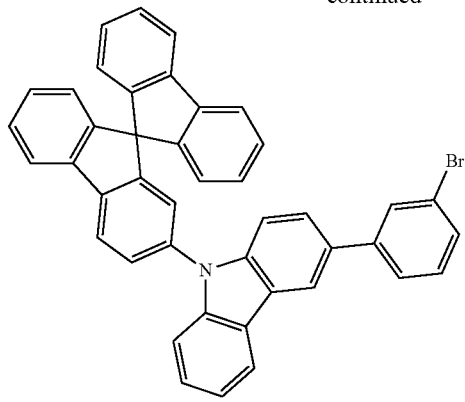

Sub 1-V-A101

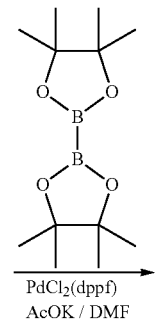

PdCl₂(dppf)
AcOK / DMF

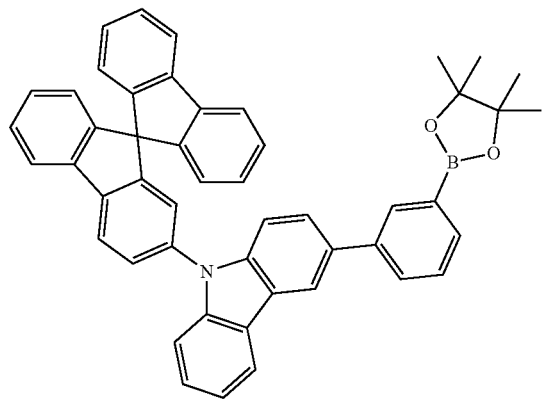

Sub 1-VI-A101

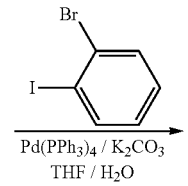

Pd(PPh₃)₄ / K₂CO₃
THF / H₂O

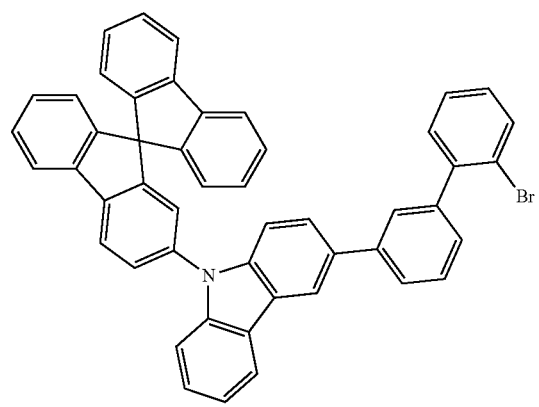

Sub 1-A101

(1) Synthesis Method of Sub 1-III-A101

Using the obtained Sub 1-II-A1 (33.01 g, 134.1 mmol) plus 2-bromo-9,9'-spirobi[fluorene] (79.53 g, 201.2 mmol), Na₂SO₄ (19.05 g, 134.1 mmol), K₂CO₃ (18.54 g, 134.1 mmol), Cu (2.56 g, 40.2 mmol), and nitrobenzene, the same procedure as described in the synthesis method of Sub 1-III-A1 was carried out to obtain 39.84 g of product (yield: 53%).

(2) Synthesis Method of Sub 1-IV-A101

Using the obtained Sub 1-III-A101 (39.84 g, 71.1 mmol) plus Bis(pinacolato)diboron (19.86 g, 78.2 mmol), Pd(dppf) Cl₂ (1.74 g, 2.1 mmol), KOAc (20.93 g, 213.2 mmol) and DMF, the same procedure as described in the synthesis method of Sub 1-IV-A1 was carried out to obtain 32.82 g of product (yield: 76%).

(3) Synthesis Method of Sub 1-V-A101

Using the obtained Sub 1-IV-A101 (32.82 g, 54 mmol) plus 1,3-dibromobenzene (19.12 g, 81 mmol), Pd(PPh₃)₄ (3.12 g, 2.7 mmol), K₂CO₃ (22.4 g, 162.1 mmol), THF and water, the same procedure as described in the synthesis method of Sub 1-V-A1 was carried out to obtain 24.42 g of product (yield: 71%).

(4) Synthesis Method of Sub 1-VI-A101

Using the obtained Sub 1-V-A101 (24.42 g, 38.4 mmol) plus Bis(pinacolato)diboron (10.72 g, 42.2 mmol), Pd(dppf)Cl$_2$ (0.94 g, 1.2 mmol), KOAc (11.29 g, 115.1 mmol) and DMF, the same procedure as described in the synthesis method of Sub 1-VI-A1 was carried out to obtain 18.88 g of product (yield: 72%).

(5) Synthesis Method of Sub 1-A101

Using the obtained Sub 1-VI-A101 (17.74 g, 25.9 mmol) plus 1-bromo-2-iodobenzene (11.01 g, 38.9 mmol), Pd(PPh$_3$)$_4$ (1.5 g, 1.3 mmol), K$_2$CO$_3$ (10.76 g, 77.8 mmol), THF and water, the same procedure as described in the synthesis method of Sub 1-A1 was carried out to obtain 10.36 g of product (yield: 56%).

23. Synthesis Method of Sub 1-A104

<Reaction Scheme 25>

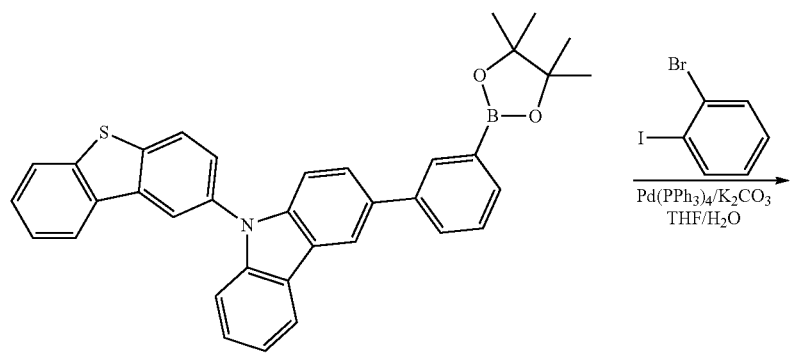

Sub 1-VI-A43 → Sub 1-A104

Using the obtained Sub 1-VI-A43 (16.13 g, 29.2 mmol) plus 1-bromo-2-iodobenzene (12.41 g, 43.9 mmol), Pd(PPh$_3$)$_4$ (1.69 g, 1.5 mmol), K$_2$CO$_3$ (12.13 g, 87.7 mmol), THF and water, the same procedure as described in the synthesis method of Sub 1-A1 was carried out to obtain 10.7 g of product (yield: 63%).

24. Synthesis Method of Sub 1-A107

<Reaction Scheme 26>

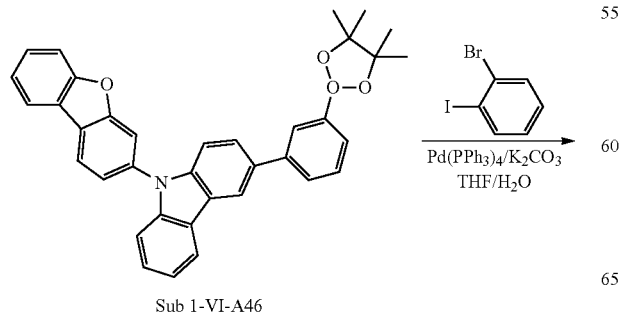

Sub 1-VI-A46 →

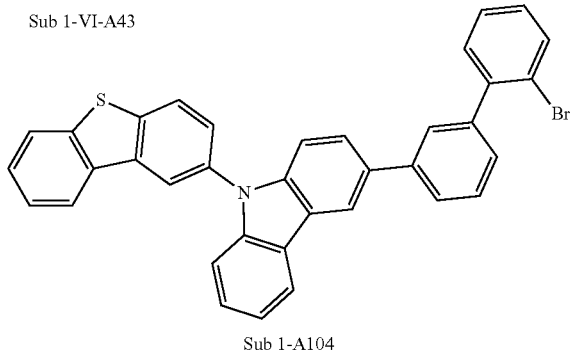

Sub 1-A107

Using the obtained Sub 1-VI-A46 (12.94 g, 24.2 mmol) plus 1-bromo-2-iodobenzene (10.26 g, 36.3 mmol), Pd(PPh$_3$)$_4$ (1.4 g, 1.2 mmol), K$_2$CO$_3$ (10.02 g, 72.5 mmol), THF and water, the same procedure as described in the synthesis method of Sub 1-A1 was carried out to obtain 8.87 g of product (yield: 65%).

Meanwhile, examples of Sub 1 compounds include, but are not limited to, the following compounds, and Field Desorption Mass Spectrometry (FD-MS) data of the Sub 1 compounds are given in Table 1 below.

Sub 1-A1
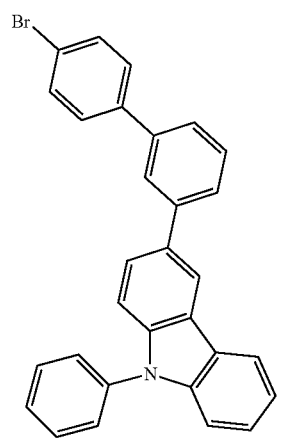
Sub 1-A2
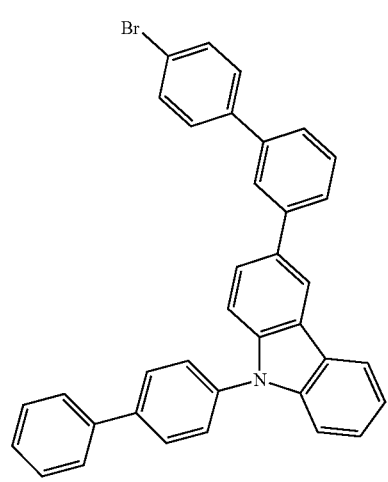
Sub 1-A3
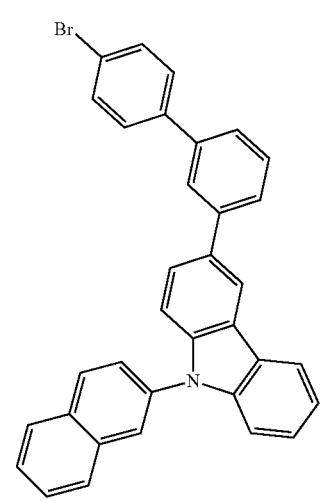
Sub 1-A4
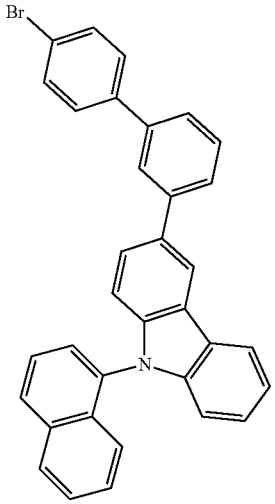
Sub 1-A5
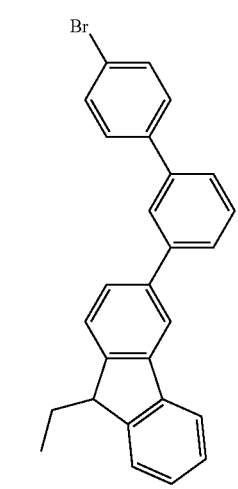
Sub 1-A6
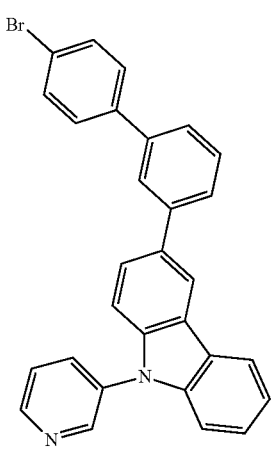

Sub 1-A7
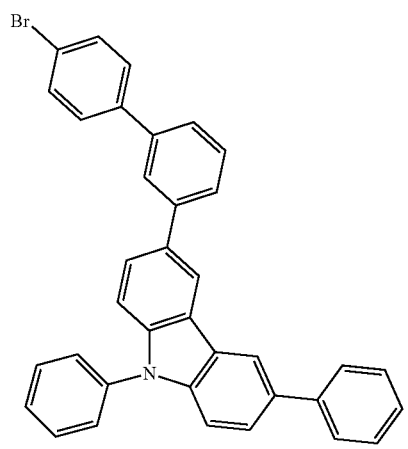
Sub 1-A8
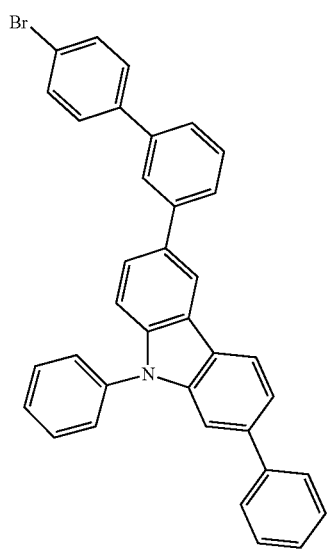
Sub 1-A10
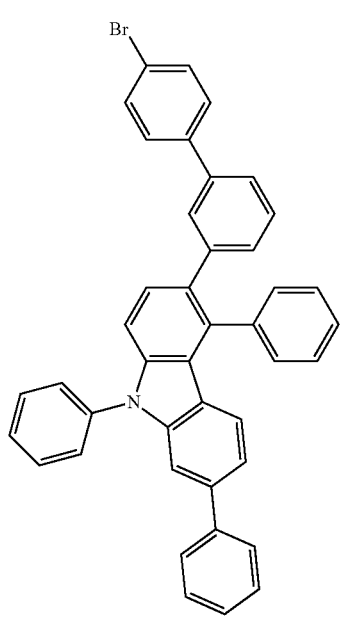
Sub 1-A11
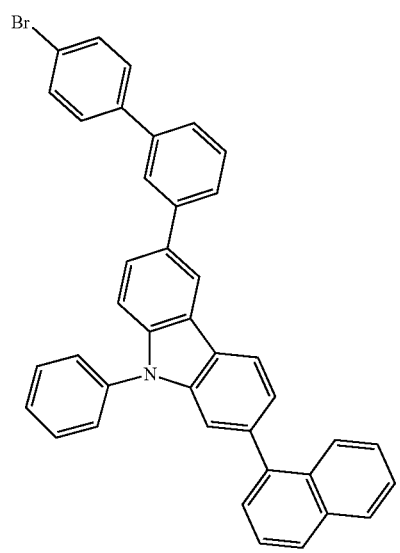
Sub 1-A13
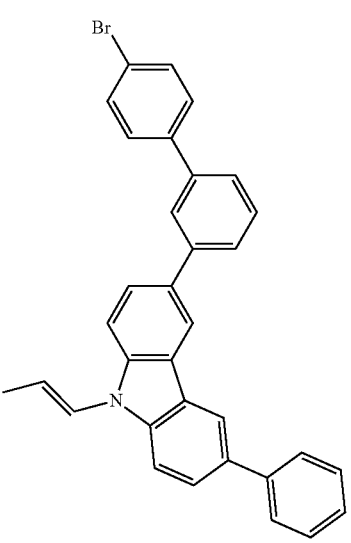
Sub 1-A14
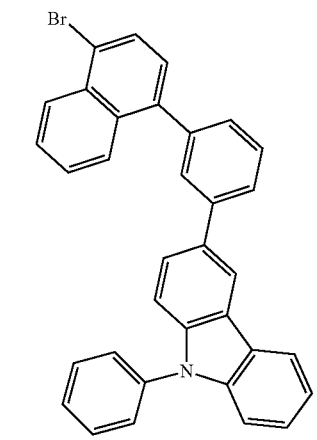

Sub 1-A18
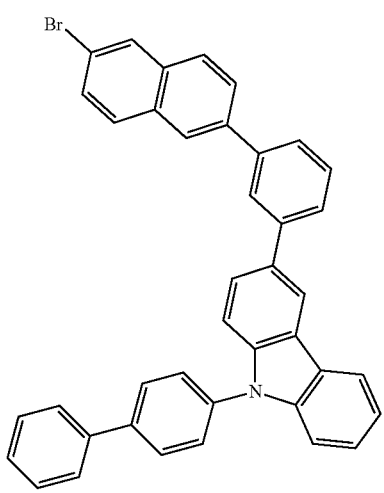
Sub 1-A21
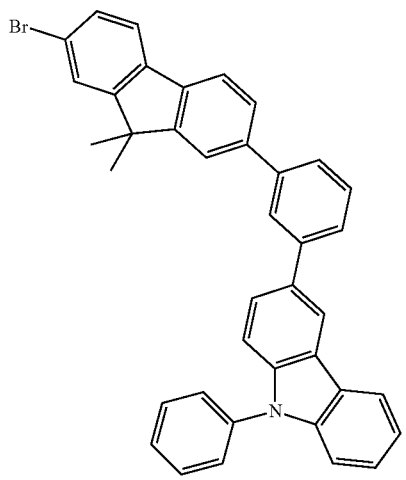
Sub 1-A22
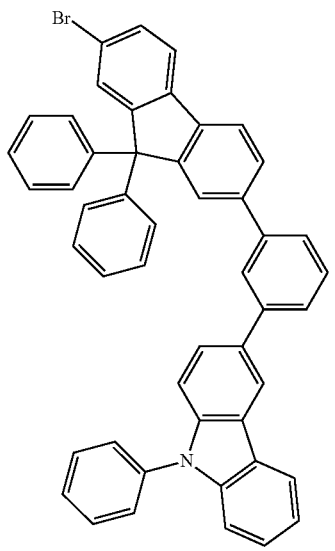
Sub 1-A23
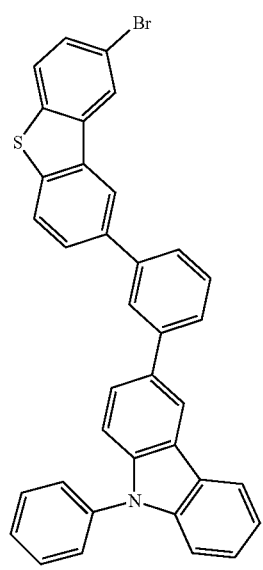
Sub 1-A24
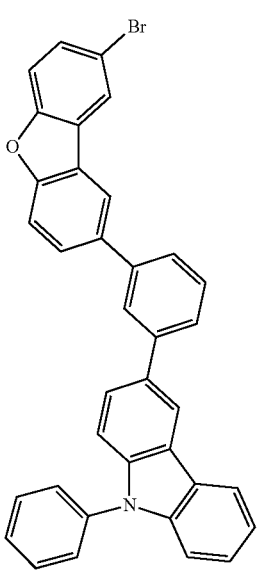
Sub 1-A25
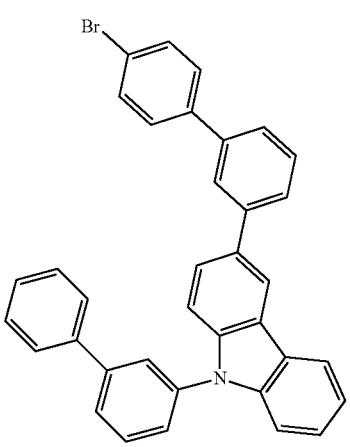

Sub 1-A26
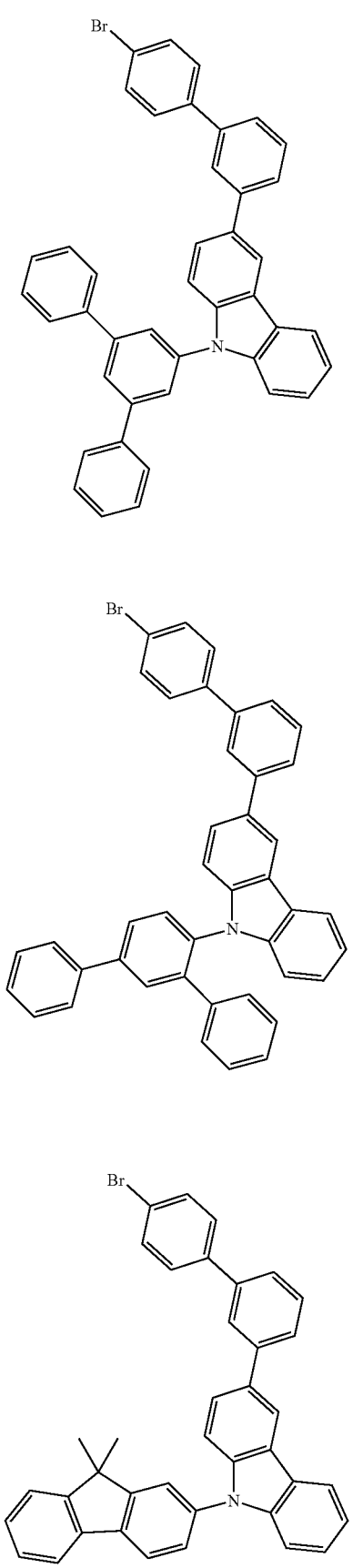
Sub 1-A27
Sub 1-A28
Sub 1-A29
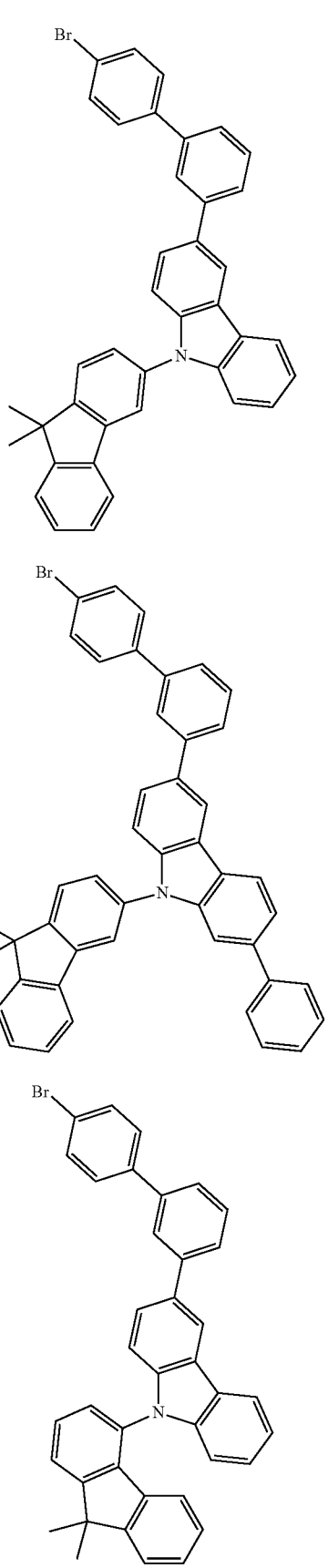
Sub 1-A30
Sub 1-A31

Sub 1-A32
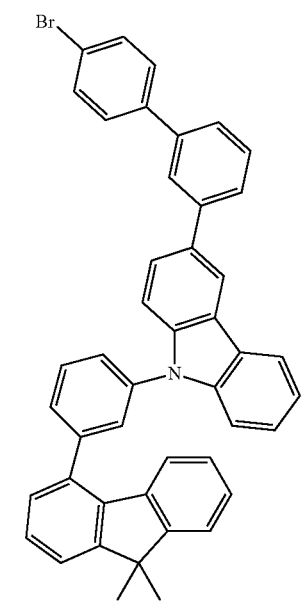
Sub 1-A33
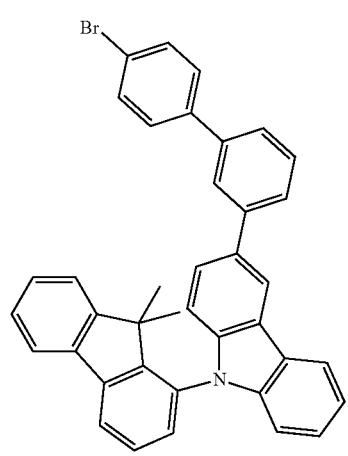
Sub 1-A34
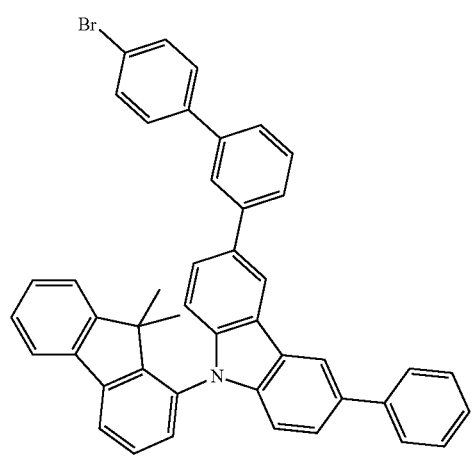
Sub 1-A35
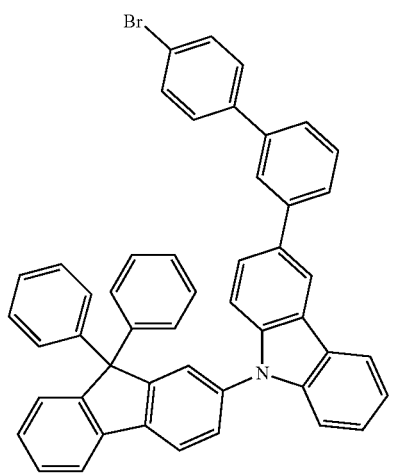
Sub 1-A36
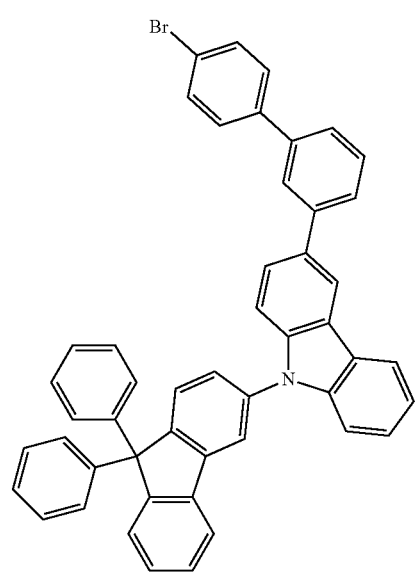
Sub 1-A37
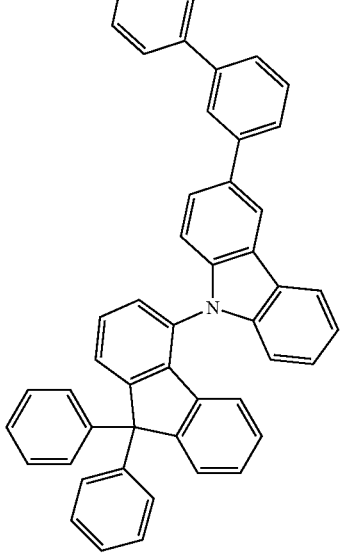

167
-continued
Sub 1-A38
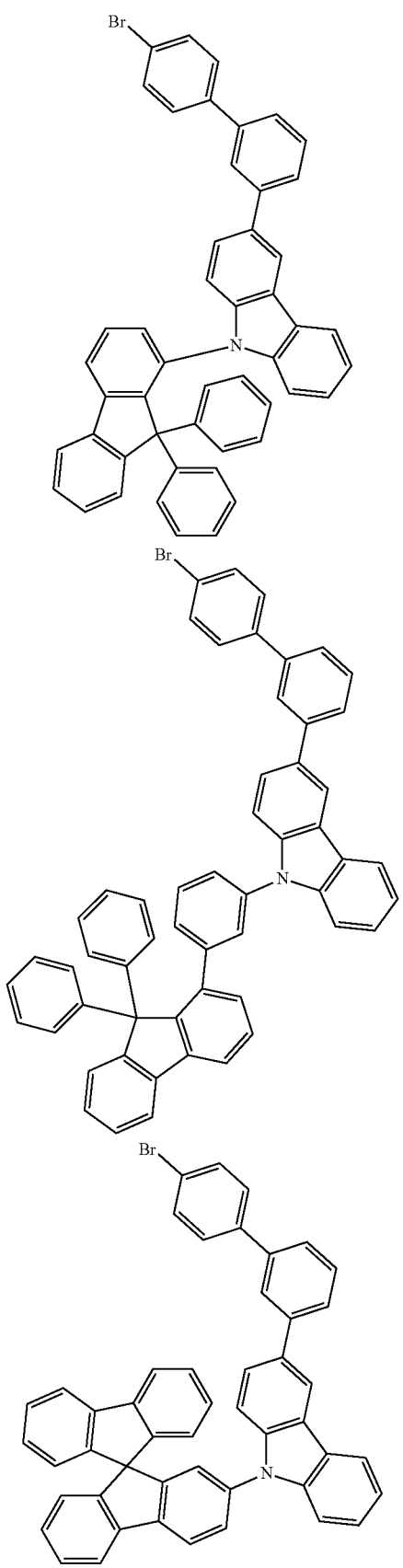
Sub 1-A39
Sub 1-A40
168
-continued
Sub 1-A41
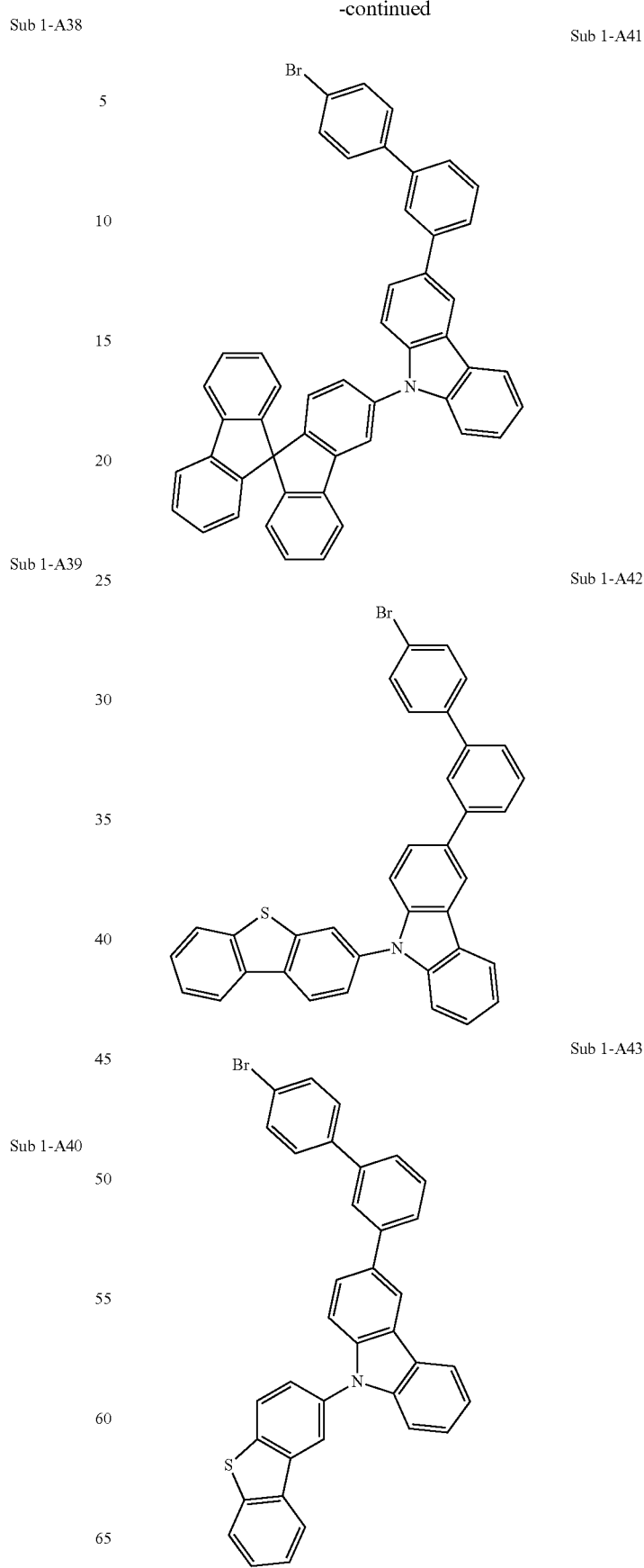
Sub 1-A42
Sub 1-A43

-continued
Sub 1-A44
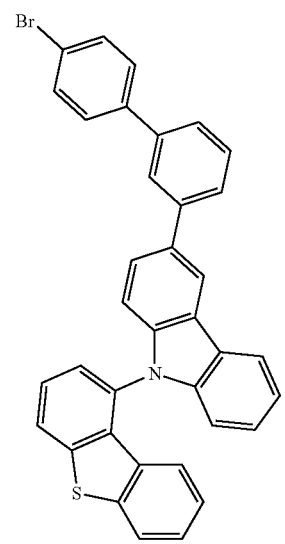
Sub 1-A45
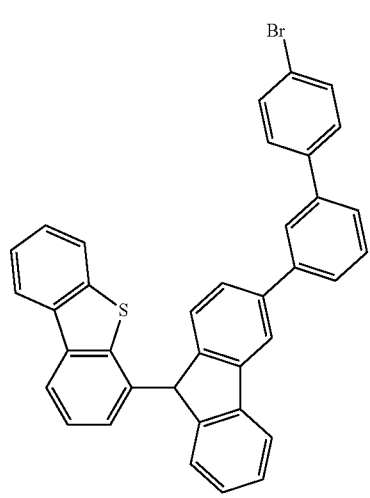
Sub 1-A46
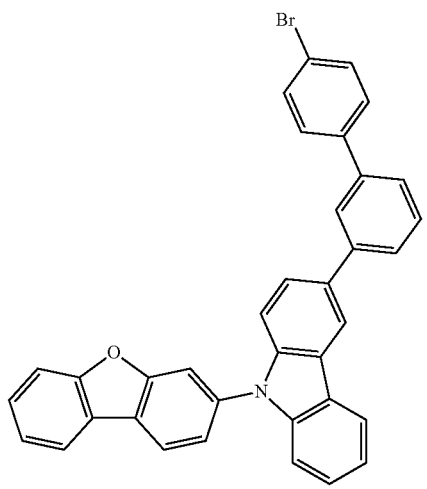
-continued
Sub 1-A47
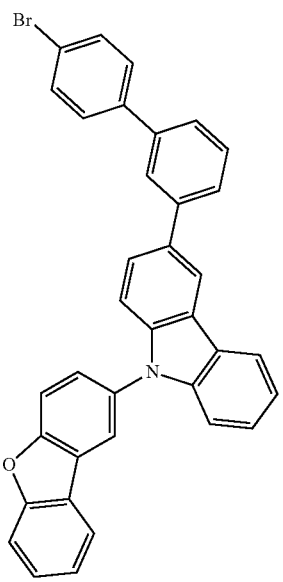
Sub 1-A48
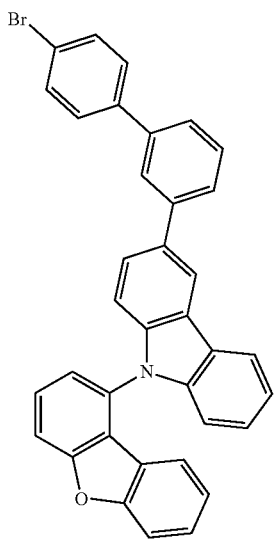
Sub 1-A49
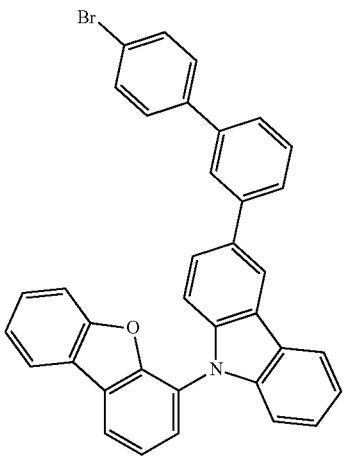

Sub 1-A50
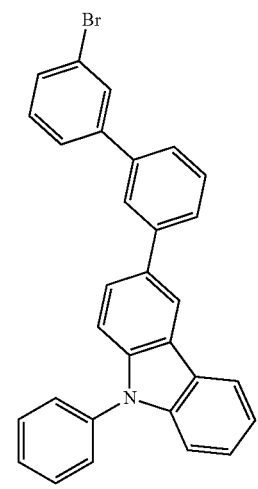
Sub 1-A51
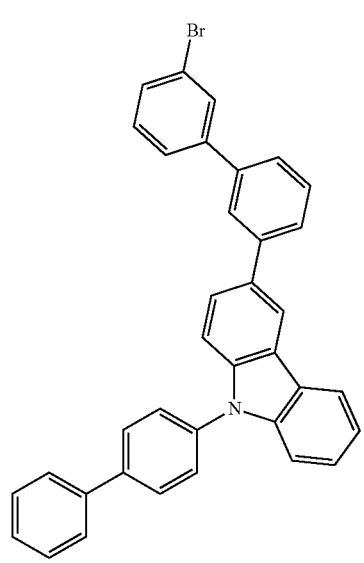
Sub 1-A52
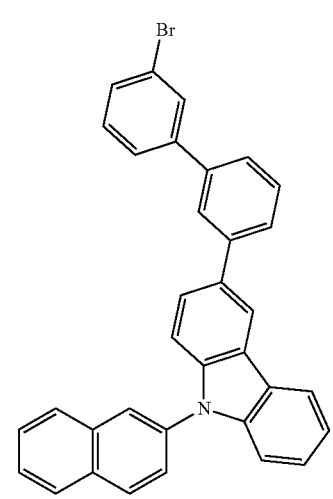
Sub 1-A53
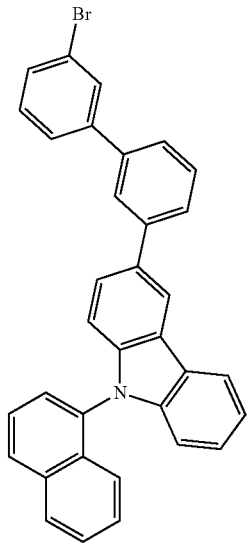
Sub 1-A54
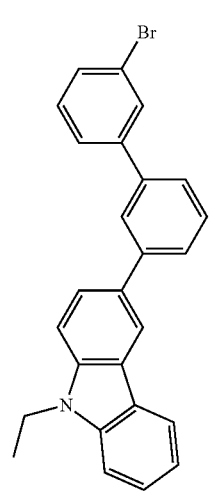
Sub 1-A55
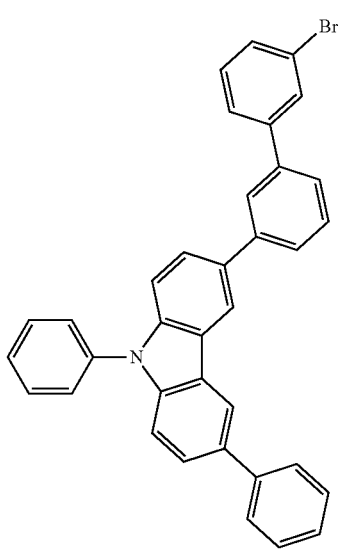

-continued
Sub 1-A56
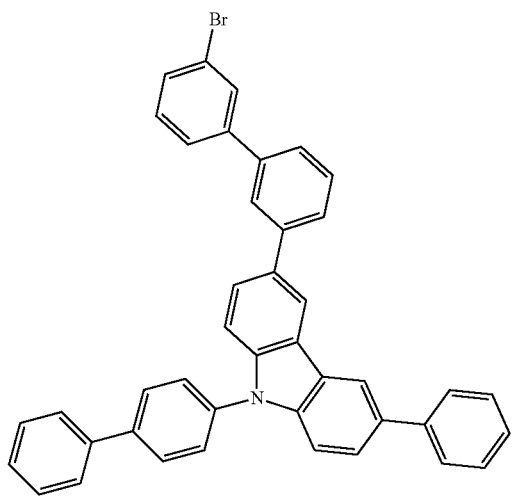
Sub 1-A57
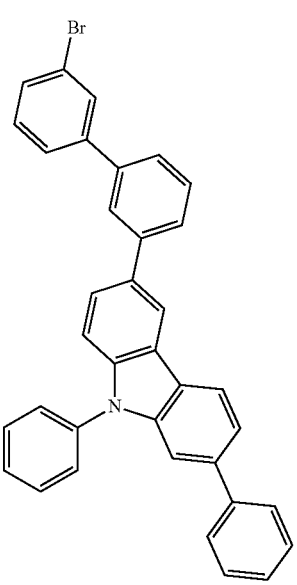
Sub 1-A58
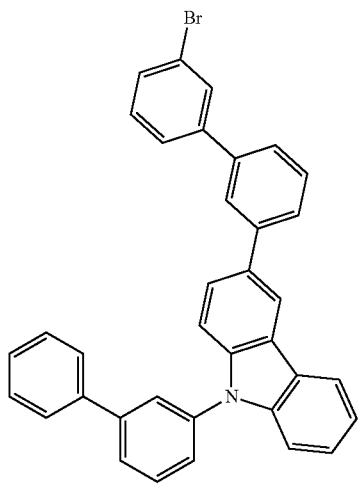
Sub 1-A59
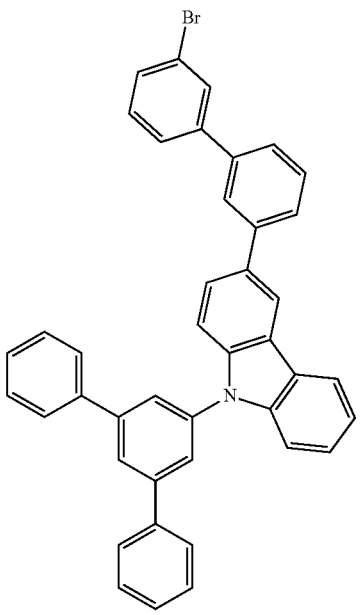
Sub 1-A60
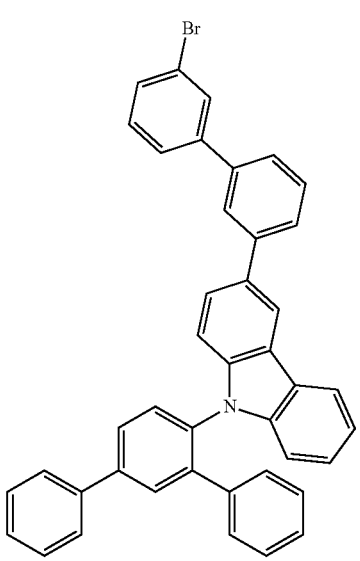
Sub 1-A61
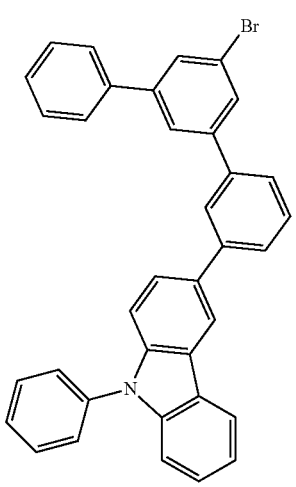

Sub 1-A62
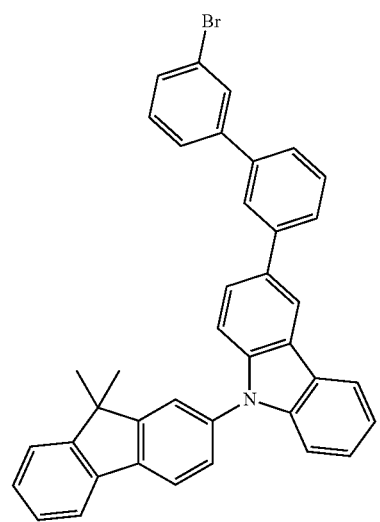
Sub 1-A63
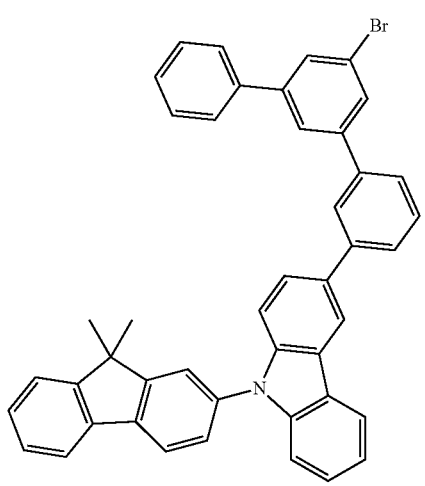
Sub 1-A64
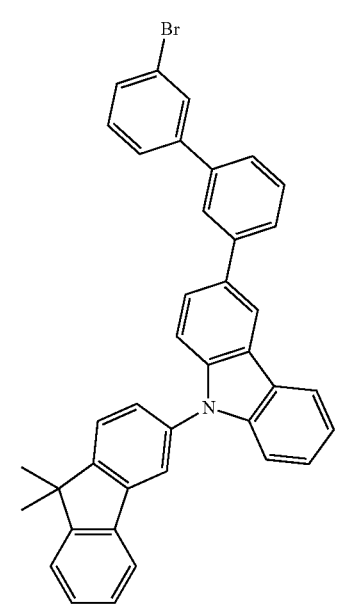
Sub 1-A65
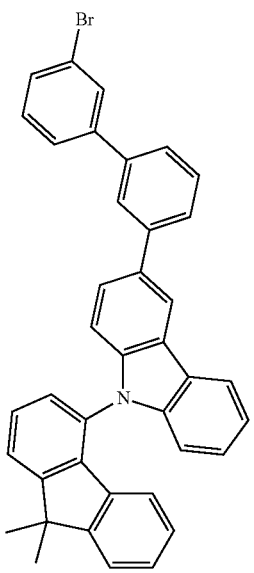
Sub 1-A66
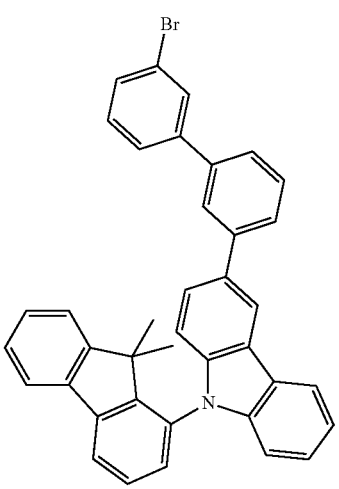
Sub 1-A67
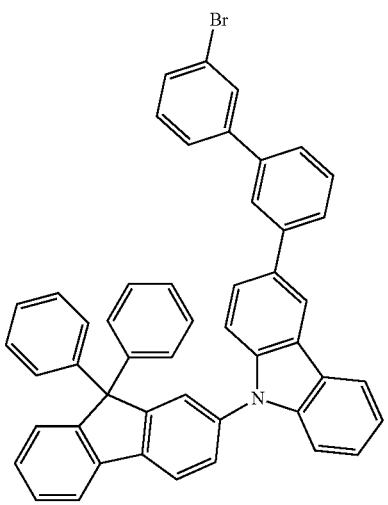

Sub 1-A68
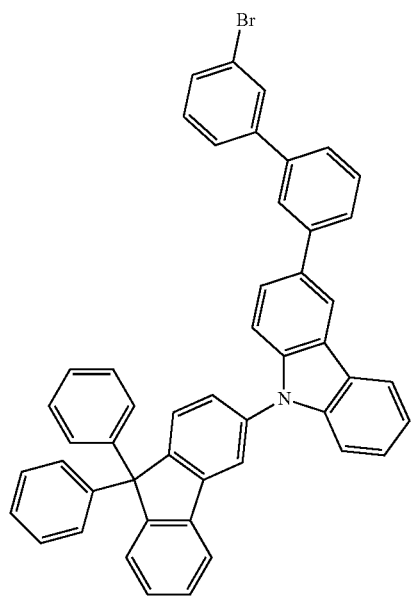
Sub 1-A69
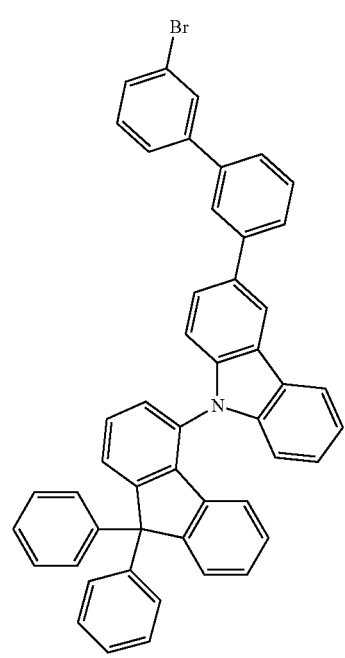
Sub 1-A70
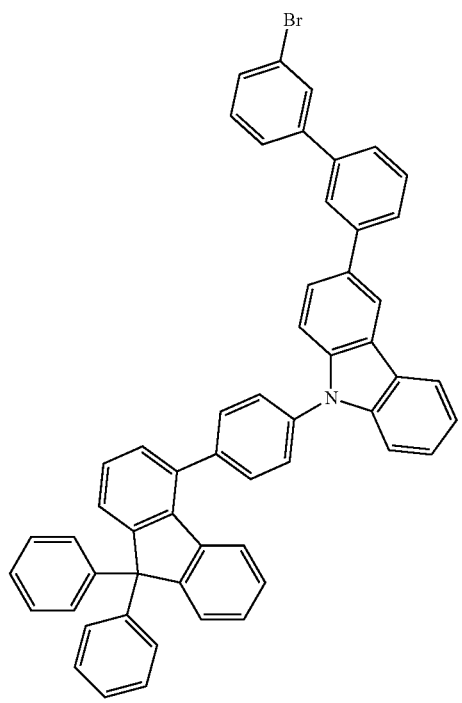
Sub 1-A71
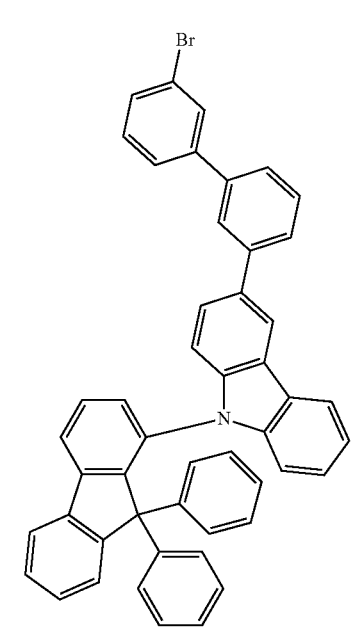

Sub 1-A72
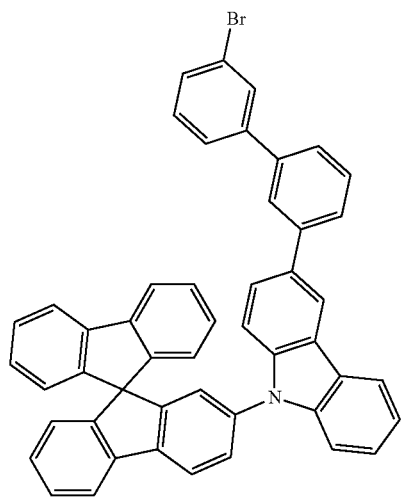
Sub 1-A73
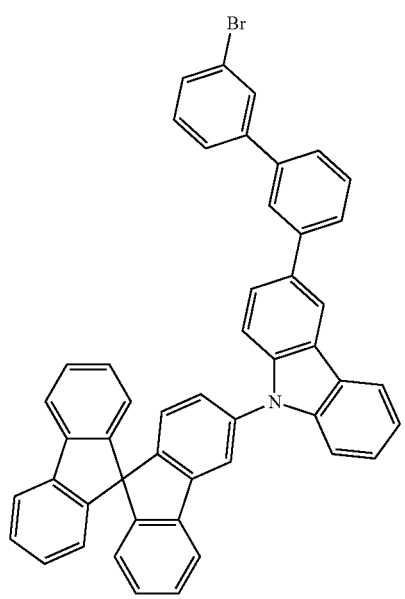
Sub 1-A75
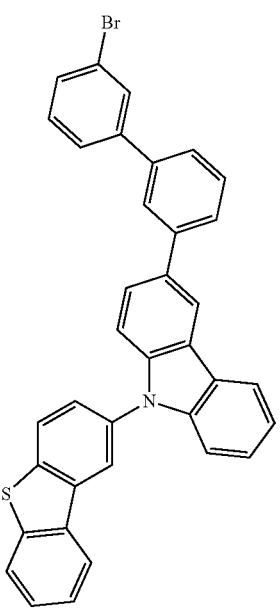
Sub 1-A75
Sub 1-A76
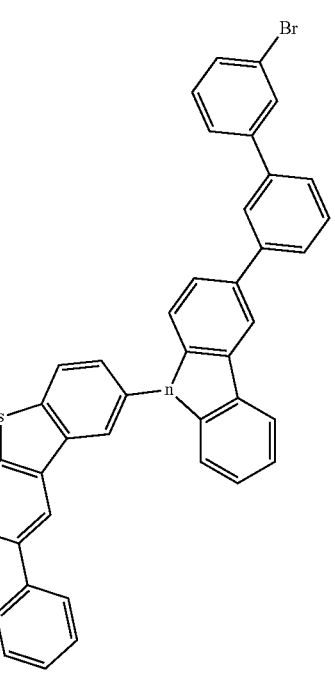

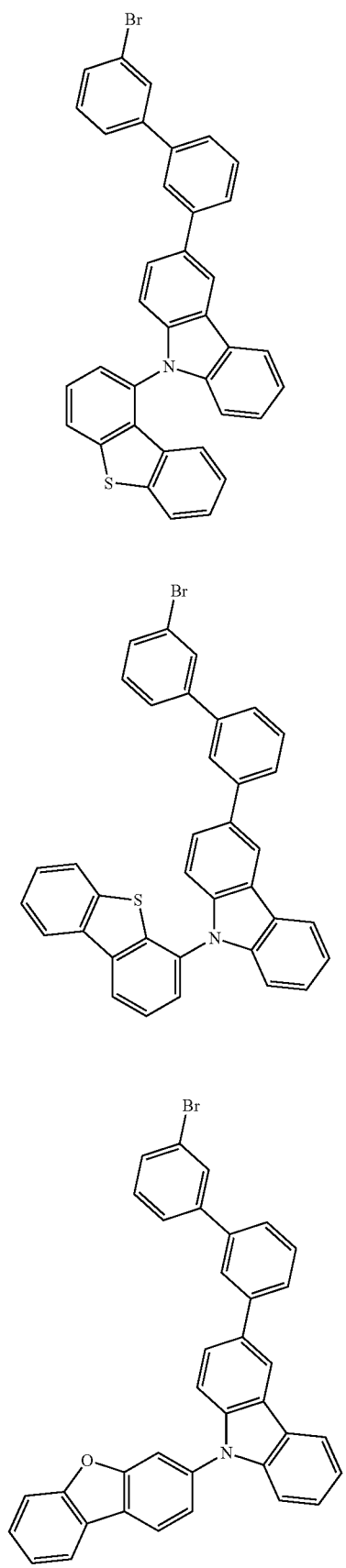
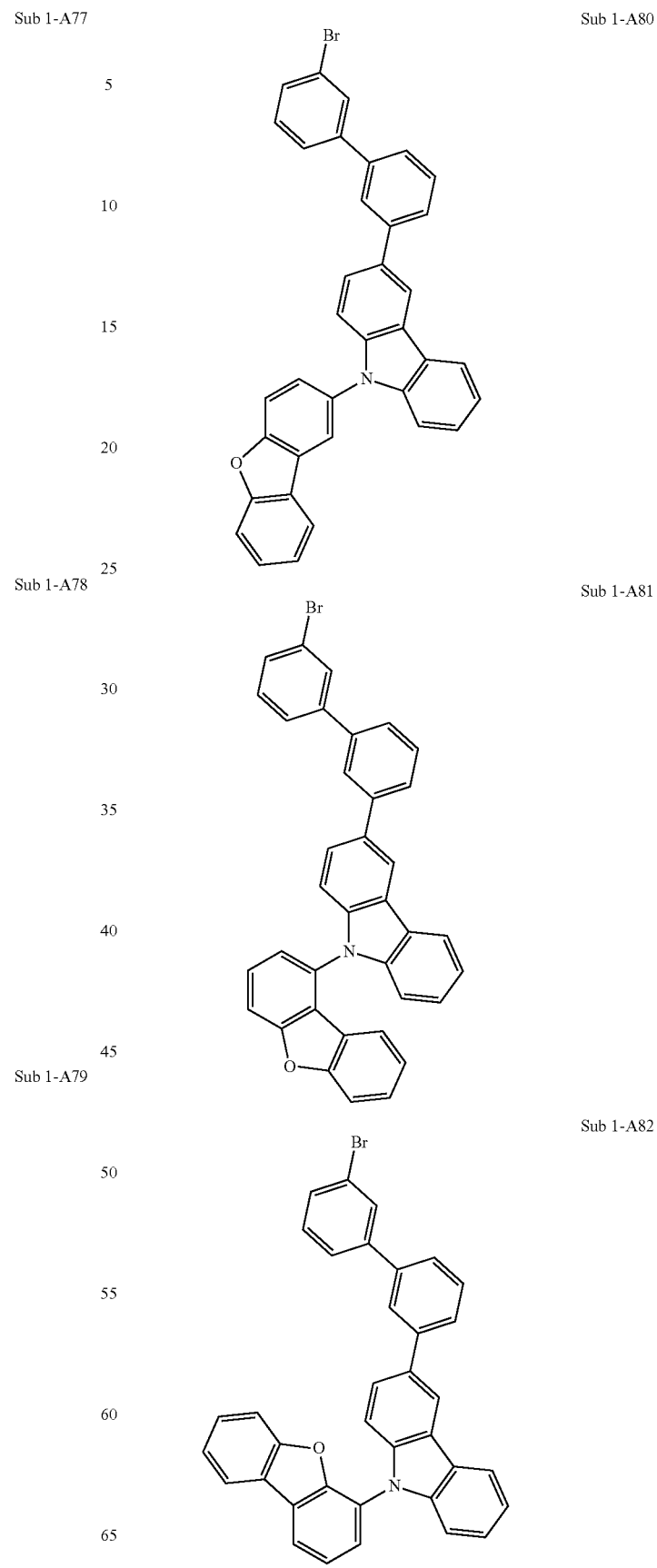

-continued
Sub 1-A83
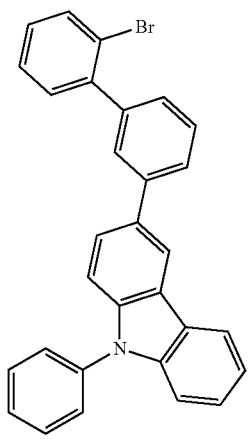
Sub 1-A84
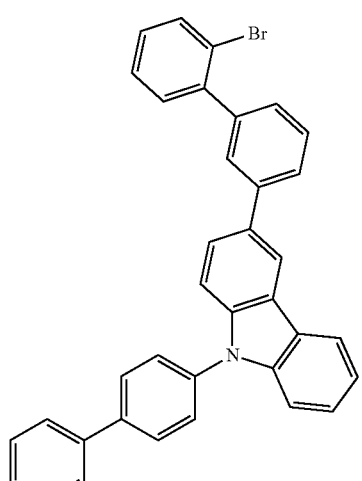
Sub 1-A85
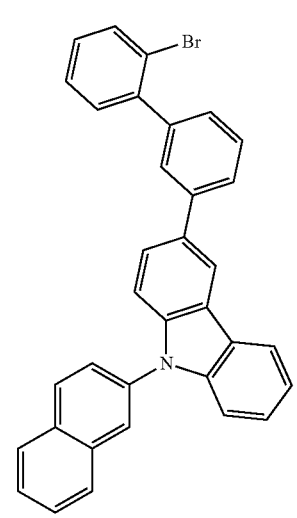
-continued
Sub 1-A86
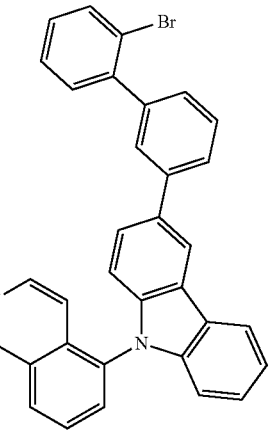
Sub 1-A87
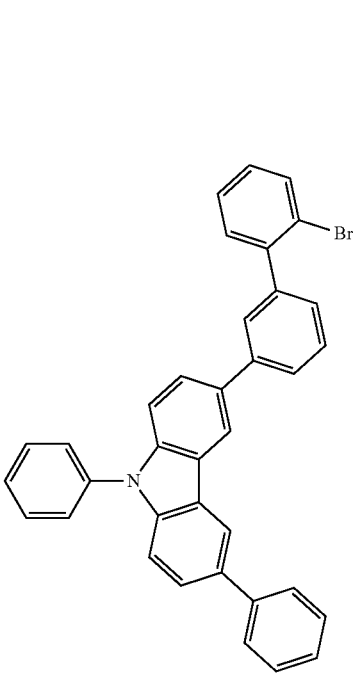
Sub 1-A88
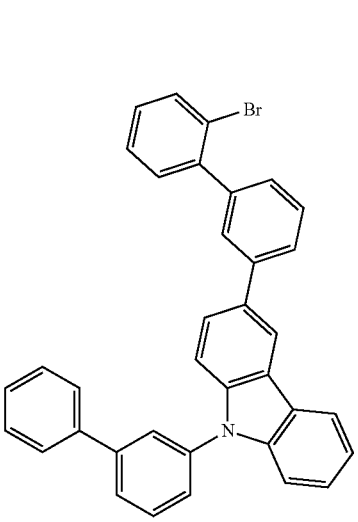

Sub 1-A89
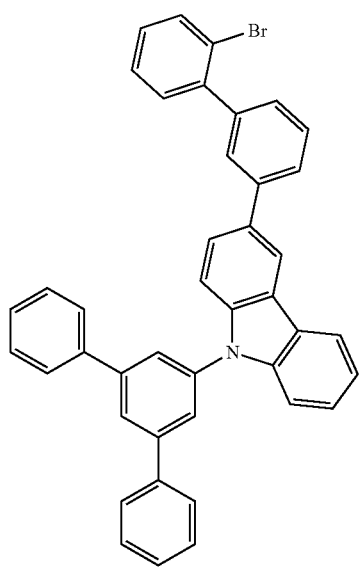
Sub 1-A90
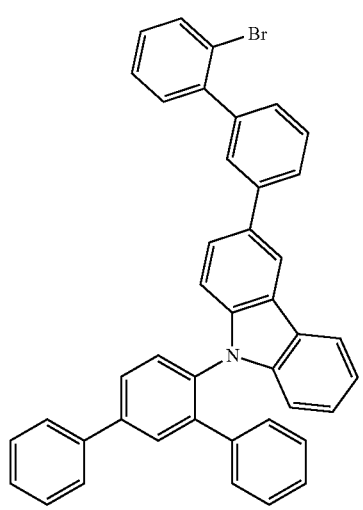
Sub 1-A91
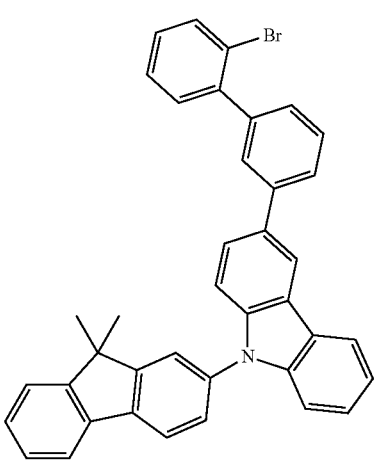
Sub 1-A92
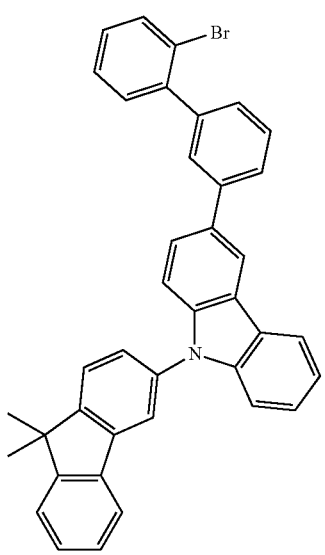
Sub 1-A93
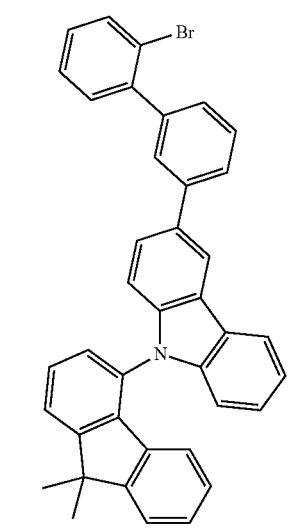
Sub 1-A94
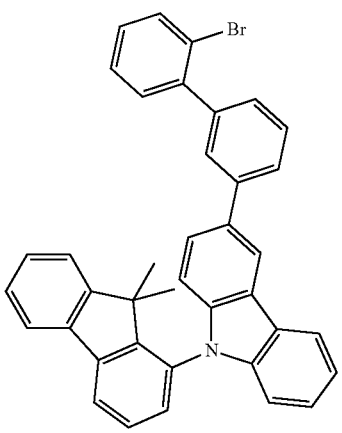

Sub 1-A95
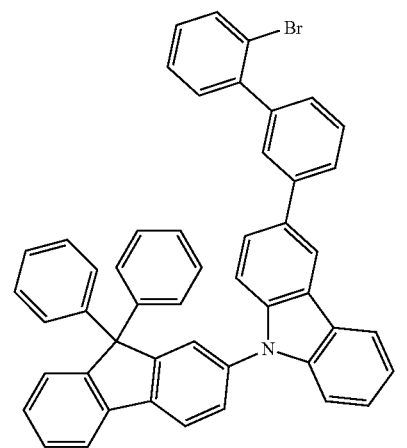
Sub 1-A96
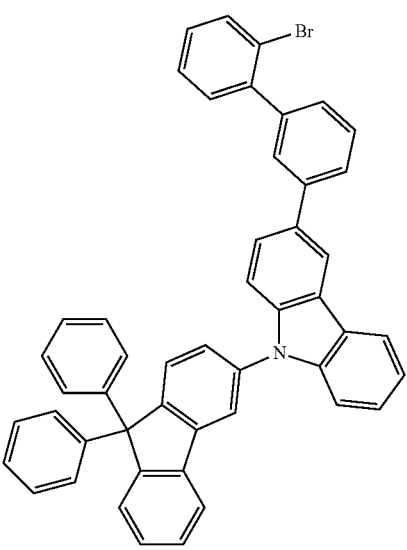
Sub 1-A97
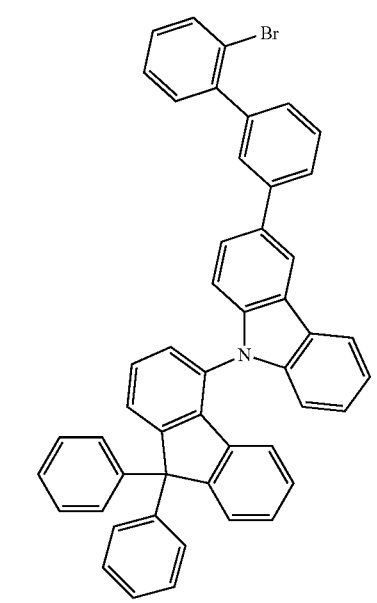
Sub 1-A98
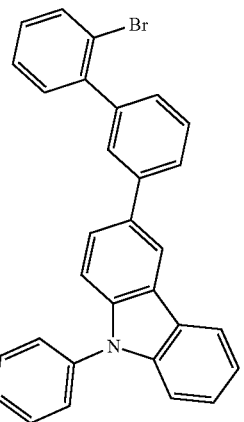
Sub 1-A99
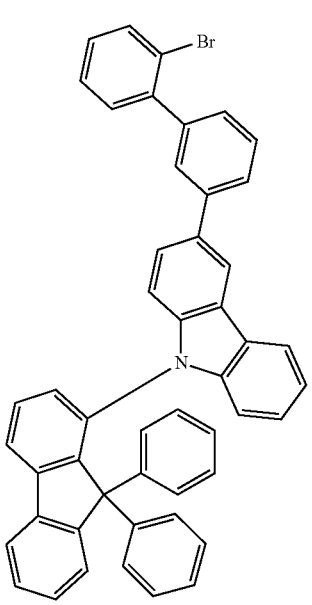

Sub 1-A100
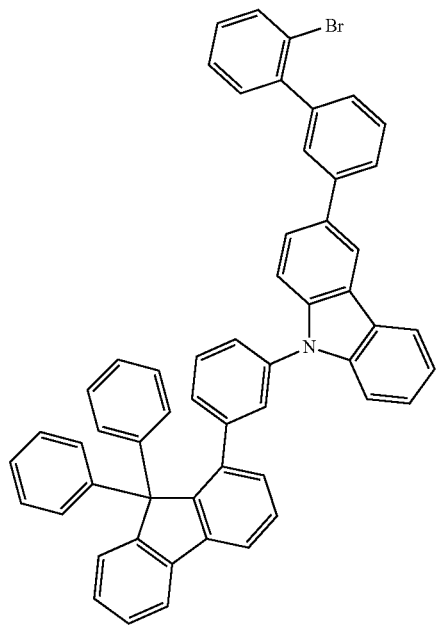
Sub 1-A101
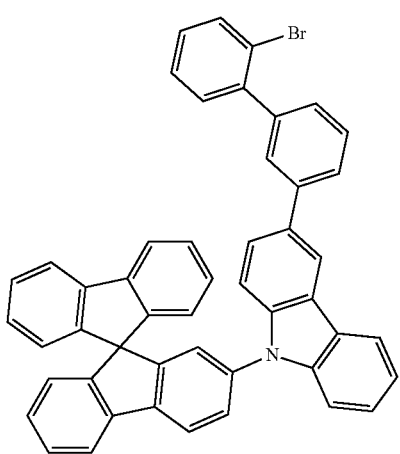
Sub 1-A102
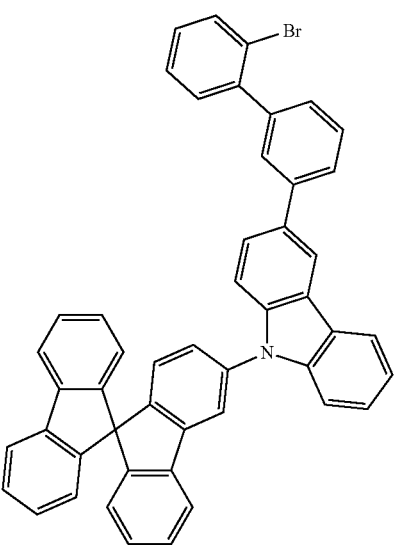
Sub 1-A103
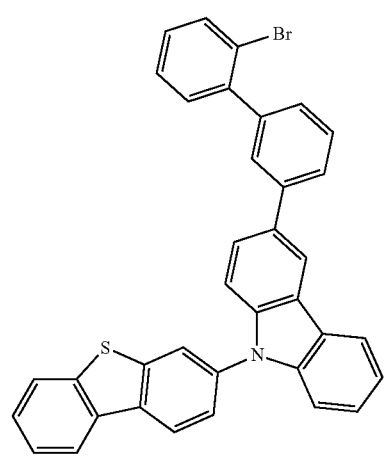
Sub A-104
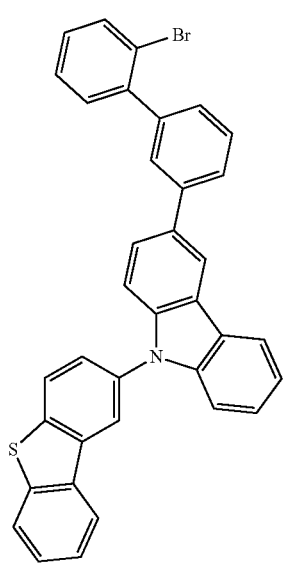

Sub 1-A105
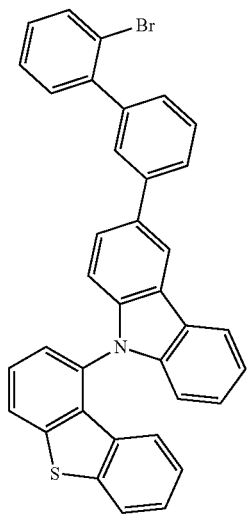
Sub 1-A106
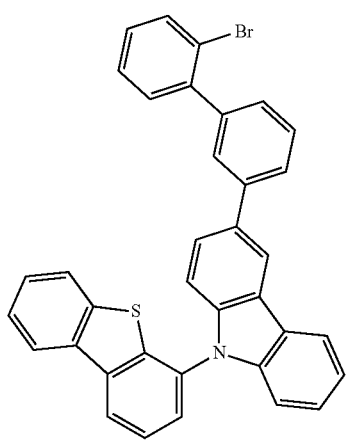
Sub 1-A107
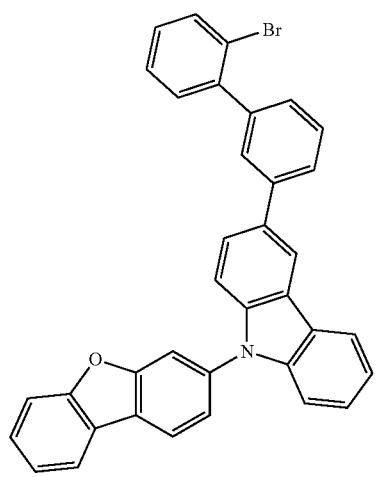
Sub 1-A108
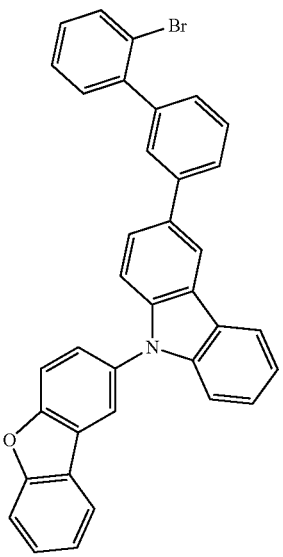
Sub 1-A109
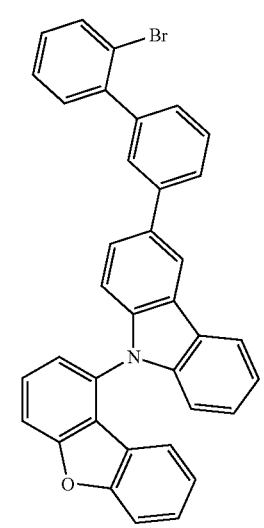
Sub 1-A110
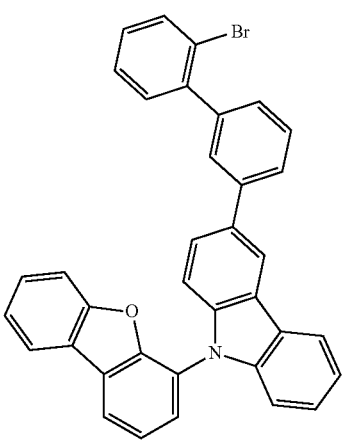

-continued
Sub 1-C1
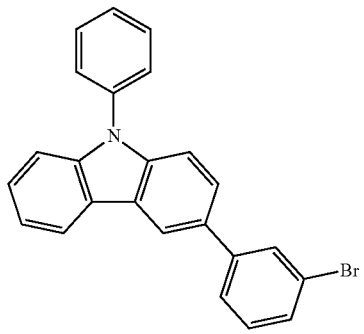
Sub 1-C2
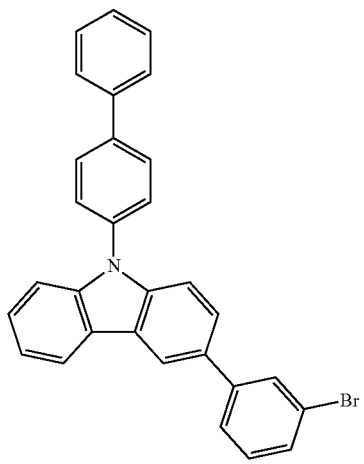
Sub 1-C3
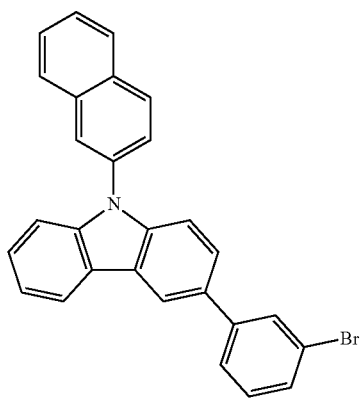
Sub 1-C4
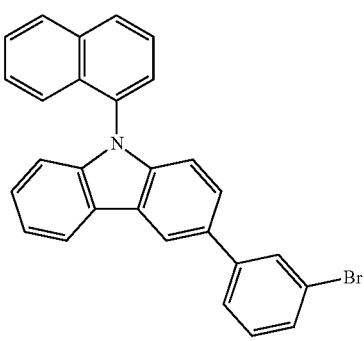
-continued
Sub 1-C5
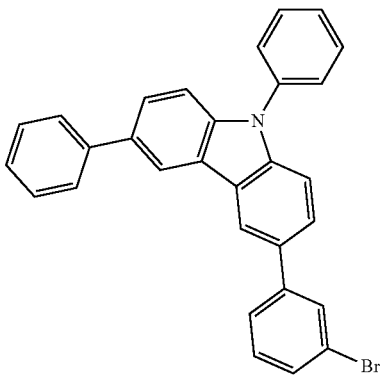
Sub 1-C6
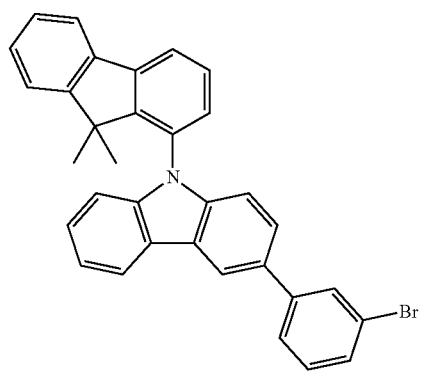
Sub 1-C7
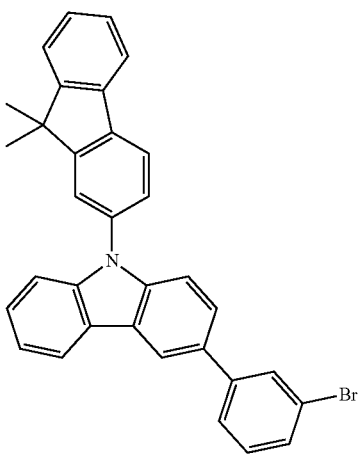
Sub 1-C8
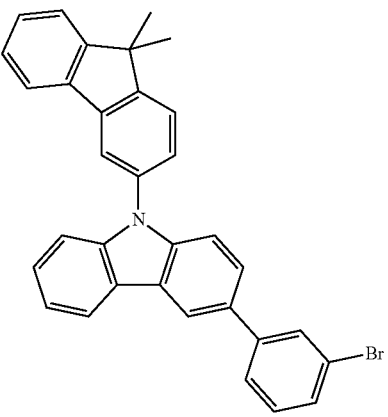

Sub 1-C9
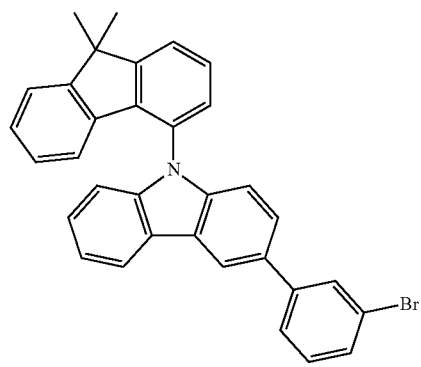
Sub 1-C10
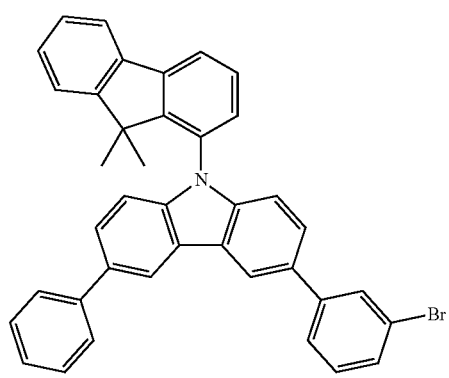
Sub 1-C11
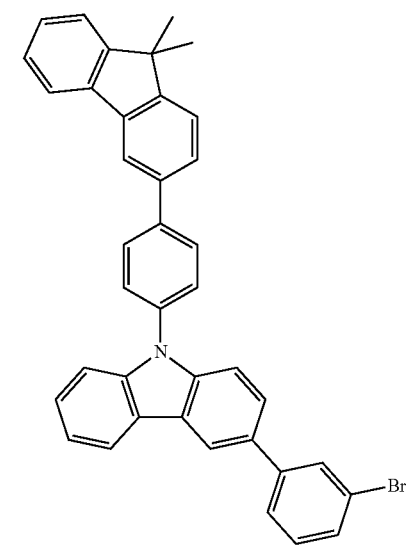
Sub 1-C12
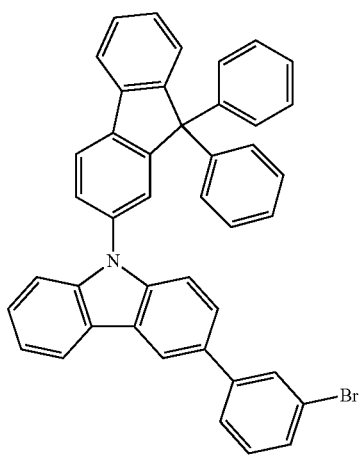
Sub 1-C13
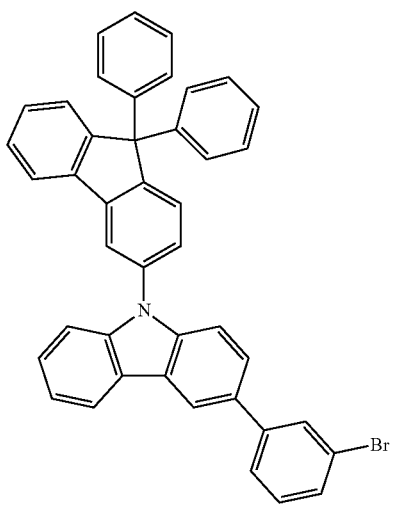
Sub 1-C14
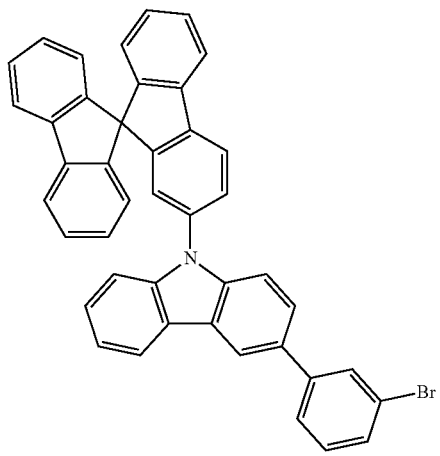

Sub 1-C15
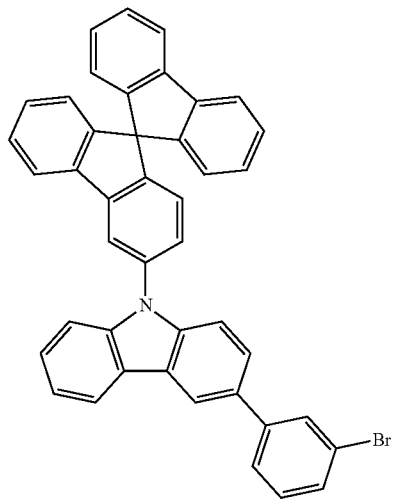
Sub 1-C16
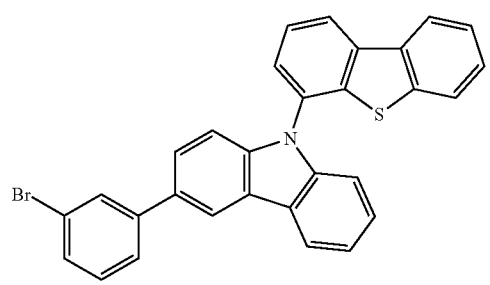
Sub 1-C17
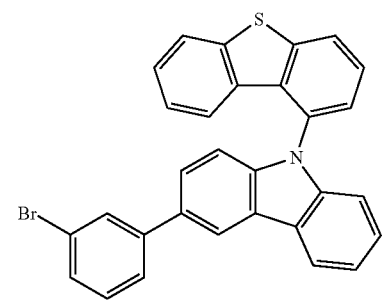
Sub 1-C18
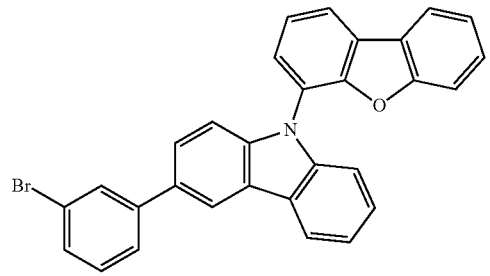
Sub 1-C19
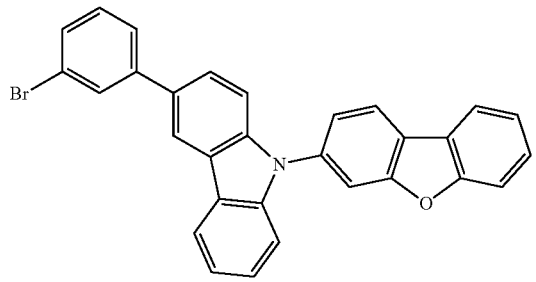
Sub 1-C20
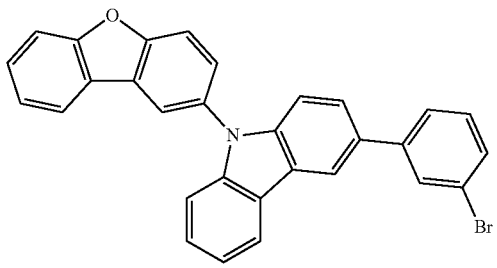
Sub 1-C21
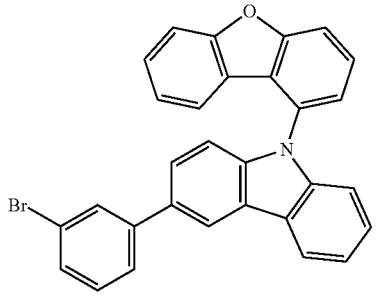
TABLE 1
| Compound | FD-MS | Compound | FD-MS |
|---|---|---|---|
| Sub1-A1 | m/z = 473.08 ($C_{30}H_{20}BrN$ = 474.39) | Sub1-A2 | m/z = 549.11 ($C_{36}H_{24}BrN$ = 550.49) |
| Sub1-A3 | m/z = 523.09 ($C_{34}H_{22}BrN$ = 524.45) | Sub1-A4 | m/z = 523.09 ($C_{34}H_{22}BrN$ = 524.45) |
| Sub1-A5 | m/z = 425.08 ($C_{26}H_{20}BrN$ = 426.35) | Sub1-A6 | m/z = 474.07 ($C_{29}H_{19}BrN_2$ = 475.38) |
| Sub1-A7 | m/z = 549.11 ($C_{36}H_{24}BrN$ = 550.49) | Sub1-A8 | m/z = 549.11 ($C_{36}H_{24}BrN$ = 550.49) |
| Sub1-A9 | m/z = 487.09 ($C_{31}H_{22}BrN$ = 488.42) | Sub1-A10 | m/z = 625.14 ($C_{42}H_{28}BrN$ = 626.58) |

TABLE 1-continued

| Compound | FD-MS | Compound | FD-MS |
|---|---|---|---|
| Sub1-A11 | m/z = 599.12 ($C_{40}H_{26}BrN$ = 600.55) | Sub1-A12 | m/z = 487.09 ($C_{31}H_{22}BrN$ = 488.42) |
| Sub1-A13 | m/z = 513.11 ($C_{33}H_{24}BrN$ = 514.45) | Sub1-A14 | m/z = 523.09 ($C_{34}H_{22}BrN$ = 524.45) |
| Sub1-A15 | m/z = 475.09 ($C_{30}H_{22}BrN$ = 476.41) | Sub1-A16 | m/z = 599.12 ($C_{40}H_{26}BrN$ = 600.55) |
| Sub1-A17 | m/z = 523.09 ($C_{34}H_{22}BrN$ = 524.45) | Sub1-A18 | m/z = 599.12 ($C_{40}H_{26}BrN$ = 600.55) |
| Sub1-A19 | m/z = 599.12 ($C_{40}H_{26}BrN$ = 600.55) | Sub1-A20 | m/z = 599.12 ($C_{40}H_{26}BrN$ = 600.55) |
| Sub1-A21 | m/z = 589.14 ($C_{39}H_{28}BrN$ = 590.55) | Sub1-A22 | m/z = 713.17 ($C_{49}H_{32}BrN$ = 714.69) |
| Sub1-A23 | m/z = 579.07 ($C_{36}H_{22}BrNS$ = 580.54) | Sub1-A24 | m/z = 563.09 ($C_{36}H_{22}BrNO$ = 564.47) |
| Sub1-A25 | m/z = 549.11 ($C_{36}H_{24}BrN$ = 550.49) | Sub1-A26 | m/z = 625.14 ($C_{42}H_{28}BrN$ = 626.58) |
| Sub1-A27 | m/z = 625.14 ($C_{42}H_{28}BrN$ = 626.58) | Sub1-A28 | m/z = 589.14 ($C_{39}H_{28}BrN$ = 590.55) |
| Sub1-A29 | m/z = 589.14 ($C_{39}H_{28}BrN$ = 590.55) | Sub1-A30 | m/z = 665.17 ($C_{45}H_{32}BrN$ = 666.65) |
| Sub1-A31 | m/z = 589.14 ($C_{39}H_{28}BrN$ = 590.55) | Sub1-A32 | m/z = 665.17 ($C_{45}H_{32}BrN$ = 666.65) |
| Sub1-A33 | m/z = 589.14 ($C_{39}H_{28}BrN$ = 590.55) | Sub1-A34 | m/z = 665.17 ($C_{45}H_{32}BrN$ = 666.65) |
| Sub1-A35 | m/z = 713.17 ($C_{49}H_{32}BrN$ = 714.69) | Sub1-A36 | m/z = 713.17 ($C_{49}H_{32}BrN$ = 714.69) |
| Sub1-A37 | m/z = 713.17 ($C_{49}H_{32}BrN$ = 714.69) | Sub1-A38 | m/z = 713.17 ($C_{49}H_{32}BrN$ = 714.69) |
| Sub1-A39 | m/z = 789.20 ($C_{55}H_{36}BrN$ = 790.79) | Sub1-A40 | m/z = 711.16 ($C_{49}H_{30}BrN$ = 712.67) |
| Sub1-A41 | m/z = 711.16 ($C_{49}H_{30}BrN$ = 712.67) | Sub1-A42 | m/z = 579.07 ($C_{36}H_{22}BrNS$ = 580.54) |
| Sub1-A43 | m/z = 579.07 ($C_{36}H_{22}BrNS$ = 580.54) | Sub1-A44 | m/z = 579.07 ($C_{36}H_{22}BrNS$ = 580.54) |
| Sub1-A45 | m/z = 579.07 ($C_{36}H_{22}BrNS$ = 580.54) | Sub1-A46 | m/z = 563.09 ($C_{36}H_{22}BrNO$ = 564.47) |
| Sub1-A47 | m/z = 563.09 ($C_{36}H_{22}BrNO$ = 564.47) | Sub1-A48 | m/z = 563.09 ($C_{36}H_{22}BrNO$ = 564.47) |
| Sub1-A49 | m/z = 563.09 ($C_{36}H_{22}BrNO$ = 564.47) | Sub1-A50 | m/z = 473.08 ($C_{30}H_{20}BrN$ = 474.39) |
| Sub1-A51 | m/z = 549.11 ($C_{36}H_{24}BrN$ = 550.49) | Sub1-A52 | m/z = 523.09 ($C_{34}H_{22}BrN$ = 524.45) |
| Sub1-A53 | m/z = 523.09 ($C_{34}H_{22}BrN$ = 524.45) | Sub1-A54 | m/z = 425.08 ($C_{26}H_{20}BrN$ = 426.35) |
| Sub1-A55 | m/z = 549.11 ($C_{36}H_{24}BrN$ = 550.49) | Sub1-A56 | m/z = 625.14 ($C_{42}H_{28}BrN$ = 626.58) |
| Sub1-A57 | m/z = 549.11 ($C_{36}H_{24}BrN$ = 550.49) | Sub1-A58 | m/z = 549.11 ($C_{36}H_{24}BrN$ = 550.49) |
| Sub1-A59 | m/z = 625.14 ($C_{42}H_{28}BrN$ = 626.58) | Sub1-A60 | m/z = 625.14 ($C_{42}H_{28}BrN$ = 626.58) |
| Sub1-A61 | m/z = 549.11 ($C_{36}H_{24}BrN$ = 550.49) | Sub1-A62 | m/z = 589.14 ($C_{39}H_{28}BrN$ = 590.55) |
| Sub1-A63 | m/z = 665.17 ($C_{45}H_{32}BrN$ = 666.65) | Sub1-A64 | m/z = 589.14 ($C_{39}H_{28}BrN$ = 590.55) |
| Sub1-A65 | m/z = 589.14 ($C_{39}H_{28}BrN$ = 590.55) | Sub1-A66 | m/z = 589.14 ($C_{39}H_{28}BrN$ = 590.55) |
| Sub1-A67 | m/z = 713.17 ($C_{49}H_{32}BrN$ = 714.69) | Sub1-A68 | m/z = 713.17 ($C_{49}H_{32}BrN$ = 714.69) |
| Sub1-A69 | m/z = 713.17 ($C_{49}H_{32}BrN$ = 714.69) | Sub1-A70 | m/z = 789.20 ($C_{55}H_{36}BrN$ = 790.79) |
| Sub1-A71 | m/z = 713.17 ($C_{49}H_{32}BrN$ = 714.69) | Sub1-A72 | m/z = 711.16 ($C_{49}H_{30}BrN$ = 712.67) |
| Sub1-A73 | m/z = 711.16 ($C_{49}H_{30}BrN$ = 712.67) | Sub1-A74 | m/z = 579.07 ($C_{36}H_{22}BrNS$ = 580.54) |
| Sub1-A75 | m/z = 579.07 ($C_{36}H_{22}BrNS$ = 580.54) | Sub1-A76 | m/z = 656.09 ($C_{41}H_{25}BrN_2S$ = 657.62) |
| Sub1-A77 | m/z = 579.07 ($C_{36}H_{22}BrNS$ = 580.54) | Sub1-A78 | m/z = 579.07 ($C_{36}H_{22}BrNS$ = 580.54) |
| Sub1-A79 | m/z = 563.09 ($C_{36}H_{22}BrNO$ = 564.47) | Sub1-A80 | m/z = 563.09 ($C_{36}H_{22}BrNO$ = 564.47) |
| Sub1-A81 | m/z = 563.09 ($C_{36}H_{22}BrNO$ = 564.47) | Sub1-A82 | m/z = 563.09 ($C_{36}H_{22}BrNO$ = 564.47) |
| Sub1-A83 | m/z = 473.08 ($C_{30}H_{20}BrN$ = 474.39) | Sub1-A84 | m/z = 549.11 ($C_{36}H_{24}BrN$ = 550.49) |
| Sub1-A85 | m/z = 523.09 ($C_{34}H_{22}BrN$ = 524.45) | Sub1-A86 | m/z = 524.09 ($C_{33}H_{21}BrN_2$ = 525.44) |
| Sub1-A87 | m/z = 549.11 ($C_{36}H_{24}BrN$ = 550.49) | Sub1-A88 | m/z = 549.11 ($C_{36}H_{24}BrN$ = 550.49) |
| Sub1-A89 | m/z = 625.14 ($C_{42}H_{28}BrN$ = 626.58) | Sub1-A90 | m/z = 625.14 ($C_{42}H_{28}BrN$ = 626.58) |
| Sub1-A91 | m/z = 589.14 ($C_{39}H_{28}BrN$ = 590.55) | Sub1-A92 | m/z = 589.14 ($C_{39}H_{28}BrN$ = 590.55) |
| Sub1-A93 | m/z = 589.14 ($C_{39}H_{28}BrN$ = 590.55) | Sub1-A94 | m/z = 589.14 ($C_{39}H_{28}BrN$ = 590.55) |
| Sub1-A95 | m/z = 713.17 ($C_{49}H_{32}BrN$ = 714.69) | Sub1-A96 | m/z = 713.17 ($C_{49}H_{32}BrN$ = 714.69) |
| Sub1-A97 | m/z = 713.17 ($C_{49}H_{32}BrN$ = 714.69) | Sub1-A98 | m/z = 789.20 ($C_{55}H_{36}BrN$ = 790.79) |
| Sub1-A99 | m/z = 713.17 ($C_{49}H_{32}BrN$ = 714.69) | Sub1-A100 | m/z = 789.20 ($C_{55}H_{36}BrN$ = 790.79) |
| Sub1-A101 | m/z = 711.16 ($C_{49}H_{30}BrN$ = 712.67) | Sub1-A102 | m/z = 711.16 ($C_{49}H_{30}BrN$ = 712.67) |
| Sub1-A103 | m/z = 579.07 ($C_{36}H_{22}BrNS$ = 580.54) | Sub1-A104 | m/z = 579.07 ($C_{36}H_{22}BrNS$ = 580.54) |
| Sub1-A105 | m/z = 579.07 ($C_{36}H_{22}BrNS$ = 580.54) | Sub1-A106 | m/z = 579.07 ($C_{36}H_{22}BrNS$ = 580.54) |
| Sub1-A107 | m/z = 563.09 ($C_{36}H_{22}BrNO$ = 564.47) | Sub1-A108 | m/z = 563.09 ($C_{36}H_{22}BrNO$ = 564.47) |
| Sub1-A109 | m/z = 563.09 ($C_{36}H_{22}BrNO$ = 564.47) | Sub1-A110 | m/z = 563.09 ($C_{36}H_{22}BrNO$ = 564.47) |
| Sub1-C1 | m/z = 397.05 ($C_{24}H_{16}BrN$ = 398.29) | Sub1-C2 | m/z = 473.08 ($C_{30}H_{20}BrN$ = 474.39) |
| Sub1-C3 | m/z = 447.06 ($C_{28}H_{18}BrN$ = 448.35) | Sub1-C4 | m/z = 447.06 ($C_{28}H_{18}BrN$ = 448.35) |
| Sub1-C5 | m/z = 473.08 ($C_{30}H_{20}BrN$ = 474.39) | Sub1-C6 | m/z = 513.11 ($C_{33}H_{24}BrN$ = 514.45) |
| Sub1-C7 | m/z = 513.11 ($C_{33}H_{24}BrN$ = 514.45) | Sub1-C8 | m/z = 513.11 ($C_{33}H_{24}BrN$ = 514.45) |
| Sub1-C9 | m/z = 513.11 ($C_{33}H_{24}BrN$ = 514.45) | Sub1-C10 | m/z = 589.14 ($C_{39}H_{28}BrN$ = 590.55) |
| Sub1-C11 | m/z = 589.14 ($C_{39}H_{28}BrN$ = 590.55) | Sub1-C12 | m/z = 637.14 ($C_{43}H_{28}BrN$ = 638.59) |
| Sub1-C13 | m/z = 637.14 ($C_{43}H_{28}BrN$ = 638.59) | Sub1-C14 | m/z = 635.12 ($C_{43}H_{26}BrN$ = 636.58) |
| Sub1-C15 | m/z = 635.12 ($C_{43}H_{26}BrN$ = 636.58) | Sub1-C16 | m/z = 503.03 ($C_{30}H_{18}BrNS$ = 504.44) |
| Sub1-C17 | m/z = 503.03 ($C_{30}H_{18}BrNS$ = 504.44) | Sub1-C18 | m/z = 487.06 ($C_{30}H_{18}BrNO$ = 488.37) |
| Sub1-C19 | m/z = 487.06 ($C_{30}H_{18}BrNO$ = 488.37) | Sub1-C20 | m/z = 487.06 ($C_{30}H_{18}BrNO$ = 488.37) |
| Sub1-C21 | m/z = 487.06 ($C_{30}H_{18}BrNO$ = 488.37) | | |

II. Synthesis Method of Sub 2

Sub 2 of Reaction Scheme 1 can be synthesized according to, but not limited to, the following Reaction Scheme 27.

<Reaction Scheme 27>

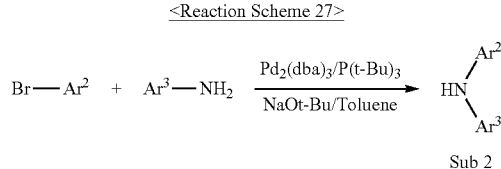

Synthesis Examples of the compounds of Sub 2 will be described in detail.

1. Synthesis Method of Sub 2-6

<Reaction Scheme 28>

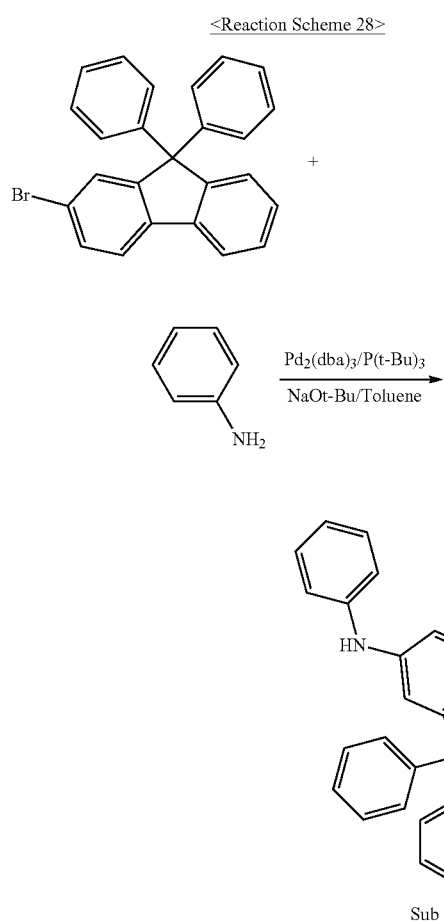

2-bromo-9,9-diphenyl-9H-fluorene (41.72 g, 105 mmol) as the starting material was dissolved in toluene in a round bottom flask, and aniline (19.56 g, 210 mmol), Pd$_2$(dba)$_3$ (2.88 g, 3.2 mmol), 50% P(t-Bu)$_3$ (4.1 ml, 8.4 mmol), and NaOt-Bu (30.28 g, 315 mmol) were added to the reaction solution, followed by stirring at 40° C. Upon completion of the reaction, the reaction product was extracted with CH$_2$Cl$_2$ and water. The extracted organic layer was dried with MgSO$_4$ and concentrated, and then the produced organic material was separated by a silica gel column and recrystallized to obtain 32.25 g of product (yield: 75%).

2. Synthesis Method of Sub 2-7

<Reaction Scheme 29>

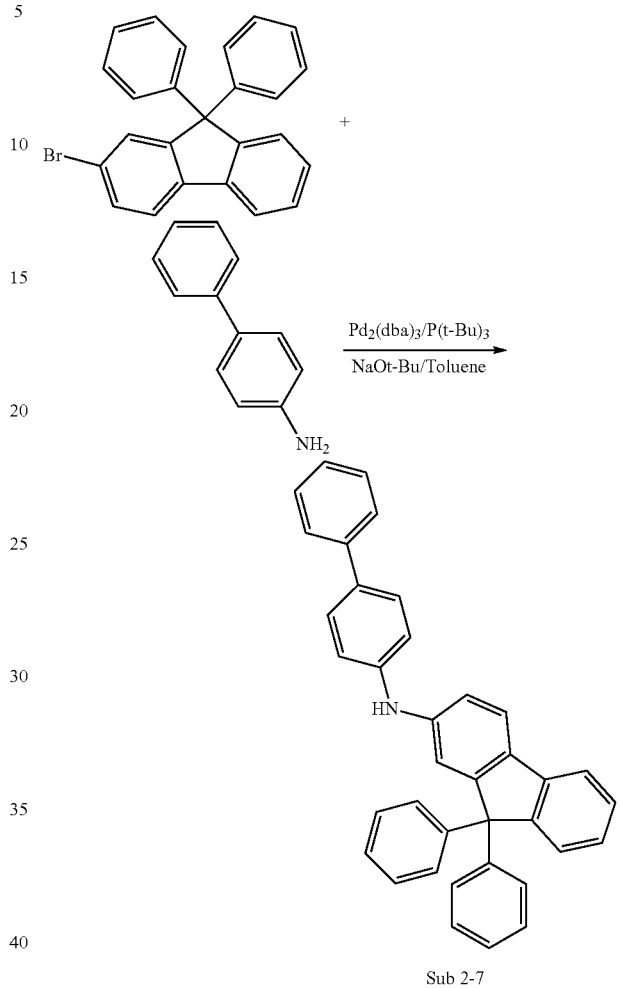

Using 2-bromo-9,9-diphenyl-9H-fluorene (15.63 g, 39.3 mmol) as the starting material and using [1,1'-biphenyl]-4-amine (13.31 g, 78.7 mmol), Pd$_2$(dba)$_3$ (1.08 g, 1.2 mmol), 50% P(t-Bu)$_3$ (1.5 ml, 3.1 mmol), NaOt-Bu (11.34 g, 118 mmol), and toluene, the same procedure as described in the synthesis method of Sub 2-6 was carried out to obtain 14.52 g of product (yield: 76%).

3. Synthesis Method of Sub 2-13

<Reaction Scheme 30>

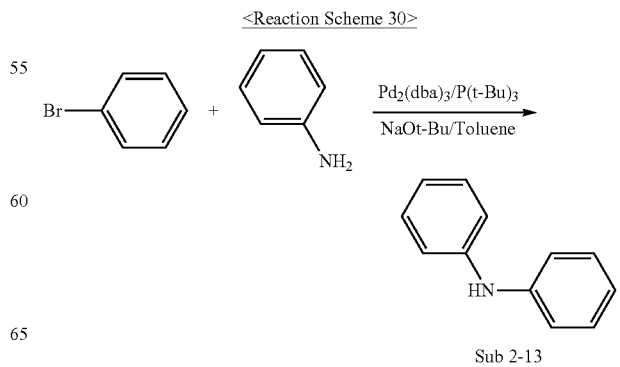

Using bromobenzene (11.82 g, 75.3 mmol) as the starting material and using aniline (14.02 g, 150.6 mmol), Pd$_2$(dba)$_3$ (2.07 g, 2.3 mmol), 50% P(t-Bu)$_3$ (2.9 ml, 6 mmol), NaOt-Bu (21.71 g, 225.8 mmol), and toluene, the same procedure as described in the synthesis method of Sub 2-6 was carried out to obtain 10.19 g of product (yield: 80%).

4. Synthesis Method of Sub 2-16

<Reaction Scheme 31>

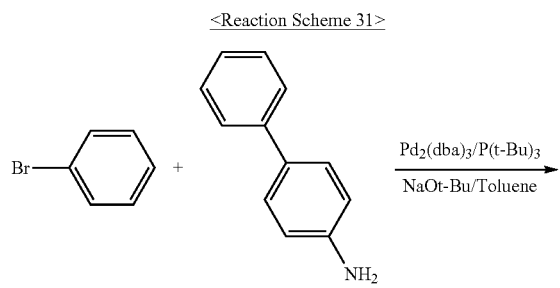

Sub 2-16

Using bromobenzene (14.93 g, 95.1 mmol) as the starting material and using [1,1'-biphenyl]-4-amine (32.18 g, 190.2 mmol), Pd$_2$(dba)$_3$ (2.61 g, 2.9 mmol), 50% P(t-Bu)$_3$ (3.7 ml, 7.6 mmol), NaOt-Bu (27.42 g, 285.3 mmol), and toluene, the same procedure as described in the synthesis method of Sub 2-6 was carried out to obtain 19.36 g of product (yield: 83%).

5. Synthesis Method of Sub 2-17

<Reaction Scheme 32>

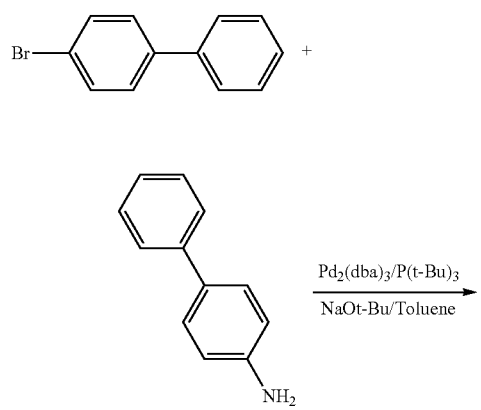

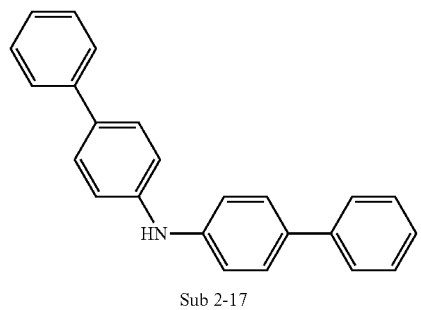

Sub 2-17

Using 4-bromo-1,1'-biphenyl (25.59 g, 109.8 mmol) as the starting material and using [1,1'-biphenyl]-4-amine (37.15 g, 219.6 mmol), Pd$_2$(dba)$_3$ (3.02 g, 3.3 mmol), 50% P(t-Bu)$_3$ (4.3 ml, 8.8 mmol), NaOt-Bu (31.65 g, 329.3 mmol), and toluene, the same procedure as described in the synthesis method of Sub 2-6 was carried out to obtain 27.87 g of product (yield: 79%).

6. Synthesis Method of Sub 2-20

Reaction Scheme 33

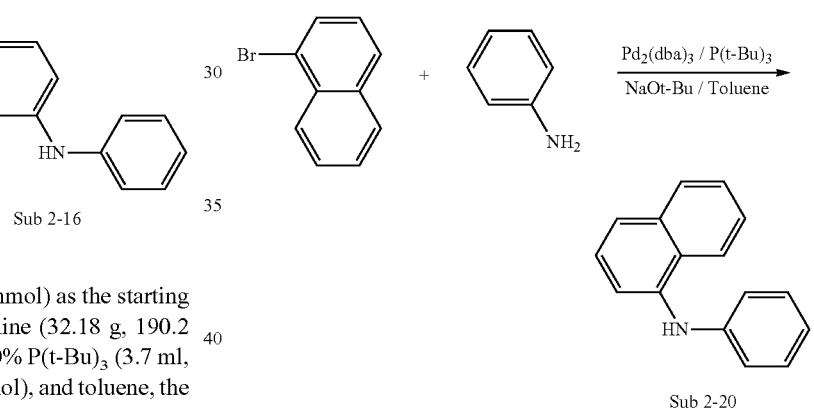

Sub 2-20

Using 1-bromonaphthalene (12.85 g, 62.1 mmol) as the starting material and using aniline (11.56 g, 124.1 mmol), Pd$_2$(dba)$_3$ (1.7 g, 1.9 mmol), 50% P(t-Bu)$_3$ (2.4 ml, 5 mmol), NaOt-Bu (17.89 g, 186.2 mmol), and toluene, the same procedure as described in the synthesis method of Sub 2-6 was carried out to obtain 10.07 g of product (yield: 74%).

7. Synthesis Method of Sub 2-40

<Reaction Scheme 34>

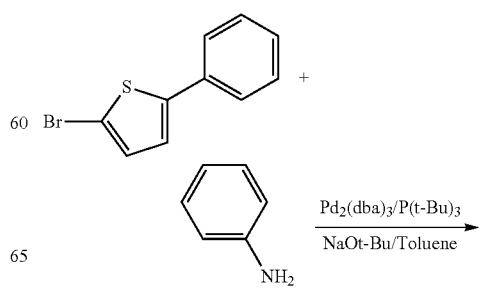

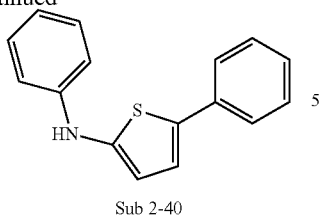

Sub 2-40

Using 2-bromo-5-phenylthiophene (14.67 g, 61.3 mmol) as the starting material and using aniline (11.43 g, 122.7 mmol), Pd$_2$(dba)$_3$ (1.69 g, 1.8 mmol), 50% P(t-Bu)$_3$ (2.4 ml, 4.9 mmol), NaOt-Bu (17.69 g, 184 mmol), and toluene, the same procedure as described in the synthesis method of Sub 2-6 was carried out to obtain 10.95 g of product (yield: 71%).

8. Synthesis Method of Sub 2-70

<Reaction Scheme 35>

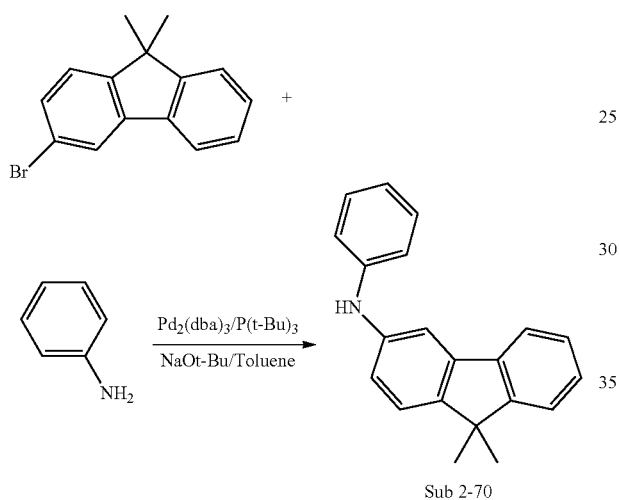

Sub 2-70

Using 3-bromo-9,9-dimethyl-9H-fluorene (15.74 g, 57.6 mmol) as the starting material and using aniline (10.73 g, 115.2 mmol), Pd$_2$(dba)$_3$ (1.58 g, 1.7 mmol), 50% P(t-Bu)$_3$ (2.2 ml, 4.6 mmol), NaOt-Bu (16.61 g, 172.9 mmol), and toluene, the same procedure as described in the synthesis method of Sub 2-6 was carried out to obtain 13.81 g of product (yield: 84%).

9. Synthesis Method of Sub 2-71

<Reaction Scheme 36>

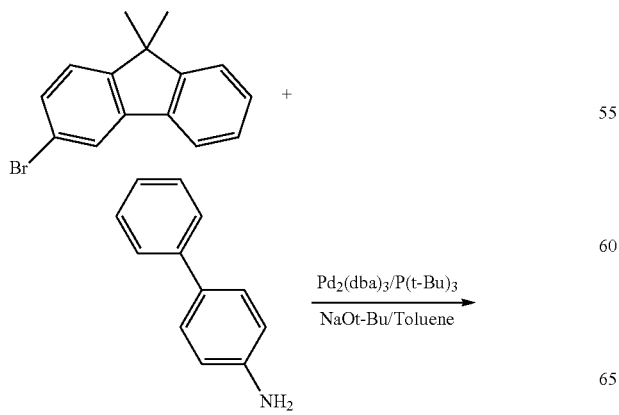

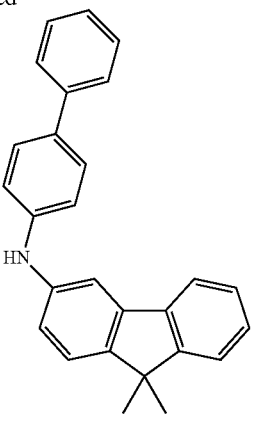

Sub 2-71

Using 3-bromo-9,9-dimethyl-9H-fluorene (9.47 g, 34.7 mmol) as the starting material and using [1,1'-biphenyl]-4-amine (11.73 g, 69.3 mmol), Pd$_2$(dba)$_3$ (0.95 g, 1 mmol), 50% P(t-Bu)$_3$ (1.4 ml, 2.8 mmol), NaOt-Bu (10 g, 104 mmol), and toluene, the same procedure as described in the synthesis method of Sub 2-6 was carried out to obtain 10.28 g of product (yield: 82%).

10. Synthesis Method of Sub 2-74

<Reaction Scheme 37>

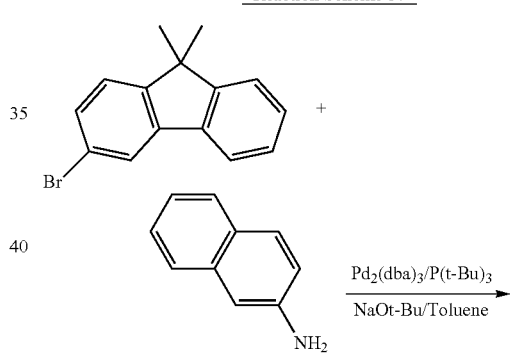

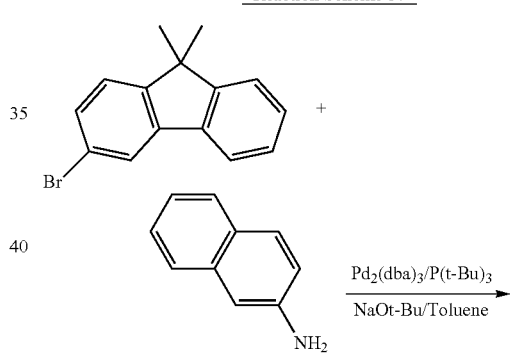

Sub 2-74

Using 3-bromo-9,9-dimethyl-9H-fluorene (11.68 g, 42.8 mmol) as the starting material and using naphthalen-2-amine (12.24 g, 85.5 mmol), Pd$_2$(dba)$_3$ (1.17 g, 1.3 mmol), 50% P(t-Bu)$_3$ (1.7 ml, 3.4 mmol), NaOt-Bu (12.33 g, 128.3 mmol), and toluene, the same procedure as described in the synthesis method of Sub 2-6 was carried out to obtain 11.04 g of product (yield: 77%).

11. Synthesis Method of Sub 2-76

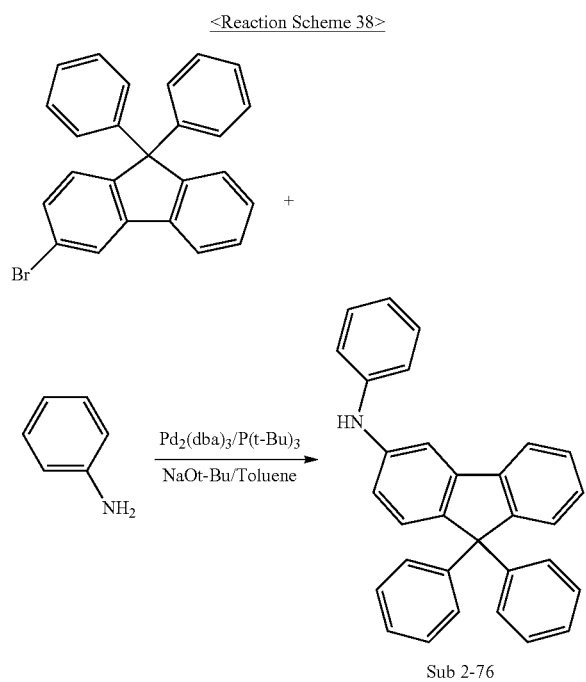 [SMILES: Brc1ccc2c(c1)-c1ccccc1C2(c1ccccc1)c1ccccc1 ; Nc1ccccc1 ; c1ccc(Nc2ccc3c(c2)-c2ccccc2C3(c2ccccc2)c2ccccc2)cc1]

Sub 2-76

Using 3-bromo-9,9-diphenyl-9H-fluorene (14.54 g, 36.6 mmol) as the starting material and using aniline (6.86 g, 73.2 mmol), $Pd_2(dba)_3$ (1.01 g, 1.1 mmol), 50% $P(t-Bu)_3$ (1.4 ml, 2.9 mmol), NaOt-Bu (10.55 g, 109.8 mmol), and toluene, the same procedure as described in the synthesis method of Sub 2-6 was carried out to obtain 11.24 g of product (yield: 75%).

12. Synthesis Method of Sub 2-81

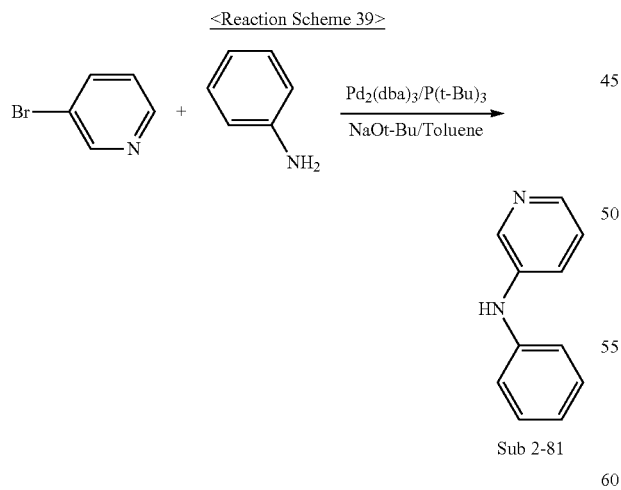

Sub 2-81

Using 3-bromopyridine (13.81 g, 87.4 mmol) as the starting material and using aniline (16.28 g, 174.8 mmol), $Pd_2(dba)_3$ (2.4 g, 2.6 mmol), 50% $P(t-Bu)_3$ (3.4 ml, 7 mmol), NaOt-Bu (25.2 g, 262.2 mmol), and toluene, the same procedure as described in the synthesis method of Sub 2-6 was carried out to obtain 9.97 g of product (yield: 67%).

13. Synthesis Method of Sub 2-82

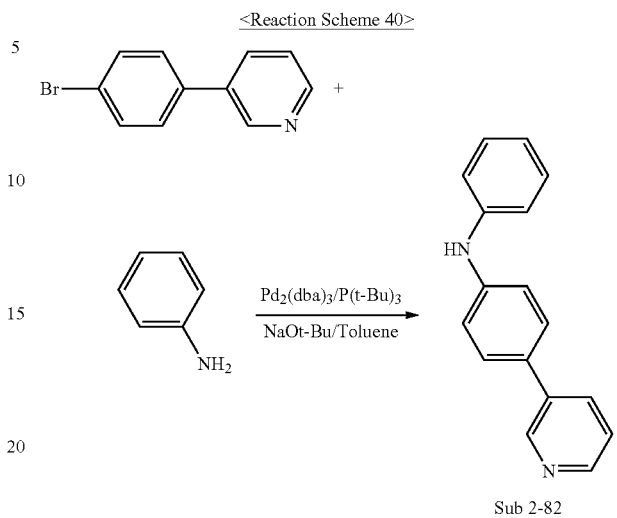

Sub 2-82

Using 3-(4-bromophenyl)pyridine (22.65 g, 96.8 mmol) as the starting material and using aniline (18.02 g, 193.5 mmol), $Pd_2(dba)_3$ (2.66 g, 2.9 mmol), 50% $P(t-Bu)_3$ (3.8 ml, 7.7 mmol), NaOt-Bu (27.9 g, 290.3 mmol), and toluene, the same procedure as described in the synthesis method of Sub 2-6 was carried out to obtain 16.44 g of product (yield: 69%).

Meanwhile, examples of Sub 2 compounds include, but are not limited to, the following compounds, and FD-MS data of the Sub 2 compounds are given in Table 2 below.

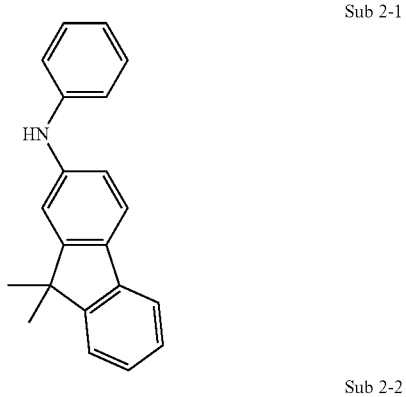

Sub 2-1

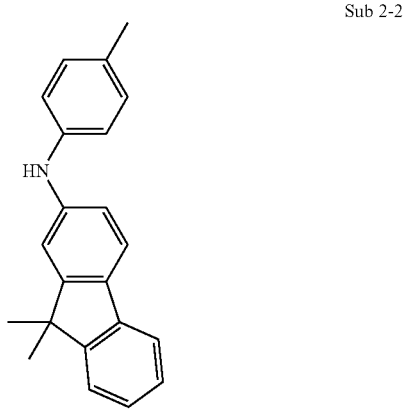

Sub 2-2

-continued
Sub 2-3
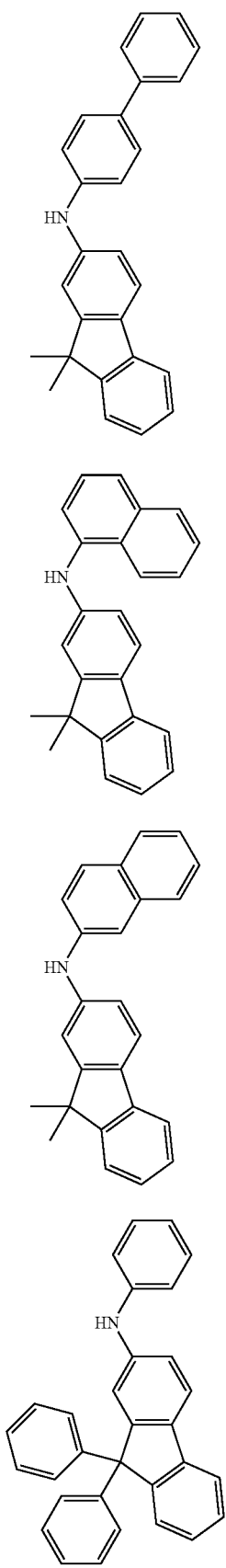
Sub 2-4
Sub 2-5
Sub 2-6
-continued
Sub 2-7
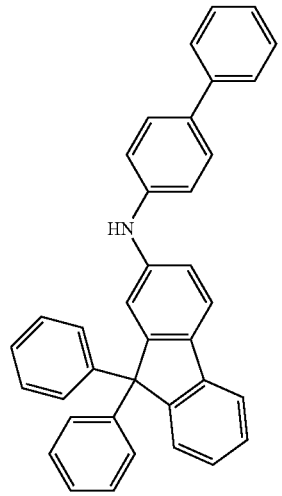
Sub 2-8
Sub 2-9

Sub 2-10
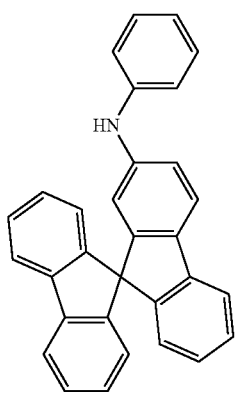
Sub 2-11
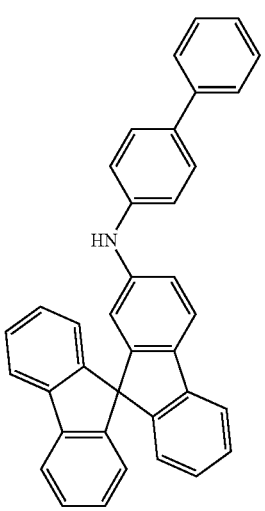
Sub 2-12
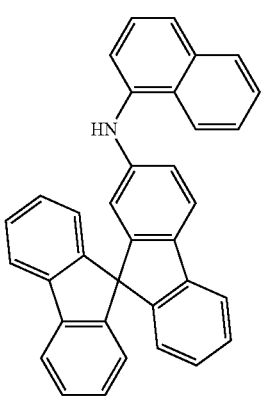
Sub 2-13
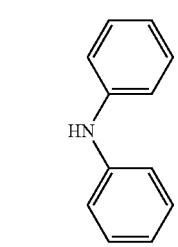
Sub 2-14
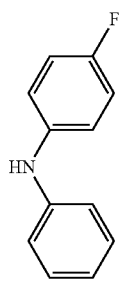
Sub 2-15
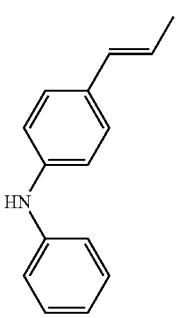
Sub 2-16
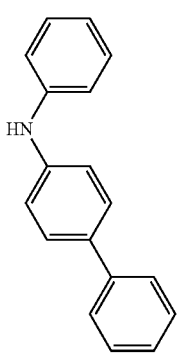
Sub 2-17
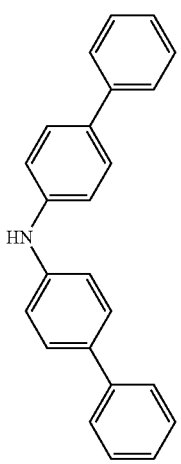

Sub 2-18
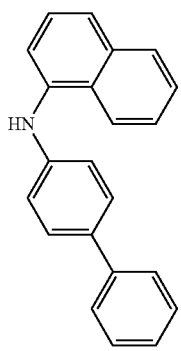
Sub 2-19
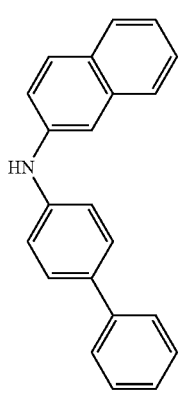
Sub 2-20
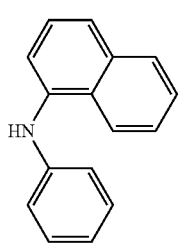
Sub 2-21
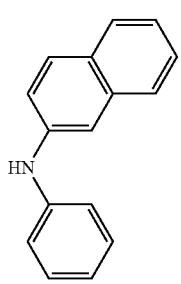
Sub 2-22
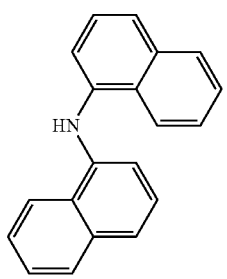
Sub 2-23
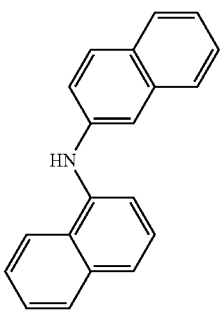
Sub 2-24
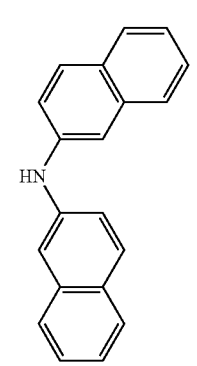
Sub 2-25
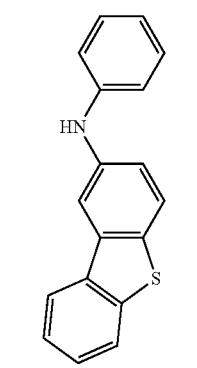
Sub 2-26
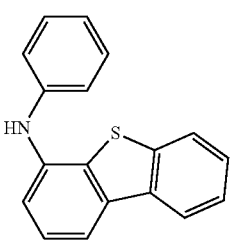

Sub 2-28
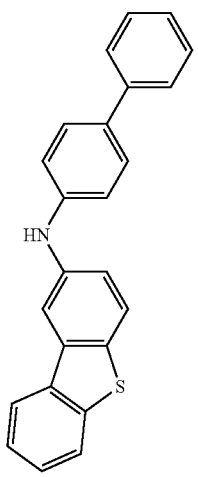
Sub 2-29
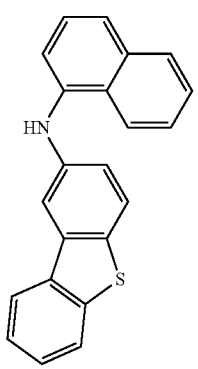
Sub 2-30
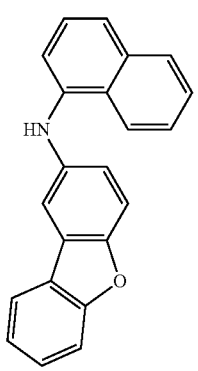
Sub 2-31
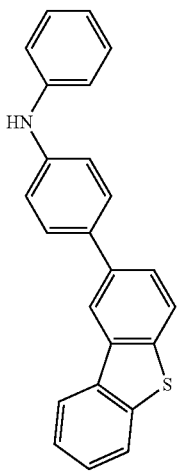
Sub 2-32
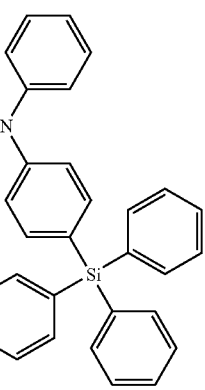
Sub 2-33
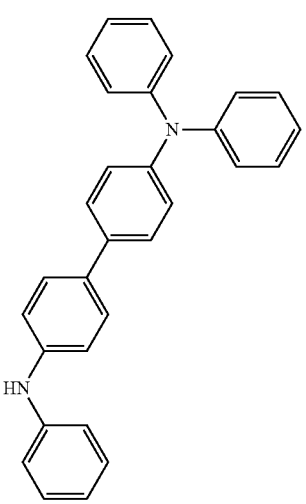

-continued
Sub 2-34
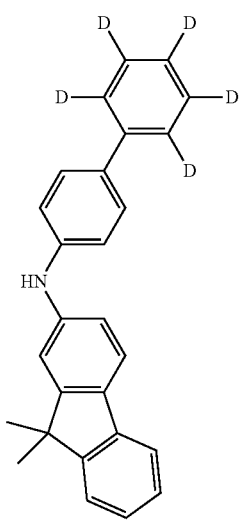
Sub 2-35
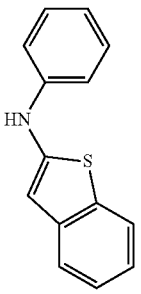
Sub 2-37
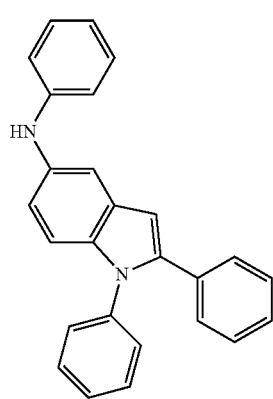
-continued
Sub 2-38
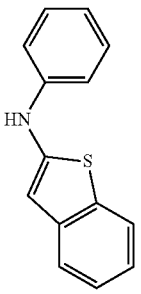
Sub 2-39
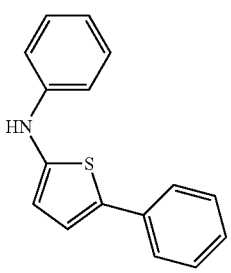
Sub 2-40
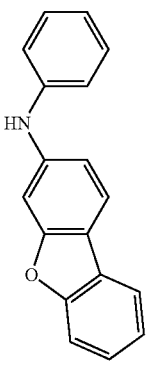
Sub 2-41
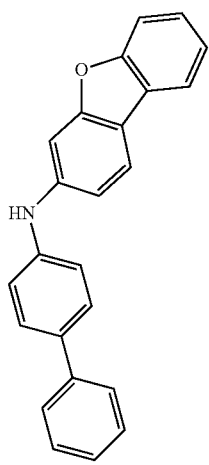
Sub 2-42
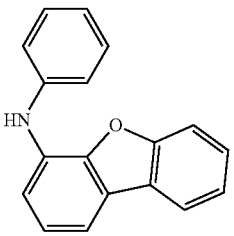

Sub 2-43
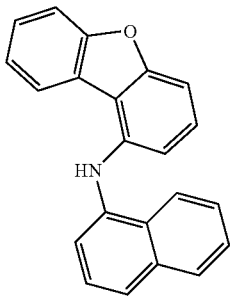
Sub 2-44
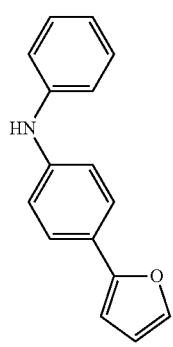
Sub 2-45
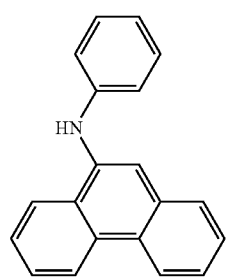
Sub 2-46
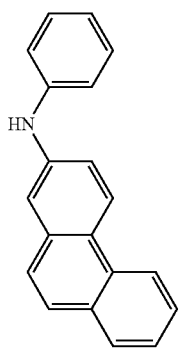
Sub 2-47
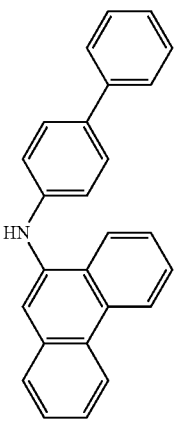
Sub 2-48
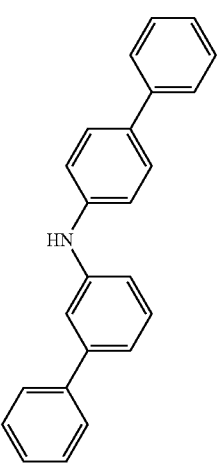
Sub 2-49
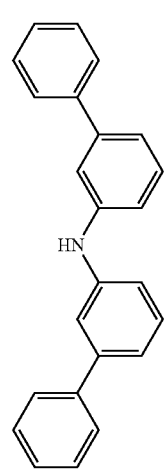

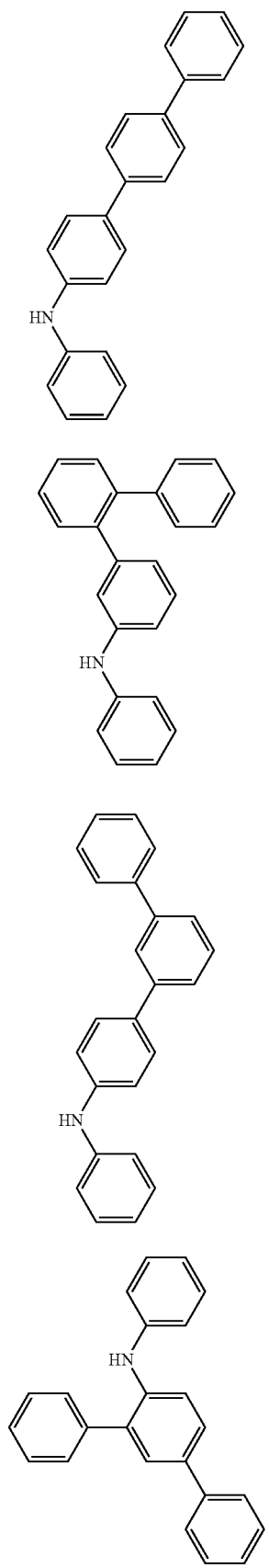
Sub 2-50
Sub 2-51
Sub 2-52
Sub 2-53
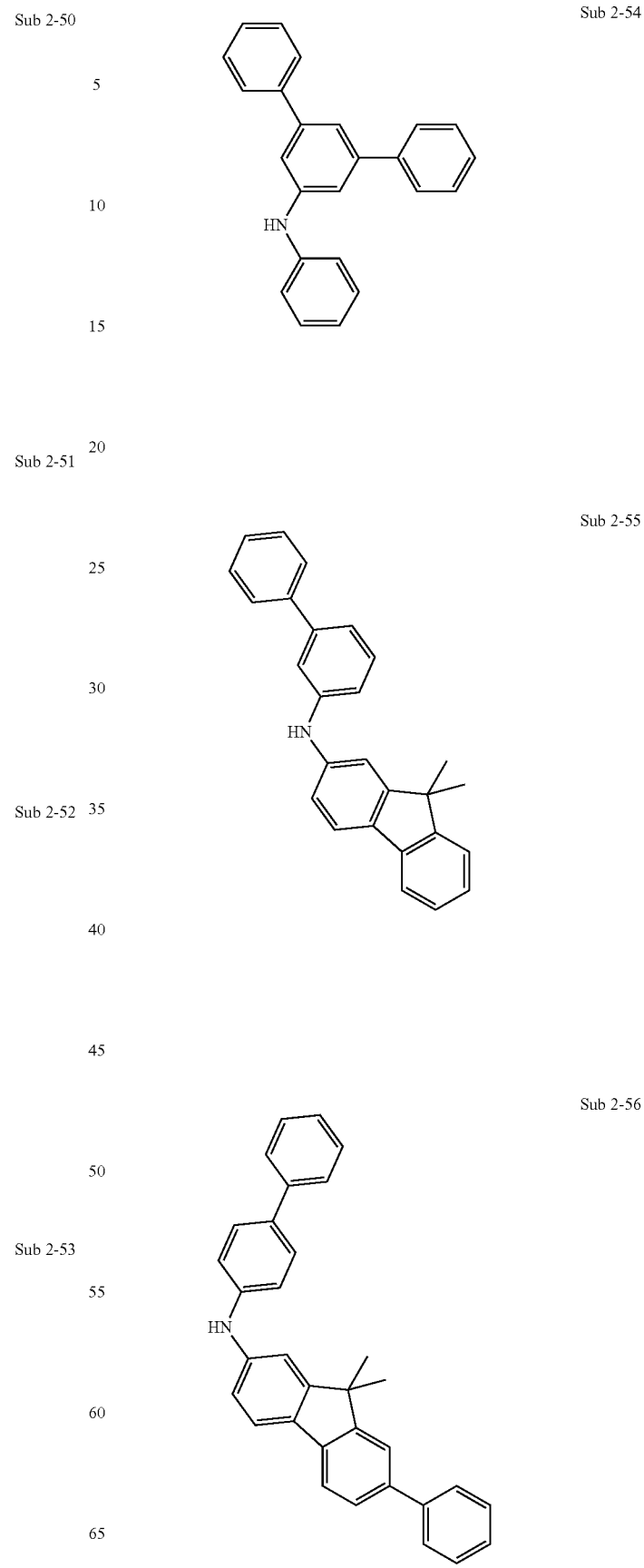
Sub 2-54
Sub 2-55
Sub 2-56

Sub 2-57
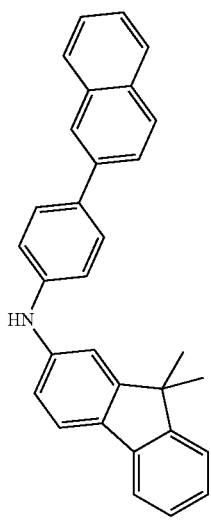
Sub 2-58
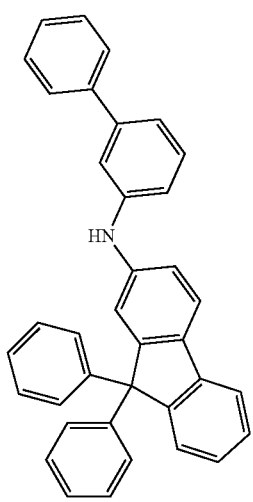
Sub 2-59
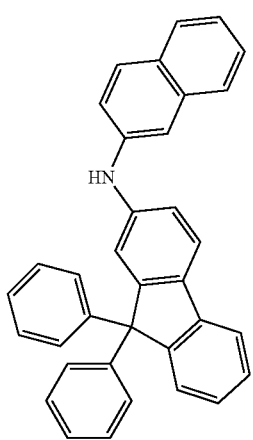
Sub 2-60
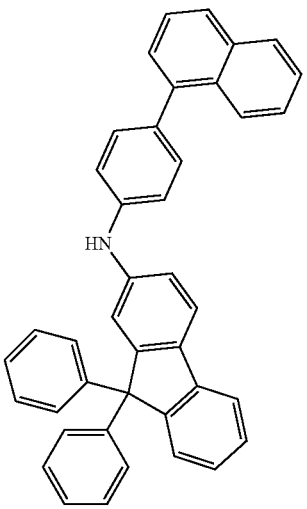
Sub 2-61
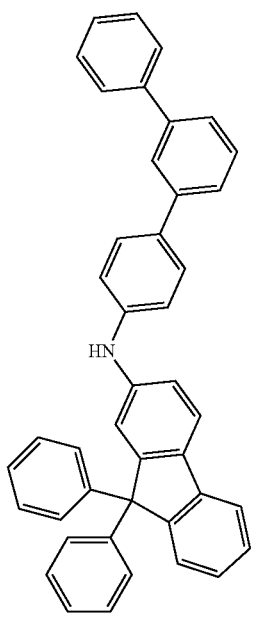
Sub 2-62
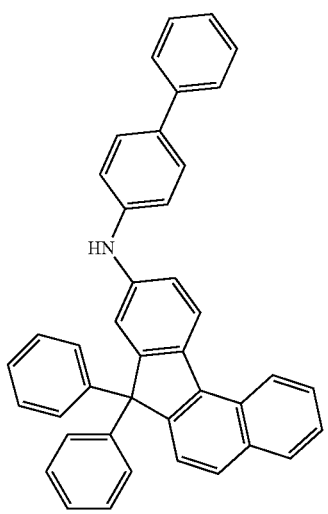

-continued
Sub 2-63
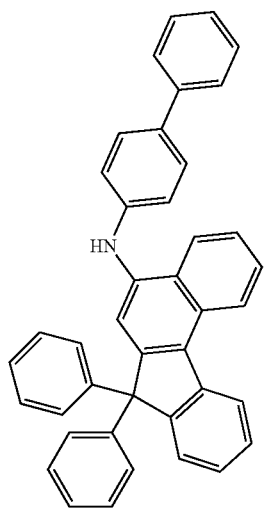
Sub 2-64
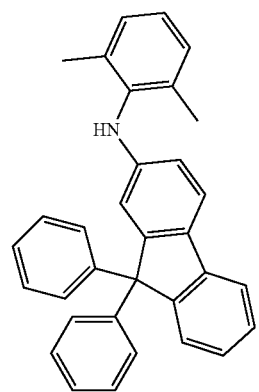
Sub 2-65
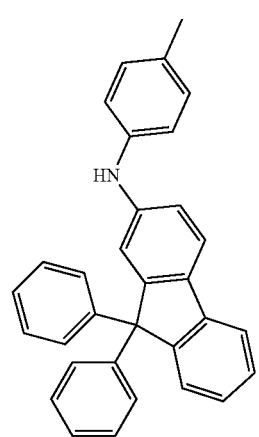
-continued
Sub 2-66
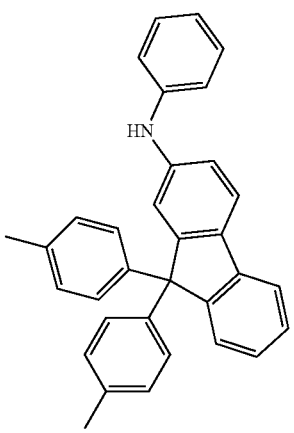
Sub 2-67
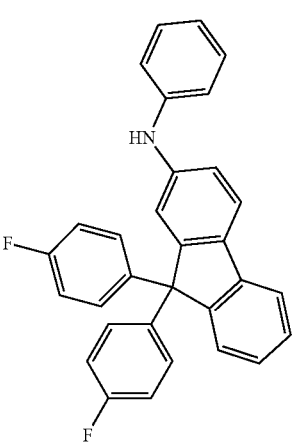
Sub 2-68
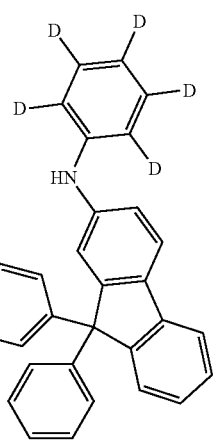
Sub 2-69
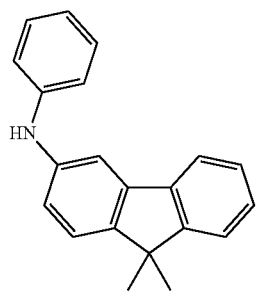

Sub 2-70
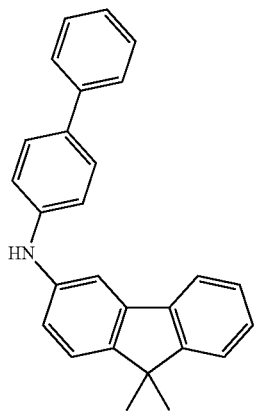
Sub 2-71
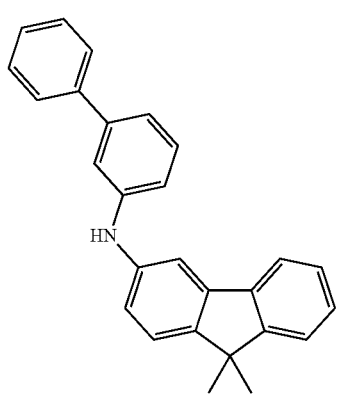
Sub 2-72
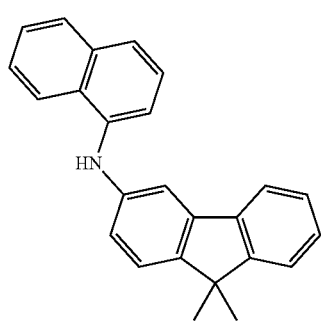
Sub 2-73
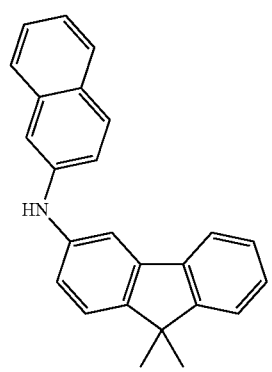
Sub 2-74
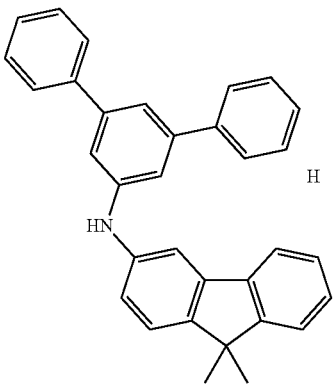
Sub 2-75
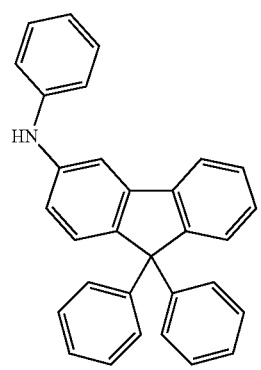
Sub 2-76
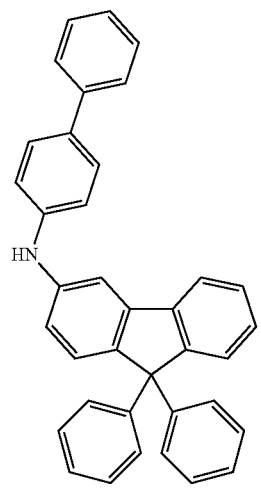
Sub 2-77
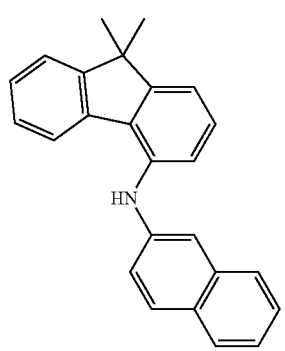

Sub 2-78
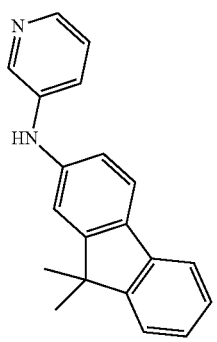
Sub 2-79
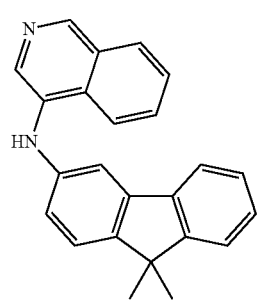
Sub 2-80
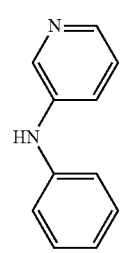
Sub 2-81
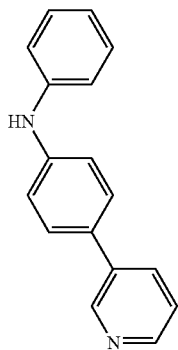
Sub 2-82
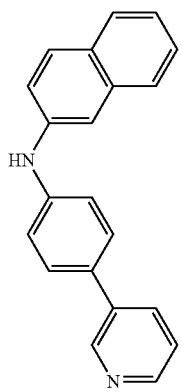
Sub 2-83
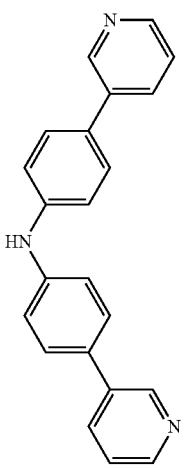
Sub 2-84
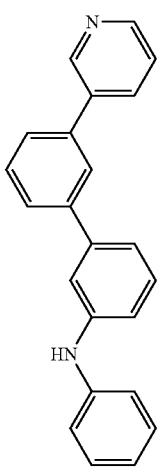
Sub 2-85
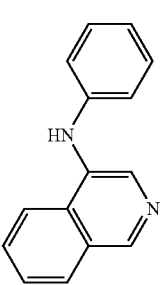

Sub 2-86

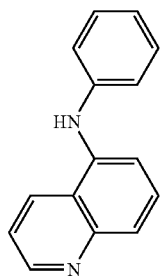

Sub 2-87

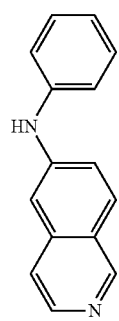

Sub 2-89

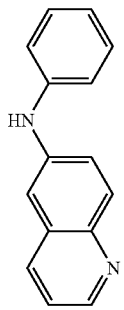

Sub 2-90

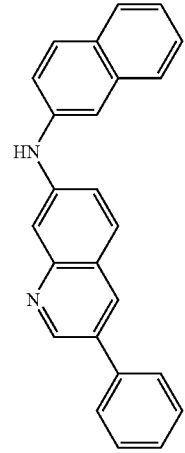

Sub 2-91

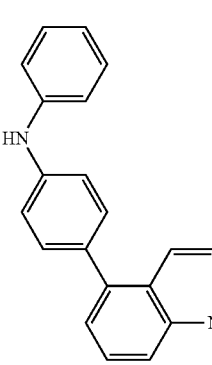

Sub 2-92

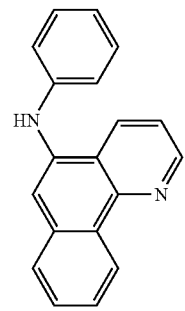

TABLE 2

| Compound | FD-MS | Compound | FD-MS |
|---|---|---|---|
| Sub 2-1 | m/z = 285.15 ($C_{21}H_{19}N$ = 285.38) | Sub 2-2 | m/z = 299.17 ($C_{22}H_{21}N$ = 299.41) |
| Sub 2-3 | m/z = 361.18 ($C_{27}H_{23}N$ = 361.48) | Sub 2-4 | m/z = 335.17 ($C_{25}H_{21}N$ = 335.44) |
| Sub 2-5 | m/z = 335.17 ($C_{25}H_{21}N$ = 335.44) | Sub 2-6 | m/z = 409.18 ($C_{31}H_{23}N$ = 409.52) |
| Sub 2-7 | m/z = 485.21 ($C_{37}H_{27}N$ = 485.62) | Sub 2-8 | m/z = 535.23 ($C_{41}H_{29}N$ = 535.68) |
| Sub 2-9 | m/z = 459.20 ($C_{35}H_{25}N$ = 459.58) | Sub 2-10 | m/z = 407.17 ($C_{31}H_{21}N$ = 407.51) |
| Sub 2-11 | m/z = 483.20 ($C_{37}H_{25}N$ = 483.60) | Sub 2-12 | m/z = 457.18 ($C_{35}H_{23}N$ = 457.56) |
| Sub 2-13 | m/z = 169.09 ($C_{12}H_{11}N$ = 169.22) | Sub 2-14 | m/z = 187.08 ($C_{12}H_{10}FN$ = 187.21) |
| Sub 2-15 | m/z = 209.12 ($C_{15}H_{15}N$ = 209.29) | Sub 2-16 | m/z = 245.12 ($C_{18}H_{15}N$ = 245.32) |
| Sub 2-17 | m/z = 321.15 ($C_{24}H_{19}N$ = 321.41) | Sub 2-18 | m/z = 295.14 ($C_{22}H_{17}N$ = 295.38) |
| Sub 2-19 | m/z = 295.14 ($C_{22}H_{17}N$ = 295.38) | Sub 2-20 | m/z = 219.10 ($C_{16}H_{13}N$ = 219.28) |
| Sub 2-21 | m/z = 219.10 ($C_{16}H_{13}N$ = 219.28) | Sub 2-22 | m/z = 269.12 ($C_{20}H_{15}N$ = 269.34) |
| Sub 2-23 | m/z = 269.12 ($C_{20}H_{15}N$ = 269.34) | Sub 2-24 | m/z = 269.12 ($C_{20}H_{15}N$ = 269.34) |
| Sub 2-25 | m/z = 275.08 ($C_{18}H_{13}NS$ = 275.37) | Sub 2-26 | m/z = 275.08 ($C_{18}H_{13}NS$ = 275.37) |
| Sub 2-27 | m/z = 259.10 ($C_{18}H_{13}NO$ = 259.30) | Sub 2-28 | m/z = 351.11 ($C_{24}H_{17}NS$ = 351.46) |
| Sub 2-30 | m/z = 325.09 ($C_{22}H_{15}NS$ = 325.43) | Sub 2-31 | m/z = 309.12 ($C_{22}H_{15}NO$ = 309.36) |
| Sub 2-32 | m/z = 351.11 ($C_{24}H_{17}NS$ = 351.46) | Sub 2-33 | m/z = 427.18 ($C_{30}H_{25}NSi$ = 427.61) |
| Sub 2-34 | m/z = 412.19 ($C_{30}H_{24}N_2$ = 412.52) | Sub 2-35 | m/z = 366.21 ($C_{27}H_{18}D_5N$ = 366.51) |
| Sub 2-37 | m/z = 410.18 ($C_{30}H_{22}N_2$ = 410.51) | Sub 2-38 | m/z = 360.16 ($C_{26}H_{20}N_2$ = 360.45) |
| Sub 2-39 | m/z = 225.06 ($C_{14}H_{11}NS$ = 225.31) | Sub 2-40 | m/z = 251.08 ($C_{16}H_{13}NS$ = 251.35) |
| Sub 2-41 | m/z = 259.10 ($C_{18}H_{13}NO$ = 259.30) | Sub 2-42 | m/z = 335.13 ($C_{24}H_{17}NO$ = 335.40) |

TABLE 2-continued

| Compound | FD-MS | Compound | FD-MS |
|---|---|---|---|
| Sub 2-43 | m/z = 259.10 ($C_{18}H_{13}NO$ = 259.30) | Sub 2-44 | m/z = 309.12 ($C_{22}H_{15}NO$ = 309.36) |
| Sub 2-45 | m/z = 235.10 ($C_{16}H_{13}NO$ = 235.28) | Sub 2-46 | m/z = 269.12 ($C_{20}H_{15}N$ = 269.34) |
| Sub 2-47 | m/z = 269.12 ($C_{20}H_{15}N$ = 269.34) | Sub 2-48 | m/z = 345.15 ($C_{26}H_{19}N$ = 345.44) |
| Sub 2-49 | m/z = 321.15 ($C_{24}H_{19}N$ = 321.41) | Sub 2-50 | m/z = 321.15 ($C_{24}H_{19}N$ = 321.41) |
| Sub 2-51 | m/z = 321.15 ($C_{24}H_{19}N$ = 321.41) | Sub 2-52 | m/z = 321.15 ($C_{24}H_{19}N$ = 321.41) |
| Sub 2-53 | m/z = 321.15 ($C_{24}H_{19}N$ = 321.41) | Sub 2-54 | m/z = 321.15 ($C_{24}H_{19}N$ = 321.41) |
| Sub 2-55 | m/z = 321.15 ($C_{24}H_{19}N$ = 321.41) | Sub 2-56 | m/z = 361.18 ($C_{27}H_{23}N$ = 361.48) |
| Sub 2-57 | m/z = 437.21 ($C_{33}H_{27}N$ = 437.57) | Sub 2-58 | m/z = 411.20 ($C_{31}H_{25}N$ = 411.54) |
| Sub 2-59 | m/z = 485.21 ($C_{37}H_{27}N$ = 485.62) | Sub 2-60 | m/z = 459.20 ($C_{35}H_{25}N$ = 459.58) |
| Sub 2-61 | m/z = 535.23 ($C_{41}H_{29}N$ = 535.68) | Sub 2-62 | m/z = 561.25 ($C_{43}H_{31}N$ = 561.71) |
| Sub 2-63 | m/z = 535.23 ($C_{41}H_{29}N$ = 535.68) | Sub 2-64 | m/z = 535.23 ($C_{41}H_{29}N$ = 535.68) |
| Sub 2-65 | m/z = 437.21 ($C_{33}H_{27}N$ = 437.57) | Sub 2-66 | m/z = 423.20 ($C_{32}H_{25}N$ = 423.55) |
| Sub 2-67 | m/z = 437.21 ($C_{33}H_{27}N$ = 437.57) | Sub 2-68 | m/z = 445.16 ($C_{31}H_{21}F_2N$ = 445.50) |
| Sub 2-69 | m/z = 414.21 ($C_{31}H_{18}D_5N$ = 414.55) | Sub 2-70 | m/z = 285.15 ($C_{21}H_{19}N$ = 285.38) |
| Sub 2-71 | m/z = 361.18 ($C_{27}H_{23}N$ = 361.48) | Sub 2-72 | m/z = 361.18 ($C_{27}H_{23}N$ = 361.48) |
| Sub 2-73 | m/z = 335.17 ($C_{25}H_{21}N$ = 335.44) | Sub 2-74 | m/z = 335.17 ($C_{25}H_{21}N$ = 335.44) |
| Sub 2-75 | m/z = 437.21 ($C_{33}H_{27}N$ = 437.57) | Sub 2-76 | m/z = 409.18 ($C_{31}H_{23}N$ = 409.52) |
| Sub 2-77 | m/z = 485.21 ($C_{37}H_{27}N$ = 485.62) | Sub 2-78 | m/z = 335.17 ($C_{25}H_{21}N$ = 335.44) |
| Sub 2-79 | m/z = 286.15 ($C_{20}H_{18}N_2$ = 286.37) | Sub 2-80 | m/z = 336.16 ($C_{24}H_{20}N_2$ = 336.43) |
| Sub 2-81 | m/z = 170.08 ($C_{11}H_{10}N_2$ = 170.21) | Sub 2-82 | m/z = 246.12 ($C_{17}H_{14}N_2$ = 246.31) |
| Sub 2-83 | m/z = 296.13 ($C_{21}H_{16}N_2$ = 296.37) | Sub 2-84 | m/z = 323.14 ($C_{22}H_{17}N_3$ = 323.39) |
| Sub 2-85 | m/z = 322.15 ($C_{23}H_{18}N_2$ = 322.40) | Sub 2-86 | m/z = 220.10 ($C_{15}H_{12}N_2$ = 220.27) |
| Sub 2-87 | m/z = 220.10 ($C_{15}H_{12}N_2$ = 220.27) | Sub 2-88 | m/z = 220.10 ($C_{15}H_{12}N_2$ = 220.27) |
| Sub 2-89 | m/z = 220.10 ($C_{15}H_{12}N_2$ = 220.27) | Sub 2-90 | m/z = 346.15 ($C_{25}H_{18}N_2$ = 346.42) |
| Sub 2-91 | m/z = 296.13 ($C_{21}H_{16}N_2$ = 296.37) | Sub 2-92 | m/z = 270.12 ($C_{19}H_{14}N_2$ = 270.33) |

III. Synthesis Method of Final Product

Sub 2 (1 eq.) was dissolved in toluene in a round bottom flask, and Sub 1 (1.2 eq.), $Pd_2(dba)_3$ (0.03 eq.), $P(t-Bu)_3$ (0.08 eq.), NaOt-Bu (3 eq.) were added to the reaction solution, followed by stirring at 100° C. Upon completion of the reaction, the reaction product was extracted with $CH_2Cl_2$ and water. The extracted organic layer was dried with $MgSO_4$ and concentrated, and then the produced organic material was separated by a silica gel column and recrystallized to obtain Final Product.

1. Synthesis Method of Product A17

<Reaction Scheme 41>

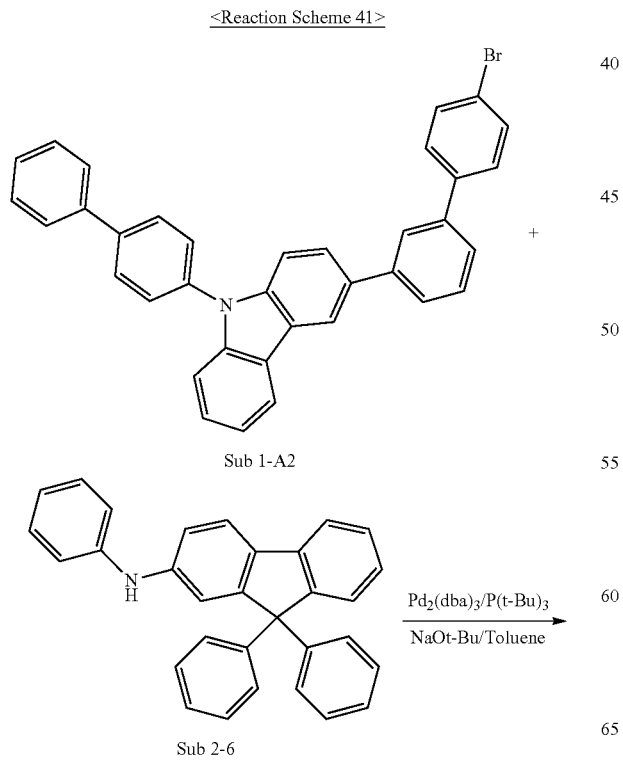

-continued

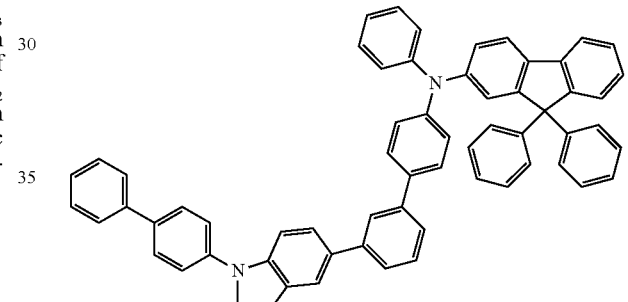

A17

The obtained Sub 2-6 (4.46 g, 10.9 mmol) was dissolved in toluene in a round bottom flask, and Sub 1-A2 (7.19 g, 13.1 mmol), $Pd_2(dba)_3$ (0.3 g, 0.3 mmol), 50% $P(t-Bu)_3$ (0.4 ml, 0.9 mmol), and NaOt-Bu (3.14 g, 32.7 mmol) were added to the reaction solution, followed by stirring at 100° C. Upon completion of the reaction, the reaction product was extracted with $CH_2Cl_2$ and water. The extracted organic layer was dried with $MgSO_4$ and concentrated, and then the produced organic material was separated by a silica gel column and recrystallized to obtain 6.8 g of product (yield: 71%).

2. Synthesis Method of Product A21

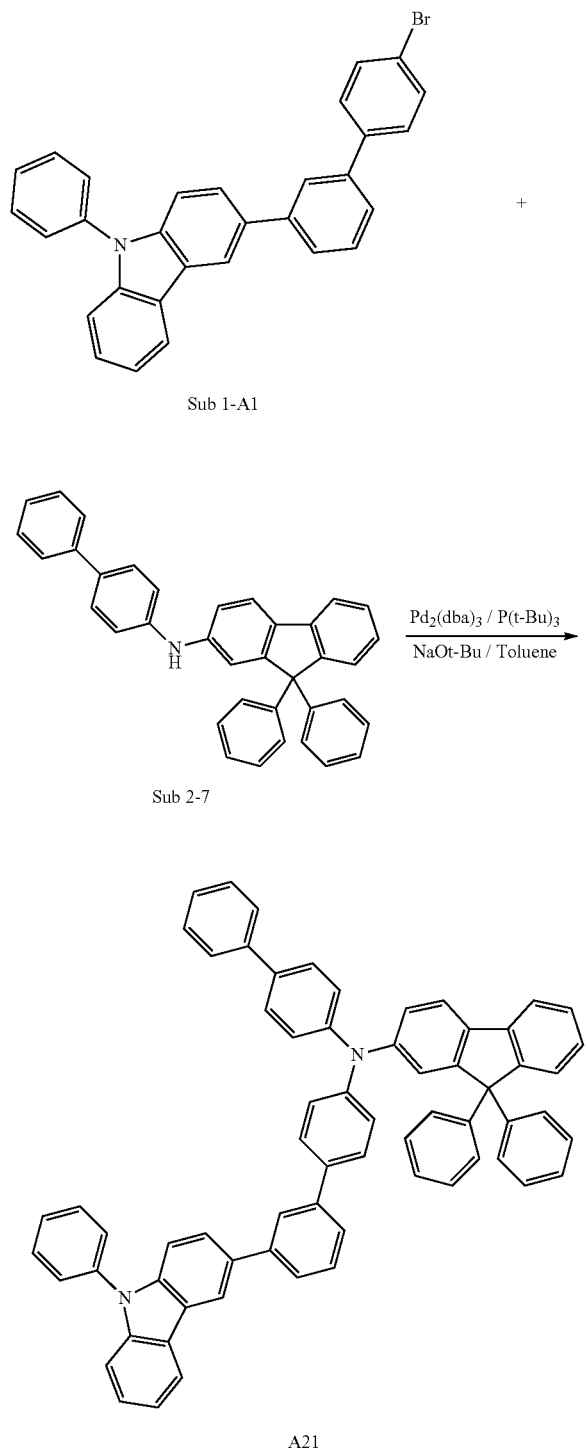

Using the obtained Sub 2-7 (7.58 g, 15.6 mmol) plus Sub 1-A1 (8.89 g, 18.7 mmol), Pd$_2$(dba)$_3$ (0.43 g, 0.5 mmol), 50% P(t-Bu)$_3$ (0.6 ml, 1.2 mmol), NaOt-Bu (4.5 g, 46.8 mmol), and toluene, the same procedure as described in the synthesis method of Product A17 was carried out to obtain 10.02 g of product (yield: 73%).

3. Synthesis Method of Product A162

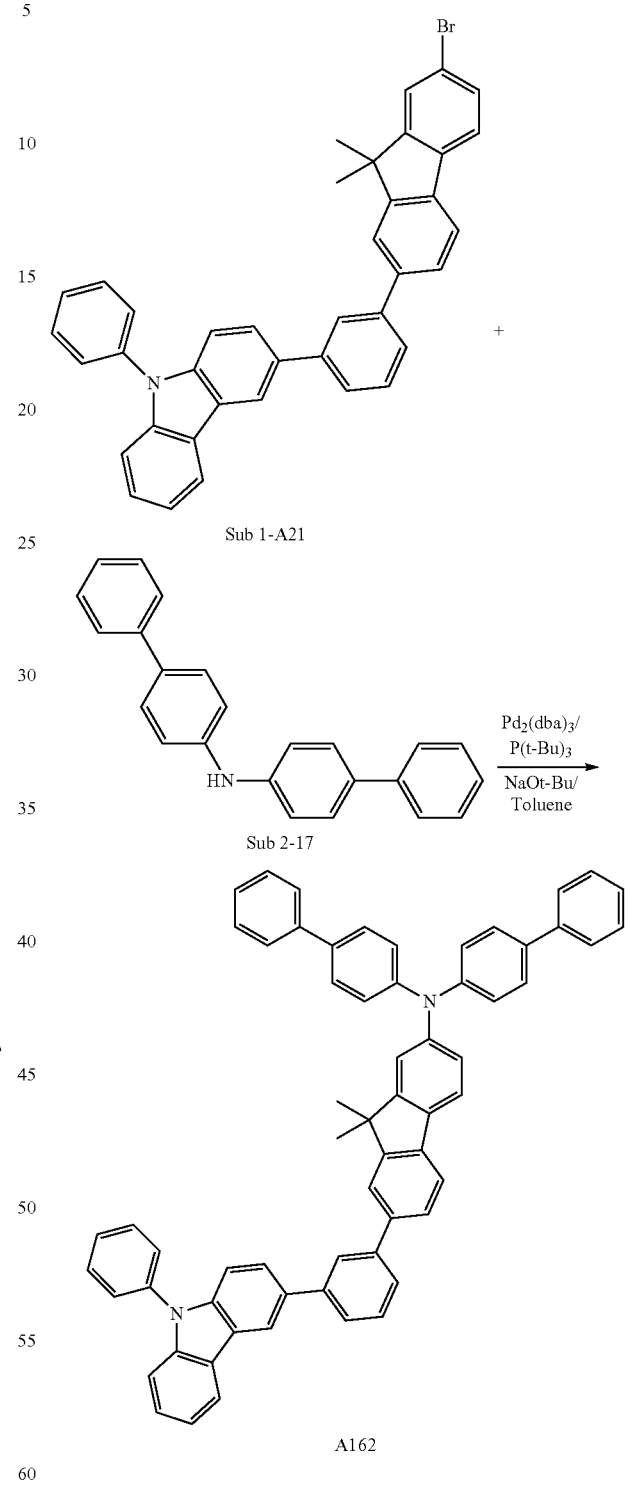

Using the obtained Sub 2-17 (5.68 g, 17.7 mmol) plus Sub 1-A21 (12.52 g, 21.2 mmol), Pd$_2$(dba)$_3$ (0.49 g, 0.5 mmol), 50% P(t-Bu)$_3$ (0.7 ml, 1.4 mmol), NaOt-Bu (5.1 g, 53 mmol), and toluene, the same procedure as described in the synthesis method of Product A17 was carried out to obtain 10.28 g of product (yield: 70%).

4. Synthesis Method of Product A183
Reaction Scheme 44
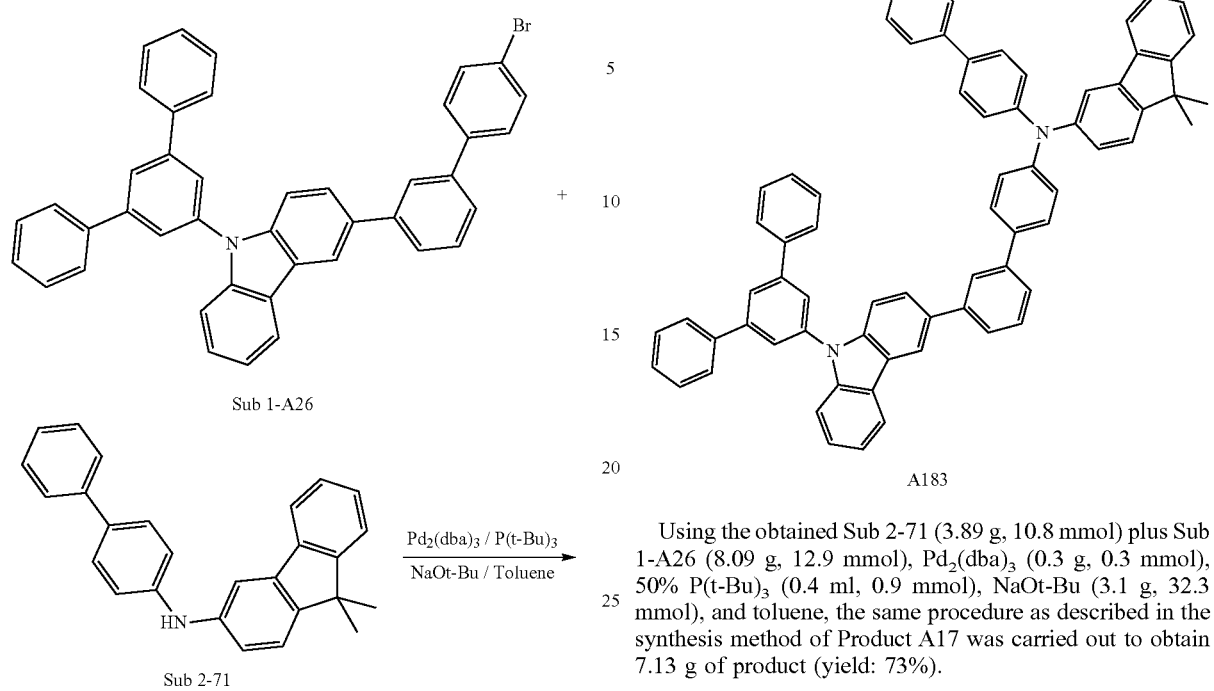
Using the obtained Sub 2-71 (3.89 g, 10.8 mmol) plus Sub 1-A26 (8.09 g, 12.9 mmol), Pd$_2$(dba)$_3$ (0.3 g, 0.3 mmol), 50% P(t-Bu)$_3$ (0.4 ml, 0.9 mmol), NaOt-Bu (3.1 g, 32.3 mmol), and toluene, the same procedure as described in the synthesis method of Product A17 was carried out to obtain 7.13 g of product (yield: 73%).
5. Synthesis Method of Product A191
<Reaction Scheme 45>
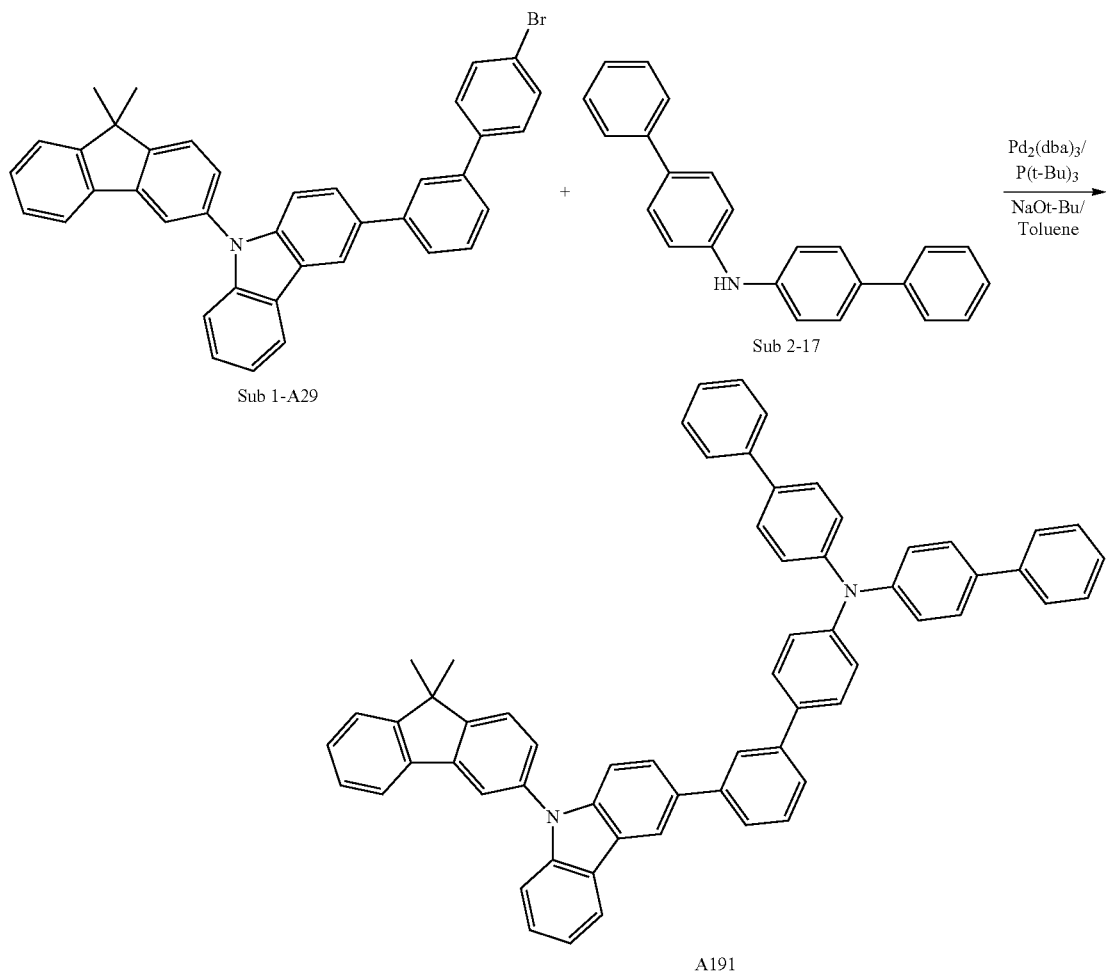

Using the obtained Sub 2-17 (3.58 g, 11.1 mmol) plus Sub 1-A29 (7.89 g, 13.4 mmol), Pd$_2$(dba)$_3$ (0.31 g, 0.3 mmol), 50% P(t-Bu)$_3$ (0.4 ml, 0.9 mmol), NaOt-Bu (3.21 g, 33.4 mmol), and toluene, the same procedure as described in the synthesis method of Product A17 was carried out to obtain 7.04 g of product (yield: 76%).

6. Synthesis Method of Product A203

Reaction Scheme 46

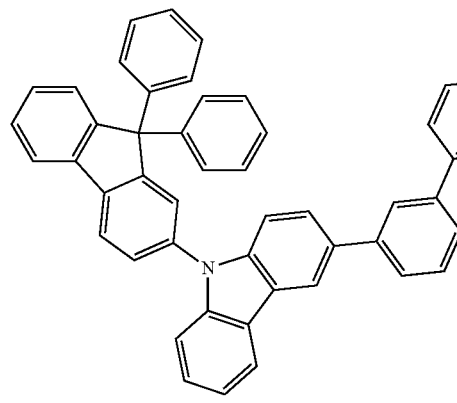

Sub 1-A35

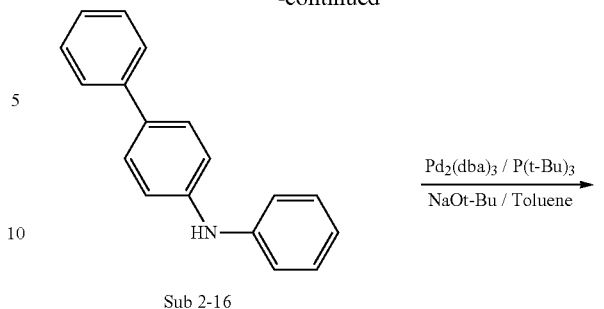

Sub 2-16

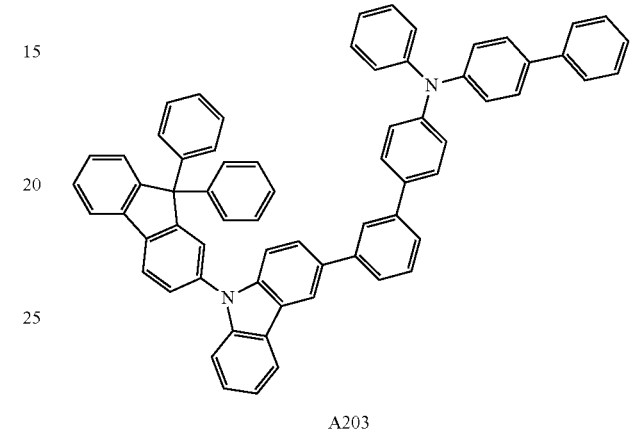

A203

Using the obtained Sub 2-16 (2.67 g, 10.9 mmol) plus Sub 1-A35 (9.33 g, 13.1 mmol), Pd$_2$(dba)$_3$ (0.3 g, 0.3 mmol), 50% P(t-Bu)$_3$ (0.4 ml, 0.9 mmol), NaOt-Bu (3.14 g, 32.7 mmol), and toluene, the same procedure as described in the synthesis method of Product A17 was carried out to obtain 6.79 g of product (yield: 71%).

7. Synthesis Method of Product A210

<Reaction Scheme 47>

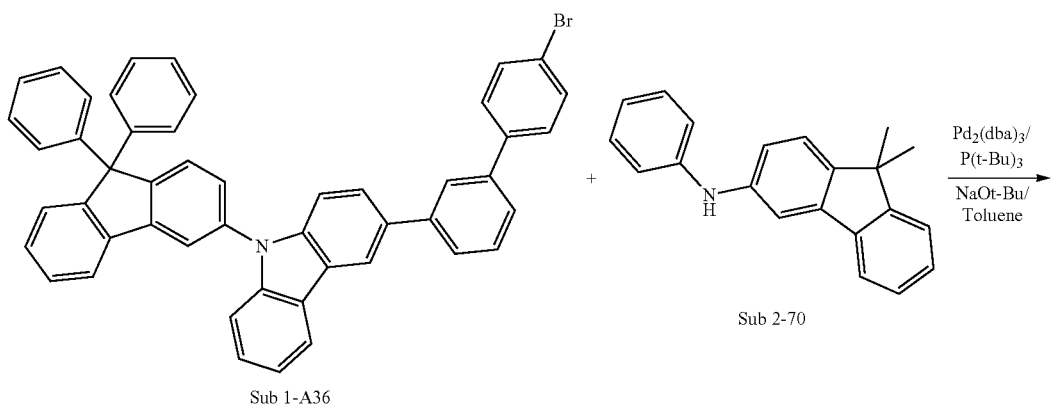

Sub 1-A36

Sub 2-70

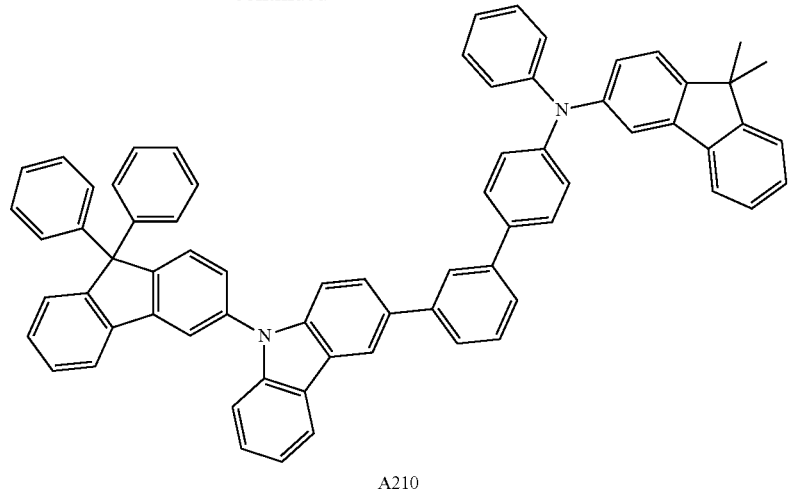
A210
Using the obtained Sub 2-70 (3.04 g, 10.7 mmol) plus Sub 1-A36 (9.14 g, 12.8 mmol), Pd$_2$(dba)$_3$ (0.29 g, 0.3 mmol), 50% P(t-Bu)$_3$ (0.4 ml, 0.9 mmol), NaOt-Bu (3.07 g, 32 mmol), and toluene, the same procedure as described in the synthesis method of Product A17 was carried out to obtain 7.25 g of product (yield: 74%).
8. Synthesis Method of Product A216
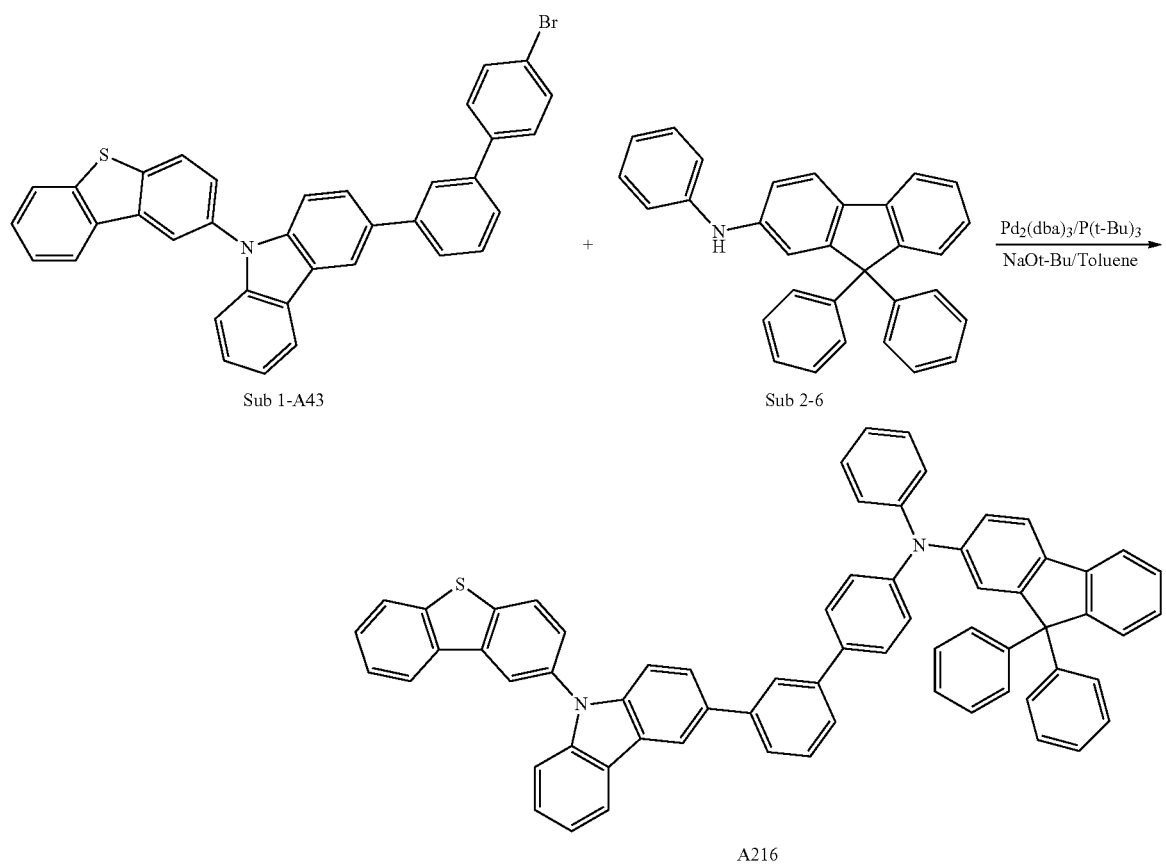

Using the obtained Sub 2-6 (4.45 g, 10.9 mmol) plus Sub 1-A43 (7.57 g, 13 mmol), Pd$_2$(dba)$_3$ (0.3 g, 0.3 mmol), 50% P(t-Bu)$_3$ (0.4 ml, 0.9 mmol), NaOt-Bu (3.13 g, 32.6 mmol), and toluene, the same procedure as described in the synthesis method of Product A17 was carried out to obtain 6.82 g of product (yield: 69%).

9. Synthesis Method of Product A219

<Reaction Scheme 49>

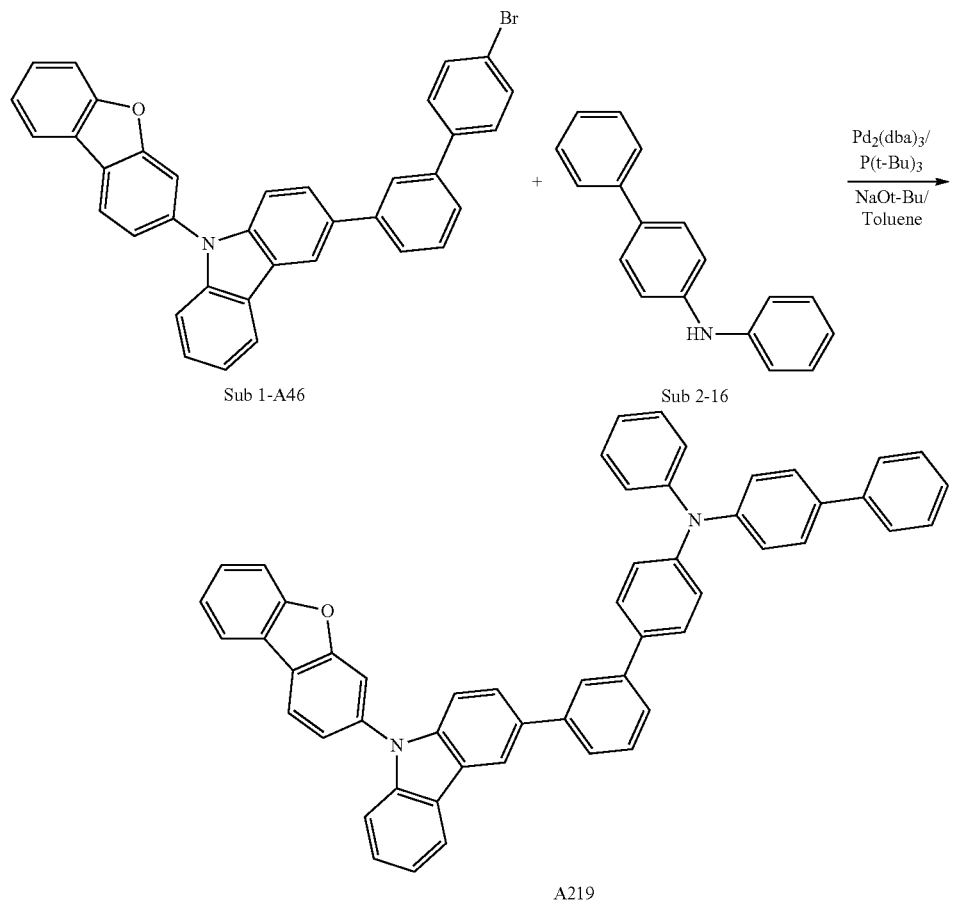

A219

Using the obtained Sub 2-16 (3.17 g, 12.9 mmol) plus Sub 1-A46 (8.75 g, 15.5 mmol), Pd$_2$(dba)$_3$ (0.35 g, 0.4 mmol), 50% P(t-Bu)$_3$ (0.5 ml, 1 mmol), NaOt-Bu (3.73 g, 38.8 mmol), and toluene, the same procedure as described in the synthesis method of Product A17 was carried out to obtain 6.97 g of product (yield: 74%).

10. Synthesis Method of Product A230

<Reaction Scheme 50>

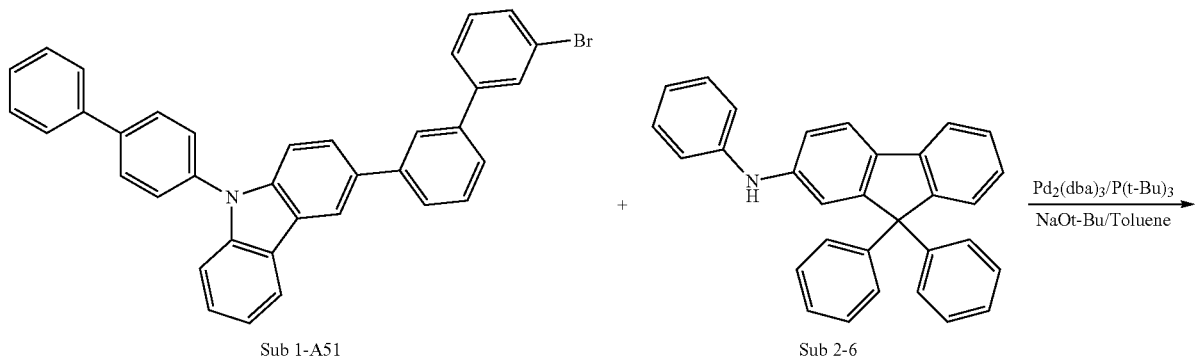

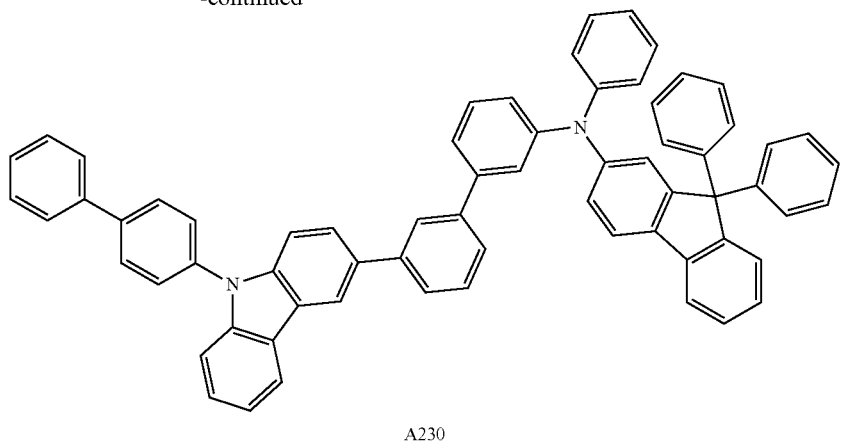

A230

Using the obtained Sub 2-6 (4.63 g, 11.3 mmol) plus Sub 1-A51 (7.47 g, 13.6 mmol), Pd$_2$(dba)$_3$ (0.31 g, 0.3 mmol), 50% P(t-Bu)$_3$ (0.4 ml, 0.9 mmol), NaOt-Bu (3.26 g, 33.9 mmol), and toluene, the same procedure as described in the synthesis method of Product A17 was carried out to obtain 7.16 g of product (yield: 72%).

11. Synthesis Method of Product A270

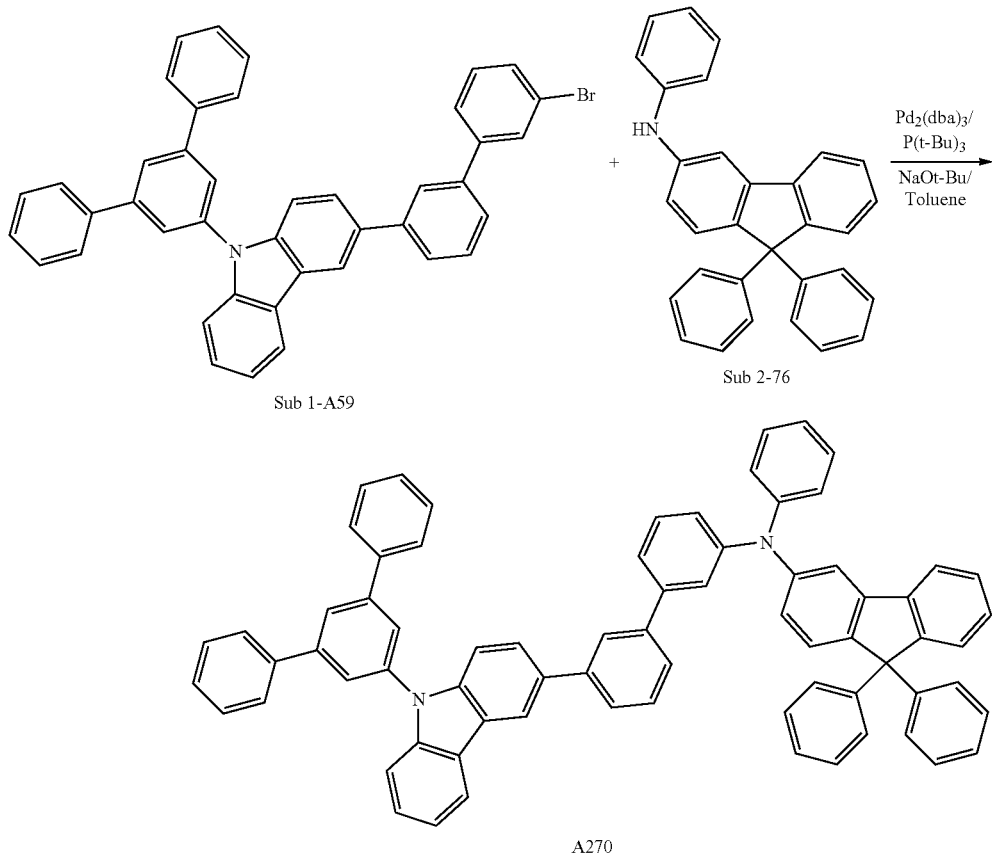

A270

Using the obtained Sub 2-76 (4.27 g, 10.4 mmol) plus Sub 1-A59 (7.84 g, 12.5 mmol), Pd$_2$(dba)$_3$ (0.29 g, 0.3 mmol), 50% P(t-Bu)$_3$ (0.4 ml, 0.8 mmol), NaOt-Bu (3.01 g, 31.3 mmol), and toluene, the same procedure as described in the synthesis method of Product A17 was carried out to obtain 6.47 g of product (yield: 65%).

12. Synthesis Method of Product A277
<Reaction Scheme 52>
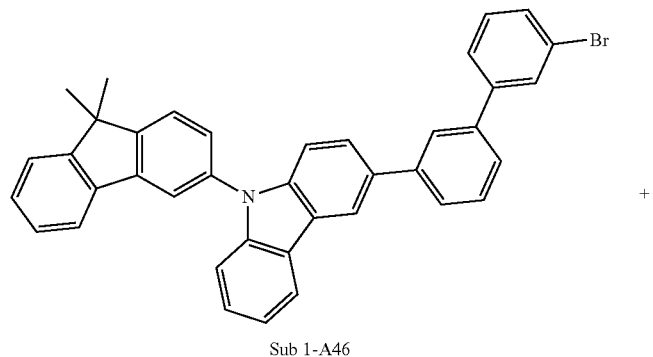
Sub 1-A46
+
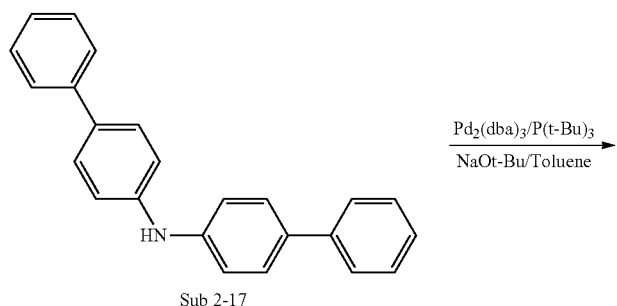
Sub 2-17
$\xrightarrow{\text{Pd}_2(\text{dba})_3/\text{P(t-Bu)}_3}{\text{NaOt-Bu/Toluene}}$
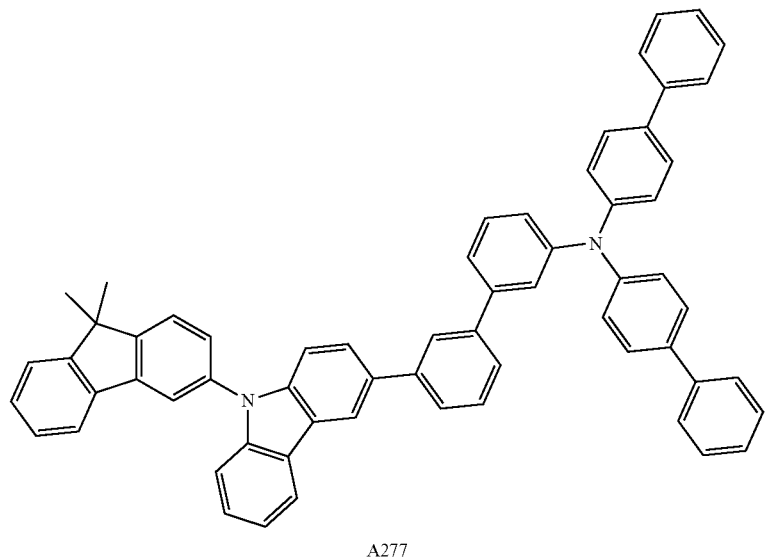
A277
Using the obtained Sub 2-17 (3.71 g, 11.5 mmol) plus Sub 1-A64 (8.18 g, 13.9 mmol), Pd₂(dba)₃ (0.32 g, 0.3 mmol), 50% P(t-Bu)₃ (0.5 ml, 0.9 mmol), NaOt-Bu (3.33 g, 34.6 mmol), and toluene, the same procedure as described in the synthesis method of Product A17 was carried out to obtain 7.39 g of product (yield: 77%).

13. Synthesis Method of Product A285
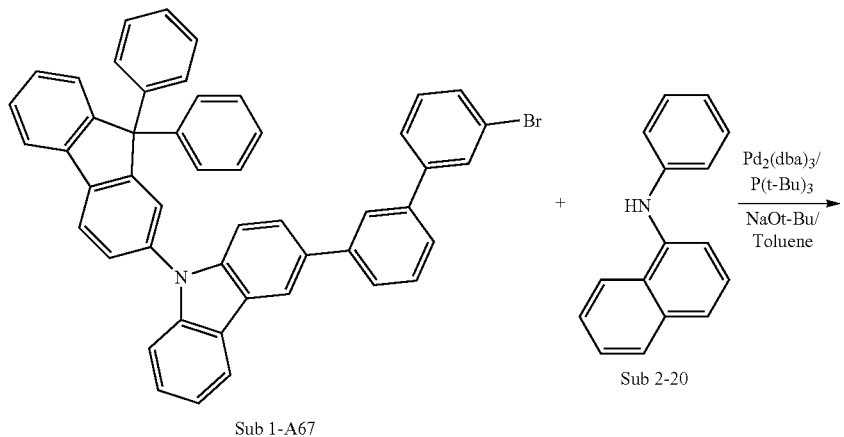
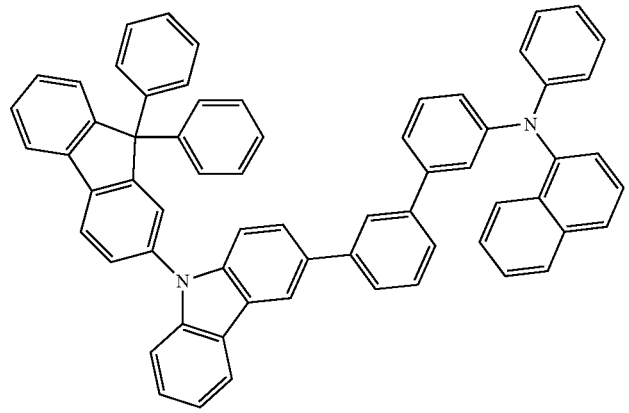
Using the obtained Sub 2-20 (2.46 g, 11.2 mmol) plus Sub 1-A67 (9.62 g, 13.5 mmol), Pd$_2$(dba)$_3$ (0.31 g, 0.3 mmol), 50% P(t-Bu)$_3$ (0.4 ml, 0.9 mmol), NaOt-Bu (3.23 g, 33.7 mmol), and toluene, the same procedure as described in the synthesis method of Product A17 was carried out to obtain 6.99 g of product (yield: 73%).
14. Synthesis Method of Product A292
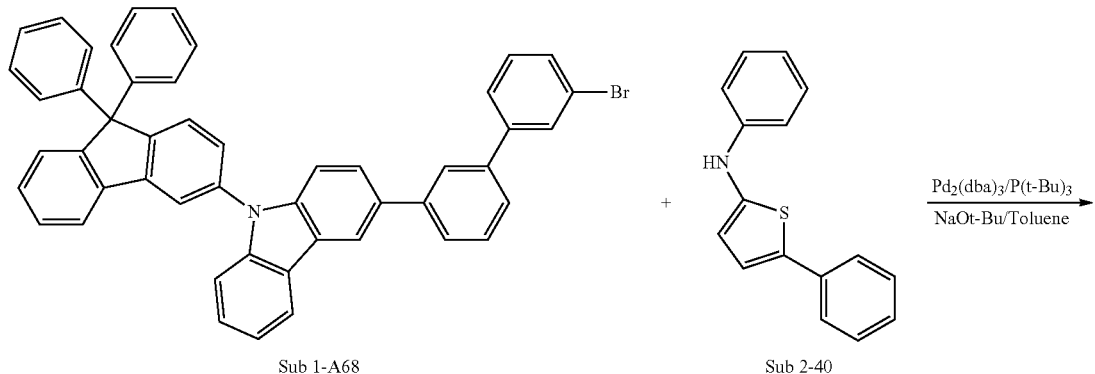

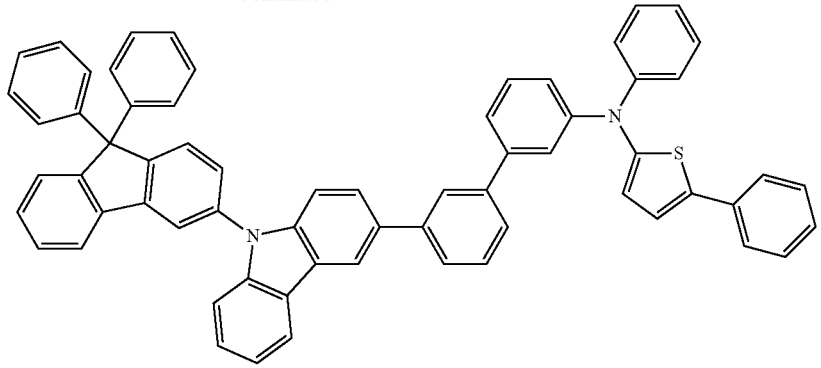

A292

Using the obtained Sub 2-40 (2.72 g, 10.8 mmol) plus Sub 1-A68 (9.28 g, 13 mmol), Pd$_2$(dba)$_3$ (0.3 g, 0.3 mmol), 50% P(t-Bu)$_3$ (0.4 ml, 0.9 mmol), NaOt-Bu (3.12 g, 32.5 mmol), and toluene, the same procedure as described in the synthesis method of Product A17 was carried out to obtain 6.42 g of product (yield: 67%).

15. Synthesis Method of Product A297

<Reaction Scheme 55>

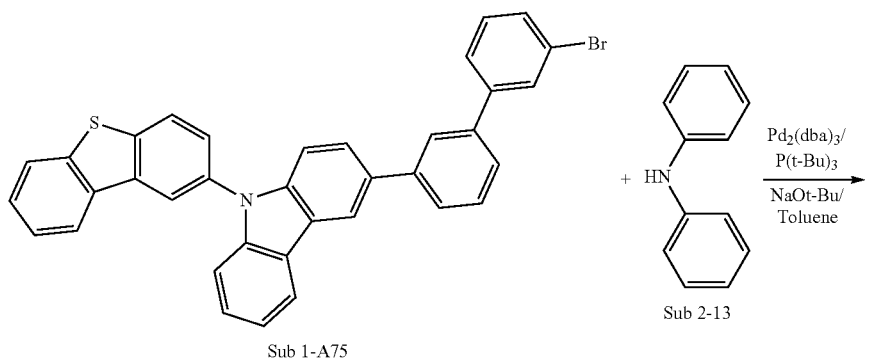

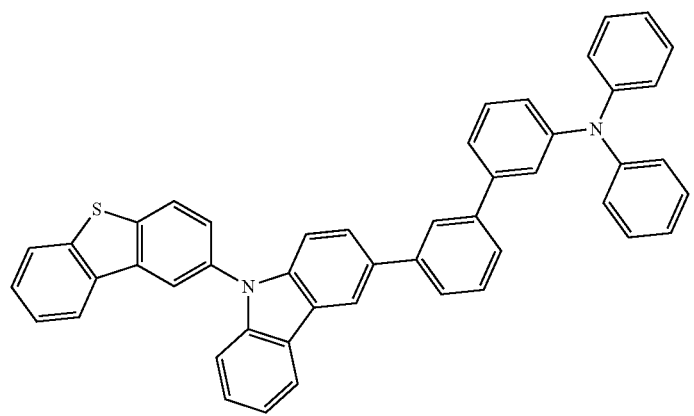

A297

Using the obtained Sub 2-13 (2.39 g, 14.1 mmol) plus Sub 1-A75 (9.84 g, 16.9 mmol), Pd$_2$(dba)$_3$ (0.39 g, 0.4 mmol), 50% P(t-Bu)$_3$ (0.6 ml, 1.1 mmol), NaOt-Bu (4.07 g, 42.4 mmol), and toluene, the same procedure as described in the synthesis method of Product A17 was carried out to obtain 6.61 g of product (yield: 70%).

16. Synthesis Method of Product A303
<Reaction Scheme 56>
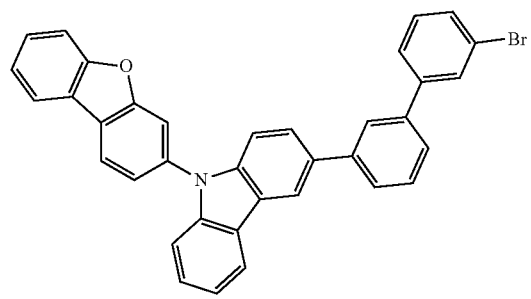
Sub 1-A79
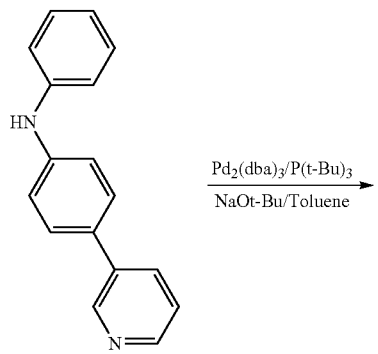
Sub 2-82
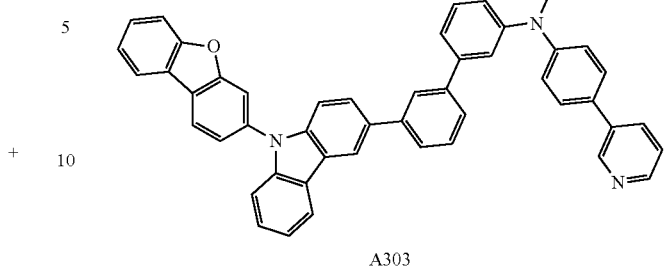
A303
Using the obtained Sub 2-82 (3.36 g, 13.6 mmol) plus Sub 1-A79 (9.24 g, 16.4 mmol), Pd₂(dba)₃ (0.37 g, 0.4 mmol), 50% P(t-Bu)₃ (0.5 ml, 1.1 mmol), NaOt-Bu (3.93 g, 40.9 mmol), and toluene, the same procedure as described in the synthesis method of Product A17 was carried out to obtain 6.07 g of product (yield: 61%).
17. Synthesis Method of Product A311
<Reaction Scheme 57>
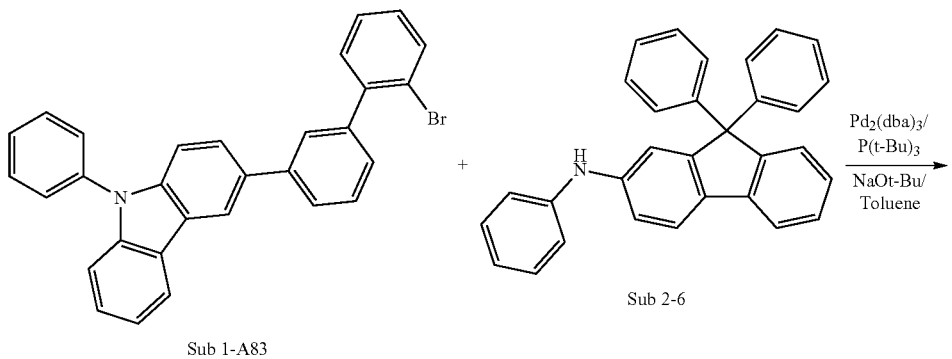
Sub 1-A83
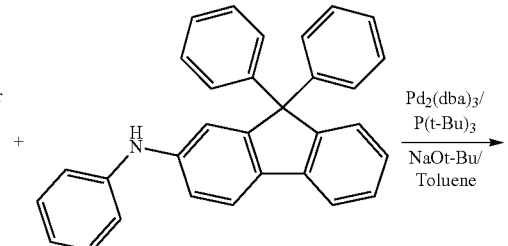
Sub 2-6
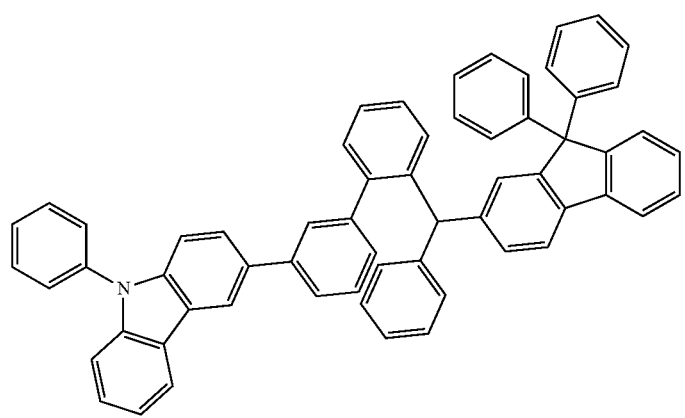
A311

Using the obtained Sub 2-6 (4.89 g, 11.9 mmol) plus Sub 1-A83 (6.8 g, 14.3 mmol), Pd$_2$(dba)$_3$ (0.33 g, 0.4 mmol), 50% P(t-Bu)$_3$ (0.5 ml, 1 mmol), NaOt-Bu (3.44 g, 35.8 mmol), and toluene, the same procedure as described in the synthesis method of Product A17 was carried out to obtain 6.42 g of product (yield: 67%).

18. Synthesis Method of Product A330

<Reaction Scheme 58>

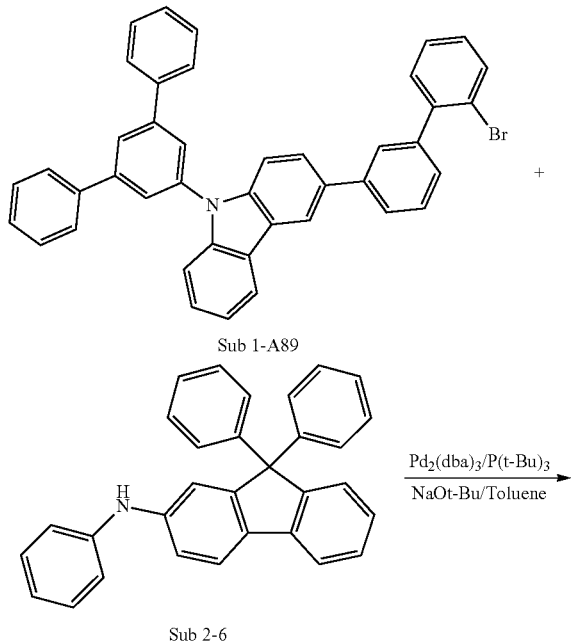

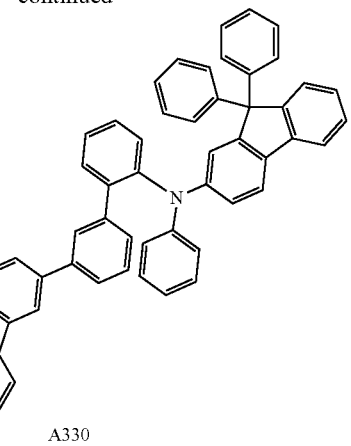

A330

Using the obtained Sub 2-6 (4.12 g, 10.1 mmol) plus Sub 1-A89 (7.56 g, 12.1 mmol), Pd$_2$(dba)$_3$ (0.28 g, 0.3 mmol), 50% P(t-Bu)$_3$ (0.4 ml, 0.8 mmol), NaOt-Bu (2.9 g, 30.2 mmol), and toluene, the same procedure as described in the synthesis method of Product A17 was carried out to obtain 6.15 g of product (yield: 64%).

19. Synthesis Method of Product A339

<Reaction Scheme 59>

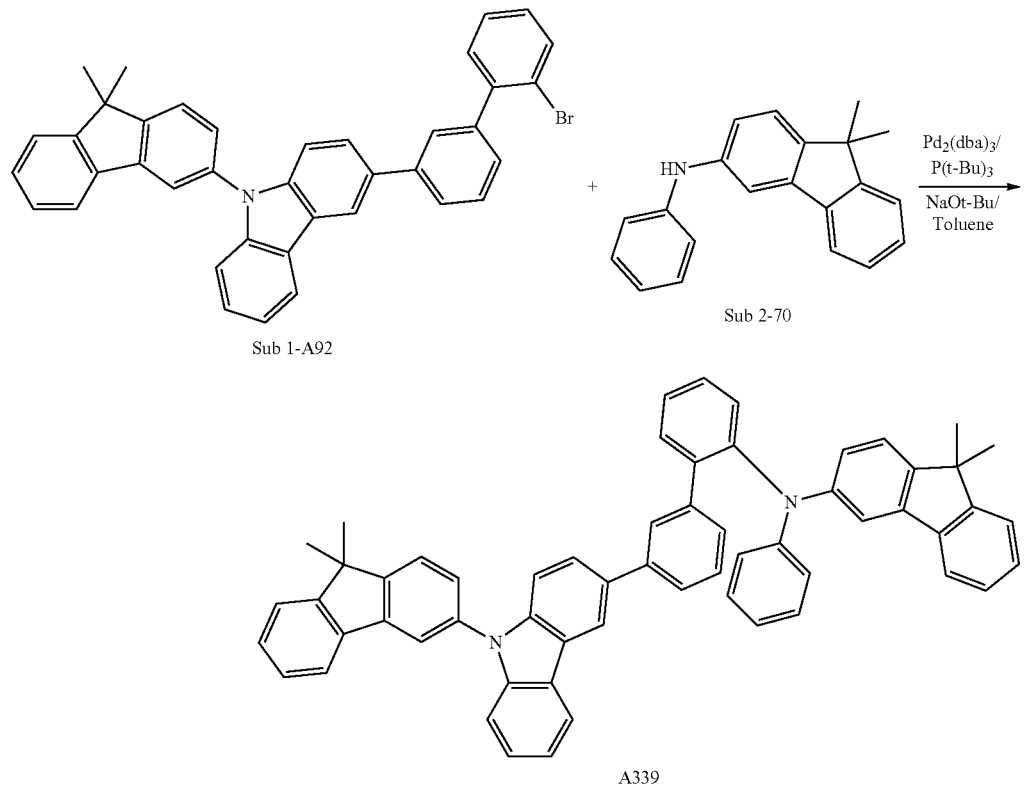

Using the obtained Sub 2-70 (3.42 g, 12 mmol) plus Sub 1-A92 (8.49 g, 14.4 mmol), Pd$_2$(dba)$_3$ (0.33 g, 0.4 mmol), 50% P(t-Bu)$_3$ (0.5 ml, 1 mmol), NaOt-Bu (3.46 g, 36 mmol), and toluene, the same procedure as described in the synthesis method of Product A17 was carried out to obtain 6.57 g of product (yield: 69%).

20. Synthesis Method of Product A348

<Reaction Scheme 60>

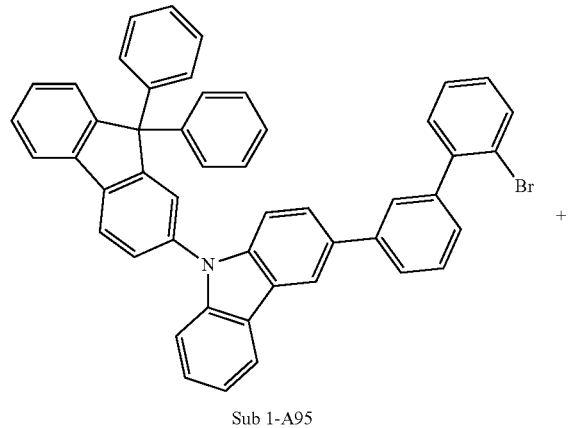

Sub 1-A95

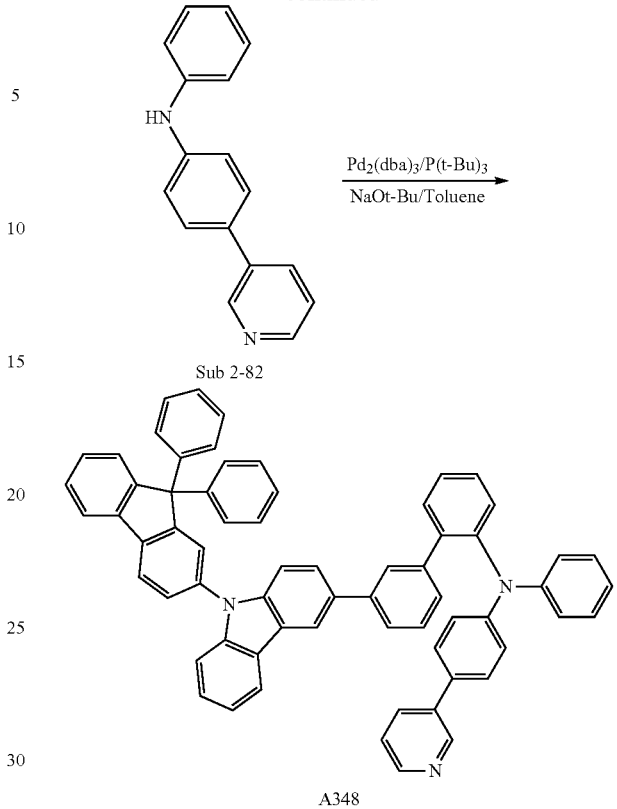

Sub 2-82

A348

Using the obtained Sub 2-82 (2.83 g, 11.5 mmol) plus Sub 1-A95 (9.85 g, 13.8 mmol), Pd$_2$(dba)$_3$ (0.32 g, 0.3 mmol), 50% P(t-Bu)$_3$ (0.4 ml, 0.9 mmol), NaOt-Bu (3.31 g, 34.5 mmol), and toluene, the same procedure as described in the synthesis method of Product A17 was carried out to obtain 5.76 g of product (yield: 57%).

21. Synthesis Method of Product A350

<Reaction Scheme 61>

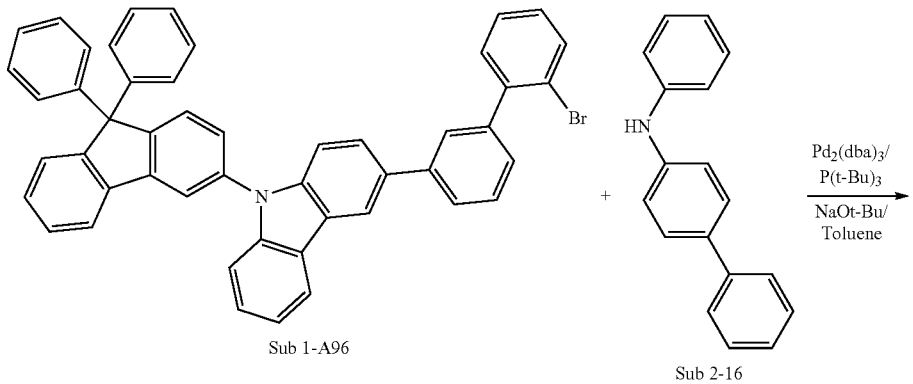

Sub 1-A96

Sub 2-16

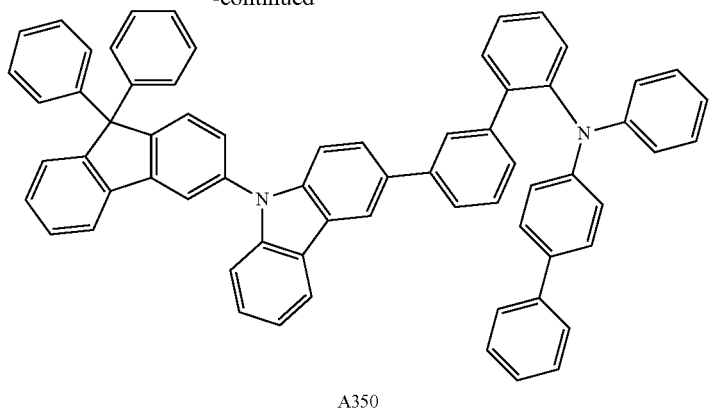

A350

Using the obtained Sub 2-16 (2.74 g, 11.2 mmol) plus Sub 1-A96 (9.58 g, 13.4 mmol), Pd$_2$(dba)$_3$ (0.31 g, 0.3 mmol), 50% P(t-Bu)$_3$ (0.4 ml, 0.9 mmol), NaOt-Bu (3.22 g, 33.5 mmol), and toluene, the same procedure as described in the synthesis method of Product A17 was carried out to obtain 6.38 g of product (yield: 65%).

22. Synthesis Method of Product A353

<Reaction Scheme 62>

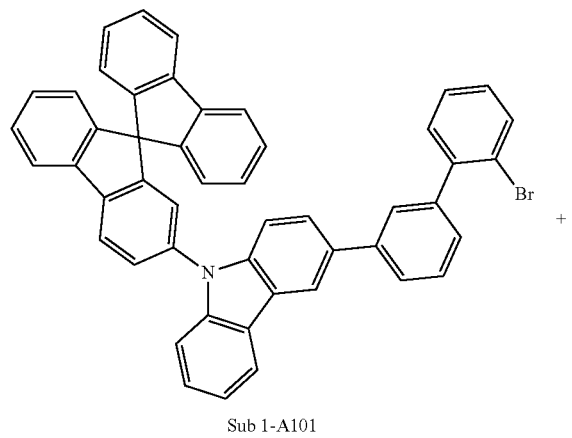

Sub 1-A101

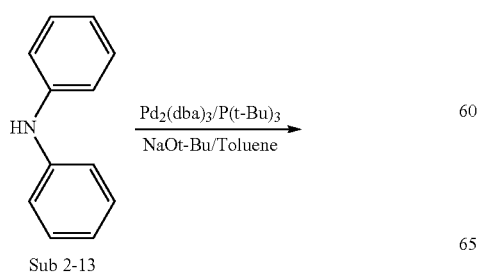

Sub 2-13

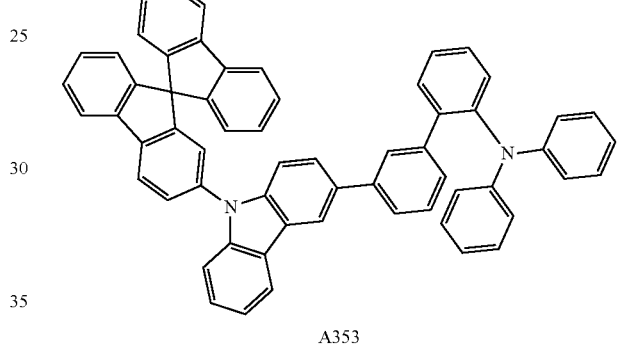

A353

Using the obtained Sub 2-13 (1.95 g, 11.5 mmol) plus Sub 1-A101 (9.85 g, 13.8 mmol), Pd$_2$(dba)$_3$ (0.32 g, 0.3 mmol), 50% P(t-Bu)$_3$ (0.4 ml, 0.9 mmol), NaOt-Bu (3.32 g, 34.6 mmol), and toluene, the same procedure as described in the synthesis method of Product A17 was carried out to obtain 6.37 g of product (yield: 69%).

23. Synthesis Method of Product A359

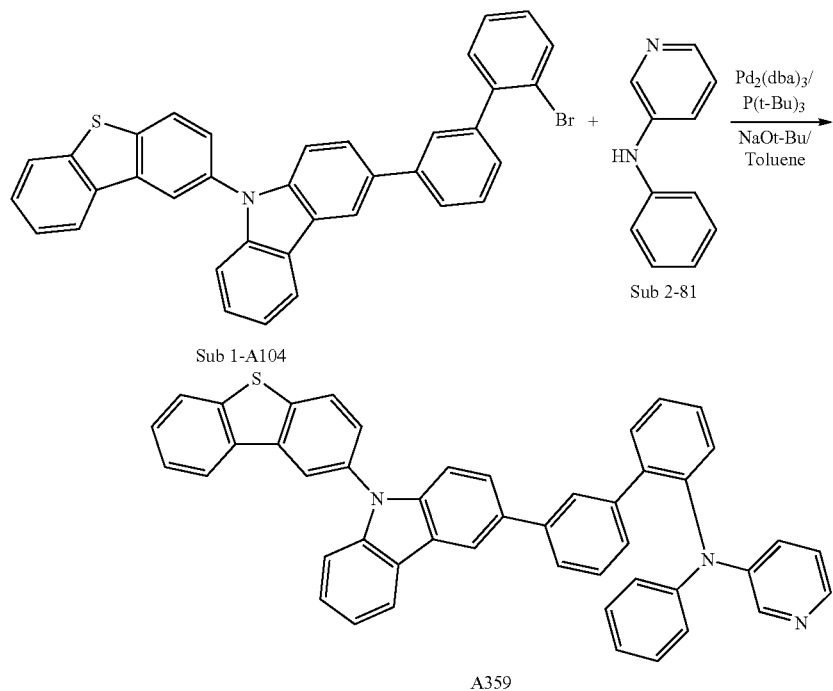

Using the obtained Sub 2-81 (2.49 g, 14.6 mmol) plus Sub 1-A104 (10.19 g, 17.6 mmol), Pd$_2$(dba)$_3$ (0.4 g, 0.4 mmol), 50% P(t-Bu)$_3$ (0.6 ml, 1.2 mmol), NaOt-Bu (4.22 g, 43.9 mmol), and toluene, the same procedure as described in the synthesis method of Product A17 was carried out to obtain 6.17 g of product (yield: 63%).

24. Synthesis Method of Product A363

<Reaction Scheme 64>

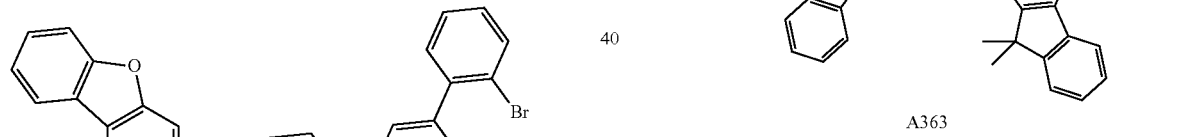

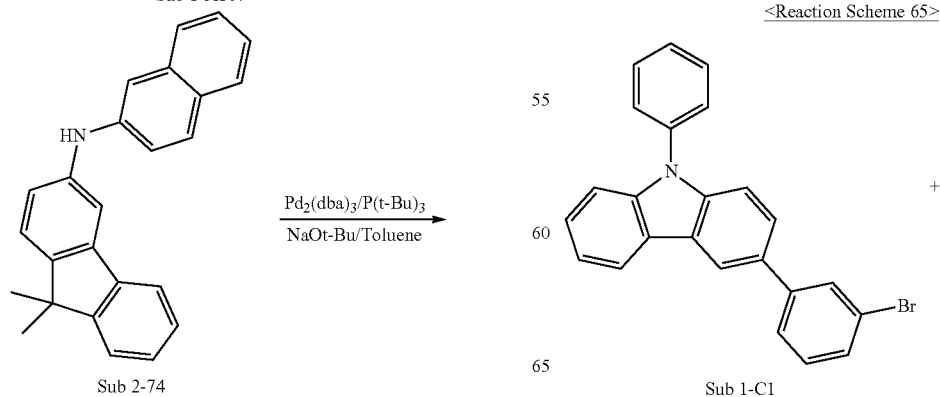

Using the obtained Sub 2-74 (4.18 g, 12.5 mmol) plus Sub 1-A107 (8.44 g, 15 mmol), Pd$_2$(dba)$_3$ (0.34 g, 0.4 mmol), 50% P(t-Bu)$_3$ (0.5 ml, 1 mmol), NaOt-Bu (3.59 g, 37.4 mmol), and toluene, the same procedure as described in the synthesis method of Product A17 was carried out to obtain 6.74 g of product (yield: 66%).

25. Synthesis Method of Product C2

<Reaction Scheme 65>

-continued

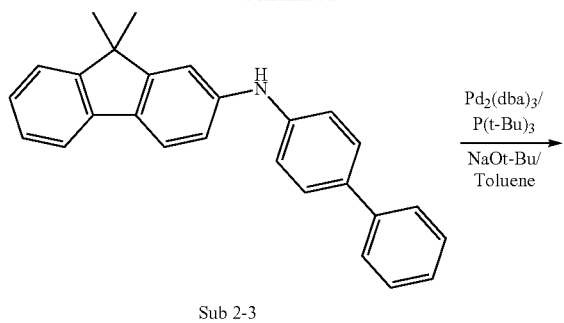

Sub 2-3

Pd₂(dba)₃/
P(t-Bu)₃
―――――→
NaOt-Bu/
Toluene

-continued

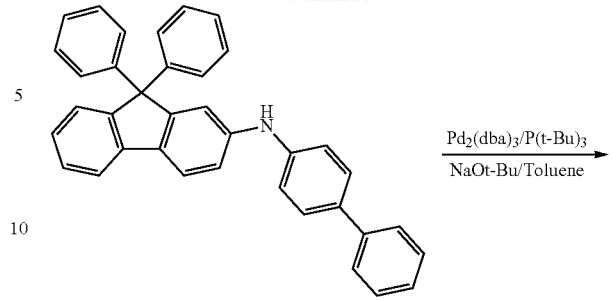

Sub 2-7

Pd₂(dba)₃/P(t-Bu)₃
―――――→
NaOt-Bu/Toluene

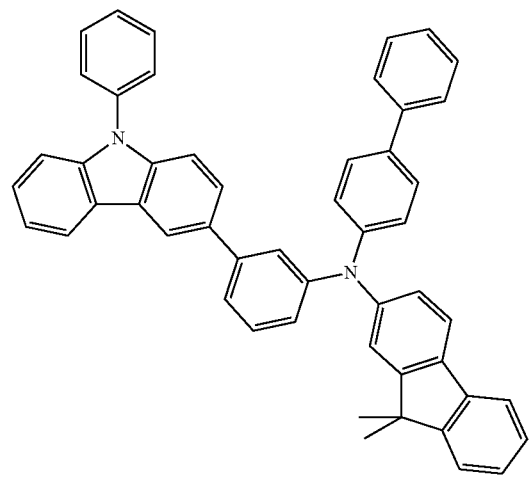

C2

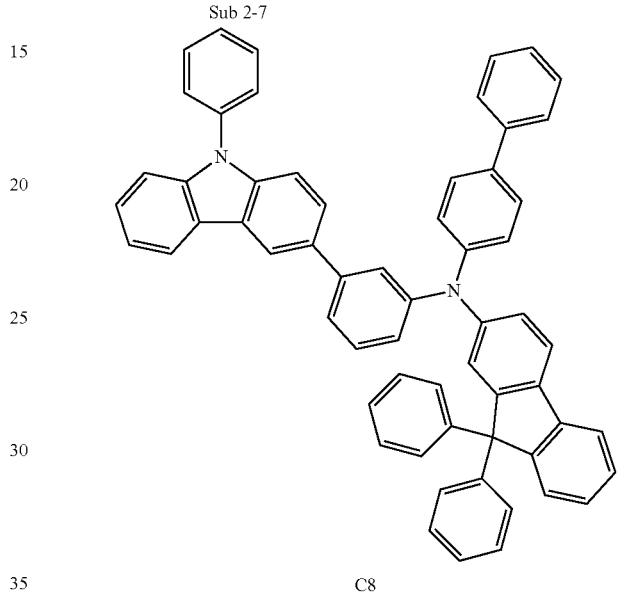

C8

Using the obtained Sub 2-3 (6 g, 16.6 mmol) plus Sub 1-C1 (7.93 g, 19.9 mmol), Pd₂(dba)₃ (1.21 g, 1.3 mmol), 50% P(t-Bu)₃ (0.7 ml, 1.66 mmol), NaOt-Bu (73.03 g, 49.8 mmol), and toluene, the same procedure as described in the synthesis method of Product A17 was carried out to obtain 8.11 g of product (yield: 72%).

26. Synthesis Method of Product C8

<Reaction Scheme 66>

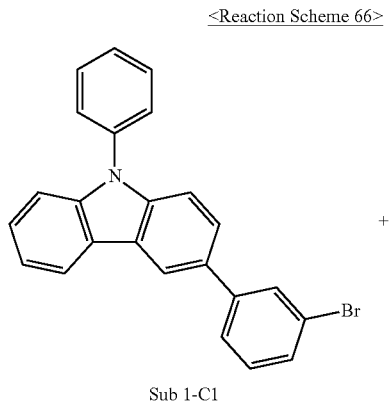

Sub 1-C1

+

Using the obtained Sub 2-7 (5.18 g, 10.7 mmol) plus Sub 1-C1 (5.1 g, 12.8 mmol), Pd₂(dba)₃ (0.29 g, 0.3 mmol), 50% P(t-Bu)₃ (0.4 ml, 0.9 mmol), NaOt-Bu (3.08 g, 32 mmol), and toluene, the same procedure as described in the synthesis method of Product A17 was carried out to obtain 6.53 g of product (yield: 76%).

27. Synthesis Method of Product C21

<Reaction Scheme 67>

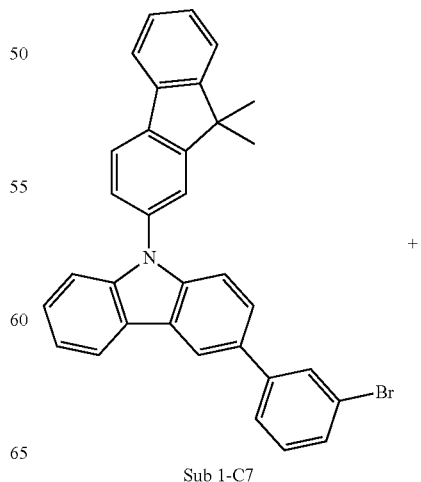

Sub 1-C7

+

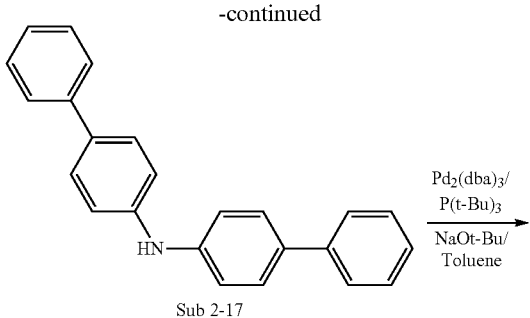

Sub 2-17

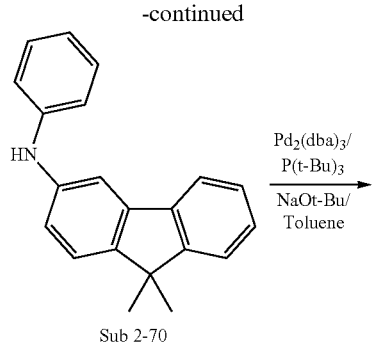

Sub 2-70

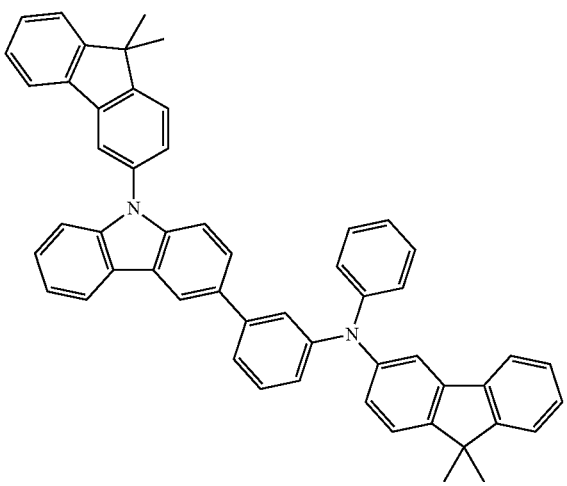

C23

C21

Using the obtained Sub 2-17 (3.59 g, 11.2 mmol) plus Sub 1-C7 (6.9 g, 13.4 mmol), Pd$_2$(dba)$_3$ (0.31 g, 0.3 mmol), 50% P(t-Bu)$_3$ (0.4 ml, 0.9 mmol), NaOt-Bu (3.22 g, 33.5 mmol), and toluene, the same procedure as described in the synthesis method of Product A17 was carried out to obtain 6.3 g of product (yield: 74%).

28. Synthesis Method of Product C23

<Reaction Scheme 68>

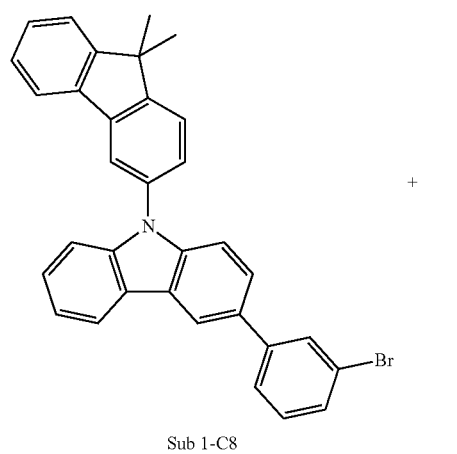

Sub 1-C8

Using the obtained Sub 2-70 (3.56 g, 12.5 mmol) plus Sub 1-C8 (7.7 g, 15 mmol), Pd$_2$(dba)$_3$ (0.34 g, 0.4 mmol), 50% P(t-Bu)$_3$ (0.5 ml, 1 mmol), NaOt-Bu (3.6 g, 37.4 mmol), and toluene, the same procedure as described in the synthesis method of Product A17 was carried out to obtain 6.92 g of product (yield: 77%).

In Table 3 below, FD-MS data of the compounds A1 to A392 and C1 to C40 prepared in the Synthesis Examples of the present invention are given.

TABLE 3

| Compound | FD-MS | Compound | FD-MS |
|---|---|---|---|
| A1 | m/z = 678.30 ($C_{51}H_{38}N_2$ = 678.86) | A2 | m/z = 754.33 ($C_{57}H_{42}N_2$ = 754.96) |
| A6 | m/z = 759.37 ($C_{57}H_{37}D_5N_2$ = 759.99) | A7 | m/z = 830.37 ($C_{63}H_{46}N_2$ = 831.05) |
| A11 | m/z = 728.32 ($C_{55}H_{40}N_2$ = 728.92) | A12 | m/z = 804.35 ($C_{61}H_{44}N_2$ = 805.02) |
| A16 | m/z = 802.33 ($C_{61}H_{42}N_2$ = 803.00) | A17 | m/z = 878.37 ($C_{67}H_{46}N_2$ = 879.10) |
| A19 | m/z = 852.35 ($C_{65}H_{44}N_2$ = 853.06) | A21 | m/z = 878.37 ($C_{67}H_{46}N_2$ = 879.10) |
| A22 | m/z = 954.40 ($C_{73}H_{50}N_2$ = 955.19) | A23 | m/z = 928.38 ($C_{71}H_{48}N_2$ = 929.15) |
| A24 | m/z = 928.38 ($C_{71}H_{48}N_2$ = 929.15) | A25 | m/z = 830.37 ($C_{63}H_{46}N_2$ = 831.05) |
| A26 | m/z = 852.35 ($C_{65}H_{44}N_2$ = 853.06) | A27 | m/z = 928.38 ($C_{71}H_{48}N_2$ = 929.15) |
| A31 | m/z = 800.32 ($C_{61}H_{40}N_2$ = 800.98) | A36 | m/z = 850.33 ($C_{65}H_{42}N_2$ = 851.04) |
| A47 | m/z = 714.30 ($C_{54}H_{38}N_2$ = 714.89) | A51 | m/z = 714.30 ($C_{54}H_{38}N_2$ = 714.89) |
| A56 | m/z = 688.29 ($C_{52}H_{36}N_2$ = 688.86) | A62 | m/z = 764.32 ($C_{58}H_{40}N_2$ = 764.95) |
| A66 | m/z = 612.26 ($C_{46}H_{32}N_2$ = 612.76) | A72 | m/z = 688.29 ($C_{52}H_{36}N_2$ = 688.86) |
| A87 | m/z = 738.30 ($C_{56}H_{38}N_2$ = 738.91) | A97 | m/z = 728.28 ($C_{54}H_{36}N_2O$ = 728.88) |
| A101 | m/z = 744.26 ($C_{54}H_{36}N_2S$ = 744.94) | A121 | m/z = 668.23 ($C_{48}H_{32}N_2S$ = 668.85) |
| A123 | m/z = 638.27 ($C_{48}H_{34}N_2$ = 638.80) | A124 | m/z = 714.30 ($C_{54}H_{38}N_2$ = 714.89) |
| A125 | m/z = 738.30 ($C_{56}H_{38}N_2$ = 738.91) | A127 | m/z = 729.31 ($C_{54}H_{39}N_3$ = 729.91) |
| A128 | m/z = 928.38 ($C_{71}H_{48}N_2$ = 929.15) | A129 | m/z = 790.33 ($C_{60}H_{42}N_2$ = 790.99) |
| A130 | m/z = 879.36 ($C_{66}H_{45}N_3$ = 880.08) | A131 | m/z = 896.36 ($C_{66}H_{48}N_2Si$ = 897.19) |
| A134 | m/z = 602.27 ($C_{45}H_{34}N_2$ = 602.76) | A135 | m/z = 656.26 ($C_{48}H_{33}FN_2$ = 656.79) |
| A142 | m/z = 612.26 ($C_{46}H_{32}N_2$ = 612.76) | A146 | m/z = 804.35 ($C_{61}H_{44}N_2$ = 805.02) |
| A161 | m/z = 802.33 ($C_{61}H_{42}N_2$ = 803.00) | A162 | m/z = 830.37 ($C_{63}H_{46}N_2$ = 831.05) |
| A165 | m/z = 820.29 ($C_{60}H_{40}N_2S$ = 821.04) | A168 | m/z = 778.30 ($C_{58}H_{38}N_2O$ = 778.94) |
| A169 | m/z = 928.38 ($C_{71}H_{48}N_2$ = 929.15) | A170 | m/z = 954.40 ($C_{73}H_{50}N_2$ = 955.19) |
| A171 | m/z = 878.37 ($C_{67}H_{46}N_2$ = 879.10) | A172 | m/z = 954.40 ($C_{73}H_{50}N_2$ = 955.19) |
| A173 | m/z = 852.35 ($C_{65}H_{44}N_2$ = 853.06) | A174 | m/z = 878.37 ($C_{67}H_{46}N_2$ = 879.10) |
| A175 | m/z = 928.38 ($C_{71}H_{48}N_2$ = 929.15) | A176 | m/z = 928.38 ($C_{71}H_{48}N_2$ = 929.15) |
| A177 | m/z = 754.33 ($C_{57}H_{42}N_2$ = 754.96) | A178 | m/z = 802.33 ($C_{61}H_{42}N_2$ = 803.00) |
| A179 | m/z = 878.37 ($C_{67}H_{46}N_2$ = 879.10) | A180 | m/z = 878.37 ($C_{67}H_{46}N_2$ = 879.10) |
| A181 | m/z = 714.30 ($C_{54}H_{38}N_2$ = 714.89) | A182 | m/z = 1004.41 ($C_{77}H_{52}N_2$ = 1005.25) |
| A183 | m/z = 906.40 ($C_{69}H_{50}N_2$ = 907.15) | A184 | m/z = 954.40 ($C_{73}H_{50}N_2$ = 955.19) |
| A185 | m/z = 820.29 ($C_{60}H_{40}N_2S$ = 821.04) | A186 | m/z = 831.36 ($C_{62}H_{45}N_3$ = 832.04) |
| A187 | m/z = 830.37 ($C_{63}H_{46}N_2$ = 831.05) | A188 | m/z = 854.37 ($C_{65}H_{46}N_2$ = 855.07) |
| A189 | m/z = 994.43 ($C_{76}H_{54}N_2$ = 995.26) | A190 | m/z = 744.31 ($C_{55}H_{40}N_2O$ = 744.92) |
| A191 | m/z = 830.37 ($C_{63}H_{46}N_2$ = 831.05) | A192 | m/z = 830.37 ($C_{63}H_{46}N_2$ = 831.05) |
| A193 | m/z = 794.37 ($C_{60}H_{46}N_2$ = 795.02) | A194 | m/z = 906.40 ($C_{69}H_{50}N_2$ = 907.15) |
| A195 | m/z = 830.37 ($C_{63}H_{46}N_2$ = 831.05) | A196 | m/z = 906.40 ($C_{69}H_{50}N_2$ = 907.15) |
| A197 | m/z = 755.33 ($C_{56}H_{41}N_3$ = 755.94) | A198 | m/z = 906.40 ($C_{69}H_{50}N_2$ = 907.15) |
| A199 | m/z = 802.33 ($C_{61}H_{42}N_2$ = 803.00) | A200 | m/z = 852.35 ($C_{65}H_{44}N_2$ = 853.06) |
| A201 | m/z = 902.37 ($C_{69}H_{46}N_2$ = 903.12) | A202 | m/z = 902.37 ($C_{69}H_{46}N_2$ = 903.12) |
| A203 | m/z = 878.37 ($C_{67}H_{46}N_2$ = 879.10) | A204 | m/z = 954.40 ($C_{73}H_{50}N_2$ = 955.19) |
| A205 | m/z = 918.40 ($C_{70}H_{50}N_2$ = 919.16) | A206 | m/z = 853.35 ($C_{64}H_{43}N_3$ = 854.05) |
| A207 | m/z = 802.33 ($C_{61}H_{42}N_2$ = 803.00) | A208 | m/z = 852.35 ($C_{65}H_{44}N_2$ = 853.06) |
| A209 | m/z = 878.37 ($C_{67}H_{46}N_2$ = 879.10) | A210 | m/z = 918.40 ($C_{70}H_{50}N_2$ = 919.16) |
| A211 | m/z = 877.35 ($C_{66}H_{43}N_3$ = 878.07) | A212 | m/z = 800.32 ($C_{61}H_{40}N_2$ = 800.98) |
| A213 | m/z = 768.26 ($C_{56}H_{36}N_2S$ = 768.96) | A214 | m/z = 936.35 ($C_{69}H_{48}N_2S$ = 937.20) |
| A215 | m/z = 820.29 ($C_{60}H_{40}N_2S$ = 821.04) | A216 | m/z = 908.32 ($C_{67}H_{44}N_2S$ = 909.14) |
| A217 | m/z = 822.28 ($C_{58}H_{38}N_4S$ = 823.01) | A218 | m/z = 794.28 ($C_{58}H_{38}N_2S$ = 795.00) |
| A219 | m/z = 728.28 ($C_{54}H_{36}N_2O$ = 728.88) | A220 | m/z = 742.26 ($C_{54}H_{34}N_2O_2$ = 742.86) |
| A221 | m/z = 829.31 ($C_{61}H_{39}N_3O$ = 829.98) | A222 | m/z = 782.33 ($C_{58}H_{42}N_2O$ = 782.97) |
| A223 | m/z = 652.25 ($C_{48}H_{32}N_2O$ = 652.78) | A224 | m/z = 942.36 ($C_{71}H_{46}N_2O$ = 943.14) |
| A225 | m/z = 678.30 ($C_{51}H_{38}N_2$ = 678.86) | A226 | m/z = 754.33 ($C_{57}H_{42}N_2$ = 754.96) |
| A227 | m/z = 754.33 ($C_{57}H_{42}N_2$ = 754.96) | A228 | m/z = 754.33 ($C_{57}H_{42}N_2$ = 754.96) |
| A229 | m/z = 802.33 ($C_{61}H_{42}N_2$ = 803.00) | A230 | m/z = 878.37 ($C_{67}H_{46}N_2$ = 879.10) |
| A231 | m/z = 878.37 ($C_{67}H_{46}N_2$ = 879.10) | A232 | m/z = 954.40 ($C_{73}H_{50}N_2$ = 955.19) |
| A233 | m/z = 928.38 ($C_{71}H_{48}N_2$ = 929.15) | A234 | m/z = 928.38 ($C_{71}H_{48}N_2$ = 929.15) |
| A235 | m/z = 852.35 ($C_{65}H_{44}N_2$ = 853.06) | A236 | m/z = 928.38 ($C_{71}H_{48}N_2$ = 929.15) |
| A237 | m/z = 562.24 ($C_{42}H_{30}N_2$ = 562.70) | A238 | m/z = 638.27 ($C_{48}H_{34}N_2$ = 638.80) |
| A239 | m/z = 638.27 ($C_{48}H_{34}N_2$ = 638.80) | A240 | m/z = 714.30 ($C_{54}H_{38}N_2$ = 714.89) |
| A241 | m/z = 714.30 ($C_{54}H_{38}N_2$ = 714.89) | A242 | m/z = 790.33 ($C_{60}H_{42}N_2$ = 790.99) |
| A243 | m/z = 878.37 ($C_{67}H_{46}N_2$ = 879.10) | A244 | m/z = 954.40 ($C_{73}H_{50}N_2$ = 955.19) |
| A245 | m/z = 830.37 ($C_{63}H_{46}N_2$ = 831.05) | A246 | m/z = 892.38 ($C_{68}H_{48}N_2$ = 893.12) |
| A247 | m/z = 830.37 ($C_{63}H_{46}N_2$ = 831.05) | A248 | m/z = 838.32 ($C_{61}H_{40}F_2N_2$ = 838.98) |
| A249 | m/z = 928.38 ($C_{71}H_{48}N_2$ = 929.15) | A250 | m/z = 1030.43 ($C_{79}H_{54}N_2$ = 1031.29) |
| A251 | m/z = 878.37 ($C_{67}H_{46}N_2$ = 879.10) | A252 | m/z = 883.40 ($C_{67}H_{41}D_5N_2$ = 884.13) |
| A253 | m/z = 878.37 ($C_{67}H_{46}N_2$ = 879.10) | A254 | m/z = 878.37 ($C_{67}H_{46}N_2$ = 879.10) |
| A255 | m/z = 954.40 ($C_{73}H_{50}N_2$ = 955.19) | A256 | m/z = 928.38 ($C_{72}H_{48}N_2$ = 929.15) |
| A257 | m/z = 802.33 ($C_{61}H_{42}N_2$ = 803.00) | A258 | m/z = 878.37 ($C_{67}H_{46}N_2$ = 879.10) |
| A259 | m/z = 878.37 ($C_{67}H_{46}N_2$ = 879.10) | A260 | m/z = 878.37 ($C_{67}H_{46}N_2$ = 879.10) |
| A261 | m/z = 614.27 ($C_{46}H_{34}N_2$ = 614.78) | A262 | m/z = 744.26 ($C_{54}H_{36}N_2S$ = 744.94) |
| A263 | m/z = 765.31 ($C_{57}H_{39}N_3$ = 765.94) | A264 | m/z = 881.38 ($C_{66}H_{47}N_3$ = 882.10) |
| A265 | m/z = 814.33 ($C_{62}H_{42}N_2$ = 815.01) | A266 | m/z = 906.40 ($C_{69}H_{50}N_2$ = 907.15) |
| A267 | m/z = 954.40 ($C_{73}H_{50}N_2$ = 955.19) | A268 | m/z = 1028.41 ($C_{79}H_{52}N_2$ = 1029.27) |
| A269 | m/z = 881.38 ($C_{66}H_{47}N_3$ = 882.10) | A270 | m/z = 954.40 ($C_{73}H_{50}N_2$ = 955.19) |
| A271 | m/z = 854.33 ($C_{64}H_{42}N_2O$ = 855.03) | A272 | m/z = 754.33 ($C_{57}H_{42}N_2$ = 754.96) |
| A273 | m/z = 830.37 ($C_{63}H_{46}N_2$ = 831.05) | A274 | m/z = 830.37 ($C_{63}H_{46}N_2$ = 831.05) |
| A275 | m/z = 918.40 ($C_{70}H_{50}N_2$ = 919.16) | A276 | m/z = 805.35 ($C_{60}H_{43}N_3$ = 806.00) |
| A277 | m/z = 830.37 ($C_{63}H_{46}N_2$ = 831.05) | A278 | m/z = 830.37 ($C_{63}H_{46}N_2$ = 831.05) |
| A279 | m/z = 844.38 ($C_{64}H_{48}N_2$ = 845.08) | A280 | m/z = 834.31 ($C_{61}H_{42}N_2S$ = 835.06) |

TABLE 3-continued

| Compound | FD-MS | Compound | FD-MS |
|---|---|---|---|
| A281 | m/z = 778.33 ($C_{59}H_{42}N_2$ = 778.98) | A282 | m/z = 946.43 ($C_{72}H_{54}N_2$ = 947.21) |
| A283 | m/z = 869.38 ($C_{65}H_{47}N_3$ = 870.09) | A284 | m/z = 870.40 ($C_{66}H_{50}N_2$ = 871.12) |
| A285 | m/z = 852.35 ($C_{65}H_{44}N_2$ = 853.06) | A286 | m/z = 878.37 ($C_{67}H_{46}N_2$ = 879.10) |
| A287 | m/z = 994.43 ($C_{76}H_{54}N_2$ = 995.26) | A288 | m/z = 903.36 ($C_{68}H_{45}N_3$ = 904.10) |
| A289 | m/z = 802.33 ($C_{61}H_{42}N_2$ = 803.00) | A290 | m/z = 878.37 ($C_{67}H_{46}N_2$ = 879.10) |
| A291 | m/z = 918.40 ($C_{70}H_{50}N_2$ = 919.16) | A292 | m/z = 884.32 ($C_{65}H_{44}N_2S$ = 885.12) |
| A293 | m/z = 916.38 ($C_{70}H_{48}N_2$ = 917.14) | A294 | m/z = 850.33 ($C_{65}H_{42}N_2$ = 851.04) |
| A295 | m/z = 744.26 ($C_{54}H_{36}N_2S$ = 744.94) | A296 | m/z = 908.32 ($C_{67}H_{44}N_2O$ = 909.14) |
| A297 | m/z = 668.23 ($C_{48}H_{32}N_2S$ = 668.85) | A298 | m/z = 898.31 ($C_{64}H_{42}N_4S$ = 899.11) |
| A299 | m/z = 774.22 ($C_{54}H_{34}N_2S_2$ = 774.99) | A300 | m/z = 820.29 ($C_{60}H_{40}N_2S$ = 821.04) |
| A301 | m/z = 908.32 ($C_{67}H_{44}N_2S$ = 909.14) | A302 | m/z = 804.31 ($C_{60}H_{40}N_2O$ = 804.97) |
| A303 | m/z = 729.28 ($C_{53}H_{35}N_3O$ = 729.86) | A304 | m/z = 768.31 ($C_{57}H_{40}N_2O$ = 768.94) |
| A305 | m/z = 752.28 ($C_{56}H_{36}N_2O$ = 752.90) | A306 | m/z = 892.35 ($C_{67}H_{44}N_2O$ = 893.08) |
| A307 | m/z = 818.33 ($C_{61}H_{42}N_2O$ = 819.00) | A308 | m/z = 804.31 ($C_{60}H_{40}N_2O$ = 804.97) |
| A309 | m/z = 754.33 ($C_{57}H_{42}N_2$ = 754.96) | A310 | m/z = 754.33 ($C_{57}H_{42}N_2$ = 754.96) |
| A311 | m/z = 802.33 ($C_{61}H_{42}N_2$ = 803.00) | A312 | m/z = 878.37 ($C_{67}H_{46}N_2$ = 879.10) |
| A313 | m/z = 954.40 ($C_{73}H_{50}N_2$ = 955.19) | A314 | m/z = 928.38 ($C_{71}H_{48}N_2$ = 929.15) |
| A315 | m/z = 852.35 ($C_{65}H_{44}N_2$ = 853.06) | A316 | m/z = 878.37 ($C_{67}H_{46}N_2$ = 879.10) |
| A317 | m/z = 562.24 ($C_{42}H_{30}N_2$ = 562.70) | A318 | m/z = 638.27 ($C_{48}H_{34}N_2$ = 638.80) |
| A319 | m/z = 638.27 ($C_{48}H_{34}N_2$ = 638.80) | A320 | m/z = 714.30 ($C_{54}H_{38}N_2$ = 714.89) |
| A321 | m/z = 878.37 ($C_{67}H_{46}N_2$ = 879.10) | A322 | m/z = 878.37 ($C_{67}H_{46}N_2$ = 879.10) |
| A323 | m/z = 800.32 ($C_{61}H_{40}N_2$ = 800.98) | A324 | m/z = 779.29 ($C_{57}H_{37}N_3O$ = 779.92) |
| A325 | m/z = 802.33 ($C_{61}H_{42}N_2$ = 803.00) | A326 | m/z = 878.37 ($C_{67}H_{46}N_2$ = 879.10) |
| A327 | m/z = 878.37 ($C_{67}H_{46}N_2$ = 879.10) | A328 | m/z = 878.37 ($C_{67}H_{46}N_2$ = 879.10) |
| A329 | m/z = 866.37 ($C_{66}H_{46}N_2$ = 867.08) | A330 | m/z = 954.40 ($C_{73}H_{50}N_2$ = 955.19) |
| A331 | m/z = 880.38 ($C_{67}H_{48}N_2$ = 881.11) | A332 | m/z = 954.40 ($C_{73}H_{50}N_2$ = 955.19) |
| A333 | m/z = 820.29 ($C_{60}H_{40}N_2S$ = 821.04) | A334 | m/z = 896.32 ($C_{66}H_{44}N_2S$ = 897.13) |
| A335 | m/z = 754.33 ($C_{57}H_{42}N_2$ = 754.96) | A336 | m/z = 794.37 ($C_{60}H_{46}N_2$ = 795.02) |
| A337 | m/z = 679.30 ($C_{50}H_{37}N_3$ = 679.85) | A338 | m/z = 83 0.37 ($C_{63}H_{46}N_2$ = 831.05) |
| A339 | m/z = 794.37 ($C_{60}H_{46}N_2$ = 795.02) | A340 | m/z = 818.33 ($C_{61}H_{42}N_2O$ = 819.00) |
| A341 | m/z = 728.32 ($C_{55}H_{40}N_2$ = 728.92) | A342 | m/z = 920.41 ($C_{70}H_{52}N_2$ = 921.18) |
| A343 | m/z = 729.31 ($C_{54}H_{39}N_3$ = 729.91) | A344 | m/z = 870.40 ($C_{66}H_{50}N_2$ = 871.12) |
| A345 | m/z = 802.33 ($C_{61}H_{42}N_2$ = 803.00) | A346 | m/z = 878.37 ($C_{67}H_{46}N_2$ = 879.10) |
| A347 | m/z = 918.40 ($C_{70}H_{50}N_2$ = 919.16) | A348 | m/z = 879.36 ($C_{66}H_{45}N_3$ = 880.08) |
| A349 | m/z = 802.33 ($C_{61}H_{42}N_2$ = 803.00) | A350 | m/z = 878.37 ($C_{67}H_{46}N_2$ = 879.10) |
| A351 | m/z = 918.40 ($C_{70}H_{50}N_2$ = 919.16) | A352 | m/z = 858.31 ($C_{63}H_{42}N_2S$ = 859.09) |
| A353 | m/z = 800.32 ($C_{61}H_{40}N_2$ = 800.98) | A354 | m/z = 916.38 ($C_{70}H_{48}N_2$ = 917.14) |
| A355 | m/z = 744.26 ($C_{54}H_{36}N_2S$ = 744.94) | A356 | m/z = 908.32 ($C_{67}H_{44}N_2O$ = 909.14) |
| A357 | m/z = 668.23 ($C_{48}H_{32}N_2S$ = 668.85) | A358 | m/z = 784.29 ($C_{57}H_{40}N_2S$ = 785.01) |
| A359 | m/z = 669.22 ($C_{47}H_{31}N_3S$ = 669.83) | A360 | m/z = 719.24 ($C_{51}H_{33}N_3S$ = 719.89) |
| A361 | m/z = 768.26 ($C_{56}H_{36}N_2S$ = 768.96) | A362 | m/z = 702.27 ($C_{52}H_{34}N_2O$ = 702.84) |
| A363 | m/z = 818.33 ($C_{61}H_{42}N_2O$ = 819.00) | A364 | m/z = 729.28 ($C_{53}H_{35}N_3O$ = 729.86) |
| A365 | m/z = 652.25 ($C_{48}H_{32}N_2O$ = 652.78) | A366 | m/z = 892.35 ($C_{67}H_{44}N_2O$ = 893.08) |
| A367 | m/z = 702.27 ($C_{52}H_{34}N_2O$ = 702.84) | A368 | m/z = 792.28 ($C_{58}H_{36}N_2O_2$ = 792.92) |
| A369 | m/z = 804.31 ($C_{60}H_{40}N_2O$ = 804.97) | A370 | m/z = 806.30 ($C_{58}H_{38}N_4O$ = 806.95) |
| A371 | m/z = 802.33 ($C_{61}H_{42}N_2$ = 803.00) | A372 | m/z = 918.40 ($C_{70}H_{50}N_2$ = 919.16) |
| A373 | m/z = 908.32 ($C_{67}H_{44}N_2S$ = 909.14) | A374 | m/z = 852.35 ($C_{65}H_{44}N_2$ = 853.06) |
| A375 | m/z = 918.40 ($C_{70}H_{50}N_2$ = 919.16) | A376 | m/z = 803.33 ($C_{60}H_{41}N_3$ = 803.99) |
| A377 | m/z = 878.37 ($C_{67}H_{46}N_2$ = 879.10) | A378 | m/z = 954.40 ($C_{73}H_{50}N_2$ = 955.19) |
| A379 | m/z = 968.41 ($C_{74}H_{52}N_2$ = 969.22) | A380 | m/z = 853.35 ($C_{64}H_{43}N_3$ = 854.05) |
| A381 | m/z = 994.43 ($C_{76}H_{54}N_2$ = 995.26) | A382 | m/z = 902.37 ($C_{69}H_{46}N_2$ = 903.12) |
| A383 | m/z = 918.40 ($C_{70}H_{50}N_2$ = 919.16) | A384 | m/z = 892.35 ($C_{67}H_{44}N_2O$ = 893.08) |
| A385 | m/z = 802.33 ($C_{61}H_{42}N_2$ = 803.00) | A386 | m/z = 1042.43 ($C_{80}H_{54}N_2$ = 1043.30) |
| A387 | m/z = 853.35 ($C_{64}H_{43}N_3$ = 854.05) | A388 | m/z = 994.43 ($C_{76}H_{54}N_2$ = 995.26) |
| A389 | m/z = 878.37 ($C_{67}H_{46}N_2$ = 879.10) | A390 | m/z = 994.43 ($C_{76}H_{54}N_2$ = 995.26) |
| A391 | m/z = 884.32 ($C_{65}H_{44}N_2S$ = 885.12) | A392 | m/z = 994.43 ($C_{76}H_{54}N_2$ = 995.26) |
| C1 | m/z = 602.27 ($C_{45}H_{34}N_2$ = 602.76) | C2 | m/z = 678.30 ($C_{51}H_{38}N_2$ = 678.86) |
| C3 | m/z = 754.33 ($C_{57}H_{42}N_2$ = 754.96) | C4 | m/z = 652.29 ($C_{49}H_{36}N_2$ = 652.82) |
| C5 | m/z = 728.32 ($C_{55}H_{40}N_2$ = 728.92) | C6 | m/z = 726.30 ($C_{55}H_{38}N_2$ = 726.90) |
| C7 | m/z = 802.33 ($C_{61}H_{42}N_2$ = 803.00) | C8 | m/z = 802.33 ($C_{61}H_{42}N_2$ = 803.00) |
| C9 | m/z = 852.35 ($C_{65}H_{44}N_2$ = 853.06) | C10 | m/z = 852.35 ($C_{65}H_{44}N_2$ = 853.06) |
| C11 | m/z = 852.35 ($C_{65}H_{44}N_2$ = 853.06) | C12 | m/z = 724.29 ($C_{55}H_{36}N_2$ = 724.89) |
| C13 | m/z = 638.27 ($C_{48}H_{34}N_2$ = 638.80) | C14 | m/z = 638.27 ($C_{48}H_{34}N_2$ = 638.80) |
| C15 | m/z = 688.29 ($C_{52}H_{36}N_2$ = 688.86) | C16 | m/z = 536.23 ($C_{40}H_{28}N_2$ = 536.66) |
| C17 | m/z = 586.24 ($C_{44}H_{30}N_2$ = 586.72) | C18 | m/z = 642.21 ($C_{46}H_{30}N_2S$ = 642.81) |
| C19 | m/z = 652.25 ($C_{48}H_{32}N_2O$ = 652.78) | C20 | m/z = 744.26 ($C_{54}H_{36}N_2S$ = 744.94) |
| C21 | m/z = 754.33 ($C_{57}H_{42}N_2$ = 754.96) | C22 | m/z = 778.33 ($C_{59}H_{42}N_2$ = 778.98) |
| C23 | m/z = 718.33 ($C_{54}H_{42}N_2$ = 718.92) | C24 | m/z = 830.37 ($C_{63}H_{46}N_2$ = 831.05) |
| C25 | m/z = 754.33 ($C_{57}H_{42}N_2$ = 754.96) | C26 | m/z = 830.37 ($C_{63}H_{46}N_2$ = 831.05) |
| C27 | m/z = 679.30 ($C_{50}H_{37}N_3$ = 679.85) | C28 | m/z = 830.37 ($C_{63}H_{46}N_2$ = 831.05) |
| C29 | m/z = 802.33 ($C_{61}H_{42}N_2$ = 803.00) | C30 | m/z = 842.37 ($C_{64}H_{46}N_2$ = 843.06) |
| C31 | m/z = 801.31 ($C_{60}H_{39}N_3$ = 801.97) | C32 | m/z = 724.29 ($C_{55}H_{36}N_2$ = 724.89) |
| C33 | m/z = 746.25 ($C_{52}H_{34}N_4S$ = 746.92) | C34 | m/z = 718.24 ($C_{52}H_{34}N_2S$ = 718.90) |
| C35 | m/z = 652.25 ($C_{48}H_{32}N_2O$ = 652.78) | C36 | m/z = 666.23 ($C_{48}H_{30}N_2O_2$ = 666.76) |
| C37 | m/z = 753.28 ($C_{55}H_{35}N_3O$ = 753.89) | C38 | m/z = 706.30 ($C_{52}H_{38}N_2O$ = 706.87) |
| C39 | m/z = 576.22 ($C_{42}H_{28}N_2O$ = 576.68) | C40 | m/z = 866.33 ($C_{65}H_{42}N_2O$ = 867.04) |

Meanwhile, even though the compounds of the present invention, represented by Chemical Formula 1, have been synthesized in the Synthesis Examples above, they are based on a Suzuki cross-coupling reaction, an Ullmann reaction, a Miyaura boration reaction, a Buchwald-Hartwig cross coupling reaction, and the like. Therefore, it should be apparent to those having ordinary skill in the art that the reactions could proceed even though substituents (such as $R^1$, $R^2$, $L^1$, $Ar^1$, $Ar^2$, and $Ar^3$) defined in Chemical Formula 1, other than those specified in the Synthesis Examples, are used.

In Reaction Scheme 2, for example, all reactions of the starting material→Sub 1-I, Sub 1-IV→Sub 1-V, and Sub 1-VI→Sub 1 are based on the Suzuki cross-coupling reaction, the reaction of Sub 1-II→Sub 1-III on the Ullmann reaction, and the reactions of Sub 1-III→Sub 1-IV and Sub 1-V→Sub 1-VI on the Miyaura boration reaction; and in Reaction Scheme 27, all the reactions of the starting material→Sub 2, and the product synthesis reactions (Reaction Schemes 41 to 68) are based on the Buchwald-Hartwig cross coupling reaction. These reactions can be conducted even with substituents that are not specifically stated.

Fabrication and Evaluation of Organic Electronic Element

[Test Example □-1] Green Organic Light Emitting Diode (a Hole Transport Layer)

Organic light emitting diodes (OLEDs) were fabricated according to a conventional method by using a compound of the present invention as a hole transport layer material. First, an ITO layer (anode) was formed on a glass substrate, and a film of 4,4',4"-Tris[2-naphthyl(phenyl)amino]triphenylamine (hereinafter abbreviated as "2-TNATA") was vacuum-deposited on the ITO layer to form a hole injection layer with a thickness of 60 nm. Subsequently, a film of the compound A1 of the present invention was vacuum-deposited on the hole injection layer to form a hole transport layer with a thickness of 60 nm. Subsequently, a light emitting layer with a thickness of 30 nm was deposited on the hole transport layer by doping the hole transport layer with the 4,4'-N,N'-dicarbazole-biphenyl (hereinafter abbreviated as "CBP") as a host material and tris(2-phenylpyridine)-iridium (hereinafter abbreviated as "Ir(ppy)$_3$") as a dopant material in a weight ratio of 90:10. Next, a film of ((1,1'-bisphenyl)-4-olato)bis(2-methyl-8-quinolinolato)aluminum (hereinafter abbreviated as "BAlq") was vacuum-deposited with a thickness of 10 nm on the light emitting layer to form a hole blocking layer, and a film of tris(8-quinolinolato)aluminum (hereinafter abbreviated as "Alq$_3$") was formed with a thickness of 40 nm to form an electron transport layer. Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Test Example □-2] to [Test Example □-308] Green Organic Light Emitting Diode (a Hole Transport Layer)

The OLED was manufactured in the same manner as described in Test Example I-1, except that any one of the compounds A2 to C40 of the present invention in the Table 4 below was used as the hole transport layer material, instead of the inventive compound A1.

Comparative Example 1

An OLED was manufactured in the same manner as described in Test Example I-1, except that Comparative Compound 1 represented below was used as the hole transport layer material, instead of the inventive compound A1.

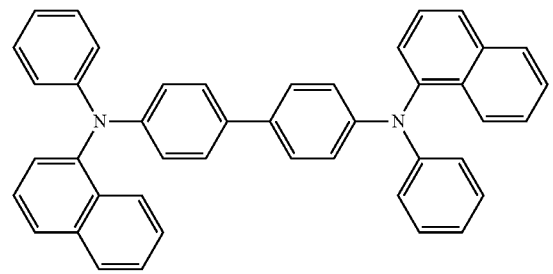

<Comparative Compound 1>

Comparative Example 2

An OLED was manufactured in the same manner as described in Test Example I-1, except that Comparative Compound 2 represented below was used as the hole transport layer material, instead of the inventive compound A1.

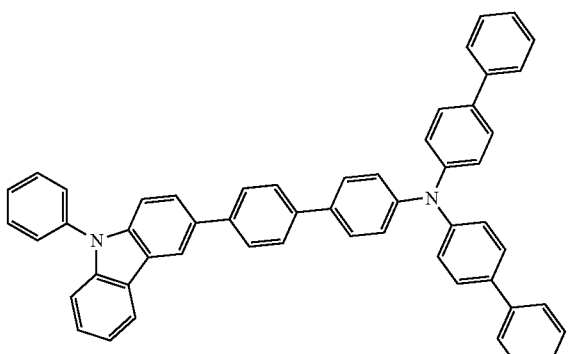

<Comparative Compound 2>

Comparative Example 3

An OLED was manufactured in the same manner as described in Test Example I-1, except that Comparative Compound 3 represented below was used as the hole transport layer material, instead of the inventive compound A1.

<Comparative Compound 3>

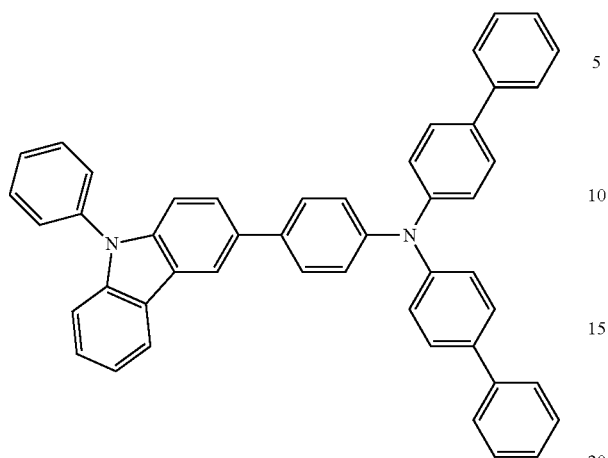

Comparative Example 4

An OLED was manufactured in the same manner as described in Test Example I-1, except that Comparative Compound 4 represented below was used as the hole transport layer material, instead of the inventive compound A1.

<Comparative Compound 4>

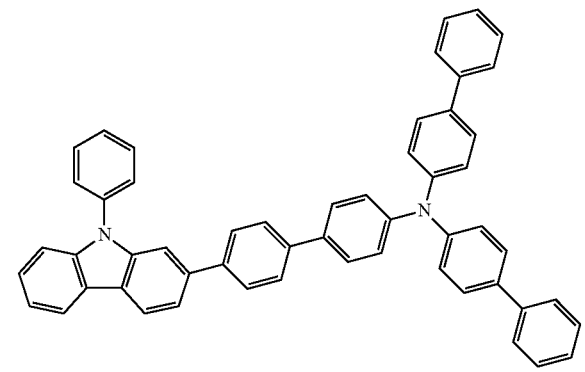

A forward bias DC voltage was applied to each of the OLEDs manufactured through Test Examples (I-1) to (I-308) and Comparative Example (1) to (4), and electroluminescence (EL characteristics of the OLED were measured by PR-650 (Photoresearch). Also, T95 life span was measured by life span measuring equipment (Mcscience) at a reference brightness of 5000 cd/m². Table 4 below shows evaluation results of OLEDs manufactured Test Examples and Comparative Examples.

TABLE 4

|  | Compound | Voltage (V) | Current Density (mA/cm²) | Brightness (cd/m²) | Efficiency (cd/A) | Lifetime T(95) | CIE x | CIE y |
|---|---|---|---|---|---|---|---|---|
| comp. Ex(1) | comp. Com1 | 6.0 | 20.8 | 5000.0 | 24.0 | 53.0 | 0.33 | 0.61 |
| comp. Ex(2) | comp. Com2 | 5.5 | 18.5 | 5000.0 | 27.1 | 80.3 | 0.33 | 0.62 |
| comp. Ex(3) | comp. Com3 | 5.5 | 18.4 | 5000.0 | 27.2 | 82.3 | 0.33 | 0.62 |
| comp. Ex(4) | comp. Com4 | 5.7 | 18.0 | 5000.0 | 27.8 | 82.3 | 0.33 | 0.62 |
| Ex. (I-1) | Com. (A1) | 5.1 | 16.1 | 5000.0 | 31.1 | 118.8 | 0.33 | 0.61 |
| Ex. (I-2) | Com. (A2) | 5.1 | 16.3 | 5000.0 | 30.6 | 115.6 | 0.33 | 0.61 |
| Ex. (I-3) | Com. (A6) | 5.3 | 15.6 | 5000.0 | 32.1 | 118.3 | 0.33 | 0.61 |
| Ex. (I-4) | Com. (A7) | 5.3 | 15.3 | 5000.0 | 32.7 | 123.7 | 0.33 | 0.62 |
| Ex. (I-5) | Com. (A11) | 5.3 | 15.7 | 5000.0 | 31.9 | 115.9 | 0.33 | 0.61 |
| Ex. (I-6) | Com. (A12) | 5.2 | 15.8 | 5000.0 | 31.6 | 116.8 | 0.33 | 0.61 |
| Ex. (I-7) | Com. (A16) | 5.1 | 15.5 | 5000.0 | 32.2 | 119.1 | 0.33 | 0.62 |
| Ex. (I-8) | Com. (A17) | 5.4 | 15.5 | 5000.0 | 32.4 | 122.3 | 0.33 | 0.61 |
| Ex. (I-9) | Com. (A19) | 5.3 | 16.5 | 5000.0 | 30.4 | 108.5 | 0.33 | 0.62 |
| Ex. (I-10) | Com. (A21) | 4.9 | 14.3 | 5000.0 | 35.1 | 137.0 | 0.33 | 0.62 |
| Ex. (I-11) | Com. (A22) | 5.4 | 15.1 | 5000.0 | 33.1 | 131.7 | 0.33 | 0.62 |
| Ex. (I-12) | Com. (A23) | 5.1 | 15.4 | 5000.0 | 32.5 | 126.5 | 0.33 | 0.62 |
| Ex. (I-13) | Com. (A24) | 5.3 | 15.5 | 5000.0 | 32.2 | 128.9 | 0.33 | 0.61 |
| Ex. (I-14) | Com. (A25) | 5.0 | 15.7 | 5000.0 | 31.8 | 125.9 | 0.33 | 0.61 |
| Ex. (I-15) | Com. (A26) | 5.3 | 15.0 | 5000.0 | 33.4 | 127.8 | 0.33 | 0.61 |
| Ex. (I-16) | Com. (A27) | 5.0 | 15.3 | 5000.0 | 32.6 | 126.8 | 0.33 | 0.62 |
| Ex. (I-17) | Com. (A31) | 5.0 | 16.2 | 5000.0 | 30.9 | 112.6 | 0.33 | 0.62 |
| Ex. (I-18) | Com. (A36) | 5.1 | 15.7 | 5000.0 | 31.7 | 113.9 | 0.33 | 0.61 |
| Ex. (I-19) | Com. (A47) | 5.3 | 16.6 | 5000.0 | 30.2 | 119.7 | 0.33 | 0.62 |
| Ex. (I-20) | Com. (A51) | 5.2 | 15.3 | 5000.0 | 32.7 | 123.7 | 0.33 | 0.62 |
| Ex. (I-21) | Com. (A56) | 5.2 | 15.6 | 5000.0 | 32.1 | 114.9 | 0.33 | 0.61 |
| Ex. (I-22) | Com. (A62) | 5.3 | 16.0 | 5000.0 | 31.3 | 111.8 | 0.33 | 0.62 |
| Ex. (I-23) | Com. (A66) | 5.1 | 15.7 | 5000.0 | 31.8 | 112.9 | 0.33 | 0.62 |
| Ex. (I-24) | Com. (A72) | 5.1 | 16.4 | 5000.0 | 30.5 | 110.9 | 0.33 | 0.61 |
| Ex. (I-25) | Com. (A87) | 5.2 | 16.3 | 5000.0 | 30.6 | 118.8 | 0.33 | 0.62 |
| Ex. (I-26) | Com. (A97) | 5.0 | 16.5 | 5000.0 | 30.3 | 118.3 | 0.33 | 0.62 |
| Ex. (I-27) | Com. (A101) | 5.2 | 15.4 | 5000.0 | 32.5 | 114.8 | 0.33 | 0.62 |
| Ex. (I-28) | Com. (A121) | 5.2 | 16.6 | 5000.0 | 30.2 | 118.2 | 0.33 | 0.61 |
| Ex. (I-29) | Com. (A123) | 5.2 | 16.3 | 5000.0 | 30.6 | 108.6 | 0.33 | 0.62 |
| Ex. (I-30) | Com. (A124) | 5.3 | 16.2 | 5000.0 | 30.9 | 112.7 | 0.33 | 0.61 |
| Ex. (I-31) | Com. (A125) | 5.3 | 16.2 | 5000.0 | 30.8 | 102.9 | 0.33 | 0.61 |
| Ex. (I-32) | Com. (A127) | 5.1 | 16.5 | 5000.0 | 30.3 | 97.1 | 0.33 | 0.62 |
| Ex. (I-33) | Com. (A128) | 5.3 | 16.4 | 5000.0 | 30.5 | 116.5 | 0.33 | 0.62 |
| Ex. (I-34) | Com. (A129) | 5.1 | 16.6 | 5000.0 | 30.2 | 104.7 | 0.33 | 0.62 |
| Ex. (I-35) | Com. (A130) | 5.4 | 16.1 | 5000.0 | 31.0 | 108.7 | 0.33 | 0.61 |

TABLE 4-continued

| | Compound | Voltage (V) | Current Density (mA/cm²) | Brightness (cd/m²) | Efficiency (cd/A) | Lifetime T(95) | CIE x | CIE y |
|---|---|---|---|---|---|---|---|---|
| Ex. (I-36) | Com. (A131) | 5.2 | 16.6 | 5000.0 | 30.2 | 98.1 | 0.33 | 0.61 |
| Ex. (I-37) | Com. (A134) | 5.3 | 16.3 | 5000.0 | 30.7 | 99.0 | 0.33 | 0.62 |
| Ex. (I-38) | Com. (A135) | 5.2 | 16.4 | 5000.0 | 30.5 | 112.9 | 0.33 | 0.62 |
| Ex. (I-39) | Com. (A142) | 5.3 | 16.3 | 5000.0 | 30.7 | 106.5 | 0.33 | 0.62 |
| Ex. (I-40) | Com. (A146) | 5.2 | 16.2 | 5000.0 | 30.8 | 118.5 | 0.33 | 0.61 |
| Ex. (I-41) | Com. (A161) | 5.1 | 16.2 | 5000.0 | 30.8 | 116.3 | 0.33 | 0.61 |
| Ex. (I-42) | Com. (A162) | 5.3 | 16.6 | 5000.0 | 30.1 | 104.0 | 0.33 | 0.61 |
| Ex. (I-43) | Com. (A165) | 5.3 | 16.4 | 5000.0 | 30.5 | 107.9 | 0.33 | 0.61 |
| Ex. (I-44) | Com. (A168) | 5.2 | 16.5 | 5000.0 | 30.4 | 103.6 | 0.33 | 0.61 |
| Ex. (I-45) | Com. (A169) | 5.1 | 15.8 | 5000.0 | 31.7 | 122.9 | 0.33 | 0.62 |
| Ex. (I-46) | Com. (A170) | 5.0 | 15.8 | 5000.0 | 31.6 | 124.1 | 0.33 | 0.61 |
| Ex. (I-47) | Com. (A171) | 5.0 | 15.5 | 5000.0 | 32.2 | 117.9 | 0.33 | 0.61 |
| Ex. (I-48) | Com. (A172) | 5.2 | 15.7 | 5000.0 | 31.8 | 115.4 | 0.33 | 0.62 |
| Ex. (I-49) | Com. (A173) | 5.2 | 15.8 | 5000.0 | 31.7 | 114.5 | 0.33 | 0.62 |
| Ex. (I-50) | Com. (A174) | 5.0 | 16.2 | 5000.0 | 31.0 | 110.6 | 0.33 | 0.61 |
| Ex. (I-51) | Com. (A175) | 5.1 | 16.1 | 5000.0 | 31.0 | 118.2 | 0.33 | 0.61 |
| Ex. (I-52) | Com. (A176) | 5.2 | 16.0 | 5000.0 | 31.3 | 117.7 | 0.33 | 0.61 |
| Ex. (I-53) | Com. (A177) | 4.9 | 15.3 | 5000.0 | 32.6 | 113.2 | 0.33 | 0.61 |
| Ex. (I-54) | Com. (A178) | 5.2 | 15.7 | 5000.0 | 31.9 | 111.2 | 0.33 | 0.61 |
| Ex. (I-55) | Com. (A179) | 5.2 | 14.9 | 5000.0 | 33.6 | 125.7 | 0.33 | 0.61 |
| Ex. (I-56) | Com. (A180) | 5.2 | 15.2 | 5000.0 | 32.9 | 127.8 | 0.33 | 0.61 |
| Ex. (I-57) | Com. (A181) | 5.2 | 15.9 | 5000.0 | 31.4 | 117.0 | 0.33 | 0.62 |
| Ex. (I-58) | Com. (A182) | 5.3 | 15.9 | 5000.0 | 31.5 | 121.8 | 0.33 | 0.62 |
| Ex. (I-59) | Com. (A183) | 5.0 | 15.6 | 5000.0 | 32.0 | 120.7 | 0.33 | 0.62 |
| Ex. (I-60) | Com. (A184) | 5.0 | 15.5 | 5000.0 | 32.3 | 112.7 | 0.33 | 0.61 |
| Ex. (I-61) | Com. (A185) | 5.0 | 15.8 | 5000.0 | 31.6 | 123.2 | 0.33 | 0.61 |
| Ex. (I-62) | Com. (A186) | 5.2 | 16.2 | 5000.0 | 30.9 | 102.8 | 0.33 | 0.62 |
| Ex. (I-63) | Com. (A187) | 5.2 | 15.6 | 5000.0 | 32.0 | 111.5 | 0.33 | 0.62 |
| Ex. (I-64) | Com. (A188) | 5.1 | 15.9 | 5000.0 | 31.4 | 120.4 | 0.33 | 0.62 |
| Ex. (I-65) | Com. (A189) | 5.3 | 16.1 | 5000.0 | 31.1 | 110.9 | 0.33 | 0.62 |
| Ex. (I-66) | Com. (A190) | 5.0 | 16.2 | 5000.0 | 30.8 | 103.4 | 0.33 | 0.62 |
| Ex. (I-67) | Com. (A191) | 5.3 | 15.0 | 5000.0 | 33.4 | 120.2 | 0.33 | 0.61 |
| Ex. (I-68) | Com. (A192) | 5.0 | 15.6 | 5000.0 | 32.1 | 119.0 | 0.33 | 0.61 |
| Ex. (I-69) | Com. (A193) | 5.3 | 15.5 | 5000.0 | 32.3 | 116.4 | 0.33 | 0.61 |
| Ex. (I-70) | Com. (A194) | 5.0 | 15.4 | 5000.0 | 32.6 | 112.6 | 0.33 | 0.61 |
| Ex. (I-71) | Com. (A195) | 5.1 | 15.4 | 5000.0 | 32.5 | 118.1 | 0.33 | 0.62 |
| Ex. (I-72) | Com. (A196) | 5.0 | 15.8 | 5000.0 | 31.6 | 120.4 | 0.33 | 0.61 |
| Ex. (I-73) | Com. (A197) | 5.2 | 16.7 | 5000.0 | 30.0 | 109.9 | 0.33 | 0.62 |
| Ex. (I-74) | Com. (A198) | 5.1 | 15.8 | 5000.0 | 31.6 | 115.8 | 0.33 | 0.61 |
| Ex. (I-75) | Com. (A199) | 5.1 | 15.2 | 5000.0 | 32.8 | 122.2 | 0.33 | 0.62 |
| Ex. (I-76) | Com. (A200) | 5.2 | 15.1 | 5000.0 | 33.2 | 122.5 | 0.33 | 0.61 |
| Ex. (I-77) | Com. (A201) | 5.1 | 15.5 | 5000.0 | 32.2 | 113.2 | 0.33 | 0.61 |
| Ex. (I-78) | Com. (A202) | 4.9 | 15.5 | 5000.0 | 32.2 | 114.5 | 0.33 | 0.61 |
| Ex. (I-79) | Com. (A203) | 5.0 | 14.7 | 5000.0 | 34.1 | 137.1 | 0.33 | 0.61 |
| Ex. (I-80) | Com. (A204) | 5.2 | 15.1 | 5000.0 | 33.2 | 127.2 | 0.33 | 0.62 |
| Ex. (I-81) | Com. (A205) | 5.1 | 15.6 | 5000.0 | 32.1 | 116.4 | 0.33 | 0.61 |
| Ex. (I-82) | Com. (A206) | 5.2 | 15.8 | 5000.0 | 31.7 | 117.2 | 0.33 | 0.61 |
| Ex. (I-83) | Com. (A207) | 5.3 | 14.6 | 5000.0 | 34.3 | 136.9 | 0.33 | 0.61 |
| Ex. (I-84) | Com. (A208) | 5.2 | 15.1 | 5000.0 | 33.1 | 122.7 | 0.33 | 0.61 |
| Ex. (I-85) | Com. (A209) | 5.2 | 14.6 | 5000.0 | 34.1 | 141.7 | 0.33 | 0.61 |
| Ex. (I-86) | Com. (A210) | 5.3 | 15.2 | 5000.0 | 32.8 | 128.7 | 0.33 | 0.61 |
| Ex. (I-87) | Com. (A211) | 5.3 | 16.5 | 5000.0 | 30.3 | 104.2 | 0.33 | 0.62 |
| Ex. (I-88) | Com. (A212) | 5.2 | 15.8 | 5000.0 | 31.6 | 118.8 | 0.33 | 0.61 |
| Ex. (I-89) | Com. (A213) | 5.2 | 16.1 | 5000.0 | 31.0 | 110.7 | 0.33 | 0.62 |
| Ex. (I-90) | Com. (A214) | 5.3 | 16.0 | 5000.0 | 31.3 | 115.2 | 0.33 | 0.62 |
| Ex. (I-91) | Com. (A215) | 5.0 | 15.9 | 5000.0 | 31.4 | 114.8 | 0.33 | 0.62 |
| Ex. (I-92) | Com. (A216) | 5.0 | 16.0 | 5000.0 | 31.3 | 119.9 | 0.33 | 0.61 |
| Ex. (I-93) | Com. (A217) | 5.2 | 16.5 | 5000.0 | 30.3 | 96.9 | 0.33 | 0.62 |
| Ex. (I-94) | Com. (A218) | 5.0 | 16.2 | 5000.0 | 30.9 | 118.1 | 0.33 | 0.62 |
| Ex. (I-95) | Com. (A219) | 5.1 | 16.0 | 5000.0 | 31.3 | 117.4 | 0.33 | 0.62 |
| Ex. (I-96) | Com. (A220) | 5.3 | 16.0 | 5000.0 | 31.2 | 115.4 | 0.33 | 0.62 |
| Ex. (I-97) | Com. (A221) | 5.1 | 16.4 | 5000.0 | 30.4 | 98.0 | 0.33 | 0.61 |
| Ex. (I-98) | Com. (A222) | 5.1 | 16.6 | 5000.0 | 30.1 | 107.0 | 0.33 | 0.61 |
| Ex. (I-99) | Com. (A223) | 5.2 | 15.8 | 5000.0 | 31.7 | 110.6 | 0.33 | 0.62 |
| Ex. (I-100) | Com. (A224) | 5.0 | 15.8 | 5000.0 | 31.7 | 120.5 | 0.33 | 0.62 |
| Ex. (I-101) | Com. (A225) | 5.0 | 15.5 | 5000.0 | 32.3 | 119.1 | 0.33 | 0.62 |
| Ex. (I-102) | Com. (A226) | 5.3 | 15.5 | 5000.0 | 32.3 | 116.2 | 0.33 | 0.61 |
| Ex. (I-103) | Com. (A227) | 4.9 | 15.3 | 5000.0 | 32.7 | 124.3 | 0.33 | 0.62 |
| Ex. (I-104) | Com. (A228) | 5.2 | 15.1 | 5000.0 | 33.1 | 126.2 | 0.33 | 0.62 |
| Ex. (I-105) | Com. (A229) | 5.0 | 15.1 | 5000.0 | 33.2 | 124.4 | 0.33 | 0.61 |
| Ex. (I-106) | Com. (A230) | 5.1 | 14.6 | 5000.0 | 34.3 | 143.7 | 0.33 | 0.62 |
| Ex. (I-107) | Com. (A231) | 4.9 | 15.2 | 5000.0 | 32.8 | 124.4 | 0.33 | 0.61 |
| Ex. (I-108) | Com. (A232) | 5.2 | 15.0 | 5000.0 | 33.4 | 129.1 | 0.33 | 0.62 |
| Ex. (I-109) | Com. (A233) | 5.0 | 15.1 | 5000.0 | 33.2 | 123.1 | 0.33 | 0.61 |
| Ex. (I-110) | Com. (A234) | 5.0 | 15.2 | 5000.0 | 32.9 | 128.6 | 0.33 | 0.61 |

TABLE 4-continued

| | Compound | Voltage (V) | Current Density (mA/cm²) | Brightness (cd/m²) | Efficiency (cd/A) | Lifetime T(95) | CIE x | CIE y |
|---|---|---|---|---|---|---|---|---|
| Ex. (I-111) | Com. (A235) | 5.0 | 15.2 | 5000.0 | 32.9 | 121.6 | 0.33 | 0.61 |
| Ex. (I-112) | Com. (A236) | 5.2 | 15.2 | 5000.0 | 32.8 | 125.7 | 0.33 | 0.61 |
| Ex. (I-113) | Com. (A237) | 5.2 | 15.1 | 5000.0 | 33.1 | 127.1 | 0.33 | 0.62 |
| Ex. (I-114) | Com. (A238) | 5.1 | 14.9 | 5000.0 | 33.5 | 129.4 | 0.33 | 0.62 |
| Ex. (I-115) | Com. (A239) | 5.0 | 15.2 | 5000.0 | 32.9 | 125.7 | 0.33 | 0.61 |
| Ex. (I-116) | Com. (A240) | 5.2 | 15.0 | 5000.0 | 33.4 | 129.9 | 0.33 | 0.61 |
| Ex. (I-117) | Com. (A241) | 4.9 | 15.1 | 5000.0 | 33.0 | 125.8 | 0.33 | 0.62 |
| Ex. (I-118) | Com. (A242) | 5.1 | 15.3 | 5000.0 | 32.8 | 121.4 | 0.33 | 0.61 |
| Ex. (I-119) | Com. (A243) | 5.1 | 15.3 | 5000.0 | 32.6 | 123.1 | 0.33 | 0.62 |
| Ex. (I-120) | Com. (A244) | 5.1 | 15.6 | 5000.0 | 32.0 | 116.8 | 0.33 | 0.61 |
| Ex. (I-121) | Com. (A245) | 5.2 | 14.9 | 5000.0 | 33.6 | 144.7 | 0.33 | 0.61 |
| Ex. (I-122) | Com. (A246) | 5.0 | 16.0 | 5000.0 | 31.2 | 123.9 | 0.33 | 0.62 |
| Ex. (I-123) | Com. (A247) | 5.2 | 16.1 | 5000.0 | 31.0 | 119.2 | 0.33 | 0.61 |
| Ex. (I-124) | Com. (A248) | 5.1 | 15.8 | 5000.0 | 31.7 | 123.1 | 0.33 | 0.62 |
| Ex. (I-125) | Com. (A249) | 4.9 | 15.4 | 5000.0 | 32.5 | 124.2 | 0.33 | 0.62 |
| Ex. (I-126) | Com. (A250) | 5.2 | 15.4 | 5000.0 | 32.4 | 113.7 | 0.33 | 0.61 |
| Ex. (I-127) | Com. (A251) | 5.0 | 15.1 | 5000.0 | 33.1 | 123.0 | 0.33 | 0.62 |
| Ex. (I-128) | Com. (A252) | 5.2 | 15.9 | 5000.0 | 31.4 | 116.0 | 0.33 | 0.61 |
| Ex. (I-129) | Com. (A253) | 5.1 | 15.3 | 5000.0 | 32.6 | 122.2 | 0.33 | 0.61 |
| Ex. (I-130) | Com. (A254) | 5.1 | 15.3 | 5000.0 | 32.7 | 125.5 | 0.33 | 0.61 |
| Ex. (I-131) | Com. (A255) | 5.0 | 14.9 | 5000.0 | 33.6 | 125.8 | 0.33 | 0.61 |
| Ex. (I-132) | Com. (A256) | 5.3 | 15.6 | 5000.0 | 32.1 | 119.9 | 0.33 | 0.62 |
| Ex. (I-133) | Com. (A257) | 5.2 | 14.9 | 5000.0 | 33.6 | 128.0 | 0.33 | 0.61 |
| Ex. (I-134) | Com. (A258) | 5.0 | 15.0 | 5000.0 | 33.3 | 121.6 | 0.33 | 0.62 |
| Ex. (I-135) | Com. (A259) | 5.0 | 14.7 | 5000.0 | 34.1 | 144.2 | 0.33 | 0.62 |
| Ex. (I-136) | Com. (A260) | 5.0 | 14.6 | 5000.0 | 34.4 | 143.7 | 0.33 | 0.62 |
| Ex. (I-137) | Com. (A261) | 5.3 | 15.8 | 5000.0 | 31.6 | 123.2 | 0.33 | 0.61 |
| Ex. (I-138) | Com. (A262) | 5.0 | 15.6 | 5000.0 | 32.0 | 112.2 | 0.33 | 0.61 |
| Ex. (I-139) | Com. (A263) | 5.0 | 15.9 | 5000.0 | 31.4 | 122.8 | 0.33 | 0.61 |
| Ex. (I-140) | Com. (A264) | 5.2 | 16.1 | 5000.0 | 31.0 | 111.1 | 0.33 | 0.62 |
| Ex. (I-141) | Com. (A265) | 5.3 | 15.6 | 5000.0 | 32.0 | 118.2 | 0.33 | 0.61 |
| Ex. (I-142) | Com. (A266) | 5.1 | 15.6 | 5000.0 | 32.1 | 114.9 | 0.33 | 0.62 |
| Ex. (I-143) | Com. (A267) | 5.0 | 15.6 | 5000.0 | 32.0 | 112.2 | 0.33 | 0.62 |
| Ex. (I-144) | Com. (A268) | 5.0 | 15.4 | 5000.0 | 32.5 | 110.5 | 0.33 | 0.61 |
| Ex. (I-145) | Com. (A269) | 5.1 | 15.9 | 5000.0 | 31.5 | 118.6 | 0.33 | 0.61 |
| Ex. (I-146) | Com. (A270) | 5.1 | 15.5 | 5000.0 | 32.2 | 111.4 | 0.33 | 0.61 |
| Ex. (I-147) | Com. (A271) | 5.0 | 15.4 | 5000.0 | 32.5 | 117.8 | 0.33 | 0.62 |
| Ex. (I-148) | Com. (A272) | 5.0 | 15.9 | 5000.0 | 31.5 | 114.6 | 0.33 | 0.62 |
| Ex. (I-149) | Com. (A273) | 5.0 | 15.0 | 5000.0 | 33.4 | 127.8 | 0.33 | 0.61 |
| Ex. (I-150) | Com. (A274) | 5.0 | 15.7 | 5000.0 | 31.9 | 120.1 | 0.33 | 0.62 |
| Ex. (I-151) | Com. (A275) | 5.0 | 15.5 | 5000.0 | 32.2 | 117.9 | 0.33 | 0.62 |
| Ex. (I-152) | Com. (A276) | 5.2 | 15.8 | 5000.0 | 31.6 | 115.7 | 0.33 | 0.61 |
| Ex. (I-153) | Com. (A277) | 5.1 | 14.7 | 5000.0 | 33.9 | 144.1 | 0.33 | 0.61 |
| Ex. (I-154) | Com. (A278) | 5.0 | 14.9 | 5000.0 | 33.5 | 128.2 | 0.33 | 0.62 |
| Ex. (I-155) | Com. (A279) | 5.3 | 15.3 | 5000.0 | 32.7 | 120.3 | 0.33 | 0.61 |
| Ex. (I-156) | Com. (A280) | 5.2 | 15.3 | 5000.0 | 32.7 | 121.8 | 0.33 | 0.61 |
| Ex. (I-157) | Com. (A281) | 5.3 | 15.5 | 5000.0 | 32.2 | 116.0 | 0.33 | 0.62 |
| Ex. (I-158) | Com. (A282) | 5.0 | 15.5 | 5000.0 | 32.4 | 124.8 | 0.33 | 0.62 |
| Ex. (I-159) | Com. (A283) | 5.2 | 16.1 | 5000.0 | 31.1 | 122.6 | 0.33 | 0.61 |
| Ex. (I-160) | Com. (A284) | 5.0 | 15.5 | 5000.0 | 32.3 | 124.8 | 0.33 | 0.62 |
| Ex. (I-161) | Com. (A285) | 5.3 | 14.9 | 5000.0 | 33.6 | 135.8 | 0.33 | 0.62 |
| Ex. (I-162) | Com. (A286) | 5.1 | 14.8 | 5000.0 | 33.7 | 136.9 | 0.33 | 0.61 |
| Ex. (I-163) | Com. (A287) | 5.2 | 15.0 | 5000.0 | 33.3 | 124.2 | 0.33 | 0.62 |
| Ex. (I-164) | Com. (A288) | 5.0 | 15.5 | 5000.0 | 32.3 | 114.6 | 0.33 | 0.62 |
| Ex. (I-165) | Com. (A289) | 5.3 | 14.1 | 5000.0 | 35.4 | 144.2 | 0.33 | 0.62 |
| Ex. (I-166) | Com. (A290) | 5.3 | 14.2 | 5000.0 | 35.3 | 144.6 | 0.33 | 0.62 |
| Ex. (I-167) | Com. (A291) | 5.2 | 14.5 | 5000.0 | 34.5 | 143.2 | 0.33 | 0.61 |
| Ex. (I-168) | Com. (A292) | 5.2 | 15.1 | 5000.0 | 33.1 | 128.9 | 0.33 | 0.61 |
| Ex. (I-169) | Com. (A293) | 5.2 | 15.3 | 5000.0 | 32.7 | 121.4 | 0.33 | 0.62 |
| Ex. (I-170) | Com. (A294) | 4.9 | 15.6 | 5000.0 | 32.1 | 115.2 | 0.33 | 0.62 |
| Ex. (I-171) | Com. (A295) | 4.9 | 15.6 | 5000.0 | 32.1 | 113.8 | 0.33 | 0.61 |
| Ex. (I-172) | Com. (A296) | 4.9 | 15.6 | 5000.0 | 32.0 | 113.8 | 0.33 | 0.62 |
| Ex. (I-173) | Com. (A297) | 5.1 | 15.6 | 5000.0 | 32.2 | 116.9 | 0.33 | 0.62 |
| Ex. (I-174) | Com. (A298) | 5.1 | 16.0 | 5000.0 | 31.2 | 113.4 | 0.33 | 0.61 |
| Ex. (I-175) | Com. (A299) | 5.2 | 15.3 | 5000.0 | 32.6 | 116.7 | 0.33 | 0.61 |
| Ex. (I-176) | Com. (A300) | 5.1 | 15.4 | 5000.0 | 32.5 | 114.6 | 0.33 | 0.61 |
| Ex. (I-177) | Com. (A301) | 5.1 | 15.7 | 5000.0 | 31.8 | 117.8 | 0.33 | 0.61 |
| Ex. (I-178) | Com. (A302) | 5.1 | 15.6 | 5000.0 | 32.0 | 121.7 | 0.33 | 0.61 |
| Ex. (I-179) | Com. (A303) | 5.1 | 16.2 | 5000.0 | 30.9 | 119.9 | 0.33 | 0.61 |
| Ex. (I-180) | Com. (A304) | 5.3 | 15.7 | 5000.0 | 31.9 | 122.7 | 0.33 | 0.62 |
| Ex. (I-181) | Com. (A305) | 5.2 | 15.6 | 5000.0 | 32.0 | 120.7 | 0.33 | 0.61 |
| Ex. (I-182) | Com. (A306) | 5.3 | 15.4 | 5000.0 | 32.4 | 110.1 | 0.33 | 0.61 |
| Ex. (I-183) | Com. (A307) | 5.3 | 15.9 | 5000.0 | 31.4 | 119.3 | 0.33 | 0.61 |
| Ex. (I-184) | Com. (A308) | 5.2 | 15.6 | 5000.0 | 32.1 | 117.7 | 0.33 | 0.61 |
| Ex. (I-185) | Com. (A309) | 5.3 | 14.9 | 5000.0 | 33.6 | 122.3 | 0.33 | 0.62 |

TABLE 4-continued

| Compound | Voltage (V) | Current Density (mA/cm²) | Brightness (cd/m²) | Efficiency (cd/A) | Lifetime T(95) | CIE x | CIE y |
|---|---|---|---|---|---|---|---|
| Ex. (I-186) Com. (A310) | 4.9 | 14.7 | 5000.0 | 34.1 | 141.2 | 0.33 | 0.61 |
| Ex. (I-187) Com. (A311) | 5.2 | 14.2 | 5000.0 | 35.3 | 142.0 | 0.33 | 0.61 |
| Ex. (I-188) Com. (A312) | 5.2 | 14.5 | 5000.0 | 34.5 | 138.0 | 0.33 | 0.62 |
| Ex. (I-189) Com. (A313) | 5.2 | 14.9 | 5000.0 | 33.6 | 142.3 | 0.33 | 0.62 |
| Ex. (I-190) Com. (A314) | 5.0 | 14.8 | 5000.0 | 33.7 | 137.3 | 0.33 | 0.61 |
| Ex. (I-191) Com. (A315) | 5.0 | 14.8 | 5000.0 | 33.8 | 140.9 | 0.33 | 0.62 |
| Ex. (I-192) Com. (A316) | 4.9 | 14.9 | 5000.0 | 33.6 | 125.7 | 0.33 | 0.62 |
| Ex. (I-193) Com. (A317) | 5.3 | 14.5 | 5000.0 | 34.4 | 143.4 | 0.33 | 0.61 |
| Ex. (I-194) Com. (A318) | 5.2 | 14.6 | 5000.0 | 34.3 | 138.3 | 0.33 | 0.61 |
| Ex. (I-195) Com. (A319) | 4.9 | 14.7 | 5000.0 | 34.1 | 138.8 | 0.33 | 0.61 |
| Ex. (I-196) Com. (A320) | 5.2 | 14.8 | 5000.0 | 33.8 | 138.7 | 0.33 | 0.61 |
| Ex. (I-197) Com. (A321) | 5.2 | 15.1 | 5000.0 | 33.1 | 128.2 | 0.33 | 0.62 |
| Ex. (I-198) Com. (A322) | 4.9 | 14.6 | 5000.0 | 34.2 | 136.7 | 0.33 | 0.62 |
| Ex. (I-199) Com. (A323) | 5.3 | 15.7 | 5000.0 | 31.9 | 113.6 | 0.33 | 0.61 |
| Ex. (I-200) Com. (A324) | 5.0 | 15.4 | 5000.0 | 32.4 | 112.8 | 0.33 | 0.62 |
| Ex. (I-201) Com. (A325) | 5.2 | 14.9 | 5000.0 | 33.6 | 138.8 | 0.33 | 0.62 |
| Ex. (I-202) Com. (A326) | 5.1 | 14.8 | 5000.0 | 33.9 | 139.7 | 0.33 | 0.61 |
| Ex. (I-203) Com. (A327) | 4.9 | 14.2 | 5000.0 | 35.3 | 143.5 | 0.33 | 0.62 |
| Ex. (I-204) Com. (A328) | 5.1 | 14.1 | 5000.0 | 35.4 | 144.0 | 0.33 | 0.62 |
| Ex. (I-205) Com. (A329) | 5.0 | 14.9 | 5000.0 | 33.6 | 129.8 | 0.33 | 0.61 |
| Ex. (I-206) Com. (A330) | 5.2 | 15.2 | 5000.0 | 33.0 | 127.2 | 0.33 | 0.61 |
| Ex. (I-207) Com. (A331) | 5.2 | 15.2 | 5000.0 | 32.9 | 120.2 | 0.33 | 0.62 |
| Ex. (I-208) Com. (A332) | 5.0 | 15.1 | 5000.0 | 33.1 | 120.5 | 0.33 | 0.61 |
| Ex. (I-209) Com. (A333) | 5.1 | 14.9 | 5000.0 | 33.5 | 128.4 | 0.33 | 0.61 |
| Ex. (I-210) Com. (A334) | 5.3 | 15.6 | 5000.0 | 32.1 | 124.4 | 0.33 | 0.61 |
| Ex. (I-211) Com. (A335) | 5.2 | 14.7 | 5000.0 | 34.0 | 139.6 | 0.33 | 0.61 |
| Ex. (I-212) Com. (A336) | 5.1 | 15.0 | 5000.0 | 33.3 | 126.8 | 0.33 | 0.62 |
| Ex. (I-213) Com. (A337) | 4.9 | 15.6 | 5000.0 | 32.0 | 115.3 | 0.33 | 0.61 |
| Ex. (I-214) Com. (A338) | 5.1 | 14.2 | 5000.0 | 35.3 | 141.4 | 0.33 | 0.62 |
| Ex. (I-215) Com. (A339) | 5.3 | 14.9 | 5000.0 | 33.6 | 128.3 | 0.33 | 0.61 |
| Ex. (I-216) Com. (A340) | 5.2 | 15.2 | 5000.0 | 32.9 | 123.5 | 0.33 | 0.62 |
| Ex. (I-217) Com. (A341) | 5.0 | 14.9 | 5000.0 | 33.5 | 129.1 | 0.33 | 0.62 |
| Ex. (I-218) Com. (A342) | 5.0 | 15.3 | 5000.0 | 32.7 | 124.3 | 0.33 | 0.62 |
| Ex. (I-219) Com. (A343) | 5.0 | 15.6 | 5000.0 | 32.1 | 118.3 | 0.33 | 0.62 |
| Ex. (I-220) Com. (A344) | 5.0 | 15.2 | 5000.0 | 32.8 | 127.4 | 0.33 | 0.61 |
| Ex. (I-221) Com. (A345) | 5.2 | 14.4 | 5000.0 | 34.6 | 144.5 | 0.33 | 0.62 |
| Ex. (I-222) Com. (A346) | 5.0 | 14.3 | 5000.0 | 35.0 | 143.1 | 0.33 | 0.62 |
| Ex. (I-223) Com. (A347) | 5.1 | 14.7 | 5000.0 | 34.0 | 135.4 | 0.33 | 0.61 |
| Ex. (I-224) Com. (A348) | 5.1 | 15.0 | 5000.0 | 33.2 | 124.1 | 0.33 | 0.62 |
| Ex. (I-225) Com. (A349) | 5.0 | 13.8 | 5000.0 | 36.3 | 146.4 | 0.33 | 0.61 |
| Ex. (I-226) Com. (A350) | 5.2 | 13.8 | 5000.0 | 36.2 | 148.3 | 0.33 | 0.61 |
| Ex. (I-227) Com. (A351) | 5.2 | 14.2 | 5000.0 | 35.2 | 142.2 | 0.33 | 0.62 |
| Ex. (I-228) Com. (A352) | 5.1 | 14.8 | 5000.0 | 33.9 | 138.9 | 0.33 | 0.61 |
| Ex. (I-229) Com. (A353) | 4.9 | 14.9 | 5000.0 | 33.5 | 124.7 | 0.33 | 0.62 |
| Ex. (I-230) Com. (A354) | 5.1 | 15.2 | 5000.0 | 32.9 | 126.1 | 0.33 | 0.61 |
| Ex. (I-231) Com. (A355) | 5.2 | 15.0 | 5000.0 | 33.4 | 122.2 | 0.33 | 0.61 |
| Ex. (I-232) Com. (A356) | 5.2 | 15.1 | 5000.0 | 33.1 | 124.4 | 0.33 | 0.62 |
| Ex. (I-233) Com. (A357) | 5.2 | 15.1 | 5000.0 | 33.1 | 124.5 | 0.33 | 0.61 |
| Ex. (I-234) Com. (A358) | 4.9 | 15.1 | 5000.0 | 33.2 | 127.1 | 0.33 | 0.61 |
| Ex. (I-235) Com. (A359) | 5.1 | 15.7 | 5000.0 | 31.8 | 117.6 | 0.33 | 0.61 |
| Ex. (I-236) Com. (A360) | 5.0 | 15.4 | 5000.0 | 32.5 | 115.4 | 0.33 | 0.62 |
| Ex. (I-237) Com. (A361) | 5.1 | 15.1 | 5000.0 | 33.1 | 121.5 | 0.33 | 0.62 |
| Ex. (I-238) Com. (A362) | 5.2 | 15.3 | 5000.0 | 32.8 | 126.0 | 0.33 | 0.62 |
| Ex. (I-239) Com. (A363) | 5.3 | 15.1 | 5000.0 | 33.2 | 120.9 | 0.33 | 0.61 |
| Ex. (I-240) Com. (A364) | 4.9 | 15.5 | 5000.0 | 32.2 | 110.0 | 0.33 | 0.61 |
| Ex. (I-241) Com. (A365) | 5.2 | 15.0 | 5000.0 | 33.4 | 128.6 | 0.33 | 0.62 |
| Ex. (I-242) Com. (A366) | 5.1 | 15.3 | 5000.0 | 32.7 | 120.7 | 0.33 | 0.62 |
| Ex. (I-243) Com. (A367) | 5.1 | 15.0 | 5000.0 | 33.3 | 125.1 | 0.33 | 0.62 |
| Ex. (I-244) Com. (A368) | 5.2 | 15.0 | 5000.0 | 33.3 | 128.9 | 0.33 | 0.61 |
| Ex. (I-245) Com. (A369) | 5.1 | 15.1 | 5000.0 | 33.1 | 129.2 | 0.33 | 0.62 |
| Ex. (I-246) Com. (A370) | 5.1 | 15.5 | 5000.0 | 32.2 | 116.9 | 0.33 | 0.61 |
| Ex. (I-247) Com. (A371) | 5.1 | 16.4 | 5000.0 | 30.4 | 98.1 | 0.33 | 0.62 |
| Ex. (I-248) Com. (A372) | 5.2 | 16.3 | 5000.0 | 30.7 | 108.9 | 0.33 | 0.62 |
| Ex. (I-249) Com. (A373) | 5.2 | 16.5 | 5000.0 | 30.4 | 112.8 | 0.33 | 0.61 |
| Ex. (I-250) Com. (A374) | 5.4 | 16.5 | 5000.0 | 30.4 | 110.9 | 0.33 | 0.61 |
| Ex. (I-251) Com. (A375) | 5.2 | 16.6 | 5000.0 | 30.1 | 118.7 | 0.33 | 0.62 |
| Ex. (I-252) Com. (A376) | 5.2 | 16.5 | 5000.0 | 30.2 | 110.2 | 0.33 | 0.61 |
| Ex. (I-253) Com. (A377) | 5.1 | 16.6 | 5000.0 | 30.2 | 98.2 | 0.33 | 0.61 |
| Ex. (I-254) Com. (A378) | 5.2 | 15.7 | 5000.0 | 31.9 | 120.8 | 0.33 | 0.62 |
| Ex. (I-255) Com. (A379) | 5.2 | 15.8 | 5000.0 | 31.7 | 115.2 | 0.33 | 0.61 |
| Ex. (I-256) Com. (A380) | 5.2 | 15.8 | 5000.0 | 31.7 | 120.3 | 0.33 | 0.62 |
| Ex. (I-257) Com. (A381) | 5.3 | 15.7 | 5000.0 | 31.8 | 121.1 | 0.33 | 0.61 |
| Ex. (I-258) Com. (A382) | 5.2 | 15.8 | 5000.0 | 31.7 | 117.6 | 0.33 | 0.61 |
| Ex. (I-259) Com. (A383) | 5.2 | 15.8 | 5000.0 | 31.6 | 124.9 | 0.33 | 0.62 |
| Ex. (I-260) Com. (A384) | 5.2 | 15.8 | 5000.0 | 31.7 | 119.5 | 0.33 | 0.62 |

TABLE 4-continued

| Compound | | Voltage (V) | Current Density (mA/cm$^2$) | Brightness (cd/m$^2$) | Efficiency (cd/A) | Lifetime T(95) | CIE x | y |
|---|---|---|---|---|---|---|---|---|
| Ex. (I-261) | Com. (A385) | 5.2 | 15.6 | 5000.0 | 32.1 | 113.8 | 0.33 | 0.61 |
| Ex. (I-262) | Com. (A386) | 5.3 | 15.6 | 5000.0 | 32.0 | 121.3 | 0.33 | 0.61 |
| Ex. (I-263) | Com. (A387) | 5.2 | 15.5 | 5000.0 | 32.2 | 116.6 | 0.33 | 0.61 |
| Ex. (I-264) | Com. (A388) | 5.2 | 15.4 | 5000.0 | 32.4 | 120.5 | 0.33 | 0.62 |
| Ex. (I-265) | Com. (A389) | 5.3 | 15.7 | 5000.0 | 31.8 | 125.9 | 0.33 | 0.61 |
| Ex. (I-266) | Com. (A390) | 5.3 | 15.4 | 5000.0 | 32.5 | 119.1 | 0.33 | 0.62 |
| Ex. (I-267) | Com. (A391) | 5.3 | 15.6 | 5000.0 | 32.0 | 115.5 | 0.33 | 0.62 |
| Ex. (I-268) | Com. (A392) | 5.2 | 15.3 | 5000.0 | 32.6 | 122.5 | 0.33 | 0.62 |
| Ex. (I-269) | Com. (C1) | 5.3 | 15.0 | 5000.0 | 33.4 | 129.9 | 0.33 | 0.61 |
| Ex. (I-270) | Com. (C2) | 5.3 | 15.7 | 5000.0 | 31.8 | 125.9 | 0.33 | 0.61 |
| Ex. (I-271) | Com. (C3) | 5.1 | 14.8 | 5000.0 | 33.8 | 115.2 | 0.33 | 0.61 |
| Ex. (I-272) | Com. (C4) | 5.2 | 15.0 | 5000.0 | 33.3 | 125.6 | 0.33 | 0.62 |
| Ex. (I-273) | Com. (C5) | 5.1 | 14.9 | 5000.0 | 33.6 | 123.6 | 0.33 | 0.61 |
| Ex. (I-274) | Com. (C6) | 5.3 | 14.9 | 5000.0 | 33.7 | 115.7 | 0.33 | 0.62 |
| Ex. (I-275) | Com. (C7) | 5.4 | 15.6 | 5000.0 | 32.1 | 126.2 | 0.33 | 0.61 |
| Ex. (I-276) | Com. (C8) | 5.3 | 15.2 | 5000.0 | 33.0 | 123.7 | 0.33 | 0.61 |
| Ex. (I-277) | Com. (C9) | 5.2 | 15.8 | 5000.0 | 31.7 | 123.8 | 0.33 | 0.61 |
| Ex. (I-278) | Com. (C10) | 5.1 | 15.8 | 5000.0 | 31.7 | 122.5 | 0.33 | 0.61 |
| Ex. (I-279) | Com. (C11) | 5.3 | 14.7 | 5000.0 | 33.9 | 137.6 | 0.33 | 0.61 |
| Ex. (I-280) | Com. (C12) | 5.2 | 14.8 | 5000.0 | 33.9 | 116.8 | 0.33 | 0.61 |
| Ex. (I-281) | Com. (C13) | 5.3 | 15.3 | 5000.0 | 32.8 | 135.1 | 0.33 | 0.62 |
| Ex. (I-282) | Com. (C14) | 5.4 | 15.8 | 5000.0 | 31.7 | 124.0 | 0.33 | 0.62 |
| Ex. (I-283) | Com. (C15) | 5.1 | 14.9 | 5000.0 | 33.5 | 133.3 | 0.33 | 0.62 |
| Ex. (I-284) | Com. (C16) | 5.0 | 15.0 | 5000.0 | 33.4 | 117.0 | 0.33 | 0.62 |
| Ex. (I-285) | Com. (C17) | 5.4 | 16.1 | 5000.0 | 31.0 | 122.4 | 0.33 | 0.61 |
| Ex. (I-286) | Com. (C18) | 5.3 | 16.0 | 5000.0 | 31.2 | 123.7 | 0.33 | 0.62 |
| Ex. (I-287) | Com. (C19) | 5.0 | 15.6 | 5000.0 | 32.1 | 127.0 | 0.33 | 0.62 |
| Ex. (I-288) | Com. (C20) | 5.1 | 15.4 | 5000.0 | 32.5 | 135.8 | 0.33 | 0.62 |
| Ex. (I-289) | Com. (C21) | 5.3 | 16.0 | 5000.0 | 31.2 | 129.1 | 0.33 | 0.61 |
| Ex. (I-290) | Com. (C22) | 5.1 | 15.6 | 5000.0 | 32.1 | 138.4 | 0.33 | 0.62 |
| Ex. (I-291) | Com. (C23) | 5.0 | 15.5 | 5000.0 | 32.2 | 115.5 | 0.33 | 0.61 |
| Ex. (I-292) | Com. (C24) | 5.2 | 15.2 | 5000.0 | 32.8 | 134.7 | 0.33 | 0.61 |
| Ex. (I-293) | Com. (C25) | 5.2 | 15.8 | 5000.0 | 31.7 | 136.9 | 0.33 | 0.61 |
| Ex. (I-294) | Com. (C26) | 5.1 | 15.7 | 5000.0 | 31.9 | 128.9 | 0.33 | 0.61 |
| Ex. (I-295) | Com. (C27) | 5.0 | 15.9 | 5000.0 | 31.4 | 119.7 | 0.33 | 0.61 |
| Ex. (I-296) | Com. (C28) | 5.3 | 15.7 | 5000.0 | 31.9 | 138.4 | 0.33 | 0.62 |
| Ex. (I-297) | Com. (C29) | 5.3 | 16.0 | 5000.0 | 31.3 | 130.1 | 0.33 | 0.62 |
| Ex. (I-298) | Com. (C30) | 5.3 | 15.2 | 5000.0 | 32.9 | 119.2 | 0.33 | 0.62 |
| Ex. (I-299) | Com. (C31) | 5.1 | 14.9 | 5000.0 | 33.6 | 129.0 | 0.33 | 0.61 |
| Ex. (I-300) | Com. (C32) | 5.1 | 15.4 | 5000.0 | 32.4 | 115.2 | 0.33 | 0.62 |
| Ex. (I-301) | Com. (C33) | 5.1 | 15.8 | 5000.0 | 31.6 | 118.9 | 0.33 | 0.62 |
| Ex. (I-302) | Com. (C34) | 5.1 | 15.5 | 5000.0 | 32.2 | 138.4 | 0.33 | 0.62 |
| Ex. (I-303) | Com. (C35) | 5.1 | 14.9 | 5000.0 | 33.5 | 133.5 | 0.33 | 0.61 |
| Ex. (I-304) | Com. (C36) | 5.2 | 15.0 | 5000.0 | 33.3 | 138.2 | 0.33 | 0.61 |
| Ex. (I-305) | Com. (C37) | 5.2 | 15.7 | 5000.0 | 31.9 | 134.1 | 0.33 | 0.61 |
| Ex. (I-306) | Com. (C38) | 5.3 | 15.2 | 5000.0 | 32.9 | 126.5 | 0.33 | 0.61 |
| Ex. (I-307) | Com. (C39) | 5.3 | 14.8 | 5000.0 | 33.9 | 137.4 | 0.33 | 0.62 |
| Ex. (I-308) | Com. (C40) | 5.3 | 15.4 | 5000.0 | 32.4 | 130.5 | 0.33 | 0.61 |

As can be seen from the results of Table 4, organic electroluminescent devices utilizing the compounds of the present invention as materials of the hole transporting layer can be operated at a relatively low driving voltage, and with significantly improved luminous efficiency and lifespan, compared to the organic electroluminescent devices utilizing Comparative Compounds 1 to 4 as materials of the hole transporting layer.

In particular, the data shows that different results are obtained according to linkage type (linear or non-linear type) as demonstrated by comparison between the compounds of the present invention (non-linear linkers) and comparative compound 2 and 4 (linear-type linkers).

The linker between carbazole and amine (—NAr$^2$Ar$^3$) allows for a deeper HOMO energy level, a higher T1 value, and higher thermal stability at a meta position (non-linear type), compared to a para position (linear type), as demonstrated by the superiority of the compounds of the present invention to Comparative Compounds 2 and 4 in terms of driving voltage, luminous efficiency, and lifespan.

A linker at a meta position (non-linear type) allows for a shorter conjugation length than that at a para position (linear type), thus guaranteeing a wider band gap and a higher T1 value.

Accordingly, the linker at a meta position (non-linear type) is believed to positively contribute to the ability to block electrons thanks to the high T1 value, and to help a hole be smoothly transported to the light emitting layer thanks to a deep HOMO energy level, so that excitons can be more easily and efficiently created in the light emitting layer. Also, the high thermal stability was observed to increase the lifespan.

When the previously described properties (the deep HOMO energy level, high T1 value, and high thermal stability) are taken into consideration, the position of the linker between the carbazole and amine (—NAr$^2$Ar$^3$) has great influence on the band gap and electrical and interfacial properties, and serves as the main factor for improving performance of the device.

Additionally, for the hole transporting layer, account must be taken of a correlation with the light emitting layer (host).

Thus, even though a similar core is used in the hole transporting layer, it would be very difficult for those having ordinary skill in the art to analogize the features of the hole transporting layer in which the compound according to the present invention is used.

[Test Example □-1] Blue Organic Light Emitting Diode (Emission-Auxiliary Layer)

Organic light emitting diodes (OLEDs) were fabricated according to a conventional method by using a compound of the present invention as an emission-auxiliary layer material. First, an ITO layer (anode) was formed on a glass substrate, and 2-TNATA was vacuum-deposited on the ITO layer to form a hole injection layer with a thickness of 60 nm. Subsequently, N,N'-Bis(1-naphthalenyl)-N,N'-bis-phenyl-(1,1'-biphenyl)-4,4'-diamine (hereinafter abbreviated as "NPB") was vacuum-deposited with a thickness of 60 nm on the hole injection layer to form a hole transport layer. Next, the inventive compound A1 was vacuum-deposited with a thickness of 20 nm on the hole transport layer to form an emission-auxiliary layer. Thereafter, a light emitting layer with a thickness of 30 nm was deposited on the emission-auxiliary layer by doping the emission-auxiliary layer with 9,10-di(naphthalen-2-yl)anthracene (hereinafter abbreviated as "ADN") as a host material and BD-052X (made by Idemitsu kosan) as a dopant material in a weight ratio of 93:7. Also, BAlq was vacuum-deposited with a thickness of 10 nm on the light emitting layer to form a hole blocking layer, and then a film of Alq$_3$ was formed with a thickness of 40 nm to form an electron injection layer. Subsequently, LiF as halogenated alkali metal was deposited with a thickness of 0.2 nm on the electron injection layer, and then Al was deposited with a thickness of 150 nm thereon to form a cathode. In this way, an OLED was completed.

[Test Example □-2] to [Test Example □-80 Blue Organic Light Emitting Diode (Emission-Auxiliary Layer)

The OLED was manufactured in the same manner as described in Test Example □-1, except that any one of the compounds A2 to A378 of the present invention in the Table 5 below was used as the Emission-Auxiliary Layer material, instead of the inventive compound A1.

Comparative Example 5

The OLED was manufactured in the same manner as described in Test Example □-1, except that Comparative Compound 2 represented above was used as the Emission-Auxiliary Layer material, instead of the inventive compound A1.

Comparative Example 6

The OLED was manufactured in the same manner as described in Test Example □-1, except that Comparative Compound 4 represented above was used as the Emission-Auxiliary Layer material, instead of the inventive compound A1.

Comparative Example 7

The OLED was manufactured in the same manner as described in Test Example □-1, except that Comparative Compound 5 represented below above was used as the Emission-Auxiliary Layer material, instead of the inventive compound A1.

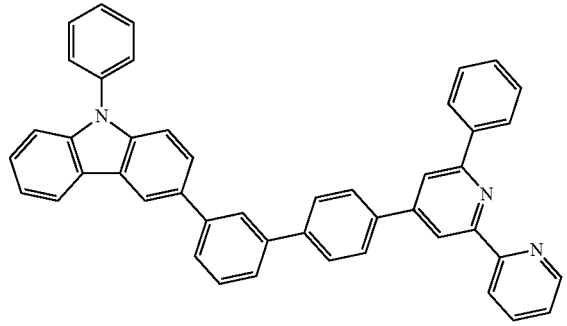

<Comparative Compound 5>

Comparative Example 8

An OLED was manufactured in the same manner as described in Test Example □-1, except that an emission-auxiliary layer was not formed.

A forward bias DC voltage was applied to each of the OLEDs manufactured through Test Examples (□-1) to (□-80) and Comparative Example (5) to (8), and electroluminescence (EL characteristics of the OLED were measured by PR-650 (Photoresearch). Also, T95 life span was measured by life span measuring equipment (Mcscience) at a reference brightness of 500 cd/m$^2$. Table 5 below shows evaluation results of OLEDs manufactured Test Examples and Comparative Examples.

TABLE 5

|  | Compound | Voltage (V) | Current Density (mA/cm$^2$) | Brightness (cd/m$^2$) | Efficiency (cd/A) | Lifetime T(95) | CIE x | y |
|---|---|---|---|---|---|---|---|---|
| comp. Ex(5) | comp. Com 2 | 5.1 | 11.4 | 500.0 | 4.4 | 86.5 | 0.14 | 0.12 |
| comp. Ex(6) | comp. Com 4 | 5.1 | 10.6 | 500.0 | 4.7 | 85.6 | 0.14 | 0.12 |
| comp. Ex(7) | comp. Com 5 | 5.5 | 12.2 | 500.0 | 4.1 | 72.3 | 0.14 | 0.13 |
| comp. Ex(8) | — | 5.0 | 14.3 | 500.0 | 3.5 | 56.4 | 0.14 | 0.15 |
| Ex. (II-1) | Com. (A1) | 5.2 | 9.0 | 500.0 | 5.5 | 113.4 | 0.14 | 0.11 |
| Ex. (II-2) | Com. (A7) | 5.0 | 8.5 | 500.0 | 5.9 | 131.2 | 0.14 | 0.11 |
| Ex. (II-3) | Com. (A17) | 5.2 | 7.0 | 500.0 | 7.1 | 142.4 | 0.14 | 0.12 |
| Ex. (II-4) | Com. (A19) | 5.2 | 9.8 | 500.0 | 5.1 | 100.1 | 0.14 | 0.12 |
| Ex. (II-5) | Com. (A21) | 5.2 | 7.1 | 500.0 | 7.1 | 141.7 | 0.14 | 0.12 |
| Ex. (II-6) | Com. (A22) | 5.2 | 7.9 | 500.0 | 6.3 | 134.0 | 0.14 | 0.11 |
| Ex. (II-7) | Com. (A23) | 5.3 | 8.3 | 500.0 | 6.0 | 121.8 | 0.14 | 0.12 |

TABLE 5-continued

| | Compound | Voltage (V) | Current Density (mA/cm²) | Brightness (cd/m²) | Efficiency (cd/A) | Lifetime T(95) | CIE x | CIE y |
|---|---|---|---|---|---|---|---|---|
| Ex. (II-8) | Com. (A26) | 5.0 | 7.9 | 500.0 | 6.3 | 133.2 | 0.14 | 0.12 |
| Ex. (II-9) | Com. (A51) | 5.2 | 8.2 | 500.0 | 6.1 | 122.2 | 0.14 | 0.12 |
| Ex. (II-10) | Com. (A66) | 5.2 | 9.2 | 500.0 | 5.4 | 120.9 | 0.14 | 0.12 |
| Ex. (II-11) | Com. (A146) | 5.2 | 9.2 | 500.0 | 5.4 | 109.0 | 0.14 | 0.12 |
| Ex. (II-12) | Com. (A162) | 5.0 | 9.8 | 500.0 | 5.1 | 111.5 | 0.14 | 0.11 |
| Ex. (II-13) | Com. (A165) | 5.3 | 9.2 | 500.0 | 5.4 | 108.5 | 0.14 | 0.11 |
| Ex. (II-14) | Com. (A169) | 5.1 | 9.3 | 500.0 | 5.4 | 113.4 | 0.14 | 0.12 |
| Ex. (II-15) | Com. (A170) | 5.2 | 9.1 | 500.0 | 5.5 | 114.2 | 0.14 | 0.11 |
| Ex. (II-16) | Com. (A171) | 5.3 | 8.4 | 500.0 | 6.0 | 125.0 | 0.14 | 0.12 |
| Ex. (II-17) | Com. (A172) | 5.1 | 8.3 | 500.0 | 6.1 | 126.9 | 0.14 | 0.11 |
| Ex. (II-18) | Com. (A174) | 5.0 | 9.2 | 500.0 | 5.5 | 111.4 | 0.14 | 0.11 |
| Ex. (II-19) | Com. (A178) | 5.0 | 8.2 | 500.0 | 6.1 | 131.5 | 0.14 | 0.11 |
| Ex. (II-20) | Com. (A179) | 5.0 | 8.1 | 500.0 | 6.2 | 133.3 | 0.14 | 0.11 |
| Ex. (II-21) | Com. (A180) | 5.0 | 8.0 | 500.0 | 6.3 | 134.1 | 0.14 | 0.12 |
| Ex. (II-22) | Com. (A183) | 5.1 | 8.3 | 500.0 | 6.1 | 125.7 | 0.14 | 0.12 |
| Ex. (II-23) | Com. (A187) | 5.2 | 8.3 | 500.0 | 6.0 | 130.1 | 0.14 | 0.12 |
| Ex. (II-24) | Com. (A191) | 5.1 | 8.1 | 500.0 | 6.2 | 124.4 | 0.14 | 0.11 |
| Ex. (II-25) | Com. (A199) | 5.1 | 7.9 | 500.0 | 6.4 | 127.7 | 0.14 | 0.11 |
| Ex. (II-26) | Com. (A203) | 5.1 | 7.7 | 500.0 | 6.5 | 135.0 | 0.14 | 0.11 |
| Ex. (II-27) | Com. (A204) | 5.0 | 8.2 | 500.0 | 6.1 | 124.8 | 0.14 | 0.12 |
| Ex. (II-28) | Com. (A209) | 5.1 | 7.5 | 500.0 | 6.6 | 135.1 | 0.14 | 0.11 |
| Ex. (II-29) | Com. (A210) | 5.1 | 8.0 | 500.0 | 6.2 | 134.9 | 0.14 | 0.11 |
| Ex. (II-30) | Com. (A212) | 5.1 | 9.1 | 500.0 | 5.5 | 119.3 | 0.14 | 0.12 |
| Ex. (II-31) | Com. (A216) | 5.3 | 8.8 | 500.0 | 5.7 | 116.9 | 0.14 | 0.11 |
| Ex. (II-32) | Com. (A219) | 5.2 | 8.8 | 500.0 | 5.7 | 123.8 | 0.14 | 0.11 |
| Ex. (II-33) | Com. (A226) | 5.0 | 8.2 | 500.0 | 6.1 | 120.7 | 0.14 | 0.11 |
| Ex. (II-34) | Com. (A227) | 5.0 | 8.4 | 500.0 | 6.0 | 115.3 | 0.14 | 0.11 |
| Ex. (II-35) | Com. (A228) | 5.0 | 8.1 | 500.0 | 6.2 | 131.2 | 0.14 | 0.12 |
| Ex. (II-36) | Com. (A229) | 5.0 | 7.9 | 500.0 | 6.3 | 130.9 | 0.14 | 0.11 |
| Ex. (II-37) | Com. (A230) | 5.1 | 7.1 | 500.0 | 7.0 | 143.0 | 0.14 | 0.11 |
| Ex. (II-38) | Com. (A231) | 5.0 | 8.0 | 500.0 | 6.2 | 130.7 | 0.14 | 0.11 |
| Ex. (II-39) | Com. (A232) | 5.1 | 8.2 | 500.0 | 6.1 | 128.4 | 0.14 | 0.12 |
| Ex. (II-40) | Com. (A234) | 5.0 | 8.1 | 500.0 | 6.2 | 125.3 | 0.14 | 0.12 |
| Ex. (II-41) | Com. (A235) | 5.1 | 7.9 | 500.0 | 6.3 | 130.2 | 0.14 | 0.11 |
| Ex. (II-42) | Com. (A238) | 5.1 | 7.9 | 500.0 | 6.4 | 136.9 | 0.14 | 0.11 |
| Ex. (II-43) | Com. (A240) | 5.0 | 7.9 | 500.0 | 6.4 | 134.4 | 0.14 | 0.12 |
| Ex. (II-44) | Com. (A241) | 5.1 | 7.9 | 500.0 | 6.3 | 129.3 | 0.14 | 0.11 |
| Ex. (II-45) | Com. (A245) | 5.1 | 7.5 | 500.0 | 6.6 | 135.7 | 0.14 | 0.11 |
| Ex. (II-46) | Com. (A251) | 5.1 | 8.1 | 500.0 | 6.2 | 134.1 | 0.14 | 0.11 |
| Ex. (II-47) | Com. (A253) | 5.1 | 8.4 | 500.0 | 6.0 | 115.5 | 0.14 | 0.12 |
| Ex. (II-48) | Com. (A254) | 5.0 | 7.9 | 500.0 | 6.3 | 125.3 | 0.14 | 0.11 |
| Ex. (II-49) | Com. (A255) | 5.2 | 7.9 | 500.0 | 6.4 | 129.6 | 0.14 | 0.11 |
| Ex. (II-50) | Com. (A257) | 5.1 | 7.9 | 500.0 | 6.4 | 133.7 | 0.14 | 0.11 |
| Ex. (II-51) | Com. (A258) | 5.2 | 7.9 | 500.0 | 6.3 | 138.7 | 0.14 | 0.11 |
| Ex. (II-52) | Com. (A259) | 5.1 | 7.4 | 500.0 | 6.7 | 134.3 | 0.14 | 0.11 |
| Ex. (II-53) | Com. (A260) | 5.0 | 7.5 | 500.0 | 6.6 | 129.1 | 0.14 | 0.12 |
| Ex. (II-54) | Com. (A270) | 5.1 | 8.3 | 500.0 | 6.0 | 126.3 | 0.14 | 0.11 |
| Ex. (II-55) | Com. (A273) | 5.2 | 8.0 | 500.0 | 6.3 | 132.5 | 0.14 | 0.12 |
| Ex. (II-56) | Com. (A277) | 5.0 | 7.5 | 500.0 | 6.6 | 133.1 | 0.14 | 0.11 |
| Ex. (II-57) | Com. (A286) | 5.1 | 7.7 | 500.0 | 6.5 | 138.8 | 0.14 | 0.12 |
| Ex. (II-58) | Com. (A290) | 5.0 | 7.1 | 500.0 | 7.0 | 142.2 | 0.14 | 0.11 |
| Ex. (II-59) | Com. (A294) | 5.2 | 8.4 | 500.0 | 5.9 | 123.1 | 0.14 | 0.11 |
| Ex. (II-60) | Com. (A297) | 5.3 | 8.2 | 500.0 | 6.1 | 124.8 | 0.14 | 0.12 |
| Ex. (II-61) | Com. (A308) | 5.1 | 8.4 | 500.0 | 5.9 | 120.0 | 0.14 | 0.12 |
| Ex. (II-62) | Com. (A310) | 5.1 | 7.3 | 500.0 | 6.9 | 131.0 | 0.14 | 0.11 |
| Ex. (II-63) | Com. (A311) | 5.0 | 7.0 | 500.0 | 7.1 | 145.2 | 0.14 | 0.11 |
| Ex. (II-64) | Com. (A312) | 5.0 | 7.1 | 500.0 | 7.0 | 141.8 | 0.14 | 0.12 |
| Ex. (II-65) | Com. (A315) | 5.0 | 7.1 | 500.0 | 7.1 | 130.5 | 0.14 | 0.12 |
| Ex. (II-66) | Com. (A318) | 5.0 | 7.3 | 500.0 | 6.9 | 143.6 | 0.14 | 0.11 |
| Ex. (II-67) | Com. (A319) | 5.1 | 7.3 | 500.0 | 6.9 | 134.6 | 0.14 | 0.11 |
| Ex. (II-68) | Com. (A320) | 5.1 | 7.1 | 500.0 | 7.0 | 133.4 | 0.14 | 0.12 |
| Ex. (II-69) | Com. (A322) | 5.1 | 7.3 | 500.0 | 6.8 | 131.5 | 0.14 | 0.12 |
| Ex. (II-70) | Com. (A325) | 5.1 | 7.1 | 500.0 | 7.0 | 141.7 | 0.14 | 0.11 |
| Ex. (II-71) | Com. (A329) | 5.1 | 7.7 | 500.0 | 6.5 | 138.9 | 0.14 | 0.11 |
| Ex. (II-72) | Com. (A335) | 5.1 | 7.2 | 500.0 | 6.9 | 138.6 | 0.14 | 0.11 |
| Ex. (II-73) | Com. (A338) | 5.2 | 6.9 | 500.0 | 7.2 | 146.3 | 0.14 | 0.11 |
| Ex. (II-74) | Com. (A345) | 5.0 | 6.9 | 500.0 | 7.3 | 148.4 | 0.14 | 0.12 |
| Ex. (II-75) | Com. (A346) | 5.1 | 7.0 | 500.0 | 7.2 | 147.4 | 0.14 | 0.11 |
| Ex. (II-76) | Com. (A350) | 5.0 | 6.7 | 500.0 | 7.5 | 151.1 | 0.14 | 0.12 |
| Ex. (II-77) | Com. (A353) | 5.0 | 7.5 | 500.0 | 6.6 | 142.9 | 0.14 | 0.12 |
| Ex. (II-78) | Com. (A361) | 5.2 | 7.6 | 500.0 | 6.6 | 141.0 | 0.14 | 0.12 |
| Ex. (II-79) | Com. (A365) | 5.2 | 7.5 | 500.0 | 6.7 | 140.1 | 0.14 | 0.11 |
| Ex. (II-80) | Com. (A378) | 5.1 | 8.1 | 500.0 | 6.2 | 134.0 | 0.14 | 0.11 |

[Test Example □-1] Green Organic Light Emitting Diode (Emission-Auxiliary Layer)

Organic light emitting diodes (OLEDs) were fabricated according to a conventional method by using a compound of the present invention as an emission-auxiliary layer material. First, an ITO layer (anode) was formed on a glass substrate, and 2-TNATA was vacuum-deposited on the ITO layer to form a hole injection layer with a thickness of 60 nm. Subsequently, NPB was vacuum-deposited with a thickness of 60 nm on the hole injection layer to form a hole transport layer. Next, the inventive compound A1 was vacuum-deposited with a thickness of 20 nm on the hole transport layer to form an emission-auxiliary layer. Thereafter, a light emitting layer with a thickness of 30 nm was deposited on the emission-auxiliary layer by doping the emission-auxiliary layer with CBP as a host material and Ir(ppy)$_3$ as a dopant material in a weight ratio of 95:5. Also, BAlq was vacuum-deposited with a thickness of 10 nm on the light emitting layer to form a hole blocking layer, and then a film of Alq$_3$ was formed with a thickness of 40 nm to form an electron injection layer. Subsequently, LiF as halogenated alkali metal was deposited with a thickness of 0.2 nm on the electron injection layer, and then Al was deposited with a thickness of 150 nm thereon to form a cathode. In this way, an OLED was completed.

[Test Example □-2] to [Test Example □-136] Green Organic Light Emitting Diode (Emission-Auxiliary Layer)

The OLED was manufactured in the same manner as described in Test Example □-1, except that any one of the compounds A2 to C16 of the present invention in the Table 6 below was used as the Emission-Auxiliary Layer material, instead of the inventive compound A1.

Comparative Example 9

The OLED was manufactured in the same manner as described in Test Example □-1, except that Comparative Compound 2 represented above was used as the Emission-Auxiliary Layer material, instead of the inventive compound A1.

Comparative Example 10

The OLED was manufactured in the same manner as described in Test Example □-1, except that Comparative Compound 3 represented above was used as the Emission-Auxiliary Layer material, instead of the inventive compound A1.

Comparative Example 11

The OLED was manufactured in the same manner as described in Test Example □-1, except that Comparative Compound 4 represented above was used as the Emission-Auxiliary Layer material, instead of the inventive compound A1.

Comparative Example 12

The OLED was manufactured in the same manner as described in Test Example □-1, except that Comparative Compound 5 represented above was used as the Emission-Auxiliary Layer material, instead of the inventive compound A1.

Comparative Example 13

An OLED was manufactured in the same manner as described in Test Example □-1, except that an emission-auxiliary layer was not formed.

A forward bias DC voltage was applied to each of the OLEDs manufactured through Test Examples (□-1) to (□-151) and Comparative Example (9) to (13), and electroluminescence (EL characteristics of the OLED were measured by PR-650 (Photoresearch). Also, T95 life span was measured by life span measuring equipment (Mcscience) at a reference brightness of 5000 cd/m$^2$. Table 6 below shows evaluation results of OLEDs manufactured Test Examples and Comparative Examples.

TABLE 6

| | Compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| comp. Ex(9) | comp. Com 2 | 6.1 | 14.8 | 5000.0 | 33.8 | 80.6 | 0.33 | 0.62 |
| comp. Ex(10) | comp. Com 3 | 6.0 | 14.6 | 5000.0 | 34.2 | 90.7 | 0.33 | 0.62 |
| comp. Ex(11) | comp. Com 4 | 6.0 | 14.5 | 5000.0 | 34.5 | 92.8 | 0.33 | 0.62 |
| comp. Ex(12) | comp. Com 5 | 6.3 | 15.1 | 5000.0 | 33.1 | 75.7 | 0.33 | 0.62 |
| comp. Ex(13) | — | 6.0 | 20.8 | 5000.0 | 24.0 | 53.0 | 0.33 | 0.61 |
| Ex. (III-1) | Com. (A1) | 6.0 | 12.1 | 5000.0 | 41.4 | 133.9 | 0.33 | 0.61 |
| Ex. (III-2) | Com. (A2) | 5.9 | 12.3 | 5000.0 | 40.8 | 134.2 | 0.33 | 0.62 |
| Ex. (III-3) | Com. (A6) | 5.9 | 11.6 | 5000.0 | 43.2 | 150.1 | 0.33 | 0.62 |
| Ex. (III-4) | Com. (A7) | 5.8 | 11.7 | 5000.0 | 42.9 | 156.9 | 0.33 | 0.61 |
| Ex. (III-5) | Com. (A11) | 5.8 | 11.7 | 5000.0 | 42.9 | 147.5 | 0.33 | 0.62 |
| Ex. (III-6) | Com. (A12) | 5.9 | 11.9 | 5000.0 | 42.0 | 149.3 | 0.33 | 0.62 |
| Ex. (III-7) | Com. (A16) | 5.9 | 11.8 | 5000.0 | 42.2 | 146.0 | 0.33 | 0.62 |
| Ex. (III-8) | Com. (A17) | 6.1 | 10.7 | 5000.0 | 46.7 | 183.5 | 0.33 | 0.61 |
| Ex. (III-9) | Com. (A19) | 5.8 | 12.4 | 5000.0 | 40.2 | 126.1 | 0.33 | 0.61 |
| Ex. (III-10) | Com. (A21) | 6.0 | 10.7 | 5000.0 | 46.6 | 178.1 | 0.33 | 0.61 |
| Ex. (III-11) | Com. (A22) | 5.9 | 11.4 | 5000.0 | 43.7 | 167.2 | 0.33 | 0.62 |
| Ex. (III-12) | Com. (A23) | 6.0 | 11.6 | 5000.0 | 43.1 | 153.4 | 0.33 | 0.61 |
| Ex. (III-13) | Com. (A24) | 5.8 | 11.6 | 5000.0 | 43.3 | 148.7 | 0.33 | 0.62 |
| Ex. (III-14) | Com. (A25) | 5.9 | 11.8 | 5000.0 | 42.5 | 152.1 | 0.33 | 0.62 |
| Ex. (III-15) | Com. (A26) | 5.9 | 11.5 | 5000.0 | 43.4 | 162.2 | 0.33 | 0.62 |
| Ex. (III-16) | Com. (A27) | 5.8 | 11.6 | 5000.0 | 43.2 | 148.3 | 0.33 | 0.62 |
| Ex. (III-17) | Com. (A47) | 5.8 | 12.5 | 5000.0 | 40.2 | 123.1 | 0.33 | 0.61 |
| Ex. (III-18) | Com. (A51) | 6.0 | 11.5 | 5000.0 | 43.3 | 156.8 | 0.33 | 0.61 |

TABLE 6-continued

| | Compound | Voltage (V) | Current Density (mA/cm$^2$) | Brightness (cd/m$^2$) | Efficiency (cd/A) | Lifetime T(95) | CIE x | y |
|---|---|---|---|---|---|---|---|---|
| Ex. (III-19) | Com. (A66) | 5.9 | 12.1 | 5000.0 | 41.3 | 134.2 | 0.33 | 0.62 |
| Ex. (III-20) | Com. (A101) | 6.1 | 13.1 | 5000.0 | 38.3 | 123.4 | 0.33 | 0.62 |
| Ex. (III-21) | Com. (A123) | 6.1 | 12.9 | 5000.0 | 38.8 | 139.3 | 0.33 | 0.61 |
| Ex. (III-22) | Com. (A124) | 5.8 | 12.2 | 5000.0 | 41.0 | 127.8 | 0.33 | 0.62 |
| Ex. (III-23) | Com. (A128) | 5.9 | 12.2 | 5000.0 | 40.9 | 136.1 | 0.33 | 0.61 |
| Ex. (III-24) | Com. (A142) | 6.0 | 12.7 | 5000.0 | 39.4 | 129.8 | 0.33 | 0.61 |
| Ex. (III-25) | Com. (A162) | 5.9 | 12.1 | 5000.0 | 41.2 | 138.7 | 0.33 | 0.62 |
| Ex. (III-26) | Com. (A165) | 5.9 | 12.6 | 5000.0 | 39.5 | 129.1 | 1.33 | 0.62 |
| Ex. (III-27) | Com. (A169) | 5.8 | 11.9 | 5000.0 | 41.9 | 149.6 | 0.33 | 0.61 |
| Ex. (III-28) | Com. (A170) | 5.9 | 11.9 | 5000.0 | 42.1 | 147.1 | 0.33 | 0.61 |
| Ex. (III-29) | Com. (A171) | 5.8 | 11.8 | 5000.0 | 42.3 | 152.5 | 0.33 | 0.61 |
| Ex. (III-30) | Com. (A172) | 6.0 | 11.5 | 5000.0 | 43.3 | 148.6 | 0.33 | 0.62 |
| Ex. (III-31) | Com. (A173) | 5.8 | 12.0 | 5000.0 | 41.7 | 143.5 | 0.33 | 0.62 |
| Ex. (III-32) | Com. (A174) | 5.9 | 12.0 | 5000.0 | 41.7 | 142.9 | 0.33 | 0.62 |
| Ex. (III-33) | Com. (A175) | 5.9 | 12.1 | 5000.0 | 41.4 | 141.4 | 0.33 | 0.61 |
| Ex. (III-34) | Com. (A176) | 5.9 | 12.1 | 5000.0 | 41.2 | 134.5 | 0.33 | 0.61 |
| Ex. (III-35) | Com. (A177) | 5.8 | 11.7 | 5000.0 | 42.9 | 148.3 | 0.33 | 0.62 |
| Ex. (III-36) | Com. (A178) | 6.0 | 11.8 | 5000.0 | 42.6 | 146.8 | 0.33 | 0.61 |
| Ex. (III-37) | Com. (A179) | 5.8 | 11.5 | 5000.0 | 43.4 | 161.0 | 0.33 | 0.61 |
| Ex. (III-38) | Com. (A180) | 6.1 | 11.4 | 5000.0 | 44.0 | 160.7 | 0.33 | 0.62 |
| Ex. (III-39) | Com. (A183) | 6.0 | 11.8 | 5000.0 | 42.4 | 147.6 | 0.33 | 0.61 |
| Ex. (III-40) | Com. (A187) | 5.8 | 11.8 | 5000.0 | 42.3 | 157.8 | 0.33 | 0.61 |
| Ex. (III-41) | Com. (A191) | 6.0 | 11.3 | 5000.0 | 44.2 | 161.2 | 0.33 | 0.61 |
| Ex. (III-42) | Com. (A199) | 5.7 | 11.3 | 5000.0 | 44.4 | 164.4 | 0.33 | 0.62 |
| Ex. (III-43) | Com. (A203) | 6.0 | 11.1 | 5000.0 | 45.2 | 174.3 | 0.33 | 0.62 |
| Ex. (III-44) | Com. (A204) | 5.7 | 11.5 | 5000.0 | 43.5 | 162.0 | 0.33 | 0.61 |
| Ex. (III-45) | Com. (A209) | 5.9 | 11.2 | 5000.0 | 44.6 | 171.4 | 0.33 | 0.62 |
| Ex. (III-46) | Com. (A210) | 5.8 | 11.5 | 5000.0 | 43.7 | 164.8 | 0.33 | 0.62 |
| Ex. (III-47) | Com. (A212) | 5.9 | 11.9 | 5000.0 | 42.1 | 149.3 | 0.33 | 0.61 |
| Ex. (III-48) | Com. (A213) | 5.9 | 12.0 | 5000.0 | 41.7 | 130.3 | 0.33 | 0.62 |
| Ex. (III-49) | Com. (A216) | 5.9 | 11.9 | 5000.0 | 42.0 | 145.1 | 0.33 | 0.61 |
| Ex. (III-50) | Com. (A218) | 5.9 | 12.1 | 5000.0 | 41.5 | 133.5 | 0.33 | 0.62 |
| Ex. (III-51) | Com. (A219) | 6.0 | 11.9 | 5000.0 | 41.9 | 136.1 | 0.33 | 0.62 |
| Ex. (III-52) | Com. (A225) | 5.8 | 11.8 | 5000.0 | 42.2 | 152.4 | 0.33 | 0.61 |
| Ex. (III-53) | Com. (A226) | 6.0 | 11.7 | 5000.0 | 42.7 | 155.2 | 0.33 | 0.61 |
| Ex. (III-54) | Com. (A227) | 5.8 | 11.8 | 5000.0 | 42.3 | 154.8 | 0.33 | 0.61 |
| Ex. (III-55) | Com. (A228) | 5.8 | 11.3 | 5000.0 | 44.3 | 164.2 | 0.33 | 0.61 |
| Ex. (III-56) | Com. (A229) | 5.8 | 11.5 | 5000.0 | 43.5 | 165.5 | 0.33 | 0.61 |
| Ex. (III-57) | Com. (A230) | 5.9 | 11.1 | 5000.0 | 45.1 | 170.9 | 0.33 | 0.61 |
| Ex. (III-58) | Com. (A231) | 5.9 | 11.3 | 5000.0 | 44.2 | 161.1 | 0.33 | 0.62 |
| Ex. (III-59) | Com. (A232) | 6.0 | 11.5 | 5000.0 | 43.4 | 157.5 | 0.33 | 0.61 |
| Ex. (III-60) | Com. (A233) | 6.0 | 11.5 | 5000.0 | 43.5 | 160.6 | 0.33 | 0.61 |
| Ex. (III-61) | Com. (A234) | 5.9 | 11.5 | 5000.0 | 43.5 | 164.6 | 0.33 | 0.62 |
| Ex. (III-62) | Com. (A235) | 6.1 | 11.4 | 5000.0 | 43.7 | 157.3 | 0.33 | 0.62 |
| Ex. (III-63) | Com. (A236) | 5.8 | 11.4 | 5000.0 | 44.0 | 158.3 | 0.33 | 0.62 |
| Ex. (III-64) | Com. (A237) | 5.8 | 11.5 | 5000.0 | 43.6 | 155.0 | 0.33 | 0.61 |
| Ex. (III-65) | Com. (A238) | 6.1 | 11.3 | 5000.0 | 44.3 | 156.0 | 0.33 | 0.62 |
| Ex. (III-66) | Com. (A239) | 5.9 | 11.3 | 5000.0 | 44.3 | 157.6 | 0.33 | 0.62 |
| Ex. (III-67) | Com. (A240) | 6.0 | 11.4 | 5000.0 | 43.9 | 167.5 | 0.33 | 0.61 |
| Ex. (III-68) | Com. (A241) | 5.9 | 11.4 | 5000.0 | 43.7 | 162.0 | 0.33 | 0.61 |
| Ex. (III-69) | Com. (A242) | 5.7 | 11.5 | 5000.0 | 43.4 | 165.5 | 0.33 | 0.62 |
| Ex. (III-70) | Com. (A243) | 5.9 | 11.8 | 5000.0 | 42.5 | 140.7 | 0.33 | 0.62 |
| Ex. (III-71) | Com. (A244) | 6.0 | 11.8 | 5000.0 | 42.5 | 140.7 | 0.33 | 0.62 |
| Ex. (III-72) | Com. (A245) | 5.8 | 11.1 | 5000.0 | 45.2 | 175.2 | 0.33 | 0.61 |
| Ex. (III-73) | Com. (A246) | 5.8 | 11.9 | 5000.0 | 42.2 | 142.0 | 0.33 | 0.61 |
| Ex. (III-74) | Com. (A247) | 5.9 | 12.1 | 5000.0 | 41.4 | 141.1 | 0.33 | 0.62 |
| Ex. (III-75) | Com. (A248) | 5.9 | 12.1 | 5000.0 | 41.2 | 133.9 | 0.33 | 0.62 |
| Ex. (III-76) | Com. (A249) | 5.8 | 11.7 | 5000.0 | 42.6 | 152.3 | 0.33 | 0.62 |
| Ex. (III-77) | Com. (A250) | 6.1 | 11.8 | 5000.0 | 42.4 | 152.4 | 0.33 | 0.62 |
| Ex. (III-78) | Com. (A251) | 6.0 | 11.4 | 5000.0 | 43.8 | 161.9 | 0.33 | 0.62 |
| Ex. (III-79) | Com. (A252) | 5.9 | 12.1 | 5000.0 | 41.5 | 135.4 | 0.33 | 0.61 |
| Ex. (III-80) | Com. (A253) | 6.0 | 11.7 | 5000.0 | 42.7 | 149.6 | 0.33 | 0.62 |
| Ex. (III-81) | Com. (A254) | 6.0 | 11.5 | 5000.0 | 43.6 | 157.4 | 0.33 | 0.61 |
| Ex. (III-82) | Com. (A255) | 5.9 | 11.3 | 5000.0 | 44.2 | 158.3 | 0.33 | 0.61 |
| Ex. (III-83) | Com. (A256) | 5.9 | 11.8 | 5000.0 | 42.3 | 148.9 | 0.33 | 0.62 |
| Ex. (III-84) | Com. (A257) | 5.8 | 11.5 | 5000.0 | 43.5 | 169.6 | 0.33 | 0.61 |
| Ex. (III-85) | Com. (A258) | 6.0 | 11.4 | 5000.0 | 43.9 | 156.6 | 0.33 | 0.61 |
| Ex. (III-86) | Com. (A259) | 5.9 | 11.0 | 5000.0 | 45.3 | 179.8 | 0.33 | 0.62 |
| Ex. (III-87) | Com. (A260) | 5.8 | 11.2 | 5000.0 | 44.5 | 170.9 | 0.33 | 0.62 |
| Ex. (III-88) | Com. (A270) | 6.0 | 11.7 | 5000.0 | 42.8 | 158.3 | 0.33 | 0.62 |
| Ex. (III-89) | Com. (A273) | 5.9 | 11.5 | 5000.0 | 43.4 | 162.0 | 0.33 | 0.62 |
| Ex. (III-90) | Com. (A274) | 5.7 | 11.8 | 5000.0 | 42.2 | 153.8 | 0.33 | 0.61 |
| Ex. (III-91) | Com. (A275) | 5.8 | 11.7 | 5000.0 | 42.9 | 153.4 | 0.33 | 0.61 |
| Ex. (III-92) | Com. (A277) | 5.8 | 11.1 | 5000.0 | 44.9 | 173.5 | 0.33 | 0.61 |
| Ex. (III-93) | Com. (A279) | 5.9 | 11.5 | 5000.0 | 43.6 | 159.3 | 0.33 | 0.61 |

TABLE 6-continued

| | Compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| Ex. (III-94) | Com. (A282) | 5.9 | 11.7 | 5000.0 | 42.8 | 147.0 | 0.33 | 0.61 |
| Ex. (III-95) | Com. (A285) | 5.9 | 11.1 | 5000.0 | 45.0 | 176.5 | 0.33 | 0.61 |
| Ex. (III-96) | Com. (A286) | 5.8 | 11.1 | 5000.0 | 45.1 | 174.1 | 0.33 | 0.61 |
| Ex. (III-97) | Com. (A289) | 5.9 | 11.0 | 5000.0 | 45.6 | 175.6 | 0.33 | 0.61 |
| Ex. (III-98) | Com. (A290) | 5.8 | 10.9 | 5000.0 | 46.1 | 179.5 | 0.33 | 0.61 |
| Ex. (III-99) | Com. (A291) | 5.9 | 11.1 | 5000.0 | 44.9 | 179.9 | 0.33 | 0.62 |
| Ex. (III-100) | Com. (A292) | 6.1 | 11.5 | 5000.0 | 43.7 | 155.3 | 0.33 | 0.62 |
| Ex. (III-101) | Com. (A294) | 6.1 | 11.8 | 5000.0 | 42.5 | 141.7 | 0.33 | 0.61 |
| Ex. (III-102) | Com. (A297) | 6.0 | 11.6 | 5000.0 | 43.1 | 151.7 | 0.33 | 0.61 |
| Ex. (III-103) | Com. (A303) | 5.9 | 12.0 | 5000.0 | 41.6 | 135.9 | 0.33 | 0.62 |
| Ex. (III-104) | Com. (A308) | 5.7 | 11.7 | 5000.0 | 42.8 | 145.4 | 0.33 | 0.61 |
| Ex. (III-105) | Com. (A309) | 5.9 | 11.4 | 5000.0 | 44.0 | 145.6 | 0.33 | 0.61 |
| Ex. (III-106) | Com. (A310) | 6.0 | 11.2 | 5000.0 | 44.6 | 170.8 | 0.33 | 0.62 |
| Ex. (III-107) | Com. (A311) | 5.9 | 10.9 | 5000.0 | 45.7 | 182.2 | 0.33 | 0.61 |
| Ex. (III-108) | Com. (A312) | 5.8 | 11.2 | 5000.0 | 44.7 | 160.9 | 0.33 | 0.61 |
| Ex. (III-109) | Com. (A313) | 6.0 | 11.1 | 5000.0 | 45.1 | 174.8 | 0.33 | 0.62 |
| Ex. (III-110) | Com. (A315) | 6.1 | 11.1 | 5000.0 | 45.2 | 165.7 | 0.33 | 0.61 |
| Ex. (III-111) | Com. (A317) | 5.8 | 11.2 | 5000.0 | 44.8 | 174.3 | 0.33 | 0.61 |
| Ex. (III-112) | Com. (A318) | 6.0 | 11.1 | 5000.0 | 45.0 | 163.3 | 0.33 | 0.61 |
| Ex. (III-113) | Com. (A319) | 5.8 | 11.1 | 5000.0 | 45.2 | 166.8 | 0.33 | 0.61 |
| Ex. (III-114) | Com. (A320) | 5.9 | 11.1 | 5000.0 | 44.9 | 168.0 | 0.33 | 0.62 |
| Ex. (III-115) | Com. (A322) | 5.8 | 11.0 | 5000.0 | 45.5 | 169.0 | 0.33 | 0.61 |
| Ex. (III-116) | Com. (A329) | 6.0 | 11.5 | 5000.0 | 43.5 | 162.5 | 0.33 | 0.61 |
| Ex. (III-117) | Com. (A330) | 5.8 | 11.3 | 5000.0 | 44.3 | 147.6 | 0.33 | 0.62 |
| Ex. (III-118) | Com. (A335) | 6.0 | 11.1 | 5000.0 | 45.0 | 164.7 | 0.33 | 0.61 |
| Ex. (III-119) | Com. (A338) | 5.7 | 11.0 | 5000.0 | 45.6 | 175.3 | 0.33 | 0.61 |
| Ex. (III-120) | Com. (A339) | 5.7 | 11.5 | 5000.0 | 43.5 | 162.0 | 0.33 | 0.61 |
| Ex. (III-121) | Com. (A345) | 5.9 | 10.8 | 5000.0 | 46.5 | 177.1 | 0.33 | 0.61 |
| Ex. (III-122) | Com. (A346) | 5.9 | 10.8 | 5000.0 | 46.1 | 178.6 | 0.33 | 0.61 |
| Ex. (III-123) | Com. (A348) | 5.8 | 11.4 | 5000.0 | 43.8 | 151.9 | 0.33 | 0.61 |
| Ex. (III-124) | Com. (A350) | 6.0 | 10.5 | 5000.0 | 47.4 | 182.5 | 0.33 | 0.62 |
| Ex. (III-125) | Com. (A351) | 5.7 | 10.9 | 5000.0 | 45.7 | 176.4 | 0.33 | 0.62 |
| Ex. (III-126) | Com. (A352) | 5.9 | 11.2 | 5000.0 | 44.6 | 171.0 | 0.33 | 0.62 |
| Ex. (III-127) | Com. (A353) | 5.8 | 11.5 | 5000.0 | 43.4 | 148.5 | 0.33 | 0.61 |
| Ex. (III-128) | Com. (A359) | 5.7 | 11.8 | 5000.0 | 42.5 | 121.5 | 0.33 | 0.61 |
| Ex. (III-129) | Com. (A361) | 6.0 | 11.5 | 5000.0 | 43.5 | 158.1 | 0.33 | 0.61 |
| Ex. (III-130) | Com. (A363) | 5.8 | 11.4 | 5000.0 | 43.7 | 164.2 | 0.33 | 0.62 |
| Ex. (III-131) | Com. (A365) | 5.7 | 11.4 | 5000.0 | 43.8 | 158.4 | 0.33 | 0.62 |
| Ex. (III-132) | Com. (A378) | 5.9 | 12.0 | 5000.0 | 41.8 | 134.2 | 0.33 | 0.61 |
| Ex. (III-133) | Com. (A381) | 5.9 | 12.0 | 5000.0 | 41.5 | 135.4 | 0.33 | 0.61 |
| Ex. (III-134) | Com. (A388) | 6.1 | 11.5 | 5000.0 | 43.5 | 139.6 | 0.33 | 0.61 |
| Ex. (III-135) | Com. (A392) | 5.7 | 11.5 | 5000.0 | 43.4 | 142.7 | 0.33 | 0.61 |
| Ex. (III-136) | Com. (C1) | 5.8 | 11.9 | 5000.0 | 42.1 | 159.2 | 0.33 | 0.61 |
| Ex. (III-137) | Com. (C2) | 5.9 | 11.4 | 5000.0 | 43.7 | 170.3 | 0.33 | 0.61 |
| Ex. (III-138) | Com. (C3) | 6.0 | 11.7 | 5000.0 | 42.7 | 161.8 | 0.33 | 0.61 |
| Ex. (III-139) | Com. (C4) | 5.8 | 11.4 | 5000.0 | 43.8 | 153.0 | 0.33 | 0.61 |
| Ex. (III-140) | Com. (C5) | 5.9 | 11.4 | 5000.0 | 43.7 | 163.5 | 0.33 | 0.61 |
| Ex. (III-141) | Com. (C6) | 5.9 | 11.8 | 5000.0 | 42.2 | 175.5 | 0.33 | 0.61 |
| Ex. (III-142) | Com. (C7) | 5.8 | 11.4 | 5000.0 | 43.9 | 157.8 | 0.33 | 0.62 |
| Ex. (III-143) | Com. (C8) | 5.8 | 11.5 | 5000.0 | 43.5 | 163.5 | 0.33 | 0.62 |
| Ex. (III-144) | Com. (C9) | 5.8 | 11.9 | 5000.0 | 42.0 | 170.0 | 0.33 | 0.62 |
| Ex. (III-145) | Com. (C10) | 5.7 | 11.2 | 5000.0 | 44.8 | 159.5 | 0.33 | 0.61 |
| Ex. (III-146) | Com. (C11) | 5.8 | 11.5 | 5000.0 | 43.7 | 162.2 | 0.33 | 0.61 |
| Ex. (III-147) | Com. (C12) | 6.0 | 11.5 | 5000.0 | 43.4 | 168.6 | 0.33 | 0.61 |
| Ex. (III-148) | Com. (C13) | 5.9 | 11.8 | 5000.0 | 42.5 | 158.0 | 0.33 | 0.61 |
| Ex. (III-149) | Com. (C14) | 5.9 | 11.4 | 5000.0 | 43.8 | 161.7 | 0.33 | 0.62 |
| Ex. (III-150) | Com. (C15) | 5.9 | 11.8 | 5000.0 | 42.2 | 177.4 | 0.33 | 0.61 |
| Ex. (III-151) | Com. (C16) | 5.9 | 11.3 | 5000.0 | 44.1 | 162.1 | 0.33 | 0.61 |

[Test Example ☐-1] Red Organic Light Emitting Diode (Emission-Auxiliary Layer)

Organic light emitting diodes (OLEDs) were fabricated according to a conventional method by using a compound of the present invention as an emission-auxiliary layer material. First, an ITO layer (anode) was formed on a glass substrate, and 2-TNATA was vacuum-deposited on the ITO layer to form a hole injection layer with a thickness of 60 nm. Subsequently, NPB was vacuum-deposited with a thickness of 60 nm on the hole injection layer to form a hole transport layer. Next, the inventive compound A1 was vacuum-deposited with a thickness of 20 nm on the hole transport layer to form an emission-auxiliary layer. Thereafter, a light emitting layer with a thickness of 30 nm was deposited on the emission-auxiliary layer by doping the emission-auxiliary layer with CBP as a host material and bis-(1-phenylisoquinolyl)iridium(☐) acetylacetonate (hereinafter abbreviated as "(piq)$_2$Ir(acac)") as a dopant material in a weight ratio of 95:5. Also, BAlq was vacuum-deposited with a thickness of 10 nm on the light emitting layer to form a hole blocking layer, and then a film of Alq$_3$ was formed with a thickness of 40 nm to form an electron injection layer. Subsequently, LiF as halogenated alkali metal was deposited with a thickness of 0.2 nm on the electron injection layer, and then Al was deposited with a thickness of 150 nm thereon to form a cathode. In this way, an OLED was completed.

[Test Example □-2] to [Test Example □-99] Red Organic Light Emitting Diode (Emission-Auxiliary Layer)

The OLED was manufactured in the same manner as described in Test Example □-1, except that any one of the compounds A2 to A392 of the present invention in the Table 7 below was used as the Emission-Auxiliary Layer material, instead of the inventive compound A1.

Comparative Example 14

An OLED was manufactured in the same manner as described in Test Example □-1, except that Comparative Compound 2 represented above was used as the Emission-Auxiliary Layer material, instead of the inventive compound A1.

Comparative Example 15

An OLED was manufactured in the same manner as described in Test Example □-1, except that Comparative Compound 3 represented above was used as the Emission-Auxiliary Layer material, instead of the inventive compound A1.

Comparative Example 16

An OLED was manufactured in the same manner as described in Test Example □-1, except that Comparative Compound 4 represented above was used as the Emission-Auxiliary Layer material, instead of the inventive compound A1.

Comparative Example 17

An OLED was manufactured in the same manner as described in Test Example □-1, except that an emission-auxiliary layer was not formed.

A forward bias DC voltage was applied to each of the OLEDs manufactured through Test Examples (□-1) to (□-99) and Comparative Example (14) to (17), and electroluminescence (EL characteristics of the OLED were measured by PR-650 (Photoresearch). Also, T95 life span was measured by life span measuring equipment (Mcscience) at a reference brightness of 2500 cd/m$^2$. Table 7 below shows evaluation results of OLEDs manufactured Test Examples and Comparative Examples.

TABLE 7

|  | Compound | (V) | Current Density (mA/cm$^2$) | Brightness (cd/m$^2$) | Efficiency (cd/A) | Lifetime T(95) | CIE x | CIE y |
|---|---|---|---|---|---|---|---|---|
| comp. Ex(14) | comp. Com 2 | 6.5 | 27.5 | 2500.0 | 9.1 | 84.7 | 0.66 | 0.32 |
| comp. Ex(15) | comp. Com 3 | 6.5 | 26.9 | 2500.0 | 9.3 | 85.3 | 0.66 | 0.32 |
| comp. Ex(16) | comp. Com 4 | 7.4 | 31.3 | 2500.0 | 8.0 | 79.6 | 0.66 | 0.32 |
| comp. Ex(17) | — | 7.0 | 33.3 | 2500.0 | 7.5 | 66.8 | 0.66 | 0.32 |
| Ex. (IV-1) | Com. (A1) | 6.8 | 21.9 | 2500.0 | 11.4 | 121.8 | 0.66 | 0.32 |
| Ex. (IV-2) | Com. (A2) | 6.6 | 22.9 | 2500.0 | 10.9 | 103.4 | 0.66 | 0.33 |
| Ex. (IV-3) | Com. (A6) | 6.5 | 21.7 | 2500.0 | 11.5 | 123.2 | 0.66 | 0.32 |
| Ex. (IV-4) | Com. (A7) | 6.7 | 21.2 | 2500.0 | 11.8 | 128.5 | 0.66 | 0.32 |
| Ex. (IV-5) | Com. (A19) | 6.6 | 23.4 | 2500.0 | 10.7 | 113.7 | 0.67 | 0.32 |
| Ex. (IV-6) | Com. (A21) | 6.7 | 19.6 | 2500.0 | 12.8 | 138.6 | 0.66 | 0.32 |
| Ex. (IV-7) | Com. (A22) | 6.6 | 20.8 | 2500.0 | 12.0 | 126.1 | 0.66 | 0.32 |
| Ex. (IV-8) | Com. (A23) | 6.6 | 21.0 | 2500.0 | 11.9 | 125.3 | 0.66 | 0.32 |
| Ex. (IV-9) | Com. (A25) | 6.5 | 21.3 | 2500.0 | 11.7 | 121.3 | 0.66 | 0.32 |
| Ex. (IV-10) | Com. (A26) | 6.7 | 20.5 | 2500.0 | 12.2 | 124.7 | 0.66 | 0.32 |
| Ex. (IV-11) | Com. (A27) | 6.6 | 21.2 | 2500.0 | 11.8 | 120.6 | 0.66 | 0.32 |
| Ex. (IV-12) | Com. (A47) | 6.7 | 23.4 | 2500.0 | 10.7 | 110.6 | 0.66 | 0.32 |
| Ex. (IV-13) | Com. (A51) | 6.6 | 20.8 | 2500.0 | 12.0 | 120.1 | 0.66 | 0.32 |
| Ex. (IV-14) | Com. (A66) | 6.7 | 22.5 | 2500.0 | 11.1 | 124.9 | 0.66 | 0.32 |
| Ex. (IV-15) | Com. (A128) | 6.8 | 23.3 | 2500.0 | 10.7 | 105.3 | 0.66 | 0.32 |
| Ex. (IV-16) | Com. (A146) | 6.6 | 23.2 | 2500.0 | 10.8 | 116.0 | 0.66 | 0.32 |
| Ex. (IV-17) | Com. (A162) | 6.7 | 22.3 | 2500.0 | 11.2 | 124.1 | 0.66 | 0.32 |
| Ex. (IV-18) | Com. (A169) | 6.7 | 22.5 | 2500.0 | 11.1 | 121.6 | 0.66 | 0.32 |
| Ex. (IV-19) | Com. (A170) | 6.7 | 21.9 | 2500.0 | 11.4 | 121.6 | 0.66 | 0.32 |
| Ex. (IV-20) | Com. (A171) | 6.6 | 20.9 | 2500.0 | 12.0 | 125.4 | 0.66 | 0.32 |
| Ex. (IV-21) | Com. (A172) | 6.7 | 21.4 | 2500.0 | 11.7 | 133.0 | 0.66 | 0.32 |
| Ex. (IV-22) | Com. (A173) | 6.7 | 22.4 | 2500.0 | 11.2 | 123.6 | 0.66 | 0.32 |
| Ex. (IV-23) | Com. (A174) | 6.8 | 21.6 | 2500.0 | 11.6 | 112.9 | 0.66 | 0.32 |
| Ex. (IV-24) | Com. (A175) | 6.7 | 22.2 | 2500.0 | 11.2 | 117.9 | 0.66 | 0.32 |
| Ex. (IV-25) | Com. (A176) | 6.6 | 21.8 | 2500.0 | 11.5 | 111.5 | 0.66 | 0.32 |
| Ex. (IV-26) | Com. (A178) | 6.7 | 21.5 | 2500.0 | 11.6 | 127.6 | 0.66 | 0.32 |
| Ex. (IV-27) | Com. (A179) | 6.6 | 20.6 | 2500.0 | 12.1 | 126.9 | 0.66 | 0.32 |
| Ex. (IV-28) | Com. (A180) | 6.6 | 20.7 | 2500.0 | 12.1 | 123.2 | 0.66 | 0.32 |
| Ex. (IV-29) | Com. (A183) | 6.7 | 21.0 | 2500.0 | 11.9 | 130.9 | 0.66 | 0.32 |
| Ex. (IV-30) | Com. (A187) | 6.7 | 21.0 | 2500.0 | 11.9 | 130.3 | 0.66 | 0.32 |
| Ex. (IV-31) | Com. (A191) | 6.7 | 20.3 | 2500.0 | 12.3 | 121.0 | 0.66 | 0.32 |
| Ex. (IV-32) | Com. (A199) | 6.6 | 20.7 | 2500.0 | 12.1 | 129.2 | 0.66 | 0.32 |
| Ex. (IV-33) | Com. (A203) | 6.6 | 19.9 | 2500.0 | 12.6 | 137.2 | 0.66 | 0.32 |
| Ex. (IV-34) | Com. (A204) | 6.7 | 20.5 | 2500.0 | 12.2 | 129.1 | 0.66 | 0.32 |
| Ex. (IV-35) | Com. (A209) | 6.6 | 19.6 | 2500.0 | 12.7 | 136.1 | 0.66 | 0.32 |
| Ex. (IV-36) | Com. (A210) | 6.7 | 20.5 | 2500.0 | 12.2 | 125.6 | 0.66 | 0.32 |
| Ex. (IV-37) | Com. (A212) | 6.8 | 21.8 | 2500.0 | 11.4 | 123.1 | 0.66 | 0.32 |

TABLE 7-continued

| | Compound | (V) | Current Density (mA/cm$^2$) | Brightness (cd/m$^2$) | Efficiency (cd/A) | Lifetime T(95) | CIE x | y |
|---|---|---|---|---|---|---|---|---|
| Ex. (IV-38) | Com. (A216) | 6.6 | 22.1 | 2500.0 | 11.3 | 120.1 | 0.66 | 0.32 |
| Ex. (IV-39) | Com. (A219) | 6.7 | 21.6 | 2500.0 | 11.6 | 121.4 | 0.66 | 0.32 |
| Ex. (IV-40) | Com. (A225) | 6.7 | 21.3 | 2500.0 | 11.8 | 126.4 | 0.66 | 0.32 |
| Ex. (IV-41) | Com. (A226) | 6.6 | 21.2 | 2500.0 | 11.8 | 128.7 | 0.66 | 0.32 |
| Ex. (IV-42) | Com. (A227) | 6.7 | 21.3 | 2500.0 | 11.7 | 119.6 | 0.66 | 0.32 |
| Ex. (IV-43) | Com. (A228) | 6.7 | 20.3 | 2500.0 | 12.3 | 126.5 | 0.66 | 0.32 |
| Ex. (IV-44) | Com. (A229) | 6.6 | 20.5 | 2500.0 | 12.2 | 138.4 | 0.66 | 0.32 |
| Ex. (IV-45) | Com. (A230) | 6.6 | 18.6 | 2500.0 | 13.5 | 143.0 | 0.66 | 0.32 |
| Ex. (IV-46) | Com. (A231) | 6.6 | 20.2 | 2500.0 | 12.4 | 135.7 | 0.66 | 0.32 |
| Ex. (IV-47) | Com. (A232) | 6.7 | 20.0 | 2500.0 | 12.5 | 132.5 | 0.66 | 0.32 |
| Ex. (IV-48) | Com. (A233) | 6.6 | 20.4 | 2500.0 | 12.2 | 126.8 | 0.66 | 0.32 |
| Ex. (IV-49) | Com. (A234) | 6.5 | 20.4 | 2500.0 | 12.2 | 131.9 | 0.66 | 0.32 |
| Ex. (IV-50) | Com. (A235) | 6.7 | 20.0 | 2500.0 | 12.5 | 130.7 | 0.66 | 0.32 |
| Ex. (IV-51) | Com. (A236) | 6.6 | 20.0 | 2500.0 | 12.5 | 129.6 | 0.66 | 0.32 |
| Ex. (IV-52) | Com. (A237) | 6.7 | 20.3 | 2500.0 | 12.3 | 133.8 | 0.66 | 0.32 |
| Ex. (IV-53) | Com. (A238) | 6.5 | 20.5 | 2500.0 | 12.2 | 132.5 | 0.66 | 0.32 |
| Ex. (IV-54) | Com. (A239) | 6.6 | 20.2 | 2500.0 | 12.4 | 131.9 | 0.66 | 0.32 |
| Ex. (IV-55) | Com. (A240) | 6.7 | 20.0 | 2500.0 | 12.5 | 127.2 | 0.66 | 0.32 |
| Ex. (IV-56) | Com. (A241) | 6.6 | 20.0 | 2500.0 | 12.5 | 129.5 | 0.66 | 0.32 |
| Ex. (IV-57) | Com. (A242) | 6.7 | 20.2 | 2500.0 | 12.4 | 136.1 | 0.66 | 0.32 |
| Ex. (IV-58) | Com. (A245) | 6.5 | 19.4 | 2500.0 | 12.9 | 139.0 | 0.66 | 0.32 |
| Ex. (IV-59) | Com. (A249) | 6.7 | 20.8 | 2500.0 | 12.0 | 127.5 | 0.66 | 0.32 |
| Ex. (IV-60) | Com. (A250) | 6.7 | 21.1 | 2500.0 | 11.9 | 123.9 | 0.66 | 0.32 |
| Ex. (IV-61) | Com. (A251) | 6.6 | 20.4 | 2500.0 | 12.3 | 136.4 | 0.66 | 0.32 |
| Ex. (IV-62) | Com. (A252) | 6.8 | 21.8 | 2500.0 | 11.5 | 121.1 | 0.66 | 0.33 |
| Ex. (IV-63) | Com. (A253) | 6.6 | 21.0 | 2500.0 | 11.9 | 125.5 | 0.66 | 0.32 |
| Ex. (IV-64) | Com. (A254) | 6.6 | 20.0 | 2500.0 | 12.5 | 131.4 | 0.66 | 0.32 |
| Ex. (IV-65) | Com. (A255) | 6.7 | 20.6 | 2500.0 | 12.1 | 125.6 | 0.66 | 0.32 |
| Ex. (IV-66) | Com. (A256) | 6.7 | 21.2 | 2500.0 | 11.8 | 115.5 | 0.66 | 0.32 |
| Ex. (IV-67) | Com. (A257) | 6.6 | 20.2 | 2500.0 | 12.4 | 132.8 | 0.66 | 0.32 |
| Ex. (IV-68) | Com. (A258) | 6.5 | 20.1 | 2500.0 | 12.5 | 138.9 | 0.66 | 0.32 |
| Ex. (IV-69) | Com. (A259) | 6.7 | 19.8 | 2500.0 | 12.6 | 136.6 | 0.66 | 0.32 |
| Ex. (IV-70) | Com. (A260) | 6.6 | 19.5 | 2500.0 | 12.8 | 126.8 | 0.66 | 0.32 |
| Ex. (IV-71) | Com. (A270) | 6.7 | 21.0 | 2500.0 | 11.9 | 119.2 | 0.66 | 0.32 |
| Ex. (IV-72) | Com. (A273) | 6.6 | 20.2 | 2500.0 | 12.4 | 131.1 | 0.66 | 0.32 |
| Ex. (IV-73) | Com. (A274) | 6.7 | 21.3 | 2500.0 | 11.7 | 120.9 | 0.66 | 0.32 |
| Ex. (IV-74) | Com. (A277) | 6.7 | 19.6 | 2500.0 | 12.8 | 126.2 | 0.66 | 0.32 |
| Ex. (IV-75) | Com. (A286) | 6.7 | 19.8 | 2500.0 | 12.6 | 133.6 | 0.66 | 0.32 |
| Ex. (IV-76) | Com. (A290) | 6.7 | 18.4 | 2500.0 | 13.6 | 140.8 | 0.66 | 0.32 |
| Ex. (IV-77) | Com. (A294) | 6.6 | 21.0 | 2500.0 | 11.9 | 116.7 | 0.66 | 0.32 |
| Ex. (IV-78) | Com. (A297) | 6.6 | 21.4 | 2500.0 | 11.7 | 118.5 | 0.66 | 0.32 |
| Ex. (IV-79) | Com. (A308) | 6.7 | 21.4 | 2500.0 | 11.7 | 128.4 | 0.66 | 0.32 |
| Ex. (IV-80) | Com. (A310) | 6.5 | 20.0 | 2500.0 | 12.5 | 132.9 | 0.66 | 0.32 |
| Ex. (IV-81) | Com. (A311) | 6.6 | 19.2 | 2500.0 | 13.1 | 130.7 | 0.66 | 0.32 |
| Ex. (IV-82) | Com. (A312) | 6.6 | 19.3 | 2500.0 | 13.0 | 132.6 | 0.66 | 0.32 |
| Ex. (IV-83) | Com. (A315) | 6.6 | 19.5 | 2500.0 | 12.8 | 142.2 | 0.66 | 0.32 |
| Ex. (IV-84) | Com. (A318) | 6.6 | 19.4 | 2500.0 | 12.9 | 141.7 | 0.66 | 0.32 |
| Ex. (IV-85) | Com. (A319) | 6.5 | 19.6 | 2500.0 | 12.7 | 132.6 | 0.66 | 0.32 |
| Ex. (IV-86) | Com. (A320) | 6.7 | 19.5 | 2500.0 | 12.8 | 137.6 | 0.66 | 0.32 |
| Ex. (IV-87) | Com. (A322) | 6.5 | 19.8 | 2500.0 | 12.6 | 137.5 | 0.66 | 0.32 |
| Ex. (IV-88) | Com. (A329) | 6.7 | 19.9 | 2500.0 | 12.6 | 125.6 | 0.66 | 0.32 |
| Ex. (IV-89) | Com. (A335) | 6.6 | 19.6 | 2500.0 | 12.7 | 143.3 | 0.66 | 0.32 |
| Ex. (IV-90) | Com. (A338) | 6.6 | 18.7 | 2500.0 | 13.4 | 140.6 | 0.66 | 0.32 |
| Ex. (IV-91) | Com. (A339) | 6.6 | 20.3 | 2500.0 | 12.3 | 122.7 | 0.66 | 0.32 |
| Ex. (IV-92) | Com. (A345) | 6.6 | 19.1 | 2500.0 | 13.1 | 141.6 | 0.66 | 0.32 |
| Ex. (IV-93) | Com. (A346) | 6.6 | 18.6 | 2500.0 | 13.4 | 143.3 | 0.66 | 0.32 |
| Ex. (IV-94) | Com. (A350) | 6.5 | 17.8 | 2500.0 | 14.0 | 145.3 | 0.66 | 0.32 |
| Ex. (IV-95) | Com. (A353) | 6.6 | 20.1 | 2500.0 | 12.5 | 122.4 | 0.66 | 0.32 |
| Ex. (IV-96) | Com. (A361) | 6.7 | 19.9 | 2500.0 | 12.5 | 129.6 | 0.66 | 0.32 |
| Ex. (IV-97) | Com. (A365) | 6.7 | 20.5 | 2500.0 | 12.2 | 127.4 | 0.66 | 0.32 |
| Ex. (IV-98) | Com. (A378) | 6.7 | 21.0 | 2500.0 | 11.9 | 121.5 | 0.66 | 0.32 |
| Ex. (IV-99) | Com. (A392) | 6.6 | 21.2 | 2500.0 | 11.8 | 123.3 | 0.67 | 0.33 |

As can be seen from the data of Tables 5 to 7, the organic electroluminescent device in which the compound according to the present invention is used as a material of an auxiliary light emitting layer has improved light emitting efficiency and a remarkably improved lifespan compared to the organic electroluminescent devices of Comparative Examples 5 to 17.

Like data of Table 4, these results showed that even when Comparative Compounds 2 to 4 having linear-type linkers are used in the auxiliary light emitting layer, both luminous efficiency and lifespan are lower, compared to the case in which the compounds of the present invention that either are in a non-linear type or have an amine group linked directly at the meta position are used in the auxiliary emitting layer. In addition, Comparative Compound 5 having a heterocyclic group rather than as a main substituent has poor luminous efficiency and longevity although it is of a non-linear structure like the compounds of the present invention.

This seems to be attributed to the fact that that the a low T1 value is generated when the heterocyclic group, instead of the amine group (—NAr$^2$Ar$^3$), is introduced, with the consequent emission of light at an interface between the light emitting layer and the auxiliary light emitting layer, rather than the inside of the light emitting layer.

As shown in the results described above, the introduction of the linker at the metal position provides the main contribution to improving the device in the performance of the auxiliary light emitting layer (blue fluorescence, green phosphorescence, and red phosphorescence), as well as the hole transporting layer, and there is similar trend therebetween.

Another feature of the compound according to the present invention is that a smaller bond angle at which linker L$^1$ is connected to amine (—NAr$^2$Ar$^3$) makes the band gap wider, and the T1 value higher. This is confirmed by the fact that a compound linked at the ortho position is higher in luminosity than that linked at the metal or para position. In addition to the improvement in luminous efficiency, the compound linked at the ortho position is expected to reduce the process time and increase the longevity of the device because it has a relatively low deposition temperature, compared to the other compounds.

Lastly, the compound according to the present invention used in the auxiliary light emitting layer causes the backbone to be further twisted upon introduction of a bulky substituent on the nitrogen (N) atom of the carbazole, which leads to a reduction in packing density between materials within the auxiliary light emitting layer while adjusting hole mobility so as to raise the luminous efficiency.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

The invention claimed is:

1. A compound represented by Formula 1 below:

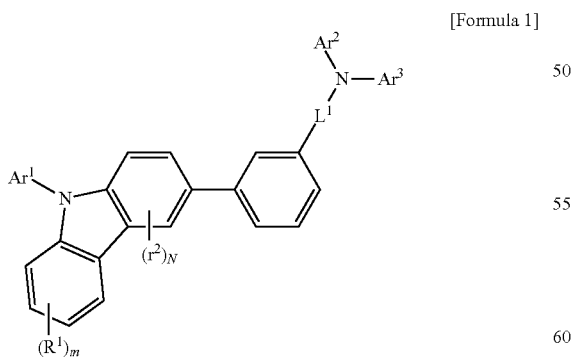

[Formula 1]

wherein,
m is an integer from 1 to 4,
n is an integer from 1 to 3,
R$^1$ is selected from the group consisting of hydrogen, deuterium, tritium, a C$_6$-C$_{60}$ aryl group, and a fluorenyl group, and R$^2$ is selected from the group consisting of hydrogen, deuterium, tritium, a C$_6$-C$_{60}$ aryl group, a fluorenyl group, and a C$_2$-C$_{60}$ heterocyclic group containing at least one heteroatom selected from the group consisting of O, N, S, Si, and P, wherein the aryl group, heterocyclic group, and fluorenyl group may be substituted by one or more substituents selected from the group consisting of halogen, a C$_1$-C$_{20}$ alkyl group, a C$_2$-C$_{20}$ alkenyl group, a C$_6$-C$_{20}$ aryl group, a C$_6$-C$_{20}$ aryl group substituted by deuterium, and a C$_2$-C$_{20}$ heterocyclic group, Ar$^1$ is selected from the group consisting of a fluorenyl group, a C$_6$-C$_{60}$ aryl group, a C$_2$-C$_{20}$ alkenyl group, a C$_2$-C$_{60}$ heterocyclic group containing at least one heteroatom selected from the group consisting of O, N, S, Si, and P, and a C$_1$-C$_{50}$ alkyl group, wherein the aryl group may be substituted by one or more substituents selected from the group consisting of deuterium, halogen, a C$_1$-C$_{20}$ alkyl group, a C$_2$-C$_{20}$ alkenyl group, a C$_6$-C$_{20}$ aryl group substituted by deuterium, and a C$_2$-C$_{20}$ heterocyclic group; and the heterocyclic group, fluorenyl group, alkyl group, and alkenyl group may be substituted by one or more substituents selected from the group consisting of deuterium, halogen, a C$_1$-C$_{20}$ alkyl group, a C$_2$-C$_{20}$ alkenyl group, a C$_6$-C$_{20}$ aryl group, a C$_6$-C$_{20}$ aryl group substituted by deuterium, and a C$_2$-C$_{20}$ heterocyclic group, L$^1$ is selected from the group consisting of a single bond, a C$_6$-C$_{60}$ arylene group, a fluorenylene group, and a C$_2$-C$_{60}$ bivalent heterocyclic group containing at least one heteroatom selected from the group consisting of O, N, S, Si, and P, wherein the arylene group, fluorenylene group, and heterocyclic group may be substituted by one or more substituents selected from the group consisting of deuterium, halogen, a C$_1$-C$_{20}$ alkyl group, a C$_2$-C$_{20}$ alkenyl group, a C$_6$-C$_{20}$ aryl group, a C$_6$-C$_{20}$ aryl group substituted by deuterium, and a C$_2$-C$_{20}$ heterocyclic group, and Ar$^2$ and Ar$^3$ are independently selected from the group consisting of a C$_6$-C$_{60}$ aryl group, a fluorenyl group, and a C$_2$-C$_{60}$ heterocyclic group containing at least one heteroatom selected from the group consisting of O, N, S, Si, and P, wherein the aryl group, heterocyclic group, and fluorenyl group may be substituted by one or more substituents selected from the group consisting of deuterium, halogen, a silane group, -L'-N(R')(R''), a C$_1$-C$_{20}$ alkyl group, a C$_2$-C$_{20}$ alkenyl group, a C$_6$-C$_{20}$ aryl group, a C$_6$-C$_{20}$ aryl group substituted by deuterium, and a C$_2$-C$_{20}$ heterocyclic group, wherein L' is selected from the group consisting of a single bond, a C$_6$-C$_{60}$ arylene group, a fluorenylene group, and a C$_2$-C$_{60}$ heterocyclic group containing at least one heteroatom selected from the group consisting of O, N, S, Si, and P; and R' and R'' are independently selected from the group consisting of a C$_6$-C$_{60}$ aryl group, a fluorenyl group, and a C$_2$-C$_{60}$ heterocyclic group containing at least one heteroatom selected from the group consisting of O, N, S, Si, and P.

2. The compound as claimed in claim 1, wherein L$^1$ is any one of the compounds below:

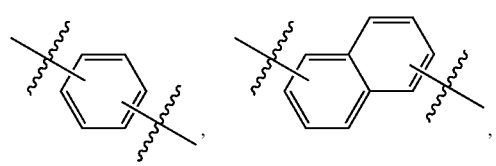

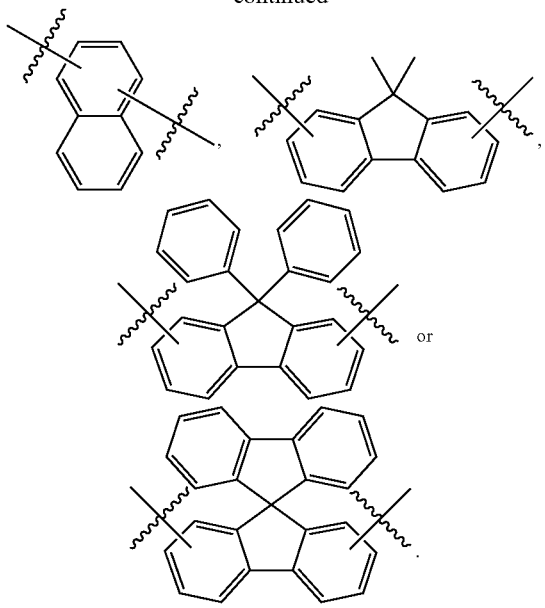

3. A compound represented by Formula 1 below:

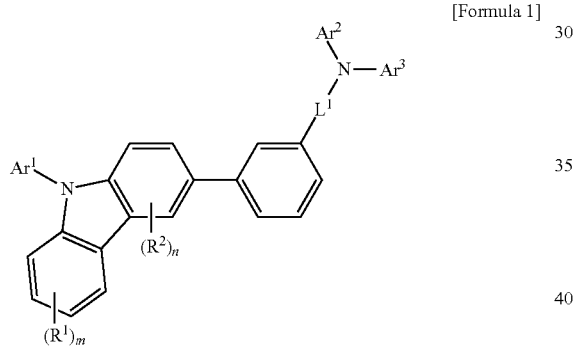

[Formula 1]

wherein
m is an integer from 1 to 4,
n is an integer from 1 to 3,
R$^1$ is selected from the group consisting of hydrogen, deuterium, tritium, a C$_6$-C$_{60}$ aryl group, and a fluorenyl group, and R$^2$ is selected from the group consisting of hydrogen, deuterium, tritium, a C$_6$-C$_{60}$ aryl group, a fluorenyl group, and a C$_2$-C$_{60}$ heterocyclic group containing at least one heteroatom selected from the group consisting of O, N, S, Si, and P, wherein the aryl group, heterocyclic group, and fluorenyl group may be substituted by one or more substituents selected from the group consisting of halogen, a C$_1$-C$_{20}$ alkyl group, a C$_2$-C$_{20}$ alkenyl group, a C$_6$-C$_{20}$ aryl group, a C$_6$-C$_{20}$ aryl group substituted by deuterium, and a C$_2$-C$_{20}$ heterocyclic group, Ar$^1$ is selected from the group consisting of a fluorenyl group, a C$_6$-C$_{60}$ aryl group, a C$_2$-C$_{20}$ alkenyl group, a C$_2$-C$_{60}$ heterocyclic group containing at least one heteroatom selected from the group consisting of O, N, S, Si, and P, and a C$_1$-C$_{50}$ alkyl group, wherein the aryl group may be substituted by one or more substituents selected from the group consisting of deuterium, halogen, a C$_1$-C$_{20}$ alkyl group, a C$_2$-C$_{20}$ alkenyl group, a C$_6$-C$_{20}$ aryl group substituted by deuterium, and a C$_2$-C$_{20}$ heterocyclic group; and the heterocyclic group, fluorenyl group, alkyl group, and alkenyl group may be substituted by one or more substituents selected from the group consisting of deuterium, halogen, a C$_1$-C$_{20}$ alkyl group, a C$_2$-C$_{20}$ alkenyl group, a C$_6$-C$_{20}$ aryl group, a C$_6$-C$_{20}$ aryl group substituted by deuterium, and a C$_2$-C$_{20}$ heterocyclic group, L$^1$ is selected from the group consisting of a single bond, a C$_6$-C$_{60}$ arylene group, a fluorenylene group, and a C$_2$-C$_{60}$ bivalent heterocyclic group containing at least one heteroatom selected from the group consisting of O, N, S, Si, and P, wherein the arylene group, fluorenylene group, and heterocyclic group may be substituted by one or more substituents selected from the group consisting of deuterium, halogen, a C$_1$-C$_{20}$ alkyl group, a C$_2$-C$_{20}$ alkenyl group, a C$_6$-C$_{20}$ aryl group, a C$_6$-C$_{20}$ aryl group substituted by deuterium, and a C$_2$-C$_{20}$ heterocyclic group, and Ar$^2$ and Ar$^3$ are independently any one of the compounds below:

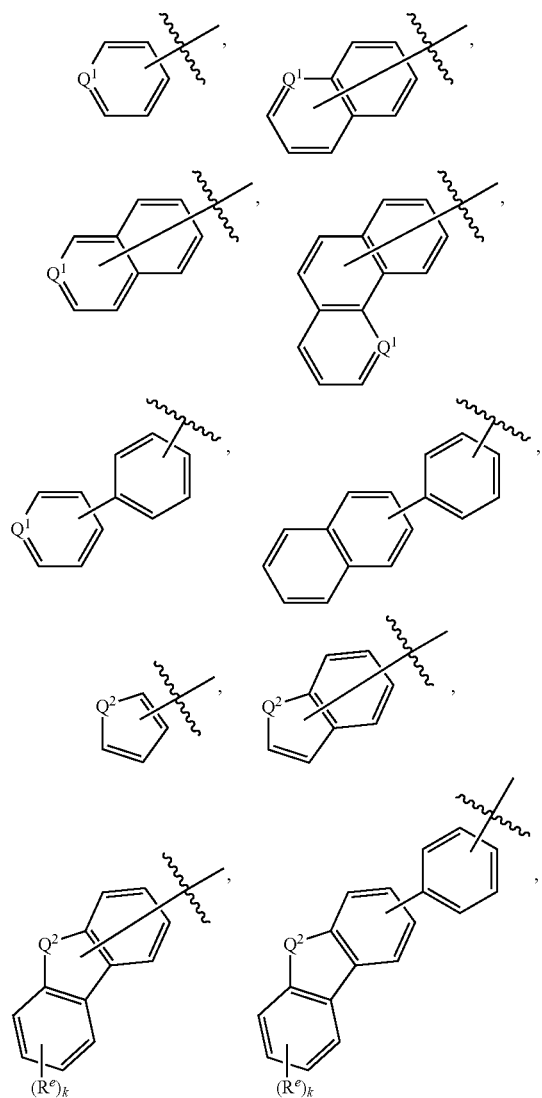

301
-continued

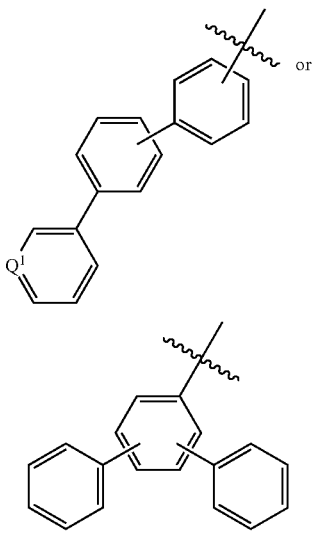

wherein, $Q^1$ is $C(R^a)$ or N, $Q^2$ is selected form the group consisting of $C(R^b)(R^c)$, $N(R^d)$, S and O, k is an integer from 1 to 4, $R^a$ and $R^e$ are independently selected from the group consisting of hydrogen, deuterium, a $C_6$-$C_{60}$ aryl group, a $C_2$-$C_{60}$ heterocyclic group containing at least one heteroatom selected from the group consisting of O, N, S, Si, and P, a $C_1$-$C_{50}$ alkyl group, a $C_2$-$C_{20}$ alkenyl group, a $C_1$-$C_{30}$ alkoxy group, and a fluorenyl group, or any two adjacent groups of $R^e$s are optionally linked together to form at least one aromatic ring, $R^b$ to $R^d$ are independently selected from the group consisting of a $C_6$-$C_{60}$ aryl group, a $C_2$-$C_{60}$ heterocyclic group containing at least one heteroatom selected from the group consisting of O, N, S, Si, and P, a $C_1$-$C_{50}$ alkyl group, a $C_2$-$C_{20}$ alkenyl group, and a $C_1$-$C_{30}$ alkoxy group, or $R^b$ and $R^c$ are optionally linked together to form at least one spiro compound.

4. A compound represented by one of Formulas below:

[Formula 2]

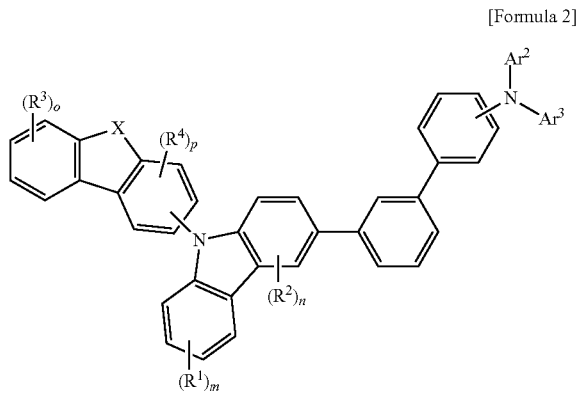

302
-continued

[Formula 3]

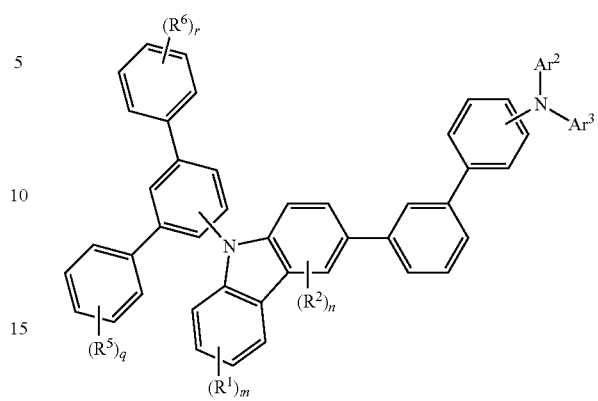

wherein, m is an integer from 1 to 4, n is an integer from 1 to 3, $R^1$ is selected from the group consisting of hydrogen, deuterium, tritium, a $C_6$-$C_{60}$ aryl group, and a fluorenyl group, and $R^2$ is selected from the group consisting of hydrogen, deuterium, tritium, a $C_6$-$C_{60}$ aryl group, a fluorenyl group, and a $C_2$-$C_{60}$ heterocyclic group containing at least one heteroatom selected from the group consisting of O, N, S, Si, and P, wherein the aryl group, heterocyclic group, and fluorenyl group may be substituted by one or more substituents selected from the group consisting of halogen, a $C_1$-$C_{20}$ alkyl group, a $C_2$-$C_{20}$ alkenyl group, a $C_6$-$C_{20}$ aryl group, a $C_6$-$C_{20}$ aryl group substituted by deuterium, and a $C_2$-$C_{20}$ heterocyclic group, $Ar^2$ and $Ar^3$ are independently selected from the group consisting of a $C_6$-$C_{60}$ aryl group, a fluorenyl group, and a $C_2$-$C_{60}$ heterocyclic group containing at least one heteroatom selected from the group consisting of O, N, S, Si, and P, wherein the aryl group, heterocyclic group, and fluorenyl group may be substituted by one or more substituents selected from the group consisting of deuterium, halogen, a silane group, -L'-N(R')(R"), a $C_1$-$C_{20}$ alkyl group, a $C_2$-$C_{20}$ alkenyl group, a $C_6$-$C_{20}$ aryl group, a $C_6$-$C_{20}$ aryl group substituted by deuterium, and a $C_2$-$C_{20}$ heterocyclic group, wherein L' is selected from the group consisting of a single bond, a $C_6$-$C_{60}$ arylene group, a fluorenylene group, and a $C_2$-$C_{60}$ heterocyclic group containing at least one heteroatom selected from the group consisting of O, N, S, Si, and P; and R' and R" are independently selected from the group consisting of a $C_6$-$C_{60}$ aryl group, a fluorenyl group, and a $C_2$-$C_{60}$ heterocyclic group containing at least one heteroatom selected from the group consisting of O, N, S, Si, and P, X is selected form the group consisting of $C(R^f)(R^g)$, S and O, $R^f$ and $R^g$ are independently selected from the group consisting of a $C_6$-$C_{60}$ aryl group, a $C_2$-$C_{60}$ heterocyclic group containing at least one heteroatom selected from the group consisting of O, N, S, Si, and P, a $C_1$-$C_{50}$ alkyl group, a $C_2$-$C_{20}$ alkenyl group, and a $C_1$-$C_{30}$ alkoxy group, or $R^f$ and $R^g$ can be are optionally linked together to form at least one spiro compound, o is an integer from 1 to 4, p is an integer from 1 to 3, q and r are independently an integer from 1 to 5, and, $R^3$ to $R^6$ are independently selected from the group consisting of hydrogen, deuterium, tritium, halogen, a $C_6$-$C_{60}$ aryl group, a $C_2$-$C_{60}$ heterocyclic group containing at least one heteroatom selected from the group consisting of O, N, S, Si, and P, a $C_1$-$C_{50}$ alkyl group, a $C_2$-$C_{20}$ alkenyl group, a $C_1$-$C_{30}$ alkoxy group, and a $C_6$-$C_{30}$ aryloxy group, or any two adjacent groups of $R^3$s to $R^6$s are optionally linked together to form at least one aromatic ring.

5. A compound represented by one of Formulas below:

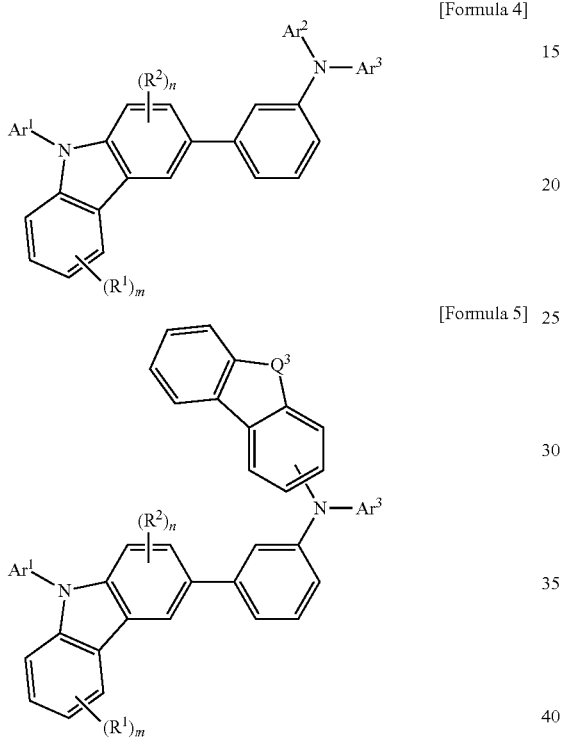

[Formula 4]

[Formula 5]

wherein
m is an integer from 1 to 4,
n is an integer from 1 to 3,
$R^1$ is selected from the group consisting of hydrogen, deuterium, tritium, a $C_6$-$C_{60}$ aryl group, and a fluorenyl group, and $R^2$ is selected from the group consisting of hydrogen, deuterium, tritium, a $C_6$-$C_{60}$ aryl group, a fluorenyl group, and a $C_2$-$C_{60}$ heterocyclic group containing at least one heteroatom selected from the group consisting of O, N, S, Si, and P, wherein the aryl group, heterocyclic group, and fluorenyl group may be substituted by one or more substituents selected from the group consisting of halogen, a $C_1$-$C_{20}$ alkyl group, a $C_2$-$C_{20}$ alkenyl group, a $C_6$-$C_{20}$ aryl group, a $C_6$-$C_{20}$ aryl group substituted by deuterium, and a $C_2$-$C_{20}$ heterocyclic group, $Ar^1$ is selected from the group consisting of a fluorenyl group, a $C_6$-$C_{60}$ aryl group, a $C_2$-$C_{20}$ alkenyl group, a $C_2$-$C_{60}$ heterocyclic group containing at least one heteroatom selected from the group consisting of O, N, S, Si, and P, and a $C_1$-$C_{50}$ alkyl group, wherein the aryl group may be substituted by one or more substituents selected from the group consisting of deuterium, halogen, a $C_1$-$C_{20}$ alkyl group, a $C_2$-$C_{20}$ alkenyl group, a $C_6$-$C_{20}$ aryl group substituted by deuterium, and a $C_2$-$C_{20}$ heterocyclic group; and the heterocyclic group, fluorenyl group, alkyl group, and alkenyl group may be substituted by one or more substituents selected from the group consisting of deuterium, halogen, a $C_1$-$C_{20}$ alkyl group, a $C_2$-$C_{20}$ alkenyl group, a $C_6$-$C_{20}$ aryl group, a $C_6$-$C_{20}$ aryl group substituted by deuterium, and a $C_2$-$C_{20}$ heterocyclic group, $Ar^2$ and $Ar^3$ are independently selected from the group consisting of a $C_6$-$C_{60}$ aryl group, a fluorenyl group, and a $C_2$-$C_{60}$ heterocyclic group containing at least one heteroatom selected from the group consisting of O, N, S, Si, and P, wherein the aryl group, heterocyclic group, and fluorenyl group may be substituted by one or more substituents selected from the group consisting of deuterium, halogen, a silane group, -L'-N(R')(R"), a $C_1$-$C_{20}$ alkyl group, a $C_2$-$C_{20}$ alkenyl group, a $C_6$-$C_{20}$ aryl group, a $C_6$-$C_{20}$ aryl group substituted by deuterium, and a $C_2$-$C_{20}$ heterocyclic group, wherein L' is selected from the group consisting of a single bond, a $C_6$-$C_{60}$ arylene group, a fluorenylene group, and a $C_2$-$C_{60}$ heterocyclic group containing at least one heteroatom selected from the group consisting of O, N, S, Si, and P; and R' and R" are independently selected from the group consisting of a $C_6$-$C_{60}$ aryl group, a fluorenyl group, and a $C_2$-$C_{60}$ heterocyclic group containing at least one heteroatom selected from the group consisting of O, N, S, Si, and P, $Q^3$ is selected form the group consisting of $C(R^h)(R^i)$, $N(R^j)$, S and O, and, $R^h$ to $R^j$ are independently selected from the group consisting of a $C_6$-$C_{60}$ aryl group, a $C_2$-$C_{60}$ heterocyclic group containing at least one heteroatom selected from the group consisting of O, N, S, Si, and P, a $C_1$-$C_{50}$ alkyl group, a $C_2$-$C_{20}$ alkenyl group, and a $C_1$-$C_{30}$ alkoxy group, or $R^h$ and $R^i$ are optionally linked together to form at least one spiro compound.

6. An organic electric element comprising the compound of claim 1.

7. The organic electric element as claimed in claim 6, wherein the organic electric element comprises a first electrode, a second electrode, and an organic material layer disposed between the first electrode and the second electrode, wherein the organic material layer comprises the compound.

8. The organic electric element as claimed in claim 7, wherein the organic material layer comprises at least one of a light emitting layer, a hole injection layer, a hole transport layer, an emission-auxiliary layer, an electron injection layer, and an electron transport layer.

9. The organic electric element as claimed in claim 7, wherein the organic electric element further comprises at least a layer to improve luminous efficiency which is formed on at least one of the sides of the first and second electrodes, which is opposite to the organic material layer.

10. The organic electric element as claimed in claim 7, wherein the organic material layer is formed by any one of the processes of spin coating, nozzle printing, inkjet printing, slot coating, dip coating and roll-to-roll.

11. An electronic device comprising a display device, which comprises the organic electric element as claimed in claim 6, and a control unit for driving the display device.

12. The electronic device as claimed in claim 11, wherein the organic electric element comprises at least one of an organic light emitting diode (OLED), an organic solar cell, an organic photo conductor (OPC), an organic transistor (organic TFT), and an element for monochromatic or white illumination.

13. The compound of claim 1, being any one of the compounds below:
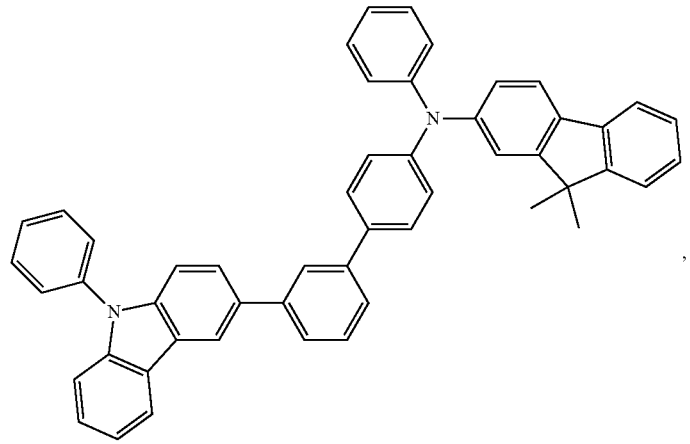
A1
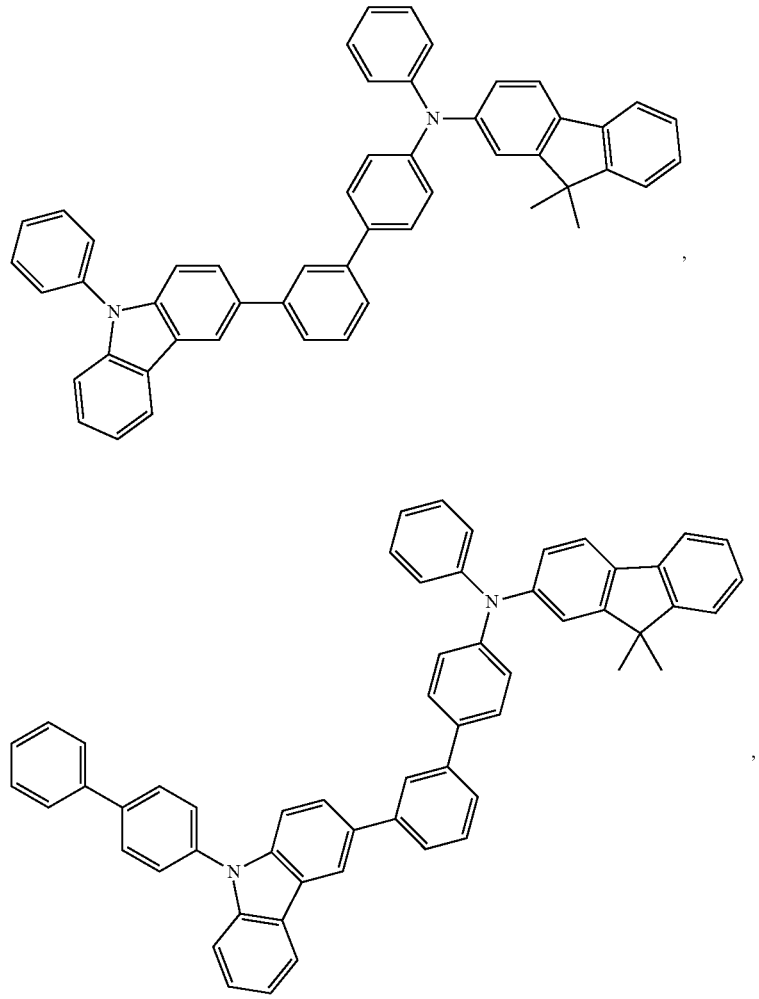
A2
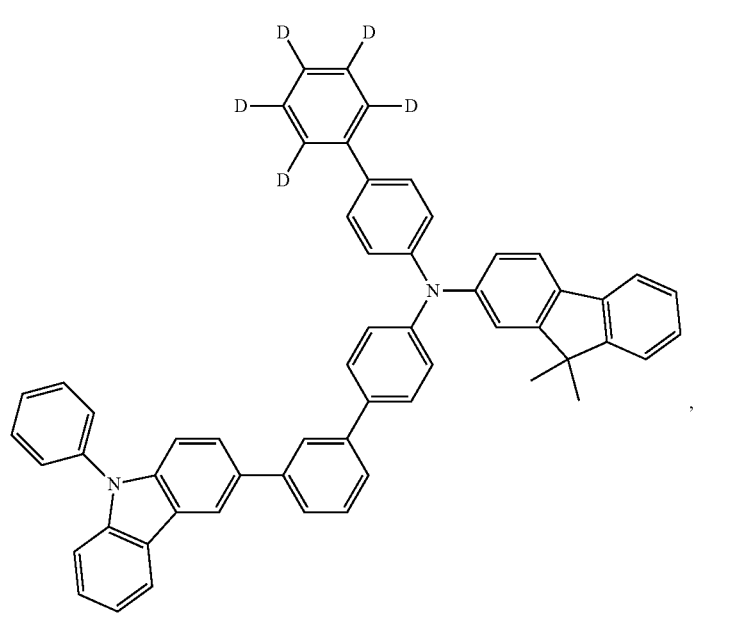
A6

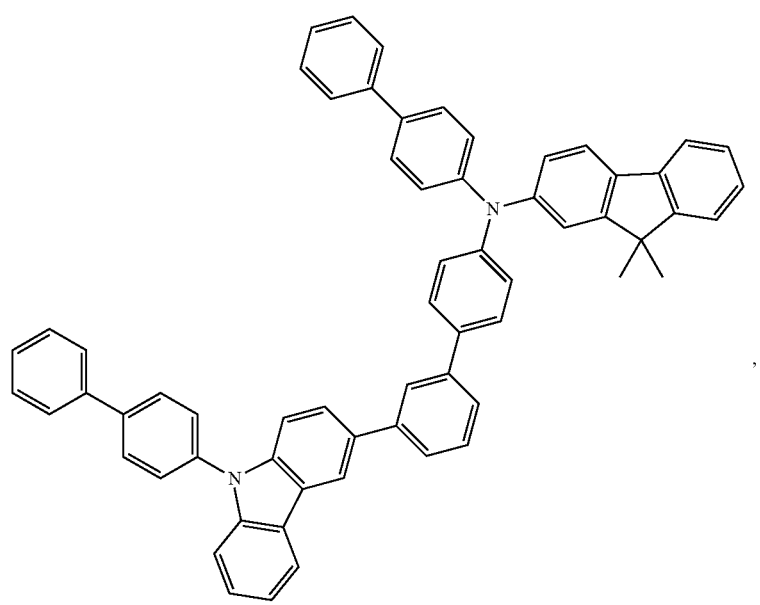
A7
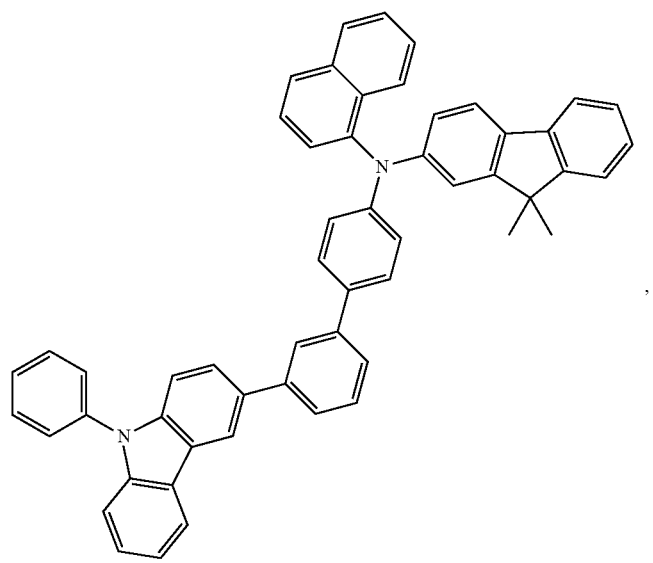
A11

-continued
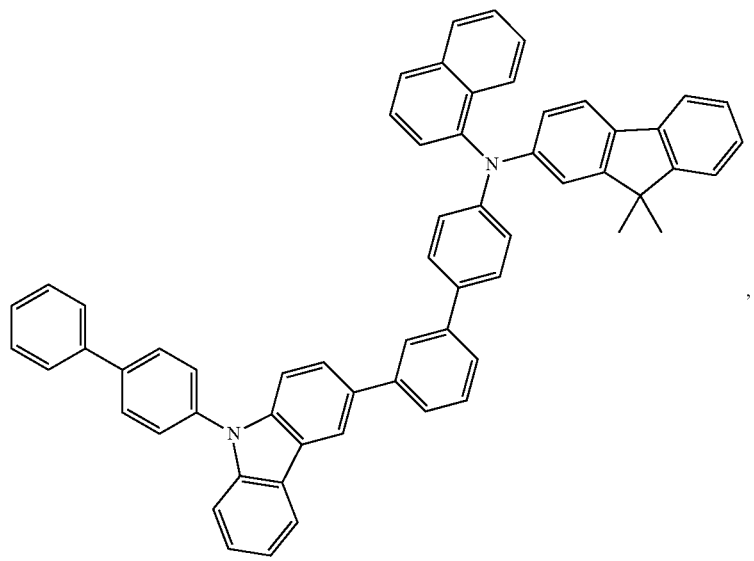
A12
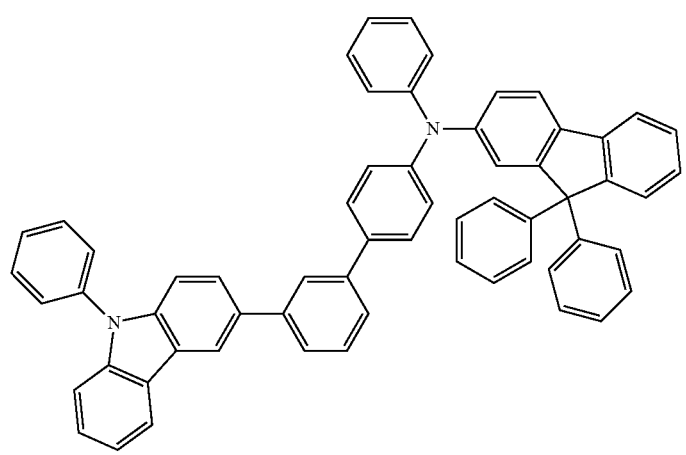
A16
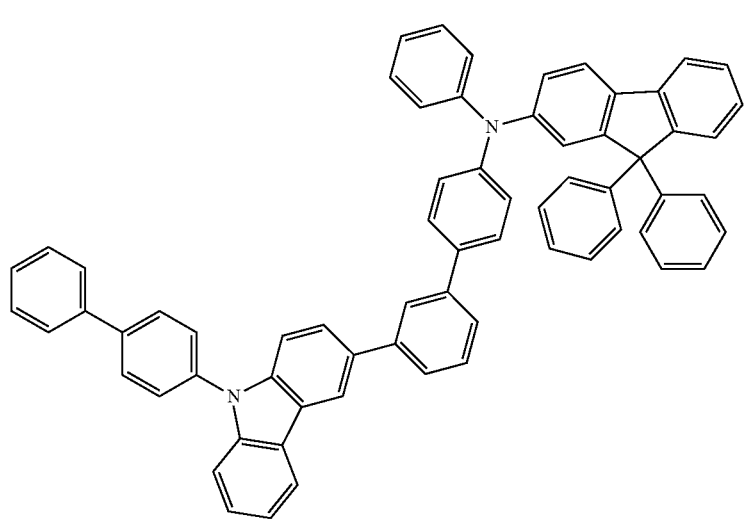
A17

-continued
A19
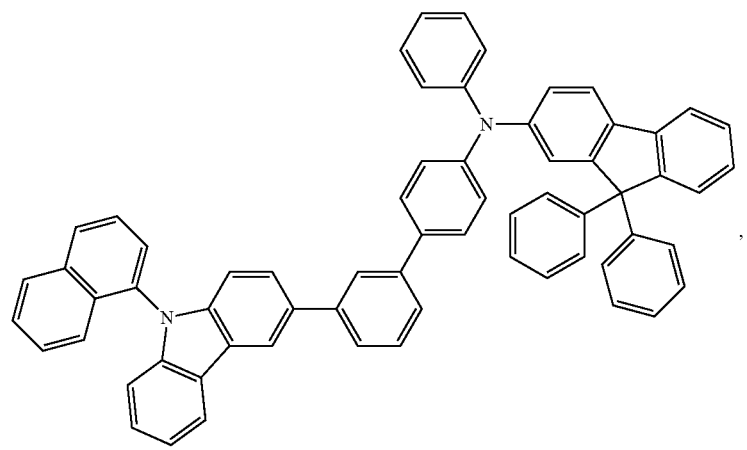
A21
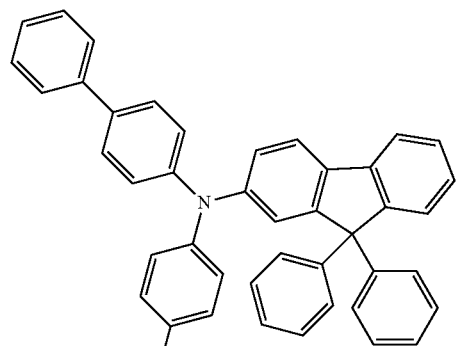
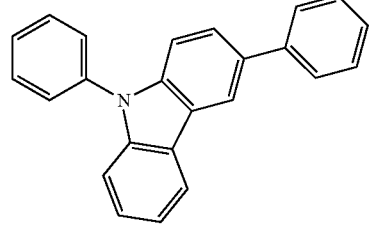
A22
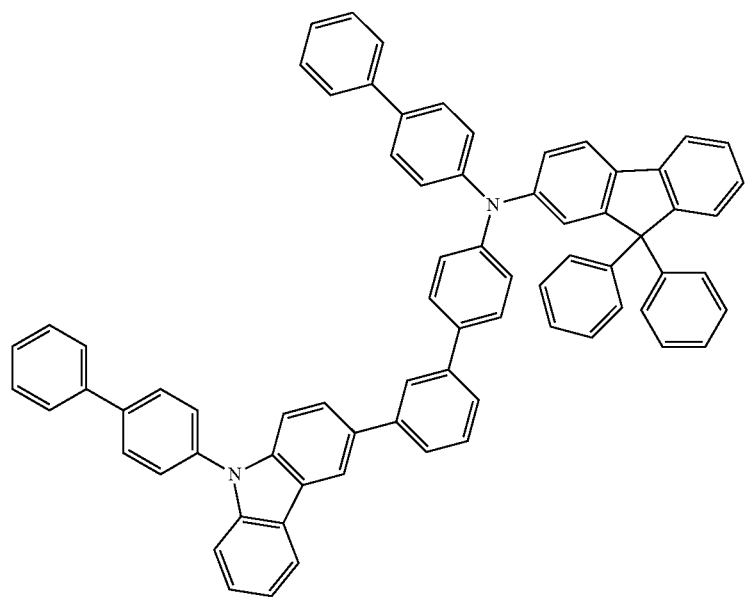

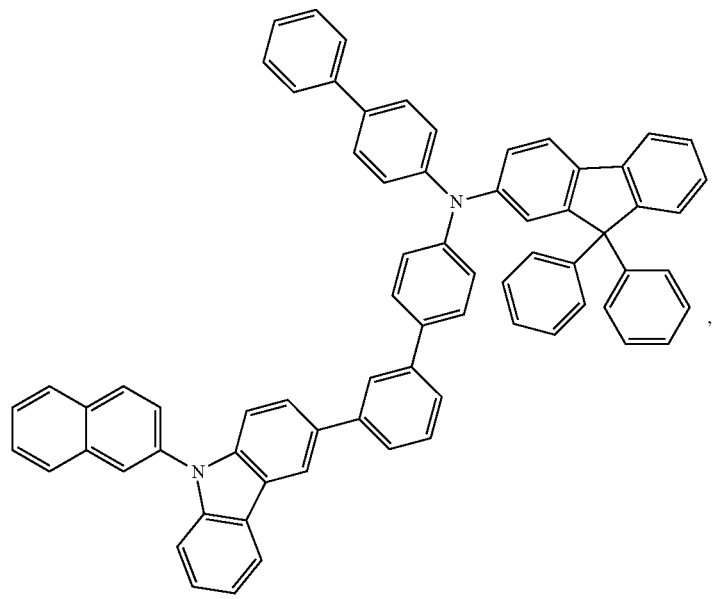
A23
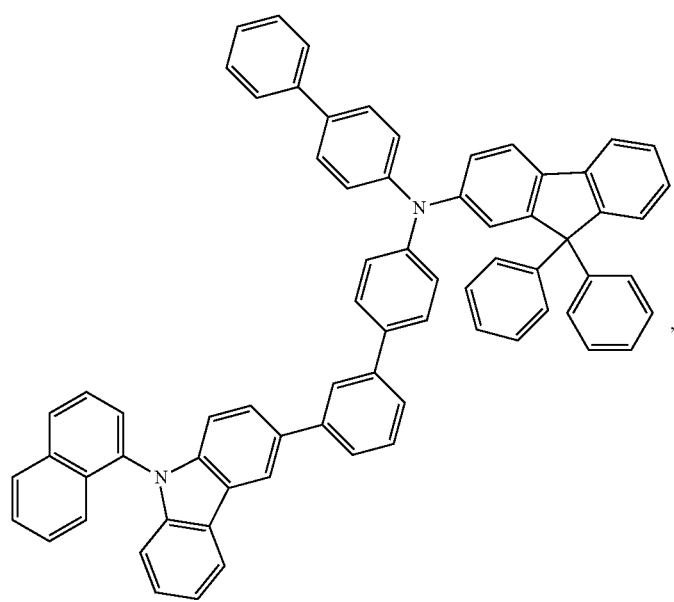
A24

-continued
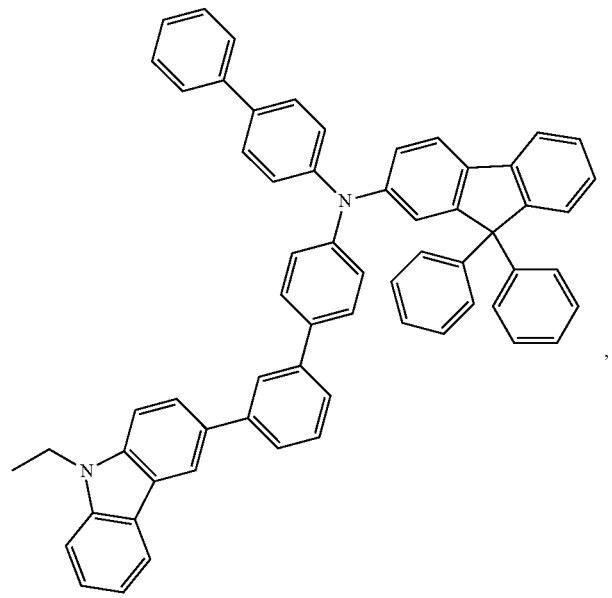
A25
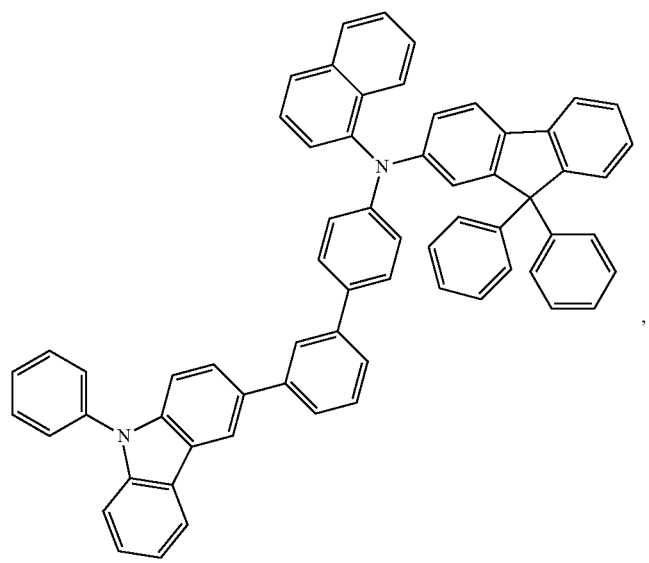
A26

-continued
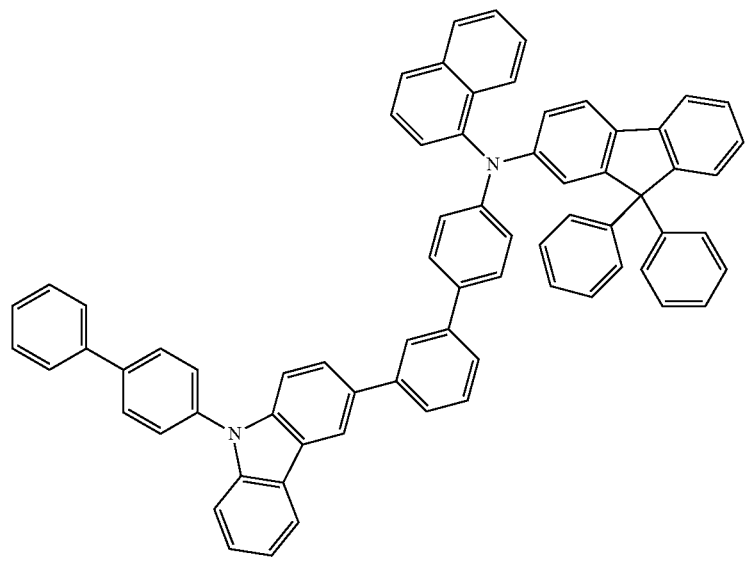
A27
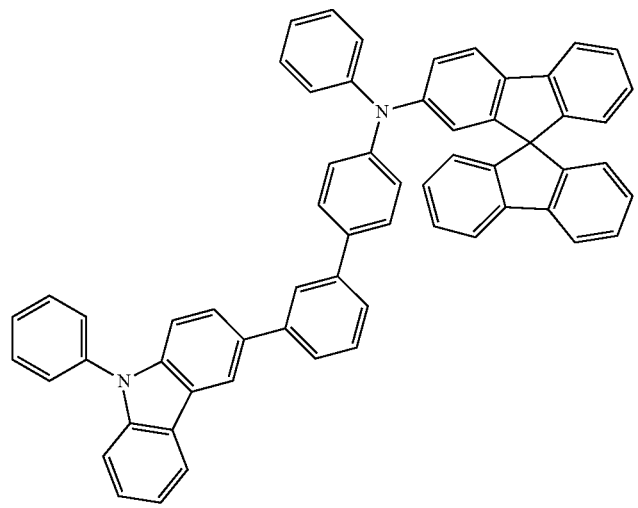
A31
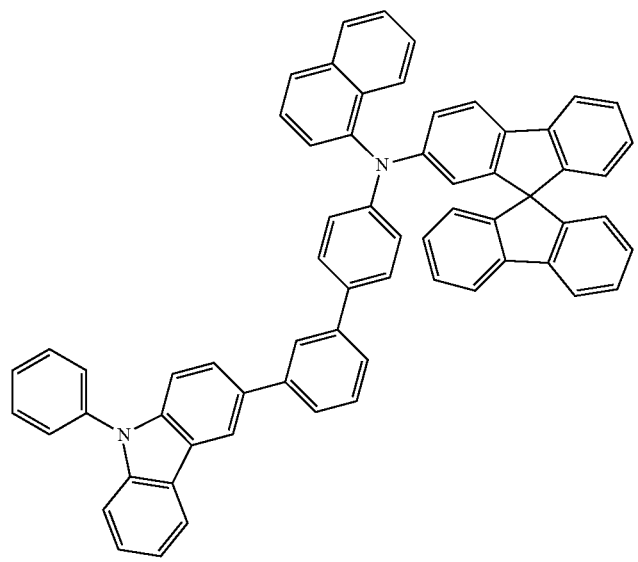
A36

-continued
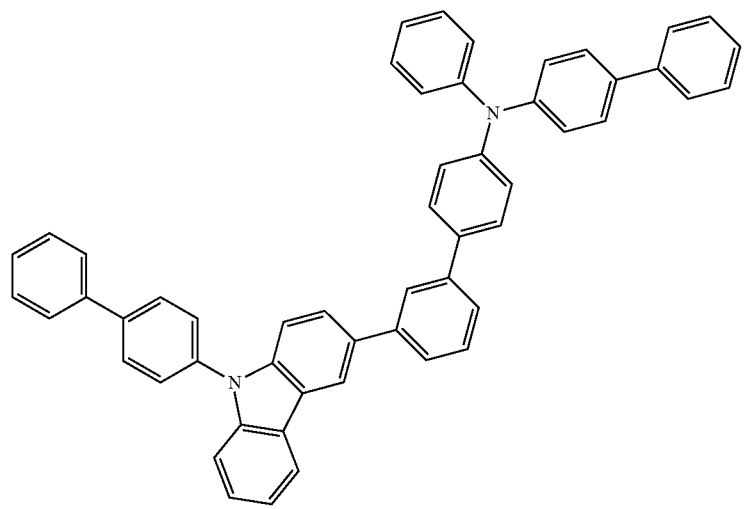
A47
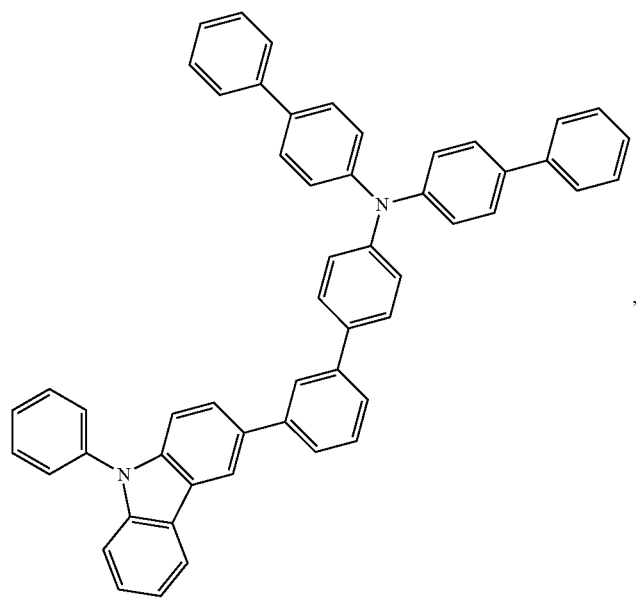
A51
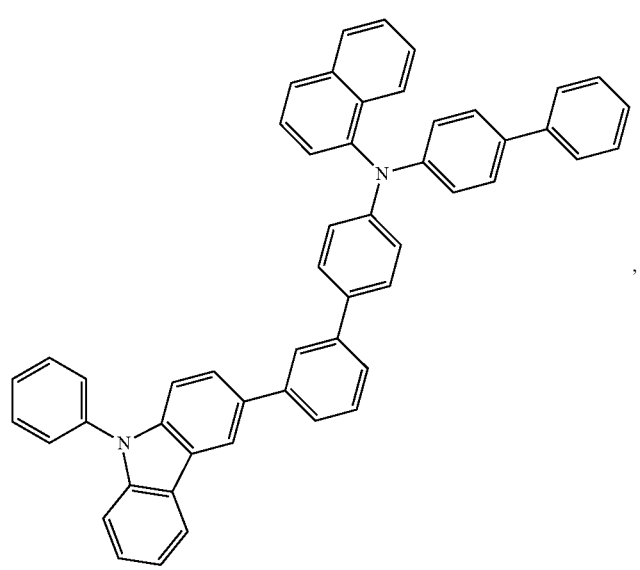
A56

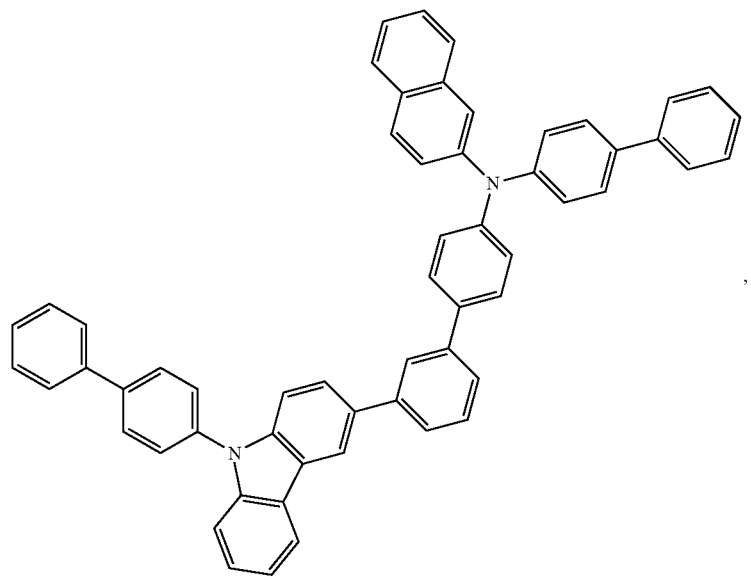
A62
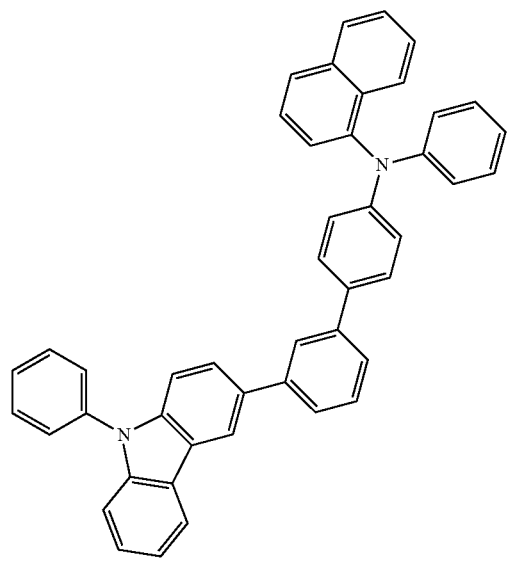
A66

-continued
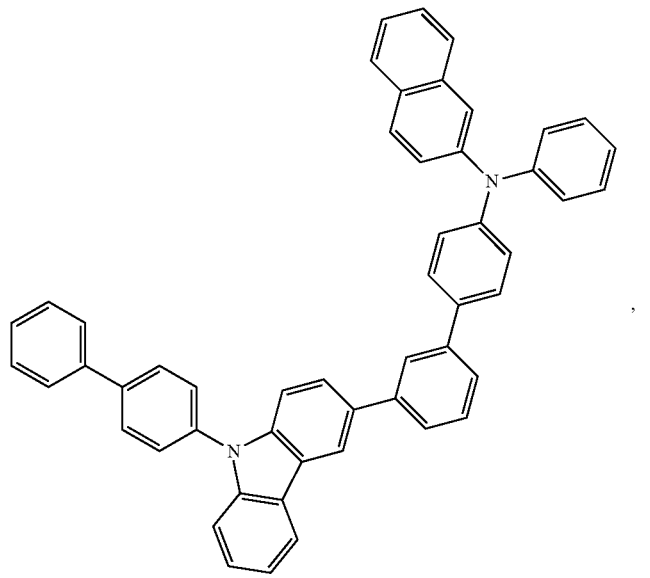
A72
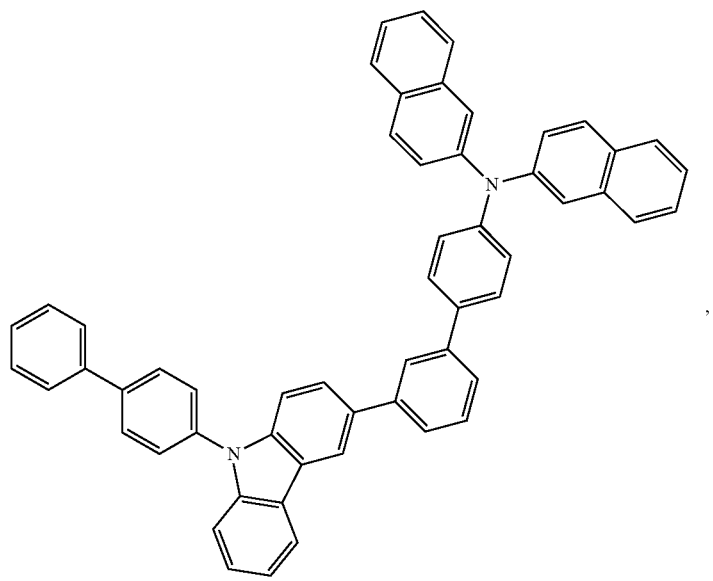
A87
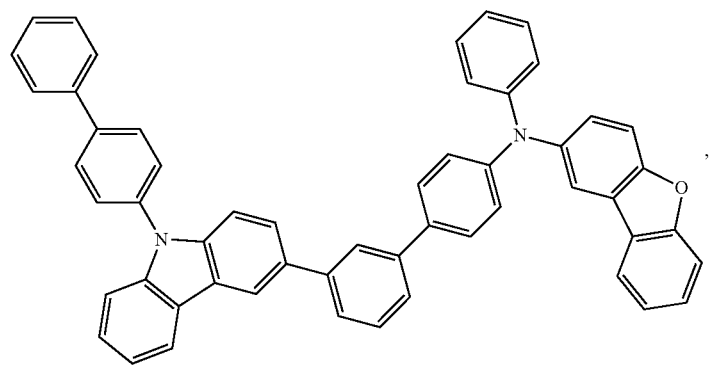
A97

-continued
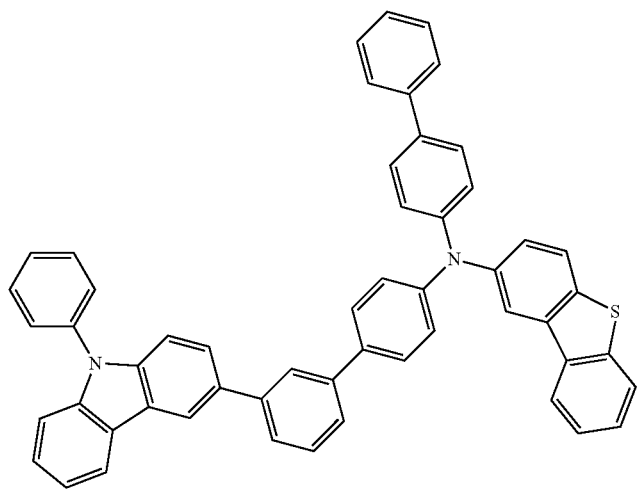
A101
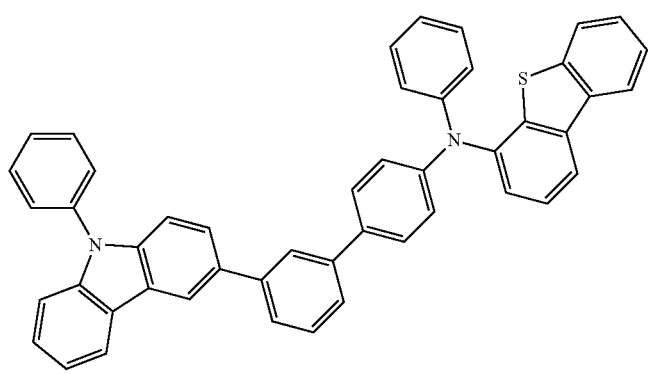
A121
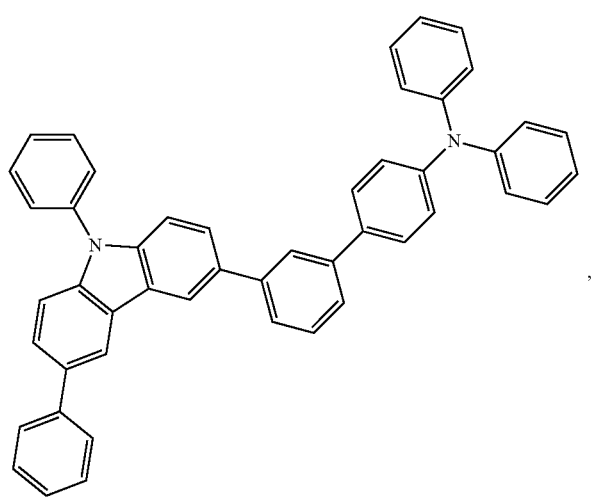
A123

A124
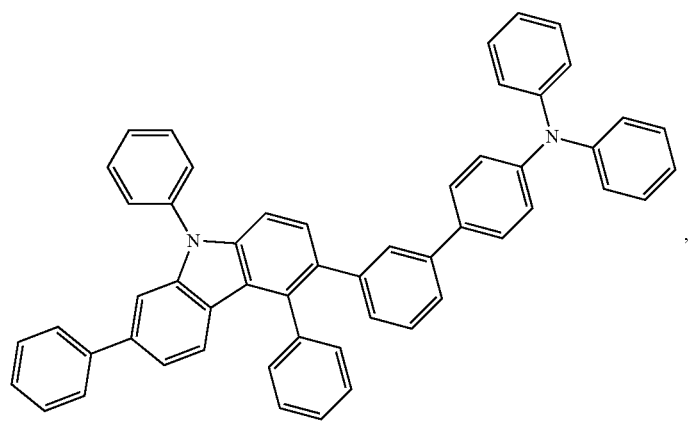
A125
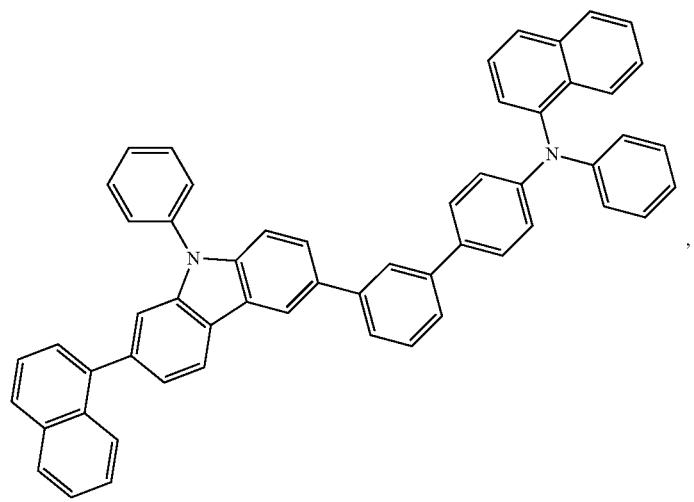
A127
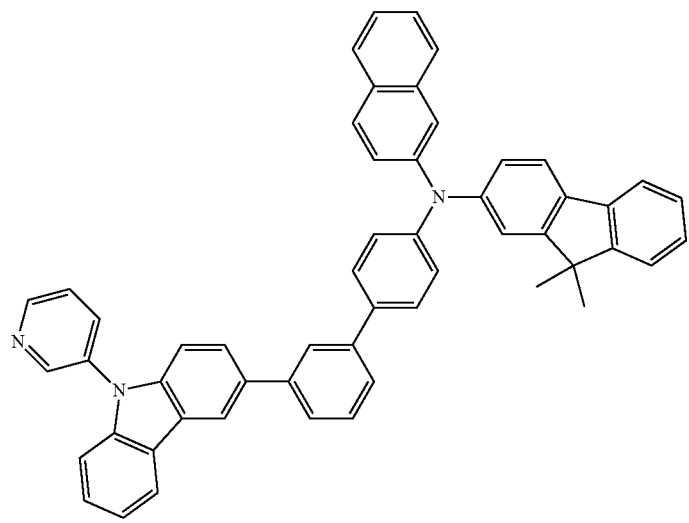

-continued
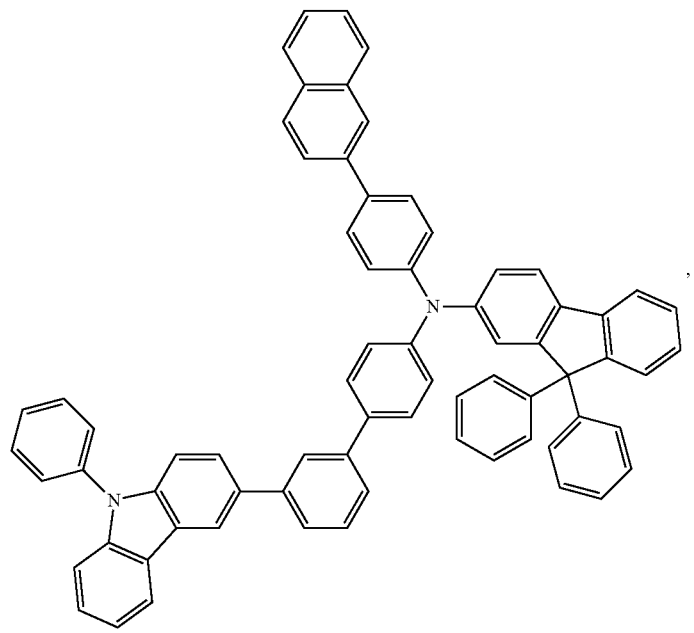
A128
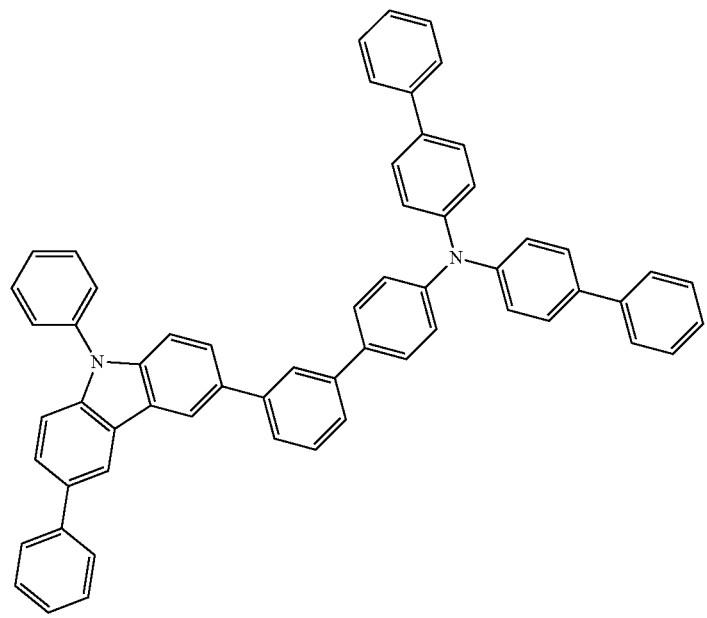
A129

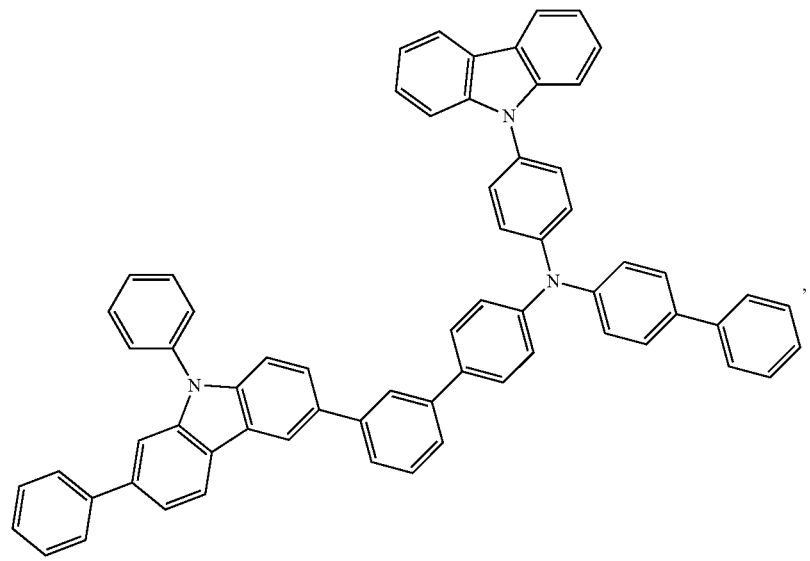
A130
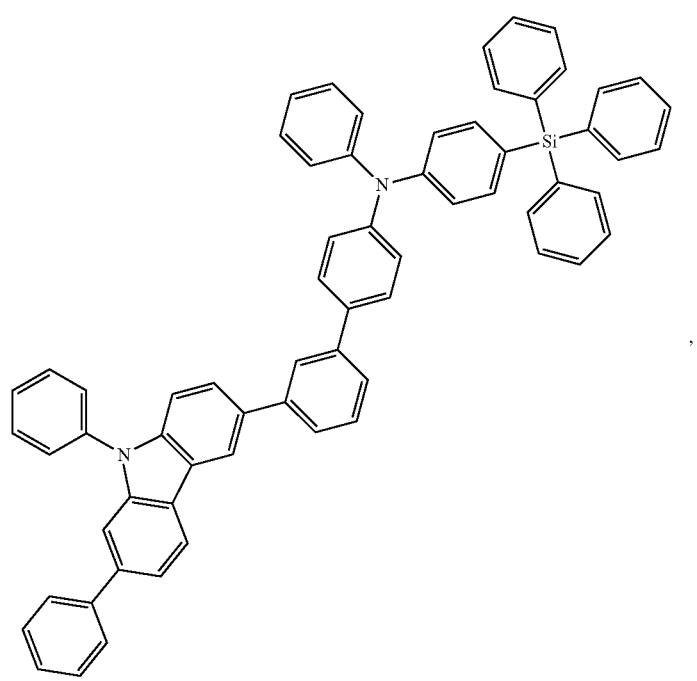
A131

-continued
A134
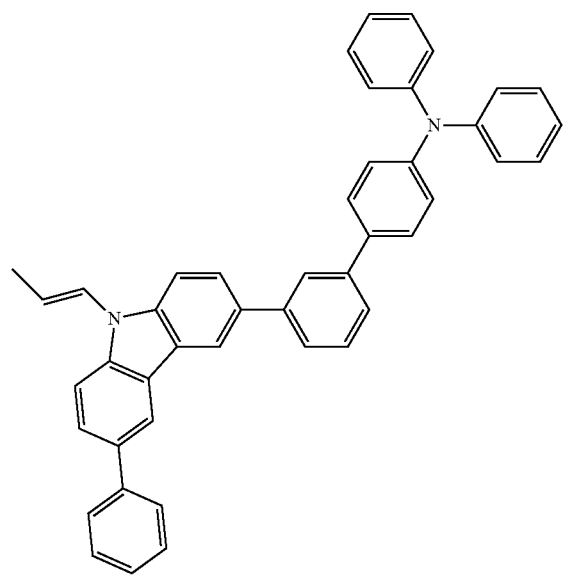
A135
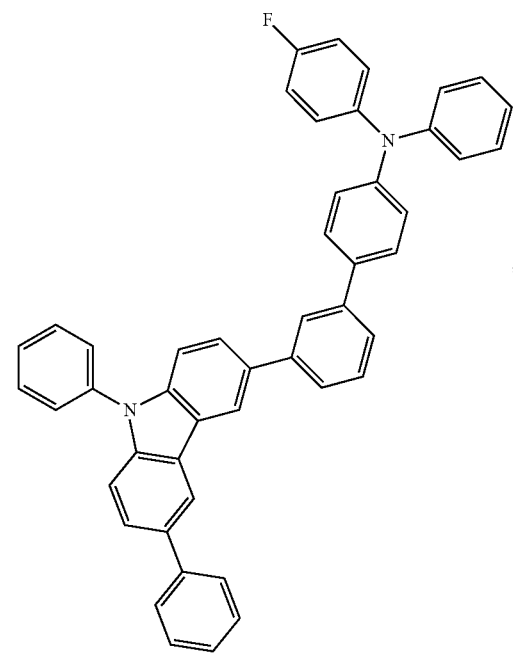
A142
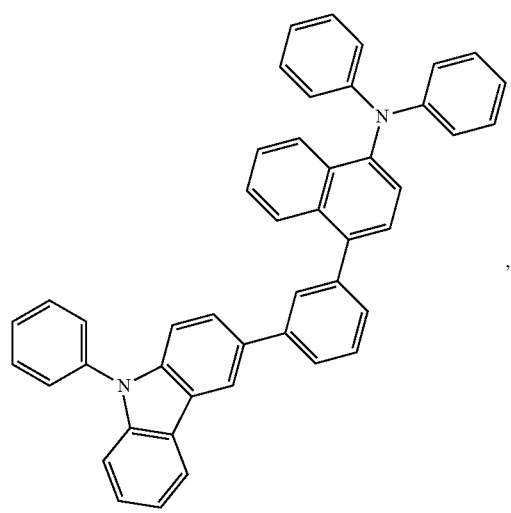

-continued
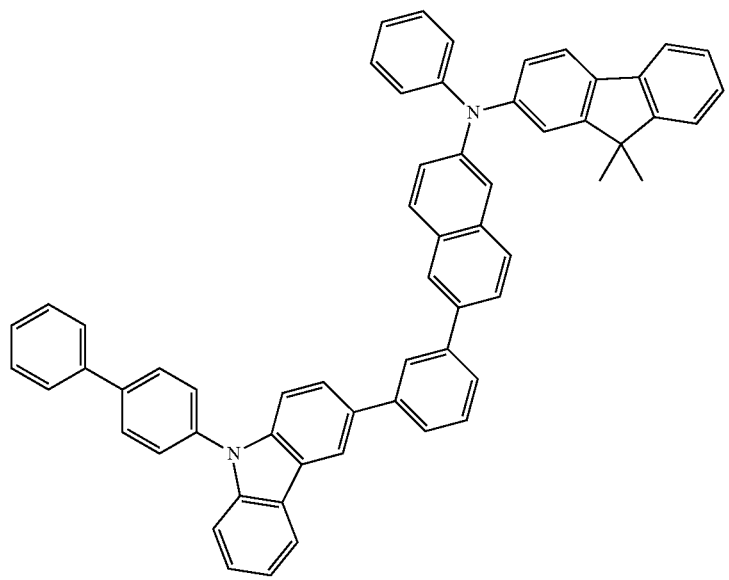
A146
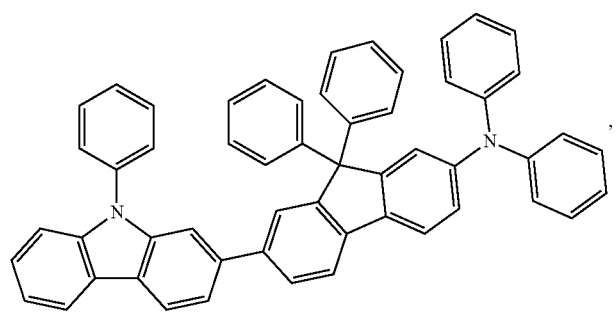
A161
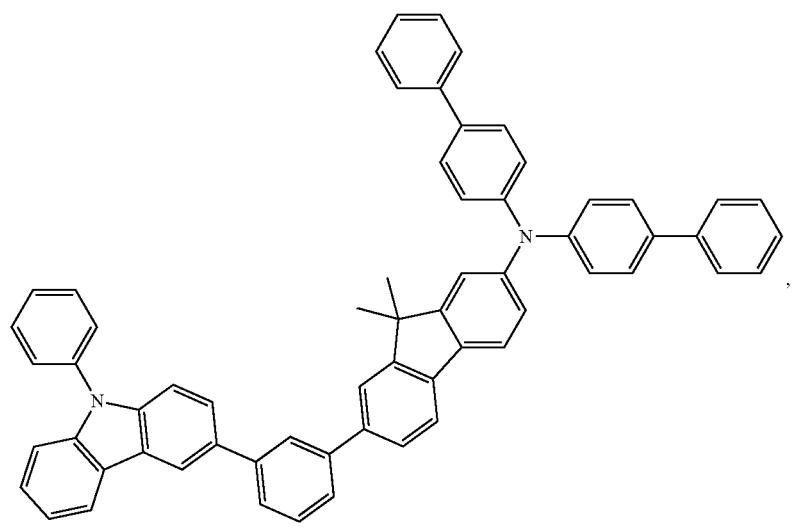
A162

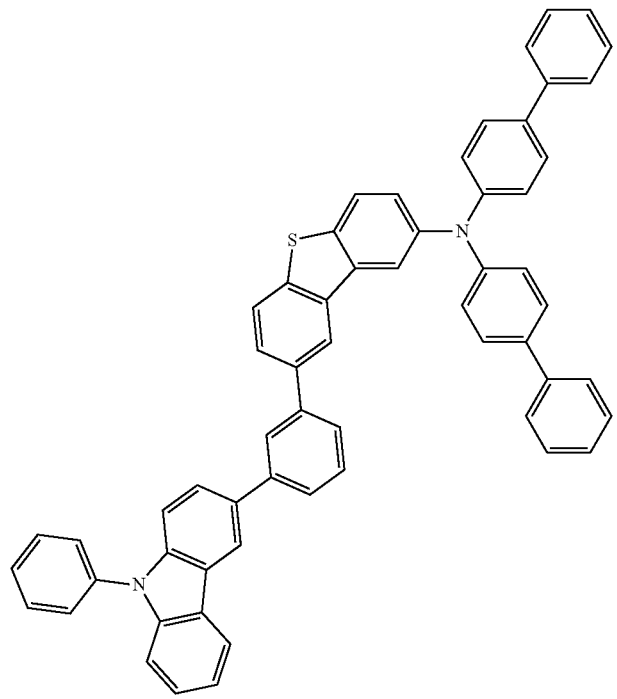
A165
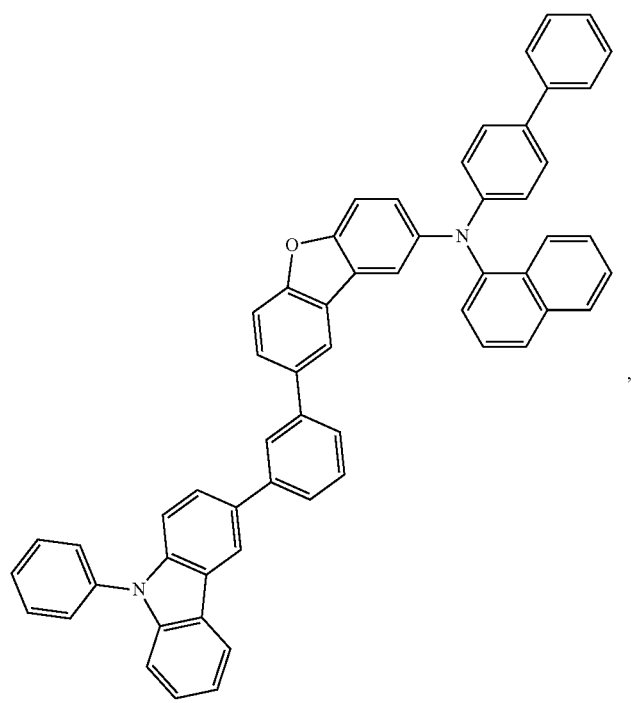
A168

-continued
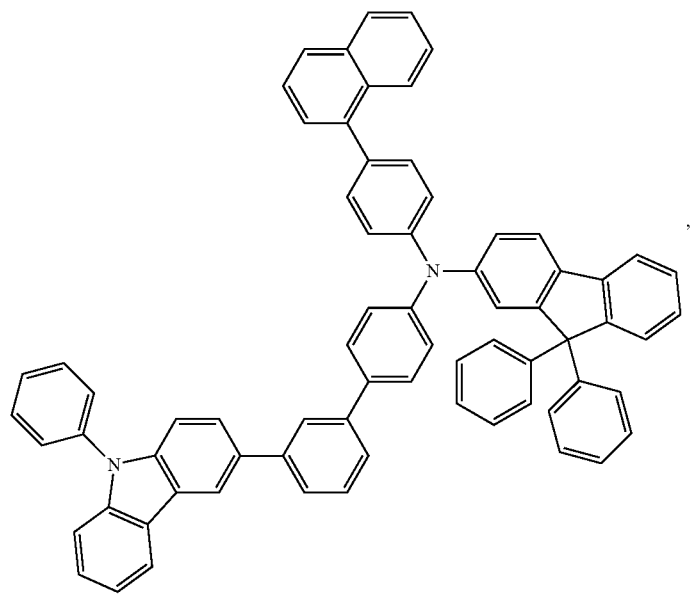
A169
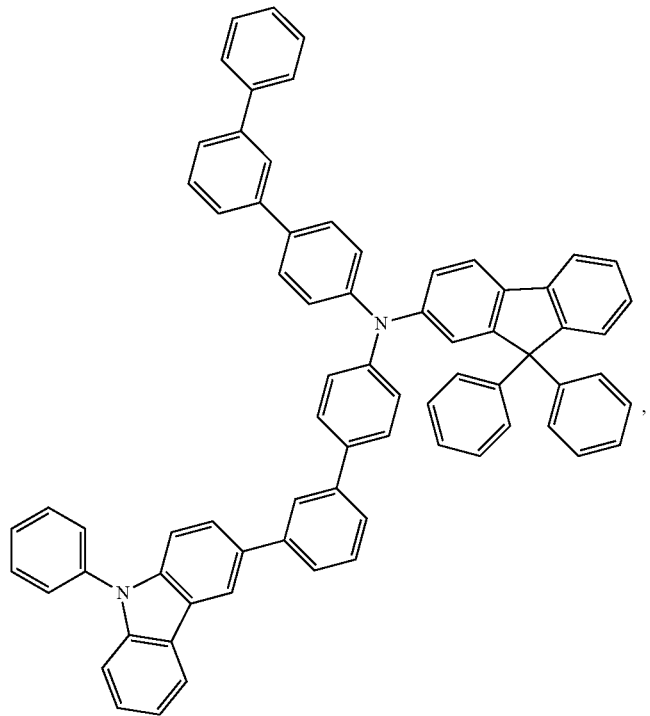
A170

-continued
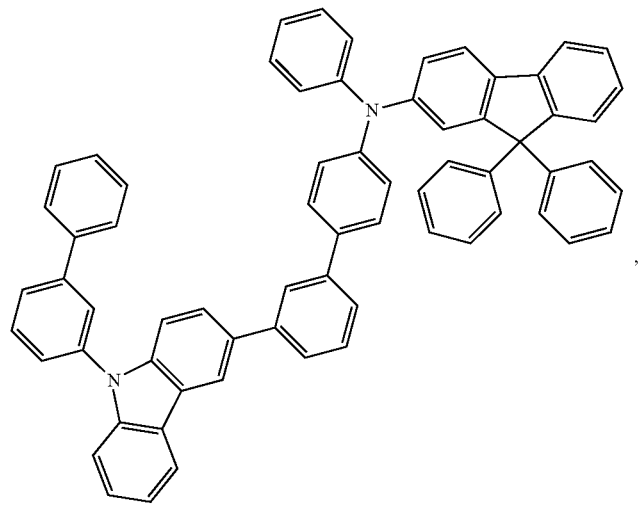
A171
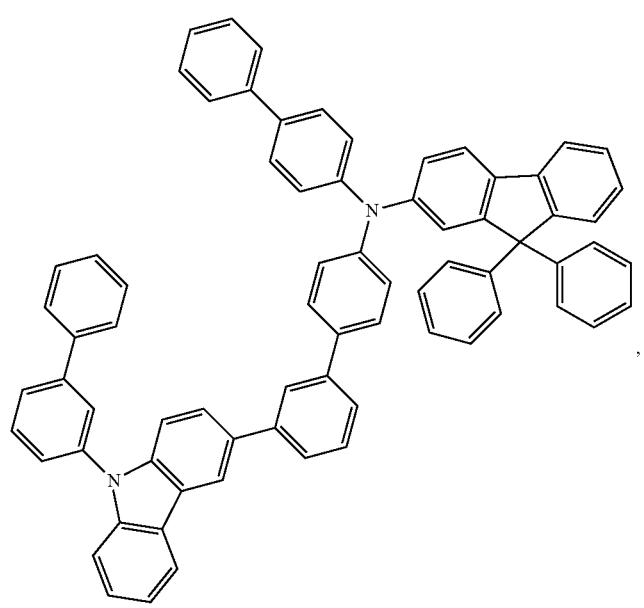
A172

-continued
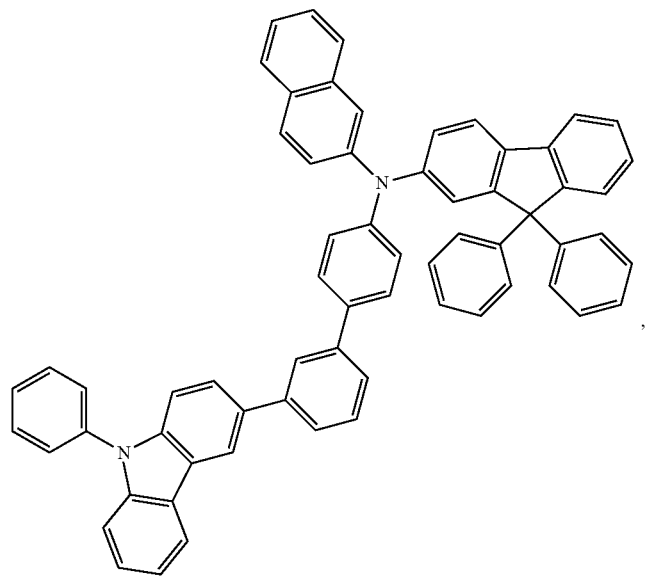
A173
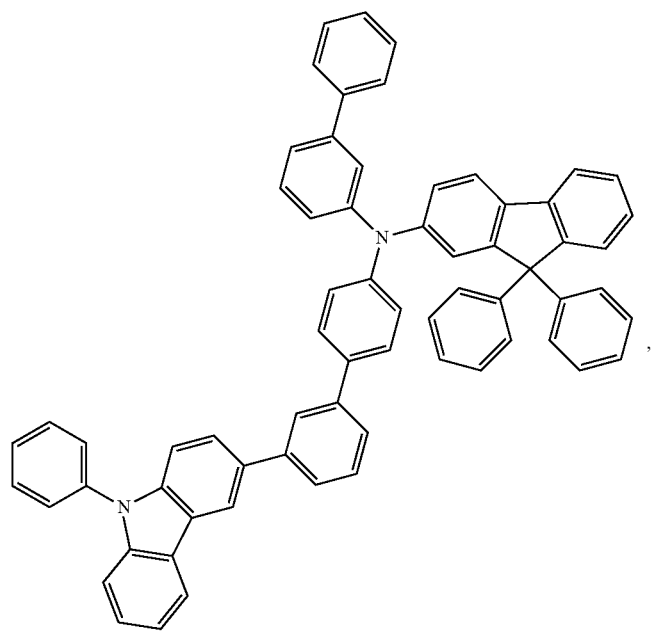
A174

-continued
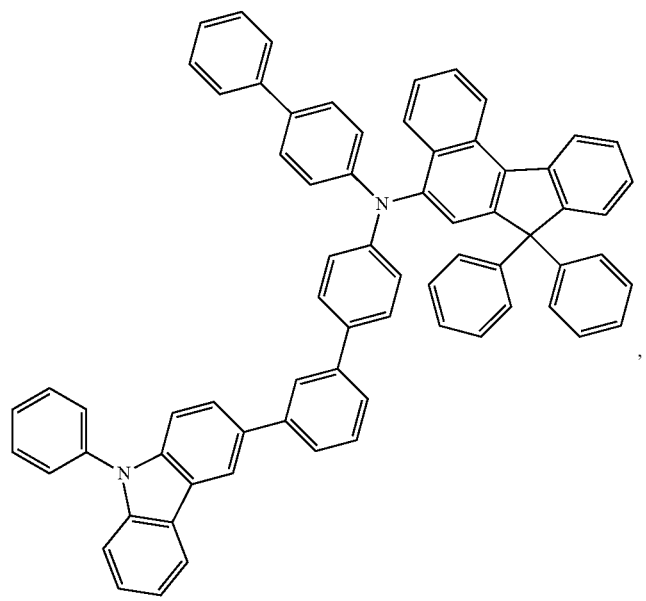
A175
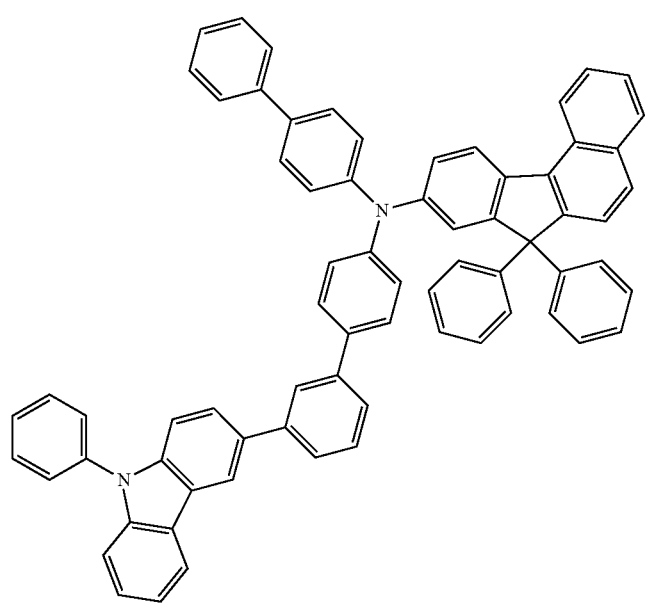
A176

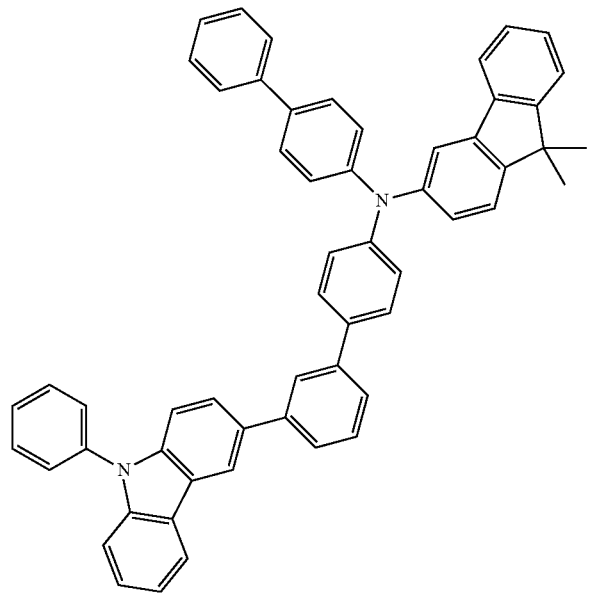
A177
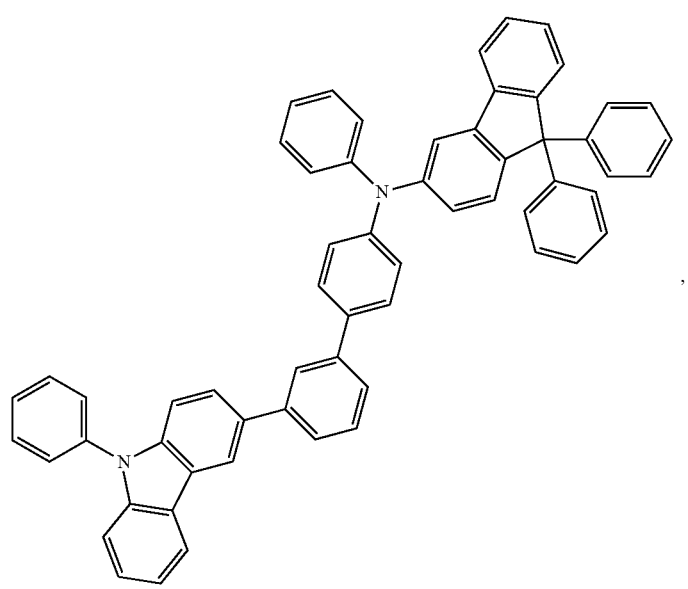
A178

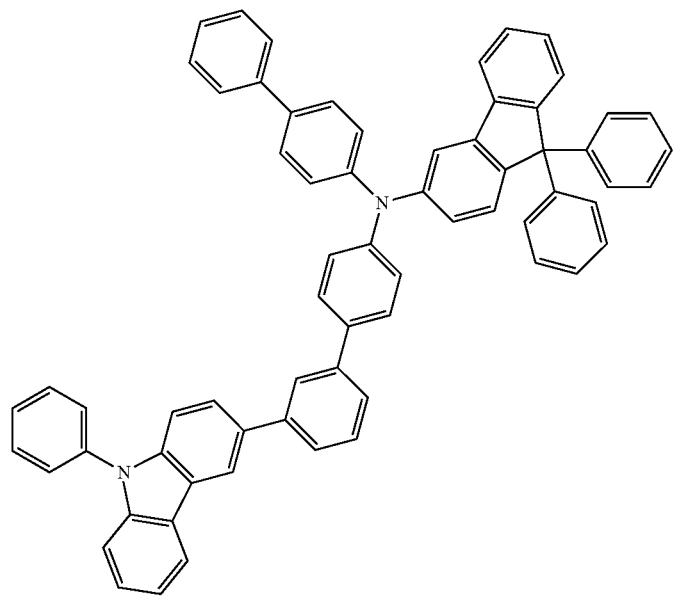
A179
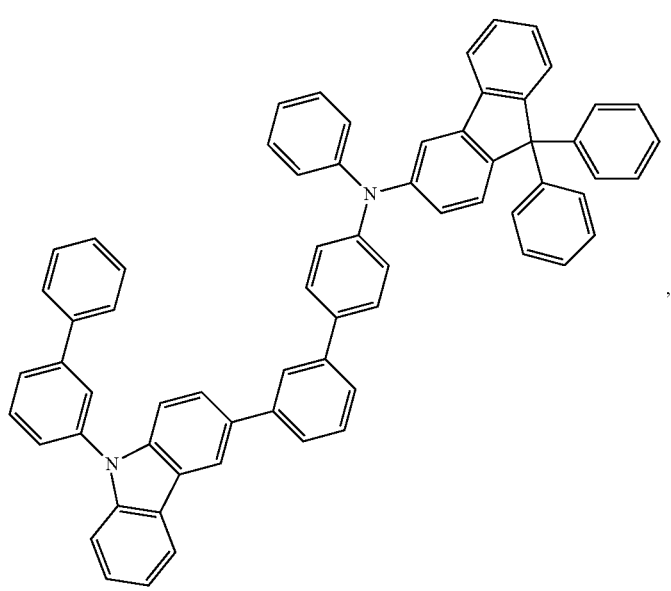
A180

-continued
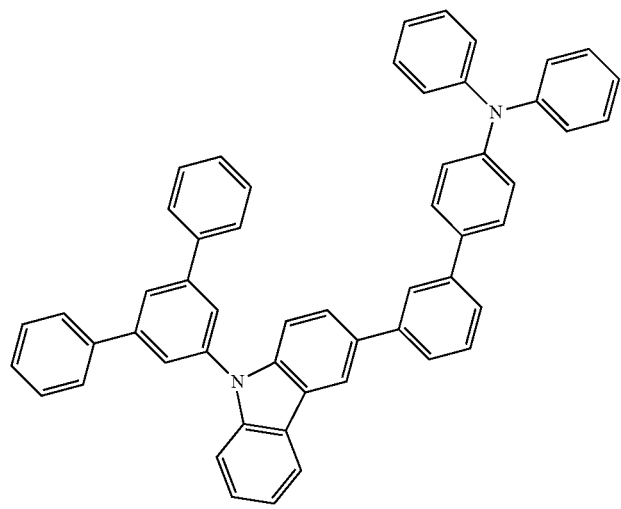
A181
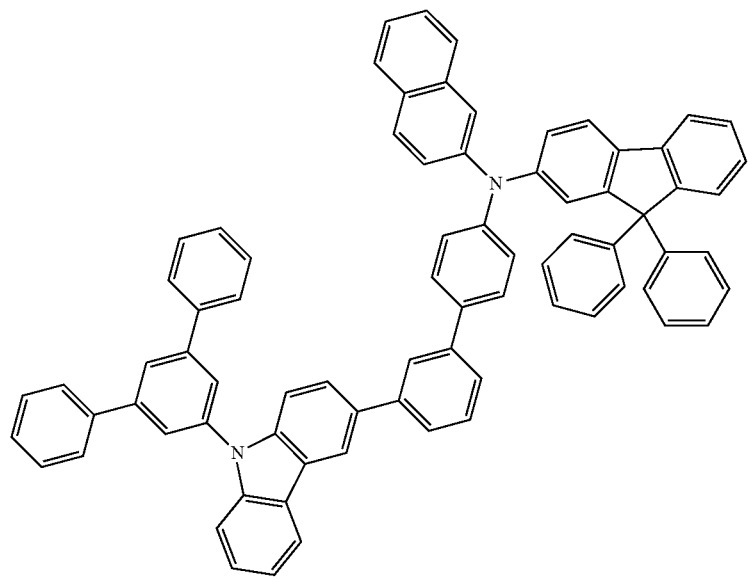
A182

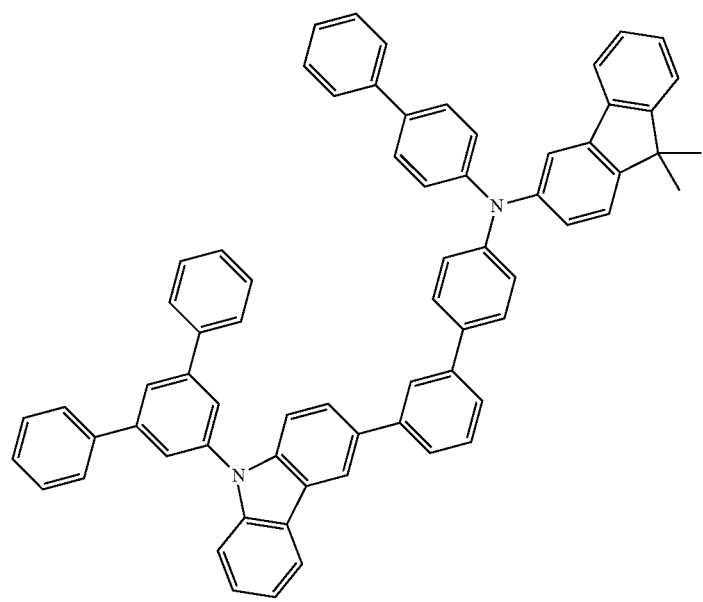
A183
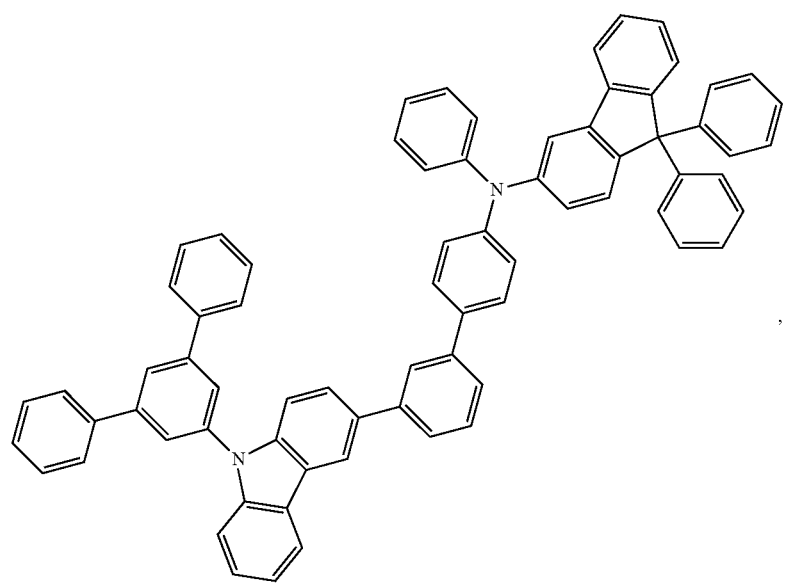
A184

-continued
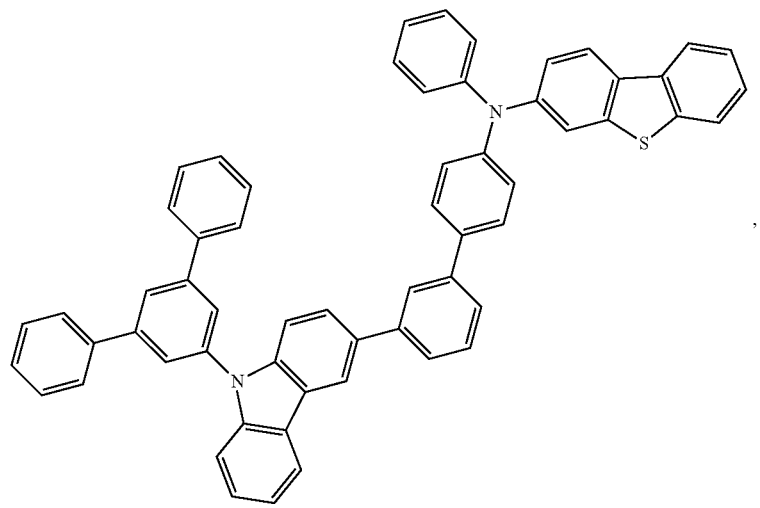
A185
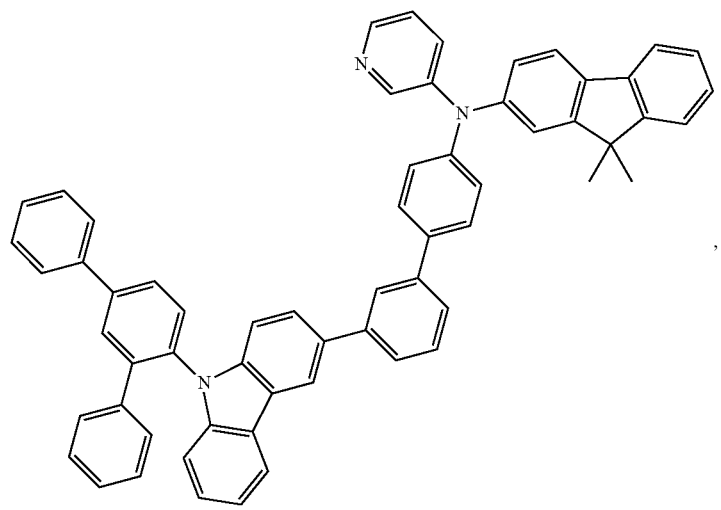
A186
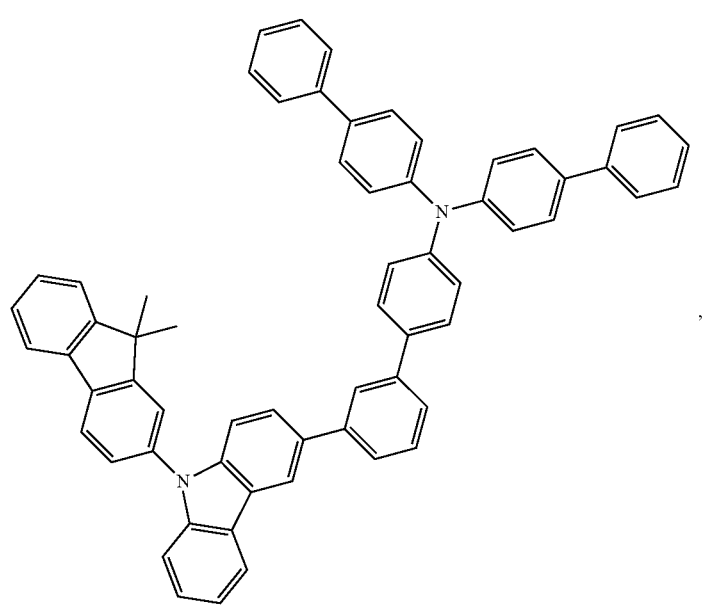
A187

-continued
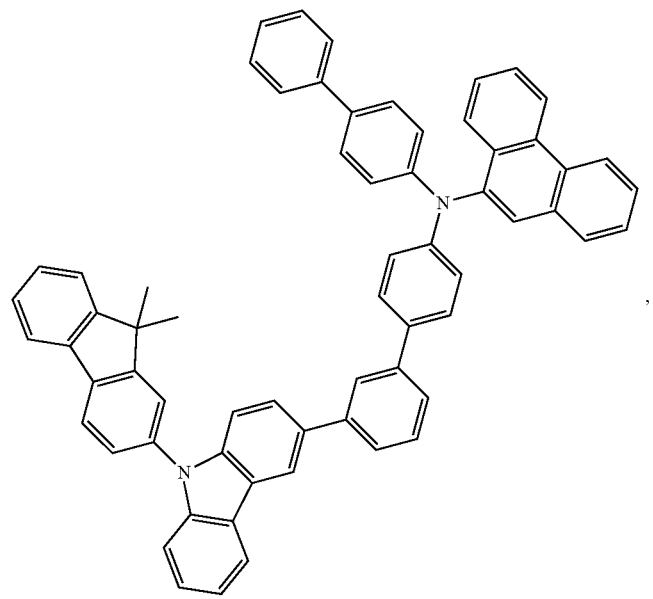
A188
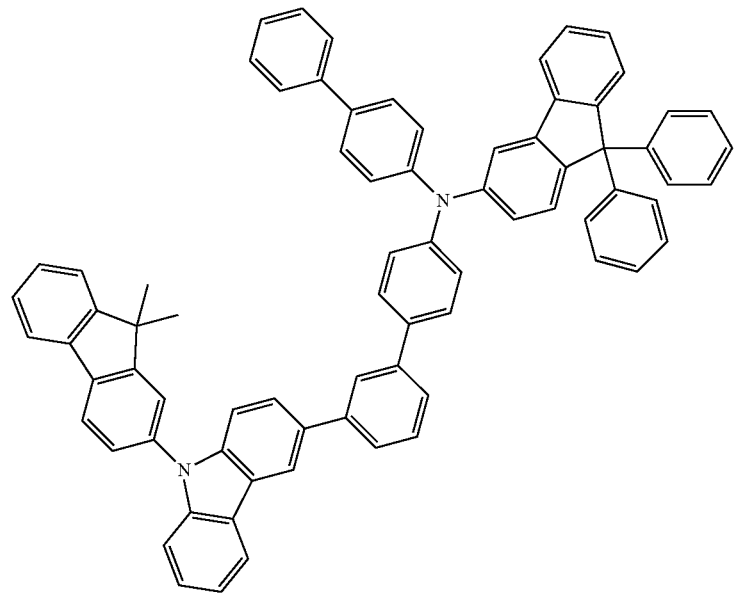
A189

-continued
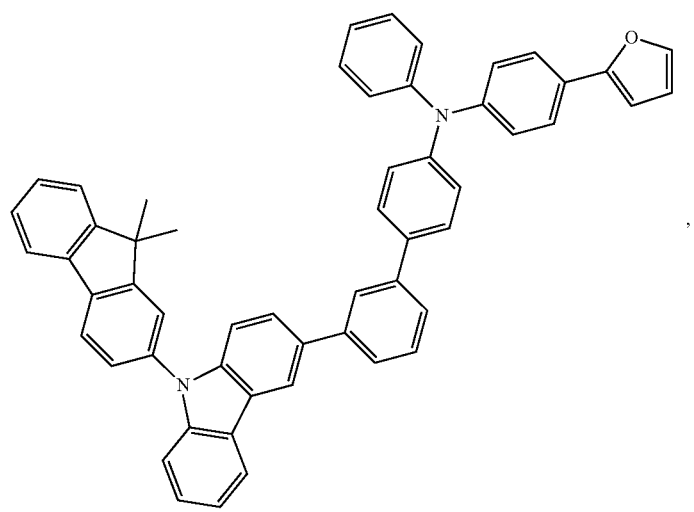
A190
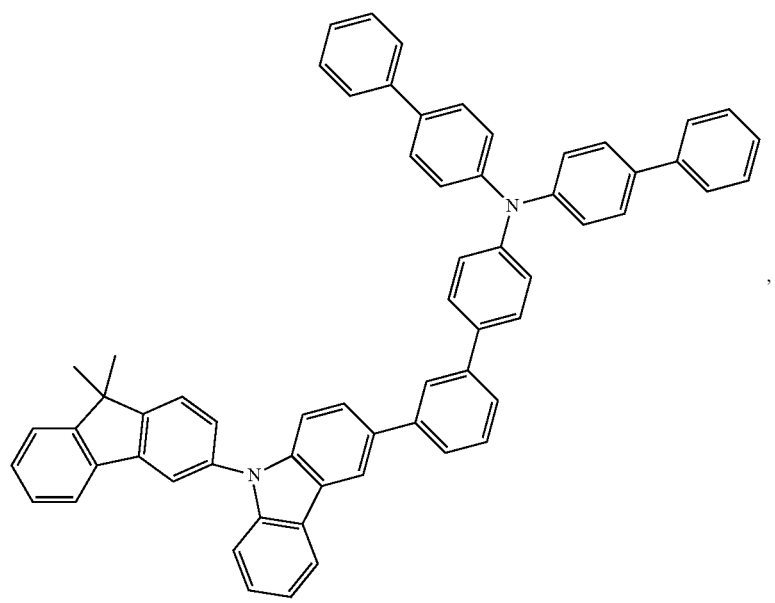
A191

-continued
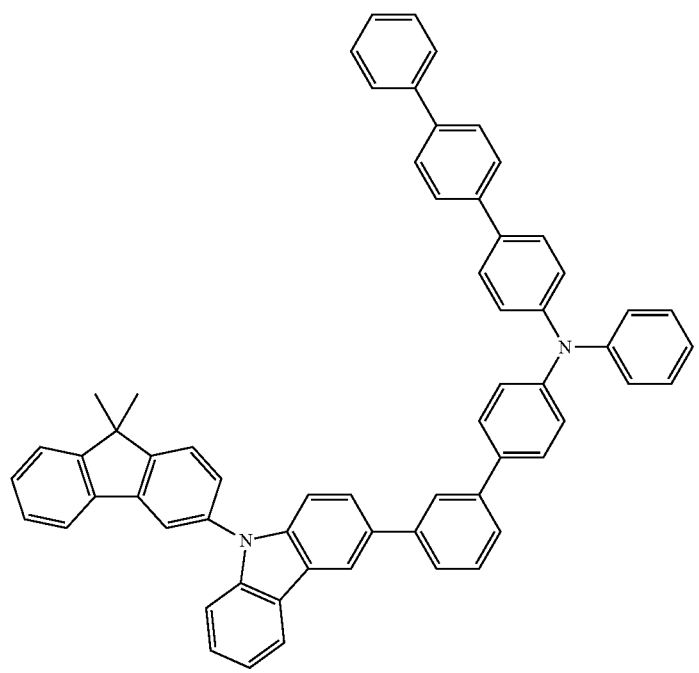
A192
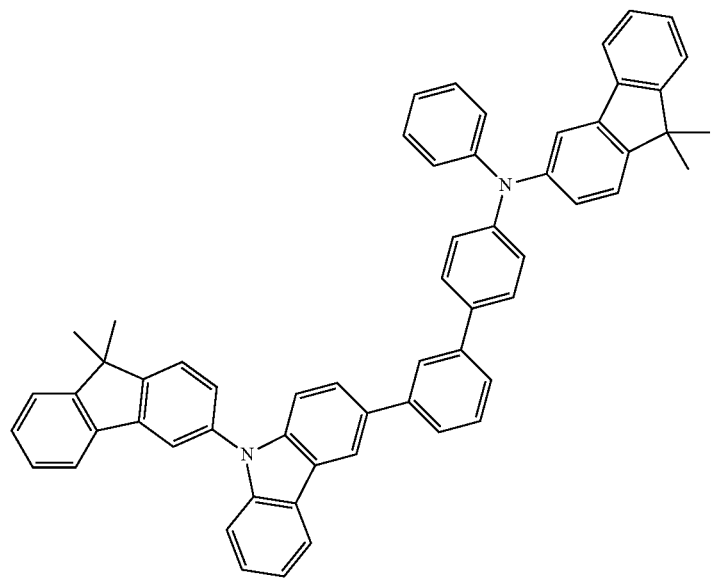
A193

-continued
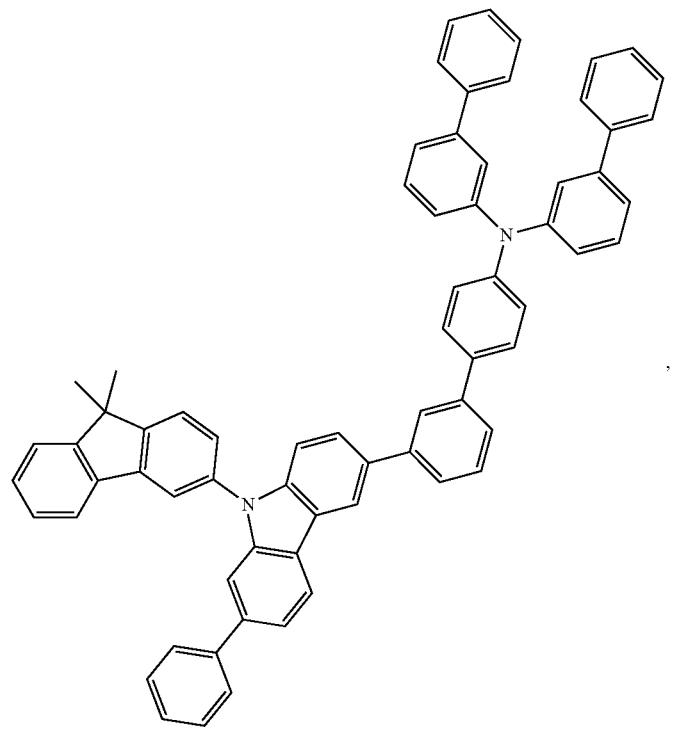
A194
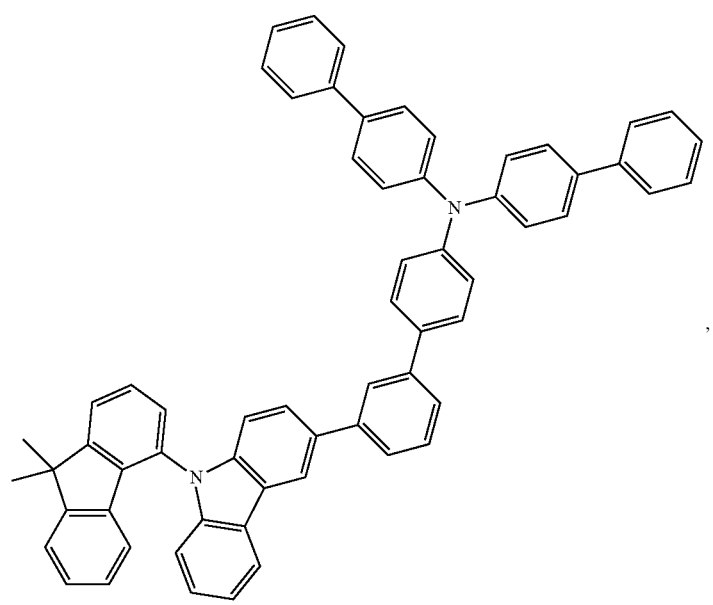
A195

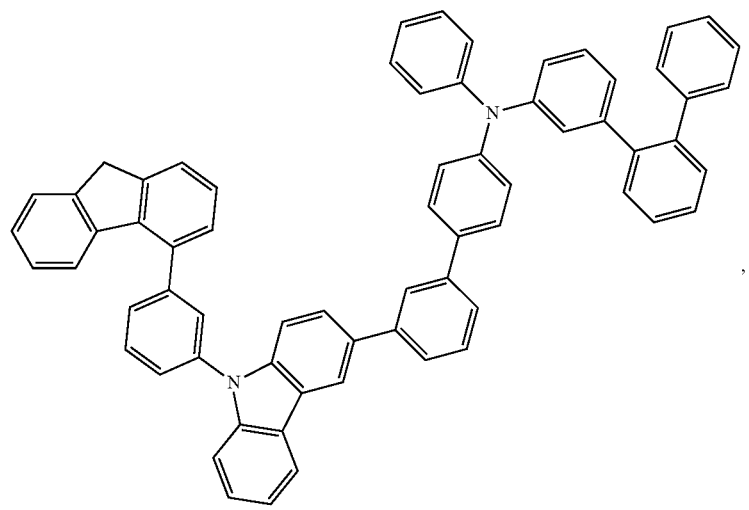
A196
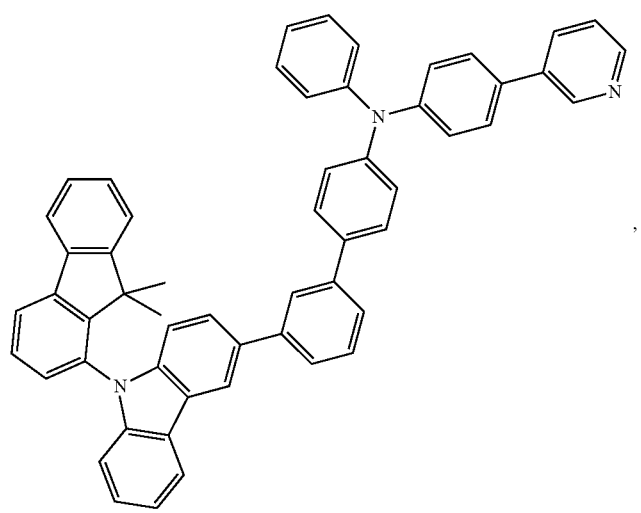
A197

-continued
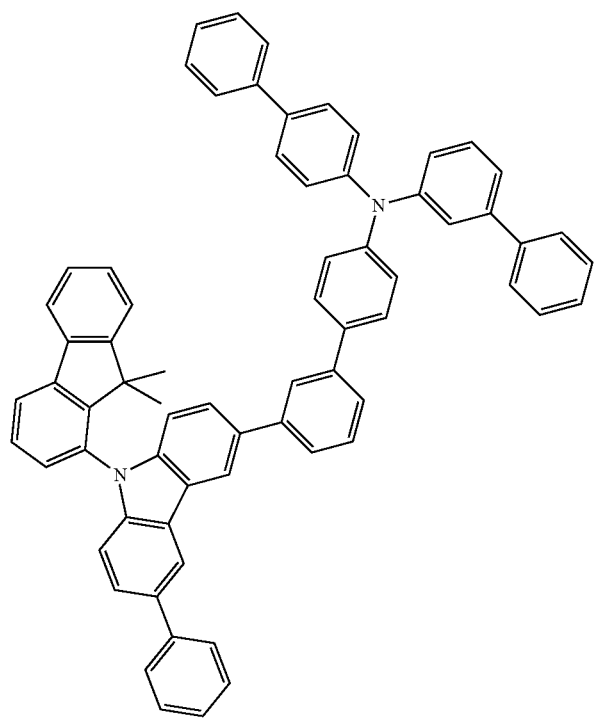
A198
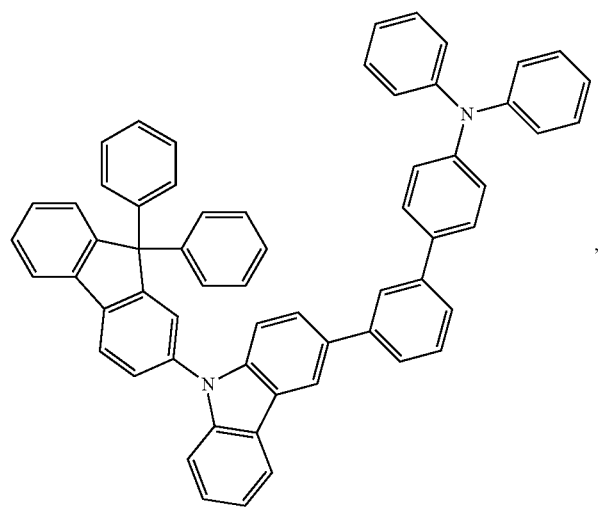
A199

-continued
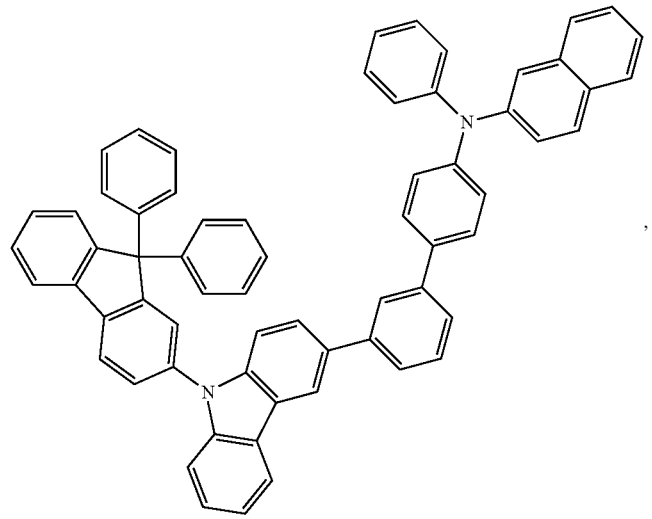
A200
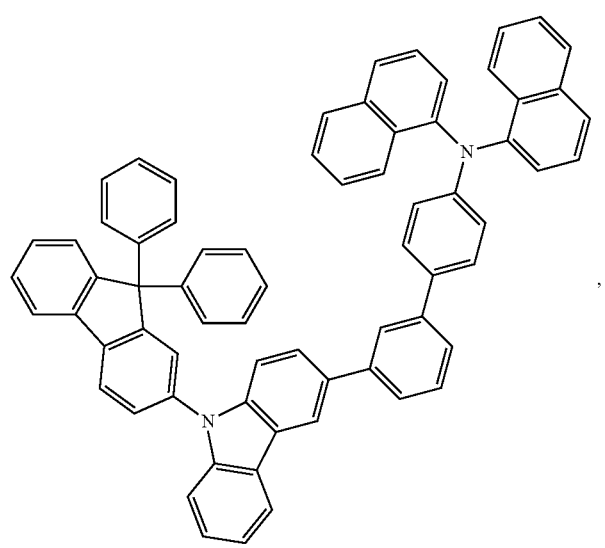
A201
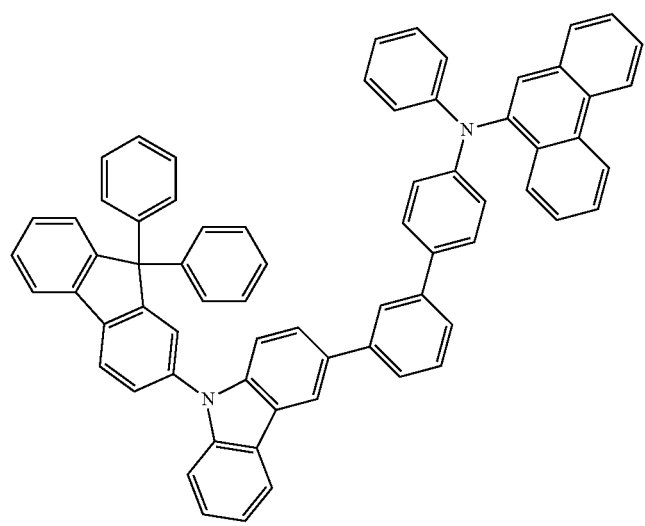
A202

-continued
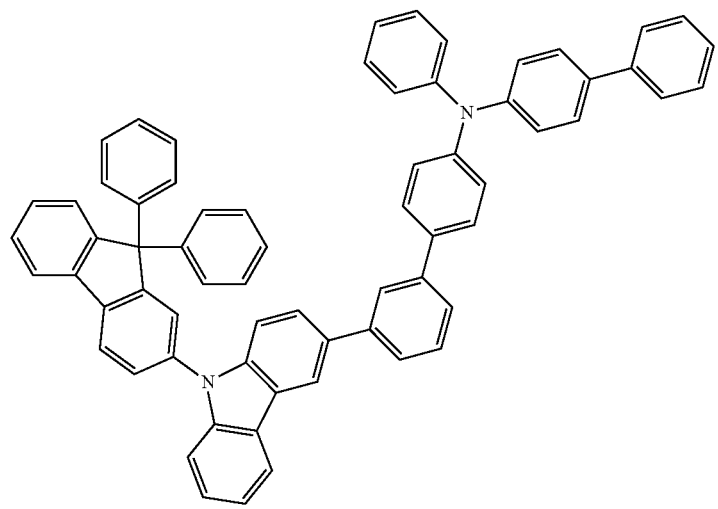
A203
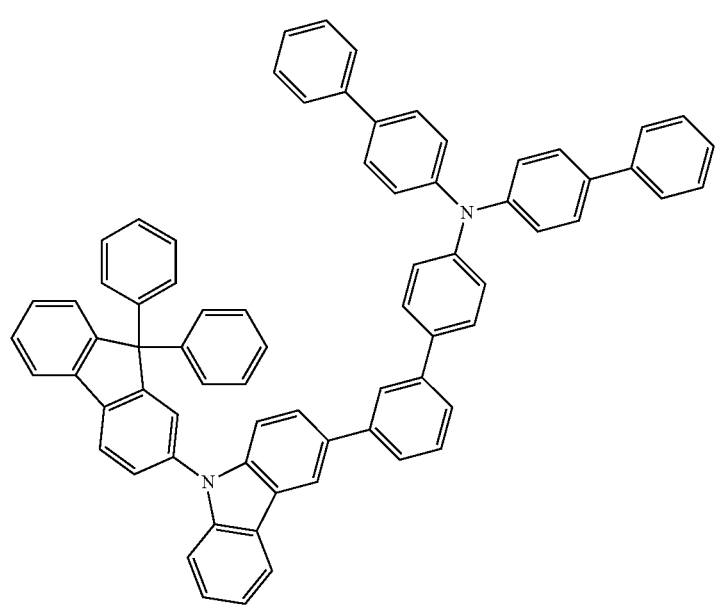
A204
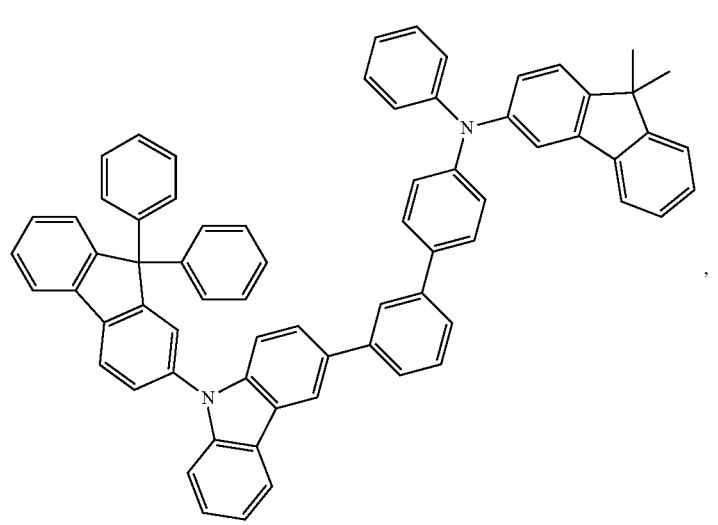
A205

A206
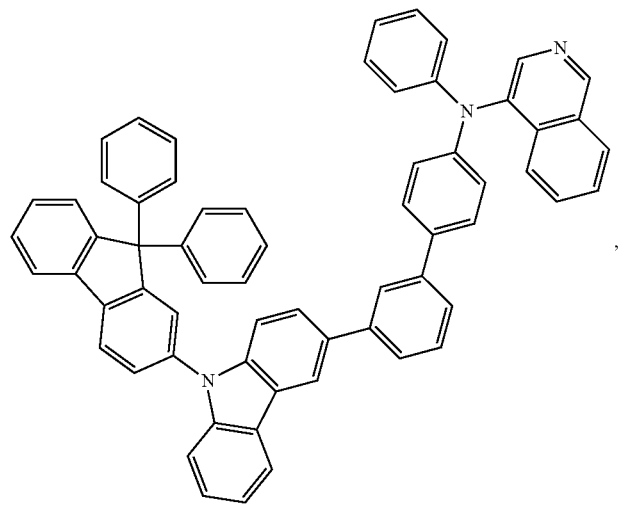
A207
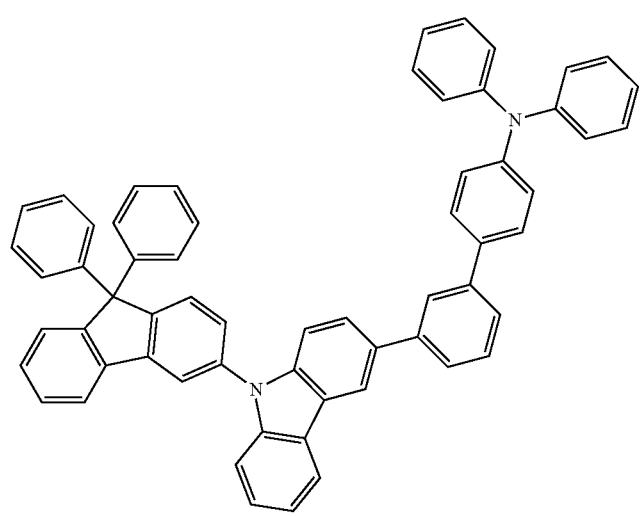
A208
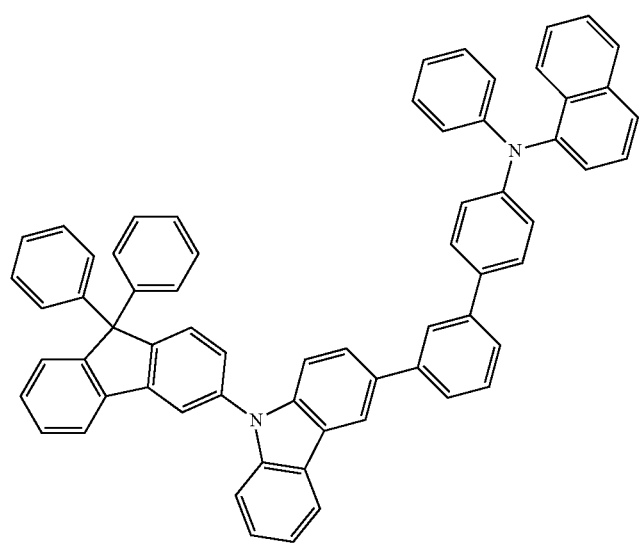

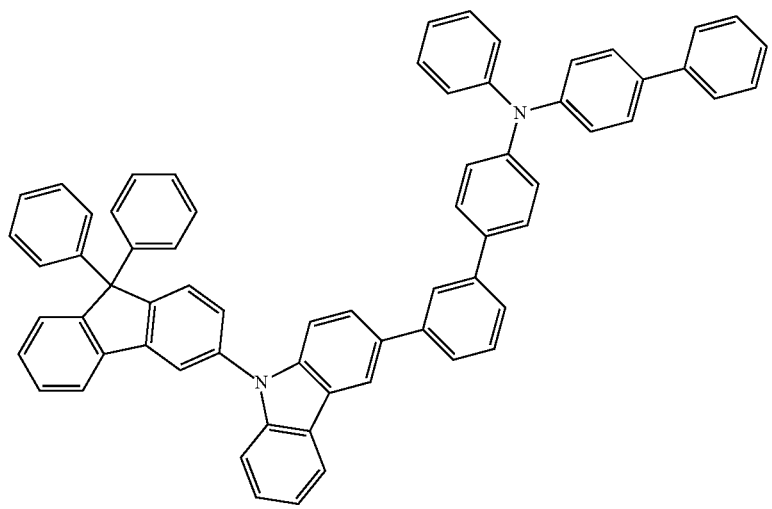
A209
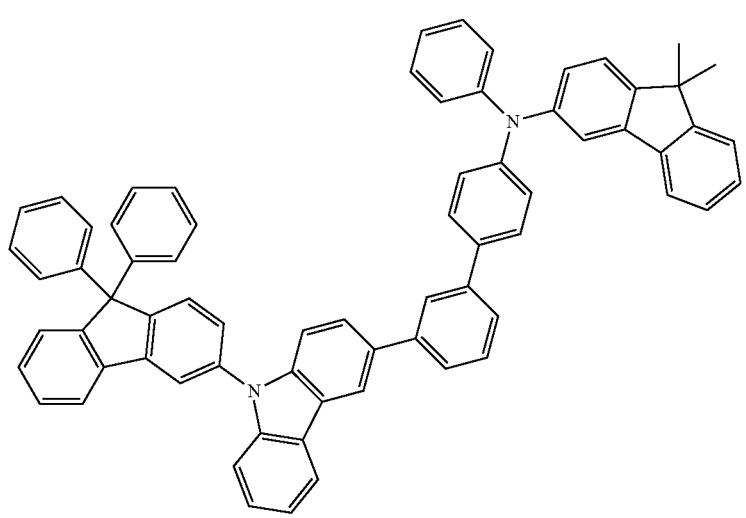
A210
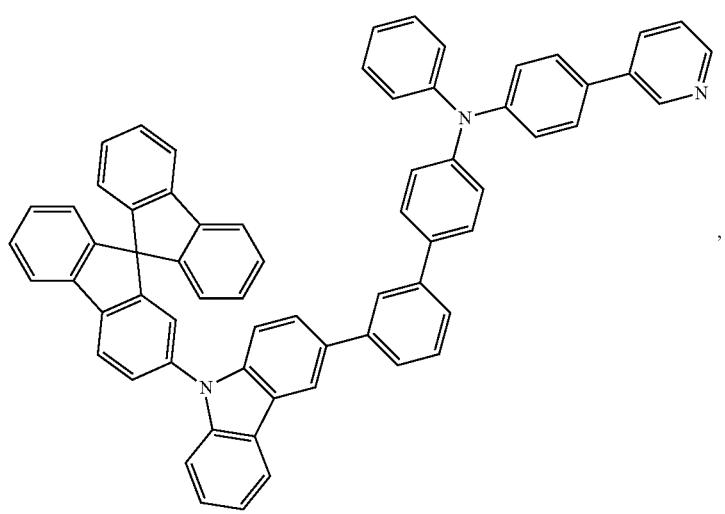
A211

-continued
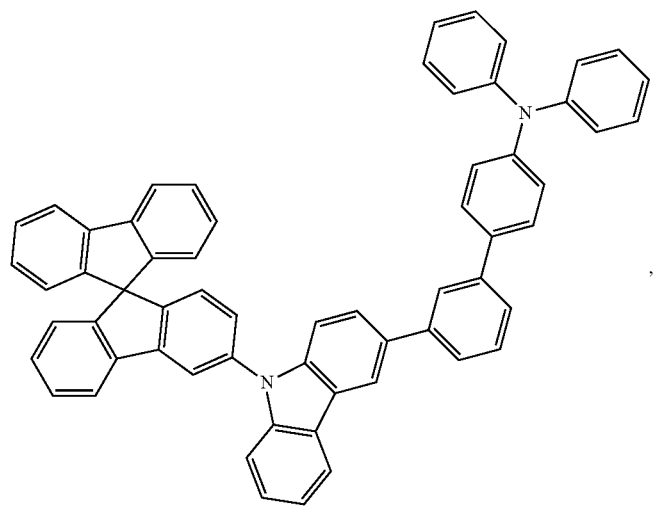
A212
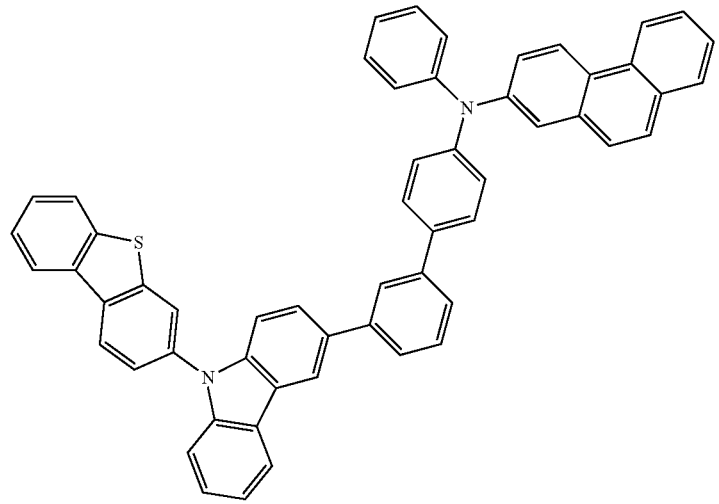
A213
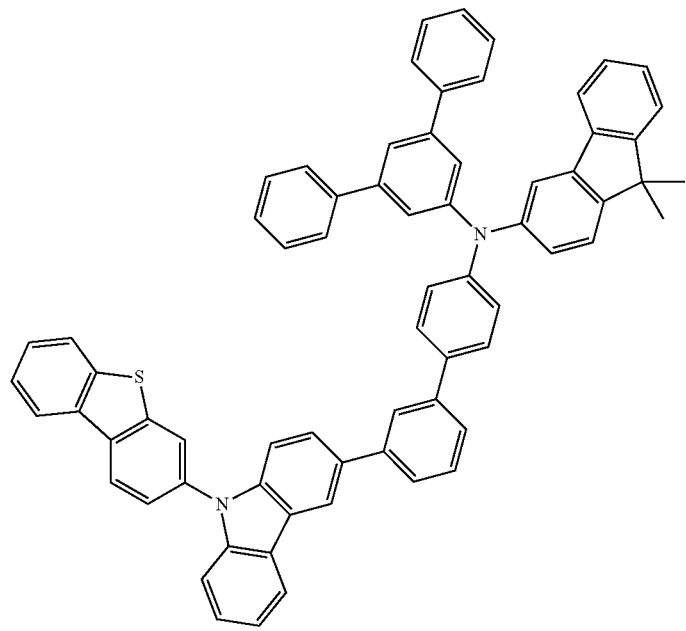
A214

-continued
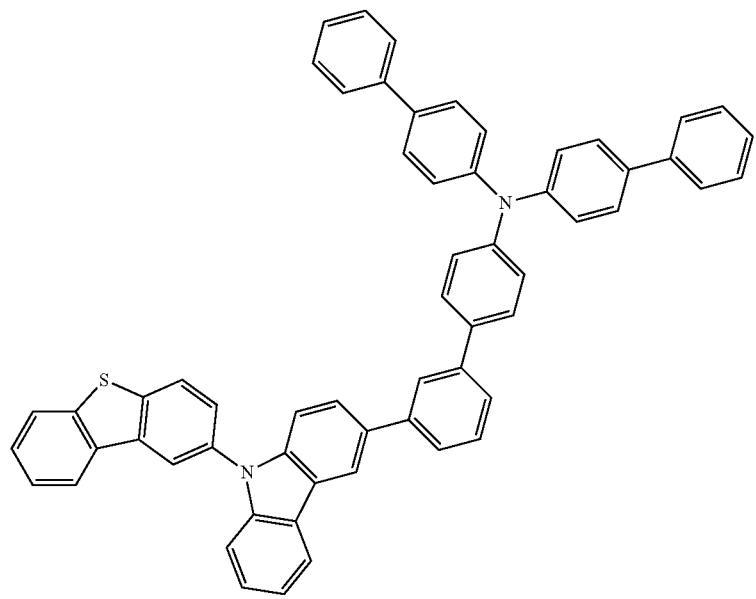
A215
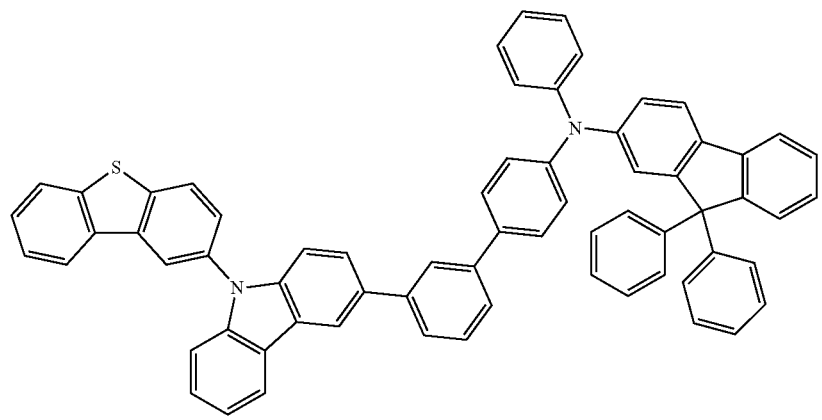
A216
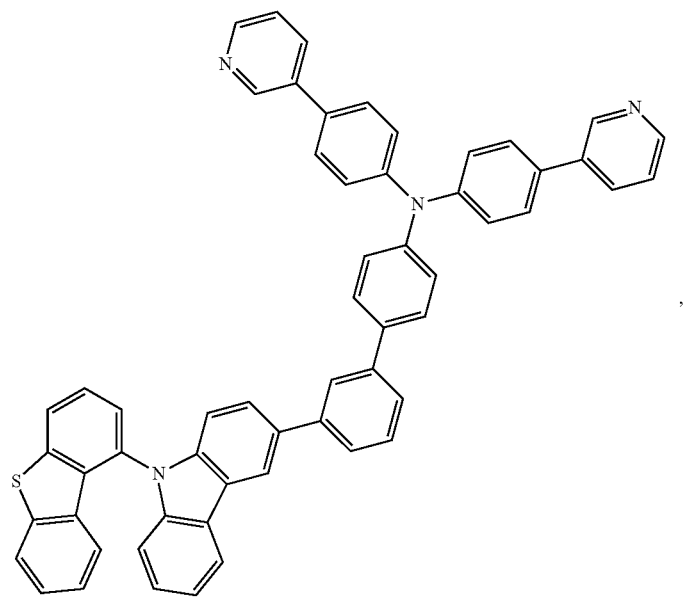
A217

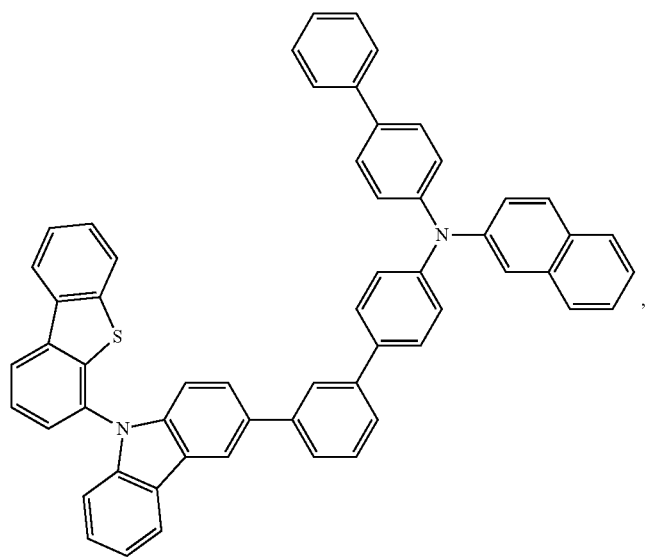
A218
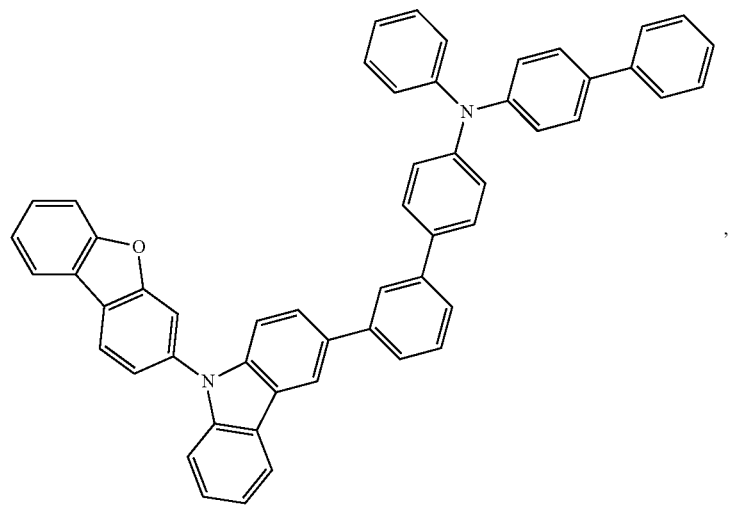
A219
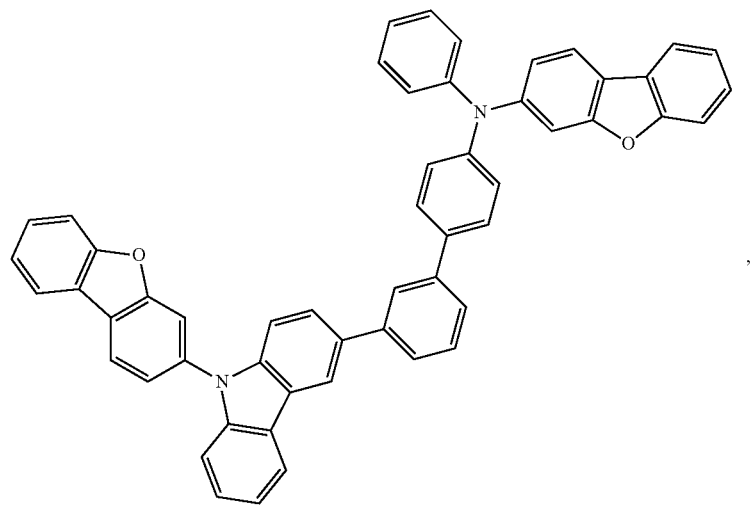
A220

-continued
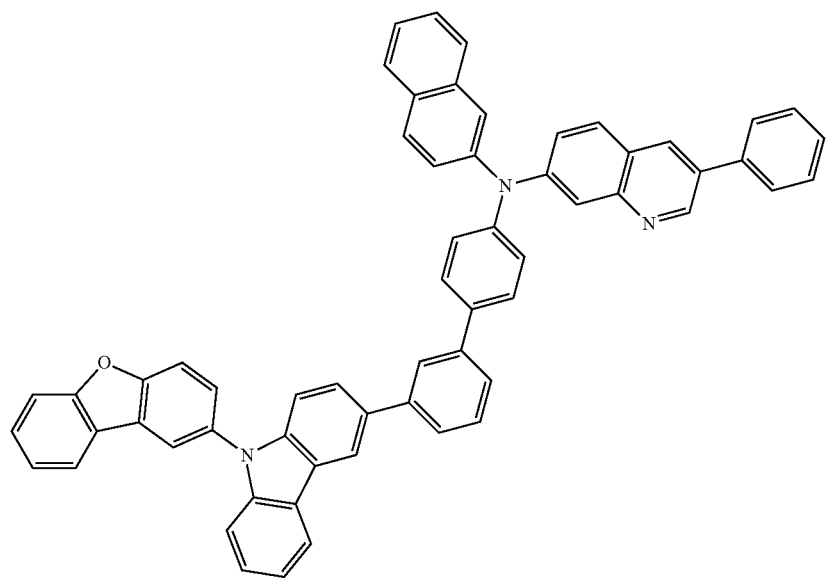
A221
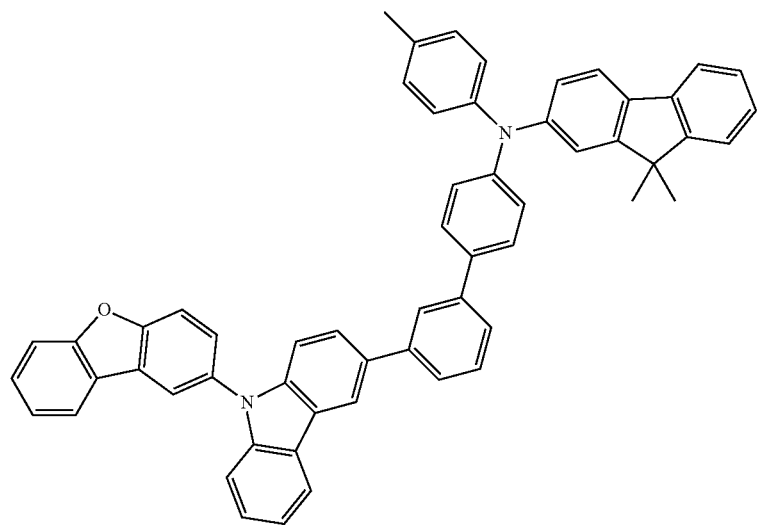
A222
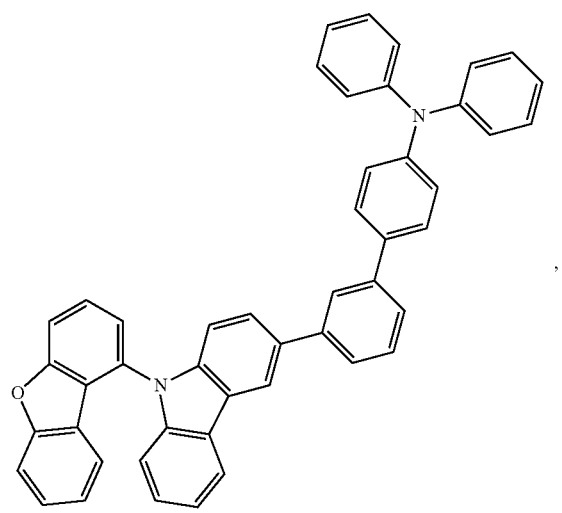
A223

-continued
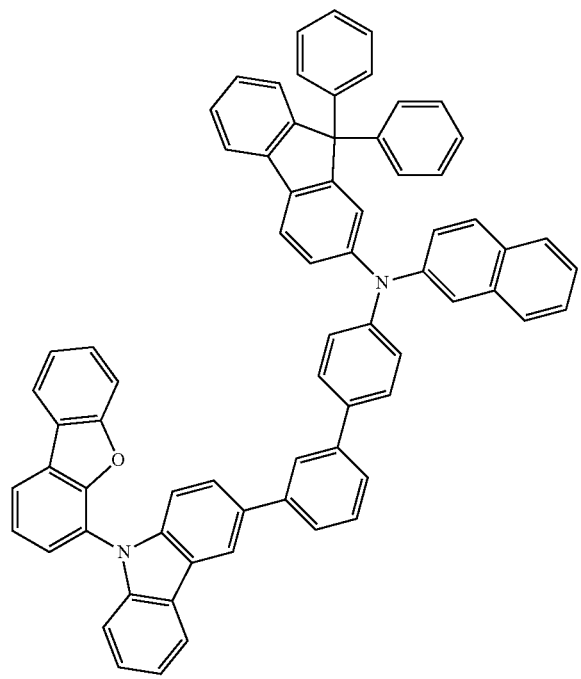
A224
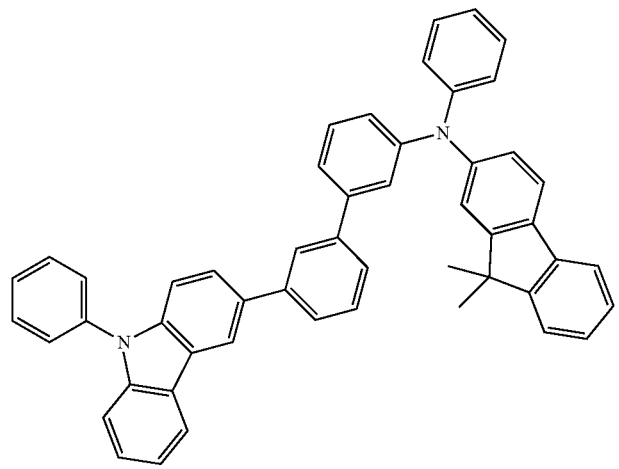
A225
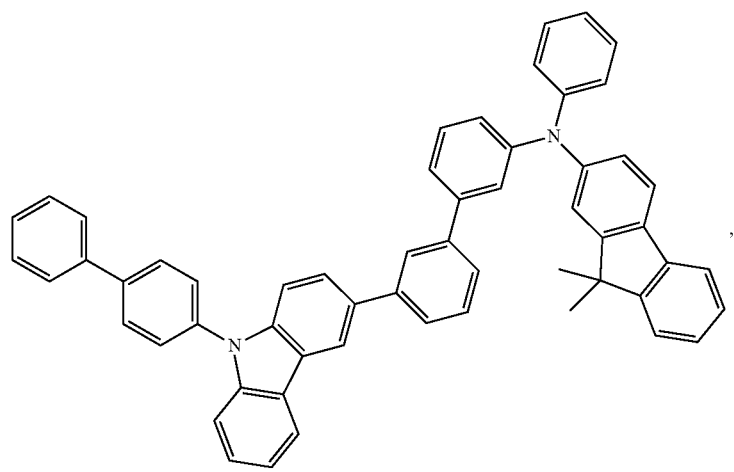
A226

-continued
A227
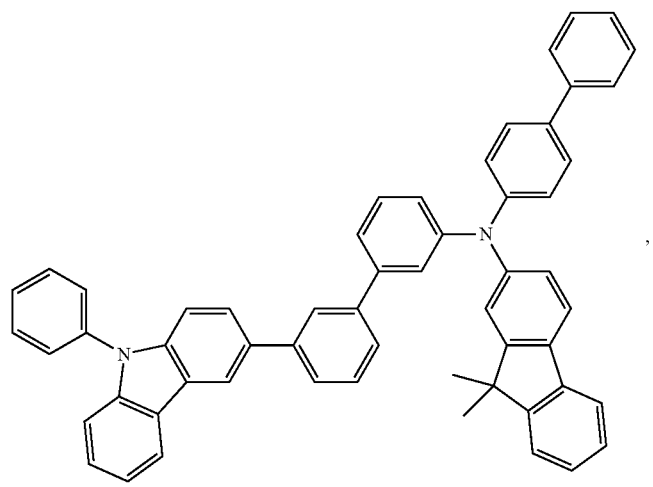
A228
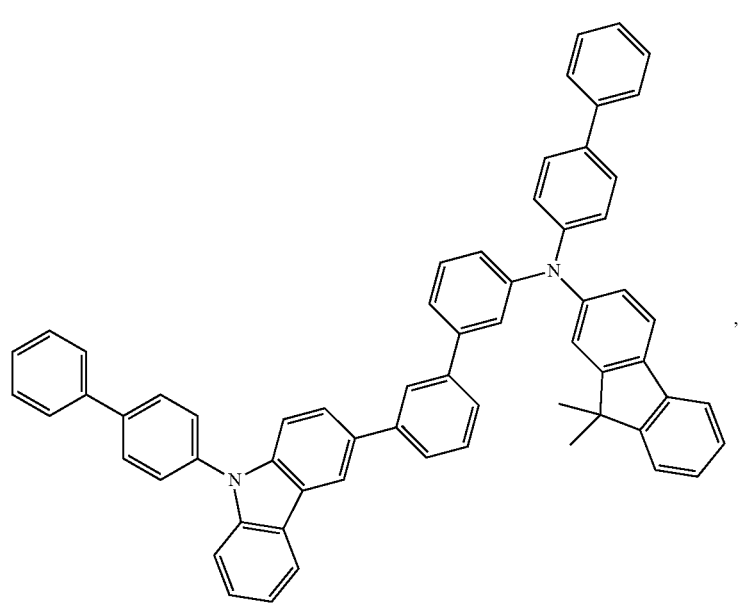
A229
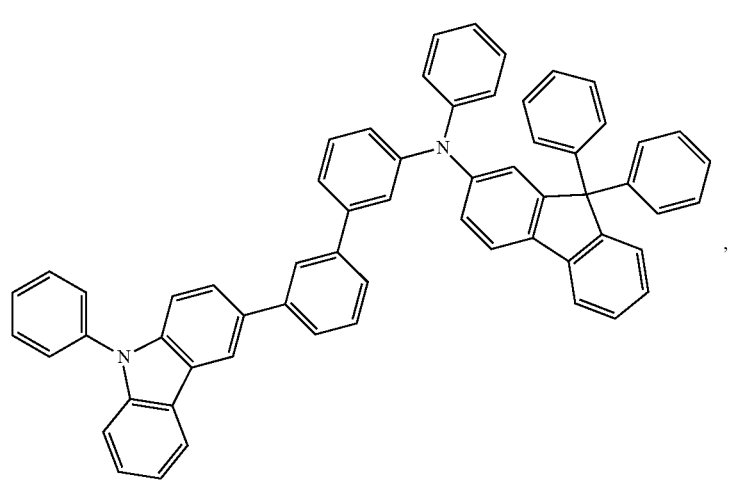

-continued
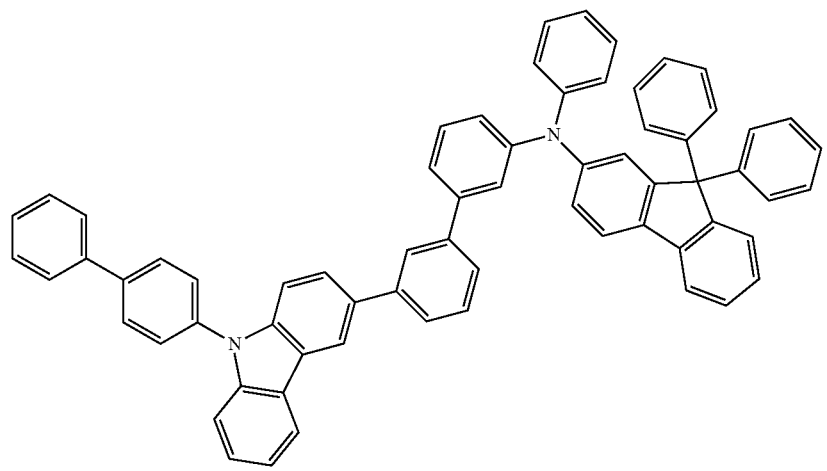
A230
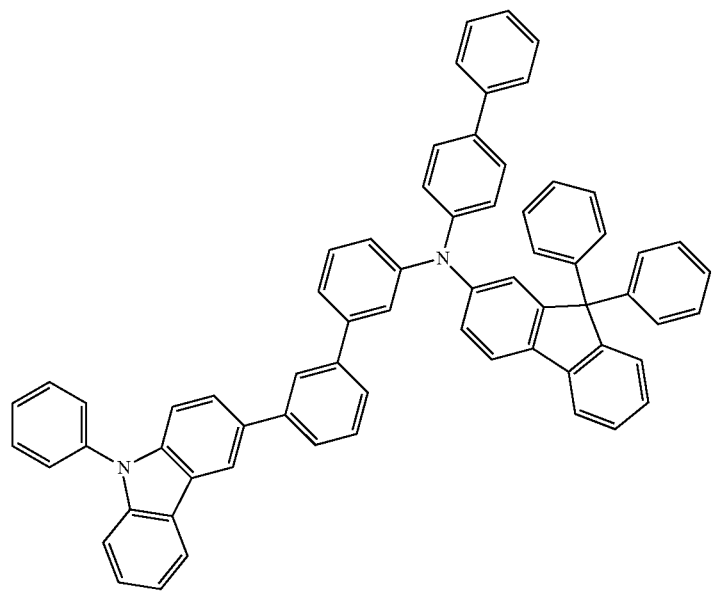
A231
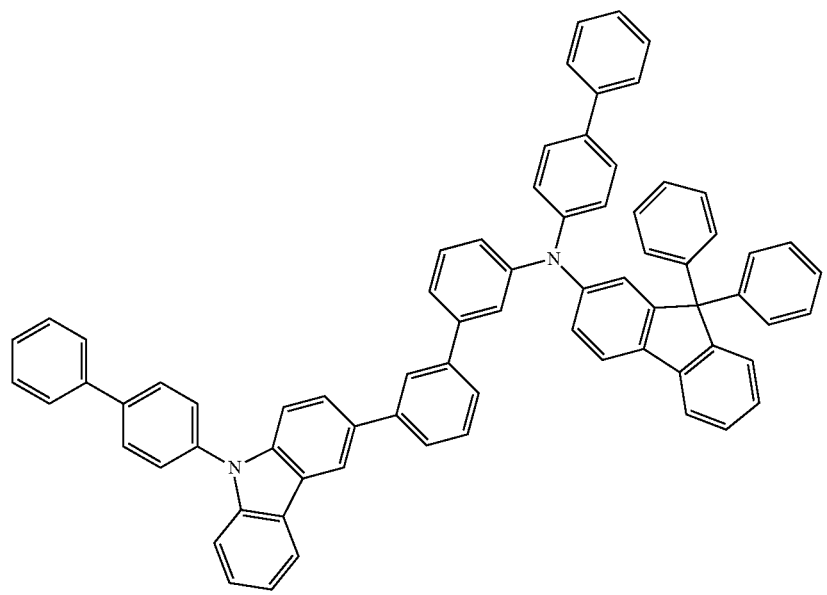
A232

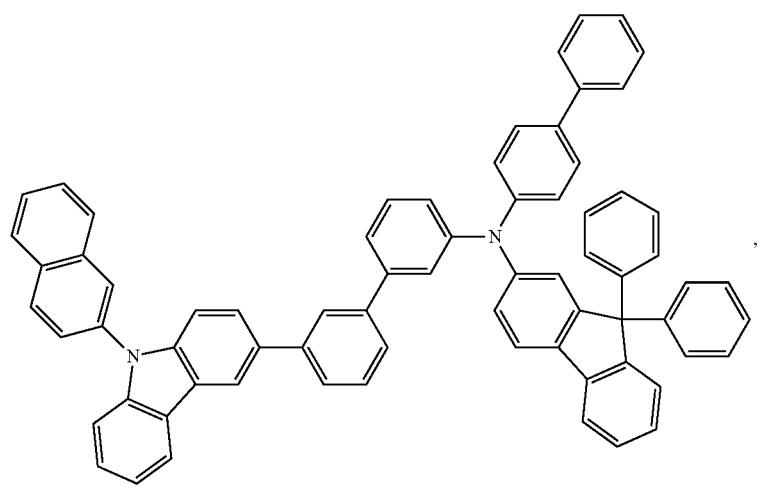
A233
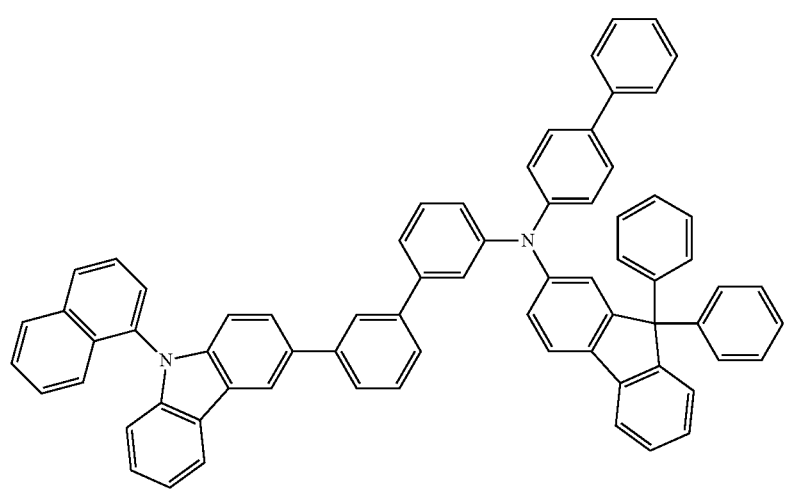
A234
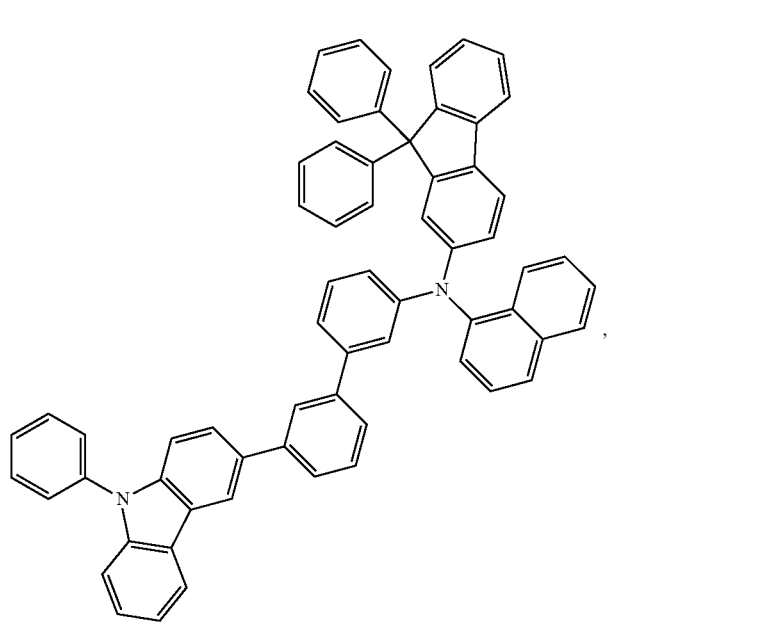
A235

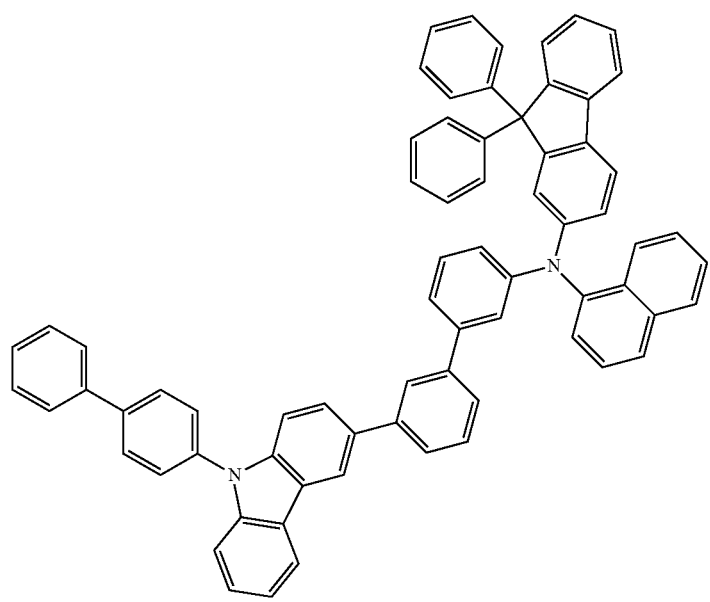
A236
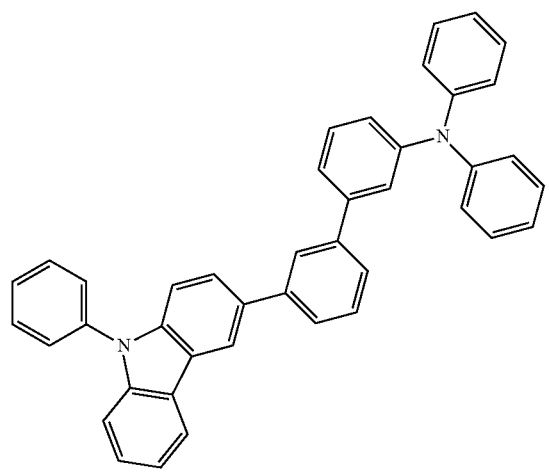
A237
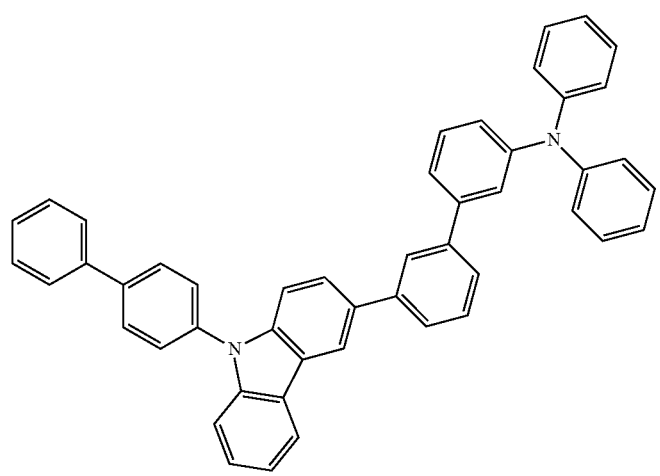
A238

-continued
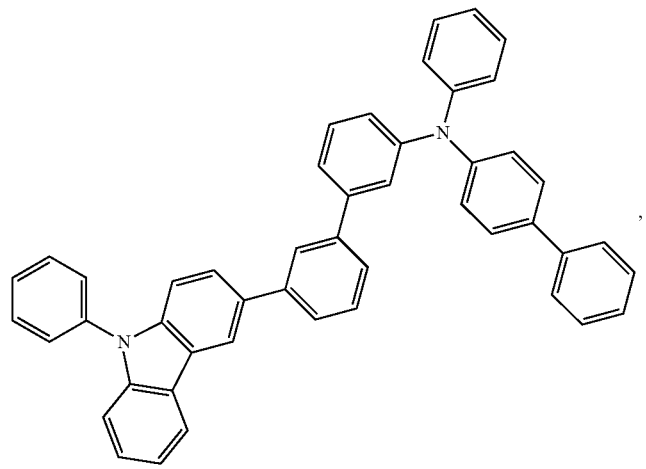
A239
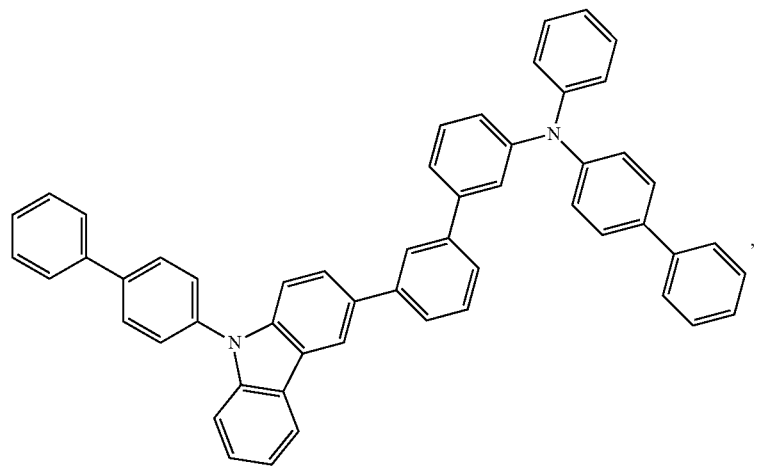
A240
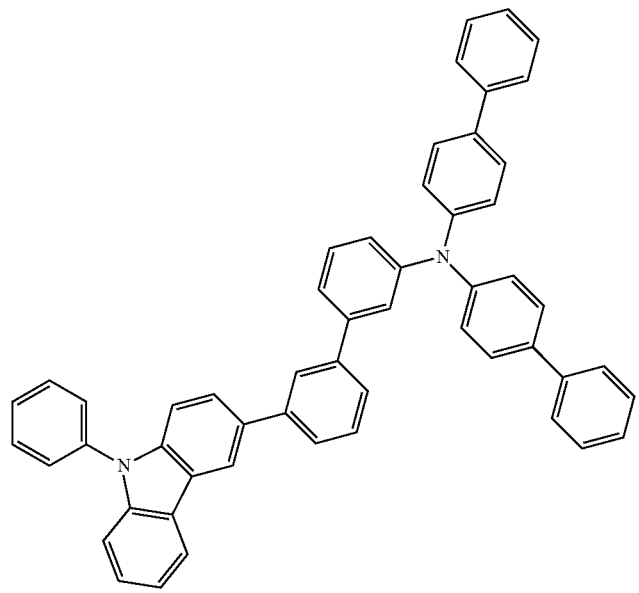
A241

-continued
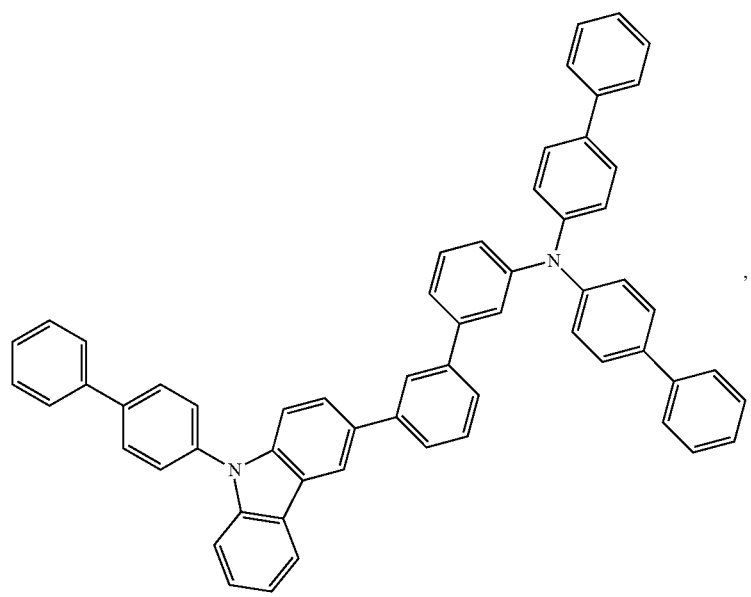
A242
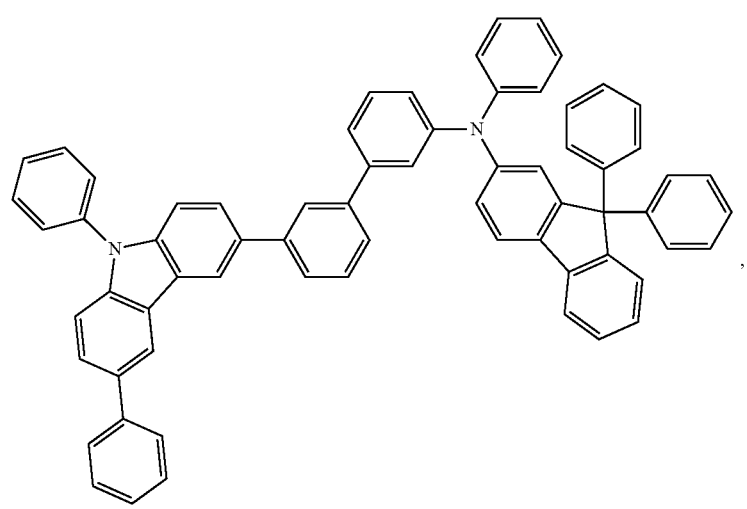
A243

A244
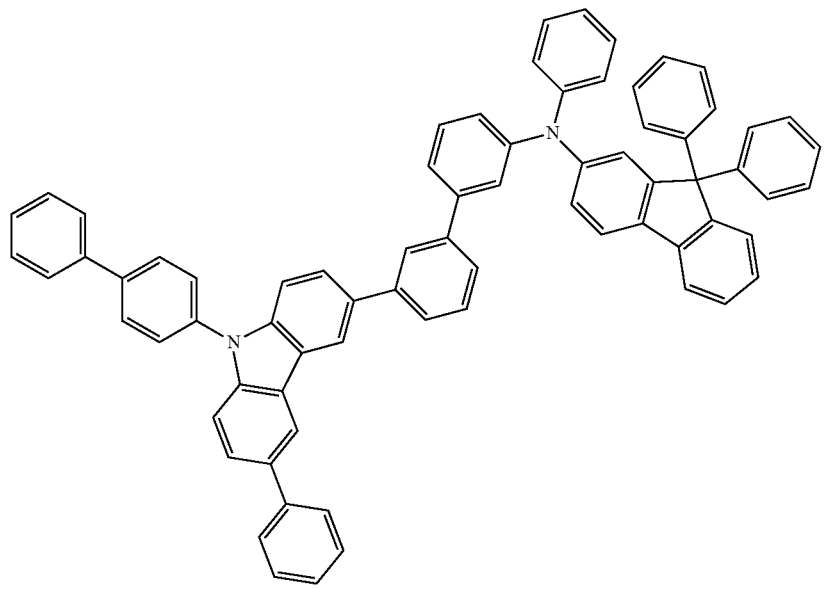
A245
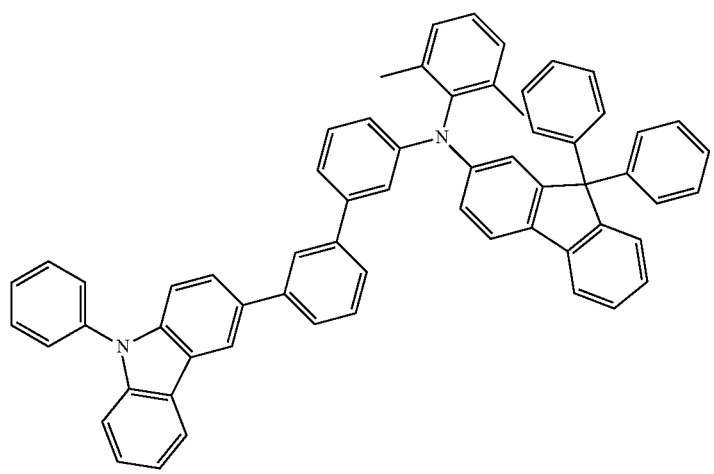
A246
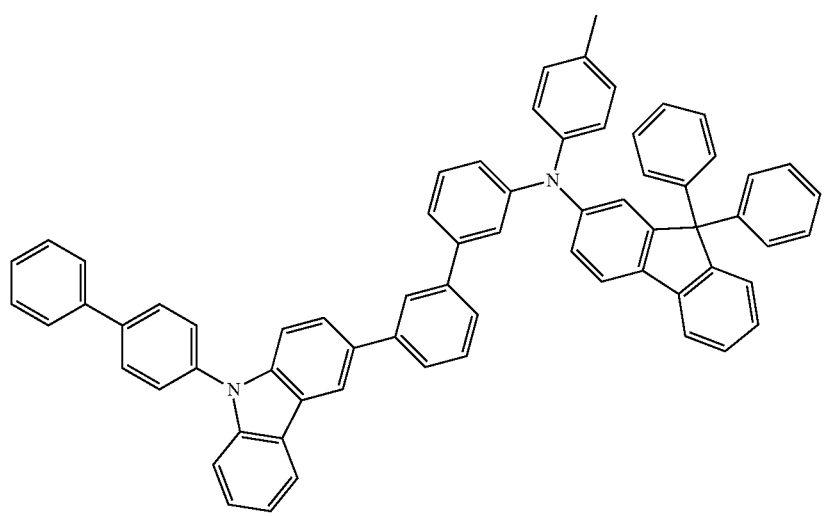

-continued
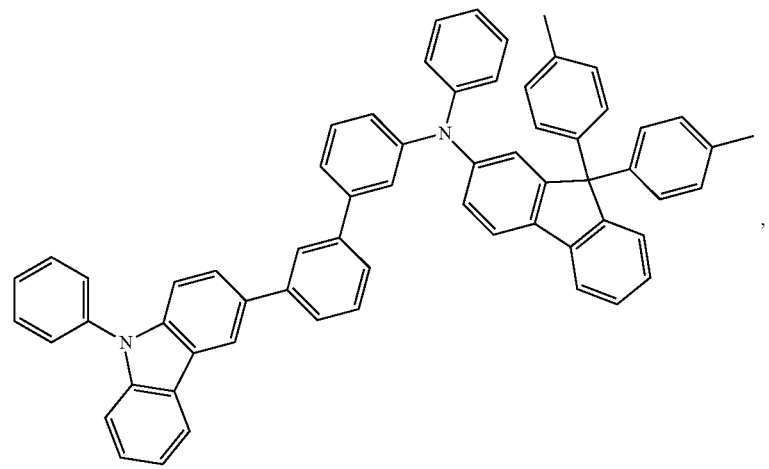
A247
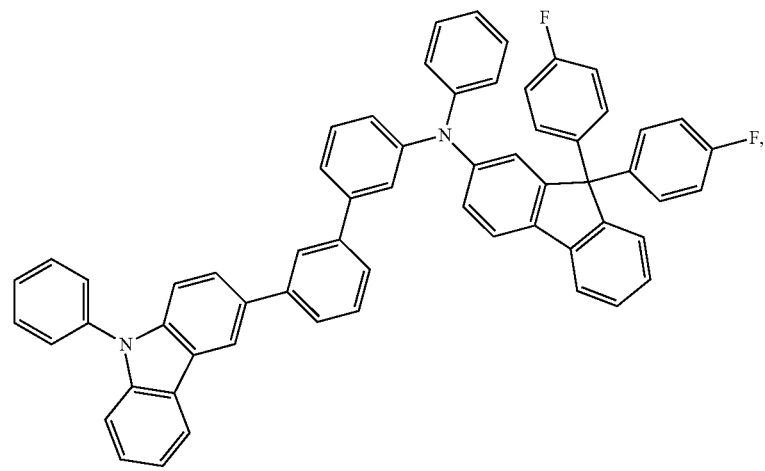
A248
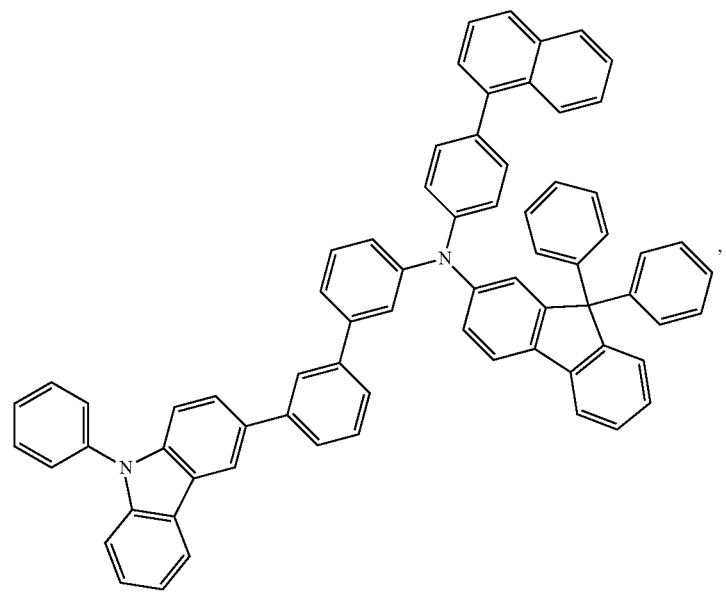
A249

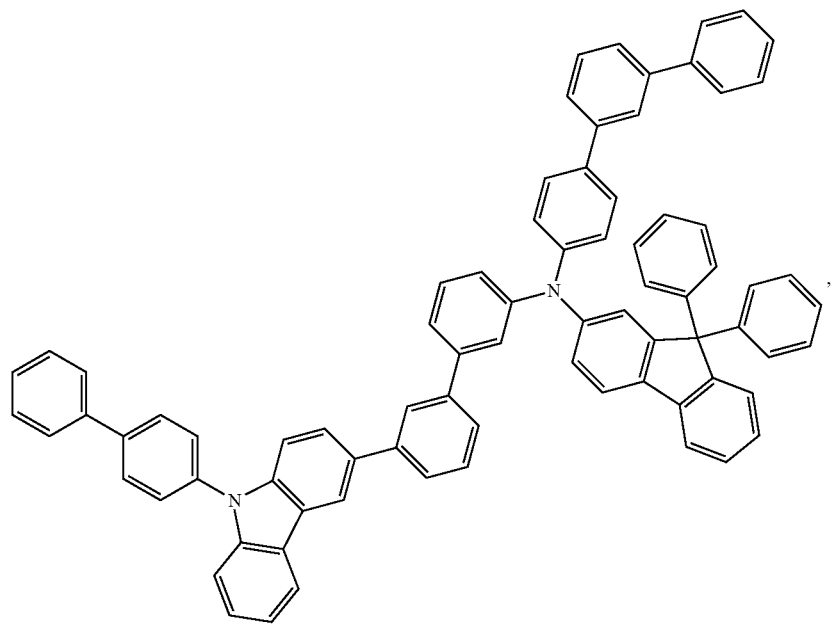
A250
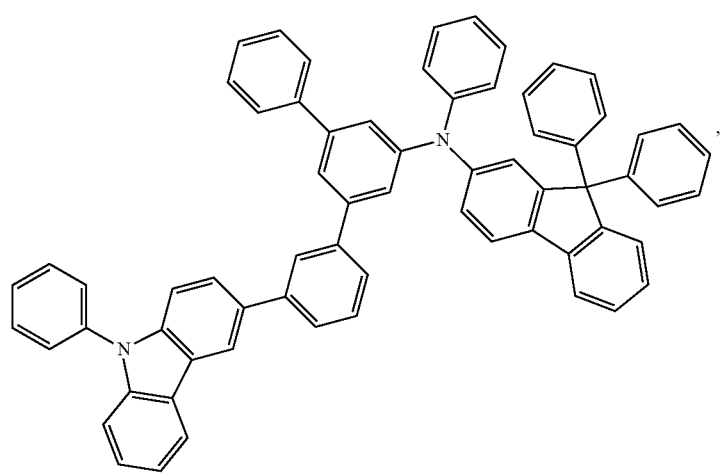
A251

-continued
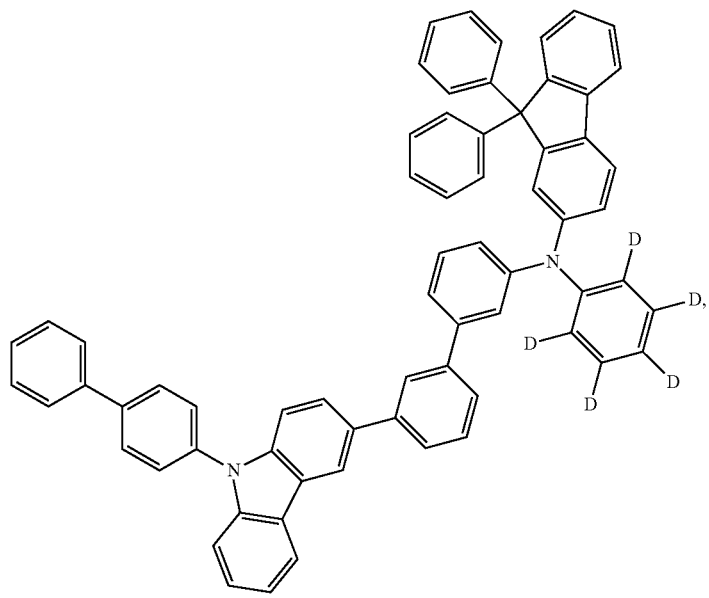
A252
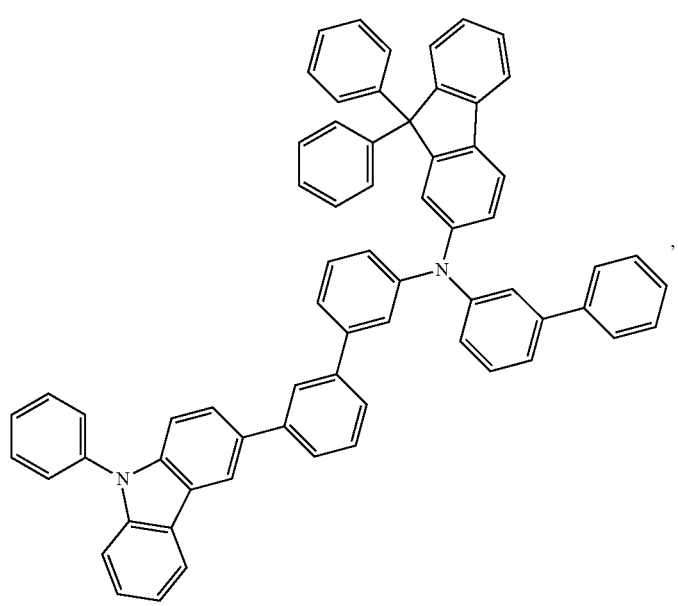
A253
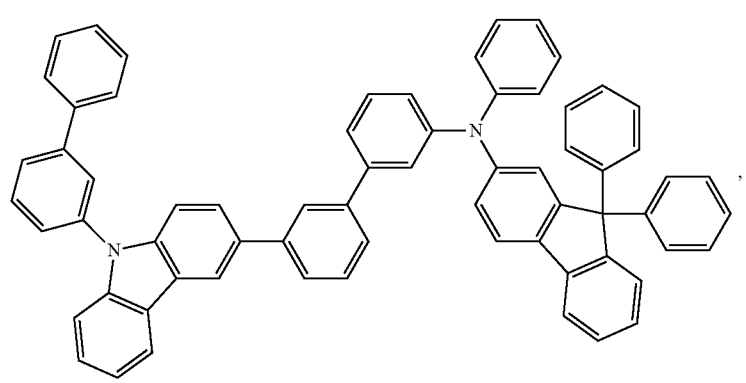
A254

-continued
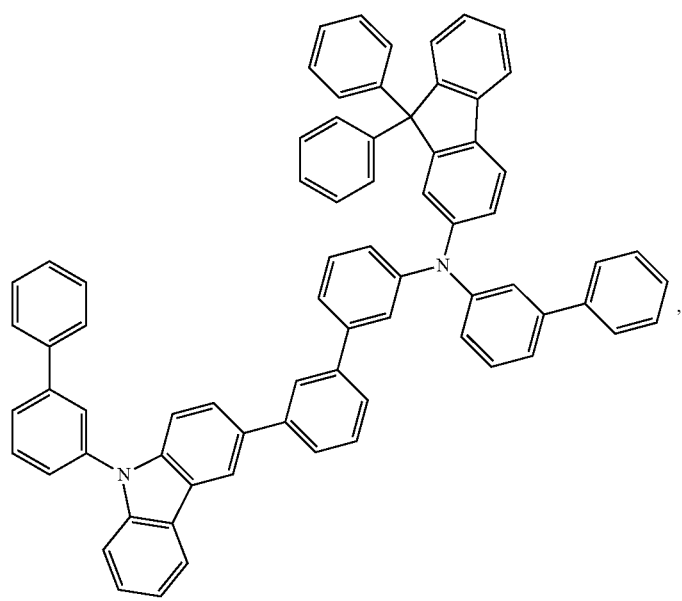
A255
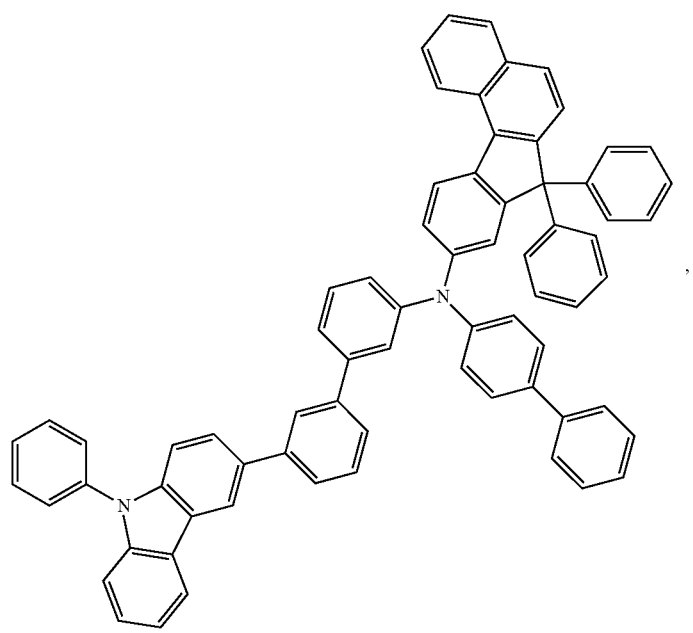
A256

-continued
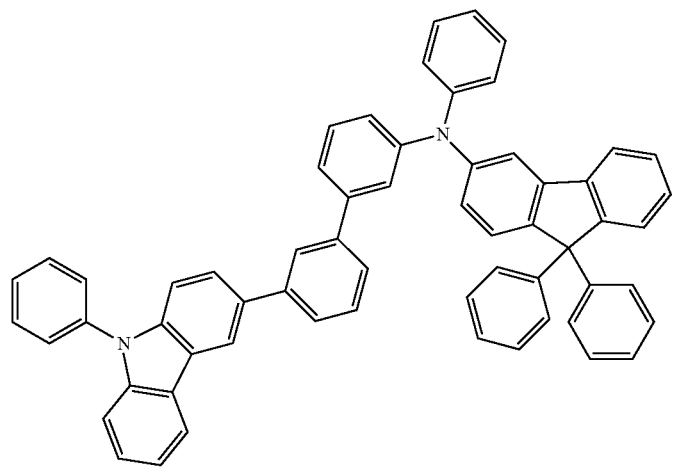
A257
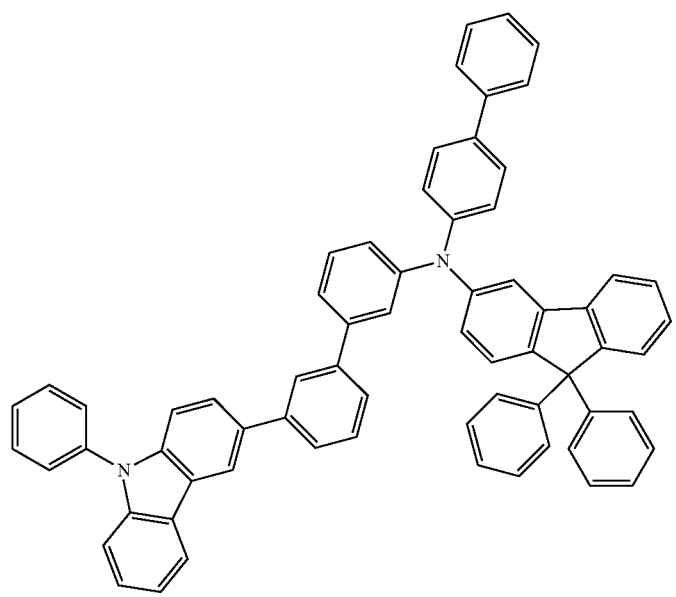
A258
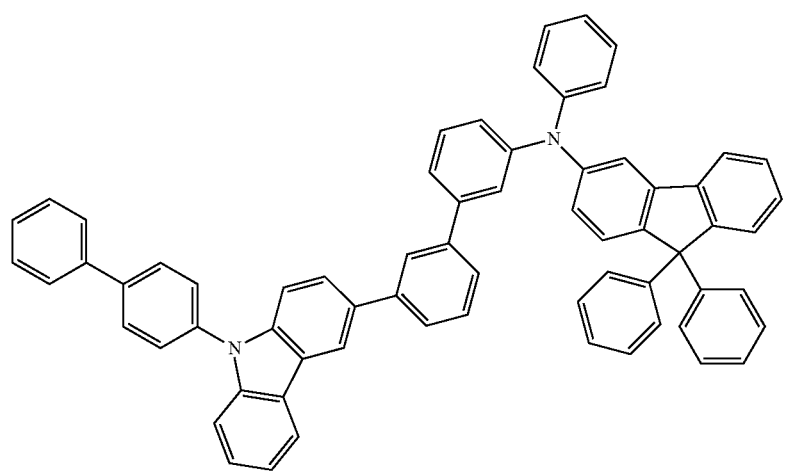
A259

-continued
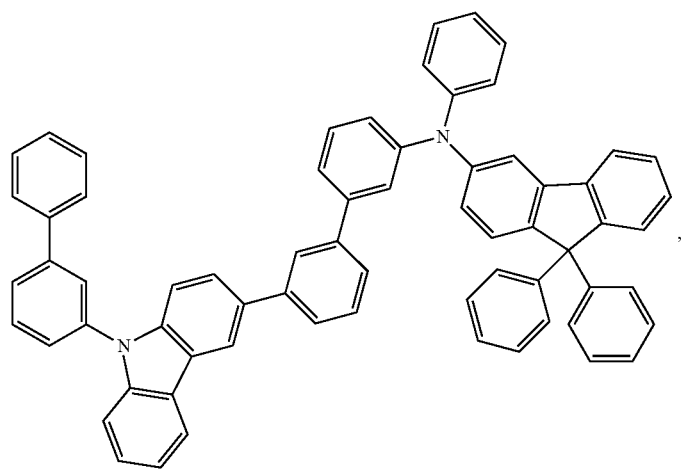
A260
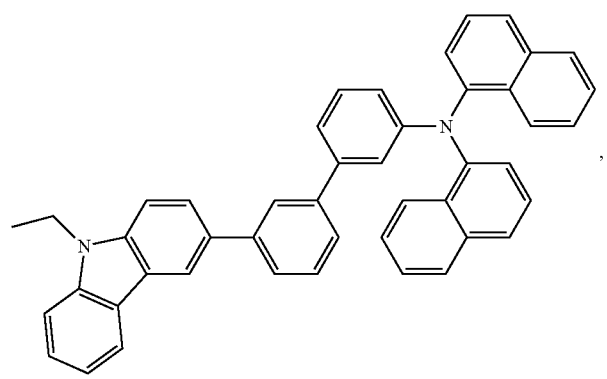
A261
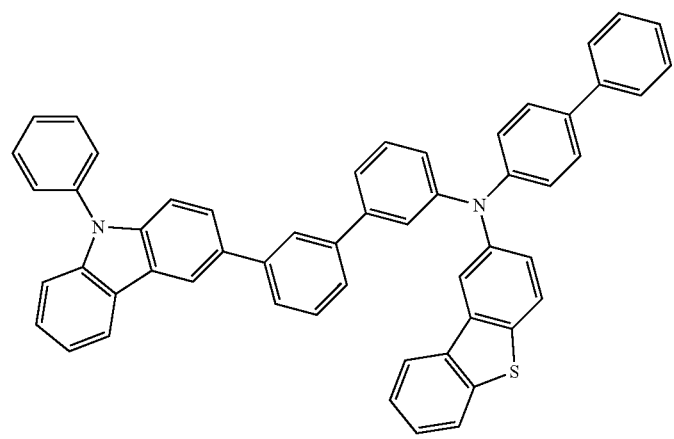
A262

-continued
A263
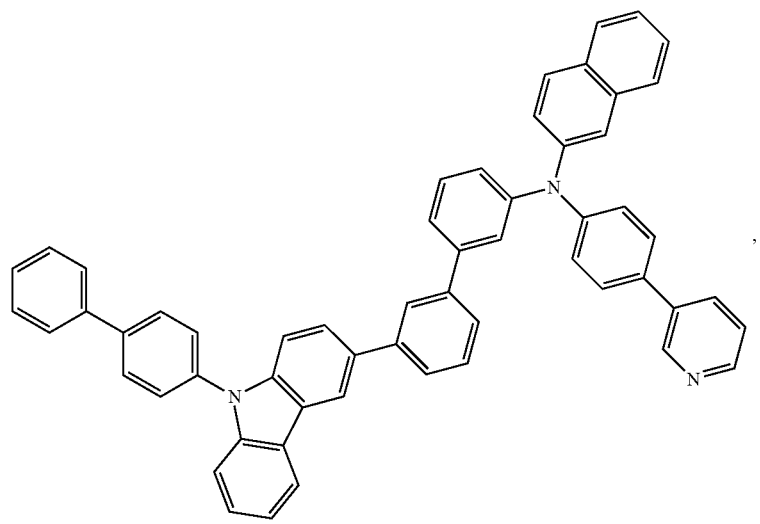
A264
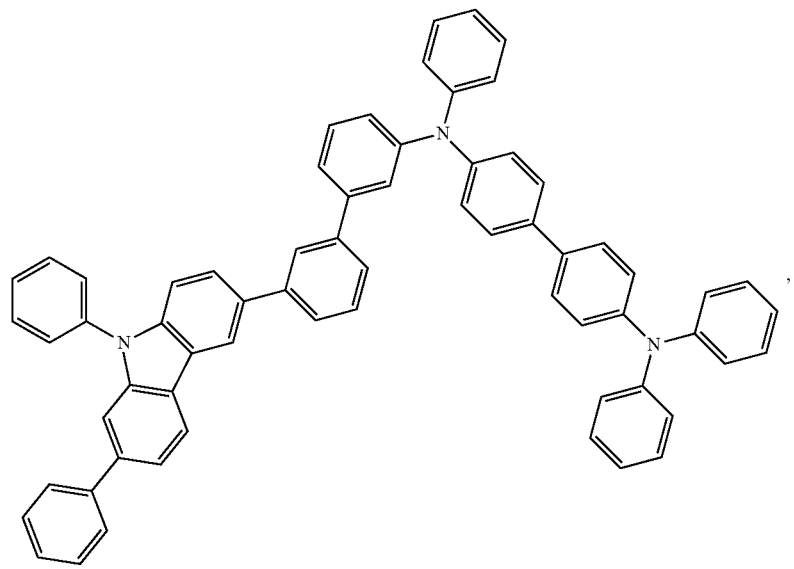
A265
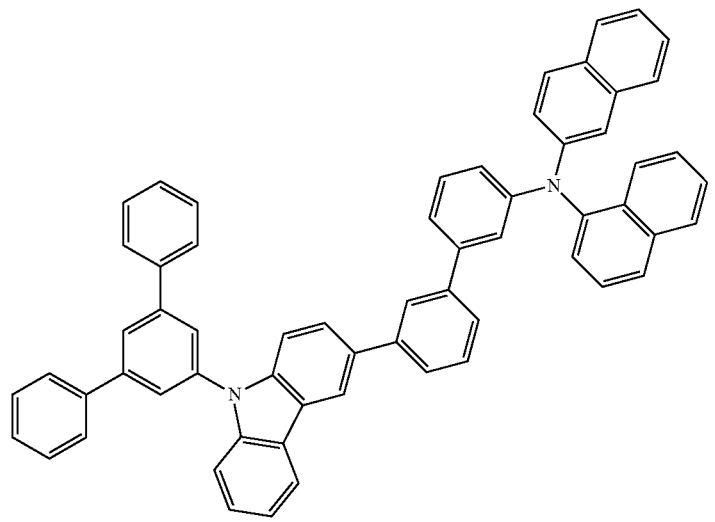

A266
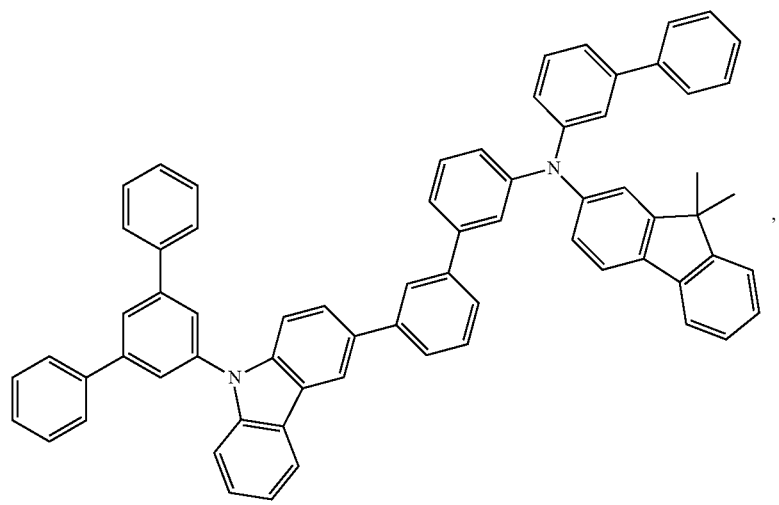
A267
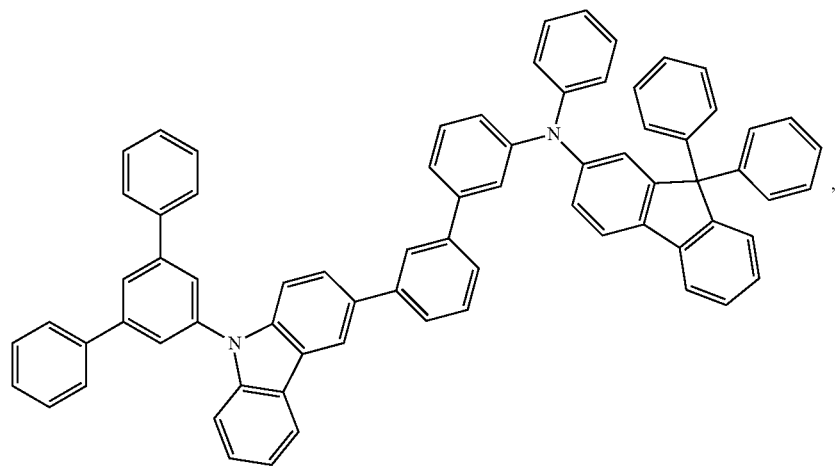
A268
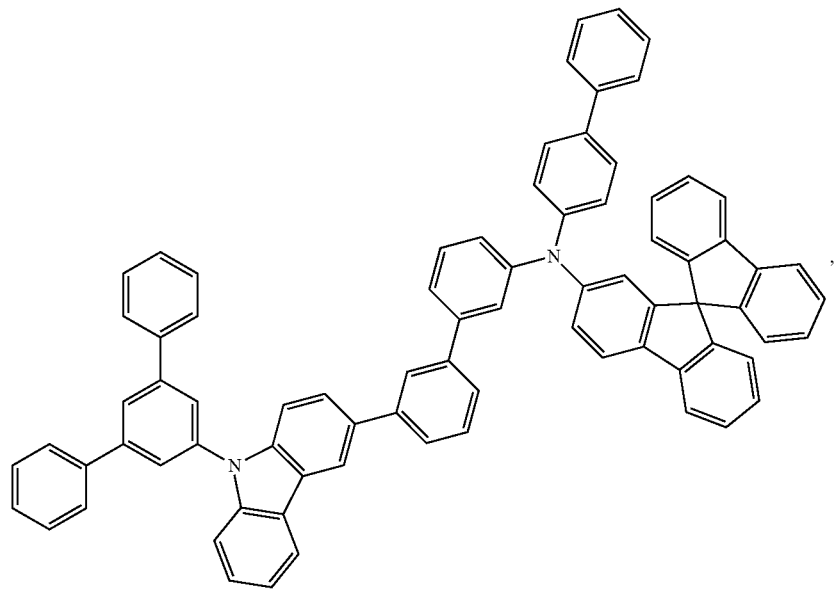

-continued
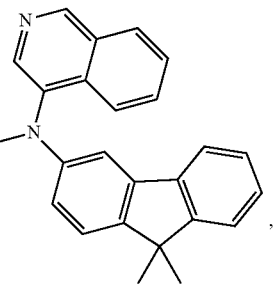
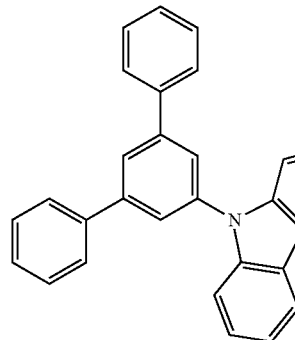
A269
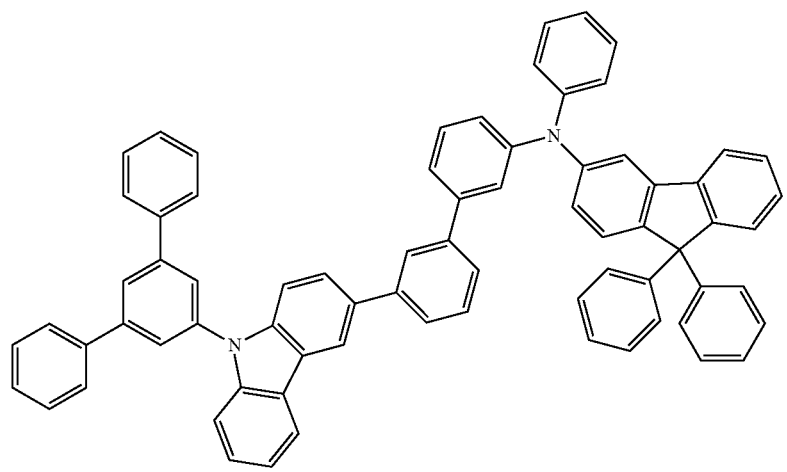
A270
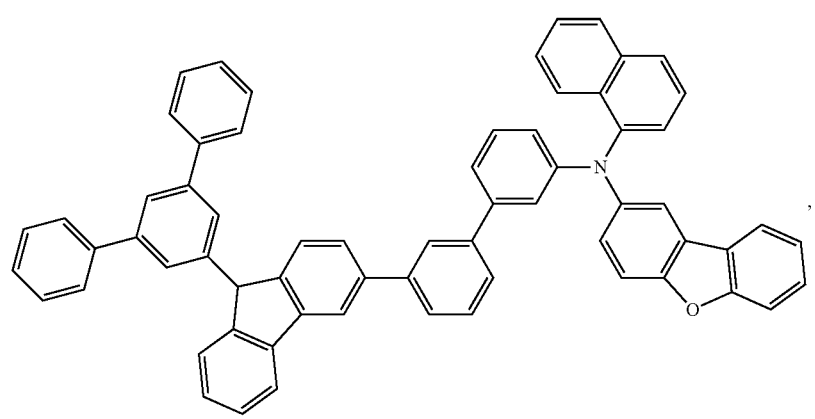
A271

A272
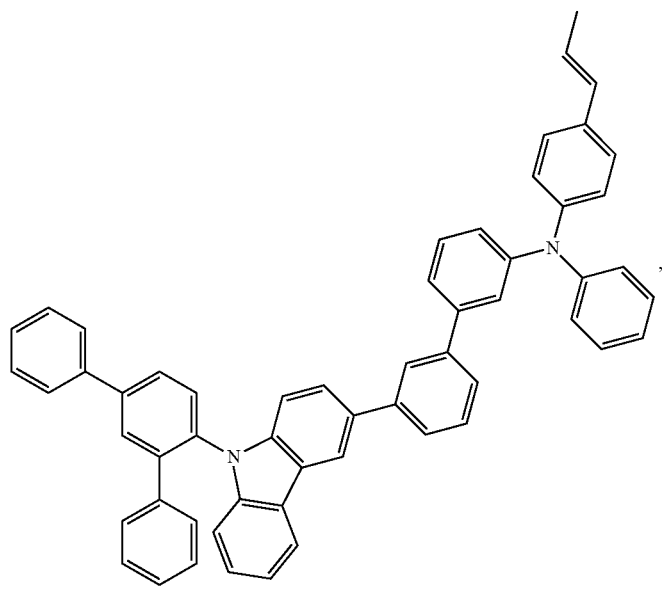
A273
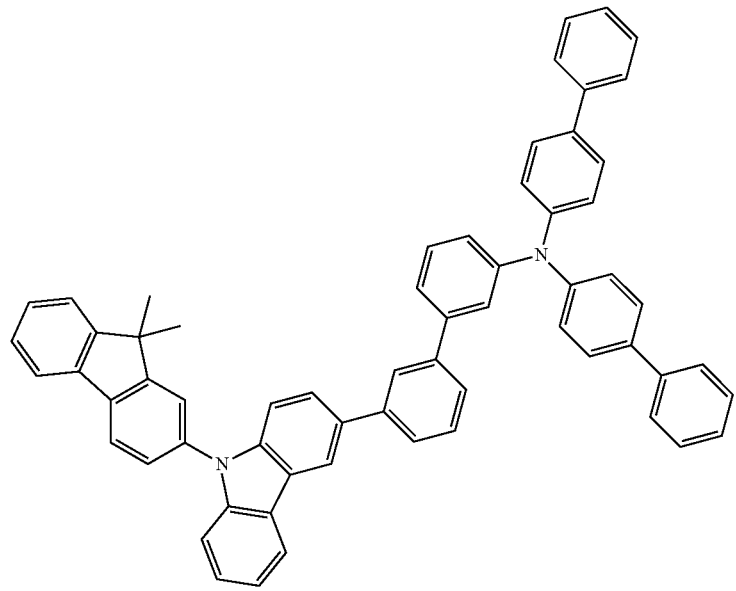
A274
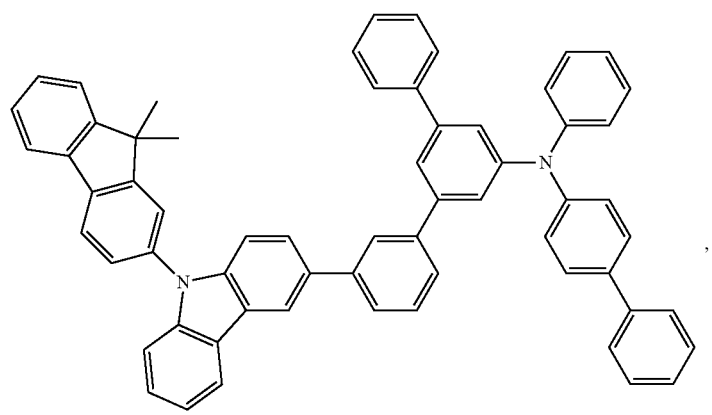

-continued
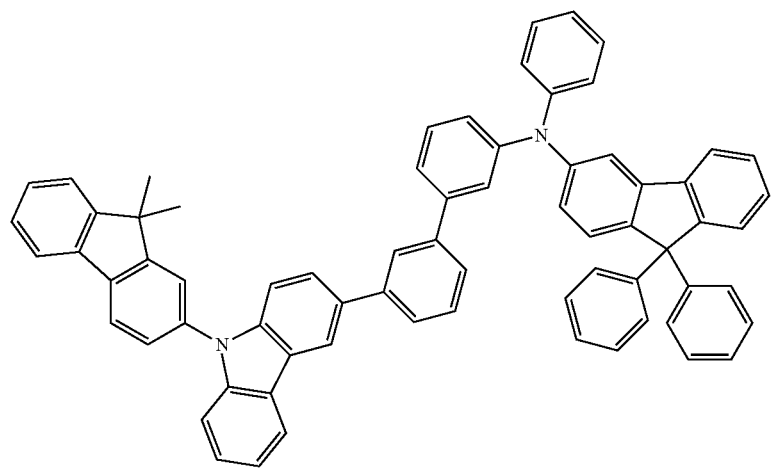
A275
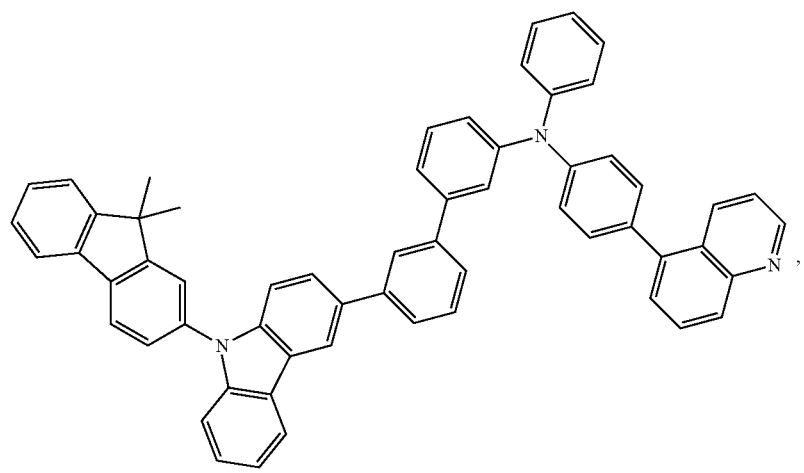
A276
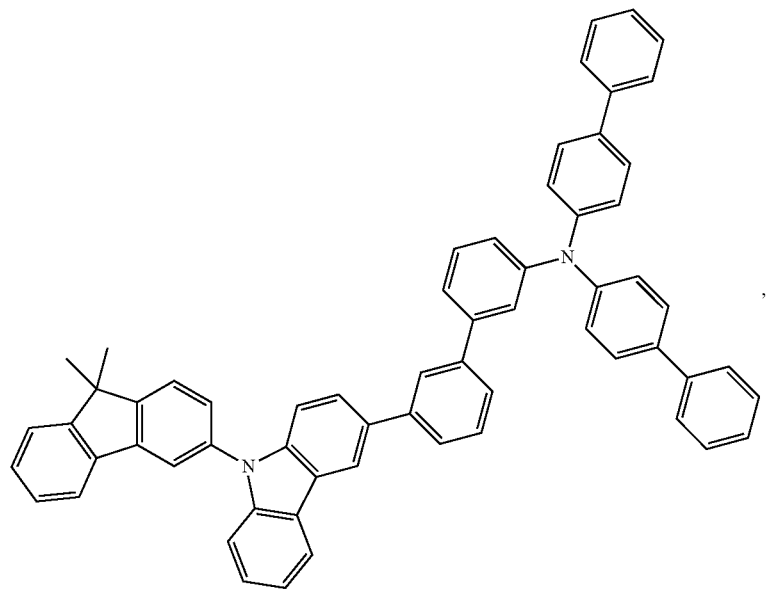
A277

-continued
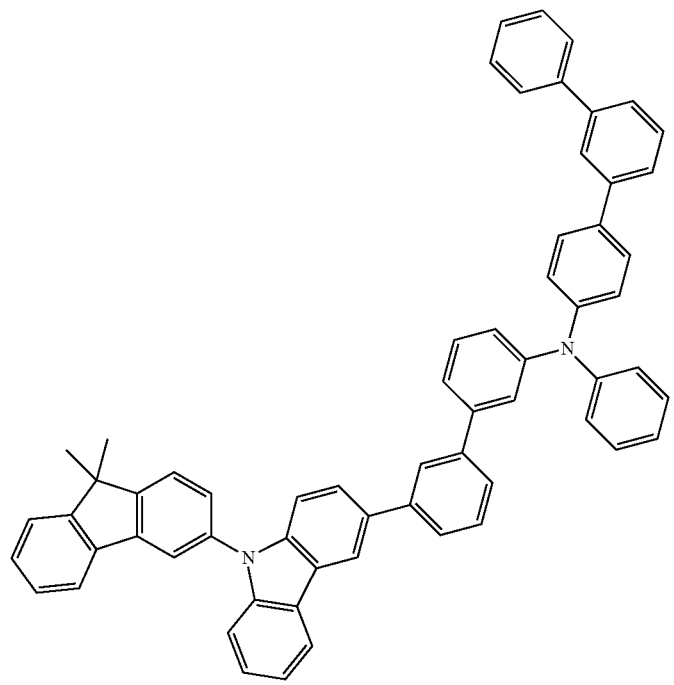
A278
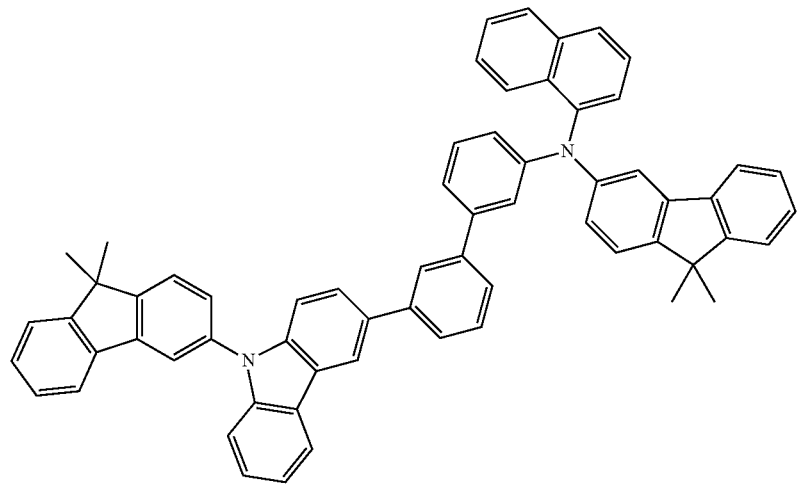
A279
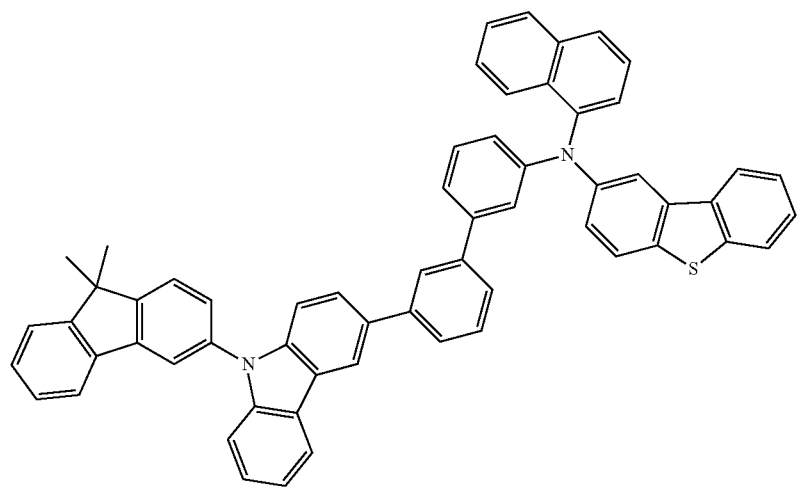
A280

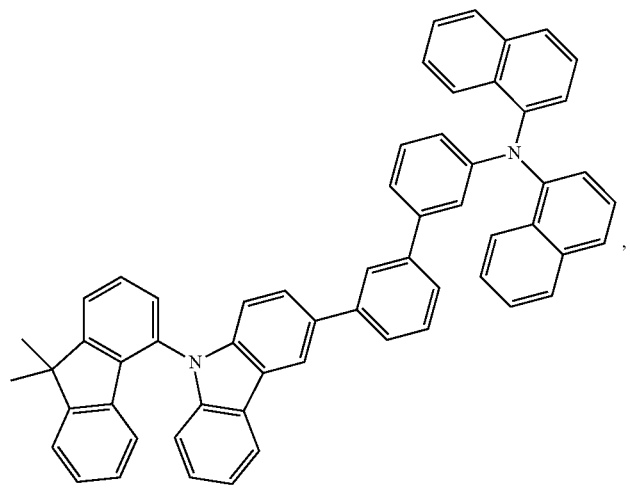 A281
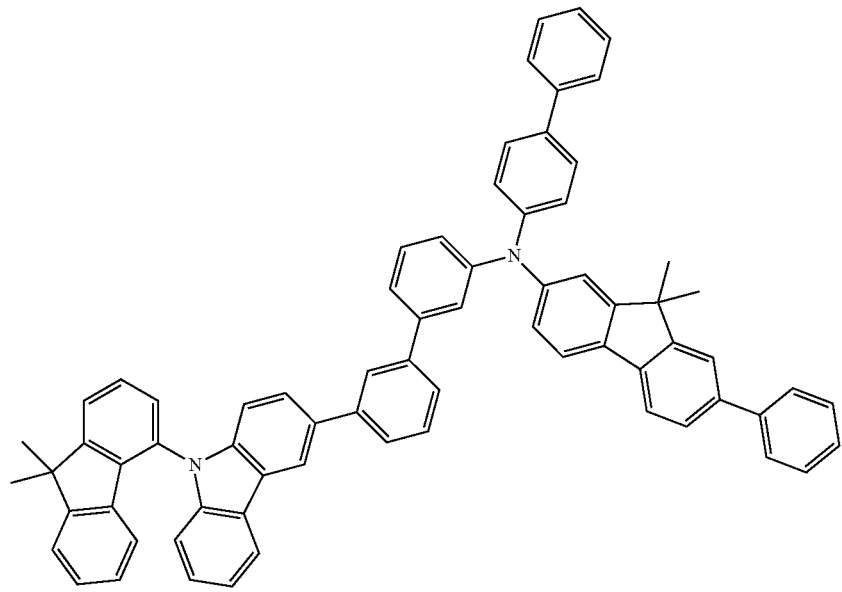 A282
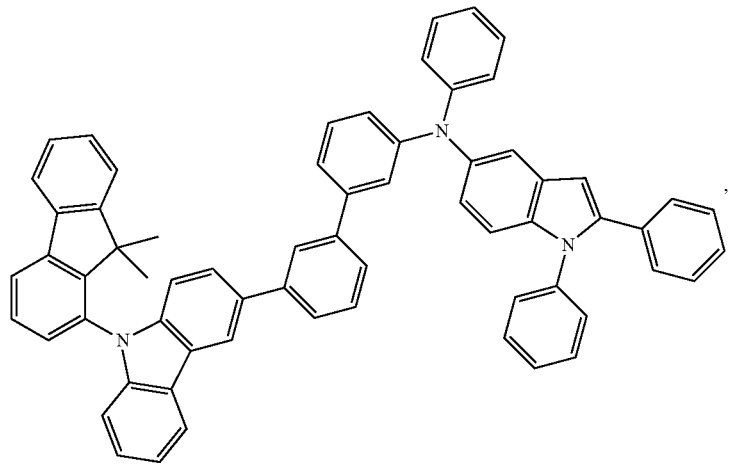 A283

-continued
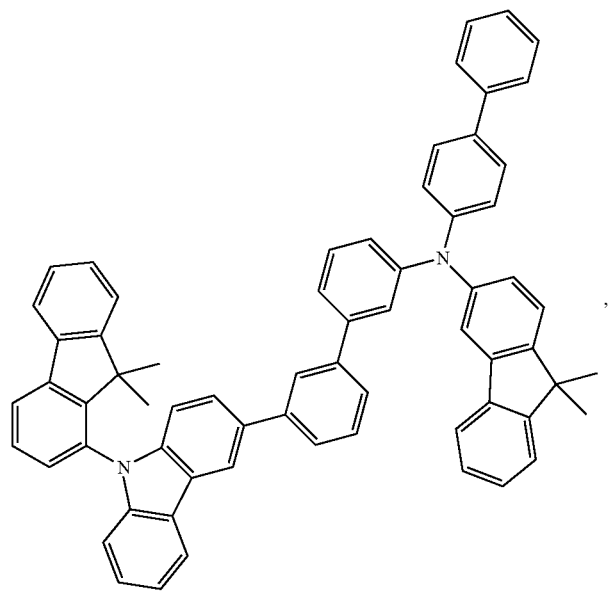
A284
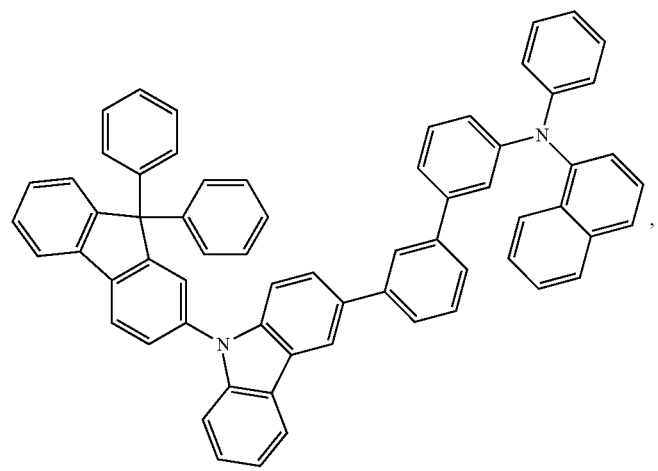
A285
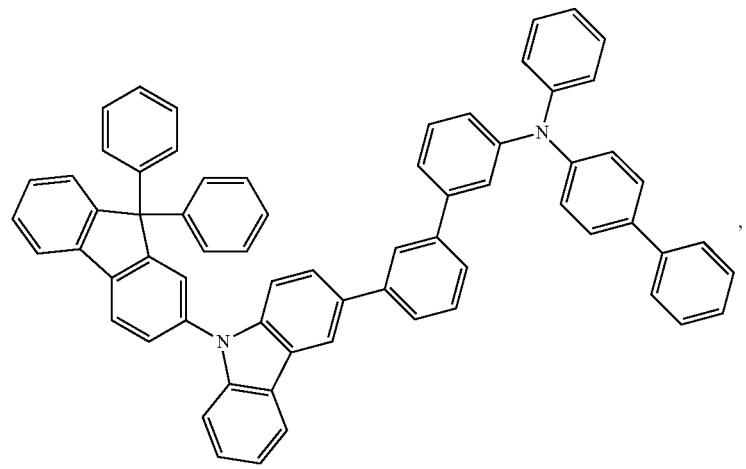
A286

-continued
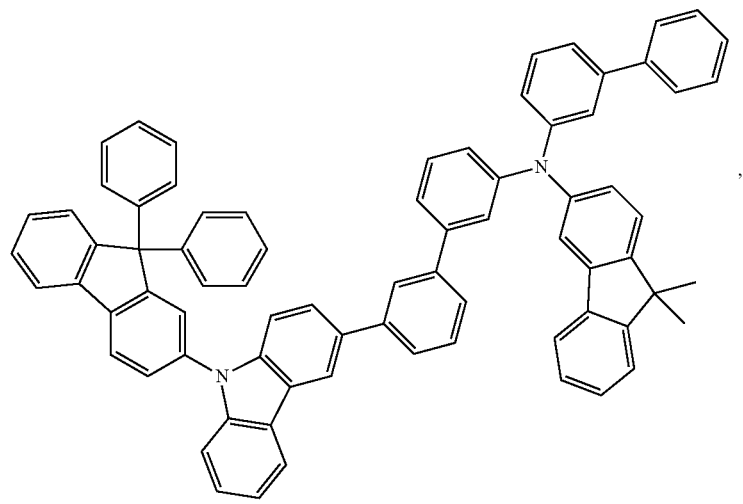
A287
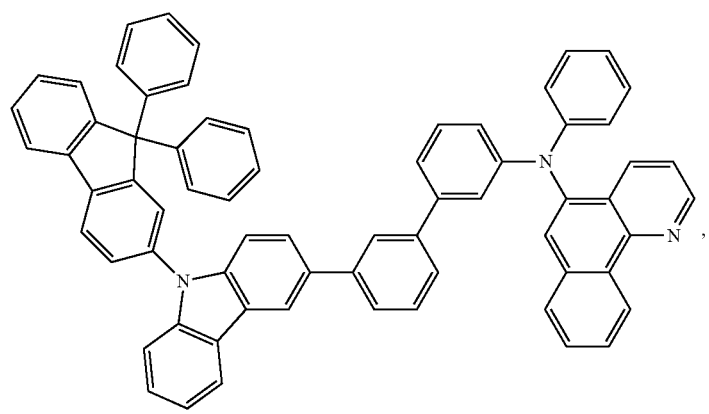
A288
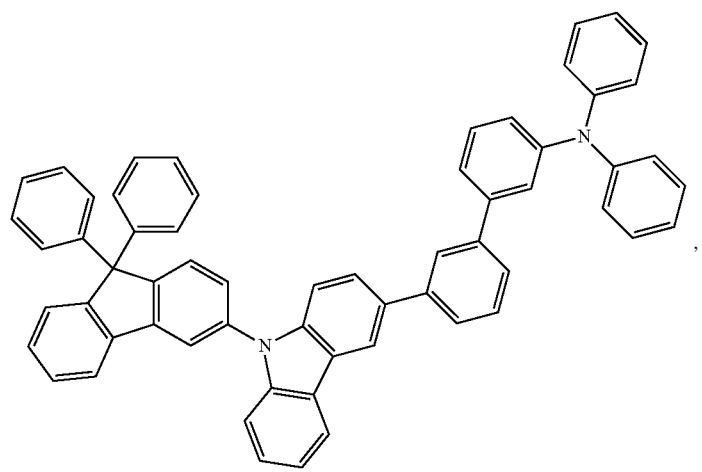
A289

-continued
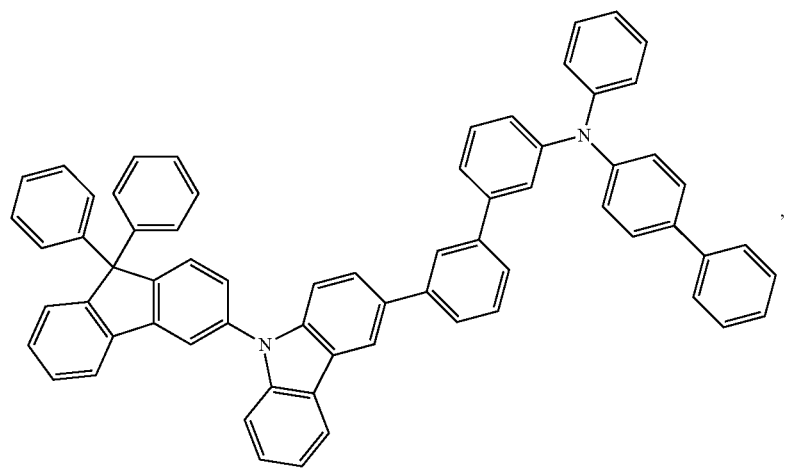
A290
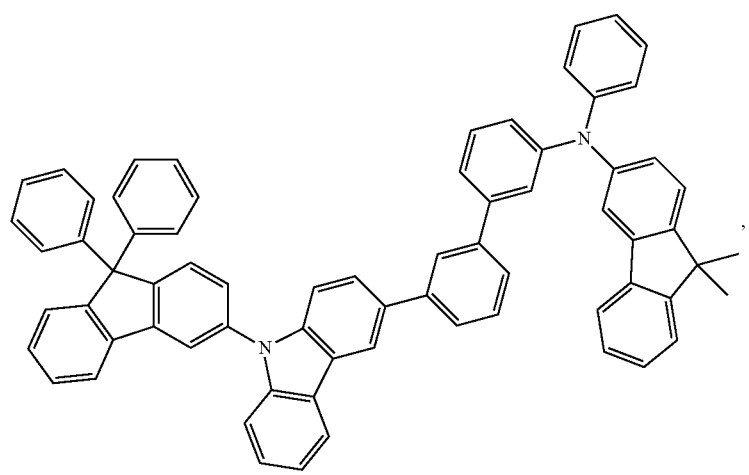
A291
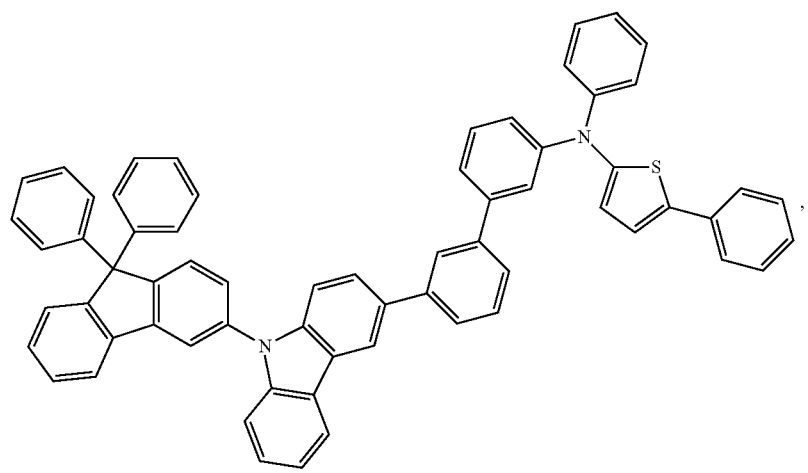
A292

A293
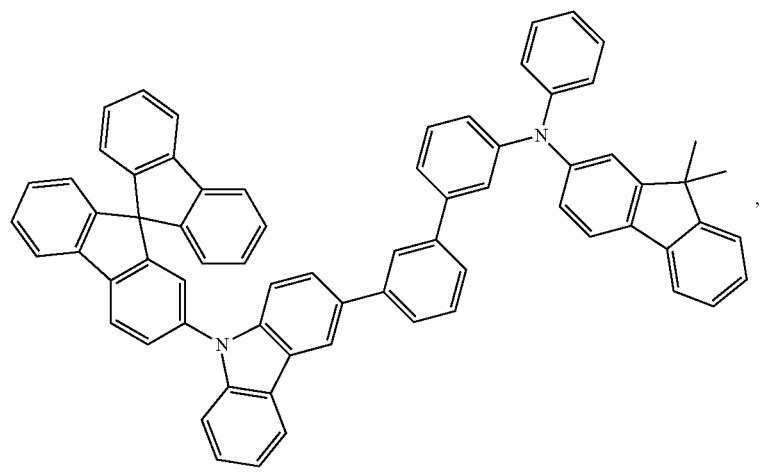
A294
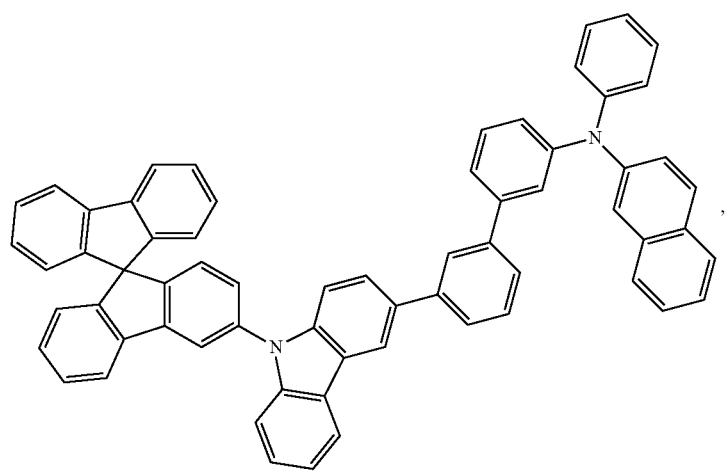
A295
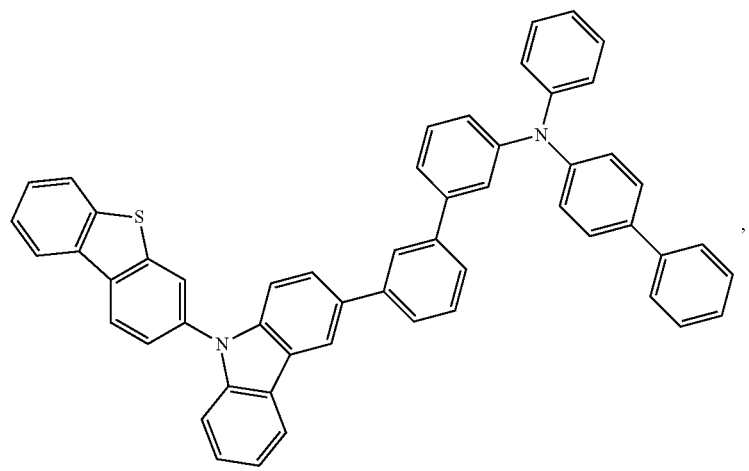

-continued
A296
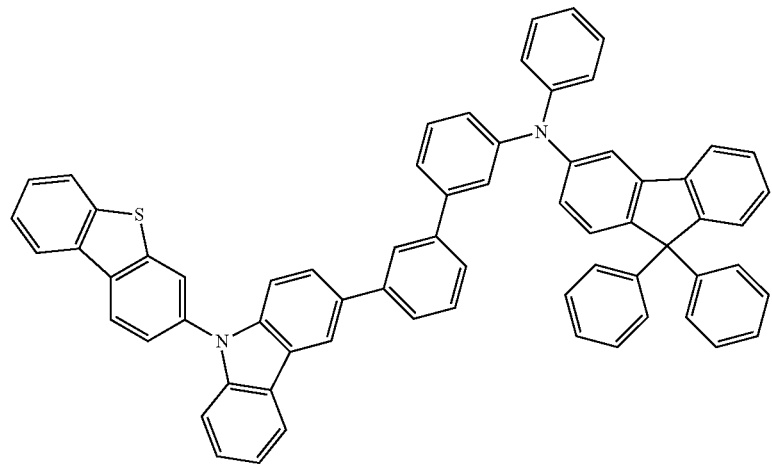
A297
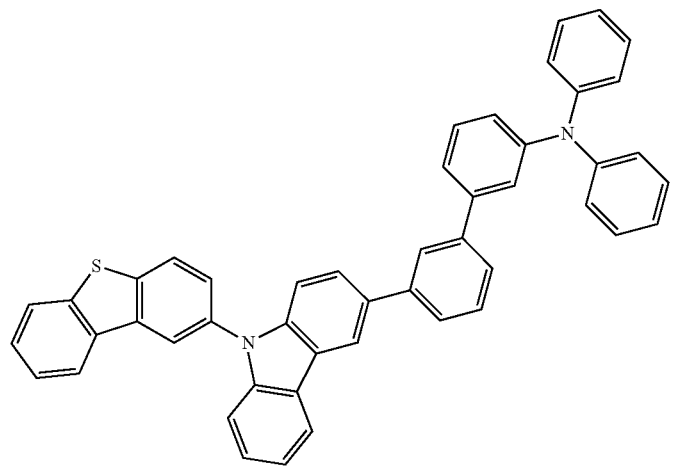
A298
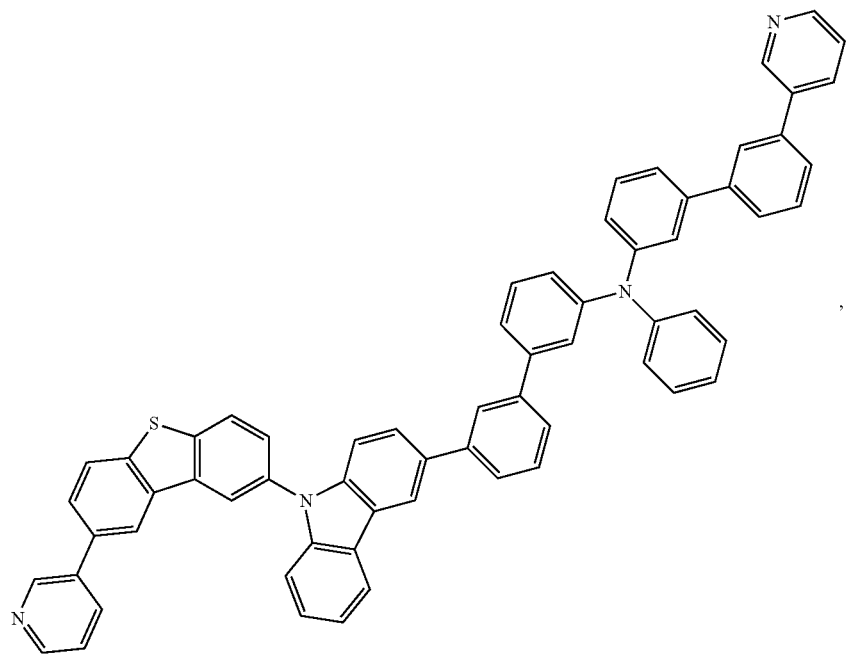

A299
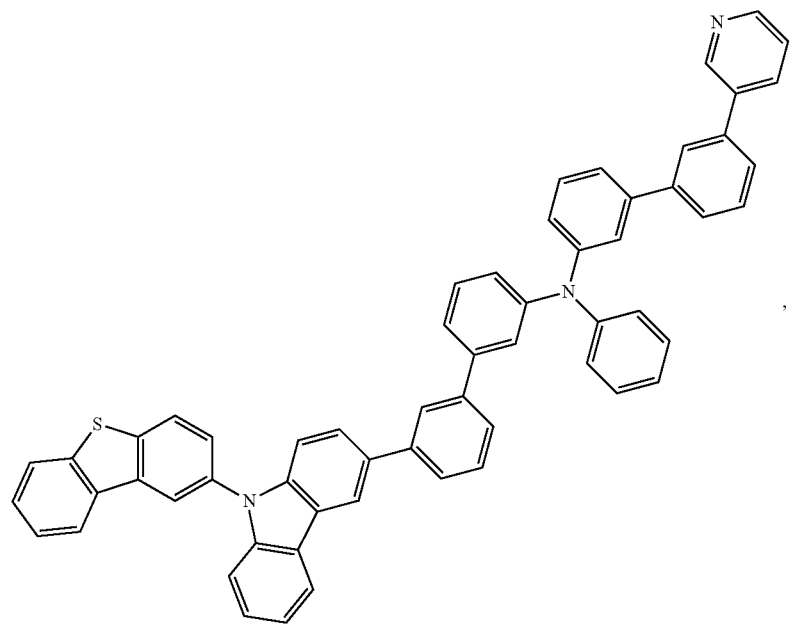
A300
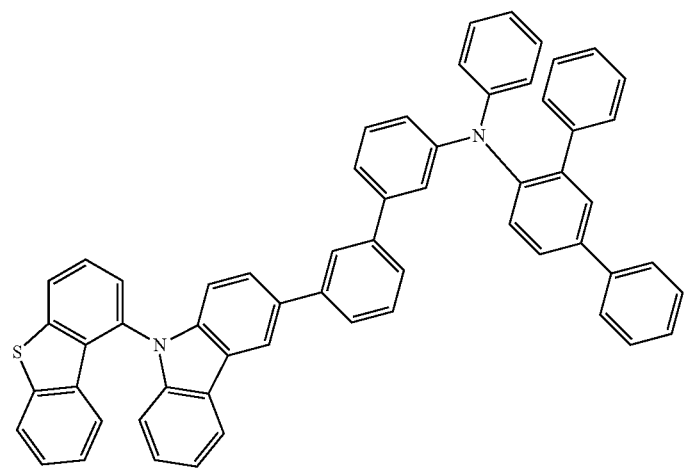
A301
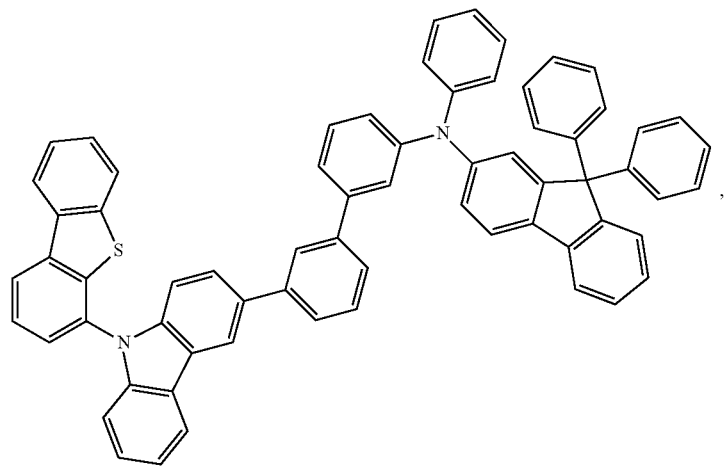

A302
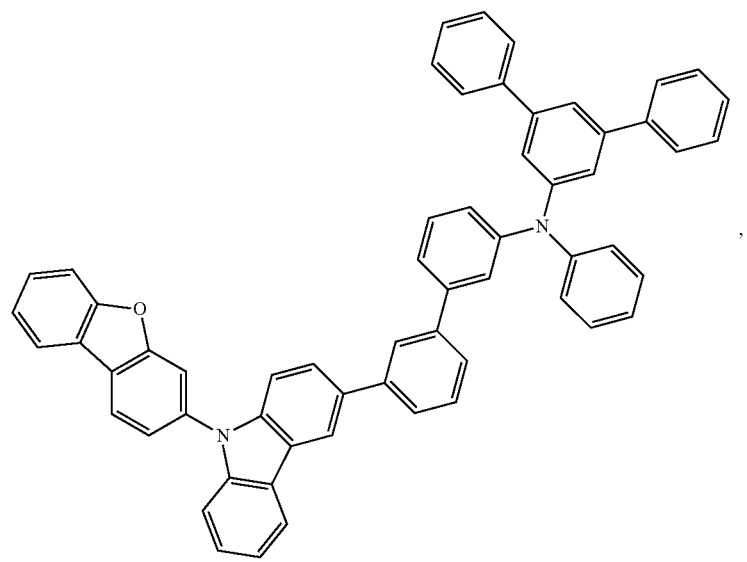
A303
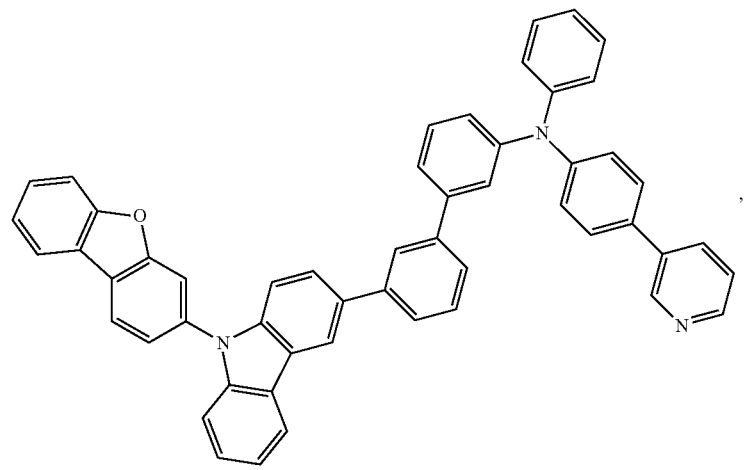
A304
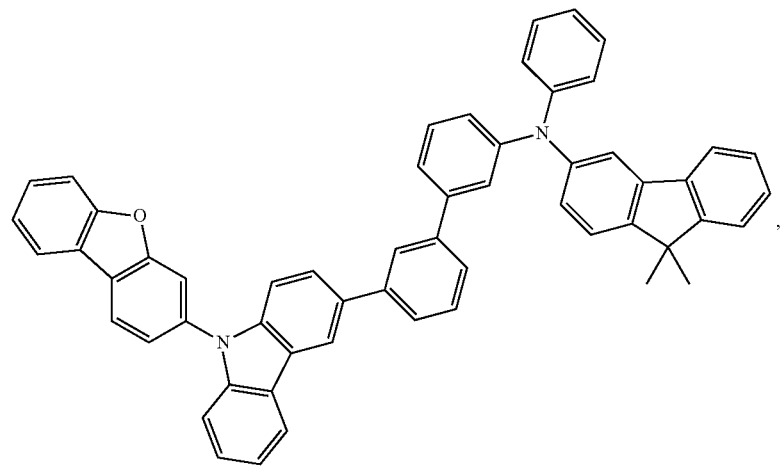

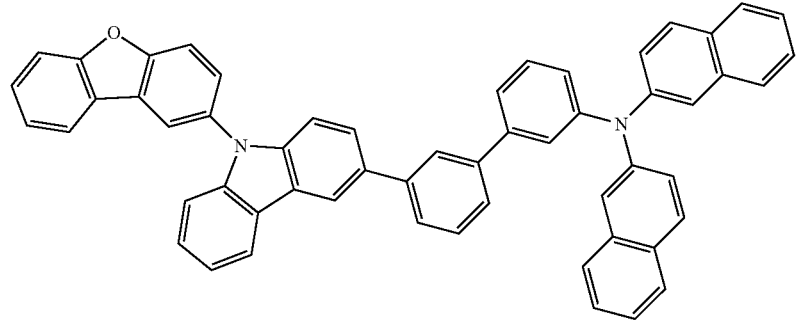
A305
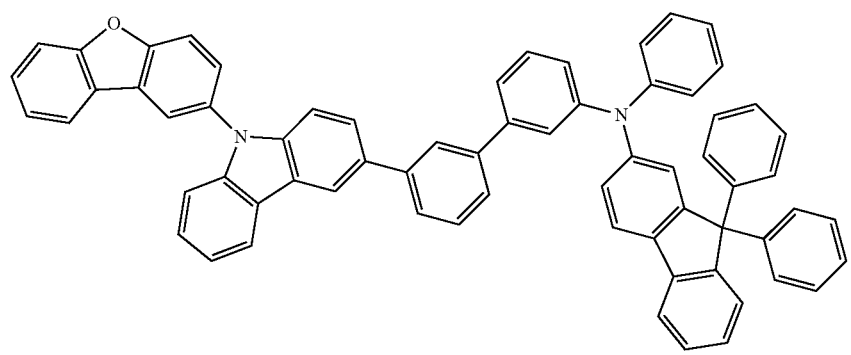
A306
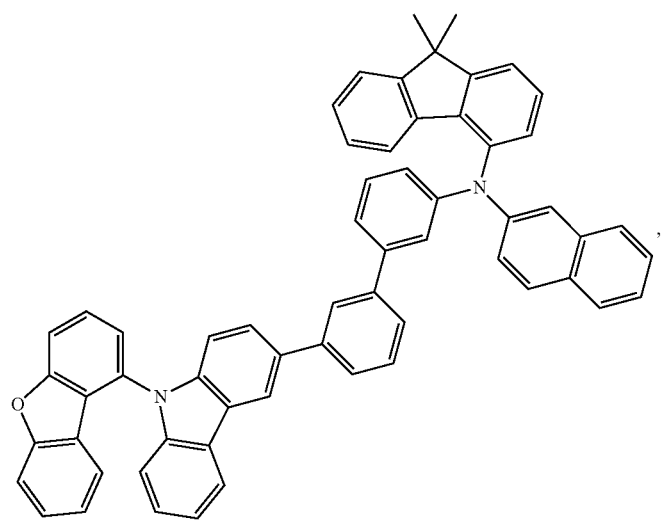
A307

-continued
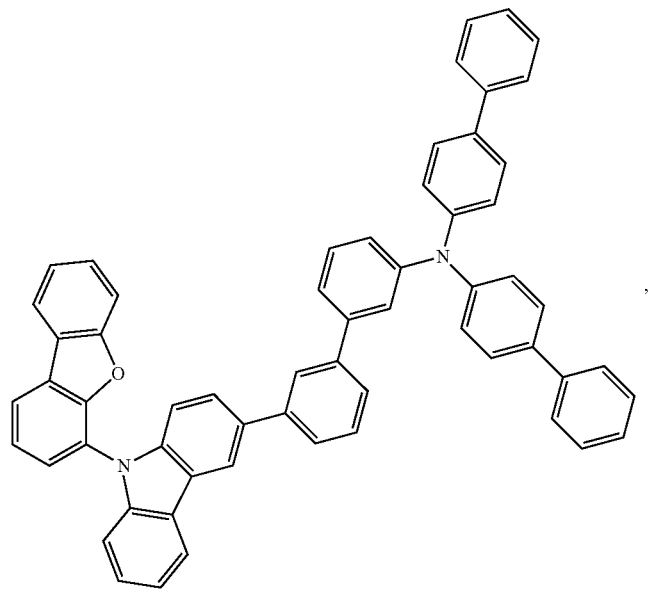
A308
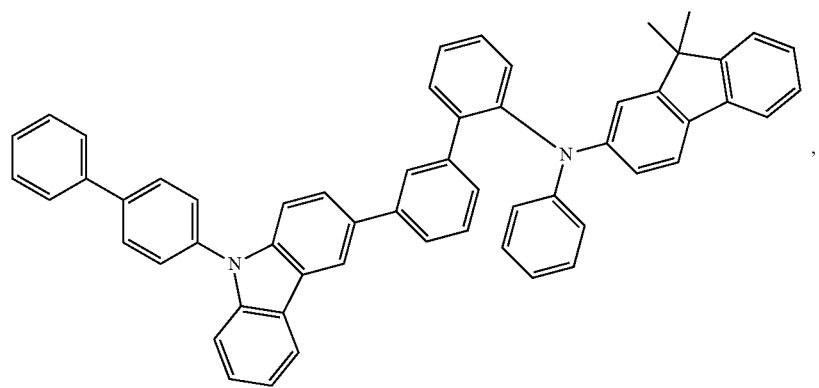
A309
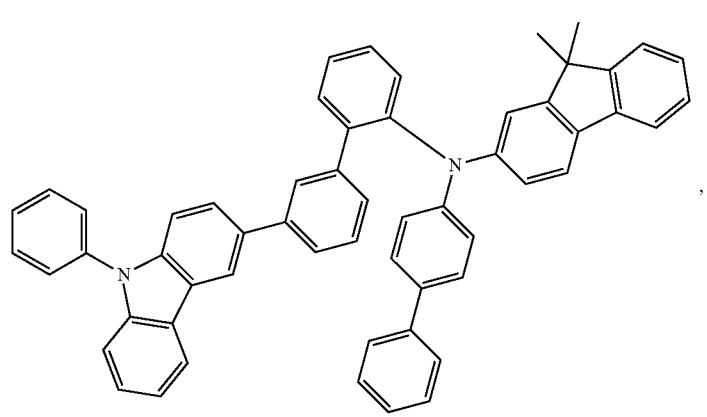
A310

A311
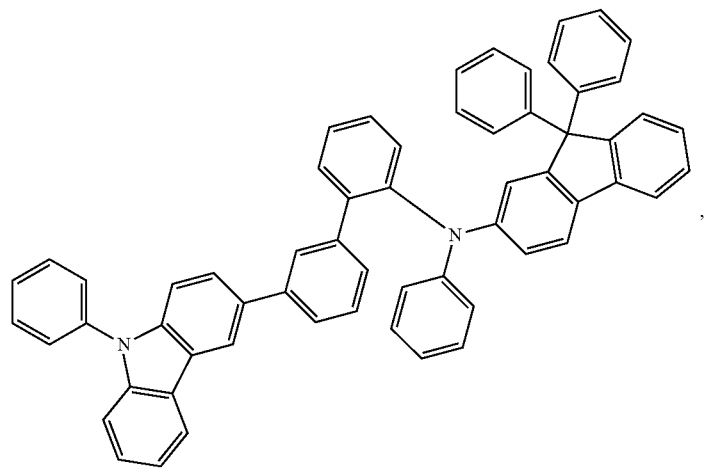
A312
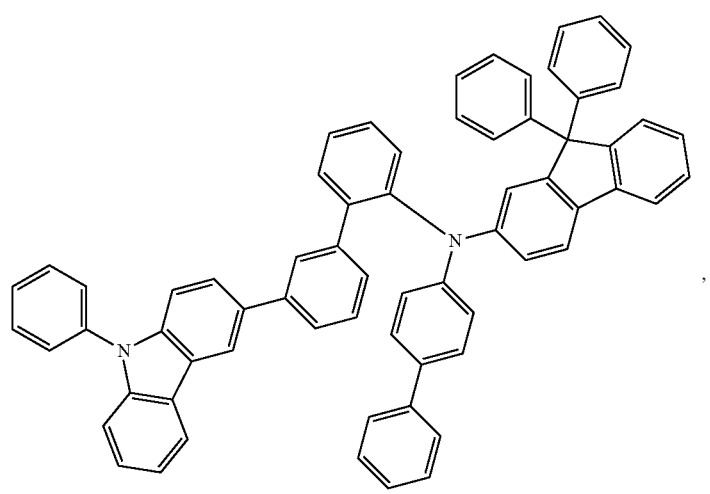
A313
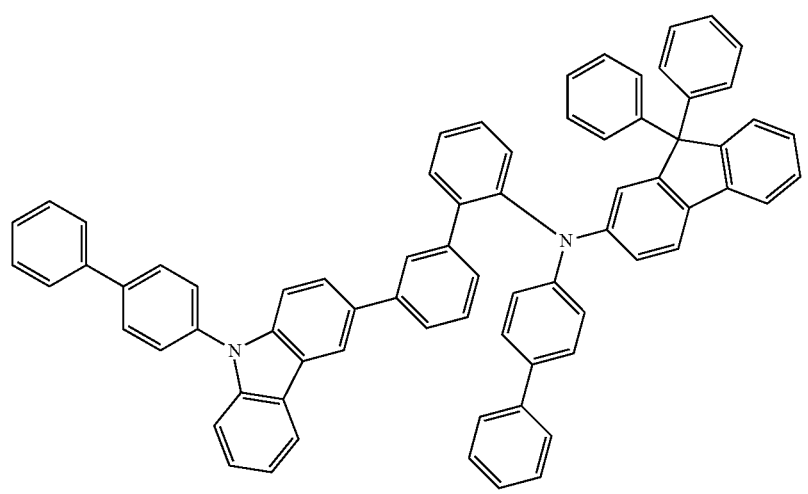

A314
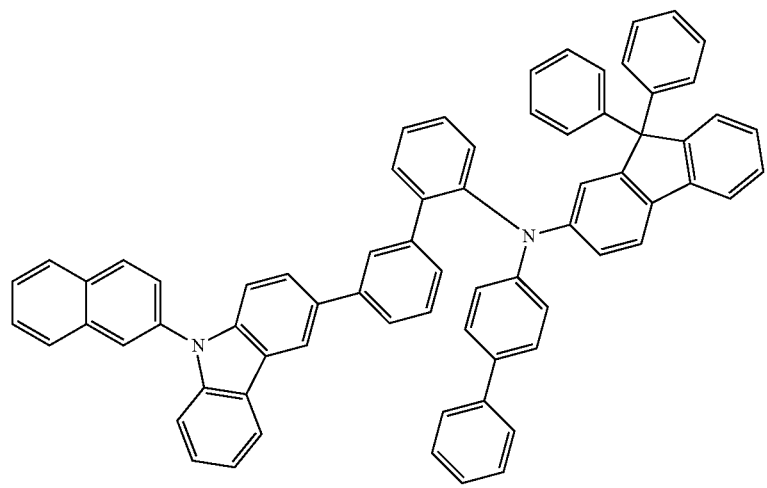
A315
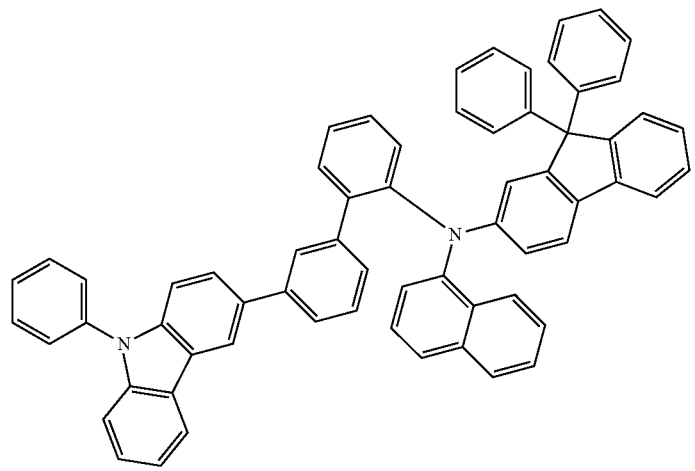
A316
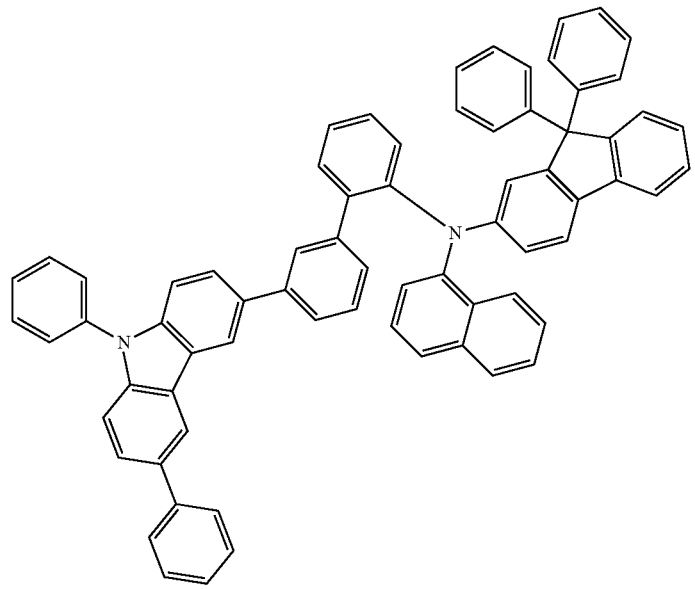

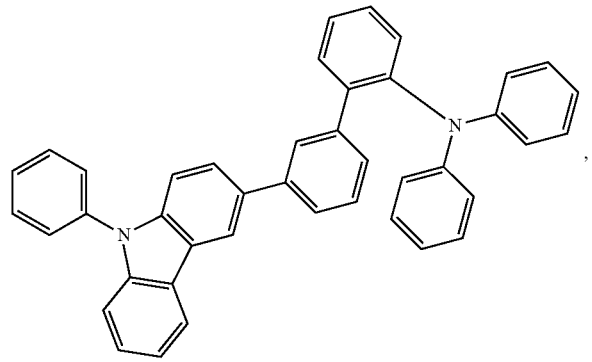 A317
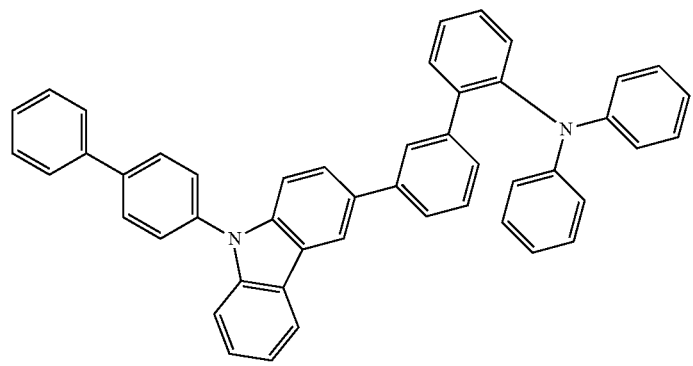 A318
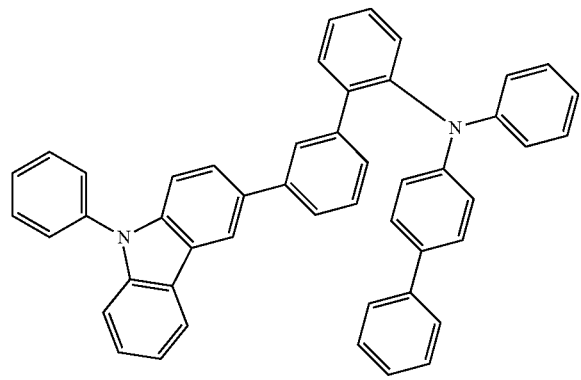 A319
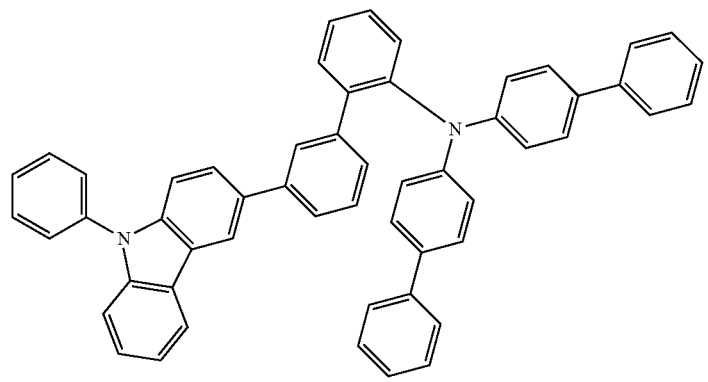 A320

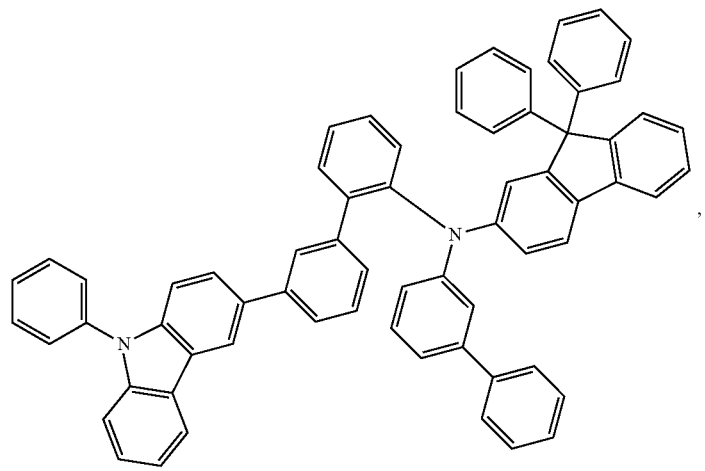
A321
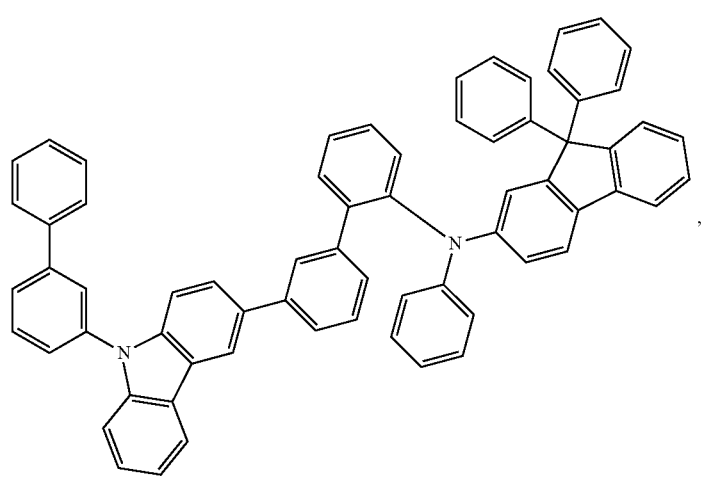
A322
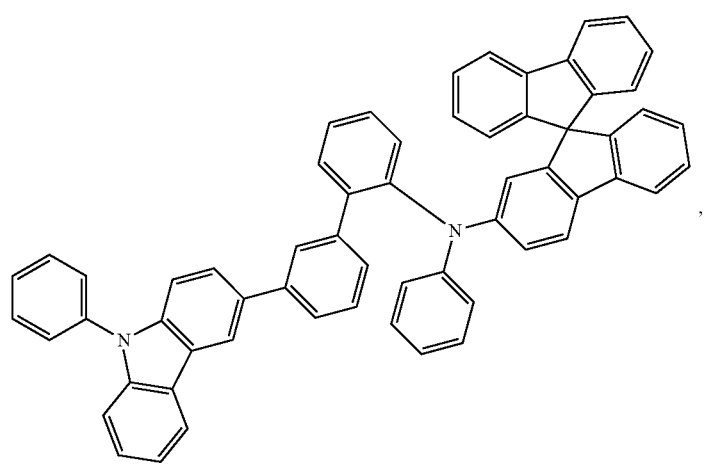
A323

-continued
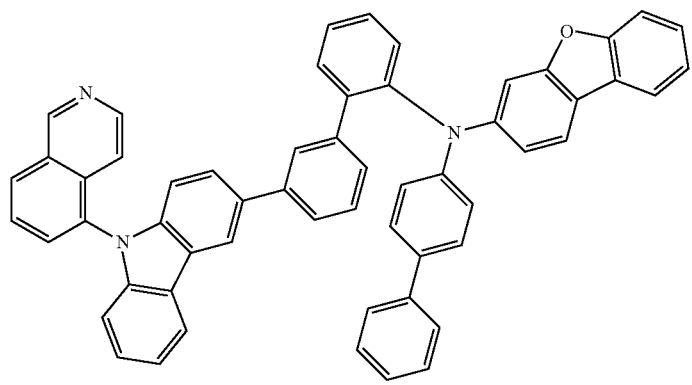
A324
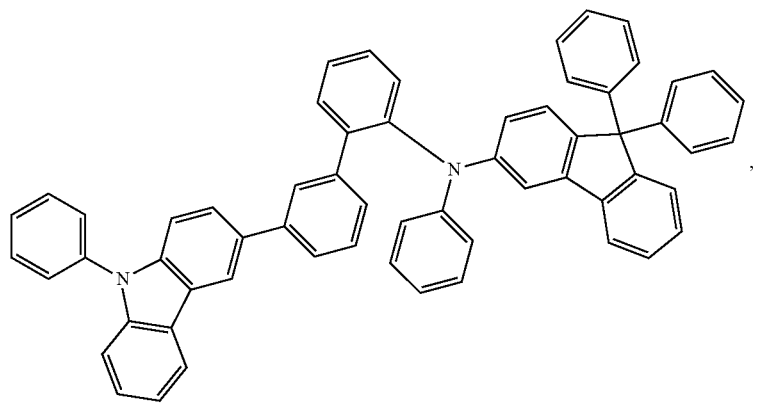
A325
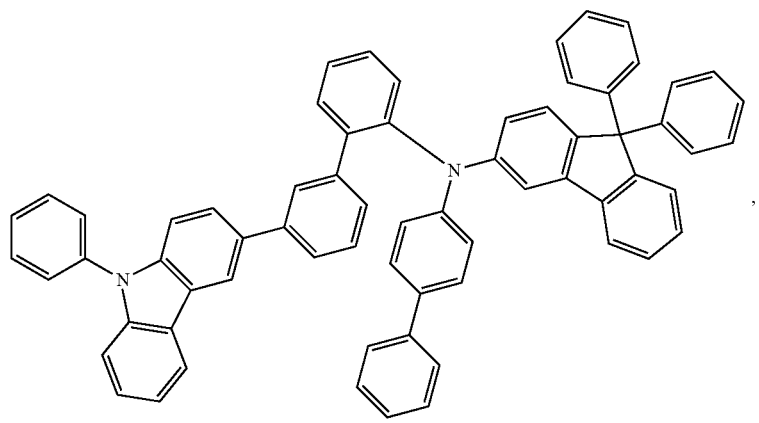
A326
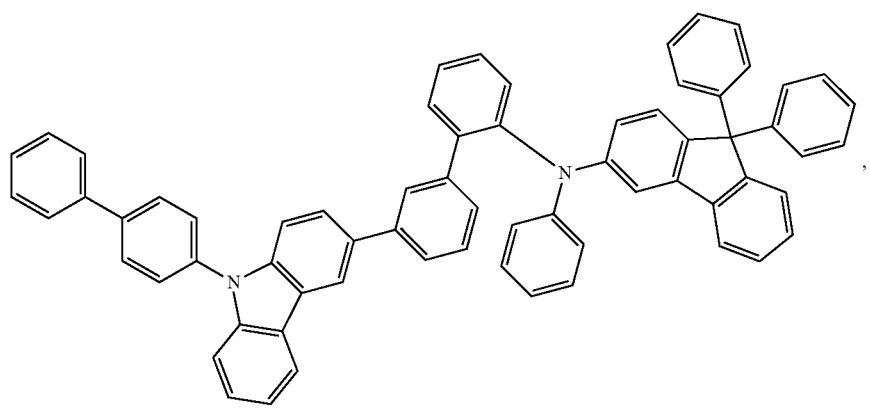
A327

-continued
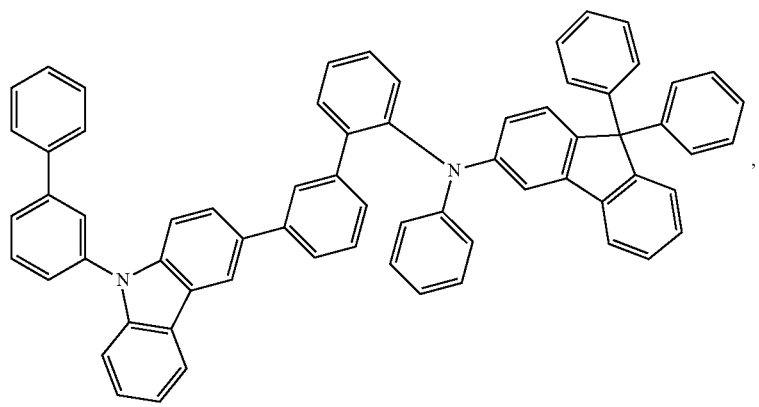
A328
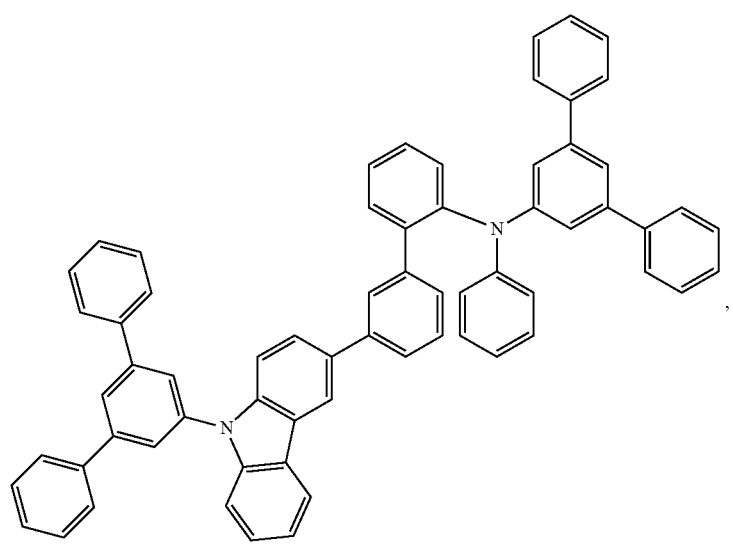
A329
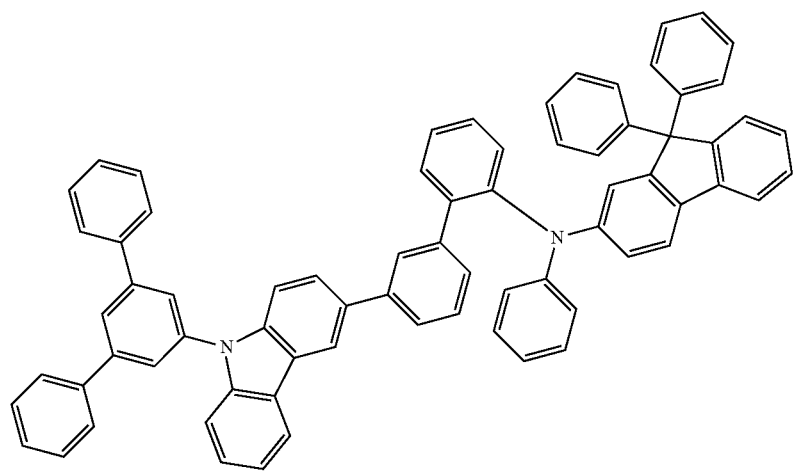
A330

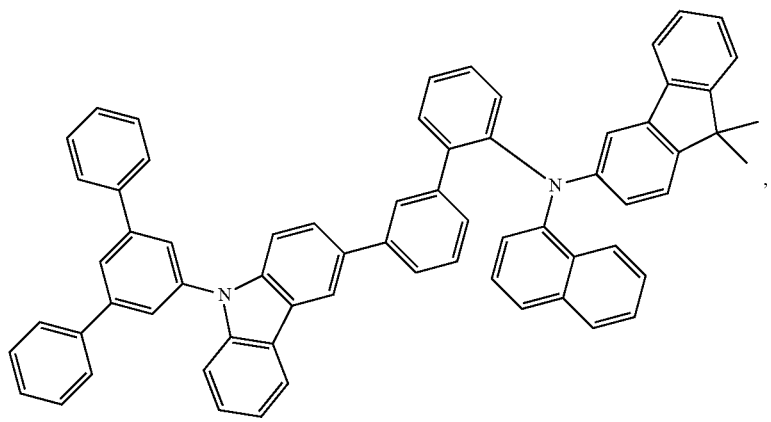
A331
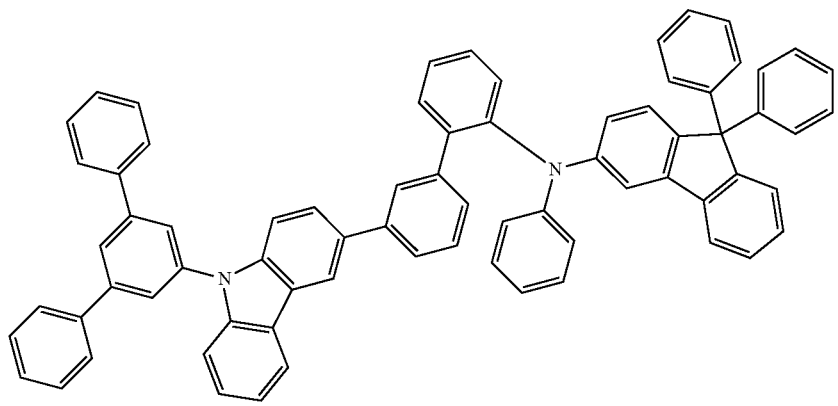
A332
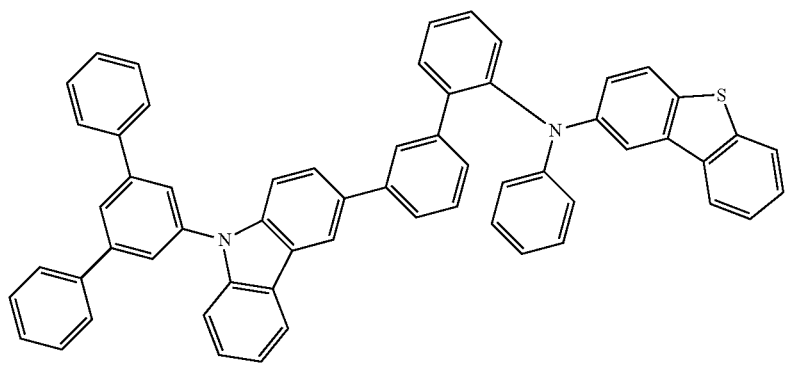
A333
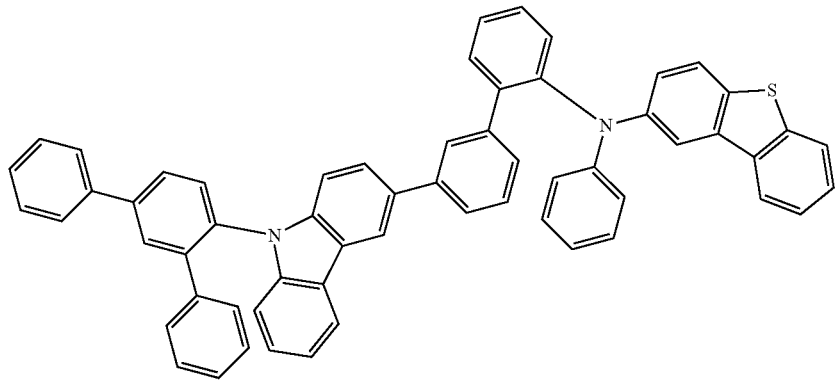
A334

-continued
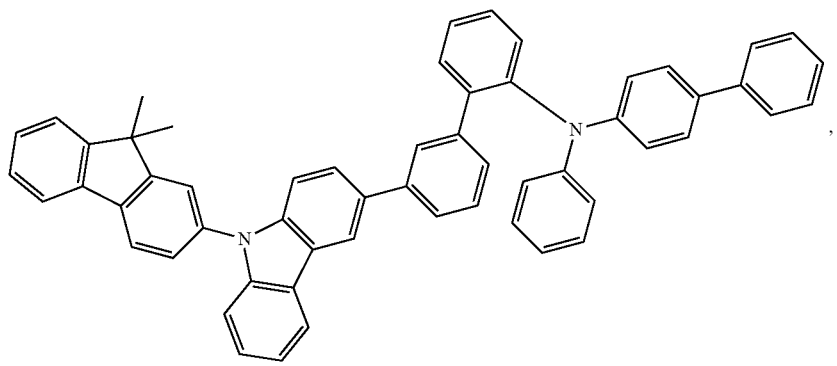
A335
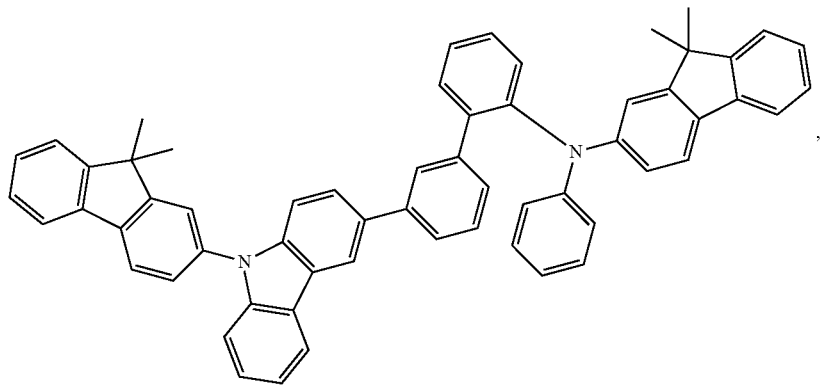
A336
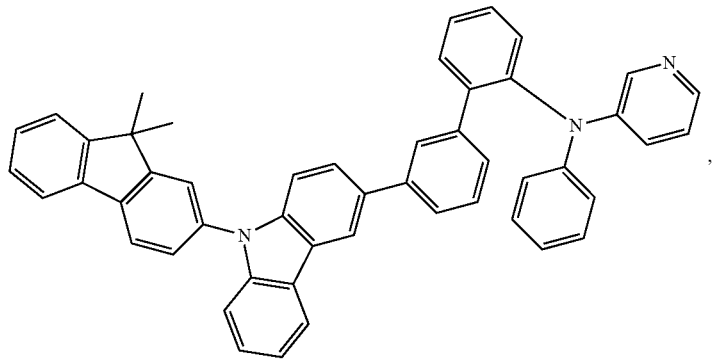
A337
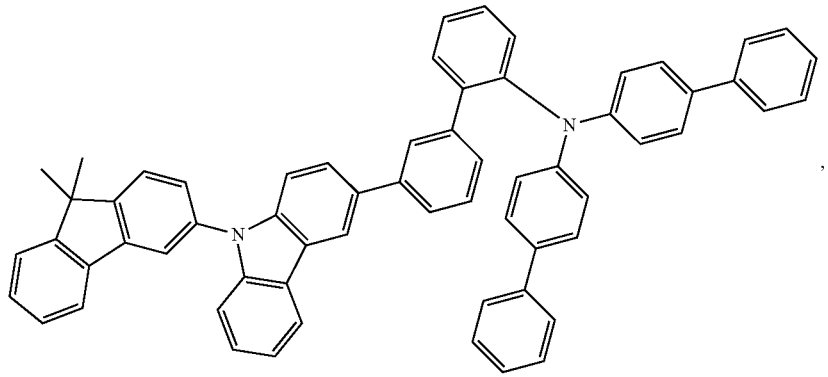
A338

-continued
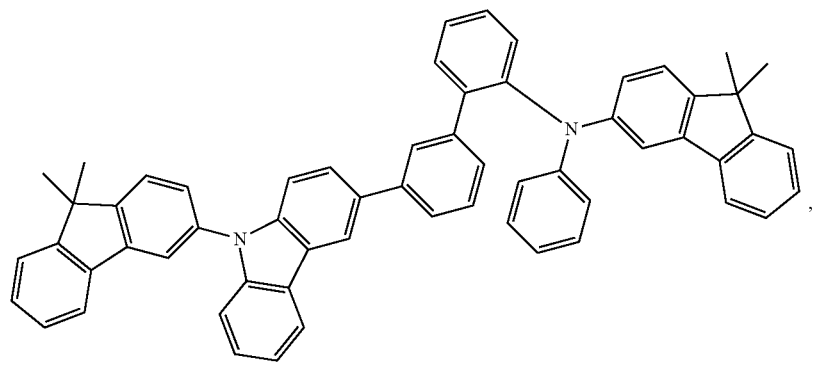
A339
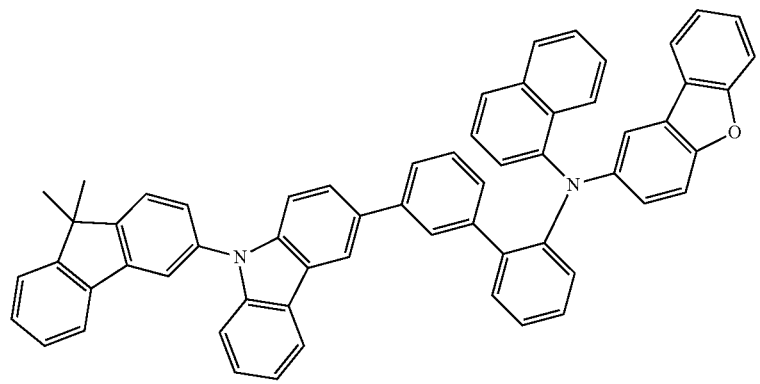
A340
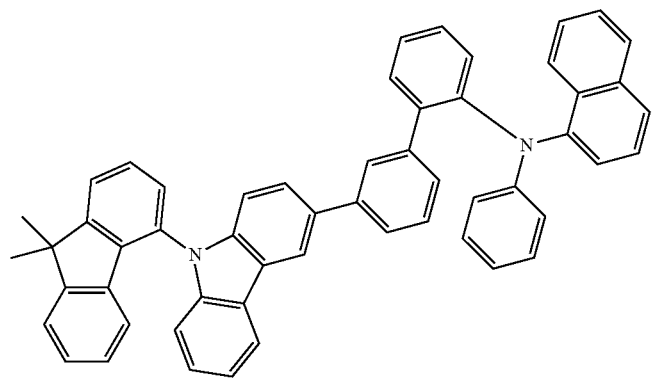
A341
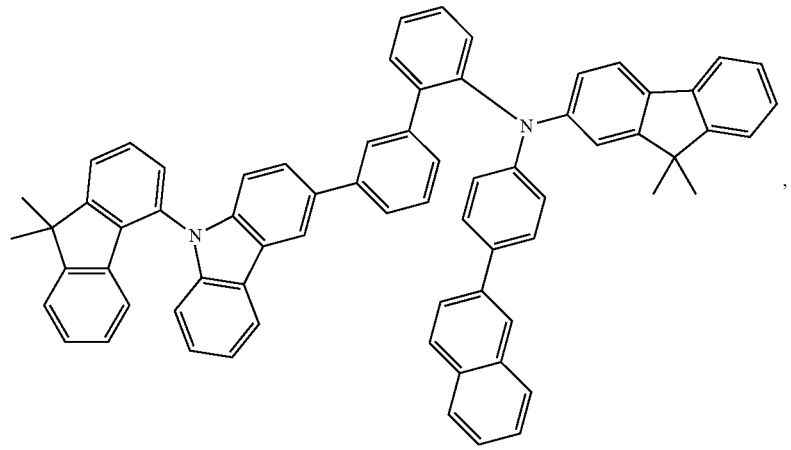
A342

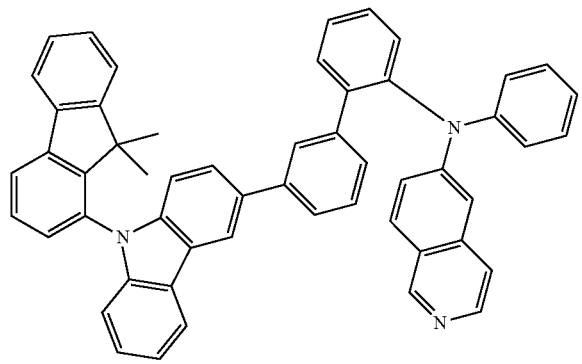
A343
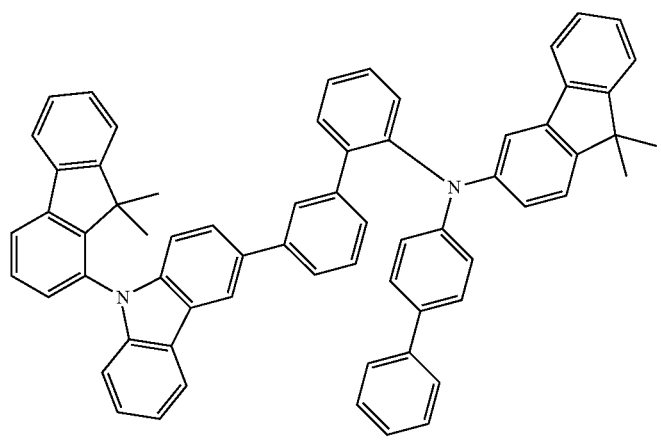
A344
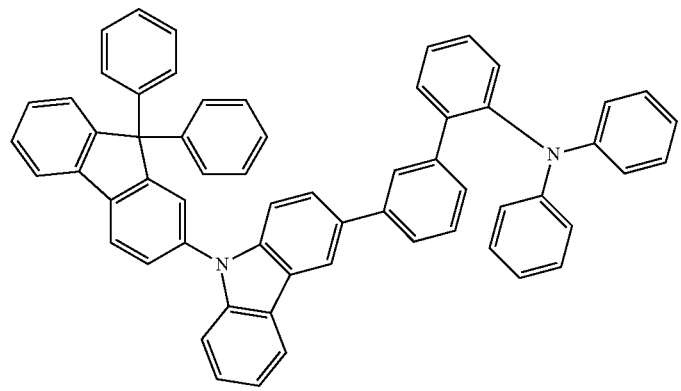
A345
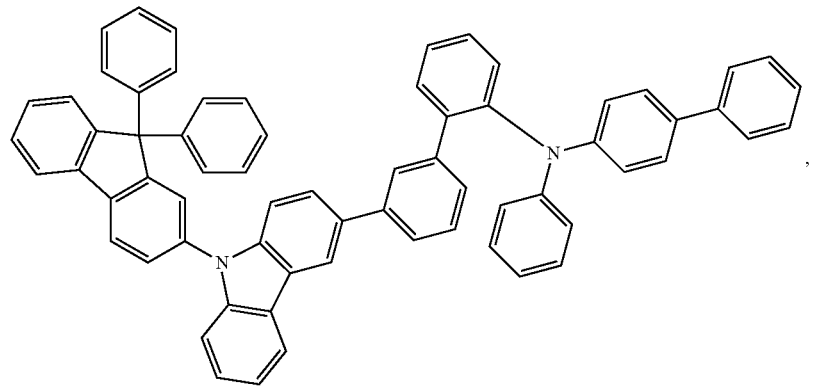
A346

-continued
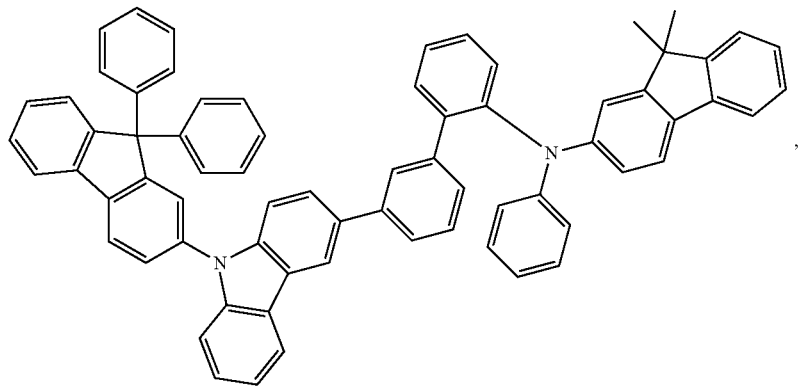
A347
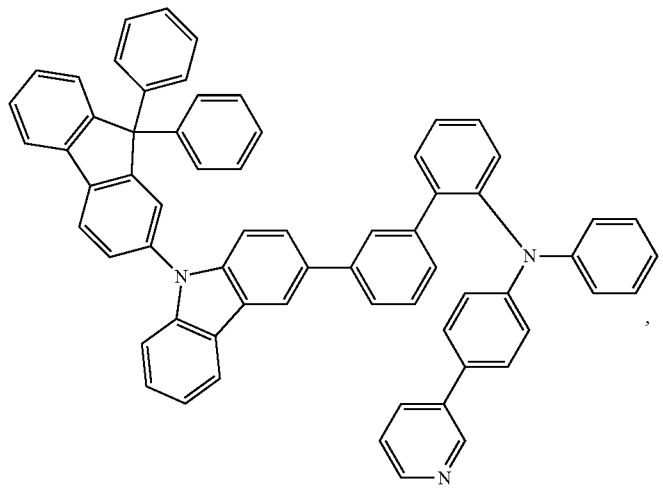
A348
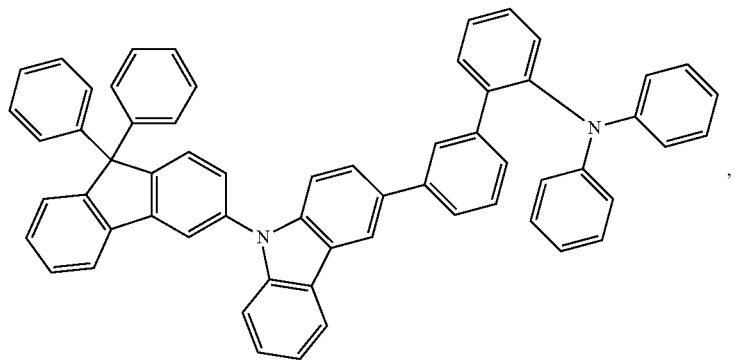
A349
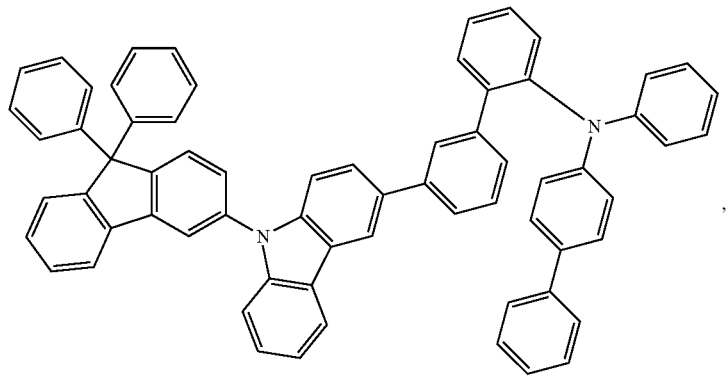
A350

-continued
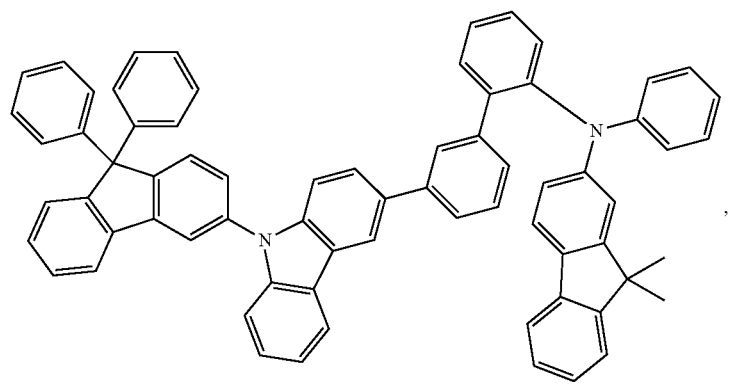
A351
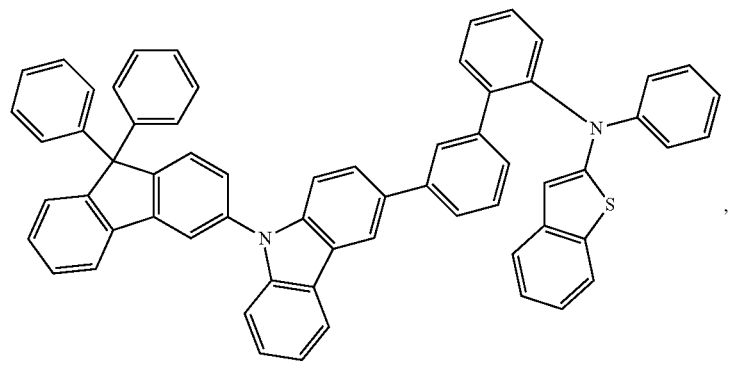
A352
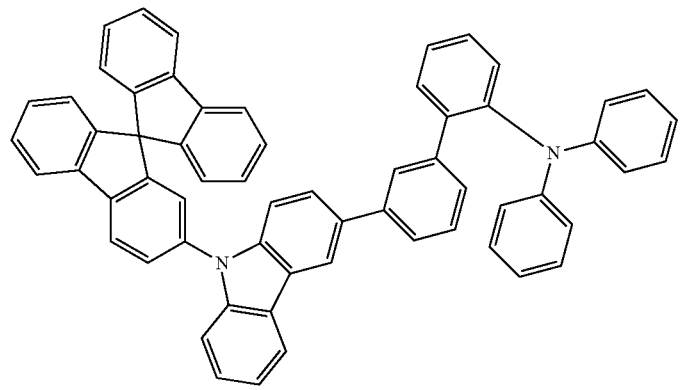
A353
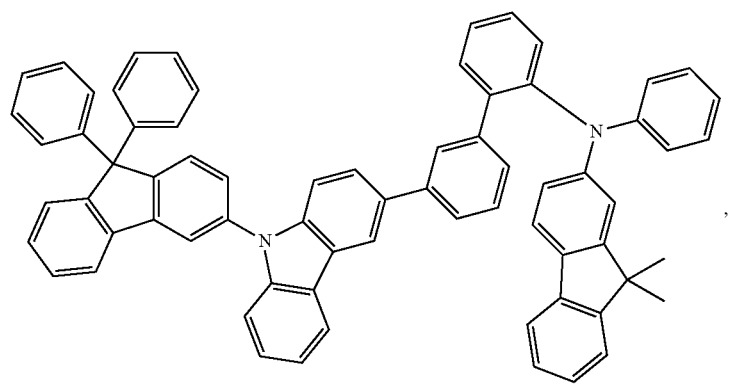
A354

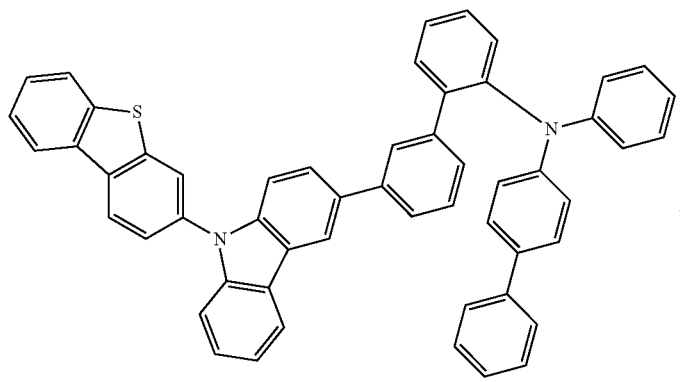
A355
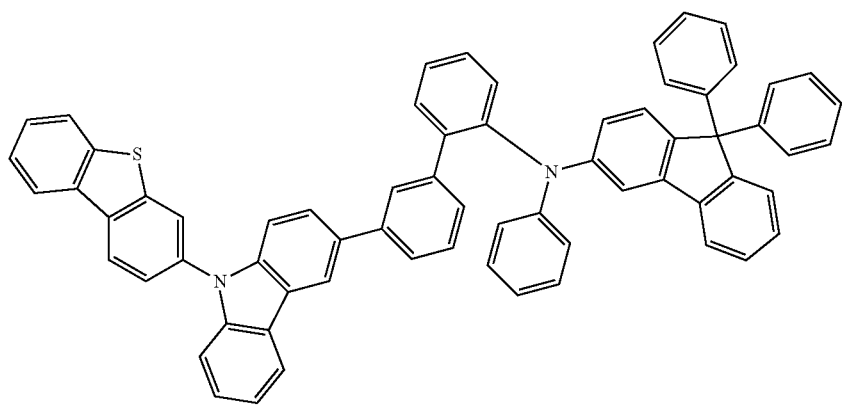
A356
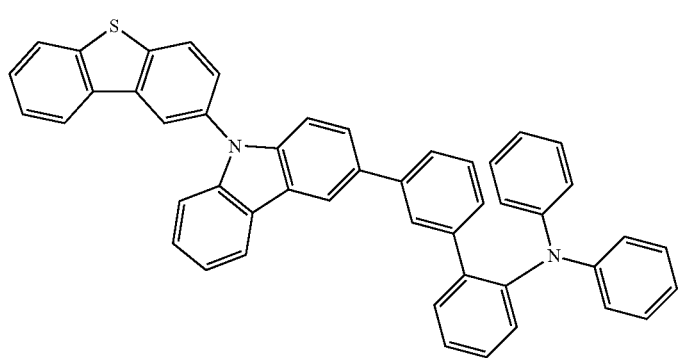
A357
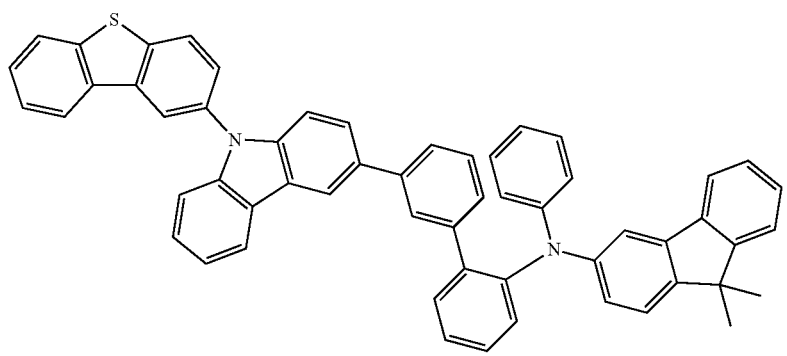
A358

-continued
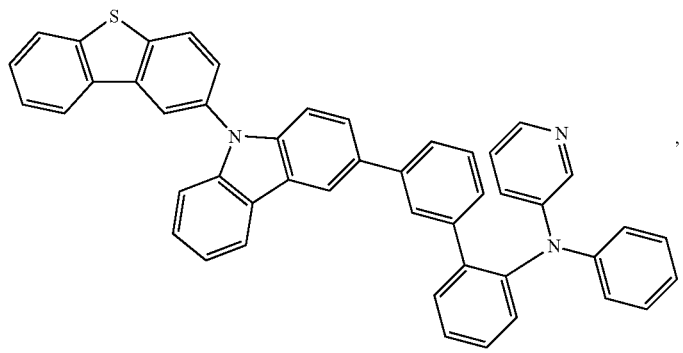
A359
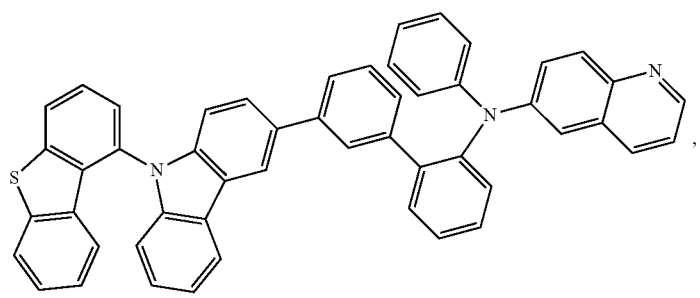
A360
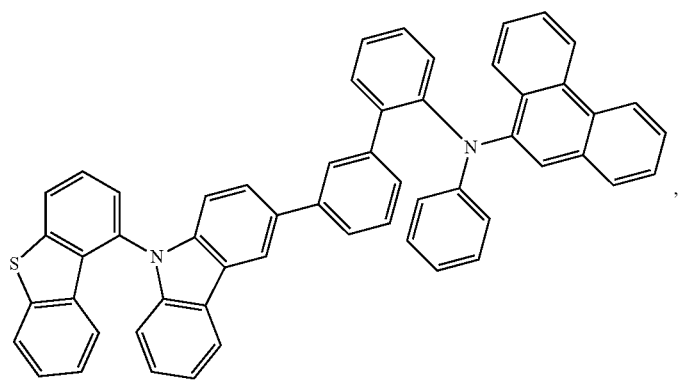
A361
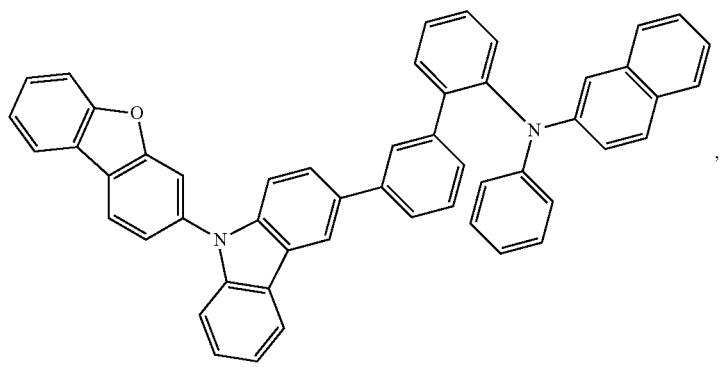
A362

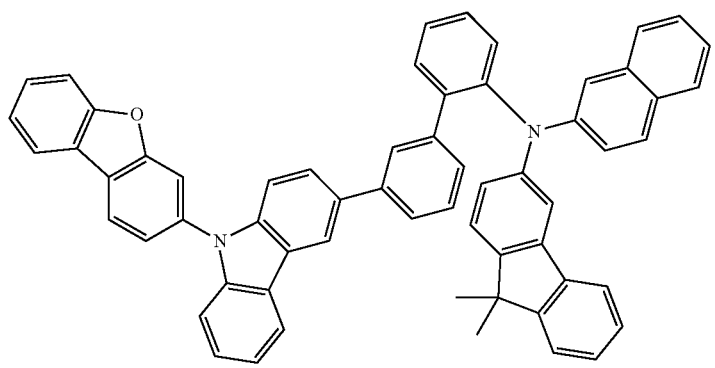
A363
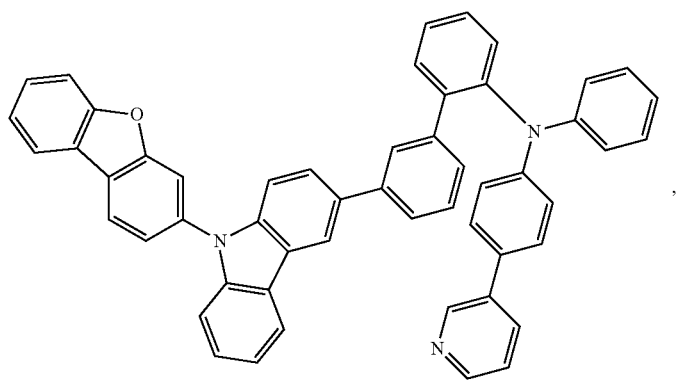
A364
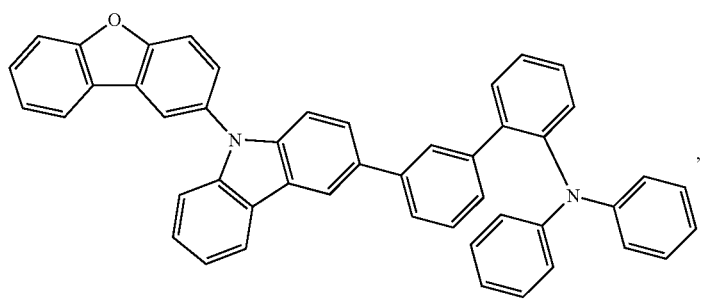
A365
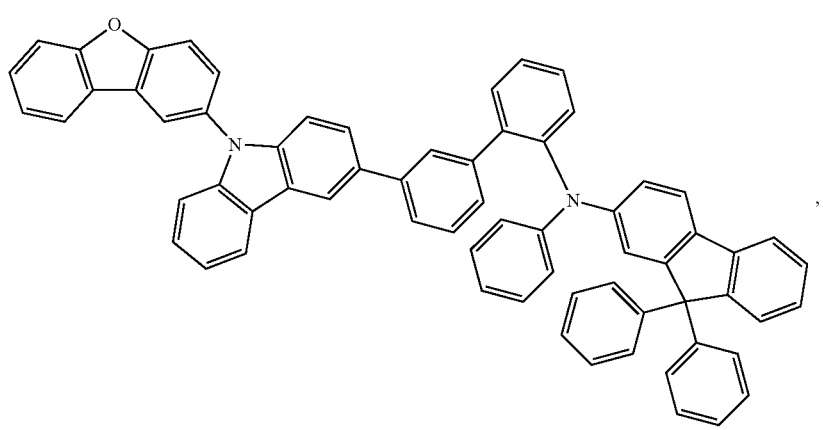
A366

A367
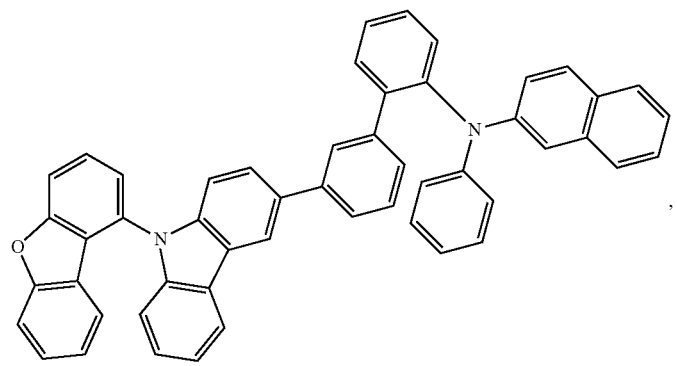
A368
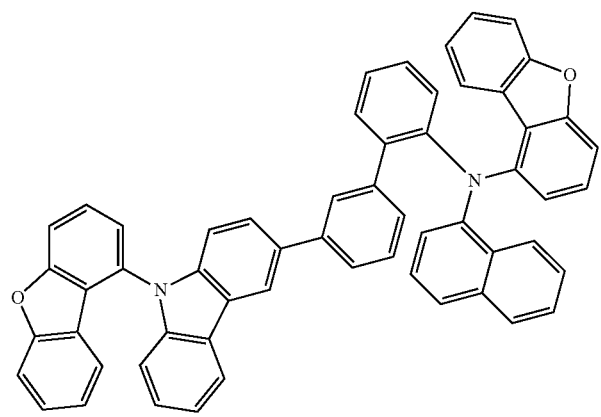
A369
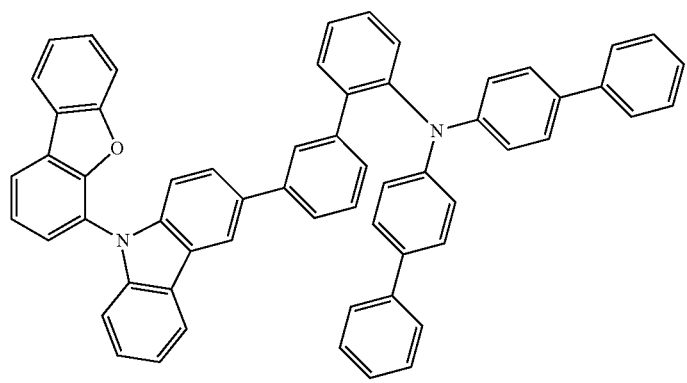
A370
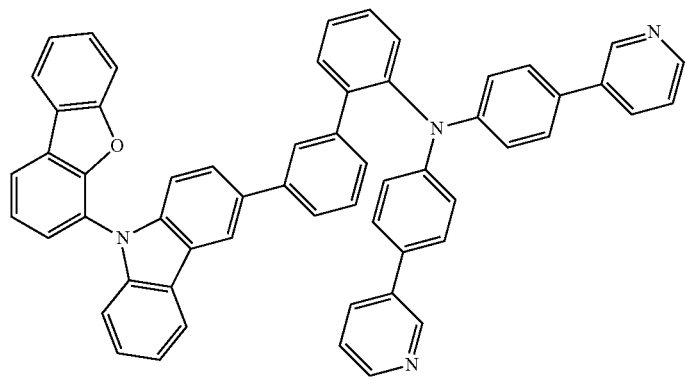

-continued
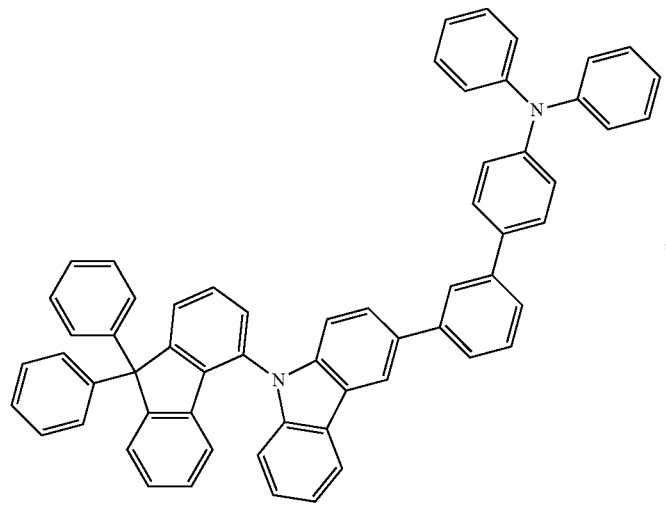
A371
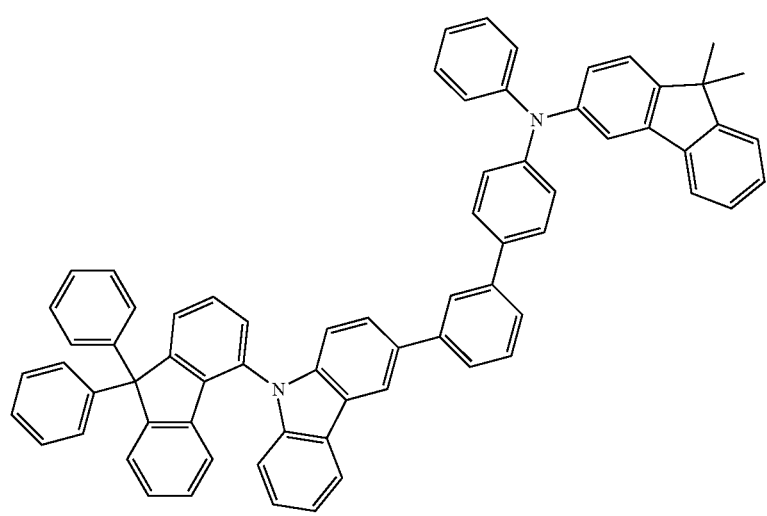
A372
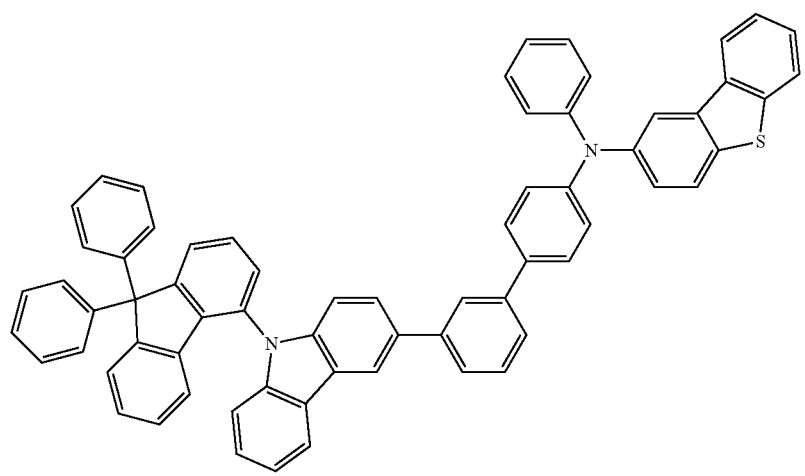
A373

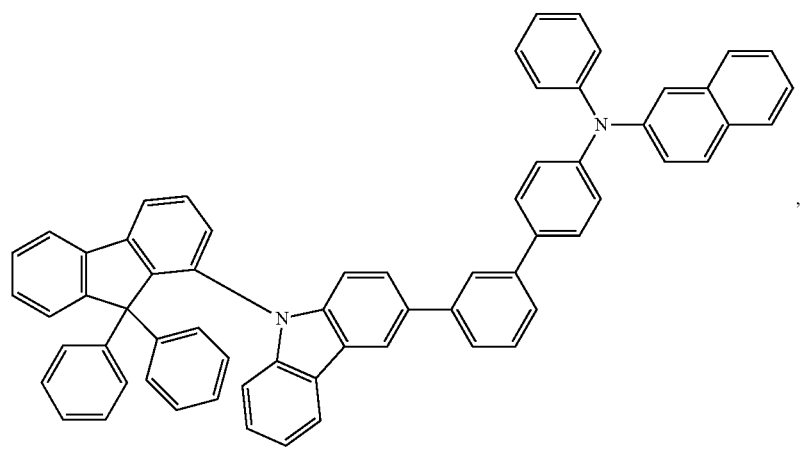
A374
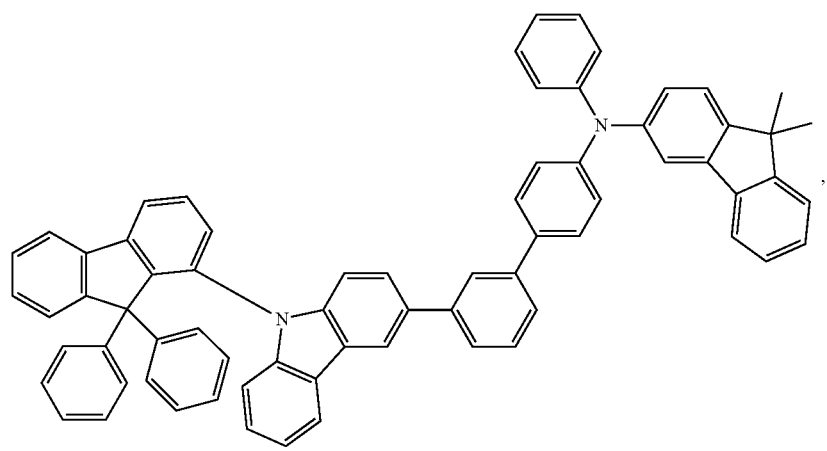
A375
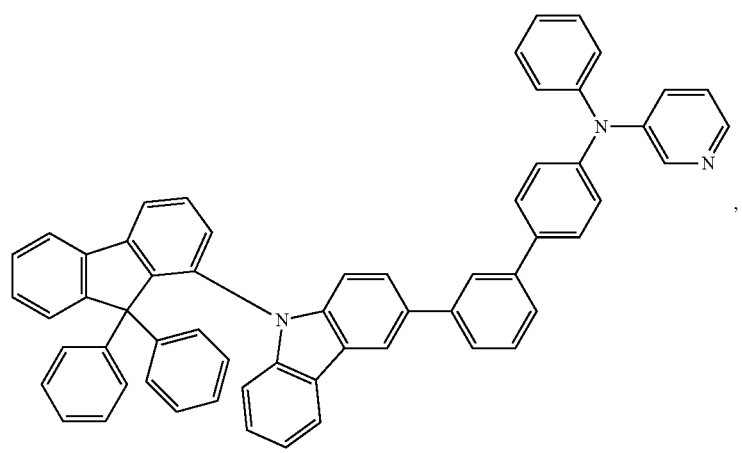
A376

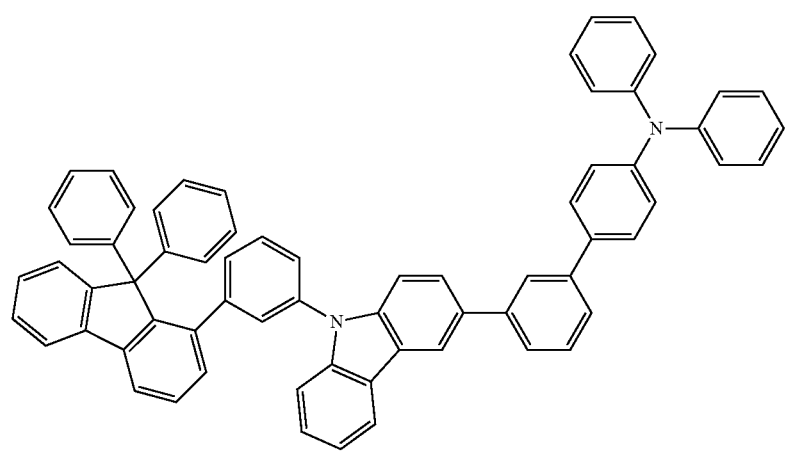
A377
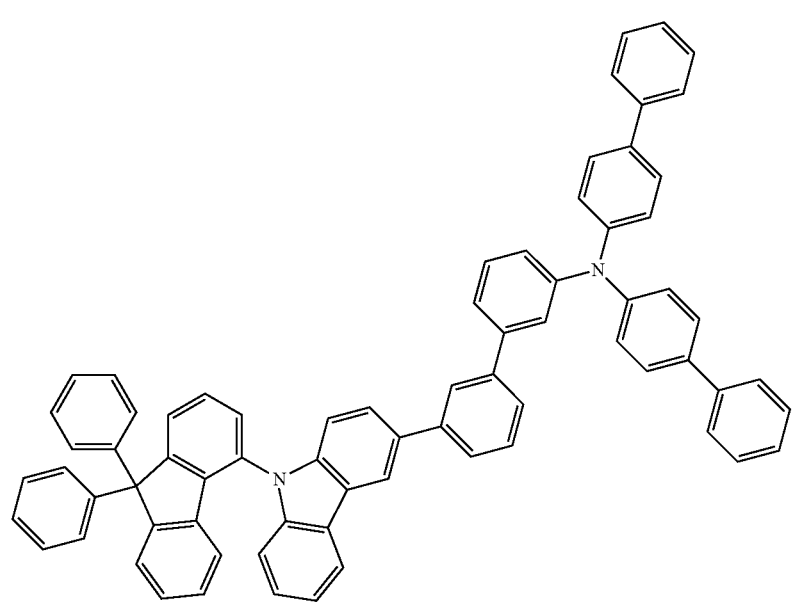
A378
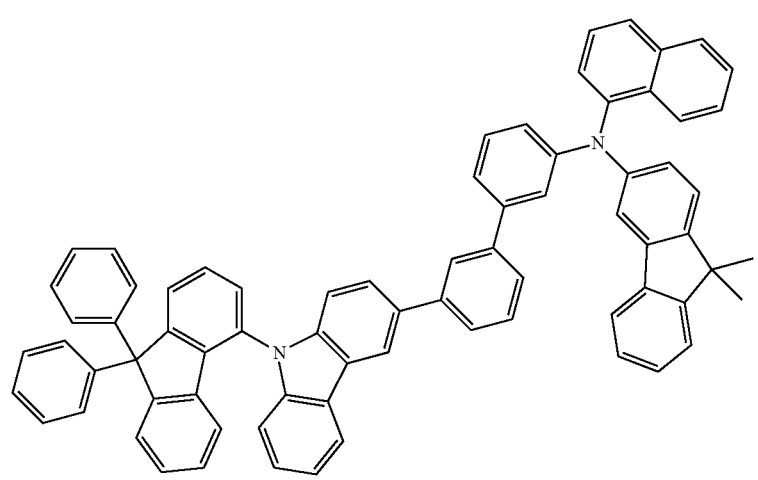
A379

-continued
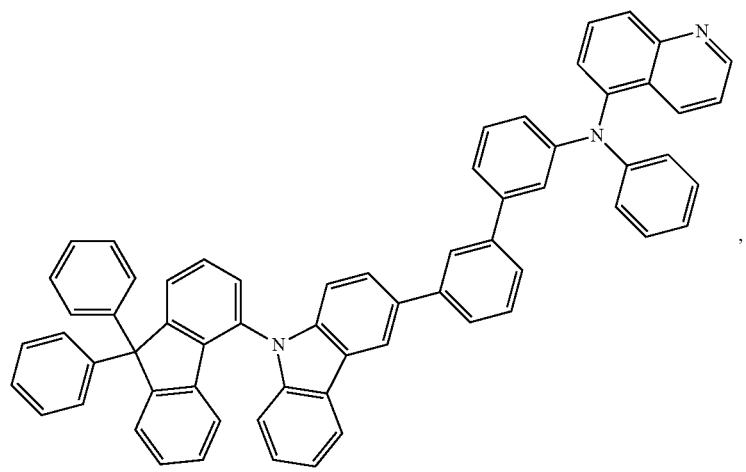
A380
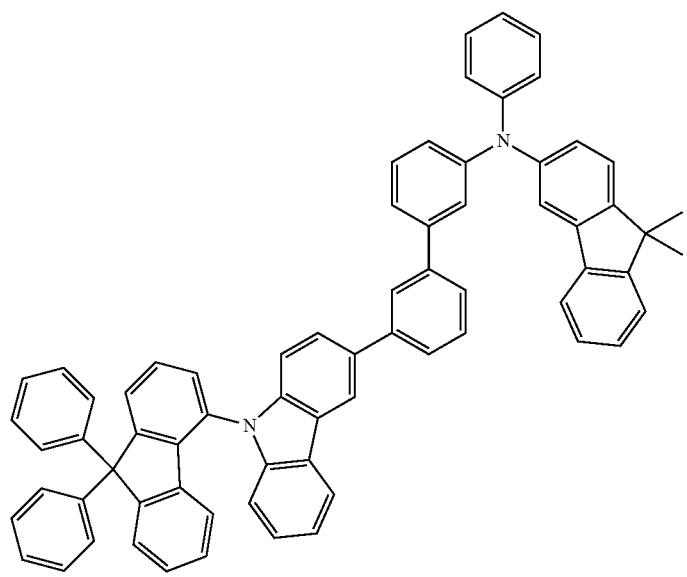
A381

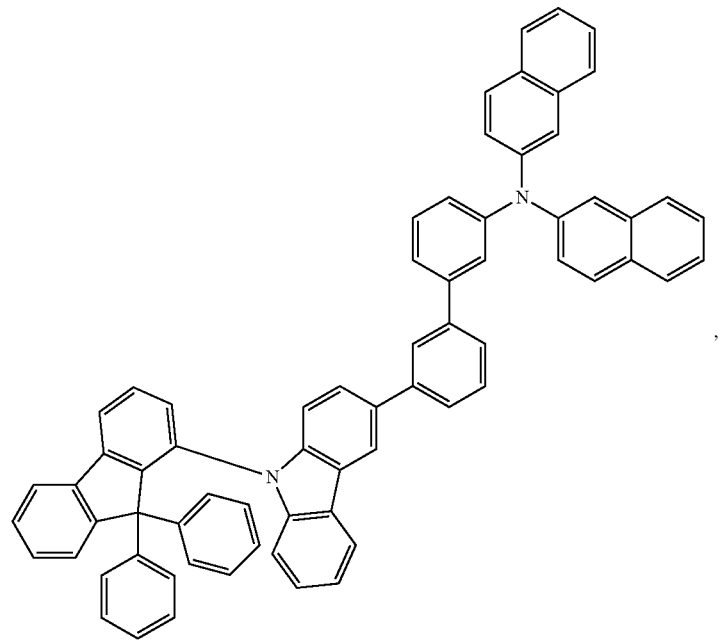
A382
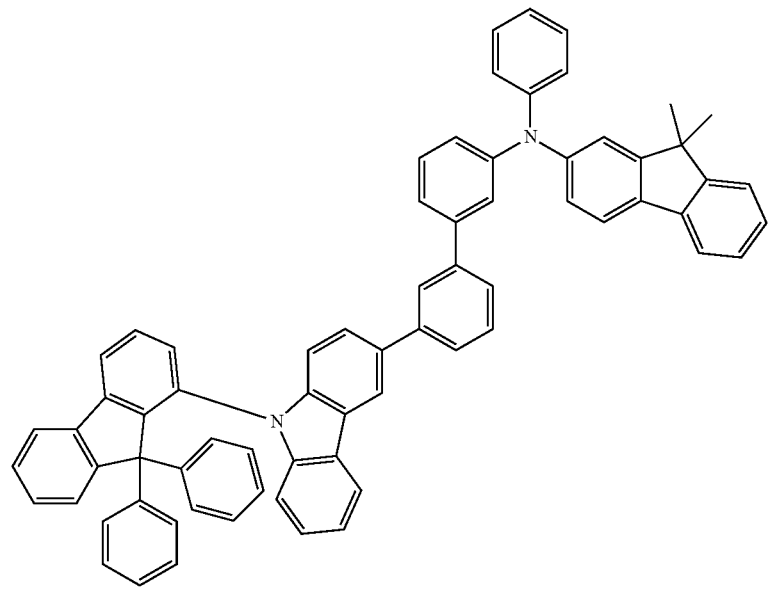
A383

-continued
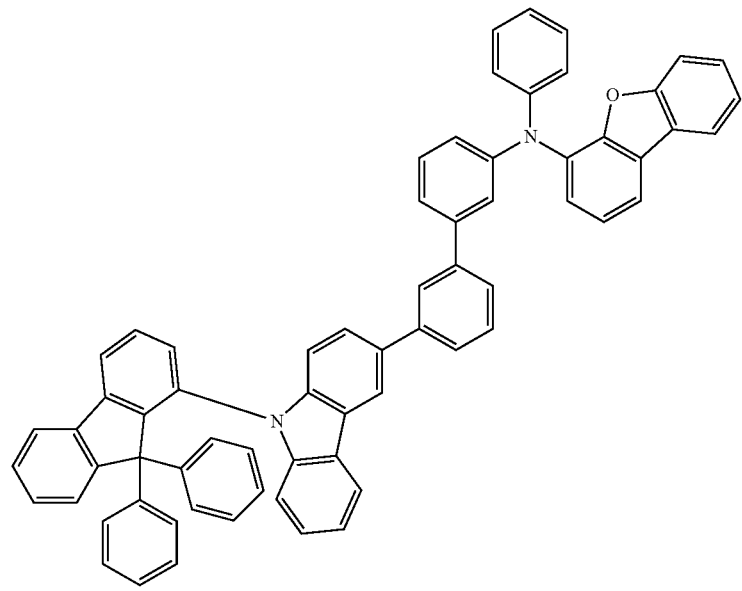
A384
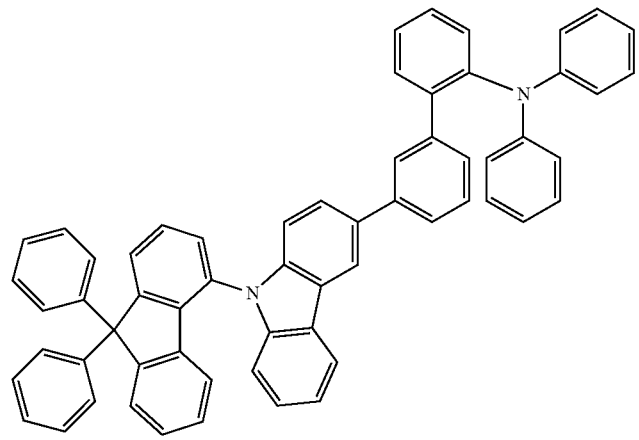
A385
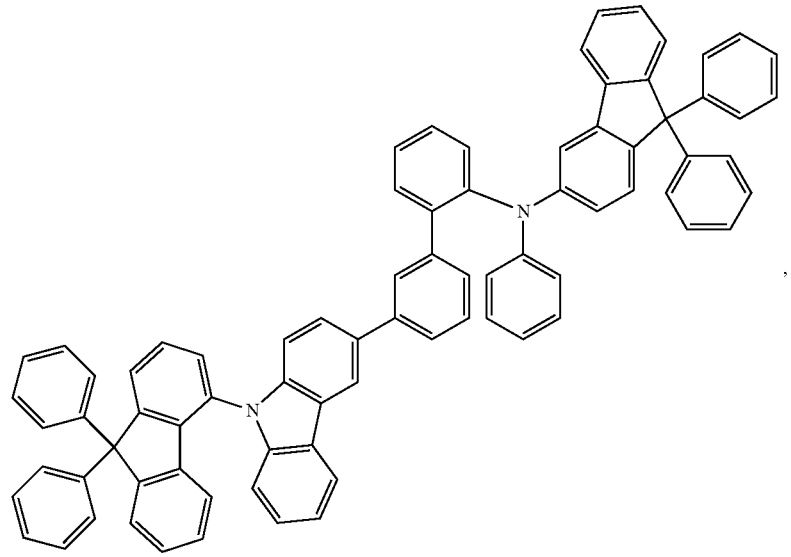
A386

-continued
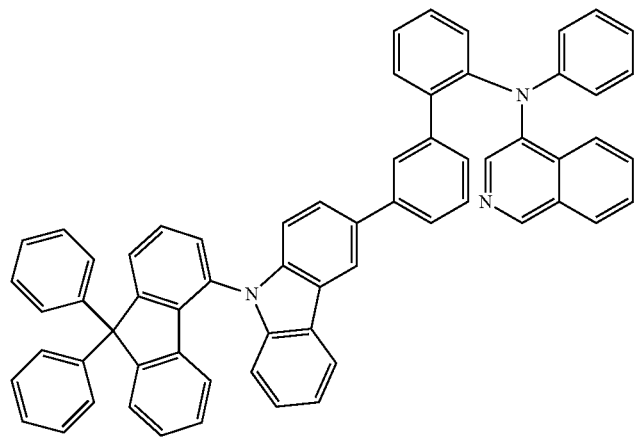
A387
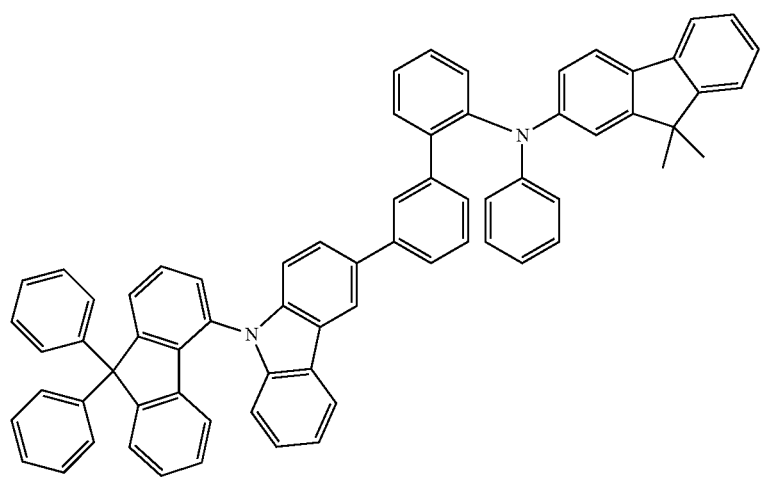
A388
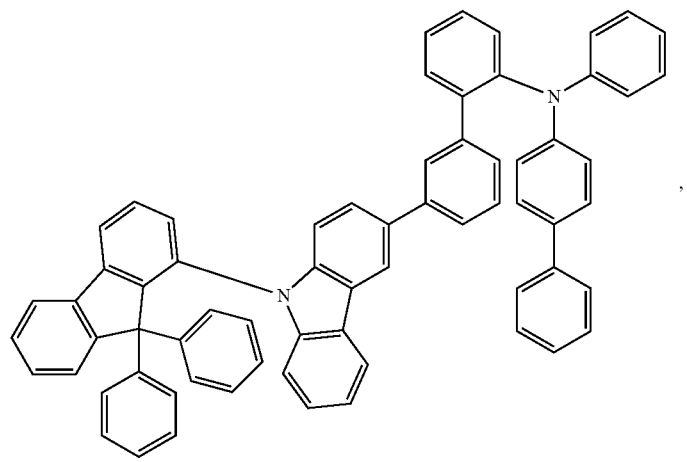
A389

-continued
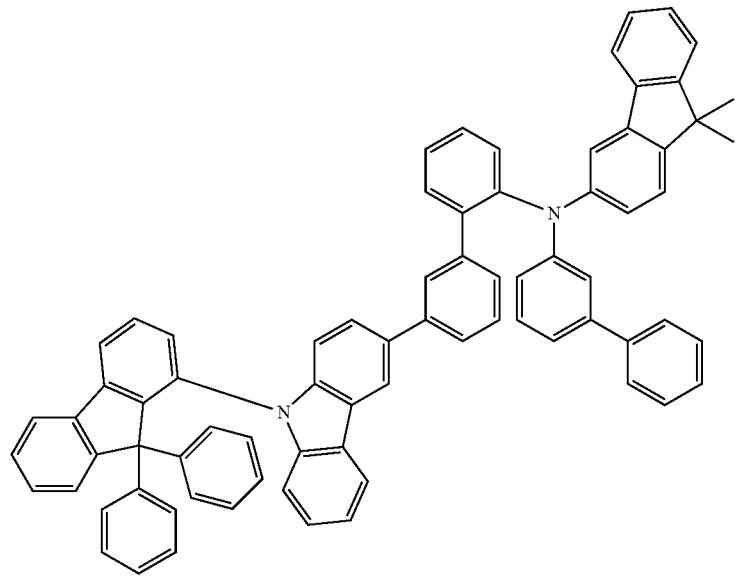
A390
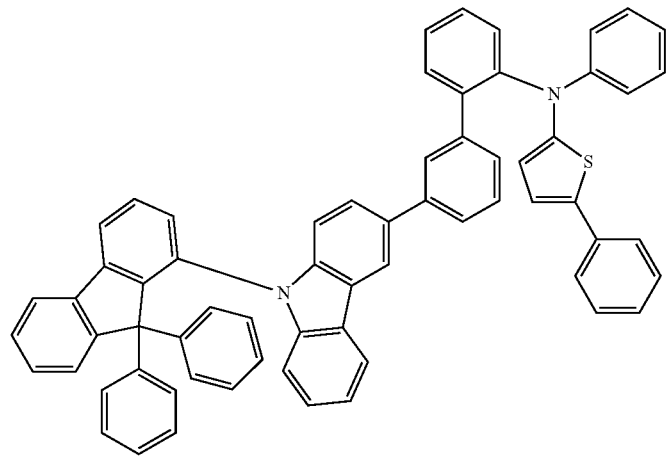
A391
or
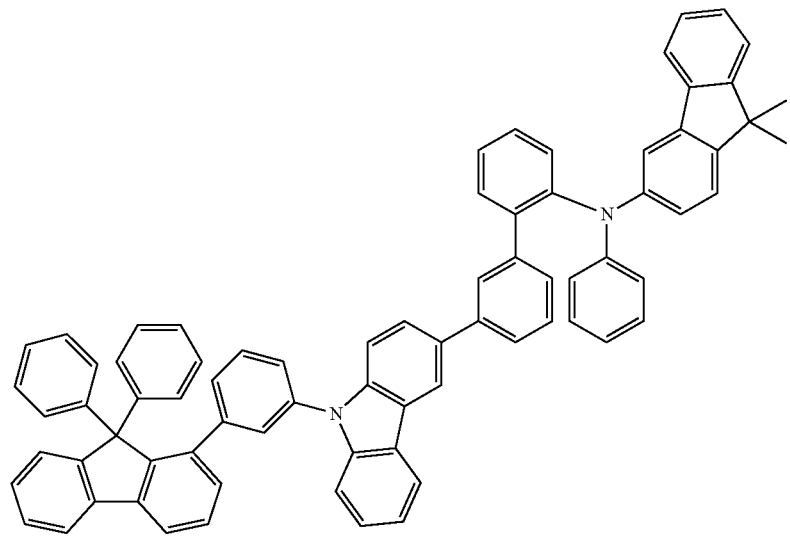
A392

-continued
493     C1
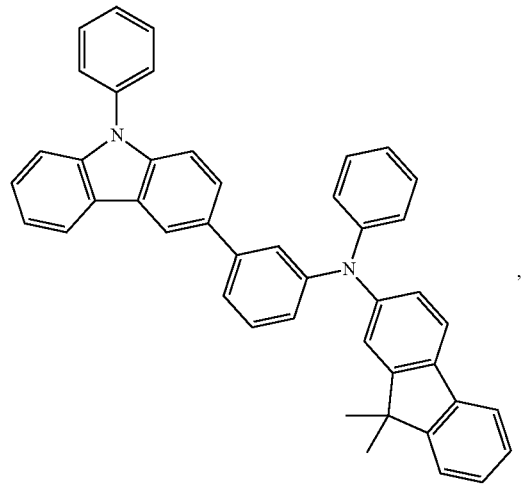
494     C2
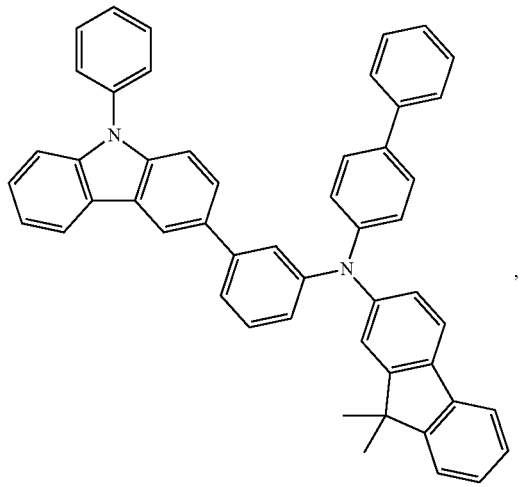
C3
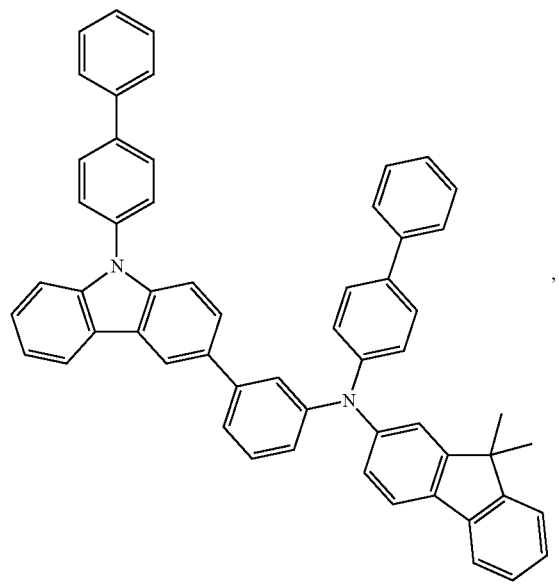
C4
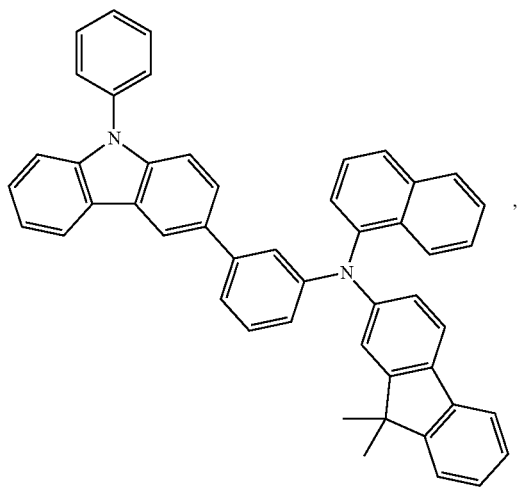

495
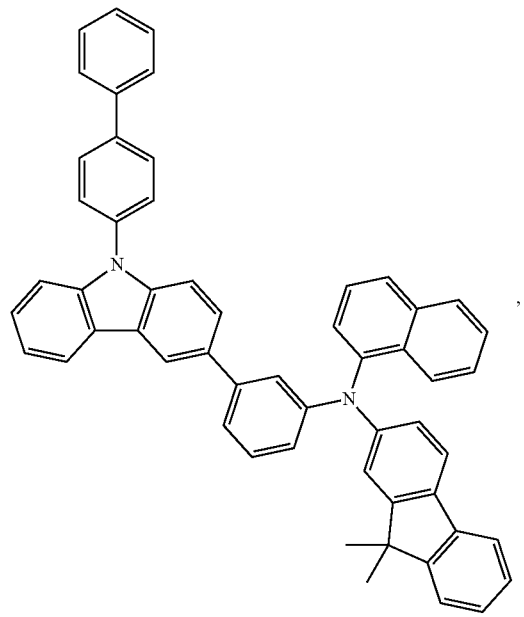
496
-continued
C5
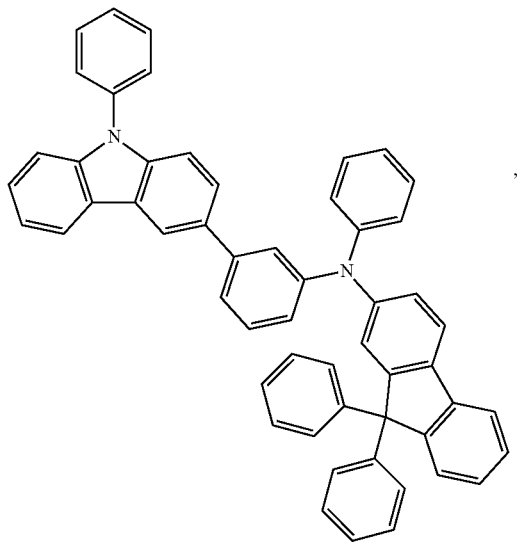
C6
C7
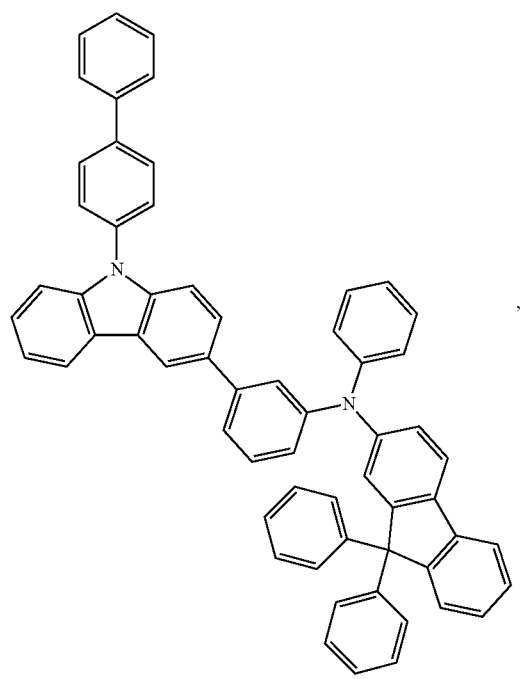
C8
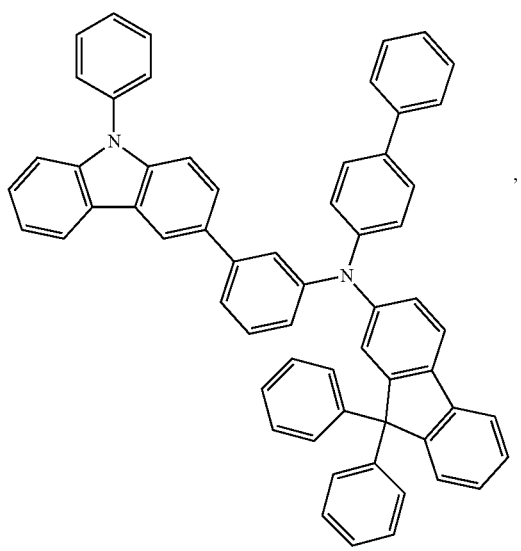

-continued
497
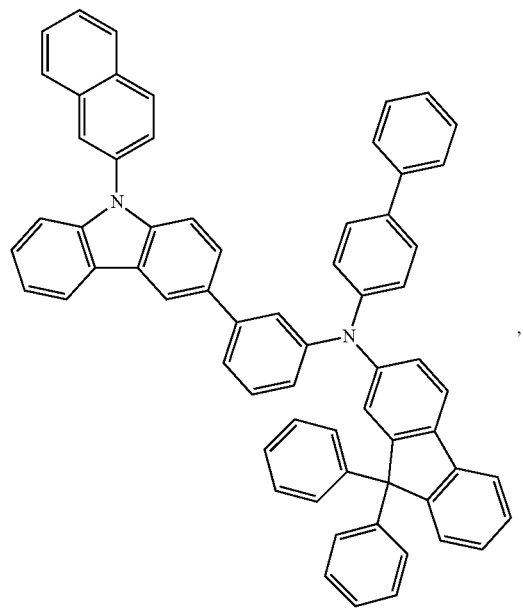
C9
498
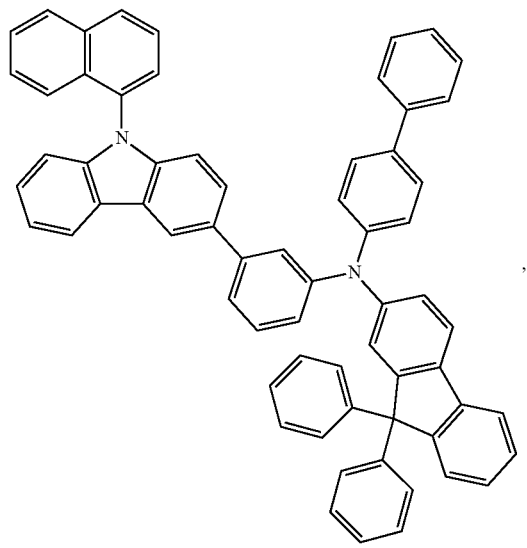
C10
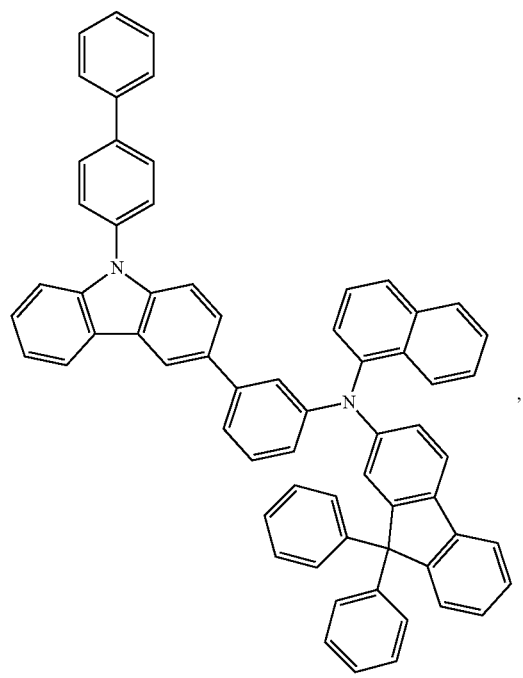
C11
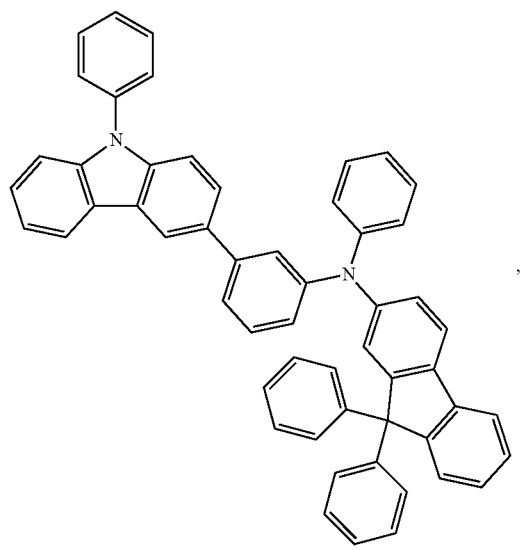
C12

-continued
C13
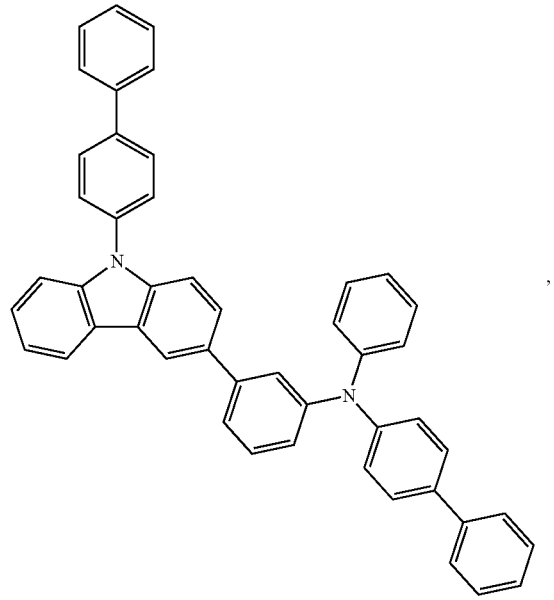
C14
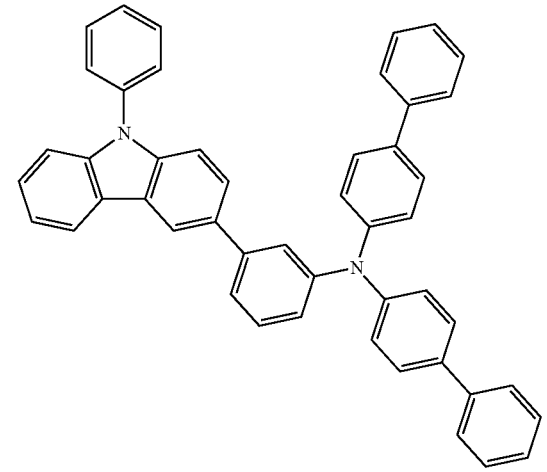
C15
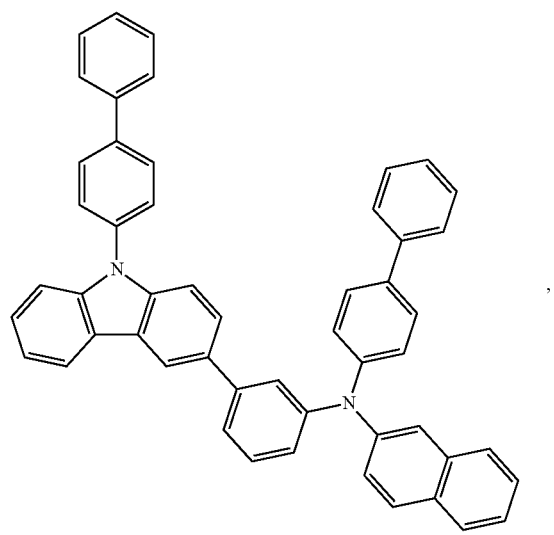
C16
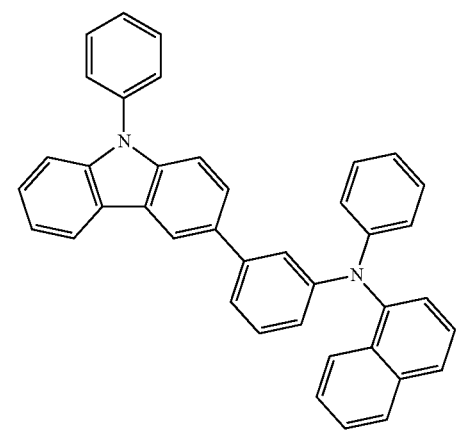
C17
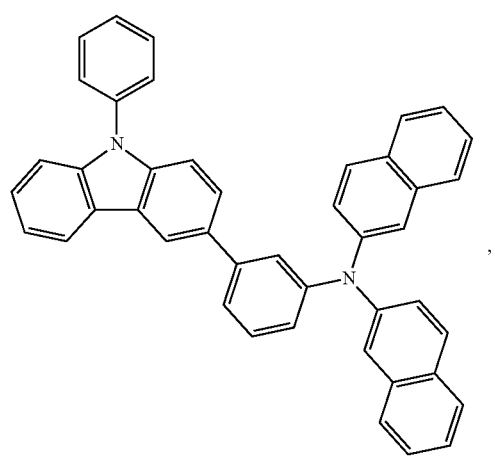

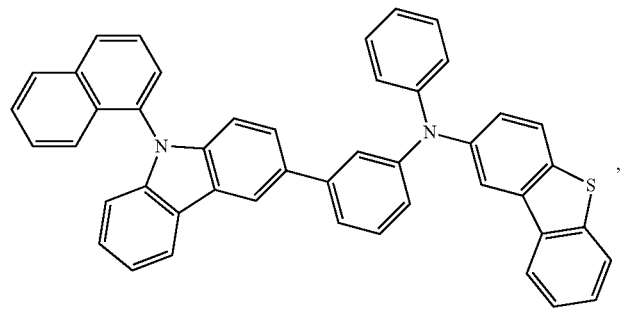
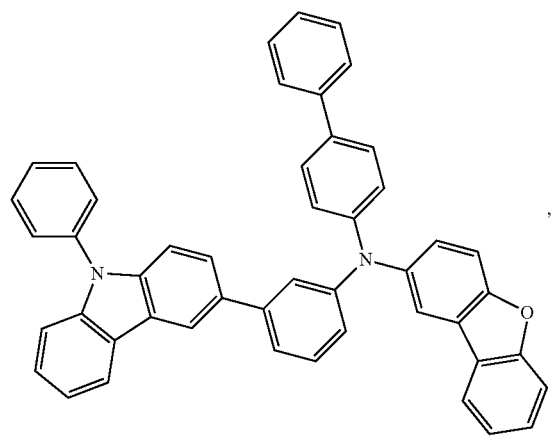
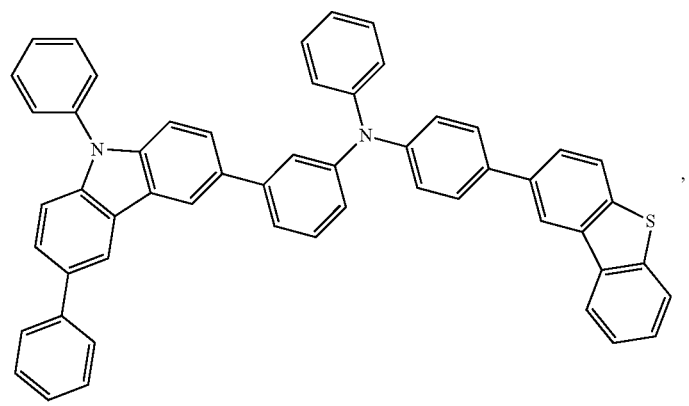

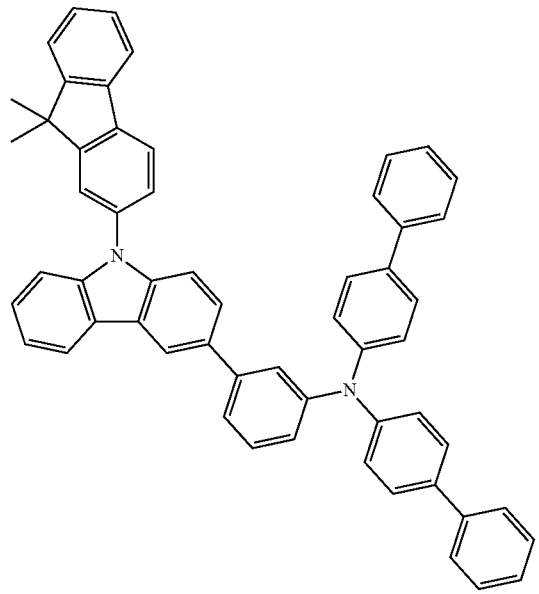
C21
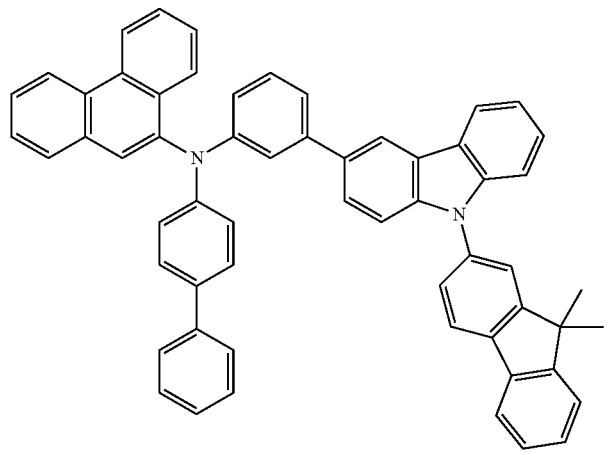
C22
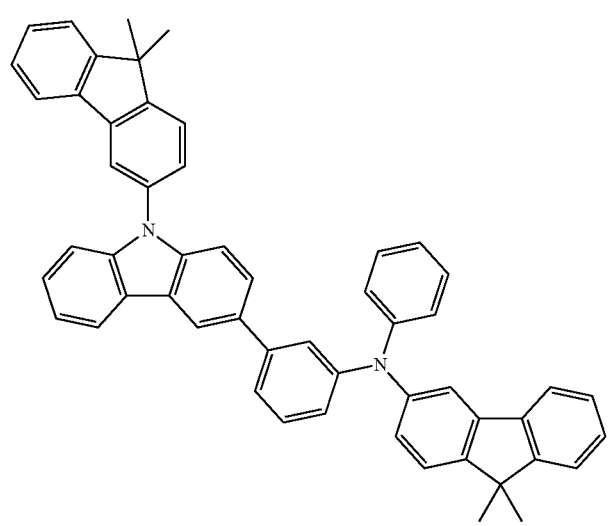
C23

-continued
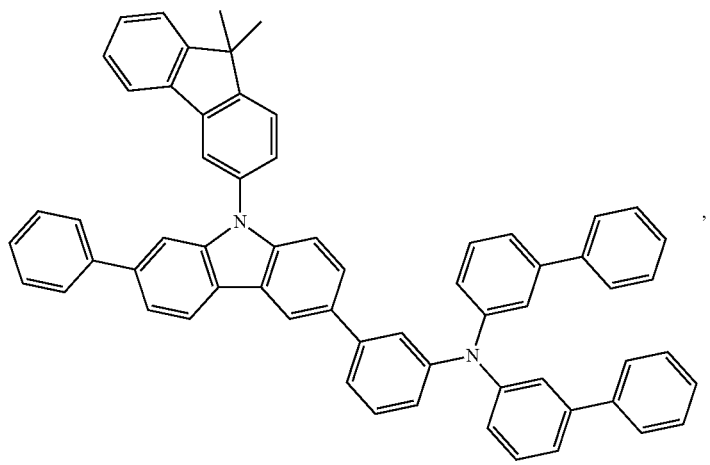
C24
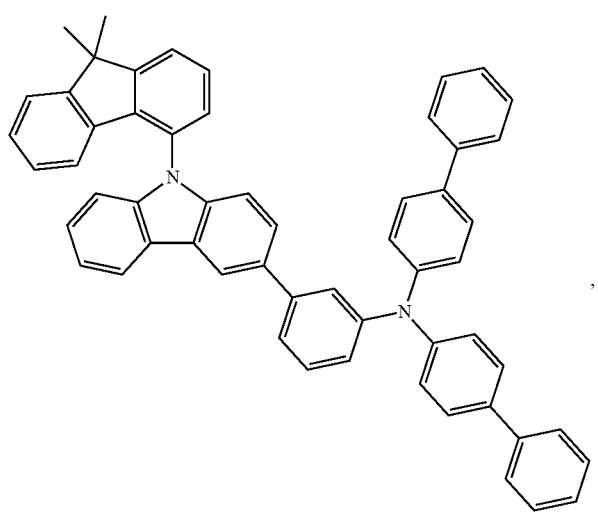
C25
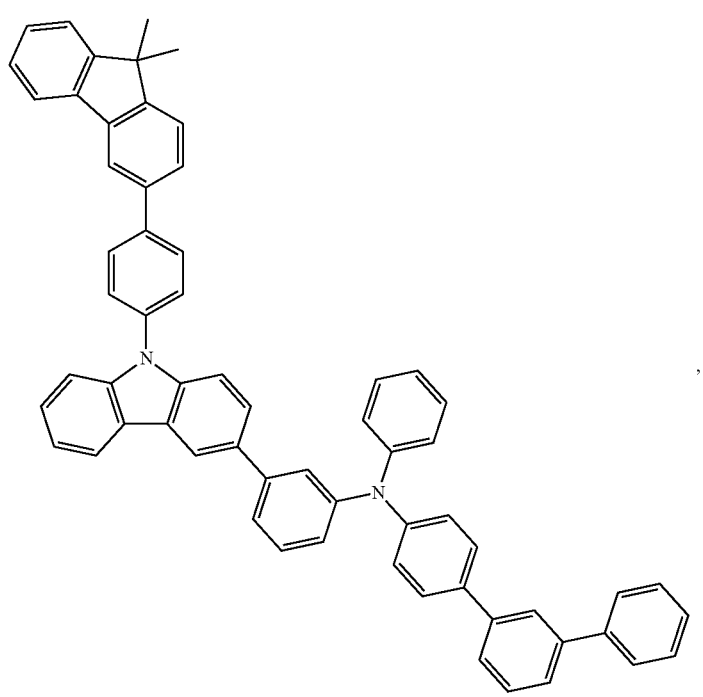
C26

-continued
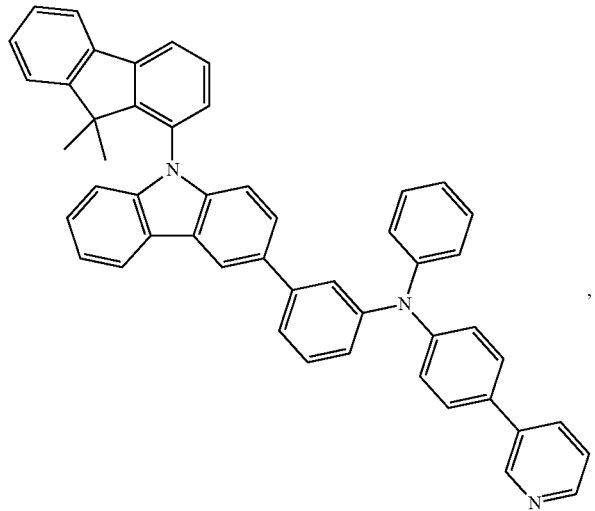
C27
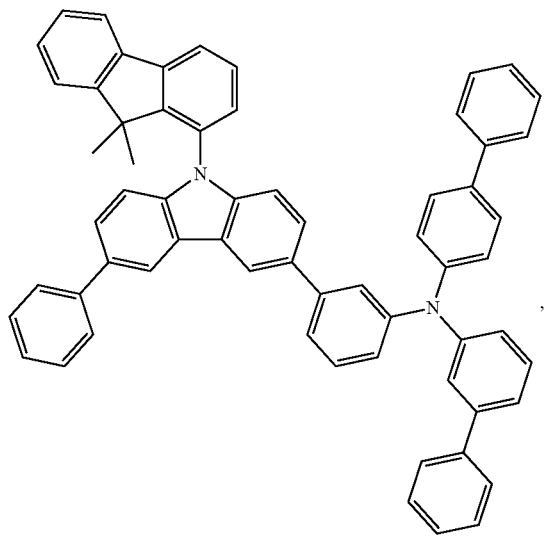
C28

-continued
C29
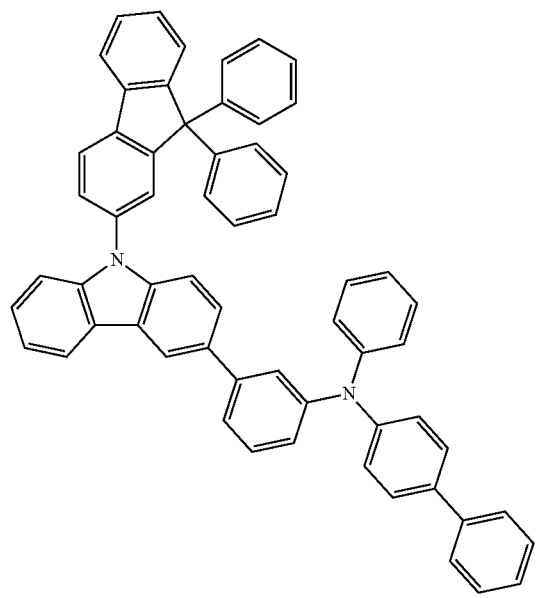
C30
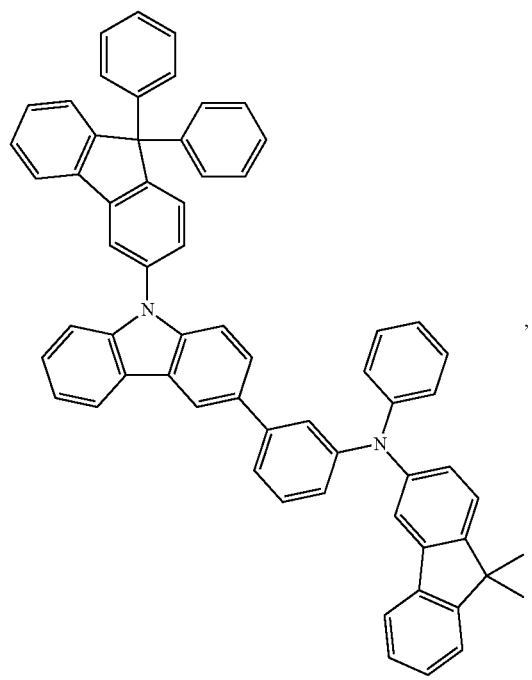
C31
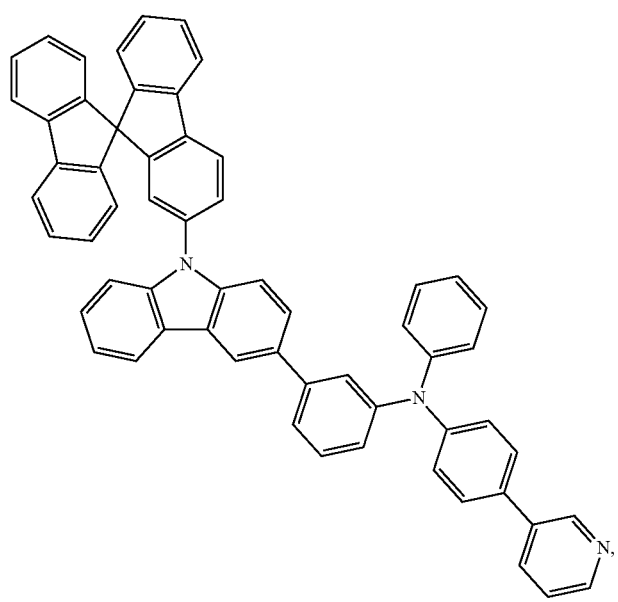

-continued
C32
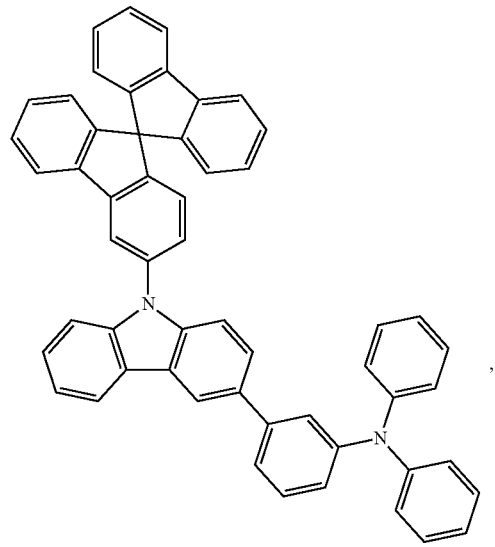
C33
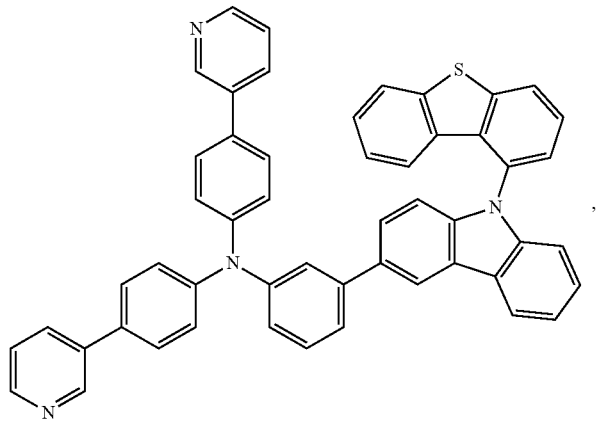
C34
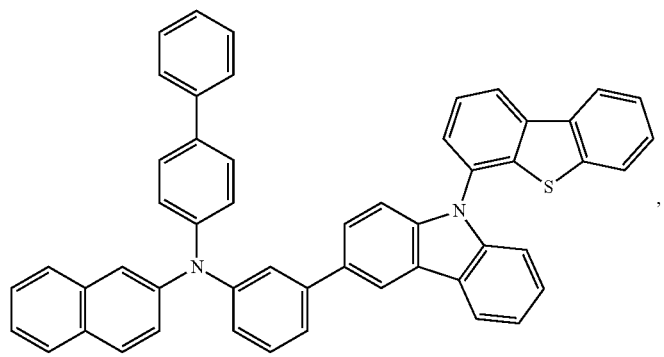
C35
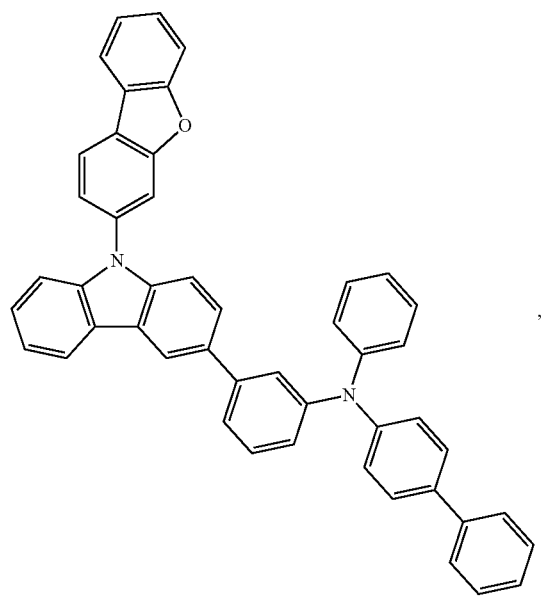
C36
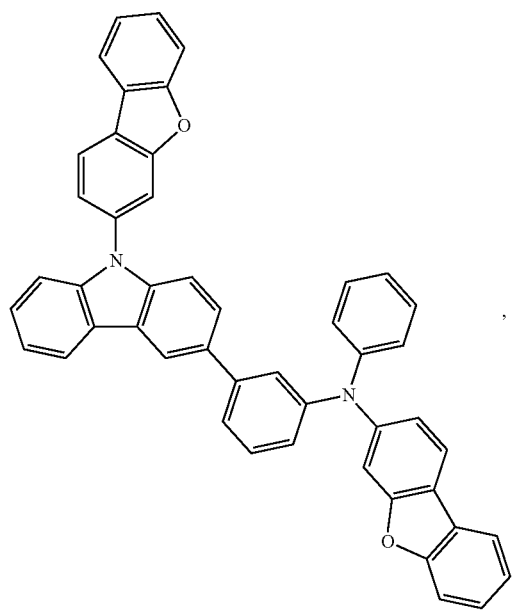

-continued
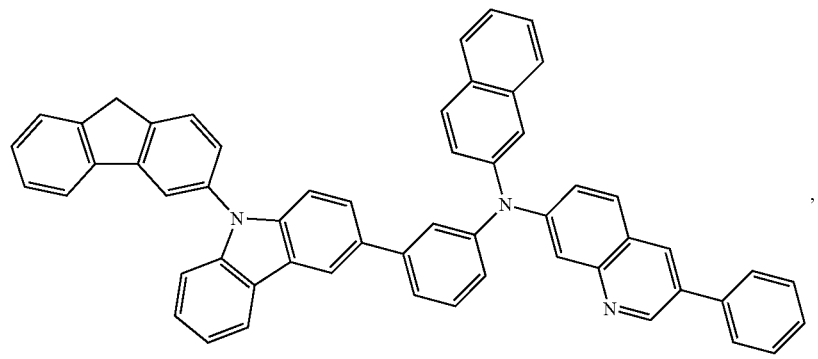
C37
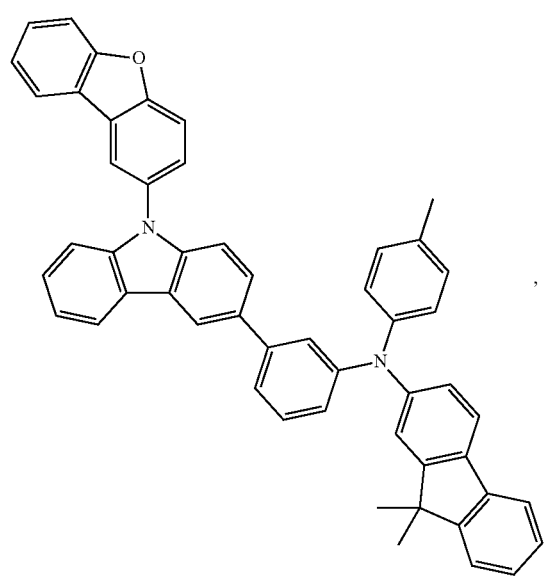
C38
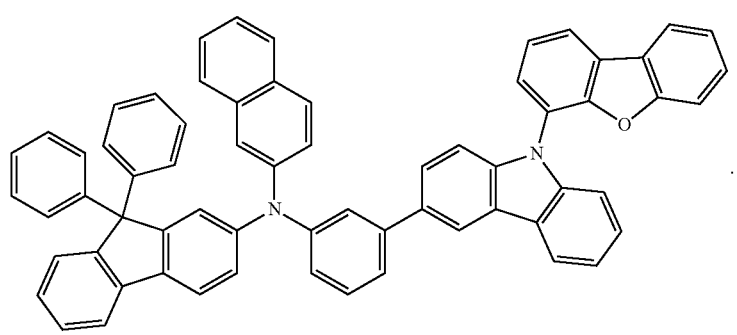
C39
or
C40
* * * * *

UNITED STATES PATENT AND TRADEMARK OFFICE
CERTIFICATE OF CORRECTION

PATENT NO. : 10,141,516 B2  
APPLICATION NO. : 14/650110  
DATED : November 27, 2018  
INVENTOR(S) : Bumsung Lee et al.

Page 1 of 1

It is certified that error appears in the above-identified patent and that said Letters Patent is hereby corrected as shown below:

In the Claims

Column 297, Claim 1, Line 46:

Please delete " 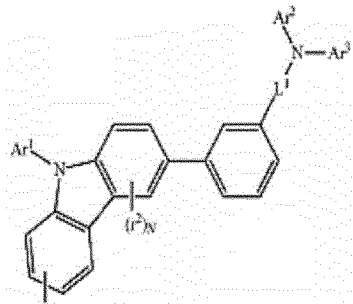 " and replace with

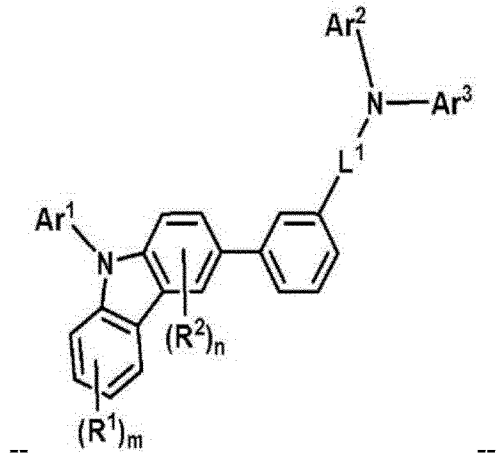

--

Signed and Sealed this  
Thirtieth Day of April, 2019

Andrei Iancu  
*Director of the United States Patent and Trademark Office*

UNITED STATES PATENT AND TRADEMARK OFFICE
CERTIFICATE OF CORRECTION

Page 1 of 1

PATENT NO. : 10,141,516 B2
APPLICATION NO. : 14/650110
DATED : November 27, 2018
INVENTOR(S) : Bumsung Lee et al.

It is certified that error appears in the above-identified patent and that said Letters Patent is hereby corrected as shown below:

Column 271, Line 31; and Column 272, Line 1:

Please delete "☐"
And replace with -- I --

Column 283, Lines 7, 37, 43, and 50; Column 284, Lines 8, 15, 40, 43, 44:

Please delete "☐"
And replace with -- II --

Column 287, Lines 1, 28, 33, 41; Column 288, Lines 8, 16, 23, 31, 34, 35:

Please delete "☐"
And replace with -- III --

Column 291, Line 56:

Please delete "☐"
And replace with -- IV --

Column 292, Line 61:

Please delete "☐"
And replace with -- III --

Column 293, Lines 6, 11, 18, 26; Column 294, Lines 8, 16, 19, 20:

Please delete "☐"
And replace with -- IV --

Signed and Sealed this
Seventh Day of January, 2020

Andrei Iancu
*Director of the United States Patent and Trademark Office* and on the first page.

EX PARTE REEXAMINATION CERTIFICATE (11809th)

United States Patent
Lee et al.

(10) Number: US 10,141,516 C1
(45) Certificate Issued: Feb. 26, 2021

(54) COMPOUND FOR ORGANIC ELECTRIC ELEMENT, ORGANIC ELECTRIC ELEMENT COMPRISING THE SAME AND ELECTRONIC DEVICE THEREOF

(71) Applicant: DUK SAN NEOLUX CO., LTD., Cheonan-si (KR)

(72) Inventors: Bumsung Lee, Cheonan-si (KR); Yeonhee Choi, Cheonan-si (KR); Daesung Kim, Yongin-si (KR); Soungyun Mun, Yongin-si (KR); Jungcheol Park, Cheonan-si (KR); Kiho So, Cheonan-si (KR); Jinho Yun, Cheonan-si (KR); Daehwan Oh, Cheonan-si (KR); Seungwon Yeo, Daejeon (KR)

(73) Assignee: DUK SAN NEOLUX CO., LTD., Cheonan-si (KR)

Reexamination Request:
No. 90/014,405, Nov. 4, 2019

Reexamination Certificate for:
Patent No.: 10,141,516
Issued: Nov. 27, 2018
Appl. No.: 14/650,110
PCT Filed: Dec. 3, 2013
PCT No.: PCT/KR2013/011089
§ 371 (c)(1),
(2) Date: Jun. 5, 2015
PCT Pub. No.: WO2014/088285
PCT Pub. Date: Jun. 12, 2014

Certificate of Correction issued Apr. 30, 2019
Certificate of Correction issued Jan. 7, 2020

(30) Foreign Application Priority Data

Dec. 6, 2012 (KR) .......... 10-2012-0141364
Nov. 1, 2013 (KR) .......... 10-2013-0132013

(51) Int. Cl.
| | | |
|---|---|---|
| C07D 209/86 | (2006.01) |
| C07D 333/76 | (2006.01) |
| H01L 51/00 | (2006.01) |
| C07D 209/82 | (2006.01) |
| C09K 11/06 | (2006.01) |
| H05B 33/14 | (2006.01) |
| C07D 405/14 | (2006.01) |
| C07D 409/04 | (2006.01) |
| C07D 409/14 | (2006.01) |
| C07D 409/12 | (2006.01) |
| G09G 3/3225 | (2016.01) |
| H01L 51/50 | (2006.01) |
| C07D 401/12 | (2006.01) |
| C07D 405/04 | (2006.01) |

(52) U.S. Cl.
CPC ........ *H01L 51/0061* (2013.01); *C07D 209/82* (2013.01); *C07D 209/86* (2013.01); *C07D 401/12* (2013.01); *C07D 405/04* (2013.01); *C07D 405/14* (2013.01); *C07D 409/04* (2013.01); *C07D 409/12* (2013.01); *C07D 409/14* (2013.01); *C09K 11/06* (2013.01); *G09G 3/3225* (2013.01); *H01L 51/006* (2013.01); *H01L 51/0072* (2013.01); *H05B 33/14* (2013.01); *C09K 2211/1007* (2013.01); *C09K 2211/1011* (2013.01); *C09K 2211/1014* (2013.01); *C09K 2211/1029* (2013.01); *C09K 2211/1088* (2013.01); *C09K 2211/1092* (2013.01); *H01L 51/0052* (2013.01); *H01L 51/0056* (2013.01); *H01L 51/0058* (2013.01); *H01L 51/0067* (2013.01); *H01L 51/0068* (2013.01); *H01L 51/0073* (2013.01); *H01L 51/0074* (2013.01); *H01L 51/5004* (2013.01); *H01L 51/5012* (2013.01); *H01L 51/5056* (2013.01); *H01L 51/5072* (2013.01); *H01L 51/5088* (2013.01); *H01L 51/5092* (2013.01); *H01L 2251/552* (2013.01); *Y02E 10/549* (2013.01)

(58) Field of Classification Search
None
See application file for complete search history.

(56) References Cited

To view the complete listing of prior art documents cited during the proceeding for Reexamination Control Number 90/014,405, please refer to the USPTO's public Patent Application Information Retrieval (PAIR) system under the Display References tab.

*Primary Examiner* — Ling X Xu

(57) ABSTRACT

Provides herein are a compound capable of improving light emitting efficiency, stability, and lifespan of the element, an organic element using the same, and an electric device for the same.

EX PARTE
REEXAMINATION CERTIFICATE

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 6-13 are cancelled.

Claims 1-3 and 5 are determined to be patentable as amended.

New claim 14 is added and determined to be patentable.

Claim 4 was not reexamined.

1. A compound represented by Formula 1 below:

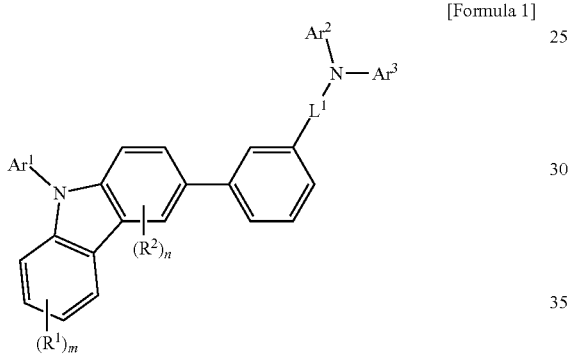

[Formula 1]

wherein[,]:
m is an integer from 1 to 4,
n is an integer from 1 to 3,
$R^1$ is selected from the group consisting of hydrogen, deuterium, tritium, a $C_6$-$C_{60}$ aryl group, and a fluorenyl group, and $R^2$ is selected from the group consisting of hydrogen, deuterium, tritium, a $C_6$-$C_{60}$ aryl group, a fluorenyl group, and a $C_2$-$C_{60}$ heterocyclic group containing at least one heteroatom selected from the group consisting of O, N, S, Si, and P, wherein the aryl group, heterocyclic group, and fluorenyl group may be substituted by one or more substituents selected from the group consisting of halogen, a $C_1$-$C_{20}$ alkyl group, a $C_2$-$C_{20}$ alkenyl group, a $C_6$-$C_{20}$ aryl group, a $C_6$-$C_{20}$ aryl group substituted by deuterium, and a $C_2$-$C_{20}$ heterocyclic group,
$Ar^1$ is selected from the group consisting of a fluorenyl group, a $C_6$-$C_{60}$ aryl group, a $C_2$-$C_{20}$ alkenyl group, a $C_2$-$C_{60}$ heterocyclic group containing at least one heteroatom selected from the group consisting of O, N, S, Si, and P, and a $C_1$-$C_{50}$ alkyl group, wherein the aryl group may be substituted by one or more substituents selected from the group consisting of deuterium, halogen, a $C_1$-$C_{20}$ alkyl group, a $C_2$-$C_{20}$ alkenyl group, a $C_6$-$C_{20}$ aryl group substituted by deuterium, and a $C_2$-$C_{20}$ heterocyclic group; and the heterocyclic group, fluorenyl group, alkyl group, and alkenyl group may be substituted by one or more substituents selected from the group consisting of deuterium, halogen, a $C_1$-$C_{20}$ alkyl group, a $C_2$-$C_{20}$ alkenyl group, a $C_6$-$C_{20}$ aryl group, a $C_6$-$C_{20}$ aryl group substituted by deuterium, and a $C_2$-$C_{20}$ heterocyclic group, $L^1$ is selected from the group consisting of a single bond, a $C_6$-$C_{60}$ arylene group, a fluorenylene group, and a $C_2$-$C_{60}$ bivalent heterocyclic group containing at least one heteroatom selected from the group consisting of O, N, S, Si, and P, wherein the arylene group, fluorenylene group, and heterocyclic group may be substituted by one or more substituents selected from the group consisting of deuterium, halogen, a $C_1$-$C_{20}$ alkyl group, a $C_2$-$C_{20}$ alkenyl group, a $C_6$-$C_{20}$ aryl group, a $C_6$-$C_{20}$ aryl group substituted by deuterium, and a $C_2$-$C_{20}$ heterocyclic group, and $Ar^2$ *is a $C_2$-$C_{60}$ heterocyclic group containing at least one heteroatom selected from the group consisting of O, N, S, Si, and P, with the proviso that a thiophene, a benzothiophene, a dibenzothiophene, a furan, a benzofuran and a dibenzofuran groups are excluded from $Ar^2$, and $Ar^3$* [are independently] *is* selected from the group consisting of a $C_6$-$C_{60}$ aryl group, a fluorenyl group, and a $C_2$-$C_{60}$ heterocyclic group containing at least one heteroatom selected from the group consisting of O, N, S, Si, and P, wherein the aryl group, heterocyclic group, and fluorenyl group may be substituted by one or more substituents selected from the group consisting of deuterium, halogen, a silane group, —L'-N (R')(R"), a $C_1$-$C_{20}$ alkyl group, a $C_2$-$C_{20}$ alkenyl group, a $C_6$-$C_{20}$ aryl group, a $C_6$-$C_{20}$ aryl group substituted by deuterium, and a $C_2$-$C_{20}$ heterocyclic group, wherein L' is selected from the group consisting of a single bond, a $C_6$-$C_{60}$ arylene group, a fluorenylene group, and a $C_2$-$C_{60}$ heterocyclic group containing at least one heteroatom selected from the group consisting of O, N, S, Si, and P; and R' and R" are independently selected from the group consisting of a $C_6$-$C_{60}$ aryl group, a fluorenyl group, and a $C_2$-$C_{60}$ heterocyclic group containing at least one heteroatom selected from the group consisting of O, N, S, Si, and P.

2. The compound as claimed in claim 1, wherein $L^1$ is any one of the compounds below:

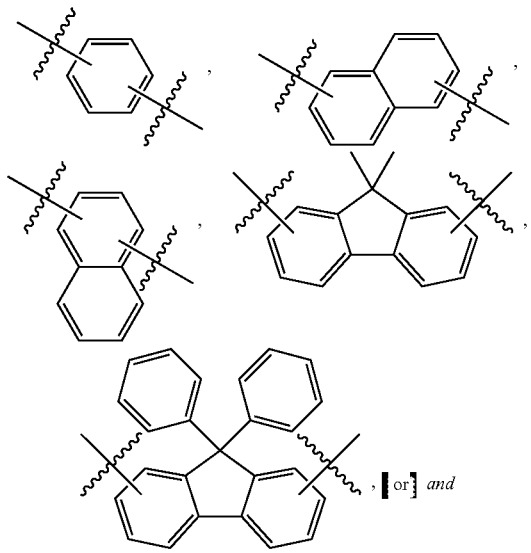

, [or] *and*

-continued

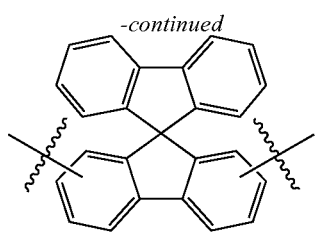

3. A compound represented by Formula 1 below:

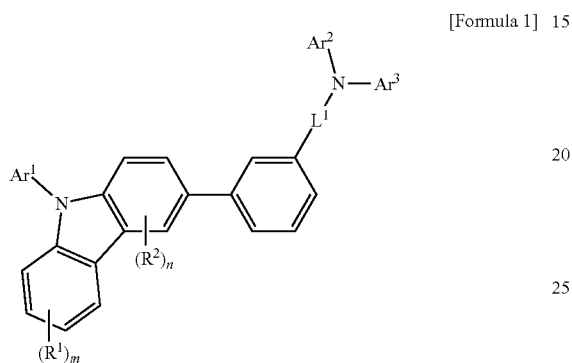

[Formula 1]

wherein:
m is an integer from 1 to 4,
n is an integer from 1 to 3,
$R^1$ is selected from the group consisting of hydrogen, deuterium, tritium, a $C_6$-$C_{60}$ aryl group, and a fluorenyl group, and $R^2$ is selected from the group consisting of hydrogen, deuterium, tritium, a $C_6$-$C_{60}$ aryl group, a fluorenyl group, and a $C_2$-$C_{60}$ heterocyclic group containing at least one heteroatom selected from the group consisting of O, N, S, Si, and P, wherein the aryl group, heterocyclic group, and fluorenyl group may be substituted by one or more substituents selected from the group consisting of halogen, a $C_1$-$C_{20}$ alkyl group, a $C_2$-$C_{20}$ alkenyl group, a $C_6$-$C_{20}$ aryl group, a $C_6$-$C_{20}$ aryl group substituted by deuterium, and a $C_2$-$C_{20}$ heterocyclic group,
$Ar^1$ is selected from the group consisting of a fluorenyl group, a $C_6$-$C_{60}$ aryl group, a $C_2$-$C_{20}$ alkenyl group, a $C_2$-$C_{60}$ heterocyclic group containing at least one heteroatom selected from the group consisting of O, N, S, Si, and P, and a $C_1$-$C_{50}$ alkyl group, wherein the aryl group may be substituted by one or more substituents selected from the group consisting of deuterium, halogen, a $C_1$-$C_{20}$ alkyl group, a $C_2$-$C_{20}$ alkenyl group, a $C_6$-$C_{20}$ aryl group substituted by deuterium, and a $C_2$-$C_{20}$ heterocyclic group; and the heterocyclic group, fluorenyl group, alkyl group, and alkenyl group may be substituted by one or more substituents selected from the group consisting of deuterium, halogen, a $C_1$-$C_{20}$ alkyl group, a $C_2$-$C_{20}$ alkenyl group, a $C_6$-$C_{20}$ aryl group, a $C_6$-$C_{20}$ aryl group substituted by deuterium, and a $C_2$-$C_{20}$ heterocyclic group,
$L^1$ is selected from the group consisting of a single bond, a $C_6$-$C_{60}$ arylene group, a fluorenylene group, and a $C_2$-$C_{60}$ bivalent heterocyclic group containing at least one heteroatom selected from the group consisting of O, N, S, Si, and P, wherein the arylene group, fluorenylene group, and heterocyclic group may be substituted by one or more substituents selected from the group consisting of deuterium, halogen, a $C_1$-$C_{20}$ alkyl group, a $C_2$-$C_{20}$ alkenyl group, a $C_6$-$C_{20}$ aryl group, a $C_6$-$C_{20}$ aryl group substituted by deuterium, and a $C_2$-$C_{20}$ heterocyclic group, [and]

$Ar^2$ *is selected from the group consisting of:*

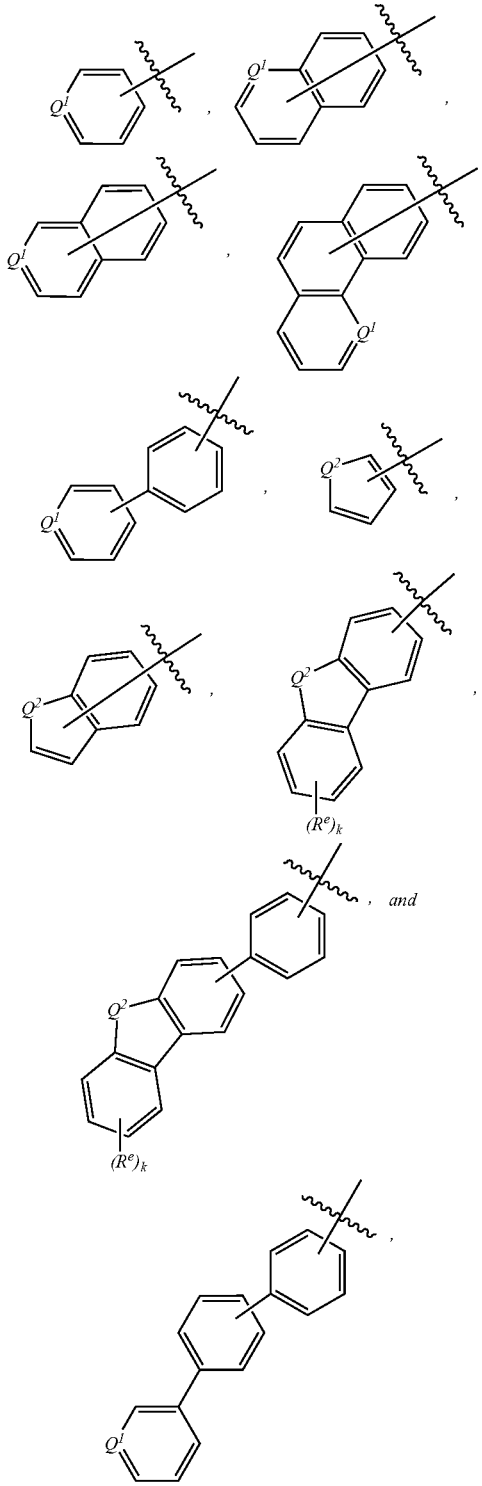

wherein:
$Q^1$ is N,
$Q^2$ is $N(R^d)$, S or O,
k is an integer from 1 to 4,
$R^e$ is selected from the group consisting of hydrogen, deuterium, a $C_6$-$C_{60}$ aryl group, a $C_2$-$C_{60}$ heterocyclic group containing at least one heteroatom selected from the group consisting of O, N, S, Si, and P, a $C_1$-$C_{50}$ alkyl group, a $C_2$-$C_{20}$ alkenyl group, a $C_1$-$C_{30}$ alkoxy group, and a fluorenyl group, or any two adjacent groups of $R^e$s are optionally linked together to form at least one aromatic ring, and
$R^d$ is selected from the group consisting of a $C_6$-$C_{60}$ aryl group, a $C_2$-$C_{60}$ heterocyclic group containing at least one heteroatom selected from the group consisting of O, N, S, Si, and P, a $C_1$-$C_{50}$ alkyl group, a $C_2$-$C_{20}$ alkenyl group, and a $C_1$-$C_{30}$ alkoxy group,
with the proviso that a thiophene, a benzothiophene, a dibenzothiophene, a furan, a benzofuran and a dibenzofuran groups are excluded from $Ar^2$, and
$Ar^3$ [are independently any one of the compounds below] is selected from the group consisting of:

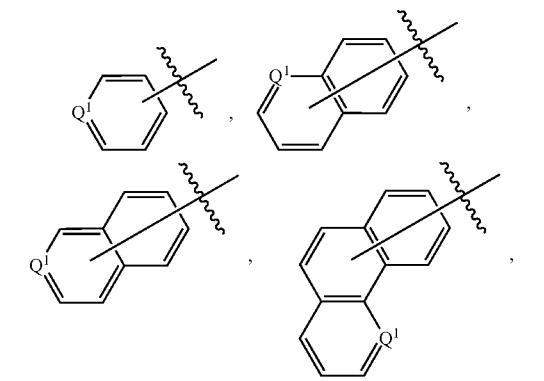

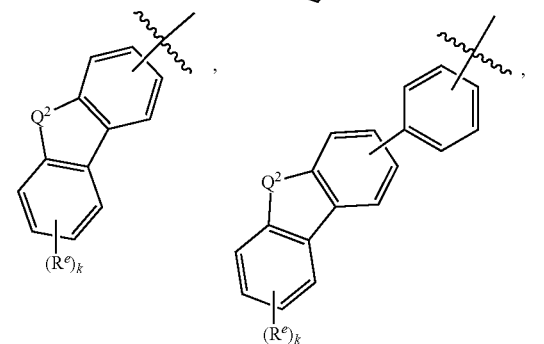

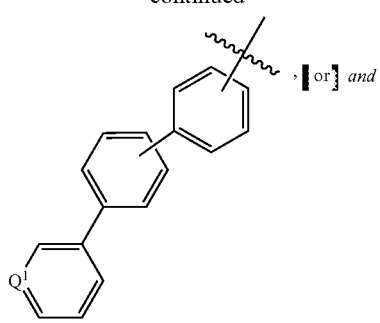

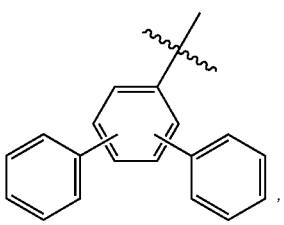

wherein[,]:

$Q^1$ is $C(R^a)$ or N, $Q^2$ is selected form the group consisting of $C(R^b)(R^c)$, $N(R^d)$, S and O, k is an integer from 1 to 4, $R^a$ and $R^e$ are independently selected from the group consisting of hydrogen, deuterium, a $C_6$-$C_{60}$ aryl group, a $C_2$-$C_{60}$ heterocyclic group containing at least one heteroatom selected from the group consisting of O, N, S, Si, and P, a $C_1$-$C_{50}$ alkyl group, a $C_2$-$C_{20}$ alkenyl group, a $C_1$-$C_{30}$ alkoxy group, and a fluorenyl group, or any two adjacent groups of $R^e$s are optionally linked together to form at least one aromatic ring, $R^b$ to $R^d$ are independently selected from the group consisting of a $C_6$-$C_{60}$ aryl group, a $C_2$-$C_{60}$ heterocyclic group containing at least one heteroatom selected from the group consisting of O, N, S, Si, and P, a $C_1$-$C_{50}$ alkyl group, a $C_2$-$C_{20}$ alkenyl group, and a $C_1$-$C_{30}$ alkoxy group, or $R^b$ and $R^c$ are optionally linked together to form at least one spiro compound.

5. A compound represented by [one of Formulas below] Formula 5:

[Formula 4]

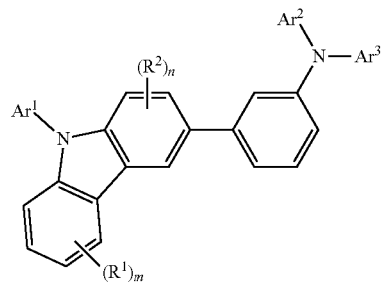

[Formula 5]

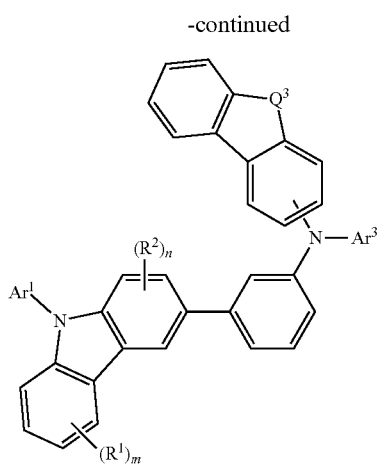

wherein[,]:
m is an integer from 1 to 4,
n is an integer from 1 to 3,
R¹ is selected from the group consisting of hydrogen, deuterium, tritium, a $C_6$-$C_{60}$ aryl group, and a fluorenyl group, and R² is selected from the group consisting of hydrogen, deuterium, tritium, a $C_6$-$C_{60}$ aryl group, a fluorenyl group, and a $C_2$-$C_{60}$ heterocyclic group containing at least one heteroatom selected from the group consisting of O, N, S, Si, and P, wherein the aryl group, heterocyclic group, and fluorenyl group may be substituted by one or more substituents selected from the group consisting of halogen, a $C_1$-$C_{20}$ alkyl group, a $C_2$-$C_{20}$ alkenyl group, a $C_6$-$C_{20}$ aryl group, a $C_6$-$C_{20}$ aryl group substituted by deuterium, and a $C_2$-$C_{20}$ heterocyclic group,
Ar¹ is selected from the group consisting of a fluorenyl group, a $C_6$-$C_{60}$ aryl group, a $C_2$-$C_{20}$ alkenyl group, a $C_2$-$C_{60}$ heterocyclic group containing at least one heteroatom selected from the group consisting of O, N, S, Si, and P, and a $C_1$-$C_{50}$ alkyl group, wherein the aryl group may be substituted by one or more substituents selected from the group consisting of deuterium, halogen, a $C_1$-$C_{20}$ alkyl group, a $C_2$-$C_{20}$ alkenyl group, a $C_6$-$C_{20}$ aryl group substituted by deuterium, and a $C_2$-$C_{20}$ heterocyclic group; and the heterocyclic group, fluorenyl group, alkyl group, and alkenyl group may be substituted by one or more substituents selected from the group consisting of deuterium, halogen, a $C_1$-$C_{20}$ alkyl group, a $C_2$-$C_{20}$ alkenyl group, a $C_6$-$C_{20}$ aryl group, a $C_6$-$C_{20}$ aryl group substituted by deuterium, and a $C_2$-$C_{20}$ heterocyclic group,
[Ar² and] Ar³ [are] is independently selected from the group consisting of a $C_6$-$C_{60}$ aryl group, a fluorenyl group, and a $C_2$-$C_{60}$ heterocyclic group containing at least one heteroatom selected from the group consisting of O, N, S, Si, and P, wherein the aryl group, heterocyclic group, and fluorenyl group may be substituted by one or more substituents selected from the group consisting of deuterium, halogen, a silane group, —L'-N(R')(R"), a $C_1$-$C_{20}$ alkyl group, a $C_2$-$C_{20}$ alkenyl group, a $C_6$-$C_{20}$ aryl group, a $C_6$-$C_{20}$ aryl group substituted by deuterium, and a $C_2$-$C_{20}$ heterocyclic group, wherein L' is selected from the group consisting of a single bond, a $C_6$-$C_{60}$ arylene group, a fluorenylene group, and a $C_2$-$C_{60}$ heterocyclic group containing at least one heteroatom selected from the group consisting of O, N, S, Si, and P; and R' and R" are independently selected from the group consisting of a $C_6$-$C_{60}$ aryl group, a fluorenyl group, and a $C_2$-$C_{60}$ heterocyclic group containing at least one heteroatom selected from the group consisting of O, N, S, Si, and P, Q³ is [selected form the group consisting of C(R^h)(R^i),] N(R^j), [S and O,] and[,]

[R^h to] R^j [are] is independently selected from the group consisting of a $C_6$-$C_{60}$ aryl group, a $C_2$-$C_{60}$ heterocyclic group containing at least one heteroatom selected from the group consisting of O, N, S, Si, and P, a $C_1$-$C_{50}$ alkyl group, a $C_2$-$C_{20}$ alkenyl group, and a $C_1$-$C_{30}$ alkoxy group[, or R^h and R^i are optionally linked together to form at least one spiro compound].

14. A compound selected from the group consisting of the following compounds:

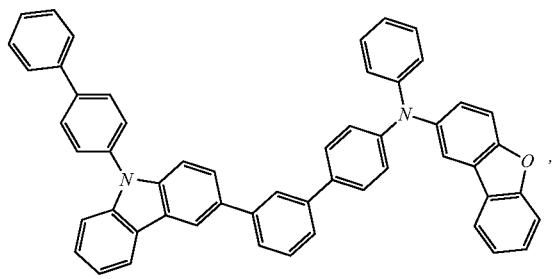

A97

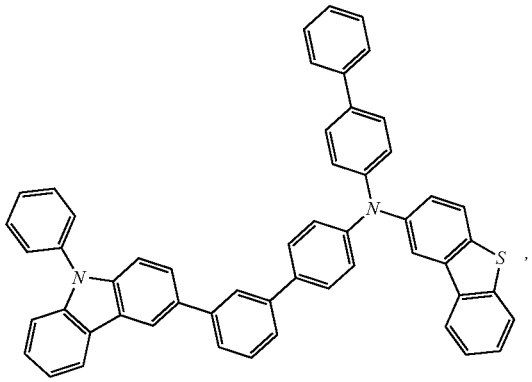

A101

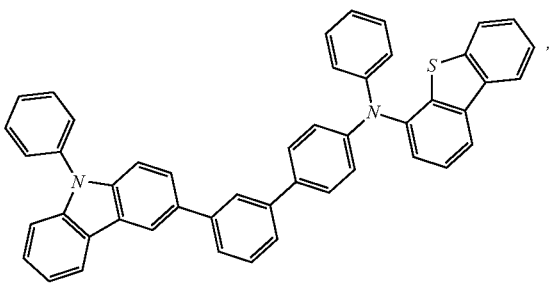

A121

-continued
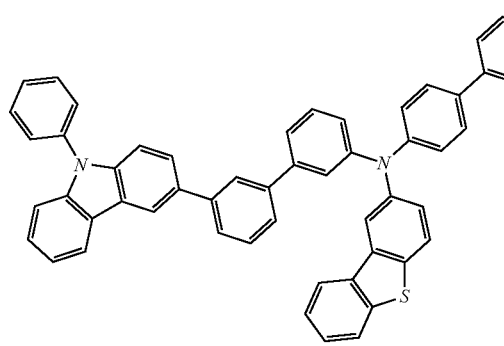
A262
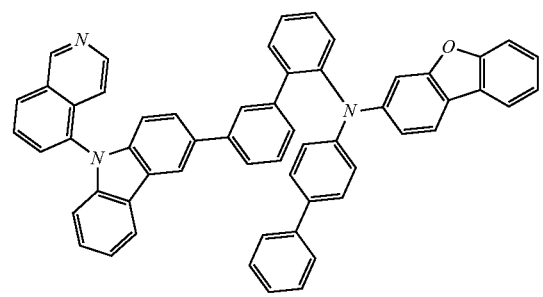
A324
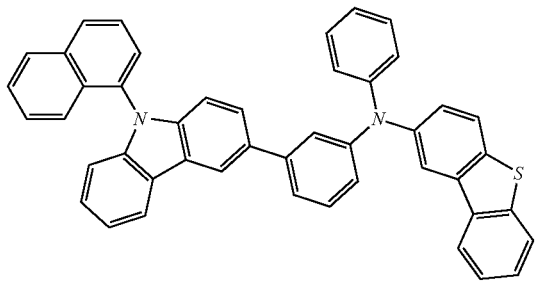
C18
and
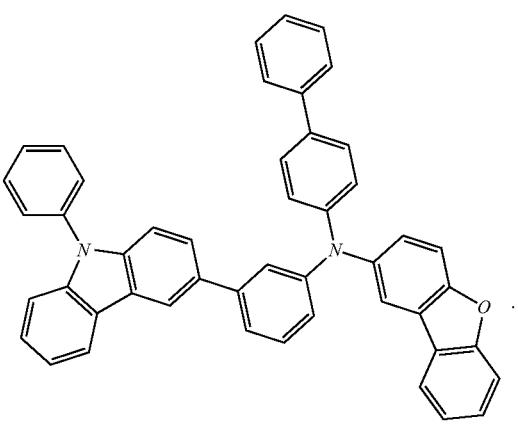
C19
* * * * *